US012459912B2

(12) United States Patent
Baggott

(10) Patent No.: US 12,459,912 B2
(45) Date of Patent: Nov. 4, 2025

(54) ADVANTAGEOUS BENZOTHIOPHENE COMPOSITIONS FOR MENTAL DISORDERS OR ENHANCEMENT

(71) Applicant: Tactogen Inc, Palo Alto, CA (US)

(72) Inventor: Matthew Baggott, Redwood City, CA (US)

(73) Assignee: TACTOGEN INC, Palo Alto, CA (US)

( * ) Notice: Subject to any disclaimer, the term of this patent is extended or adjusted under 35 U.S.C. 154(b) by 483 days.

(21) Appl. No.: 18/093,773

(22) Filed: Jan. 5, 2023

(65) Prior Publication Data

US 2023/0159487 A1 May 25, 2023

Related U.S. Application Data

(63) Continuation of application No. PCT/US2021/040570, filed on Jul. 6, 2021.

(60) Provisional application No. 63/149,208, filed on Feb. 12, 2021, provisional application No. 63/069,135, filed on Aug. 23, 2020, provisional application No. 63/048,640, filed on Jul. 6, 2020.

(51) Int. Cl.
*C07D 333/58* (2006.01)
*A61P 25/22* (2006.01)
*C07D 333/56* (2006.01)

(52) U.S. Cl.
CPC ............ *C07D 333/58* (2013.01); *A61P 25/22* (2018.01); *C07D 333/56* (2013.01)

(58) Field of Classification Search
CPC .................................................... C07D 333/58
See application file for complete search history.

(56) References Cited

U.S. PATENT DOCUMENTS

| | | | |
|---|---|---|---|
| 2,916,495 | A | 12/1959 | Edgerton et al. |
| 5,462,965 | A | 10/1995 | Roba et al. |
| 10,058,534 | B2 | 8/2018 | Burks et al. |
| 2008/0200541 | A1 | 8/2008 | Gross et al. |
| 2009/0264474 | A1 | 10/2009 | Branum et al. |
| 2010/0041673 | A1 | 2/2010 | Ramakrishna et al. |
| 2011/0118263 | A1 | 5/2011 | Li et al. |
| 2013/0203752 | A1 | 8/2013 | Blough et al. |
| 2015/0045356 | A1 | 2/2015 | Yamashita et al. |
| 2019/0321359 | A1 | 10/2019 | Yamashita et al. |
| 2020/0000747 | A1 | 1/2020 | Golan |
| 2022/0096429 | A1 | 3/2022 | Liechti |

FOREIGN PATENT DOCUMENTS

| | | | |
|---|---|---|---|
| EP | 3312184 A1 | 4/2018 | |
| GB | 855115 | 11/1960 | |
| WO | WO 1994/029290 A1 | 12/1994 | |
| WO | WO 2008/047883 A1 | 4/2008 | |
| WO | WO 2009/117097 A1 | 9/2009 | |
| WO | WO 2021/173273 A1 | 1/2021 | |
| WO | WO 2021/257169 A1 | 12/2021 | |
| WO | WO 2022/031566 A1 | 2/2022 | |
| WO | WO 2022/106947 A1 | 5/2022 | |
| WO | WO 2022/109050 A1 | 5/2022 | |
| WO | WO 2022/120289 A1 | 6/2022 | |

OTHER PUBLICATIONS

CAS Registry No. 1893062-76-4, which entered STN on Apr. 19, 2016 (Year: 2016).*
US, U.S. Pat. No. 11,767,305, A1, U.S. Appl. No. 18/077,966, Matthew Baggott, Sep. 26, 2023.
US, 2023/0159487, A1, U.S. Appl. No. 18/093,773, Matthew Baggott, May 25, 2023.
US, 2023/0257347, A1, U.S. Appl. No. 18/123,812, Matthew Baggott, Aug. 17, 2023.
US, 2024/0083864, A1, U.S. Appl. No. 18/371,935, Matthew Baggott, Mar. 14, 2024.
STN US Registry. Mar. 18, 2021. Columbus, Ohio, US. CAS RN:2613382-32-2.
STN US Registry. Aug. 1, 2017. Columbus, Ohio, US. CAS RN: 2106849-09-4.
US, 2023/0150963, A1, U.S. Appl. No. 18/077,966, Matthew Baggott, May 18, 2023.
US, 2023/0183199, A1, U.S. Appl. No. 18/106,273, Matthew Baggott, Jun. 15, 2023.
US, U.S. Appl. No. 18/123,812, Matthew Baggott, filed Mar. 20, 2023.
Kadkhodaei Kian et al. "Separation of 1-15 enantiomers of new psychoactive substances by high-performance liquid chromatography", Journal of Separation Science, vol. 41, No. 6, pp. 1274-1286, XP055785621, De ISSN: 1615-9306, DOI: 10.1002/jssc.201701239 Retrieved from the Internet: URL:https://api.wiley.com/onlinelibrary/tdm/v1/articles/10.1002%2Fjssc.201701239> Abstract; table 1, Mar. 1, 2018.
Shimshoni Jakob A. et al. "Neurochernical binding profiles of novel indole and benzofuran MDMA analogues", Naunyn-Schmiedeberg's Archives of Pharmacology, Springer, De, vol. 390, No. 1, pp. 15-24, XP036122857, ISSN: 0028-1298, DOI: 10.1007/S00210-016-1297-4, Abstract; figure 1, Sep. 20, 2016.
US, 2024/0308999, A1, U.S. Appl. No. 18/653,750, Matthew Baggott, Sep. 19, 2024.
US, 2024/0335414, A1, U.S. Appl. No. 18/737,589, Baggott et al., Oct. 10, 2024.
US, U.S. Appl. No. 18/737,506, Baggott et al., filed Jun. 7, 2024.
US, U.S. Appl. No. 18/893,750, Matthew Baggott, filed Sep. 23, 2024.
US, U.S. Appl. No. 18/895,095, Matthew Baggott, filed Sep. 24, 2024, Matthew Baggott.

(Continued)

*Primary Examiner* — Matthew P Coughlin
(74) *Attorney, Agent, or Firm* — Knowles Intellectual Property Strategies, LLC

(57) ABSTRACT

Pharmaceutically active benzothiophene compounds and their pharmaceutically acceptable salts and salt mixtures and pharmaceutically acceptable compositions for the treatment of mental disorders or for mental enhancement, including for entactogenic therapy, and generally for modulating central nervous system activity.

38 Claims, 11 Drawing Sheets

(56) References Cited

OTHER PUBLICATIONS

Barnet, Gene, et al. Quantitative structure activity relationships of analgesics, narcotic antagonists, and hallucinogens, National Institute on Drug Abuse, Research 22 Monograph Series, Apr. 20-22, 1978.
Baggott, Matthew J. et al. Effects of 3,4-methylenedioxymethamphetamine on socioemotional feelings, authenticity, and autobiographical disclosure in healthy volunteers in a controlled setting. J Psychopharmacol. Feb. 15, 2016;30(4):378-87.
Berge, Stephen M. Pharmaceutical Salts, vol. 66, No. 1, Journal of Pharmaceuticals Sciences, Jan. 1977.
Campaigne, E. et al. Benzo[b]thiophene Derivatives, XII. Synthesis of some 3-Benzo[b]thienylalkylamines and comparison of their central nervous system activity with tryptamine isosteres, vol. 11, 1049-1053, Sep. 1968.
Carleton, R. Nicholas, Brief Fear of Negative Evaluation Scale—Revised, Depression and Anxiety 23:297-303, May 10, 2006.
De Brouwer, Geoffrey, et al. A critical inquiry into marble-burying as a preclinical screening paradigm of relevance for anxiety and obsessive-compulsive disorder: Mapping the way forward, Cognitive, Affective, & Behavioral Neuroscience (2019) 19:1-39 (published Oct. 25, 2018).
Brandt, Simon D. et al. Systhesis and analytical characterizations of Novel (2-aminopropyl)benzo[b]thiophene (APBT) based stimulants, Drug Test Anal. May 5, 2020;12:1109-1125.
Feduccia Allison A. et al. Breakthrough for Trauma Treatment: Safety and Efficacy of MDMA-Assisted Psychotherapy Compared to Paroxetine and Sertraline. Frontiers Psychiatry. Sep. 12, 2019;10:650.
Glennon, Richard A. et al. 5-HT and 5-HT2 Binding characteristics of 1-(2,5-Dimethoxy-4-bromophenyl)-2-aminopropane analogues, J. Med. Chem. Feb. 1, 1986, 29, 194-199.
Heifets, Boris D. et al. Distinct neural mechanisms for the prosocial and rewarding properties of MDMA, Science Translational Medicine, Research Article, Dec. 11, 2019.
Hysek Cedric M. et al. MDMA enhances emotional empathy and prosocial behavior. Soc Cogn Affect Neurosci. Nov. 2014;9(11):1645-52 (published Oct. 28, 2013).
International Search Report and Written Opinion for PCT/US21/40570 dated Jul. 6, 2021, 10 pages.
Iovino Michele et al. Vasopressin secretion control: central neural pathways, neurotransmitters and effects of drugs. Curr Pharm Des. 2012;18(30):4714-24.
Joyce, B. Matthew, Adderal produces increased striatal dopamine release and a prolonged time course compared to amphetamine isomers, Psychophamacology, 2007, 191:669-677 (published Oct. 10, 2006).
Jiddou, Haila, et al. Novel benzofuran and benzohiophene molecules substitute for the discriminative stimulus effects of 3,4-methylenodioxmethamphetamine (MDMA) in male Sprague-Dawley rares, Society for Neuroscience (SfN) Annual Meeting, San Diego, Nov. 14, 2022, and SfN Annual meeting at Western Michigan University Jun. 9, 2023.
Keri, Rangappa S. et al. An overview of benzo[b]thiophene-based medicinal chemical, European Journal of Medicinal Chemistry, 138, 10002-1033, Jul. 22, 2017.
Kedrowski, Sean M. A. et al. 1-Oxo-6-hydroxytryptamine: A surprisingly potent agonist of the 5-HT3 (Serotonin) Receptor, Organic Letters, Aug. 16, 2007, vol. 9, No. 17, 3205-3207 (published online Jul. 18, 2007).
Luethi, Dino et al. Designer drugs: mechanism of action and adverse effects, Archives of Toxicology 94:1085-1133, Apr. 6, 2020.
Ly, Calvin et al. Psychedelics Promote Structural and Functional Neural Plasticity. Cell Reports. Jun. 12, 2018, 23 (11): 3170-3182.
Ilic, Marija, et al. Cell-Based Radiotracer Binding and Uptake Inhibition Assays: A Comparison of In Vitro Methods to Assess the Potency of Drugs That Target Monoamine Transporters, Frontiers in Pharmacology, vol. 11, Article 673, May 19, 2020.
Masand, PS; and Gupta, S. Selective serotonin-reuptake inhibitors: an update. Harv Rev Psychiatry. Jul.-Aug. 1999;7(2):69-84.
Nenajdenko, Valentine G. et al. A new convenient approach to chiral β-aryl) heteroaryl)alkylamines, Tetrahedron: Assymmetry 12; 2517-2527, Oct. 15, 2001.
Nichols, David E. e al. 2,3-Dihydrobenzofuran analogues of hallucinogenic phenethylamines, J. Med. Chem. , vol. 34, No. 276-281, Jan. 1, 1991.
Olson, David E. Psychoplastogens: A promising class of plasticity-promoting neurotherapeutics, Journal of Experimental Neuroscience vol. 12: 1-4, Sep. 19, 2018.
Pacifici, Roberta et al. Paroxetine inhibits acute effects of 3,4-methylenedioxymethamphetamine on the immune system in humans, The Journal of Pharmacology and Experimental Therapeutics, Apr. 2004, vol. 309, No. 1, 285-292, (published online Jan. 13, 2004).
S. Perez-Silanes, et al. Synthesis of New 5-substitutedbenzo[b]thiophene derivative, J. Heterocyclic Chem., 38, 1025-1030, 2001.
Pitts, Elizabeth G. et al. (±)-MDMA and its enantiomers: potential therapeutic advantages of R(−)-MDMA. Psychopharmacology (Berl). Feb. 2018;235(2):377-392.
Pool, Eva et al. Measuring wanting and liking from animals to humans: A systematic review, Neuroscience and Biobehavioral Reviews124-142, Feb. 3, 2016.
Poos, George I. et al. Chapter 5, Anorexigenic Agents, 44-47, 1966.
Ramos, Linnet et al. Acute Prosocial Effects of Oxytocin and Vasopressin When Given Alone or in Combination with 3,4-Methylenedioxymethamphetamine in Rats: Involvement of the V1A Receptor, Neuropsychopharmacology 38, 2249-2259, May 16, 2013.
Ray, Thomas S. Psychedelics and the Human Receptorome, vol. 5, Issue 2, Feb. 2, 2010.
Rudin, Deborah et al. (2-Aminopropyl)benzo[β]thiophenes (APBTs) are novel monoamine transporter ligands that lack stimulant effects but display psychedelic-like activity in mice, American College of Neuropsychopharmacology, Nov. 8, 2021.
Sessa, Ben et al. A Review of 3,4-methylenedioxymethamphetamine (MDMA)-Assisted Psychotherapy. Front in Psychiatry;10:138, Mar. 20, 2019.
Spitzer, Manfred et al. Enantio-selective cognitive and brain activation effects of N-ethyl-3,4-methylenedioxyamphetamine in humans. Neuropharmacology. Aug. 2001;41(2):263-71.
Studerus, Erich et al. Prediction of psilocybin response in healthy volunteers, PLos One, vol. 7, Issue 2, Feb. 2012.
Studerus, Erich, et al. Acute, subacute and long-term subjective effects of psilocybin in healthy humans: A pooled analysis of experimental studies, Journal of Psychopharmacology, Nov. 2011, vol. 25, Issue 11, 1434-1452. (published online Sep. 20, 2010).
Vallejos, Gabriel, Heteroarylisopropylamines as MAO inhibitors, Bioorganic & Medicinal Chemistry, 4450-4457, Jul. 15, 2005.
Vollenweider, Franz X. et al. Psychological and cardiovascular effects and short-term sequelae of MDMA ("ecstasy") in MDMA-naïve healthy volunteers. Neuropsychopharmacology, 19(4):241-51, Oct. 1998.
Tatsumi, Masahiko et al. Pharmacological profile of neuroleptics at human monoamine transporters, European Journal of Pharmacology 368 . 277-283, Mar. 5, 1999.
Wee, Sunmee et al. Relationship between the serotonergic activity and reinforcing effects of a series of amphetamine analogs. J Pharmacol Exp Ther. May 2005;313(2):848-54. (published online Jan. 26, 2005).

* cited by examiner serotonin
or 5-HT dopamine noradrenaline citalopram fluoxetine paroxetine sertraline bupropion escitalopram methamphetamine amphetamine

MDMA

MDA

MBDB

MDEA

5-MAPBT

5-EAPBT

Bk-5-MAPBT

Bk-5-EAPBT

5-MBPBT

5-EBPBT

Bk-5-MBPBT

Bk-5-EBPBT

5-MAPDBT

5-EAPDBT

Bk-5-MAPDBT

Bk-5-EAPDBT

5-MBPDBT

5-EBPDBT

Bk-5-MBPDBT

Bk-5-EBPDBT

6-MAPBT

6-EAPBT

Bk-6-MAPBT

Bk-6-EAPBT

6-MBPBT

6-EBPBT

Bk-6-MBPBT

Bk-6-EBPBT

6-MAPDBT

6-EAPDBT

Bk-6-MAPDBT

Bk-6-EAPDBT

6-MBPDBT

6-EBPDBT

Bk-6-MBPDBT

Bk-6-EBPDBT

5-MAPBT

6-MAPBT

ADVANTAGEOUS BENZOTHIOPHENE COMPOSITIONS FOR MENTAL DISORDERS OR ENHANCEMENT

CROSS-REFERENCE TO RELATED APPLICATIONS

This application is a continuation of International Application No. PCT/US2021/040570, filed in the U.S. Receiving Office on Jul. 6, 2021, which claims the benefit of U.S. Provisional Application No. 63/048,640, filed Jul. 6, 2020; U.S. Provisional Application No. 63/069,135, filed Aug. 23, 2020; and U.S. Provisional Application No. 63/149,208, filed Feb. 12, 2021. The entirety of each of these applications is hereby incorporated by reference herein for all purposes.

FIELD OF THE INVENTION

The present invention is in area of pharmaceutically active benzothiophene compounds and compositions for the treatment of mental disorders or for mental enhancement, including for entactogenic therapy. The present invention also includes more generally benzothiophene compounds, compositions, and methods for modulating central nervous system activity and treating central nervous system disorders.

BACKGROUND

Mental disorders, including Post-Traumatic Stress Disorder (PTSD), are more common in society than most recognize, as they can be silent or hidden. The U.S. National Institute of Mental Health (NIMH) reports that 70% of all adults have experienced at least one traumatic event in their lives, and 20% of these people will develop PTSD. NIMH estimates that about 3.6% of U.S. adults have PTSD in a one-year period. PTSD can significantly impair a person's ability to function at work, at home, and socially. While many people associate PTSD with veterans and combat, in fact, it is prevalent in all aspects of society.

The World Health Organization reports that depression is a serious medical disorder affecting at least 264 million people globally of all ages. When long lasting and with even moderate intensity or severe intensity, depression can become a serious health condition. It is a leading cause of disability and if not treated can lead to suicidal thoughts and ideation which can progress to suicide as well as addiction. According to WHO, suicide is the second leading cause of death globally in 15-29 year olds.

Other mental disorders that can profoundly affect a person's ability to function normally in society include anxiety disorders such as generalized anxiety disorder, phobia, panic disorder, separation anxiety disorder, stress-related disorders, adjustment disorder, dissociative disorder, eating disorders (e.g., bulimia, anorexia, etc.), attention deficit disorder, sleep disorders, disruptive disorders, neurocognitive disorders, obsessive compulsive disorders, and personality disorders, among others.

While medications are available or in clinical testing for a range of mental disorders, these disorders remain a large burden of disease globally and are insufficiently treated. Further, many of the medications have a long ramp-up time of weeks or more, during which period some patients needing therapy stop the medication out of impatience or the belief the medication does not work.

Many mental disorders are caused by, affected by and/or may be treated by altered levels of neurotransmitters, which are chemicals that transmit a signal from a neuron across the synapse to another neuron. Brain neurotransmitter systems include the serotonin system, the noradrenaline (norepinephrine) system, the dopamine system and the cholinergic system. Dopamine, serotonin, and noradrenaline (norepinephrine) are classed as phenylethylamines, and noradrenaline is also a catecholamine. Drugs that prevent a neurotransmitter from binding to its receptor are called receptor antagonists. Drugs that bind to a receptor and mimic the normal neurotransmitter are receptor agonists. Other drugs interfere with the deactivation of a neurotransmitter after it has been released, which prolongs its action. This can be accomplished by blocking the re-uptake of the transmitter (reuptake inhibitor) or by inhibiting enzymes that degrade the transmitter. A direct agonist binds directly to its associated receptor site. An indirect agonist increases the binding of a neurotransmitter at the target receptor by stimulating the release or preventing the reuptake of the neurotransmitter.

Dopamine receptors are involved in many neurological processes such as motivation, pleasure, cognition, memory, learning, and fine motor control. It is the primary neurotransmitter involved in the reward pathway. Drugs that increase dopamine may produce euphoria. Some widely used drugs such as methamphetamines alter the functioning of the dopamine transporter (DAT), which is responsible for removing dopamine from the neural synapse.

Norepinephrine, also called noradrenaline, mobilizes the body for activity, and is at a high level during stress or danger. It focuses attention and increases arousal and alertness.

Serotonin (5-hydroxytryptamine or "5-HT") receptors influence various neurological functions such as aggression, anxiety, appetite, cognition, learning, memory, mood, and sleep. 5-HT receptors are the target of FDA approved drugs and unapproved drugs, including antidepressants, antipsychotics, hallucinogens (psychedelics), and entactogens (empathogens). There are seven families of 5-HT receptors, and each has subtypes, creating a highly complex signaling system. For example, when 5-$HT_{2A}$ is agonized it often induces hallucinogenic effects (for example, perceptual distortions, delusions, depersonalization, derealization, and labile mood), whereas 5-$HT_{2B}$, which is more predominantly in the periphery than in the brain, when chronically agonized, can cause toxicity such as valvulopathy. In contrast, 5-$HT_{1B}$ when agonized regulates neurons in the ventral striatum and likely contributes to the social effects of entactogens.

Current treatments for a range of mental disorders typically involve the use of selective serotonin reuptake inhibitors (SSRIs), such as citalopram (Celexa), escitalopram (Lexapro), fluoxetine (Prozac), paroxetine (Paxil) and sertraline (Zoloft). SSRIs block the reabsorption (i.e., reuptake) of serotonin into neurons, thereby increasing levels of serotonin in the brain. However, SSRIs are generally slow to achieve clinically meaningful benefit, requiring weeks to produce therapeutic effects. Moreover, many patients are nonresponders and show no benefit at all (Masand et al., Harv. Rev. Psychiatry, 1999, 4: 69-84; Rosen et al., J. Clin. Psychopharmacol., 1999, 19: 67-85).

Bupropion (Wellbutrin), in contrast, is an anti-depressant that is a norepinephrine-dopamine reuptake inhibitor, which provides more stimulant effects, including weight loss.

Another class of drugs for treatment of CNS mental disorders is monoamine releasers. Monoamine releasers induce the release of one or more monoamine neurotransmitters (e.g., dopamine, serotonin, or epinephrine) from neurons in the brain. Monoamine releasers rapidly modulate the brain systems that are more slowly affected by SSRIs. However, their stimulant and euphoric effects frequently lead them to have high abuse liability. Hence, although the monoamine releasers based on the phenethylamine structure, such as amphetamine (Benzedrine, Dexedrine) and methamphetamine (Obetrol, Pervitin), were widely employed as antidepressants in the mid-20th century, such agents are now used much more cautiously, and primarily treat attention deficit hyperactivity disorder (ADHD).

In the search for alternatives to the flawed existing CNS mental disorder therapies, new classes of pharmacological agent have been investigated. Entactogens (empathogens) have received recent attention as promising agents to solve some of these serious health problems. Entactogens increase feelings of authenticity and emotional openness while decreasing social anxiety (Baggott et al., Journal of Psychopharmacology 2016, 30.4: 378-87). Entactogens are typically monoamine releasers that appear to produce their effects in part by releasing serotonin, which stimulates serotonergic receptors in the hypothalamus and nucleus accumbens areas of the brain (Ramos et al., Neuropsychopharmacology 2013, 38(11):2249-59; Heifets et al., Science translational medicine. 2019, 11:522). Entactogens are distinguished from drugs that are primarily hallucinogenic or psychedelic, and from stimulants, such as amphetamine. The most well-known entactogen is MDMA (3,4-methylenedioxymethamphetamine). Other examples of entactogens are MDA, MBDB, MDOH, and MDEA, however, these drugs do have varying and complex effects that result in part from binding to a range of 5-HT receptors.

MDMA is currently in human clinical trials in the United States (clinicaltrials.gov; NCT03537014) and Europe for approval for use in psychotherapy sessions for severe PTSD and has been suggested as useful for aiding social cognition (Preller & Vollenweider, Frontiers in Psychiatry, 2019, 10; Hysek et al., Social cognitive and affective neuroscience, 2015, 9.11, 1645-52). The FDA granted breakthrough therapy designation for the trial and has also agreed to an expanded access program, both indicative of promising results (Feduccia et al., Frontiers in Psychiatry, 2019, 10: 650; Sessa et al., Frontiers in Psychiatry, 2019, 10: 138). While MDMA has significant therapeutic potential, it has a number of features that potentially make it contraindicated for some patients. This includes its ability to produce acute euphoria, acute hypertensive effects, risk of hyponatremia, and oxidative and metabolic stress.

It is an object of the present invention to provide advantageous compositions and their use and manufacture for the treatment of mental disorders and enhancement. Additional objects are to provide drugs with a more rapid onset to be used in a clinical setting such as counseling or a home setting, which open the patient to empathy, sympathy and acceptance. A further object is to provide effective treatments for a range of CNS disorders.

SUMMARY OF THE INVENTION

The present invention provides multiple embodiments of described benzothiophene compounds and their pharmaceutically acceptable salts and salt mixtures thereof, pharmaceutical compositions, and methods to treat mental disorders and more generally central nervous disorders, as well as for mental enhancement comprising administering an effective amount to a host, typically a human, as further described herein. Benzothiophenes present a previously unstudied pharmacophore for entactogens. The benzothiophene ring provides advantageous pharmacological properties that are desirable as therapeutics for the treatment of mental disorders, particularly as psychotherapeutics and neurotherapeutics.

The embodiments of the invention are presented to meet the goal of assisting persons with mental disorders, who desire mental enhancement or suffer from other CNS disorders by providing milder therapeutics that are fast acting and that reduce the properties that decrease the patient experience, are counterproductive to the therapy, or are undesirably toxic. One goal of the invention is to provide therapeutic compositions that increase empathy, sympathy, openness and acceptance of oneself and others, which can be taken, if necessary, as part of therapeutic counseling sessions, or when necessary, episodically, or even consistently, as prescribed by a healthcare provider.

It has been surprisingly discovered that the benzothiophene compounds and compositions of the present invention demonstrate properties that indicate the compounds are fast-acting. This represents a significant improvement over SSRIs, the current standard of care for many CNS and psychological disorders. The slow onset of effects is one of the most pronounced shortcomings of SSRI therapeutics. In contrast, in one embodiment, the compounds of the present invention act as fast-acting treatments, which represents a significant advance for clinical use. It is advantageous to use a fast-acting therapeutic in a clinical therapeutic setting that typically lasts for one, two, or several hours.

The entactogenic properties of the presently described compounds can be assessed by multiple published methods, including but not limited to those described in Example 8 (Evaluation of Entactogenic Effect of Decreased Neuroticism) and Example 9 (Evaluation of Entactogenic Effect of Authenticity).

In one aspect, the invention provides the compound 6-MAPBT, an enantiomerically enriched mixture or pure enantiomers of R-6-MAPBT or S-6-MAPBT or a pharmaceutically acceptable salt or salt mixture thereof for any of the uses thereof as described herein. In certain aspects, a pharmaceutical composition is provided that comprises 6-MAPBT or a pure R- or S-enantiomer or enantiomerically enriched mixture thereof:

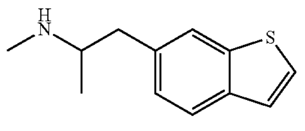

6-MAPBT

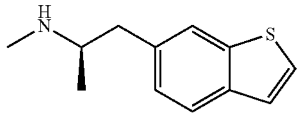

R-6-MAPBT

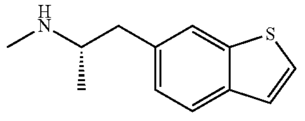

S-6-MAPBT

In certain aspects of this embodiment, the invention provides enantiomerically enriched or enantiomerically pure, R-5-MAPBT or S-5-MAPBT, or a pharmaceutically acceptable salt or salt mixture thereof, or for any use thereof as described herein.

While the racemic compound 5-MAPBT is registered as CAS #2613382-32-2 by a vendor supply company, it is without details or without any references to any use or synthesis. In certain embodiments, the racemic 5-MAPBT or its pharmaceutical salt or salt mixture is used in an effective amount for any of the methods described herein, optionally in a pharmaceutical composition.

In certain aspects, a pure R- or S-enantiomer or an enantiomerically enriched mixture of the R- or S-enantiomer of 5-MAPBT or its pharmaceutically acceptable salt or salt mixture or pharmaceutical composition is provided for any of the uses described herein:

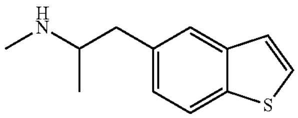

5-MAPBT

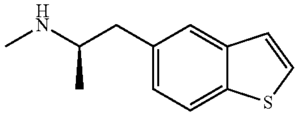

R-5-MAPBT

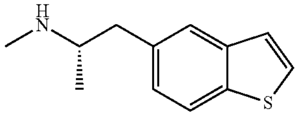

S-5-MAPBT

In certain embodiments, isolated enantiomers of the compounds of the present invention show improved binding at the desired receptors and transporters relevant to the goal of treatment for the mental disorder or for mental enhancement. In certain embodiments, a tuned enantiomerically enriched mixture containing both R- and S-enantiomers in unequal amounts shows improved binding at the desired receptors and transporters relevant to the goal of treatment for the mental disorder or for mental enhancement.

Accordingly, in one embodiment, an enantiomerically enriched mixture of the S-enantiomer or pure enantiomer of S-5-MAPBT or enantiomerically enriched mixture of the S-enantiomer or pure enantiomer of S-6-MAPBT increases the serotonin-receptor-dependent therapeutic effects and minimizes unwanted nicotinic effects or dopaminergic effects when administered to a host in need thereof, for example a mammal, including a human, relative to the racemic form.

In another embodiment, an enantiomerically enriched mixture of the R-enantiomer or pure enantiomer of R-5-MAPBT or an enantiomerically enriched mixture of the R-enantiomer or pure enantiomer of R-6-MAPBT increases nicotinic-receptor-dependent or dopaminergic-receptor dependent therapeutic effects while minimizing unwanted effects, when administered to a host in need thereof, including a mammal, for example, a human.

In certain embodiments enantiomerically enriched mixtures of 5-MAPBT that are non-racemic have a relatively greater amount of some therapeutic effects (such as emotional openness) while having lesser effects associated with abuse liability (such as perceptible 'good drug effects'). Additionally, abuse liability is attenuated to the extent that the substance also increases extracellular serotonin (see, e.g., Wee et al., Journal of Pharmacology and Experimental Therapeutics, 2005, 313(2), 848-854). Therefore, one aspect of the present invention is a balanced enantiomerically enriched mixture of S-5-MAPBT and R-5-MAPBT optionally as a salt or salt mixture or a balanced enantiomerically enriched mixture of S-6-MAPBT and R-6-MAPBT optionally as a salt or salt mixture that achieves a predetermined combination of emotional therapeutic effects and perceptible mood effects. The effect can be modulated as desired for optimal therapeutic effect.

Accordingly, in one embodiment, an enantiomerically enriched mixture of the S-enantiomer or pure enantiomer of S-5-MAPBT or an enantiomerically enriched mixture of the S-enantiomer or pure enantiomer of S-6-MAPBT or a pharmaceutically acceptable salt or salt mixture thereof balances emotional openness and perceptible mood effects when administered to a host in need thereof, for example a mammal, including a human.

Accordingly, in one embodiment, S-5-MAPBT or S-6-MAPBT balances emotional openness and perceptible mood effects when administered to a host in need thereof, for example a mammal, including a human.

Additional non-limiting examples of unwanted effects that can be minimized by carefully selecting the balance of enantiomers in an enantiomerically enriched mixture include hallucinogenic effects, psychoactive effects (such as excess stimulation or sedation), physiological effects (such as transient hypertension or appetite suppression), toxic effects (such as to the brain or liver), effects contributing to abuse liability (such as euphoria or dopamine release), and/or other side effects.

Another aspect of the present invention is the reduced side effect and toxicity profile of the compounds and compositions of the present invention. The benzothiophene ring of the compounds, pure R- or S-enantiomers, and enantiomerically-enriched mixtures of the present invention is less prone to metabolic breakdown, for example by CYP enzymes, than other entactogens. This property can result in the reduction of the number of toxic or unintended compounds produced in the course of eliminating the active pharmaceutical agent from the body.

In yet other embodiments, the present invention includes enantiomerically enriched mixtures, or their pharmaceutically acceptable salts or salt mixtures, and uses as further described herein, of the R- or S-enantiomer of the racemic structure selected from:

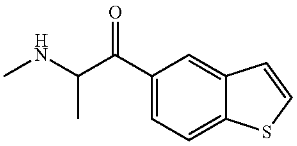

Bk-5-MAPBT

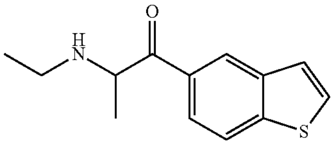

Bk-5-EAPBT and

-continued

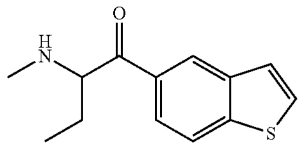

Bk-5-MBPBT .

The enantiomers of Bk-5-MAPBT are registered in the ZINC20 database as ZINC691801808 for the R-enantiomer and ZINC691801812 for the S-enantiomer, however, there are no references with the entry describing their uses or synthesis. The enantiomers of Bk-5-EAPBT are registered in the ZINC20 database as ZINC707988078 for the R-enantiomer and ZINC707988082 for the S-enantiomer however, there are no references with the entry describing their use or synthesis. The enantiomers of Bk-5-MBPBT are registered in the ZINC20 database as ZINC691789113 for the R-enantiomer and ZINC691789115 for the S-enantiomer however, there are no references with the entry describing their use or synthesis.

In yet other embodiments, the present invention includes a compound or a pharmaceutically acceptable salt or salt mixture thereof, a pharmaceutical composition thereof or a method of use as further described herein selected from:

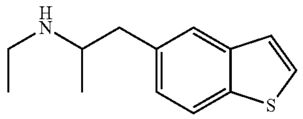

5-EAPBT

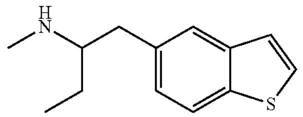

5-MBPBT

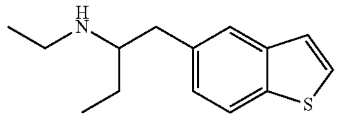

5-EBPBT

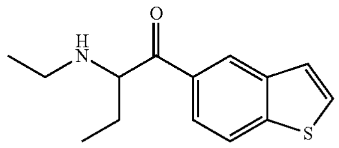

Bk-5-EBPBT

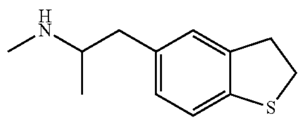

5-MAPDBT

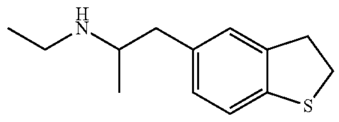

5-EAPDBT

-continued

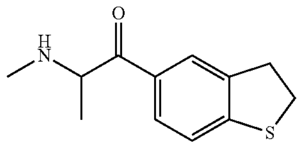

Bk-5-MAPDBT

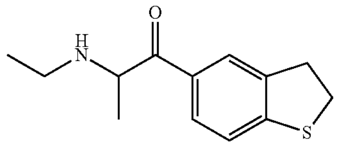

Bk-5-EAPDBT

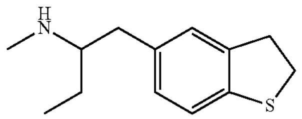

5-MBPDBT

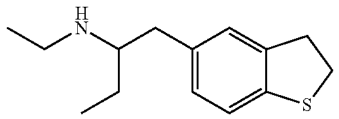

5-EBPDBT

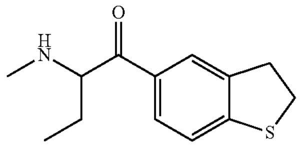

Bk-5-MBPDBT

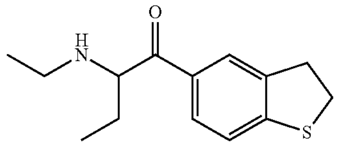

Bk-5-EBPDBT

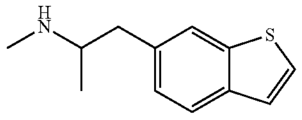

6-MAPBT

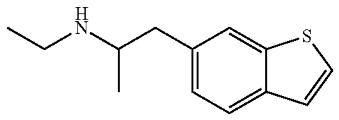

6-EAPBT

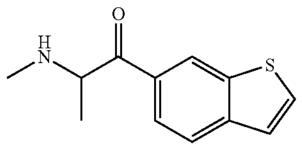

Bk-6-MAPBT

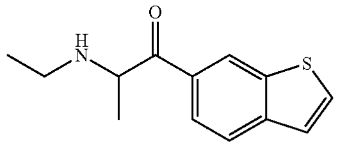

Bk-6-EAPBT

-continued

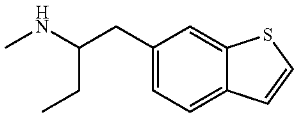

6-MBPBT

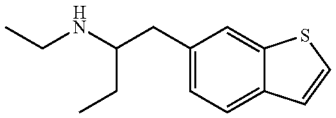

6-EBPBT

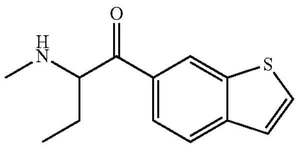

Bk-6-MBPBT

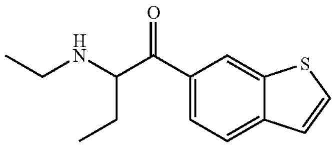

Bk-6-EBPBT

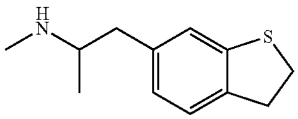

6-MAPDBT

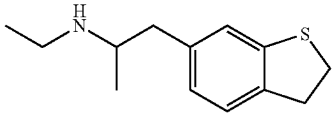

6-EAPDBT

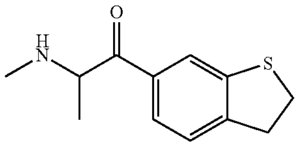

Bk-6-MAPDBT

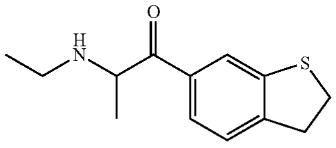

Bk-6-EAPDBT

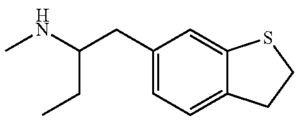

6-MBPDBT

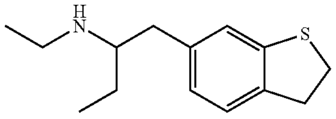

6-EBPDBT

-continued

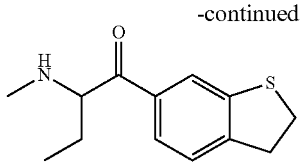

and

Bk-6-MBPDBT

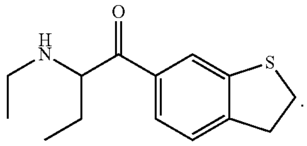

Bk-6-EBPDBT

In yet other embodiments, the present invention provides an enantiomerically enriched mixture of the R- and S-enantiomers of a compound of Formula C or a pharmaceutically acceptable salt or salt mixture thereof, for any of the uses described herein by administering to a patient, such as a human, the enantiomerically enriched compound in an effective amount to achieve the desired effect:

Formula C

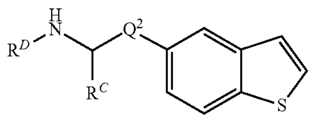

wherein:

$R^C$ is selected from $-CH_3$, $-CH_2Y$, $-CHY_2$, $-CY_3$, $-CH_2CH_2Y$, $-CH_2CHY_2$, $-CH_2CY_3$, $-CH_2CH_3$, $-CH_2OH$, or $-CH_2CH_2OH$;

$R^D$ is selected from $-CH_3$ and $-CH_2CH_3$;

$Q^2$ is selected from:

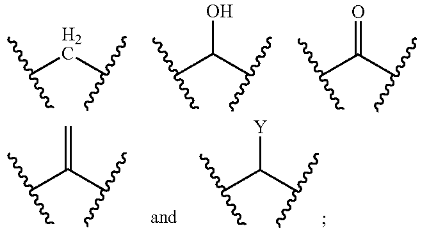

and ;

and

Y is halogen.

In yet other embodiments, the present invention provides a pure or enantiomerically enriched mixture of the R- or S-enantiomer of a compound of Formula A, Formula B, or Formula D, or a pharmaceutically acceptable salt or salt mixture thereof, for any of the uses described herein by administering to a patient, such as a human, the enantiomerically enriched compound in an effective amount to achieve the desired effect:

Formula A

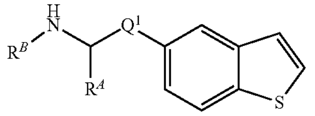

-continued

Formula B

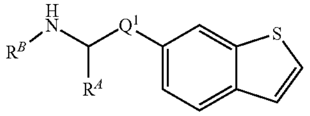

Formula D

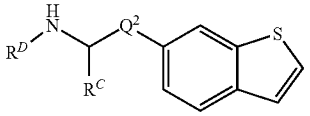

wherein:

$R^A$ and $R^B$ are independently selected from $—CH_3$ and $—CH_2CH_3$;

$R^C$ is selected from $—CH_3$, $—CH_2Y$, $—CHY_2$, $—CY_3$, $—CH_2CH_2Y$, $—CH_2CHY_2$, $—CH_2CY_3$, $—CH_2CH_3$, $—CH_2OH$, or $—CH_2CH_2OH$;

$R^D$ is selected from $—CH_3$ and $—CH_2CH_3$;

$Q^1$ is selected from

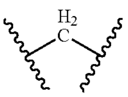 and 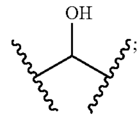;

$Q^2$ is selected from:

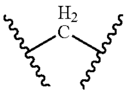 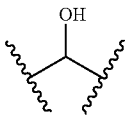 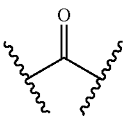

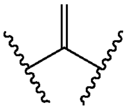 and 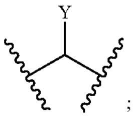;

and

Y is halogen.

The present invention includes compounds with beneficial selectivity profiles for neurotransmitter transporters. The balance of weakly activating NET (to reduce acute cardiovascular toxicity risk) and decreasing the DAT to SERT ratio over the racemate (to increase therapeutic effect relative to addictive liability) is a desirable feature of an entactogenic therapy displayed by the compounds and compositions of the present invention.

An enantiomerically enriched mixture is a mixture that contains one enantiomer in a greater amount than the other. The term enantiomerically enriched mixture includes either the mixture enriched with the R-enantiomer or enriched with the S-enantiomer. Accordingly, unless context clearly indicates otherwise, the term "enantiomerically enriched mixture" can be understood to mean "enantiomerically enriched mixture of the R- or S-enantiomer." An enantiomerically enriched mixture of an S-enantiomer contains at least 55% of the S-enantiomer, and, typically at least about 60%, 65%, 70%, 75%, 80%, 85%, 90%, 95% of the S-enantiomer. An enantiomerically enriched mixture of an R-enantiomer contains at least 55% of the R-enantiomer, and typically at least about 60%, 65%, 70%, 75%, 80%, 85%, 90%, 95% of the R-enantiomer. The specific ratio of S or R enantiomer can be selected for the need of the patient according to the health care specialist to balance the desired effect.

The term enantiomerically enriched mixture as used herein does not include either a racemic mixture or a pure enantiomer.

The present invention also provides new medical uses for the described compounds, including but not limited to, administration in an effective amount to a host in need thereof such as a human for post-traumatic stress disorder, depression, dysthymia, anxiety, generalized anxiety, social anxiety, panic, adjustment disorders, feeding and eating disorders, binge behaviors, body dysmorphic syndromes, addiction, drug abuse or dependence disorders, substance use disorders, disruptive behavior disorders, impulse control disorders, gaming disorders, gambling disorders, memory loss, dementia of aging, attention deficit hyperactivity disorder, personality disorders, attachment disorders, autism or dissociative disorders or any other disorder described herein, including in the Background. One particular treatment is for adjustment disorder, which is highly prevalent in society and currently insufficiently addressed. In nonlimiting aspects, the compound used in the treatment includes, for example, a pure or enantiomerically enriched composition of R- or S-enantiomer of 5-MAPBT, 6-MAPBT, 5-MBPBT, 6-MBPBT, 6-Bk-MAPBT, or Bk-6-MBPBT, or a combination thereof. In nonlimiting aspects, the compound used in the treatment includes, for example, an enriched composition of R- or S-enantiomer of a compound shown in FIG. 2.

It has been discovered that several of the benzothiophene derivatives of the current invention are direct $5\text{-HT}_{1B}$ agonists. Very few substances are known that are $5\text{-HT}_{1B}$ agonists and also 5-HT releasers and these have significant toxicities. For example, meta-chlorophenylpiperazine (mCPP) is one example but is anxiogenic and induces headaches, limiting any clinical use.

However, MDMA itself does not bind directly to the $5\text{-HT}_{1B}$ (Ray. 2010. *PloS one,* 5(2), e9019). $5\text{-HT}_{1B}$ agonism is noteworthy because indirect stimulation of these receptors, secondary to elevated extracellular serotonin, has been hypothesized to be required for the prosocial effects of MDMA (Heifets et al. 2019. *Science translational medicine,* 11(522)), while other aspects of entactogen effects have been attributed to monoamine release (e.g., Luethi & Liechti. 2020. *Archives of toxicology,* 94(4), 1085-1133). Thus, the unique ratios of $5\text{-HT}_{1B}$ stimulation and monoamine release displayed by the disclosed compounds enable different profiles of therapeutic effects that appear not achieved by MDMA or other known entactogens.

The general pharmacology of entactogen enantiomers and enantiomeric compositions has been poorly understood to date. They have been difficult to separate, and it is not currently easily predicted what the therapeutic effects of individual enantiomers or enantiomerically enriched compositions might be based on individual complex receptor binding. Further, trends in the contribution of individual enantiomers often do not translate to other members of the same class of compounds. For example, the S-(+)-enantiomer of MDMA is more psychoactive than the R-(−)-enantiomer, but in 3,4-methylenedioxyamphetamine (MDA, differing from MDMA only by the absence of an N-methyl group), the S-(+)-enantiomer is less active than its corresponding R-(−)-enantiomer (Anderson et al., NIDA Res Monogr, 1978, 22: 8-15; Nichols. J. Psychoactive Drugs, 1986, 18: 305-13).

In the case of amphetamine, a non-entactogenic stimulant, it has been observed that an enantiomerically enriched mixture of enantiomers displays properties superior to the racemic mix or either enantiomer alone (Joyce et al., Psychopharmacology, 2007, 191: 669-677). The drug Adderall is a paradigm example of a mixture of enantiomers of amphetamine. The mixture has equal parts racemic amphetamine and dextroamphetamine salt mixtures (sulfate, aspartate, and saccharate) which results in an approximately 3:1 ratio between the dextroamphetamine and levoamphetamine. The two enantiomers are different enough to give Adderall an effect profile different from the racemate or the d-enantiomer. However, to date, it has not been reported or predictable what properties a mixture of enantiomers of the entactogenic compounds described herein would produce or how to use the mixture in therapy.

Understanding the pharmacology of the entactogen enantiomers is further complicated by the fact that the therapeutic effects of entactogens are not identical to the more readily identifiable psychoactive effects. Moreover, different enantiomers may differ in potency and activity in dissimilar and unpredictable ways. For instance, when the enantiomers of 3,4-methylenedioxy-N-ethylamphetamine (MDE) were compared in humans, it was concluded that the therapeutic effects of MDE were due to the S-(+)-enantiomer while the R-(−)-enantiomer primarily contributed to unwanted and toxic effects (Spitzer et al., Neuropharmacology, 2001, 41.2: 263-271). In contrast, it has been argued that the R-(−)-enantiomer of MDMA may maintain the therapeutic effects of (±)-MDMA with a reduced side effect profile (Pitts et al., Psychopharmacology, 2018, 235.2: 377-392). Thus, it is not possible to predict which enantiomers will best retain or provide therapeutic activity. To the inventor's knowledge, there have not yet been any studies characterizing the pharmacological effects, much less the entactogenic properties, of the isolated enantiomers of a benzothiophene entactogen before this invention.

As described in the non-limiting illustrative Example 7, in one embodiment, the compounds of the present invention are rapid releasers of serotonin. This mechanism of action works in parallel with the inhibition of serotonin reuptake. The combination of inhibiting reuptake and increasing release significantly raises levels of serotonin and enhances therapeutic effect.

Further, select compounds of the present invention retain antagonism of the serotonin transporter (SERT), which is believed to be the principal mechanism of action for SSRIs. In this way the present invention provides compounds and methods that act in a similar way to the current standard of care for many CNS disorders including mental disorders, but do not present the crucial drawback of delayed onset.

In addition, some compounds of the present invention act as partial DAT substrates, with high concentrations producing limited dopamine release in comparison to the reference releaser amphetamine. For example, 5-EAPBT dopamine release (details provided in non-limiting illustrative Example 7) has an $E_{max}$ below that of the reference releaser, meaning that this compound is more limited in the amount of dopamine it can release even at high doses. This indicates that 5-EAPBT will display further reductions in abuse liability beyond those predictable from its DAT to SERT ratio. This demonstrated lower abuse liability is a beneficial improvement of the present invention.

For at least three of the molecules disclosed herein, the potency at stimulating 5-$HT_{1B}$ is similar to (or lower than) their potency for releasing 5-HT. Specifically, 5-MAPBT has an $EC_{50}$ of 23 nM for releasing 5-HT and an $EC_{50}$ of 38 nM at 5-$HT_{1B}$, while 6-MAPBT has an $EC_{50}$ of 57 nM for releasing 5-HT and an $EC_{50}$ of 24 nM at 5-$HT_{1B}$, and BK-5-MAPBT has an $EC_{50}$ of 101 nM for releasing 5-HT and an $EC_{50}$ of 59 nM at 5-$HT_{1B}$. Thus, in certain embodiments, the unique ratios of 5-$HT_{1B}$ stimulation and monoamine release displayed by the disclosed compounds enable different profiles of therapeutic effects that cannot be achieved by MDMA or other known entactogens.

Finally, the compounds of the present invention show a 5-HT selectivity pattern that is important to therapeutic use. Agonism of the 5-$HT_{2A}$ receptor can cause feelings of fear (ranging from mild anxiety to panic) and hallucinations, but agonism of 5-$HT_{1B}$ is believed to be tied to the pro-social effects of entactogens (Studerus et al. 2011. Journal of psychopharmacology, 25(11), 1434-1452; Studerus et al. 2012. PloS one, 7(2), p.e30800; Heifets et al. 2019. Science translational medicine, 11(522)).

It has been surprisingly discovered that compounds of the present invention can be selected to be poor agonists of 5-$HT_{2A}$ while retaining activity toward 5-$HT_{1B}$. For example, as described in the non-limiting illustrative Example 5, the compounds show strong selectivity for 5-$HT_{1B}$ agonism over 5-$HT_{2A}$ agonism. Some compounds showed no measurable $EC_{50}$ for 5-$HT_{2A}$ up to 30 μM. Importantly, the 5-$HT_{1B}$ agonist activity effect occurs through direct action on the receptor, rather than as an indirect consequence of serotonin release. This is an unexpected discovery because this property has not been observed in an entactogen, including MDMA, before. In one embodiment, the selectivity of the 5-$HT_{1B}$ receptor over 5-$HT_{2A}$ receptor allows for a more relaxed and therapeutically productive experience for the patient undergoing treatment with a compound of the present invention. In other embodiments, a compound or composition of the present invention is provided in an effective amount to treat a host, typically a human, with a CNS disorder that can be either a neurological condition (one that is typically treated by a neurologist) or a psychiatric condition (one that is typically treated by a psychiatrist). Neurological disorders are typically those affecting the structure, biochemistry, or normal electrical functions of the brain, spinal cord or other nerves. Psychiatric conditions are more typically thought of as mental disorders, which are primarily abnormalities of thought, feeling or behavior that cause significant distress or impairment of personal functioning.

Thus, the disclosed compounds can be used in an effective amount to improve neurological or psychiatric functioning in a patient in need thereof. Neurological indications include, but are not limited to, improved neuroplasticity, including treatment of stroke, brain trauma, dementia, and neurodegenerative diseases. MDMA has an $EC_{50}$ of 7.41 nM for promoting neuritogenesis and an $E_{max}$ approximately twice that of ketamine, which has fast acting psychiatric benefits that are thought to be mediated by its ability to promote neuroplasticity, including the growth of dendritic spines, increased synthesis of synaptic proteins, and strengthening synaptic responses (Ly et al. Cell reports 23, no. 11 (2018): 3170-3182; FIG. S3). The compounds of the current invention can similarly be considered psychoplastogens, that is, small molecules that are able to induce rapid neuroplasticity (Olson, 2018, Journal of experimental neuroscience, 12, 1179069518800508). For example, in certain embodiments, the disclosed compounds and compositions can be used to improve stuttering and other dyspraxias or to treat Parkinson's disease or schizophrenia.

The term "improving psychiatric function" is intended to include mental health and life conditions that are not traditionally treated by neurologists but sometimes treated by psychiatrists and can also be treated by psychotherapists, life coaches, personal fitness trainers, meditation teachers, counselors, and the like. For example, it is contemplated that the disclosed compounds will allow individuals to effectively contemplate actual or possible experiences that would normally be upsetting or even overwhelming. This includes individuals with fatal illnesses planning their last days and the disposition of their estate. This also includes couples discussing difficulties in their relationship and how to address them. This also includes individuals who wish to more effectively plan their career.

In other embodiments, the compositions and compounds of the present invention may be used in an effective amount to treat a host, typically a human, to modulate an immune or inflammatory response. The compounds disclosed herein alter extracellular serotonin, which is known to alter immune functioning. MDMA produces acute time-dependent increases and decreases in immune response (e.g., Pacifici et al. 2004. Journal of Pharmacology and Experimental Therapeutics, 309(1), 285-292).

In other embodiments, the invention provides an active compound for any of the uses described herein of Formula I, Formula II, Formula III, Formula IV, Formula V, Formula VI, Formula VII, Formula VIII, or Formula IX, or a pharmaceutically acceptable salt or salt mixture or composition thereof. The compounds of Formula I, Formula II, Formula III, Formula IV, Formula V, Formula VI, Formula VII, Formula VIII, and Formula IX, are:

(I)

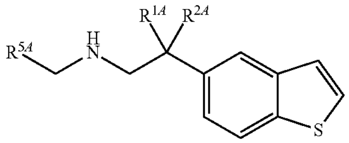

(II)

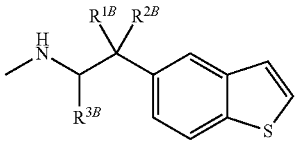

(III)

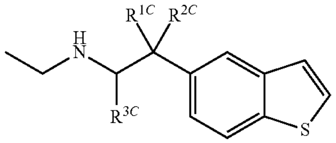

(IV)

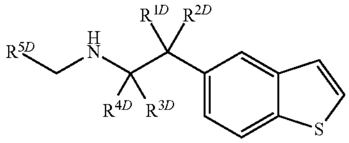

(V)

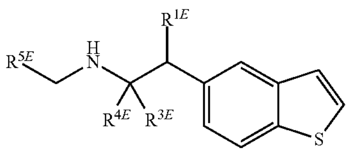

(VI)

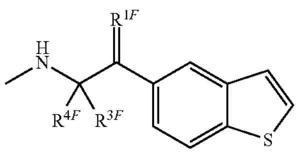

-continued (VII)

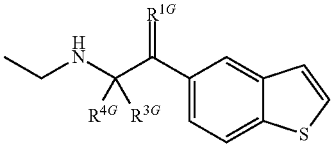

(VIII)

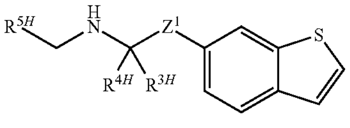

(IX)

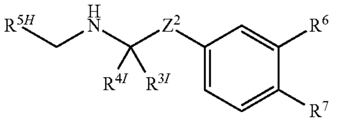

wherein:

$Z^1$ is selected from

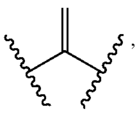, 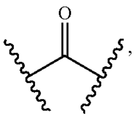, and 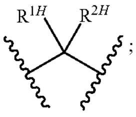;

$Z^2$ is selected from

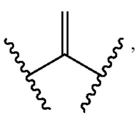, 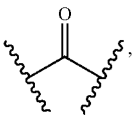, and 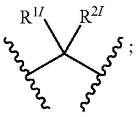;

$R^{1A}$, $R^{1D}$, and $R^{2D}$ are independently selected from —X, —OH, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{1B}$, $R^{1C}$, $R^{1E}$, $R^{1H}$, $R^{1I}$, $R^{2B}$, $R^{2C}$, $R^{2H}$, and $R^{2I}$ are independently selected from —H, —X, —OH, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{1F}$ and $R^{1G}$ are independently selected from $CH_2$ and O;

$R^{2A}$ is selected from —H, —X, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein if $R^{1A}$ is —OH, $R^{2A}$ is not —H or $C_1$ alkyl;

$R^{3B}$ is selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl; wherein if $R^{3B}$ is $C_1$ alkyl and one of $R^{2B}$ and $R^{1B}$ is —H, then the other of $R^{2B}$ and $R^{1B}$ cannot be —H or —OH;

$R^{3C}$ is selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl; wherein if $R^{3C}$ is $C_1$ alkyl and one of $R^{2C}$ and $R^{1C}$ is —H, then the other of $R^{2C}$ and $R^{1C}$ cannot be —OH or $C_1$ alkyl;

$R^{3D}$, $R^{3F}$, and $R^{4D}$ are independently selected from —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{3E}$ and $R^{4E}$ are independently selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein when $R^{3E}$ and $R^{4E}$ are both $C_1$ alkyl, $R^{1E}$ cannot be —OH or —F;

$R^{3G}$ and $R^{4G}$ are independently selected from —H, —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein if $R^{1G}$ is O and one of $R^{3G}$ and $R^{4G}$ is —H, then the other of $R^{3G}$ and $R^{4G}$ cannot be —H or $C_1$ alkyl;

$R^{3H}$, $R^{3I}$, $R^{4H}$, and $R^{4I}$ are independently selected from —H, —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{4F}$ is selected from —H, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein if $R^{4F}$ is —H and $R^{1F}$ is O, then $R^{3F}$ cannot be $C_1$ or $C_2$ alkyl;

$R^{5A}$, $R^{5D}$, $R^{5E}$, and $R^{5H}$ are independently selected from —H or —$CH_3$;

$R^{5I}$ is selected from —H and —$CH_3$, wherein if $R^{3I}$, $R^{4I}$, and $R^{5I}$ are all —H, then $Z^2$ cannot be

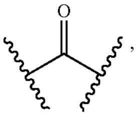, 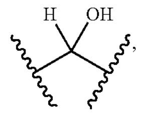, or 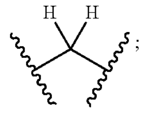;

$R^6$ and $R^7$ are taken together as —$SCH_2CH_2$— or —$CH_2CH_2S$—; and

X is independently selected from —F, —Cl, and —Br.

The invention additionally provides an active compound as an enantiomerically enriched mixture or pure enantiomer for any of the uses described herein of Formula VIII, Formula X, Formula XI, Formula XII, or Formula XIII, or a pharmaceutically acceptable salt or salt mixture or composition thereof. The compounds Formula VIII, Formula X, Formula XI, Formula XII, and Formula XIII are:

(VIII)

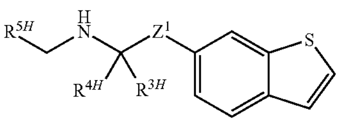

(X)

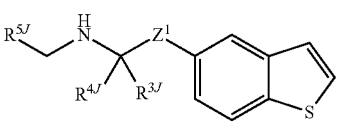

(XI)

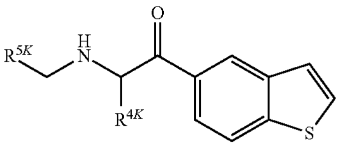

-continued (XII)

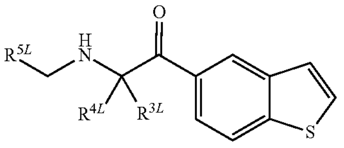

(XIII)

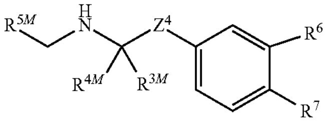

wherein:

$Z^1$ is selected from

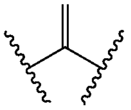, 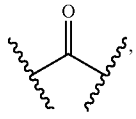, and 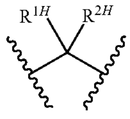;

$Z^3$ is selected from

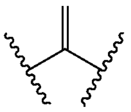 and 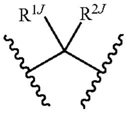;

$Z^4$ is selected from

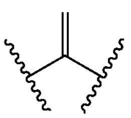, 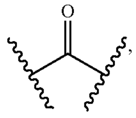, and 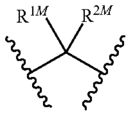;

$R^{1H}$, $R^{1J}$, $R^{1M}$, $R^{2H}$, $R^{2J}$, and $R^{2M}$ are independently selected from —H, —X, —OH, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{3H}$, $R^{3J}$, $R^{3M}$, $R^{4H}$, $R^{4J}$, and $R^{4M}$ are independently selected from —H, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{3L}$ and $R^{4L}$ are independently selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{4K}$ is selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_2$-$C_4$ alkyl;

$R^{5H}$, $R^{5L}$, and $R^{5M}$ are independently selected from —H and —$CH_3$;

$R^{5J}$ is selected from —H and —$CH_3$, wherein if $R^{5J}$ is

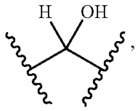 [SMILES: *C(*)O]

and one of $R^{3J}$ and $R^{4J}$ is —H, then the other of $R^{3J}$ and $R^{4J}$ cannot be $C_1$ alkyl;

$R^{5K}$ is selected from —H and —$CH_3$, wherein if $R^{5K}$ is —H, then $R^{4K}$ cannot be $C_2$ alkyl;

$R^6$ and $R^7$ are taken together as —$SCH_2CH_2$— or —$CH_2CH_2S$—; and

X is independently selected from —F, —Cl, and —Br.

The invention additionally provides enantiomerically enriched mixtures for any of the uses described herein of Formula XIV, or a pharmaceutically acceptable salt or salt mixture or composition thereof. The enantiomerically enriched mixtures of Formula XIV are:

(XIV)

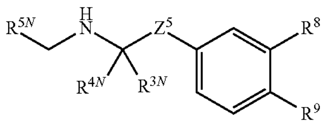

wherein:

$Z^5$ is selected from

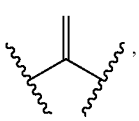,
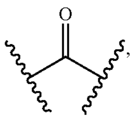, and
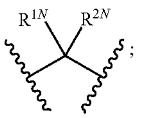;

$R^{1N}$ and $R^{2N}$ are independently selected from —H, —X, —OH, —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{3N}$ and $R^{4N}$ are independently selected from —H, —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{5N}$ is selected from —H and —$CH_3$;

$R^8$ and $R^9$ are taken together as —$SCH_2CH_2$—, —$CH_2CH_2S$—, —SCH═CH—, or —CH═CHS—; and X is independently selected from —F, —Cl, and —Br.

In certain embodiments, a compound of Formulas A-D or Formulas I-XVI is used as described herein in enantiomerically enriched form of the R- or S-enantiomer to achieve the goals of the invention. In other embodiments, the compound is used as a racemate or a pure enantiomer.

The invention additionally includes methods to treat a neurological or psychiatric central nervous system disorder as further described herein, including a mental disorder, or to provide a mental enhancement, with a compound of Formula A, Formula B, Formula C, Formula D, Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt or salt mixture thereof.

In other embodiments, the present invention includes a method for treating any of the disorders described herein, such as a central nervous system disorder, in a host in need thereof comprising administering an effective amount of a compound of Formula XV or its salt or salt mixture, optionally in a pharmaceutically acceptable composition, selected from:

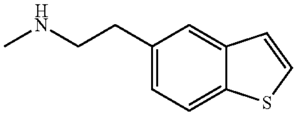

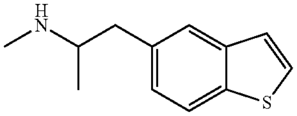

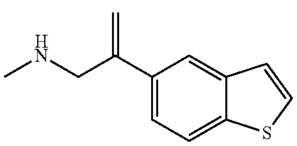

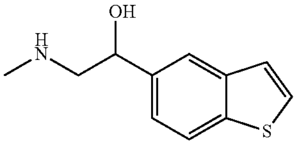

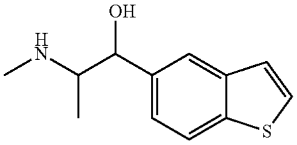

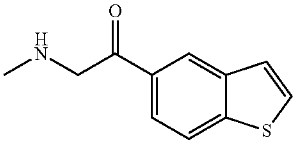

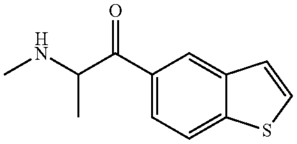

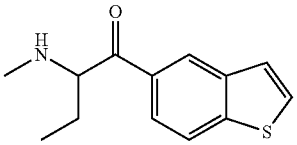

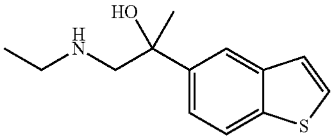

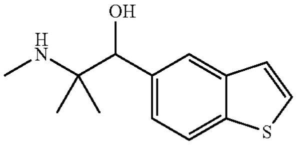

-continued

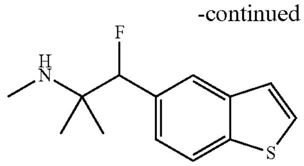

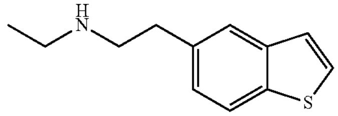

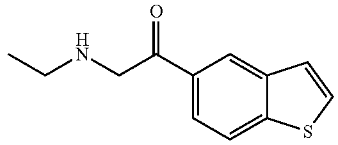

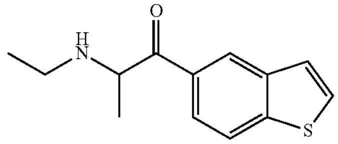

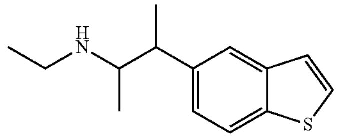

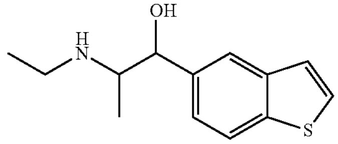

and

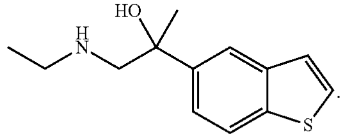

.

In other embodiments, the present invention includes a method for treating any of the disorders described herein, such as a central nervous system disorder, in a host in need thereof comprising administering an effective amount of a compound of Formula XVI or its pharmaceutically acceptable salt or salt mixture, optionally in a pharmaceutically acceptable composition, which is:

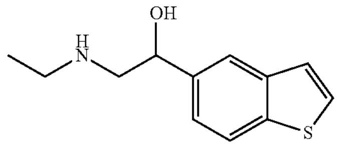

In certain embodiments, any of the selected compounds or mixtures of the present invention are administered to a human patient in an effective amount in conjunction with psychotherapy, cognitive enhancement, or life coaching (pharmacotherapy), or as part of routine medical therapy.

Any of the compounds, including the enantiomerically enriched compounds, can be used in the form of a pharmaceutically acceptable salt or a salt mixture. Nonlimiting examples include those wherein the pharmaceutically acceptable salt(s) is selected from HCl, sulfate, aspartate, saccharate, phosphate, oxalate, acetate, amino acid anion, gluconate, maleate, malate, citrate, mesylate, nitrate or tartrate, or a mixture thereof.

The present invention thus includes at least the following aspects:

(i) A compound of 6-MAPBT, 5-MBPBT, 6-MBPBT, Bk-6-MAPBT, Bk-6-MBPBT, Formula I, Formula II, Formula III, Formula IV, Formula V, Formula VI, Formula VII, Formula VIII, or Formula IX, or a pharmaceutically acceptable salt or salt mixture, isotopic derivative, or prodrug thereof;

(ii) An enantiomerically enriched or pure compound of 5-MAPBT, 6-MAPBT, 5-MBPBT, 6-MBPBT, Bk-6-MAPBT, Bk-6-MBPBT, Formula I, Formula II, Formula III, Formula IV, Formula V, Formula VI, Formula VII, Formula VIII, Formula IX, Formula X, Formula XI, Formula XII, or Formula XIII, or a pharmaceutically acceptable salt, or salt mixture, an isotopic derivative, or prodrug thereof, or diastereomerically enriched form, as relevant;

(iii) An enantiomerically enriched mixture of Formula XIV, XV or XVI, Formula A, Formula B, Formula C, Formula D, or compound shown in FIG. 2, or a pharmaceutically acceptable salt, or salt mixture, an isotopic derivative, or prodrug thereof, or diastereomerically enriched form, as relevant;

(iv) A pharmaceutical composition comprising an effective patient-treating amount of a compound of (i), (ii) or (iii) or a pharmaceutically acceptable salt or salt mixture, isotopic derivative, or prodrug thereof, optionally with a pharmaceutically acceptable carrier or diluent or any of the uses described herein;

(v) The pharmaceutically acceptable composition of (iv) in a solid or liquid, systemic, oral, topical or parenteral dosage form;

(vi) A method for treating a patient with any neurological or psychological CNS disorder as described herein that includes administering an effective amount of a compound of (i), (ii) or (iii) to a patient such as a human in need thereof, (vii) A method for treating any neurological or psychological CNS disorder comprising administering an effective amount of a compound of (i), (ii) or (iii) or a pharmaceutically acceptable salt, isotopic derivative, or prodrug thereof, as described herein, to a patient, typically a human, in need thereof;

(viii) A compound of (i), (ii) or (iii) or a pharmaceutically acceptable salt, salt mixture, isotopic derivative, or prodrug thereof, for use to treat any disorder as described herein in an effective amount as further described herein;

(ix) A compound of (i), (ii) or (iii) for use in the manufacture of a medicament for the treatment of any of the disorders described herein;

(x) Use of a compound of (i), (ii) or (iii) or a pharmaceutically acceptable salt, salt mixture, isotopic derivative, or prodrug thereof, to treat any disorder as described herein in an effective amount as further described herein;

(xi) Processes for the preparation of therapeutic products that contain an effective amount of a compound of (i), (ii) or (iii) or a pharmaceutically acceptable salt or salt mixtures, isotopic derivatives, or prodrugs thereof, as described herein.

DETAILED DESCRIPTION OF THE INVENTION

Figure 1:
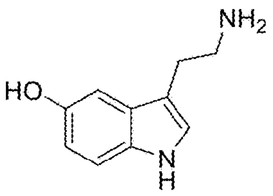
FIG. 1 provides the structures and names of several compounds referred to herein.
Figure 1:
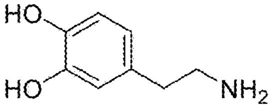
Figure 1:
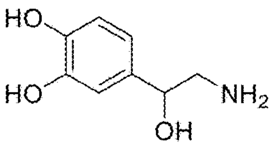
Figure 1:
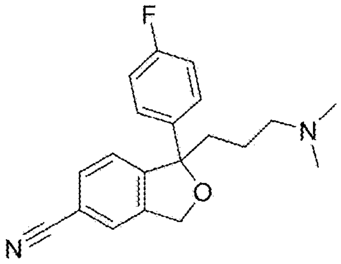
Figure 1:
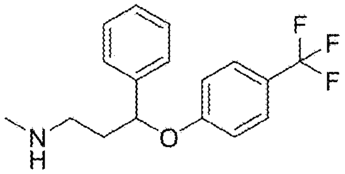
Figure 1:
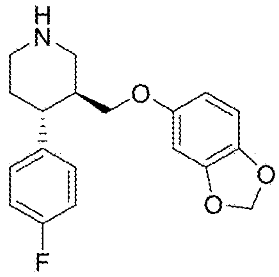
Figure 1:
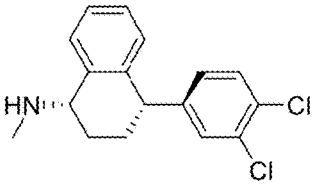
Figure 1:
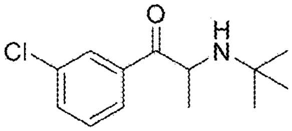
Figure 1:
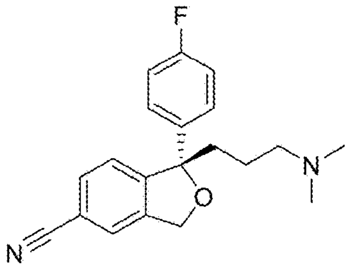
Figure 1:
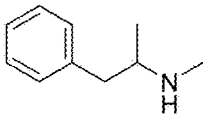
Figure 1:
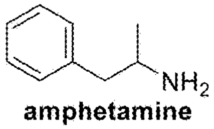
Figure 1:
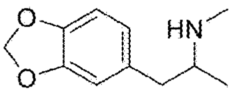
Figure 1:
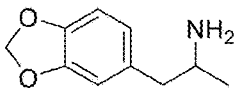
Figure 1:
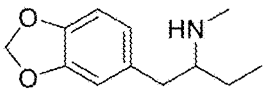
Figure 1:
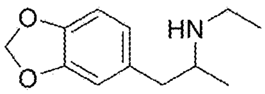

The present invention provides multiple embodiments of the described benzothiophene compounds, compositions, and methods to treat mental disorders, and more generally central nervous disorders, as well as for mental enhancement. The benzothiophene compounds of the present invention provide advantageous pharmacological properties that are highly desirable as therapeutics for the treatment of mental disorders, particularly as psychotherapeutics and neurotherapeutics.

The embodiments of the invention are presented to meet the goal of assisting persons with mental disorders, who desire mental enhancement, or who suffer from other CNS disorders by providing milder therapeutics that are fast acting and that reduce the properties that decrease the patient experience, are counterproductive to the therapy, or are undesirably toxic. One goal of the invention is to provide therapeutic compositions that increase empathy, sympathy, openness and acceptance of oneself and others, which can be taken if necessary as part of therapeutic counseling sessions, when necessary episodically or even consistently, as prescribed by a healthcare provider.

It has been surprisingly discovered that the benzothiophene compositions of the present invention demonstrate properties that indicate the compounds will be fast-acting. This represents a significant improvement over SSRIs, the current standard of care for many CNS and psychological disorders. The slow onset of effects is one of the most pronounced shortcomings of SSRI therapeutics. In contrast, in one embodiment, the compounds of the present invention act as a fast-acting treatment, which represents a significant advance for clinical use. It is advantageous to use a fast-acting therapeutic in a clinical therapeutic setting that typically lasts for one or two hours.

I. Definitions

When introducing elements of the present invention or the typical embodiments thereof, the articles "a," "an," "the," and "said" are intended to mean that there are one or more of the elements. The terms "comprising," "including," and "having" are intended to be inclusive and not exclusive (i.e., there may be other elements in addition to the recited elements). Thus, the terms "including," "may include," and "include," as used herein mean, and are used interchangeably with, the phrase "including but not limited to."

Where a range of values is provided, it is understood that the upper and lower limit, and each intervening value between the upper and lower limit of the range is encompassed within the embodiments.

Unless defined otherwise, all technical and scientific terms herein have the meaning as commonly understood by one of ordinary skill in the art to which this invention belongs. In the event there is a plurality of definitions for a term herein, those in this section prevail unless stated otherwise. Further definitions that may assist the reader to understand the disclosed embodiments are as follows, and such definitions may be used to interpret the defined terms, when those terms are used herein. However, the examples given in the definitions are generally non-exhaustive and must not be construed as limiting the invention. It also will be understood that a substituent should comply with chemical bonding rules and steric compatibility constraints in relation to the particular molecule to which it is attached.

"Compounds" refers to compounds encompassed by structural formulas disclosed herein (e.g., Formula A or Formula I), and includes any specific compounds within these formulas whose structure is disclosed herein. Although sometimes referred to using different terms, and sometimes used interchangeably with "structures," compounds will be understood to include the conjugates, codrugs, and prodrugs of the invention. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers, or diastereomers. Accordingly, the chemical structures depicted herein encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. Further, it should be understood when partial structures of the compounds of the invention are illustrated, that brackets or dashes indicate the point of attachment of the partial structure to the rest of the molecule.

"Composition of the invention" refers to at least one compound of the invention and a pharmaceutically acceptable vehicle with which the compound is administered to a patient. When administered to a patient, the compounds of the invention are administered in isolated form, which means separated from a synthetic organic reaction mixture.

An enantiomerically enriched mixture is a mixture that contains one enantiomer in a greater amount than the other. An enantiomerically enriched mixture of an S-enantiomer contains at least 55% of the S-enantiomer, and, typically at least about 60%, 65%, 70%, 75%, 80%, 85%, 90%, or 95% or more of the S-enantiomer. An enantiomerically enriched mixture of an R-enantiomer contains at least 55% of the R-enantiomer, and typically at least about 60%, 65%, 70%, 75%, 80%, 85%, 90% or 95% of the R-enantiomer. The specific ratio of S or R enantiomer can be selected for the need of the patient according to the health care specialist to balance the desired effect.

The term enantiomerically enriched mixture as used in this application does not include a racemic mixture and does not include a pure isomer. Notwithstanding, it should be understood that any compound described herein in enantiomerically enriched form can be used as a pure isomer if it achieves the goal of any of the specifically itemized methods of treatment described herein, including but not limited to 5-MAPBT, 6-MAPBT, 5-MBPBT, 6-MBPBT, 5-Bk-5-MAPBT, 6-Bk-MAPBT, Bk-5-MBPBT, Bk-6-MBPBT, or a compound shown in FIG. 2.

The term "CNS disorder" as used herein refers to either a neurological condition (one that is typically treated by a neurologist) or a psychiatric condition (one that is typically treated by a psychiatrist). Neurological disorders are typically those affecting the structure, biochemistry or normal electrical functioning of the brain, spinal cord or other nerves. Psychiatric conditions are more typically thought of as mental disorders, which are primarily abnormalities of thought, feeling or behavior that cause significant distress or impairment of personal functioning. Thus, the disclosed compounds can be used in an effective amount to improve neurological or psychiatric functioning in a patient in need thereof. Neurological indications include, but are not limited to improved neuroplasticity, including treatment of stroke, brain trauma, dementia, and neurodegenerative diseases. Compounds of the current invention can be considered psychoplastogens, that is, small molecules that are able to induce rapid neuroplasticity. For example, in certain embodiments, the disclosed compounds and compositions can be used to improve stuttering and other dyspraxias or to treat Parkinson's disease or schizophrenia.

The term "improving psychiatric function" is intended to include mental health and life conditions that are not traditionally treated by neurologists but sometimes treated by psychiatrists and can also be treated by psychotherapists, life coaches, personal fitness trainers, meditation teachers, counselors, and the like. For example, it is contemplated that the disclosed compounds will allow individuals to effectively contemplate actual or possible experiences that would normally be upsetting or even overwhelming. This includes individuals with fatal illness planning their last days and the disposition of their estate. This also includes couples discussing difficulties in their relationship and how to address them. This also includes individuals who wish to more effectively plan their career.

The term "inadequate functioning of neurotransmission" is used synonymously with a CNS disorder that adversely affects normal healthy neurotransmission.

Figure 2:
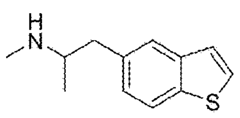
FIG. 2 provides the names and structures of select entactogenic compounds referred to herein.
Figure 2:
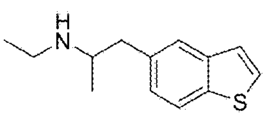
Figure 2:
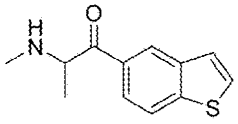
Figure 2:
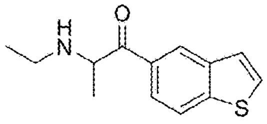
Figure 2:
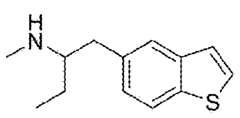
Figure 2:
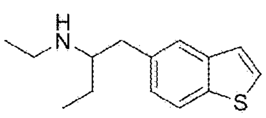
Figure 2:
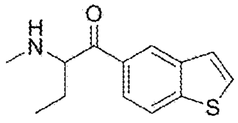
Figure 2:
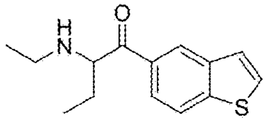
Figure 2:
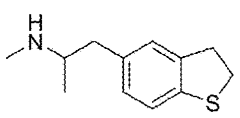
Figure 2:
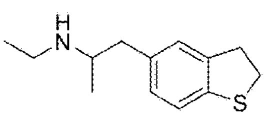
Figure 2:
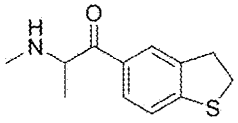
Figure 2:
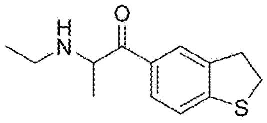
Figure 2:
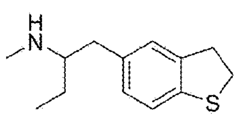
Figure 2:
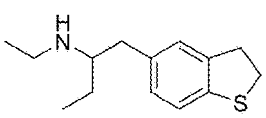
Figure 2:
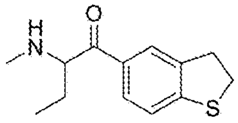
Figure 2:
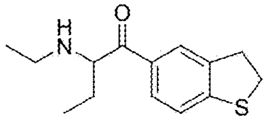
Figure 2:
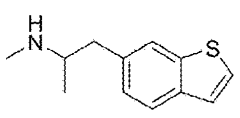
Figure 2:
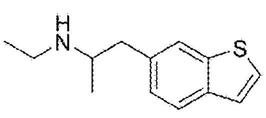
Figure 2:
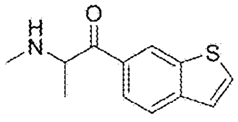
Figure 2:
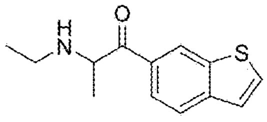
Figure 2:
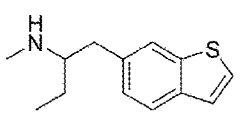
Figure 2:
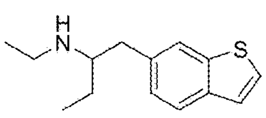
Figure 2:
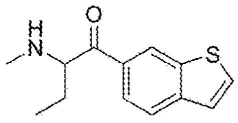
Figure 2:
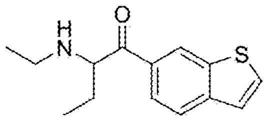
Figure 2:
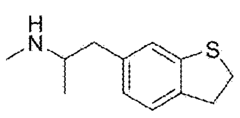
Figure 2:
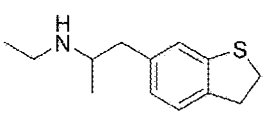
Figure 2:
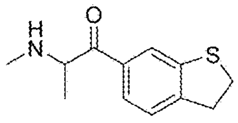
Figure 2:
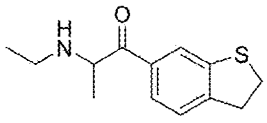
Figure 2:
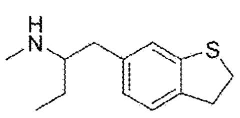
Figure 2:
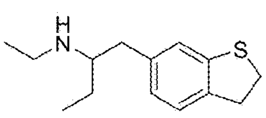
Figure 2:
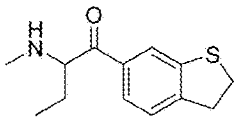
Figure 2:
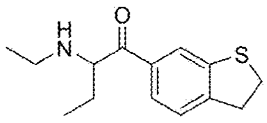
Figure 3:
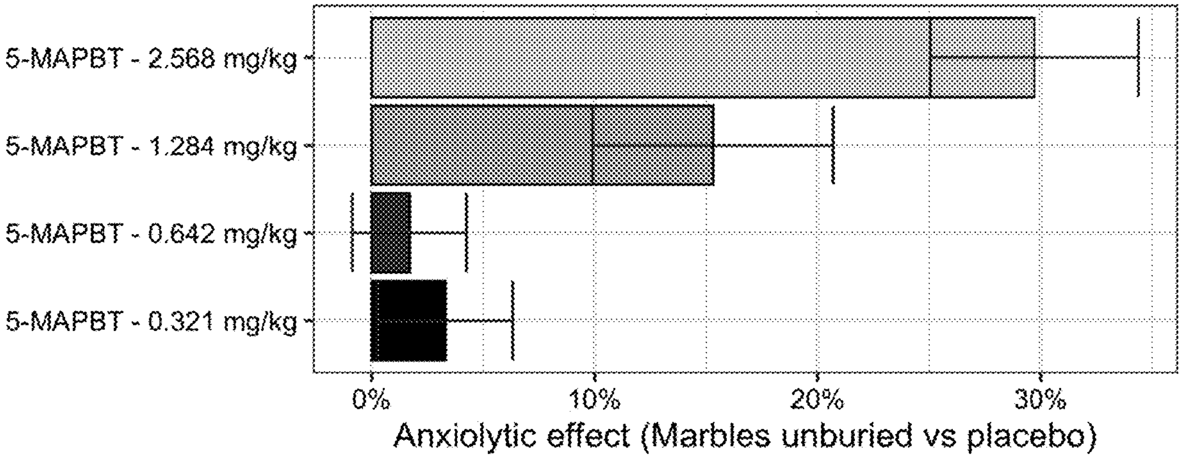
FIG. 3 is a chart showing results from the marble burying assay to measure decreased anxiety and neuroticism resulting from treatment with 5-MAPBT. The x-axis of the chart displays anxiolytic effect, described as the percent of marbles left unburied versus placebo. The y-axis gives the compound and dose. Error bars indicate 95% confidence intervals. Details and procedural information for this assay are described in Example 4.
Figure 4:
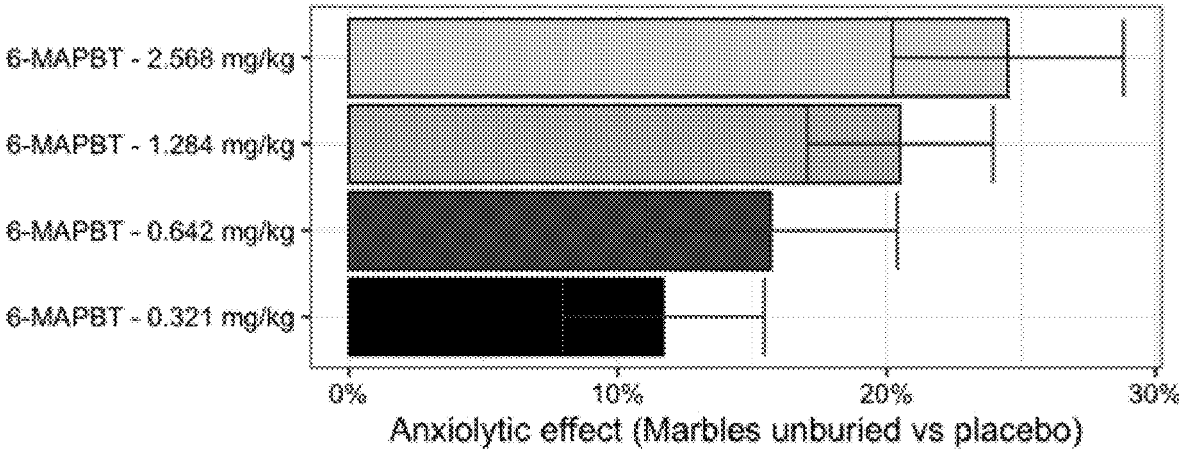
FIG. 4 is a chart showing results from the marble burying assay to measure decreased anxiety and neuroticism resulting from treatment with 6-MAPBT. The x-axis of the chart displays anxiolytic effect, described as the percent of marbles left unburied versus placebo. The y-axis gives the compound and dose. Error bars indicate 95% confidence intervals. Details and procedural information for this assay are described in Example 4.
Figure 5:
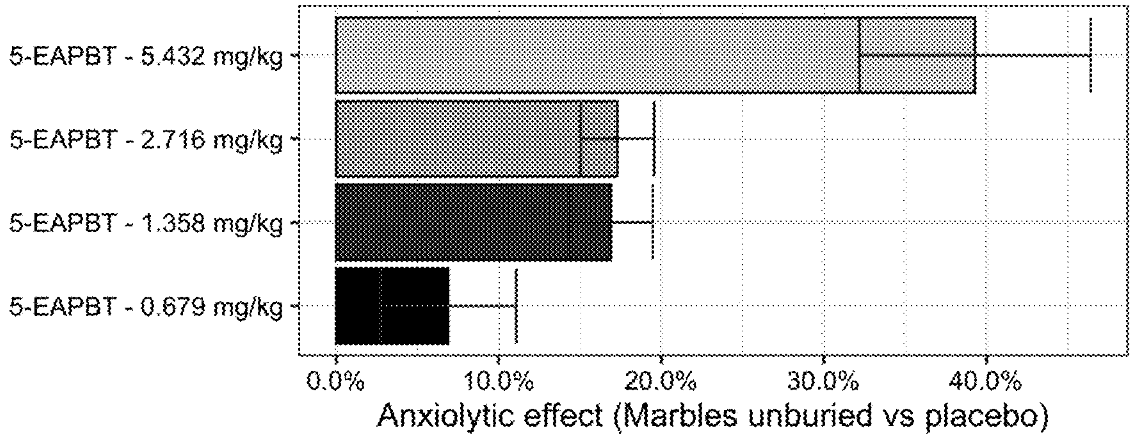
FIG. 5 is a chart showing results from the marble burying assay to measure decreased anxiety and neuroticism resulting from treatment with 5-EAPBT. The x-axis of the chart displays anxiolytic effect, described as the percent of marbles left unburied versus placebo. The y-axis gives the compound and dose. Error bars indicate 95% confidence intervals. Details and procedural information for this assay are described in Example 4.
Figure 6:
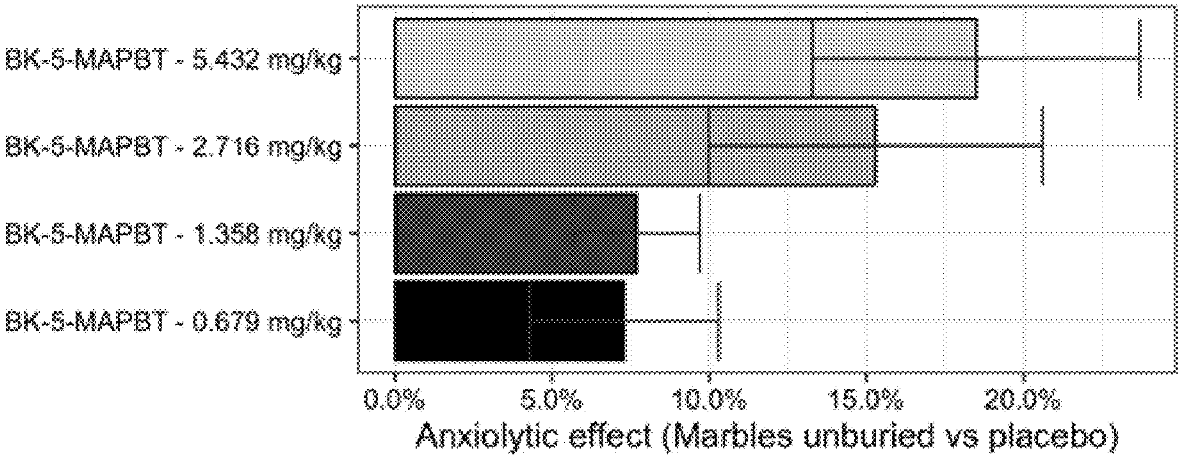
FIG. 6 is a chart showing results from the marble burying assay to measure decreased anxiety and neuroticism resulting from treatment with Bk-5-MAPBT. The x-axis of the chart displays anxiolytic effect, described as the percent of marbles left unburied versus placebo. The y-axis gives the compound and dose. Error bars indicate 95% confidence intervals. Details and procedural information for this assay are described in Example 4.

The present invention also includes compounds, including enantiomerically enriched compounds and their use, such as 5-MAPBT, 6-MAPBT, 5-MBPBT, 6-MBPBT, Bk-5-MAPBT, Bk-6-MAPBT, Formula A, Formula B, Formula C, Formula D, Formula I, Formula II, Formula III, Formula IV, Formula V, Formula VI, Formula VII, Formula VIII, Formula IX, Formula X, Formula XI, Formula XII, Formula XII, Formula XIII, Formula XIV, Formula XV, Formula XVI, and compounds shown in FIG. 2, with at least one desired isotopic substitution of an atom, at an amount above the natural abundance of the isotope, i.e., isotopically enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, fluorine and chlorine such as $^{2}H$, $^{3}H$, $^{11}C$, $^{13}C$, $^{14}C$, $^{13}N$, $^{15}N$, $^{17}O$, $^{18}O$, $^{18}F$, $^{36}Cl$, and respectively. In one non-limiting embodiment, isotopically labelled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively, or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is at least 60, 70, 80, 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in a compounds or compositions described herein. In one non-limiting embodiment, the substitution of a hydrogen atom for a deuterium atom occurs within a group selected from any of $Q^1$, $Q^2$, $Z^1$, $Z^2$, $Z^3$, $Z^4$, $Z^5$, $R^4$, $R^B$, $R^C$, $R^D$, $R^1$, $R^2$, $R^3$, $R^4$, $R^5$, $R^6$, $R^7$, $R^8$, or $R^9$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). The compounds of the invention also include isotopically labeled compounds where one or more atoms have an atomic mass different from the atomic mass conventionally found in nature. Examples of isotopes that may be incorporated into the compounds of the invention include $^2H$, $^3H$, $^{13}C$, $^{14}C$, $^{13}N$, $^{15}N$ $^{18}O$, $^{17}O$, $^{31}P$, $^{32}P$ $^{35}S$, $^{18}F$, and $^{36}Cl$.

For example, the methyl group on the nitrogen of 5-MAPBT, 6-MAPBT, 5-MBPBT, 6-MBPBT, Bk-5-MAPBT, and Bk-6-MAPBT is subject to metabolic removal, which produces pharmacologically active metabolites. In some embodiments, 5-MAPBT or 6-MAPBT is prepared with deuterium replacing some or all of the three hydrogens on the N-methyl group. In one embodiment, 5-MBPBT or 6-MBPBT is prepared with deuterium replacing some or all of the three hydrogens on the N-methyl group. In one embodiment, Bk-5-MAPBT or Bk-6-MAPBT is prepared with deuterium replacing some or all of the three hydrogens on the N-methyl group. This creates a higher activation energy for bond cleavage and a slower formation of the methyl metabolites. Analogously, the two hydrogens on the thiophene ring may be replaced with one or two deuteriums to decrease metabolic opening of the thiophene ring and formation of hydroxyl-substituted metabolites.

Similarly, the methyl or ethyl group on the nitrogen of Formula A, Formula B, Formula C, or Formula D of the invention is subject to metabolic removal, which produces pharmacologically active metabolites. In one embodiment, Formula A or Formula B is prepared with deuterium replacing some or all of the three, four, or five hydrogens on the N-methyl or N-ethyl group. In one embodiment, Formula C or Formula D is prepared with deuterium replacing some or all of the three, four, or five hydrogens on the N-methyl or N-ethyl group. The primary amines of Formula A, Formula B, Formula C and Formula D of the invention retain therapeutic effects while presenting a different profile of pharmacological effects. Accordingly, the present disclosure also includes the primary amine variants of Formula A, Formula B, Formula C and Formula D, where applicable.

The methyl or ethyl group on the nitrogen of a compound shown in FIG. 2 of the invention is subject to metabolic removal, which produces pharmacologically active metabolites. In one embodiment, a compound shown in FIG. 2 is prepared with deuterium replacing some or all of the three, four, or five hydrogens on the N-methyl or N-ethyl group. The primary amines of the compounds shown in FIG. 2 of the invention retain therapeutic effects while presenting a different profile of pharmacological effects. Accordingly, the present disclosure also includes the primary amine variants of the compounds shown in FIG. 2, where applicable.

The methyl or ethyl group on the nitrogen where applicable of Formula I, Formula II, Formula III, Formula IV, Formula V, Formula VI, Formula VII, Formula VIII, Formula IX, Formula X, Formula XI, Formula XII, Formula XIII, and Formula XIV is also subject to metabolic removal, which produces pharmacologically active metabolites. In one embodiment, Formula I, Formula II, Formula III, Formula IV, Formula V, Formula VI, Formula VII, Formula VIII, Formula IX, Formula X, Formula XI, Formula XII, Formula XIII, Formula XIV Formula XV, or Formula XVI is prepared with deuterium replacing some or all of the three, four, or five hydrogens on the N-ethyl or N-methyl group. The primary amines of Formula I, Formula II, Formula III, Formula IV, Formula V, Formula VI, Formula VII, Formula VIII, Formula IX, Formula X, Formula XI, Formula XII, Formula XIII, and Formula XIV of the invention retain therapeutic effects while presenting a different profile of pharmacological effects.

The term "isotopically-labeled" analog refers to an analog that is a "deuterated analog", a "$^{13}C$-labeled analog," or a "deuterated/$^{13}C$-labeled analog." The term "deuterated analog" means a compound described herein, whereby a H-isotope, i.e., hydrogen/protium ($^1H$), is substituted by a H-isotope, e.g., deuterium ($^2H$). Deuterium substitution can be partial or complete. Partial deuterium substitution means that at least one hydrogen is substituted by at least one deuterium. In certain embodiments, the isotope is at least 60, 70, 80 90, 95 or 99% or more enriched in an isotope at any location of interest. In some embodiments it is deuterium that is 90, 95 or 99% enriched at a desired location. Unless indicated to the contrary, the deuteration is at least 80% at the selected location. Deuteration of the nucleoside can occur at any replaceable hydrogen that provides the desired results.

"Alkyl" refers to a saturated or unsaturated, branched, straight-chain, or cyclic monovalent hydrocarbon radical derived by the removal of one hydrogen atom from a single carbon atom of a parent alkane, alkene or alkyne. Typical alkyl groups include methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Alkyl will be understood to include cyclic alkyl radicals such as cyclopropyl, cyclobutyl, and cyclopentyl.

"Alkyl" includes radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl,"

and "alkynyl" are used. In certain embodiments, an alkyl group comprises from 1 to 26 carbon atoms, typically from 1 to 10 carbon atoms.

"Halogen" or "halo" means fluoro (F), chloro (Cl), bromo (Br), or iodo (I). For groups containing two or more halogens, such as $—CHY_2$ or $—CY_3$, and for example "where Y is halogen," it will be understood that each Y independently will be selected from the group of halogens.

"Hydroxy" means the radical —OH.

"Oxo" means the divalent radical =O.

"Stereoisomers" includes enantiomers, diastereomers, the components of racemic mixtures, and combinations thereof. Stereoisomers can be prepared or separated as described herein or by using other methods.

"Isomers" includes stereo and geometric isomers, as well as diastereomers. Examples of geometric isomers include cis isomers or trans isomers across a double bond. Other isomers are contemplated among the compounds of the present disclosure. The isomers may be used either in pure form or in admixture with other isomers of the compounds described herein.

"Agonism" refers to the activation of a receptor or enzyme by a modulator, or agonist, to produce a biological response.

"Agonist" refers to a modulator that binds to a receptor or enzyme and activates the receptor to produce a biological response. As a nonlimiting example, "$5HT_{1B}$ agonist" can be used to refer to a compound that exhibits an $EC_{50}$ with respect to $5HT_{1B}$ activity of no more than about 10, 25 or even 50 μM. In some embodiments, "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

"Antagonism" refers to the inactivation of a receptor or enzyme by a modulator, or antagonist. Antagonism of a receptor, for example, is when a molecule binds to the receptor and does not allow activity to occur.

"Antagonist" or "neutral antagonist" refers to a modulator that binds to a receptor or enzyme and blocks a biological response. An antagonist has no activity in the absence of an agonist or inverse agonist but can block the activity of either, causing no change in the biological response.

"DAT to SERT ratio" refers to the tendency of a substance (e.g., a compound or a drug) to increase extracellular dopamine versus increasing extracellular 5-HT concentrations. Higher numbers of this ratio indicate a greater increase of dopamine than serotonin, while lower number indicate an increasing 5-HT more than dopamine. The exact numbers depend on the assay used. The ratio is calculated herein as $(DAT\ EC_{50})^{-1}/(SERT\ EC_{50})^{-1}$. Some publications use $IC_{50S}$ for inhibiting uptake instead of $EC_{50S}$ for causing release to calculate this ratio, which will often yield very different results for substances that are monoamine releasers. Thus, it is important to review the numbers in view of the assay and measurement used.

"$IC_{50}$" refers to the concentration of a substance (e.g., a compound or a drug) that is required for 50% inhibition of a biological process. For example, $IC_{50}$ refers to the half maximal (50%) inhibitory concentration (IC) of a substance as determined in a suitable assay. Similarly, $EC_{50}$ refers to the concentration of a substance that provokes a response halfway between the baseline activity and maximum response. In some instances, an $IC_{50}$ or $EC_{50}$ is determined in an in vitro assay system. In some embodiments as used herein, $IC_{50}$ (or $EC_{50}$) refers to the concentration of a modulator that is required for 50% inhibition (or excitation) of a receptor, for example, $5HT_{1B}$.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., positive allosteric modulator) of a G protein-coupled receptor (e.g., $5\text{-}HT_{1B}$) are modulators of the receptor.

"Neuroplasticity" refers to the ability of the brain to change its structure and/or function throughout a subject's life. Examples of the changes to the brain include, but are not limited to, the ability to adapt or respond to internal and/or external stimuli, such as due to an injury, and the ability to produce new neurites, dendritic spines, and synapses.

"Treating" or "treatment" of a disease, as used in context, includes (i) inhibiting the disease, i.e., arresting or reducing the development or progression of the disease or its clinical symptoms; or (ii) relieving the disease, i.e., causing regression of the disease or its clinical symptoms. Inhibiting the disease, for example, would include prophylaxis. Hence, one of skill in the art will understand that a therapeutic amount necessary to effect treatment for purposes of this invention will, for example, be an amount that provides for objective indicia of improvement in patients having clinically diagnosable symptoms. Other such measurements, benefits, and surrogate or clinical endpoints, whether alone or in combination, would be understood to those of ordinary skill.

"Therapeutic effect" means the responses(s) in a mammal after treatment that are judged to be desirable and beneficial. Hence, depending on the CNS disorder to be treated, or improvement in CNS functioning sought, those responses shall differ, but would be readily understood by those of ordinary skill.

The term "hallucinations" or "hallucinogenic effects" includes but is not limited to perceptual distortions, delusions, depersonalization, derealization and/or labile mood. These effects can include dysphoria of intensities ranging from controllable anxiety to uncontrollable panic.

II. Compounds of the Present Invention

Smith Kline & French Laboratories disclosed primary amine benzothiophenes as CNS agents in 1960 (GB855115A). Brandt and colleagues recently reviewed what little is known of the pharmacology of primary (2-aminopropyl) benzothiophenes and suggested they might act as stimulants (Brandt et al., Drug testing and analysis, 2020 12(8):1109-25). The compound 1-(1-benzothiophen-3-yl) propan-2-amine (3-APBT, SKF 6678) reportedly inhibited MAO-A (IC50=16.2±0.4 μM) but not MAO-B (Vallejos et al., Bioorganic & medicinal chemistry. 2005 13(14):4450-7) and acted to reduce appetite (Poos, Annual Reports in Medicinal Chemistry 1967 2: 44-47.). To the inventor's knowledge, the benzothiophenes disclosed herein have not been proposed as entactogens and most have not been previously contemplated or synthesized.

The chiral carbon typically referred to in this application is the carbon alpha to the amine in the phenylethylamine motif (i.e., the benzothiophenyl ethyl amine motif). Of course, the compounds can have additional chiral centers that result in diastereomers. Notwithstanding, in the present application, the primary chiral carbon referred to in the term "enantiomerically enriched" is that carbon alpha to the amine in the provided structures.

In one aspect, the invention provides the compound 6-MAPBT, enantiomerically enriched mixtures or pure enantiomers of R-6-MAPBT or R-6-MAPBT or a pharmaceutically acceptable salt or salt mixture thereof. In certain aspects, a pharmaceutical composition is provided that comprises 6-MAPBT or a pure R- or S-enantiomer or enantiomerically enriched mixture thereof:

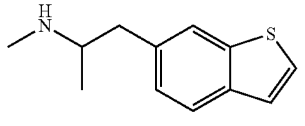

6-MAPBT

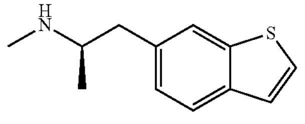

R-6-MAPBT

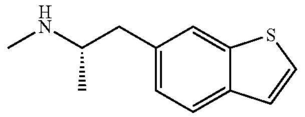

S-6-MAPBT

In one aspect of this embodiment, the invention provides pharmaceutical compositions comprising enantiomerically enriched or enantiomerically pure, R-5-MAPBT, S-5-MAPBT, or a pharmaceutically acceptable salt or salt mixture thereof, where the racemic compound is registered as CAS #2613382-32-2 but without any references to use or synthesis. In certain aspects, a pharmaceutical composition is provided that comprises a pure R- or S-enantiomer or an enantiomerically enriched mixture of the R- or S-enantiomer of 5-MAPBT:

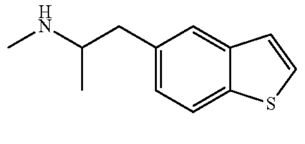

5-MAPBT

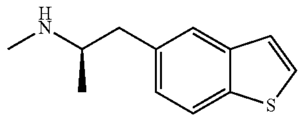

R-5-MAPBT

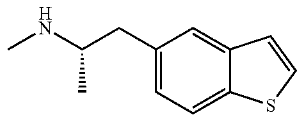

S-5-MAPBT

In certain embodiments, isolated enantiomers of the compounds of the present invention show improved binding at the desired receptors and transporters relevant to the goal of treatment for the mental disorder or for mental enhancement.

An enantiomerically enriched mixture is a mixture that contains one enantiomer in a greater amount than the other. An enantiomerically enriched mixture of an S-enantiomer contains at least 55% of the S-enantiomer, and, typically at least about 60%, 65%, 70%, 75%, 80%, 85%, 90%, or 95% or more of the S-enantiomer. An enantiomerically enriched mixture of an R-enantiomer contains at least 55% of the R-enantiomer, and typically at least about 60%, 65%, 70%, 75%, 80%, 85%, 90% or 95% of the R-enantiomer. The specific ratio of S or R enantiomer can be selected for the need of the patient according to the health care specialist to balance the desired effect.

The term enantiomerically enriched mixture as used in this application does not include a racemic mixture and does not include a pure isomer. Notwithstanding, it should be understood that any compound described herein in enantiomerically enriched form can be used as a pure isomer (or a racemic form) if it achieves the goal of any of the specifically itemized methods of treatment described herein, including but not limited to 5-MAPBT, 6-MAPBT, 5-MBPBT, 6-MBPBT, 5-Bk-5-MAPBT, 6-Bk-MAPBT, Bk-5-MBPBT, Bk-6-MBPBT, or a compound shown in FIG. 2.

It has been discovered that it is useful to have an S- or R-enantiomerically enriched mixture of these entactogenic compounds that is not a racemic mixture. Enantiomerically enriched mixtures that have a greater amount of the one enantiomer of 5-MAPBT or 6-MAPBT potentially maximize serotonin-receptor-dependent therapeutic effects, whereas the enantiomerically enriched opposite enantiomer of 5-MAPBT or 6-MAPBT potentially increases nicotinic-receptor-dependent therapeutic effects relative to the racemic mixture Therefore, one aspect of the present invention is a balanced mixture of S-5-MAPBT and R-5-MAPBT or a balanced mixture of S-6-MAPBT and R-6-MAPBT that achieves a predetermined combination of serotonin-receptor-dependent therapeutic effects and nicotinic-receptor-dependent or dopaminergic therapeutic effects. The effect can be modulated as desired for optimal therapeutic effect.

Non-limiting examples of unwanted effects that can be minimized by carefully selecting the balance of enantiomers include hallucinogenic effects (for example, perceptual distortions, delusions, depersonalization, derealization, and labile mood), psychoactive effects (including excess stimulation or sedation), physiological effects (including transient hypertension or appetite suppression), toxic effects (including to the brain or liver), effects contributing to abuse liability (including euphoria or dopamine release), and/or other side effects.

Accordingly, in one embodiment, an enantiomerically enriched mixture of the S-enantiomer or pure enantiomer of S-5-MAPBT or an enantiomerically enriched mixture of the S-enantiomer or pure enantiomer of S-6-MAPBT balances therapeutic effects (such as emotional openness and perceptible mood effects) while having lesser effects associated with abuse liability (such as perceptible 'good drug effects' or desire for more drug, which can lead to abuse; Pool et al. 2016. Neuroscience & Biobehavioral Reviews, 63, pp. 124-142) when administered to a host in need thereof, for example a mammal, including a human. The enantiomerically enriched mixture or pure enantiomer achieves a predetermined combination of emotional therapeutic effects and perceptible mood effects. The effect can be modulated as desired for optimal therapeutic effect.

Accordingly, in another embodiment, an enantiomerically enriched mixture of the R-enantiomer or pure enantiomer of R-5-MAPBT or an enantiomerically enriched mixture of the R-enantiomer or pure enantiomer of R-6-MAPBT balances therapeutic effects (such as emotional openness and perceptible mood effects) while having lesser effects associated with abuse liability (such as perceptible 'good drug effects' or desire for more drug, which can lead to abuse; Pool et al. 2016. Neuroscience & Biobehavioral Reviews, 63, pp. 124-142) when administered to a host in need thereof, for example a mammal, including a human. The enantiomerically enriched mixture or pure enantiomer achieves a predetermined combination of emotional therapeutic effects and perceptible mood effects. The effect can be modulated as desired for optimal therapeutic effect.

In yet other embodiments, the present invention includes enantiomerically enriched mixtures of the R- or S-enantiomer of the racemic structure selected from:

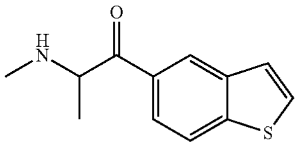

Bk-5-MAPBT

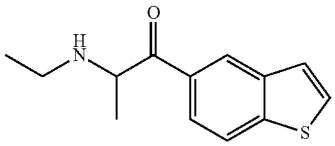

and

Bk-5-EAPBT

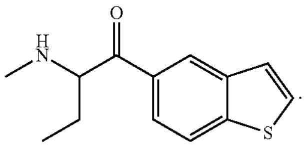

Bk-5-MBPBT

In yet other embodiments, the present invention includes compounds selected from:

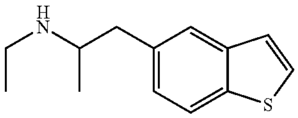

5-EAPBT

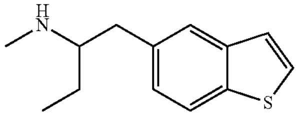

5-MBPBT

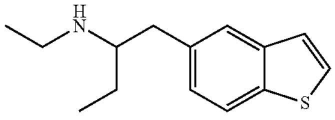

5-EBPBT

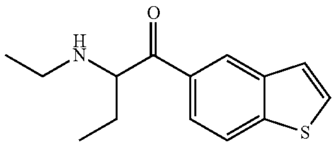

Bk-5-EBPBT

-continued

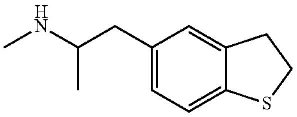

5-MAPDBT

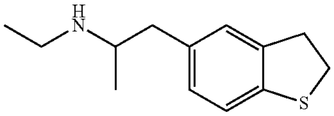

5-EAPDBT

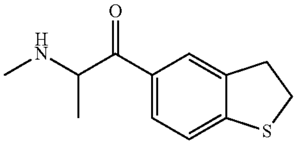

Bk-5-MAPDBT

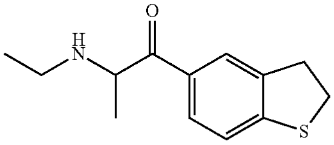

Bk-5-EAPDBT

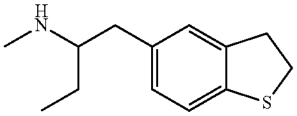

5-MBPDBT

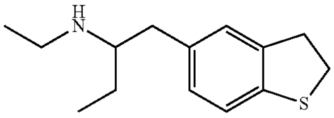

5-EBPDBT

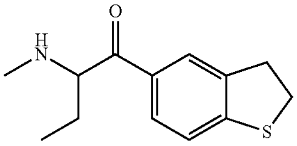

Bk-5-MBPDBT

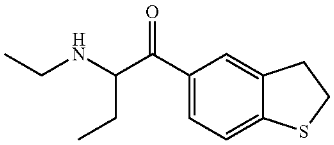

Bk-5-EBPDBT

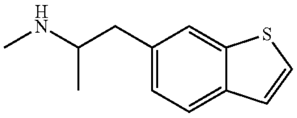

6-MAPBT

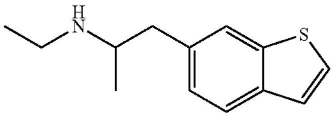

6-EAPBT

-continued

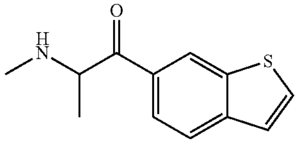

Bk-6-MAPBT

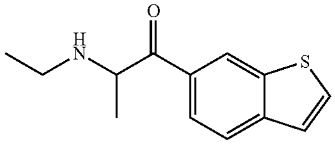

Bk-6-EAPBT

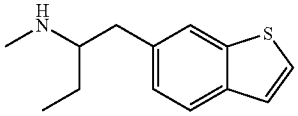

6-MBPBT

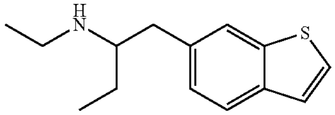

6-EBPBT

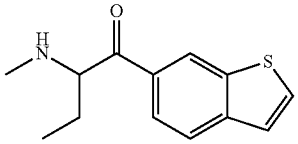

Bk-6-MBPBT

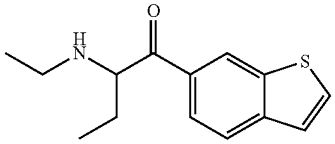

Bk-6-EBPBT

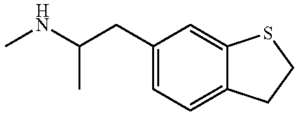

6-MAPDBT

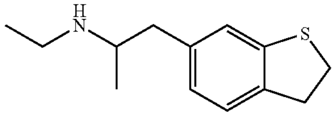

6-EAPDBT

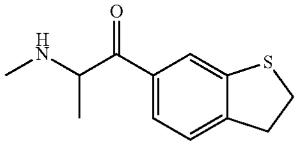

Bk-6-MAPDBT

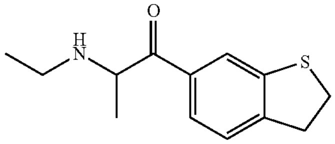

Bk-6-EAPDBT

-continued

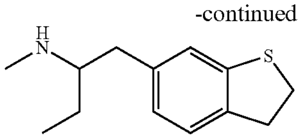

6-MBPDBT

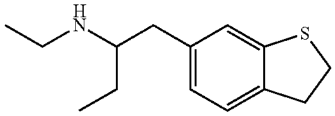

6-EBPDBT

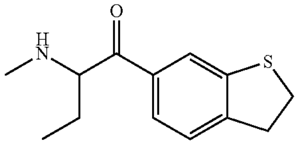

and

Bk-6-MBPDBT

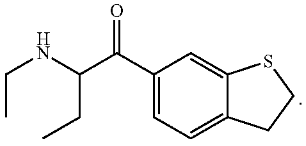

Bk-6-EBPDBT

In yet other embodiments, the present invention provides an enantiomerically enriched mixture of the R- and S-enantiomers of a compound of Formula C or a pharmaceutically acceptable salt or salt mixture thereof, for any of the uses described herein by administering to a patient, such as a human, the enantiomerically enriched compound in an effective amount to achieve the desired effect:

Formula C

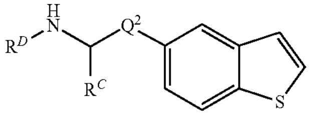

wherein:

$R^C$ is selected from $-CH_3$, $-CH_2Y$, $-CHY_2$, $-CY_3$, $-CH_2CH_2Y$, $-CH_2CHY_2$, $-CH_2CY_3$, $-CH_2CH_3$, $-CH_2OH$, or $-CH_2CH_2OH$;

$R^D$ is selected from $-CH_3$ and $-CH_2CH_3$;

$Q^2$ is selected from:

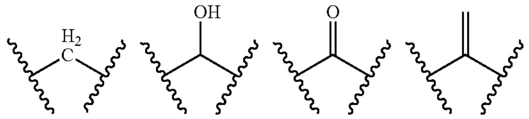

and

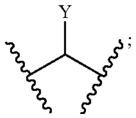

;

and

Y is halogen.

In yet other embodiments, the present invention provides a pure or enantiomerically enriched mixture of the R- or S-enantiomer of a compound of Formula A, Formula B, or Formula D, or a pharmaceutically acceptable salt or salt mixture thereof, for any of the uses described herein by administering to a patient, such as a human, the enantiomerically enriched compound in an effective amount to achieve the desired effect:

Formula A

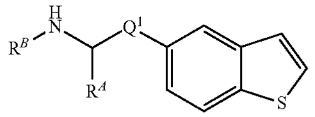

Formula B

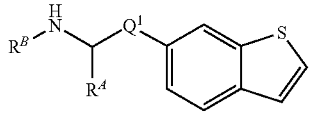

Formula D

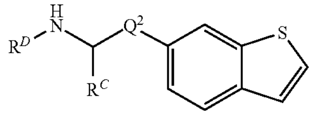

wherein:

$R^A$ and $R^B$ are independently selected from —$CH_3$ and —$CH_2CH_3$;

$R^C$ is selected from —$CH_3$, —$CH_2Y$, —$CHY_2$, —$CY_3$, —$CH_2CH_2Y$, —$CH_2CHY_2$, —$CH_2CY_3$, —$CH_2CH_3$, —$CH_2OH$, or —$CH_2CH_2OH$;

$R^D$ is selected from —$CH_3$ and —$CH_2CH_3$;

$Q^1$ is selected from

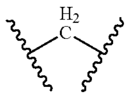 and 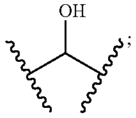;

$Q^2$ is selected from:

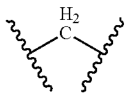 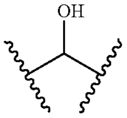 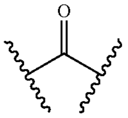 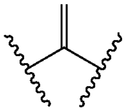

and 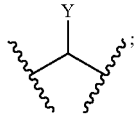;

and

Y is halogen.

The present invention also provides new medical uses for the compounds, pure R- or S-enantiomers or enantiomerically enriched mixtures of Formulas I-XVI, Formulas A-D, 5-MAPBT, 6-MAPBT, 5-MBPBT, 6-MBPBT, 5-Bk-5-MAPBT, 6-Bk-MAPBT, Bk-5-MBPBT, Bk-6-MBPBT, or shown in FIG. 2, by administering an effective amount to a patient such as a human to treat a CNS disorder including but not limited to, the treatment of post-traumatic stress disorder, depression, dysthymia, anxiety, generalized anxiety, social anxiety, panic, post-traumatic stress disorder, adjustment disorders, feeding and eating disorders, binge behaviors, body dysmorphic syndromes, addiction, drug abuse or dependence disorders, substance use disorders, disruptive behavior disorders, impulse control disorders, gaming disorders, gambling disorders, memory loss, dementia of aging, attention deficit hyperactivity disorder, personality disorders, attachment disorders, autism or dissociative disorders or any other disorder described herein, including in the Background.

It has been discovered that several of the benzothiophene derivatives of the current invention are direct $5\text{-HT}_{1B}$ agonists. Very few substances are known that are $5\text{-HT}_{1B}$ agonists and also 5-HT releasers and of those, some show significant toxicities. For example, m-chlorophenylpiperazine (mCPP) is one example but is anxiogenic and induces headaches, limiting any clinical use. MDMA itself does not bind to the $5\text{-HT}_{1B}$ (Ray. 2010. *PloS one,* 5(2), e9019). $5\text{-HT}_{1B}$ agonism is noteworthy because indirect stimulation of these receptors, secondary to elevated extracellular serotonin, has been hypothesized to be required for the prosocial effects of MDMA (Heifets et al. 2019. *Science translational medicine,* 11(522)), while other aspects of entactogen effects have been attributed to monoamine release (e.g., Luethi & Liechti. 2020. *Archives of Toxicology,* 94(4), 1085-1133). For at least three of the molecules disclosed herein, the potency at stimulating $5\text{-HT}_{1B}$ is similar to (or lower than) their potency for releasing 5-HT. Specifically, 5-MAPBT has an $EC_{50}$ of 23 nM for releasing 5-HT and an $EC_{50}$ of 38 nM at $5\text{-HT}_{1B}$, while 6-MAPBT has an $EC_{50}$ of 57 nM for releasing 5-HT and an $EC_{50}$ of 24 nM at $5\text{-HT}_{1B}$, and BK-5-MAPBT has an $EC_{50}$ of 101 nM for releasing 5-HT and an $EC_{50}$ of 59 nM at $5\text{-HT}_{1B}$. Thus, the unique ratios of $5\text{-HT}_{1B}$ stimulation and monoamine release displayed by the disclosed compounds enable different profiles of therapeutic effects that cannot be achieved by MDMA or other known entactogens.

The compounds of the present invention show a 5-HT selectivity pattern that is important to therapeutic use. Various subtypes of 5-HT receptor can induce different felt experiences on a patient. Agonism of the $5\text{-HT}_{2A}$ receptor can cause feelings of fear (ranging from mild anxiety to panic) and hallucinations, but agonism of $5\text{-HT}_{1B}$ is believed to be tied to the pro-social effects of entactogens. Various subtypes of 5-HT receptor can also contribute to different toxicity risks for a patient. Administration of MDMA and other serotonergic drugs is associated with elevated acute risk of hyponatremia. It is known that stimulation of $5\text{-HT}_2$ receptors is an important trigger of release of antidiuretic hormone (Iovino et al. Current pharmaceutical design 18, no. 30 (2012): 4714-4724).

It has been surprisingly discovered that the compounds of the present invention can be poor agonists of $5\text{-HT}_{2A}$, but exhibit activity toward $5\text{-HT}_{1B}$. For example, as described in the non-limiting illustrative Example 5, all the tested compounds show excellent selectivity for $5\text{-HT}_{1B}$ agonist activity over $5\text{-HT}_{2A}$ agonist activity. For some tested compounds, the $5\text{-HT}_{2A}$ agonist activity was too weak to detect an $EC_{50}$ below 30 μM. Importantly, $5\text{-HT}_{1B}$ agonist activity effect occurs through direct action on the receptor, rather than as an indirect consequence of serotonin release. This is an unexpected discovery because this property has not been observed in an entactogen, including MDMA, before. In one embodiment, the selectivity toward the $5\text{-HT}_{1B}$ receptor over $5\text{-HT}_{2A}$ receptor allows for a more relaxed and therapeutically productive experience for the patient undergoing treatment with a compound of the present invention.

The unique ratios of $5\text{-HT}_{1B}$ stimulation and 5-HT release displayed by selected disclosed compounds enable different profiles of therapeutic effects and side effects that may not be achieved by MDMA or other known entactogens. An undesirable effect of releasing 5-HT can be hyponatremia or loss of appetite. Drugs such as d-fenfluramine that release 5-HT by interacting with SERT and thereby increase agonism of all serotonin receptors have been used as anorectics. Similarly, MDMA is known to acutely suppress appetite (see, e.g., Vollenweider et al. Neuropsychopharmacology 19, no. 4 (1998): 241-251.).

Accordingly, as described in the non-limiting illustrative Example 7, compounds of the present invention have the ability to release 5-HT with potencies ($EC_{50S}$) below 1 μM and as low as 0.0023 μM. In another embodiment, therefore, the selectivity toward the $5\text{-HT}_{1B}$ receptor over SERT-mediated 5-HT release allows for a therapeutically productive experience for the patient undergoing treatment with a compound of the present invention with fewer other side effects from serotonin release, such as loss of appetite or risk of hyponatremia.

In certain embodiments, the compounds and compositions of the present invention present a reduced side effect and toxicity profile compared to other entactogens. The chemical structure of the compounds, pure R- or S-enantiomers, and enantiomerically-enriched mixtures of the present invention is less prone to metabolic breakdown, for example by CYP enzymes, than other entactogens. This property reduces the number of toxic or unintended compounds produced in the course of eliminating the active pharmaceutical agent from the body.

The present invention also includes compounds with beneficial selectivity profiles for neurotransmitter transporters. The balance of weakly activating NET (to reduce cardiovascular toxicity risk) and having a relatively low DAT to SERT ratio (to increase therapeutic effect relative to addictive liability) is a desirable feature of an entactogenic therapy displayed by the compounds and compositions of the present invention. Every tested compound displayed a DAT to SERT ratio less than one, indicating each compound is more selective for SERT (therapeutic effect) than DAT (addictive liability) as described in the non-limiting illustrative Example 7.

In other embodiments, the invention provides an active compound of Formula I, Formula II, Formula III, Formula IV, Formula V, Formula VI, Formula VII, Formula VIII, or Formula IX:

(I)

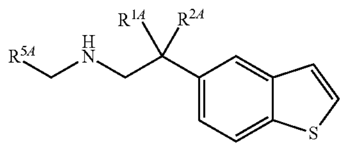

(II)

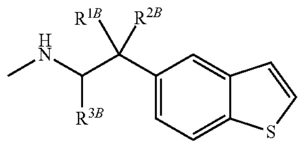

(III)

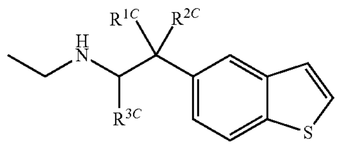

-continued (IV)

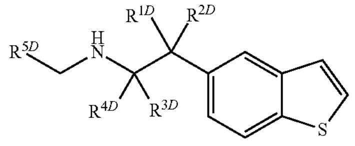

(V)

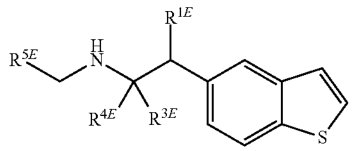

(VI)

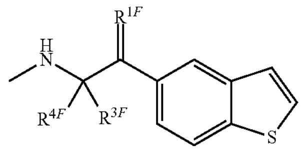

(VII)

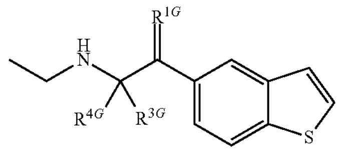

(VIII)

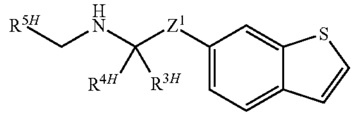

(IX)

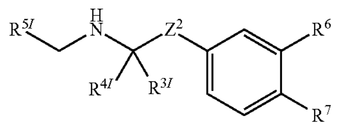

wherein:

$Z^1$ is selected from

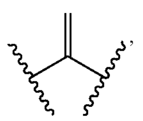, 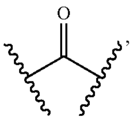, and 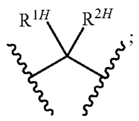;

$Z^2$ is selected from

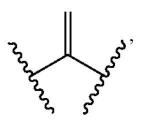, 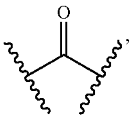, and 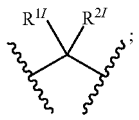;

$R^{1A}$, $R^{1D}$, and $R^{2D}$ are independently selected from —X, —OH, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{1B}$, $R^{1C}$, $R^{1E}$, $R^{1H}$, $R^{1I}$, $R^{2B}$, $R^{2C}$, $R^{2H}$, and $R^{2I}$ are independently selected from —H, —X, —OH, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{1F}$ and $R^{1G}$ are independently selected from $CH_2$ and O;

$R^{2A}$ is selected from —H, —X, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein if $R^{1A}$ is —OH, $R^{2A}$ is not —H or $C_1$ alkyl;

$R^{3B}$ is selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl; wherein if $R^{3B}$ is $C_1$ alkyl and one of $R^{2B}$ and $R^{1B}$ is —H, then the other of $R^{2B}$ and $R^{1B}$ cannot be —H or —OH;

$R^{3C}$ is selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl; wherein if $R^{3C}$ is $C_1$ alkyl and one of $R^{2C}$ and $R^{1C}$ is —H, then the other of $R^{2C}$ and $R^{1C}$ cannot be —OH or $C_1$ alkyl;

$R^{3D}$, $R^{3F}$, and $R^{4D}$ are independently selected from —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{3E}$ and $R^{4E}$ are independently selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein when $R^{3E}$ and $R^{4E}$ are both $C_1$ alkyl, $R^{1E}$ cannot be —OH or —F;

$R^{3G}$ and $R^{4G}$ are independently selected from —H, —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein if $R^{1G}$ is O and one of $R^{3G}$ and $R^{4G}$ is —H, then the other of $R^{3G}$ and $R^{4G}$ cannot be —H or $C_1$ alkyl;

$R^{3H}$, $R^{3I}$, $R^{4H}$, and $R^{4I}$ are independently selected from —H, —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{4F}$ is selected from —H, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein if $R^{4F}$ is —H and $R^{1F}$ is O, then $R^{3F}$ cannot be $C_1$ or $C_2$ alkyl;

$R^{5A}$, $R^{5D}$, $R^{5E}$, and $R^{5H}$ are independently selected from —H or —$CH_3$;

$R^{5I}$ is selected from —H and —$CH_3$, wherein if $R^{3I}$, $R^{4I}$, and $R^{5I}$ are all —H, then $Z^2$ cannot be

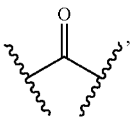, 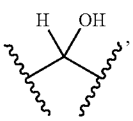, or 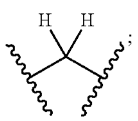;

$R^6$ and $R^7$ are taken together as —$SCH_2CH_2$— or —$CH_2CH_2S$—; and

X is independently selected from —F, —Cl, and —Br.

The compounds of Formulas I-IX can be used as racemic mixtures, enantiomerically or diastereomerically enriched or pure isomers, as desired to achieve the goal of therapy.

In further embodiments, the invention includes pure R- or S-enantiomers and enantiomerically enriched mixtures of Formula VIII, Formula X, Formula XI, Formula XII, and Formula XIII or a pharmaceutically acceptable salt or salt mixture thereof:

(VIII)

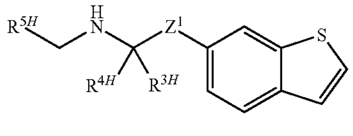

(X)

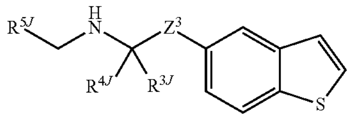

(XI)

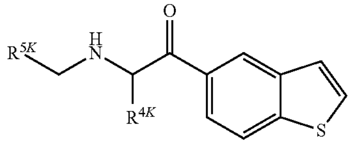

(XII)

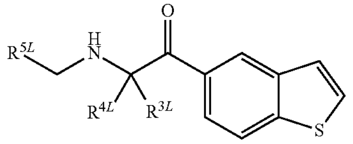

(XIII)

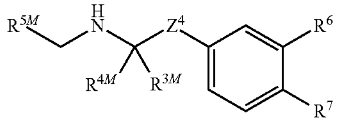

wherein:

$Z^1$ is selected from

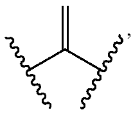, 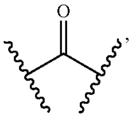, and 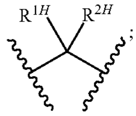;

$Z^3$ is selected from

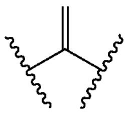 and 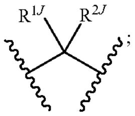;

$Z^4$ is selected from

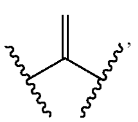, 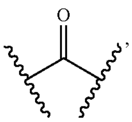, and 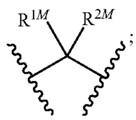;

$R^{1H}$, $R^{1J}$, $R^{1M}$, $R^{2H}$, $R^{2J}$, and $R^{2M}$ are independently selected from —H, —X, —OH, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{3H}$, $R^{3J}$, $R^{3M}$, $R^{4H}$, $R^{4J}$, and $R^{4M}$ are independently selected from —H, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{3L}$ and $R^{4L}$ are independently selected from $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_1$-$C_4$ alkyl;

$R^{4K}$ is selected from $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_2$-$C_4$ alkyl;

$R^{5H}$, $R^{5L}$, and $R^{5M}$ are independently selected from —H and $—CH_3$;

$R^{5J}$ is selected from —H and $—CH_3$, wherein if $R^5$ is —H, $Z^3$ is

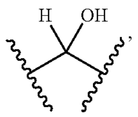, and one of $R^{3J}$ and $R^{4J}$ is —H, then the other of $R^{3J}$ and $R^{4J}$ cannot be $C_1$ alkyl;

$R^{5K}$ is selected from —H and $—CH_3$, wherein if $R^{5K}$ is —H, then $R^{4K}$ cannot be $C_2$ alkyl;

$R^6$ and $R^7$ are taken together as $—SCH_2CH_2—$ or $—CH_2CH_2S—$; and

X is independently selected from —F, —Cl, and —Br.

In further embodiments, the invention includes enantiomerically enriched mixtures of compounds of Formula XIV:

(XIV)

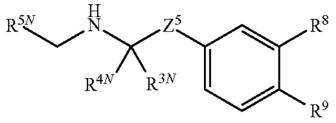

wherein:

$Z^5$ is selected from

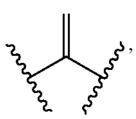, 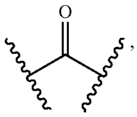, and 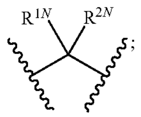;

$R^{1N}$ and $R^{2N}$ are independently selected from —H, —X, —OH, $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_1$-$C_4$ alkyl;

$R^{3N}$ and $R^{4N}$ are independently selected from —H, $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_1$-$C_4$ alkyl;

$R^{5N}$ is selected from —H and $—CH_3$;

$R^8$ and $R^9$ are taken together as $—SCH_2CH_2—$, $—CH_2CH_2S—$, $—SCH{=}CH—$, or $—CH{=}CHS—$; and X is independently selected from —F, —Cl, and —Br.

In certain aspects of these embodiments, one or more selected compounds of Formulas I-XVI or Formulas A-D can be improved or "tuned" by administering an effective amount to a host such as a human, in need thereof, in a composition of a pure enantiomer (or diastereomer, where relevant), or alternatively, an enantiomerically enriched composition that has an abundance of one enantiomer over the other. In this way, as described above, the enantiomeric forms act differently from each other on various 5-HT receptors, dopamine receptors, nicotinic acetylcholine receptors, and norepinephrine receptors, producing variable effects, and that those effects can be selected for based on desired outcome for the patient.

In certain embodiments, any of the selected compounds or mixtures of the present invention is administered to a patient in an effective amount in conjunction with psychotherapy, cognitive enhancement, or life coaching (pharmacotherapy), or as part of routine medical therapy.

The present invention also provides compounds that in certain embodiments can be used in methods for the modulation of CNS activity and/or a method for treatment of CNS disorders, including, but not limited to post-traumatic stress and adjustment disorders, comprising administering a compound of Formula A, Formula B, Formula C or Formula D or a pharmaceutically acceptable salt thereof:

Formula A

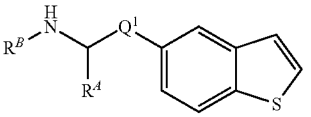

Formula B

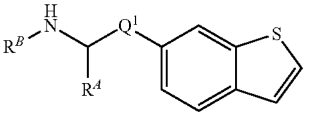

Formula C

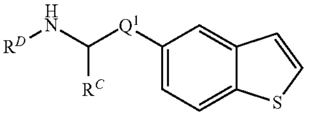

Formula D

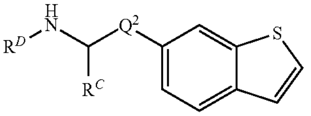

wherein:

$R^A$ and $R^B$ are independently selected from $—CH_3$ and $—CH_2CH_3$;

$R^C$ is selected from $—CH_3$, $—CH_2Y$, $—CHY_2$, $—CY_3$, $—CH_2CH_2Y$, $—CH_2CHY_2$, $—CH_2CY_3$, $—CH_2CH_3$, $—CH_2OH$, or $—CH_2CH_2OH$;

$R^D$ is selected from $—CH_3$ and $—CH_2CH_3$;

$Q^1$ is selected from

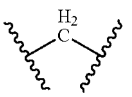 and 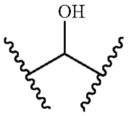;

$Q^2$ is selected from:

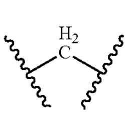 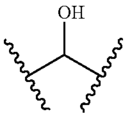 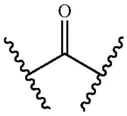

-continued

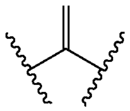 and 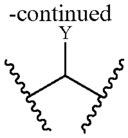 ;

and

Y is halogen.

The compounds may be provided in a composition that is enantiomerically enriched, such as a mixture of enantiomers in which one enantiomer is present in excess, in particular to the extent of 60% or more, 70% or more, 75% or more, 80% or more, 90% or more, 95% or more, or 97% or more, or alternatively, as a pure isomer.

Exemplary, but non-exhaustive, embodiments of Formulas C and D are given in Table 1 below.

In other embodiments, the present invention includes a method for treating any of the disorders described herein, such as a central nervous system disorder, in a host in need thereof comprising administering an effective amount of a compound of Formula XV or its salt or salt mixture, optionally in a pharmaceutically acceptable composition, selected from:

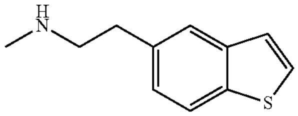

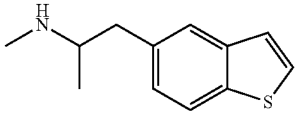

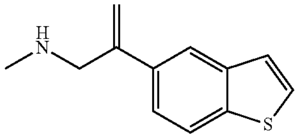

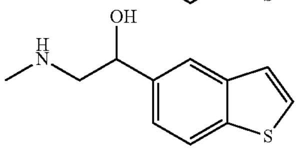

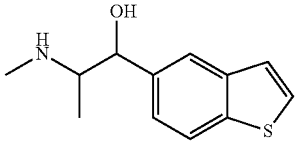

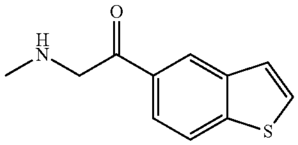

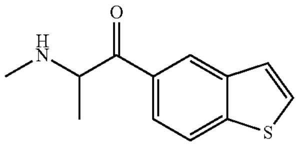

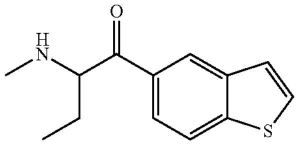

-continued

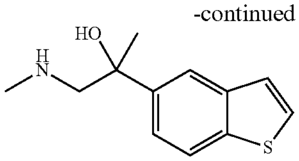

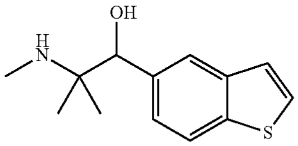

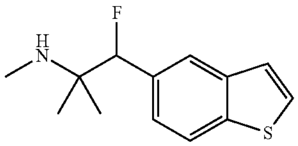

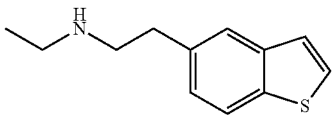

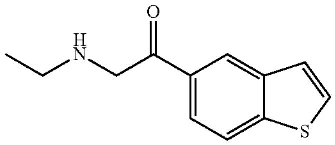

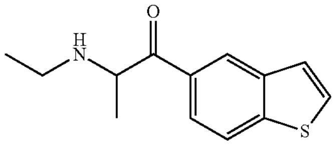

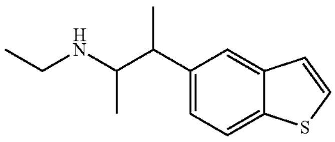

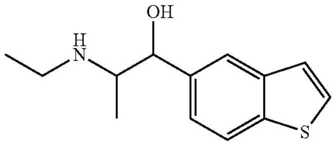 and

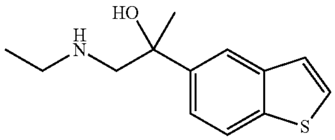.

In other embodiments, the present invention includes a method for treating any of the disorders described herein, such as a central nervous system disorder, in a host in need thereof comprising administering an effective amount of a compound of Formula XVI or its pharmaceutically acceptable salt or salt mixture, optionally in a pharmaceutically acceptable composition, which is:

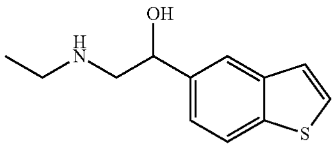

TABLE 1

| Exemplary Embodiments of Formulas C and D | | | | |
|---|---|---|---|---|
| Entry | Formula | $R^D$ | $R^C$ | $Q^2$ |
| 1 | C or D | CH3 | CH3 | 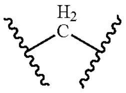 |
| 2 | C or D | CH3 | CH2CH3 | 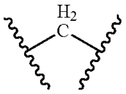 |
| 3 | C or D | CH2CH3 | CH3 | 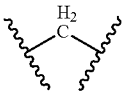 |
| 4 | C or D | CH2CH3 | CH2CH3 | 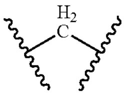 [SMILES: *C*] |
| 5 | C or D | CH3 | CH3 | 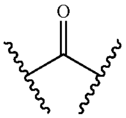 [SMILES: *C(*)=O] |
| 6 | C or D | CH3 | CH2CH3 | 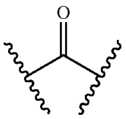 [SMILES: *C(*)=O] |
| 7 | C or D | CH2CH3 | CH3 | 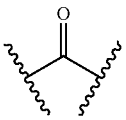 [SMILES: *C(*)=O] |
| 8 | C or D | CH2CH3 | CH2CH3 | 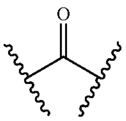 [SMILES: *C(*)=O] |
| 9 | C or D | CH3 | CH3 | 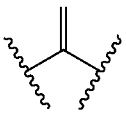 [SMILES: *C(*)=C] |
| 10 | C or D | CH3 | CH2CH3 | 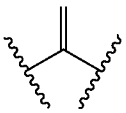 [SMILES: *C(*)=C] |
| 11 | C or D | CH2CH3 | CH3 | 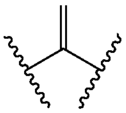 [SMILES: *C(*)=C] |
| 12 | C or D | CH2CH3 | CH2CH3 | 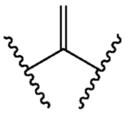 [SMILES: *C(*)=C] |

TABLE 1-continued

| Exemplary Embodiments of Formulas C and D | | | | |
|---|---|---|---|---|
| Entry | Formula | $R^D$ | $R^C$ | $Q^2$ |
| 13 | C or D | CH3 | CH2Br | 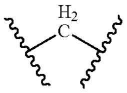 |
| 14 | C or D | CH3 | CH2CH2Br | 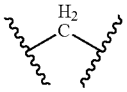 |
| 15 | C or D | CH2CH3 | CH2Br | 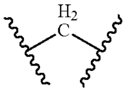 |
| 16 | C or D | CH2CH3 | CH2CH2Br | 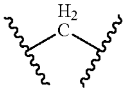 |
| 17 | C or D | CH3 | CH2Br | 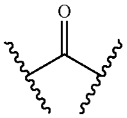 [SMILES: *C(*)=O] |
| 18 | C or D | CH3 | CH2CH2Br | 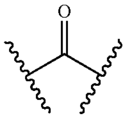 [SMILES: *C(*)=O] |
| 19 | C or D | CH2CH3 | CH2Br | 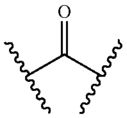 [SMILES: *C(*)=O] |
| 20 | C or D | CH2CH3 | CH2CH2Br | 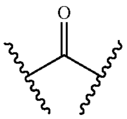 [SMILES: *C(*)=O] |
| 21 | C or D | CH3 | CH2Br | 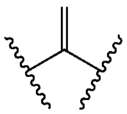 [SMILES: *C(*)=C] |
| 22 | C or D | CH3 | CH2CH2Br | 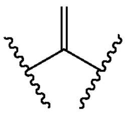 [SMILES: *C(*)=C] |
| 23 | C or D | CH2CH3 | CH2Br | 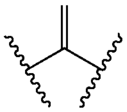 [SMILES: *C(*)=C] |
| 24 | C or D | CH2CH3 | CH2CH2Br | 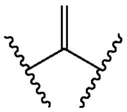 [SMILES: *C(*)=C] |

TABLE 1-continued

| Exemplary Embodiments of Formulas C and D | | | | |
|---|---|---|---|---|
| Entry | Formula | $R^D$ | $R^C$ | $Q^2$ |
| 25 | C or D | CH3 | CH2F | 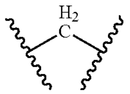 |
| 26 | C or D | CH3 | CH2CH2F | 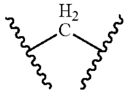 |
| 27 | C or D | CH2CH3 | CH2F | 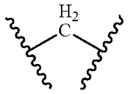 [SMILES: *C*] |
| 28 | C or D | CH2CH3 | CH2CH2F | 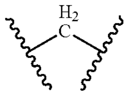 |
| 29 | C or D | CH3 | CH2F | 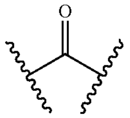 [SMILES: *C(*)=O] |
| 30 | C or D | CH3 | CH2CH2F | 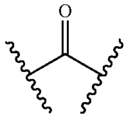 [SMILES: *C(*)=O] |
| 31 | C or D | CH2CH3 | CH2F | 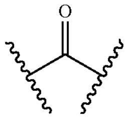 [SMILES: *C(*)=O] |
| 32 | C or D | CH2CH3 | CH2CH2F | 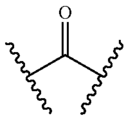 [SMILES: *C(*)=O] |
| 33 | C or D | CH3 | CH2F | 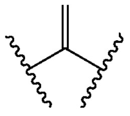 [SMILES: *C(*)=C] |
| 34 | C or D | CH3 | CH2CH2F | 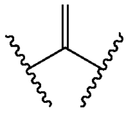 [SMILES: *C(*)=C] |
| 35 | C or D | CH2CH3 | CH2F | 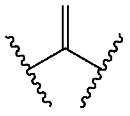 [SMILES: *C(*)=C] |
| 36 | C or D | CH2CH3 | CH2CH2F | 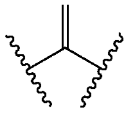 [SMILES: *C(*)=C] |

Where diastereomers exist, the compounds can be used in any diastereomeric form or mixture of forms that provides the appropriate therapeutic effect for the patient, as taught herein. Therefore, in one embodiment, the compounds of the present invention can be administered in a racemic mixture, as the R-enantiomer, as the S-enantiomer, or as an enantiomerically enriched mixture, or a diastereomeric form.

The following compound illustrations indicate where primary stereocenters exist when the designated R group is not hydrogen. In certain embodiments, the enantiomers of the present invention include compounds of Formula I:

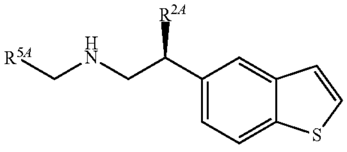

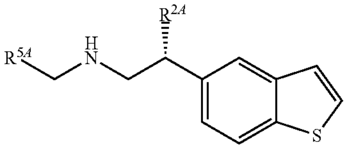

for example, wherein $R^{1A}$ is hydrogen (not shown) and $R^{2A}$ is not hydrogen.

In certain embodiments, the enantiomers of the present invention include compounds of Formula II:

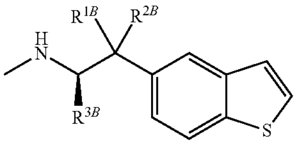

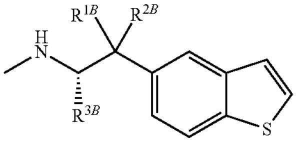

wherein $R^{3B}$ is not hydrogen, and the other variables are as defined above.

In certain embodiments, the enantiomers of the present invention include compounds of Formula III:

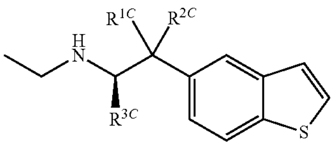

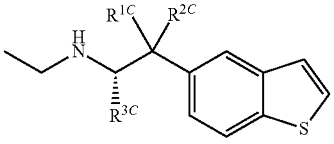

wherein $R^{3C}$ is not hydrogen, and the other variables are as described above.

In certain embodiments, the enantiomers of the present invention include compounds of Formula IV:

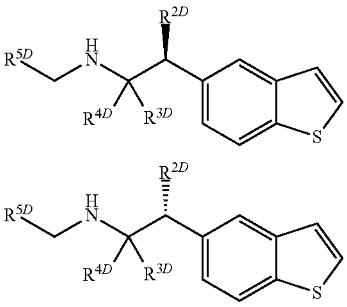

for example, wherein $R^{1D}$ is hydrogen (not shown) and $R^{2D}$ is not hydrogen, or

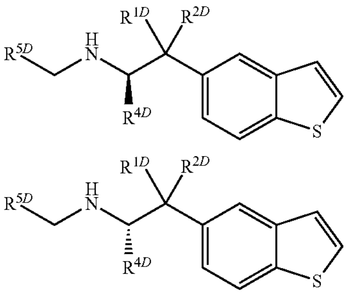

wherein $R^{3D}$ is hydrogen (not shown) and $R^{4D}$ is not hydrogen.

In certain embodiments, the enantiomers of the present invention include compounds of Formula V:

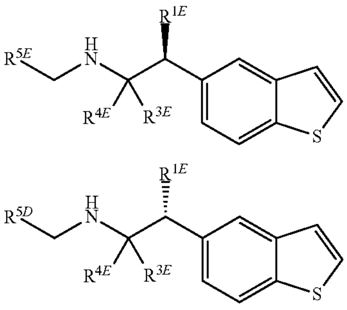

for example, wherein $R^{1E}$ is not hydrogen.

In certain embodiments, the enantiomers of the present invention include compounds of Formula VI:

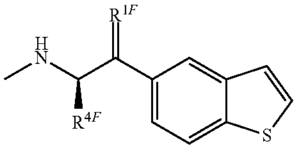

-continued

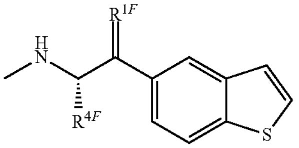

for example, wherein $R^{3F}$ is hydrogen (not shown) and $R^{4F}$ is not hydrogen.

In certain embodiments, the enantiomers of the present invention include compounds of Formula VII:

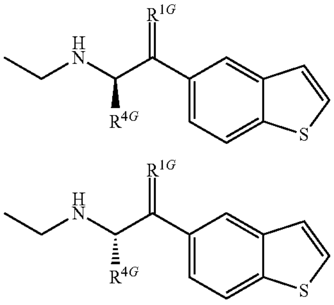

for example, wherein $R^{3G}$ is hydrogen (not shown) and $R^{4G}$ is not hydrogen.

In certain embodiments, the enantiomers of the present invention include compounds of Formula VIII:

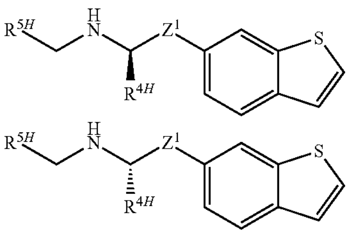

for example, wherein $R^{3H}$ is hydrogen (not shown) and $R^{4H}$ is not hydrogen.

In certain embodiments, the enantiomers of the present invention include compounds of Formula IX:

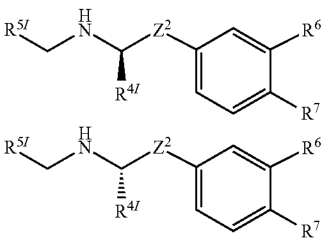

for example, wherein $R^{3I}$ is hydrogen (not shown) and $R^{4I}$ is not hydrogen.

In certain embodiments, the enantiomers of the present invention include compounds of Formula X:

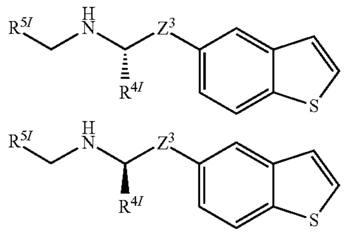

for example, wherein $R^{3J}$ is hydrogen (not shown) and $R^{4J}$ is not hydrogen.

In certain embodiments, the enantiomers of the present invention include compounds of Formula XI:

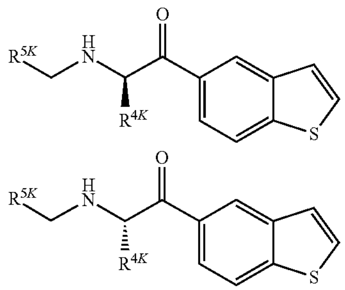

for example, wherein $R^{4K}$ is not hydrogen.

In certain embodiments, the enantiomers of the present invention include compounds of Formula XII:

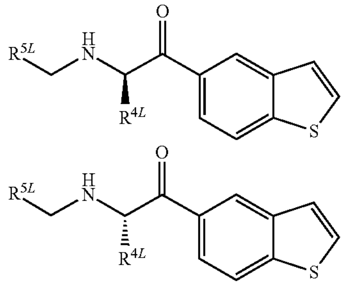

for example, wherein $R^{3L}$ is hydrogen (not shown) and $R^{4L}$ is not hydrogen.

In certain embodiments, the enantiomers of the present invention include compounds of Formula XIII:

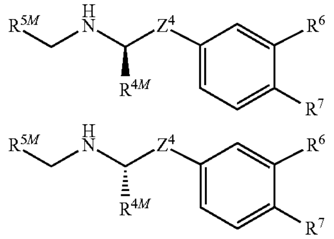

for example, wherein $R^{3M}$ is hydrogen (not shown) and $R^{4M}$ is not hydrogen.

In certain embodiments, the enantiomers of the present invention include compounds of Formula XIV:

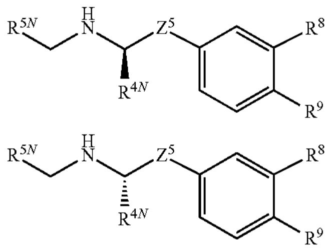

for example, wherein $R^{3N}$ is hydrogen (not shown) and $R^{4N}$ is not hydrogen.

In certain embodiments, the present invention is an enantiomerically enriched mixture of a racemic compound selected from:

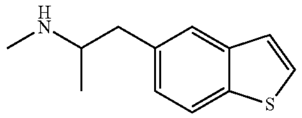

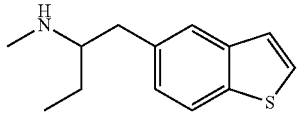

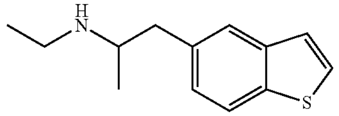

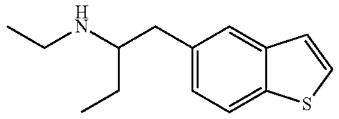

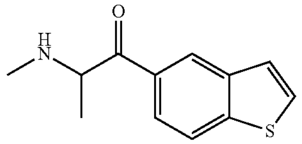

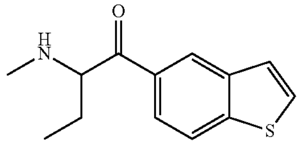

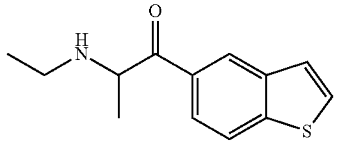

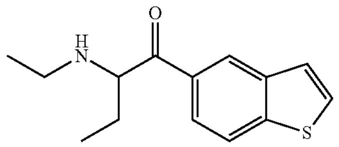

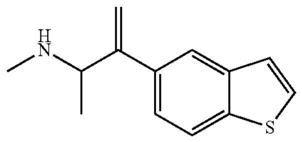

-continued
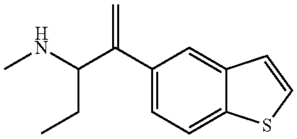
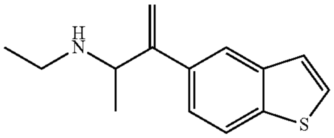
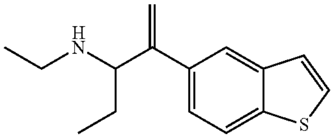
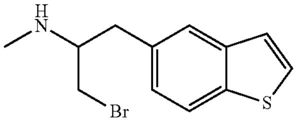
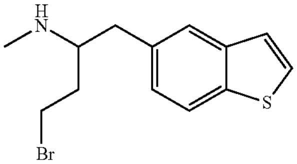
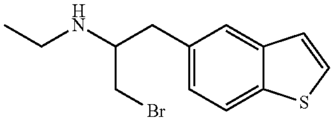
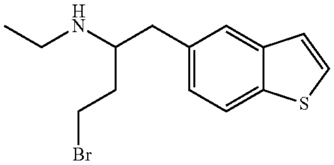
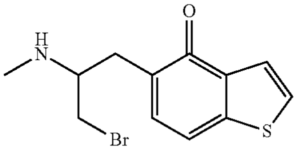
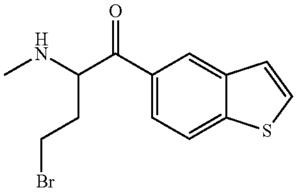
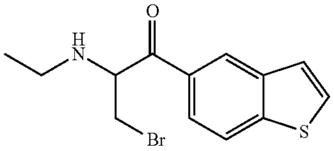
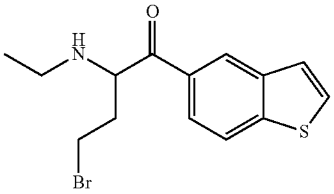
-continued
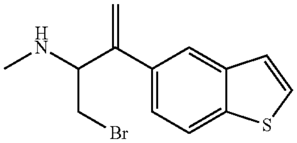
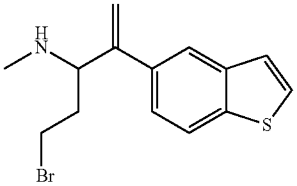
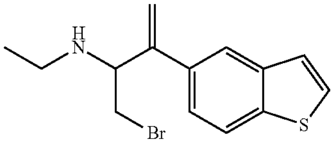
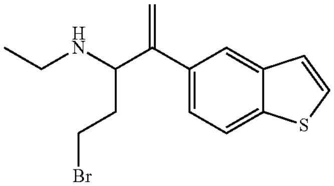
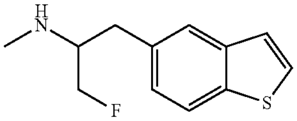
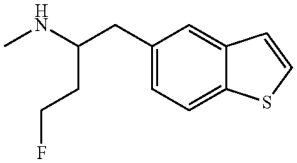
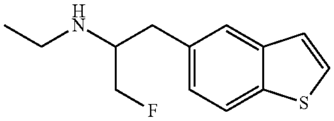
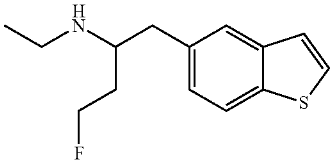
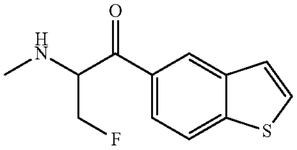
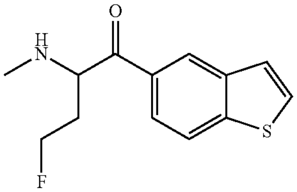
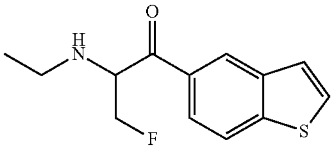

-continued
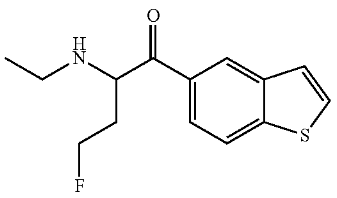
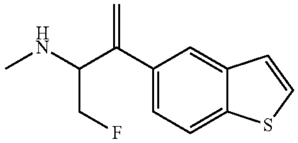
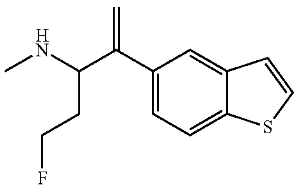
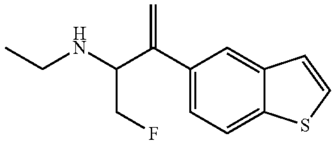
and
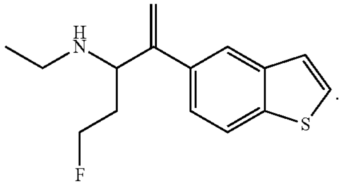
.
In certain embodiments, the present invention is an enantiomerically enriched mixture of a racemic compound selected from:
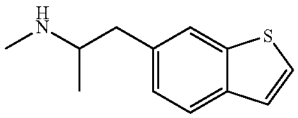
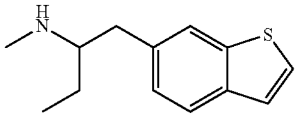
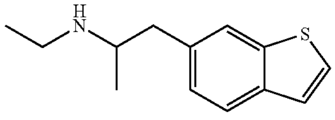
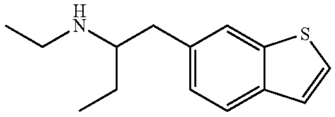
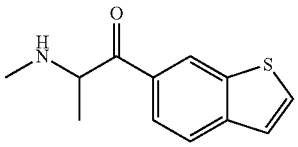
-continued
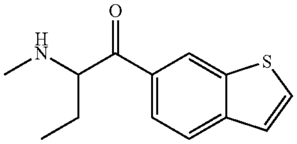
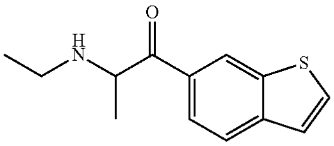
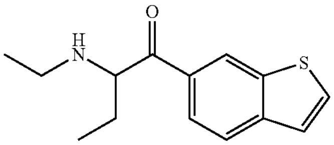
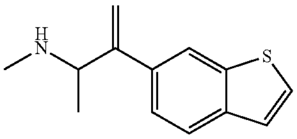
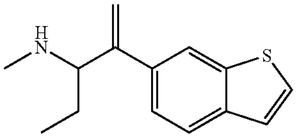
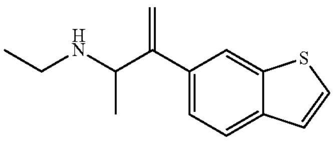
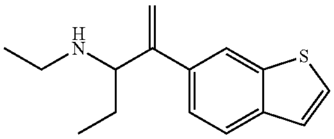
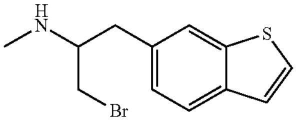
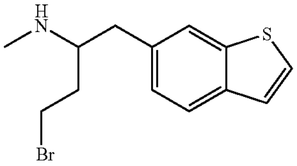
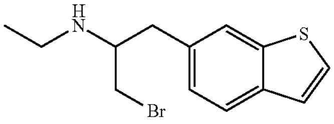
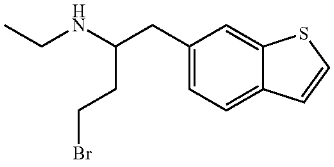
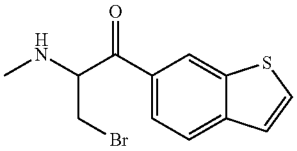

-continued
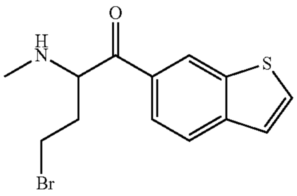
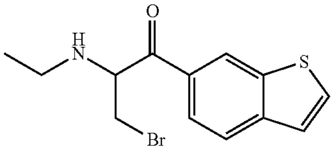
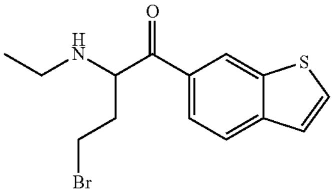
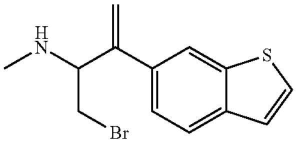
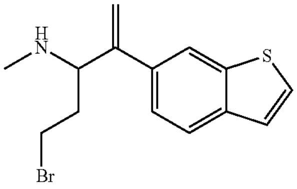
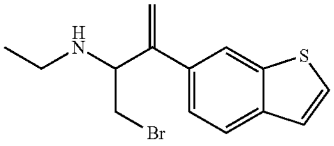
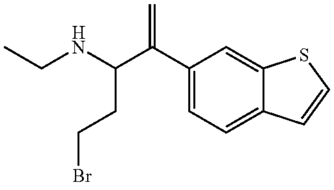
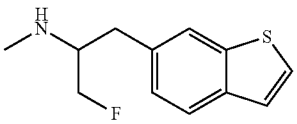
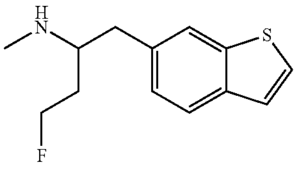
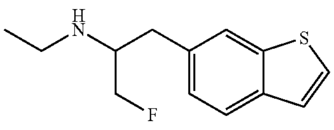
-continued
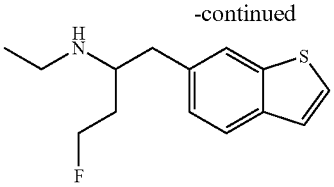
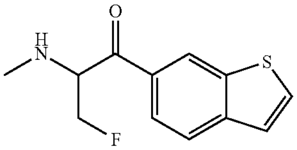
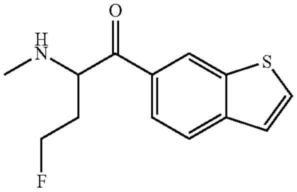
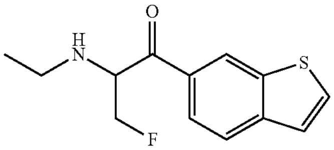
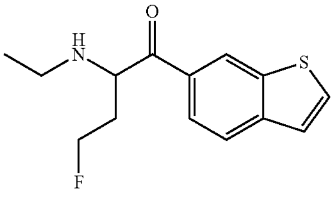
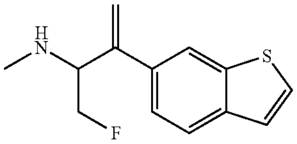
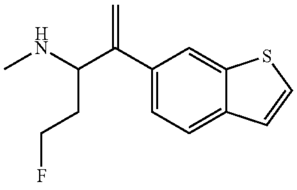
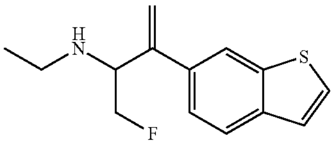
and
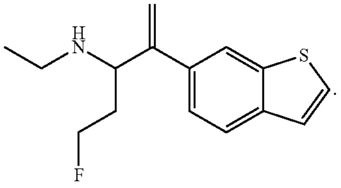
In certain embodiments, the present invention is an enantiomerically enriched mixture or pure enantiomer of a compound selected from:

-continued
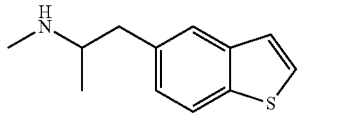
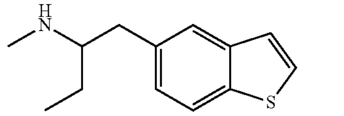
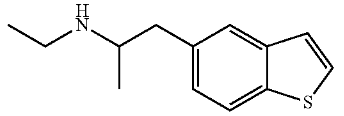
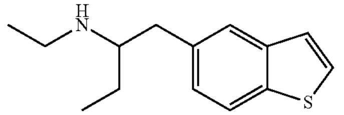
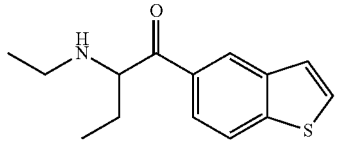
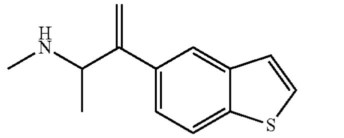
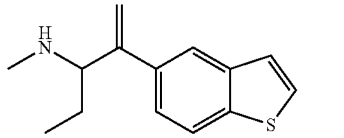
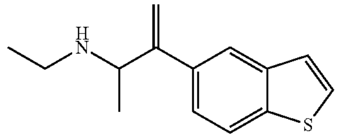
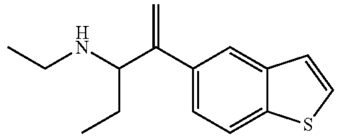
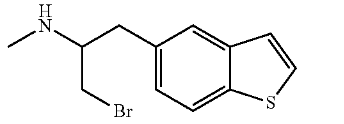
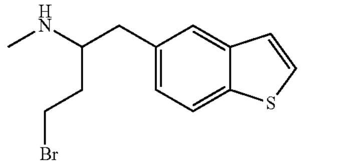
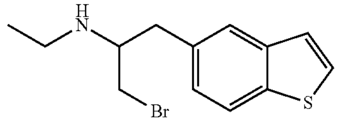
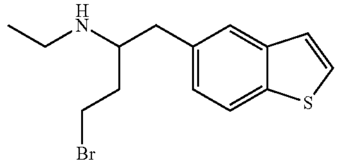
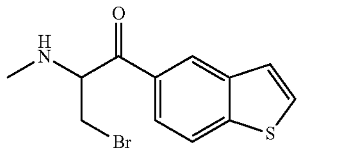
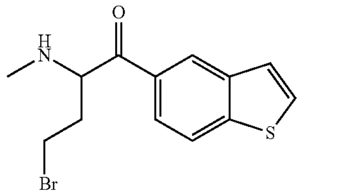
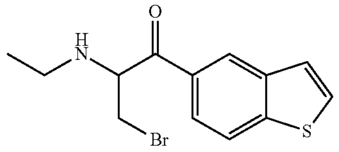
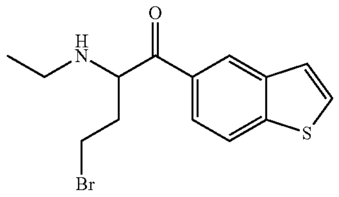
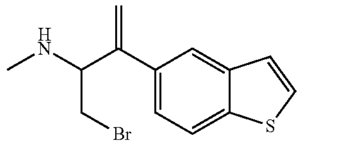
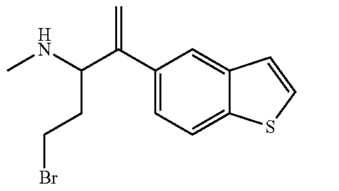
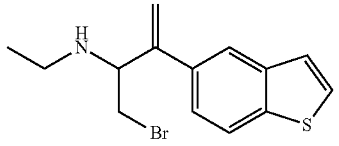
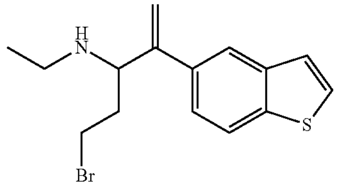
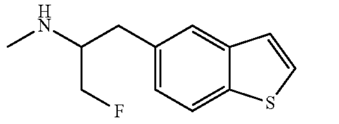
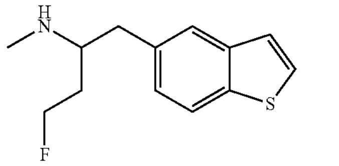

-continued
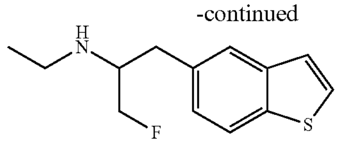
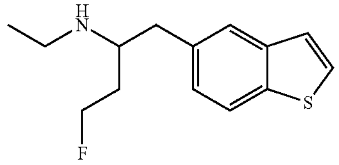
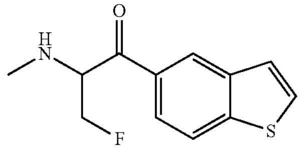
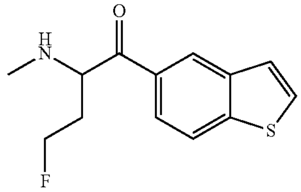
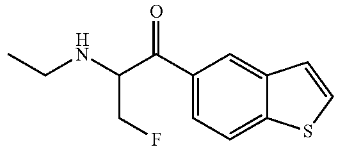
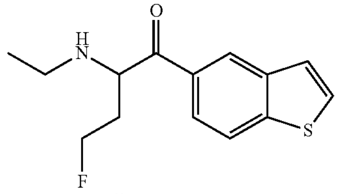
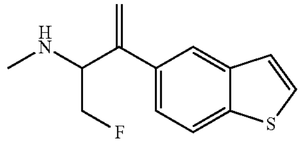
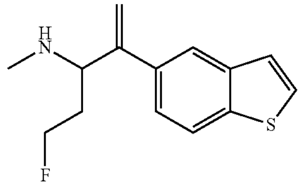
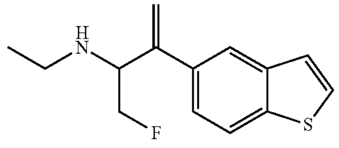
and
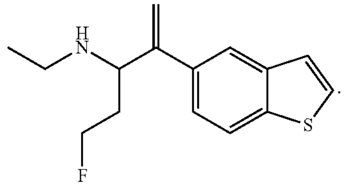
.
In certain embodiments, the present invention is an enantiomerically enriched mixture or pure enantiomer of a compound selected from:
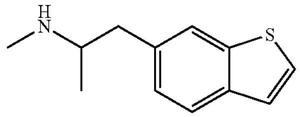
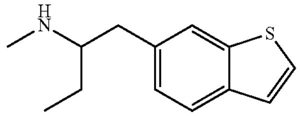
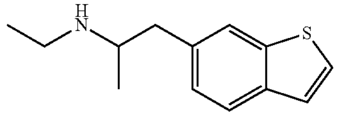
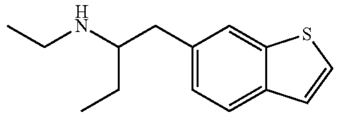
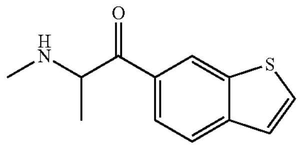
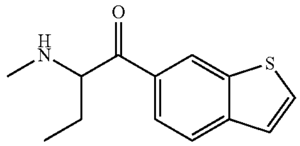
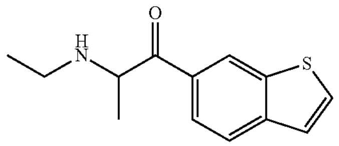
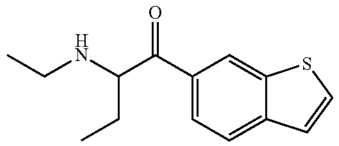
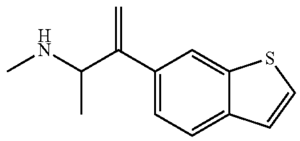
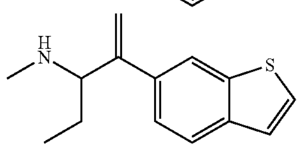
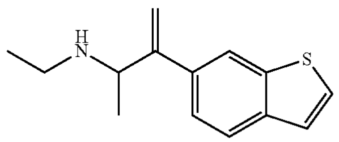
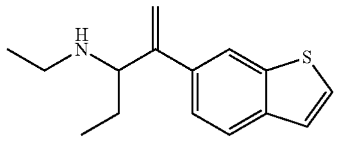
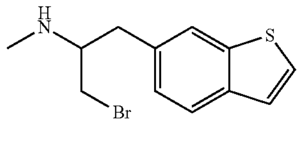

-continued
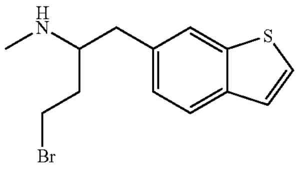
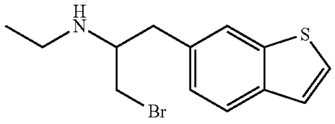
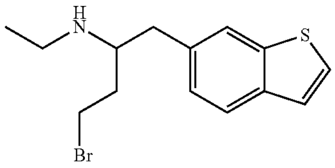
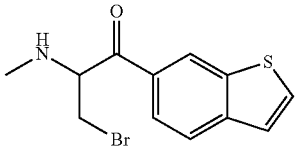
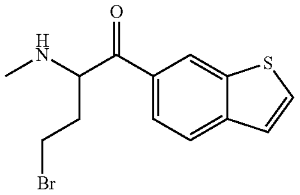
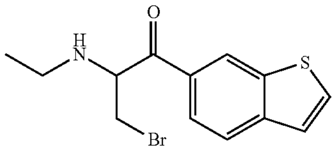
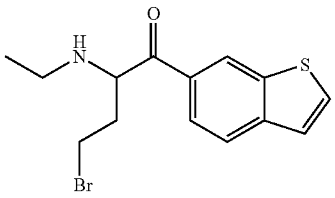
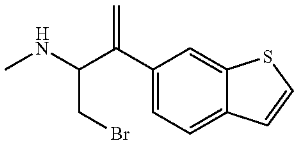
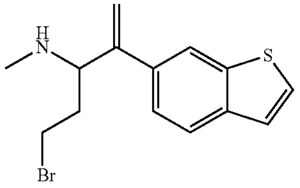
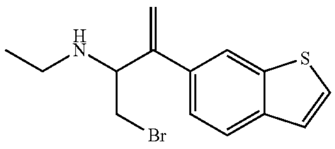
-continued
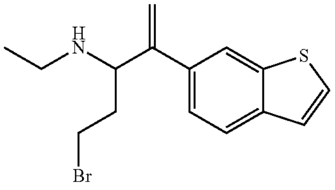
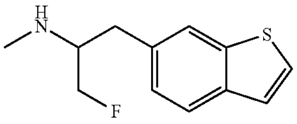
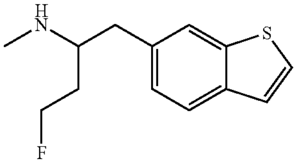
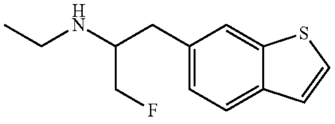
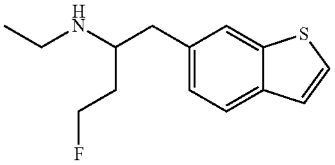
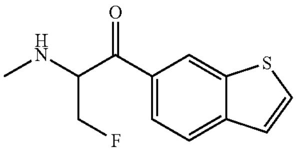
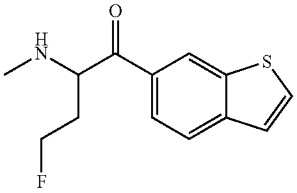
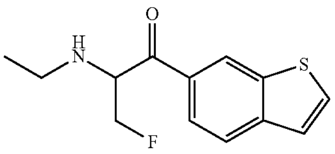
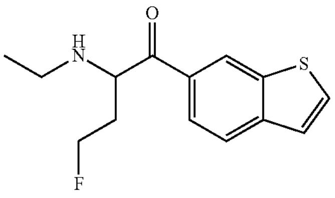
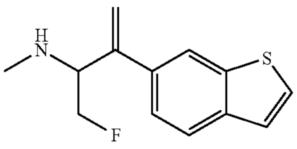

-continued
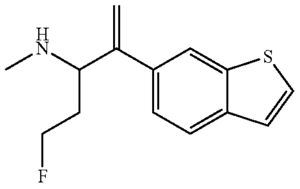
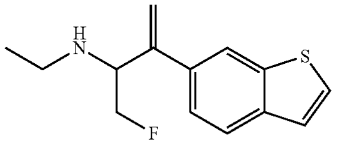
and
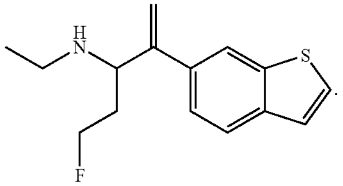
In certain embodiments, the present invention is a compound selected from:
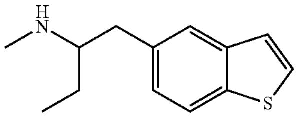
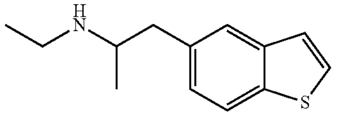
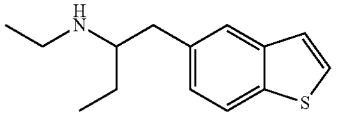
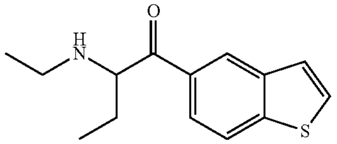
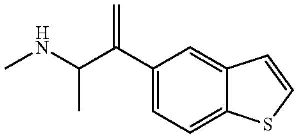
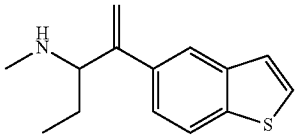
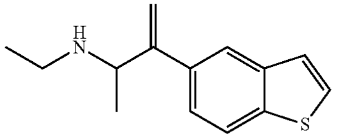
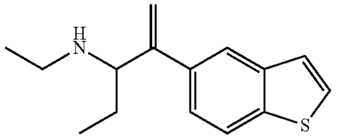
-continued
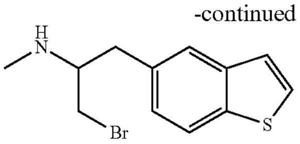
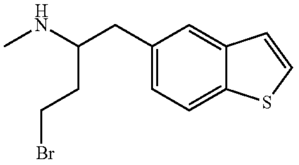
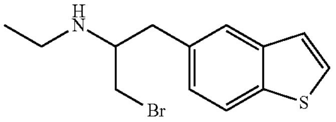
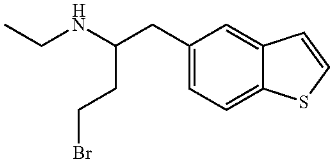
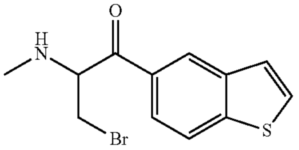
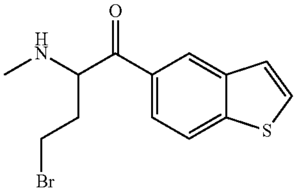
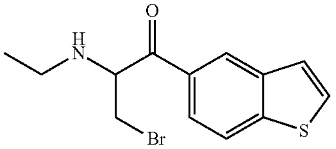
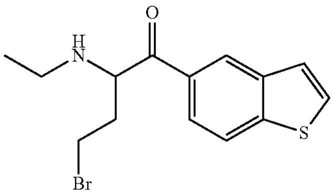
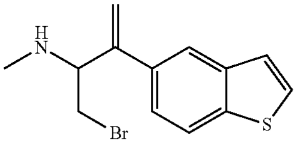
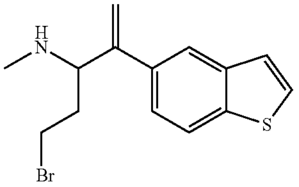
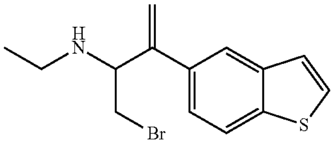

-continued
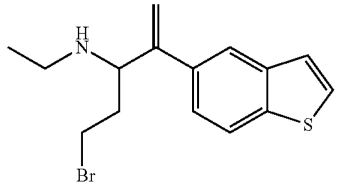
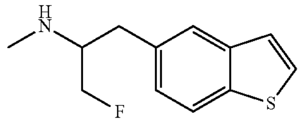
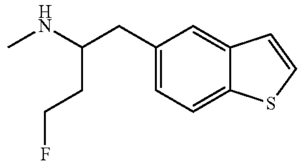
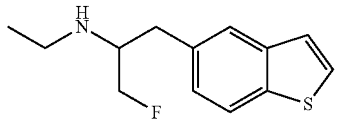
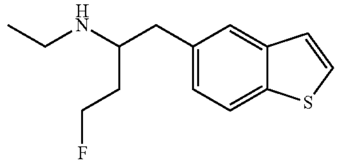
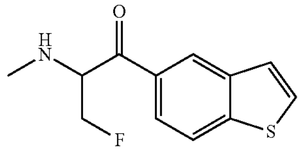
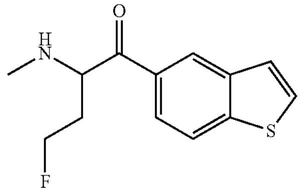
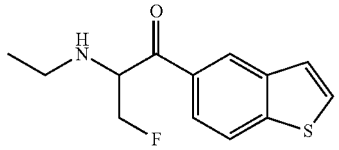
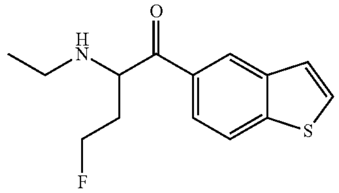
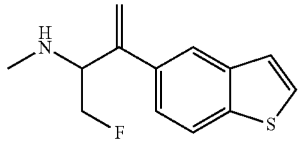
-continued
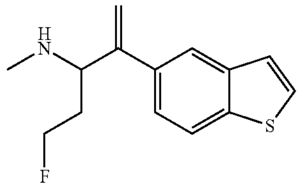
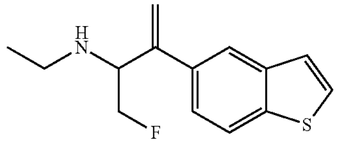
and
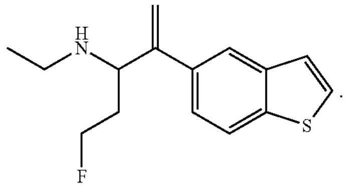
In certain embodiments, the present invention is a compound selected from:
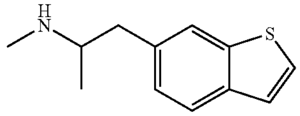
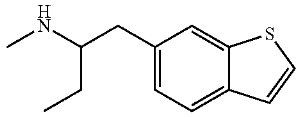
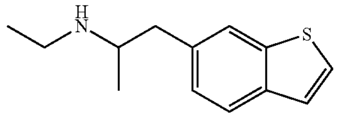
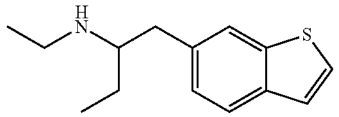
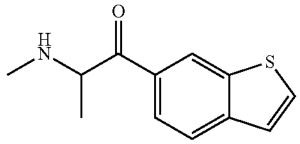
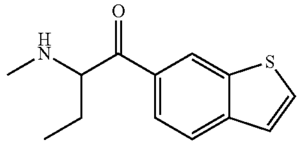
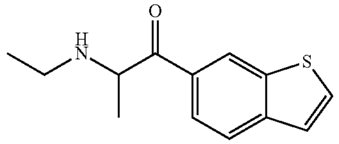
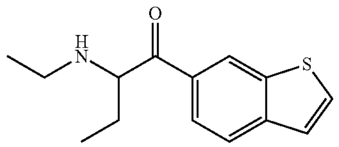

-continued
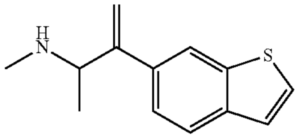
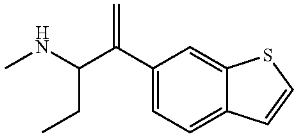
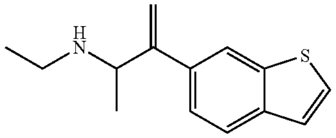
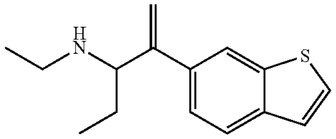
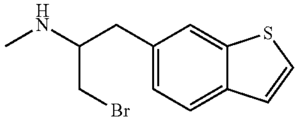
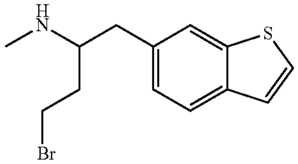
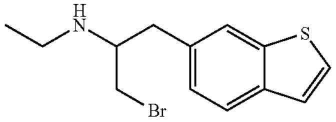
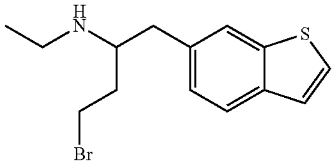
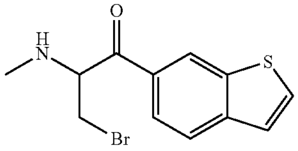
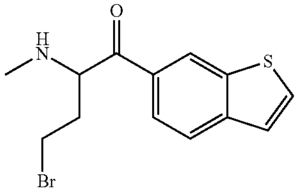
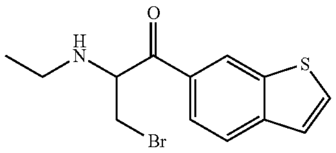
-continued
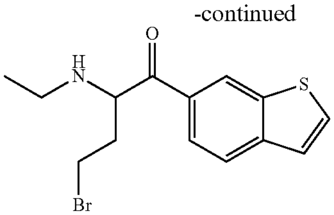
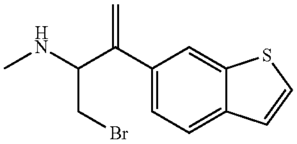
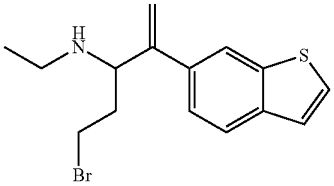
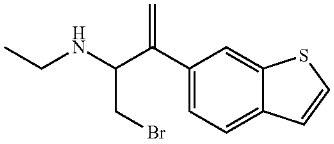
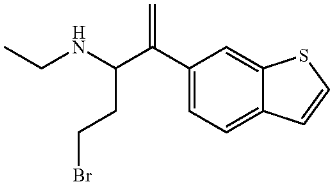
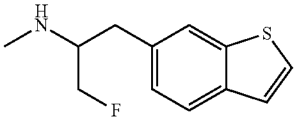
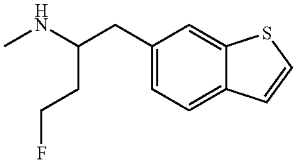
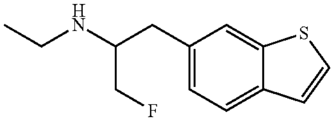
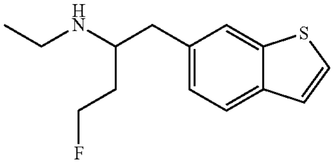
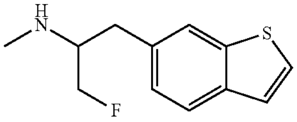
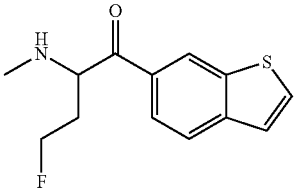

-continued
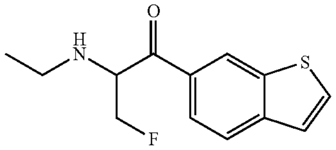
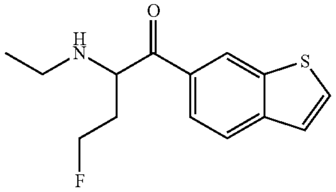
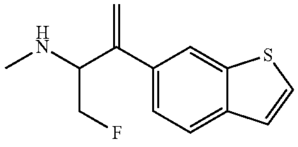
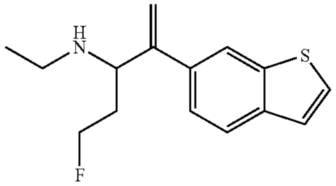
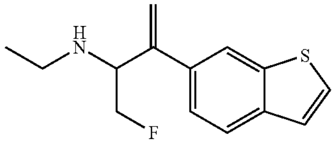
and
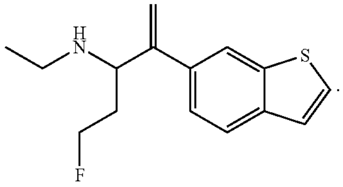
In certain embodiments, the compound of the present invention is selected from:
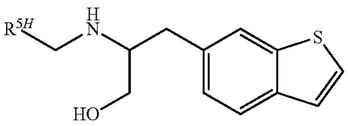
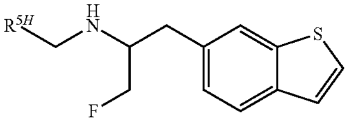
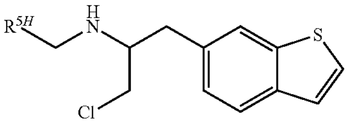
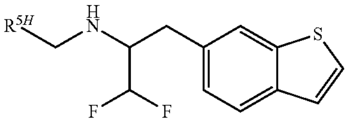
-continued
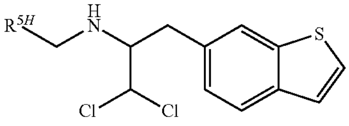
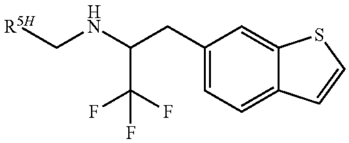
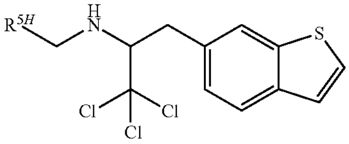
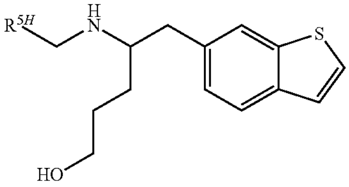
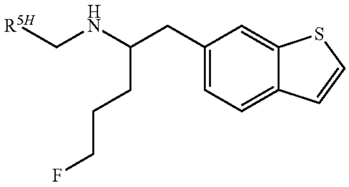
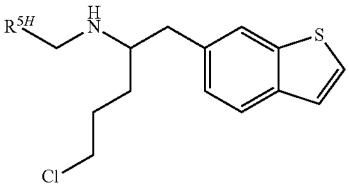
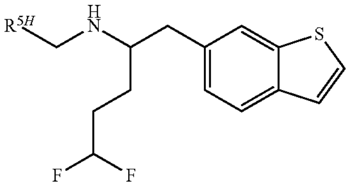
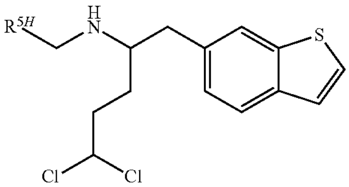
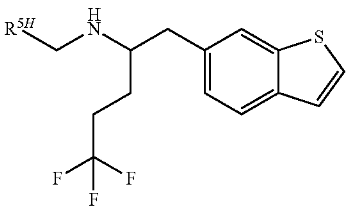

-continued
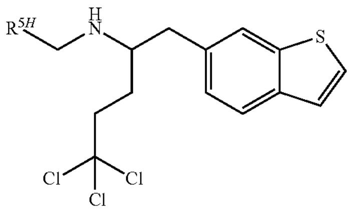
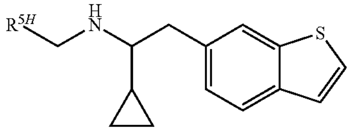
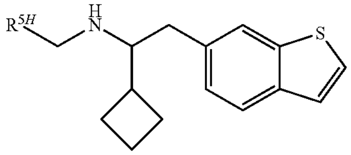
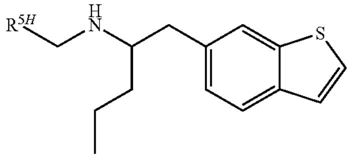
and
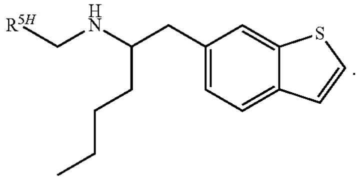
In certain embodiments, the compound of the present invention is selected from:
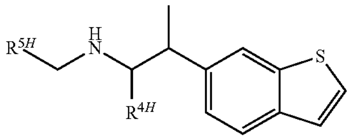
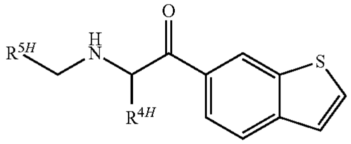
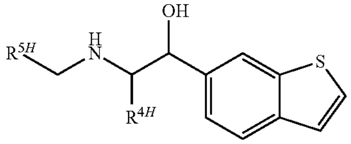
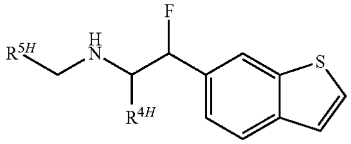
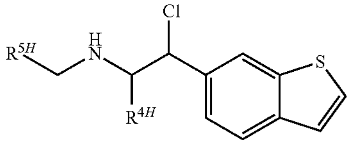
-continued
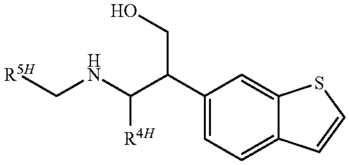
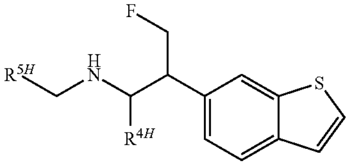
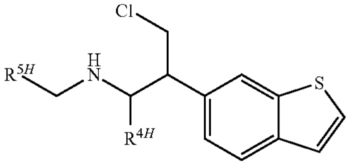
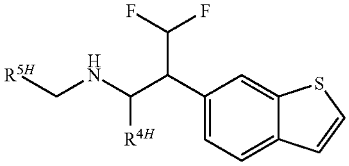
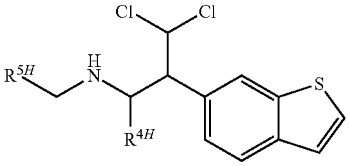
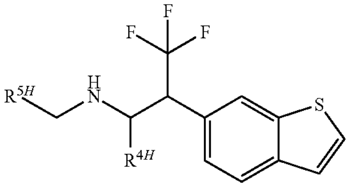
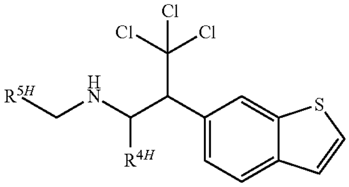
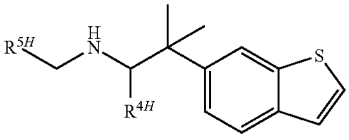
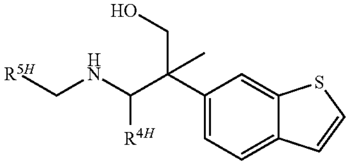
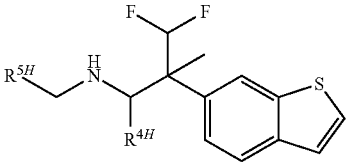

-continued
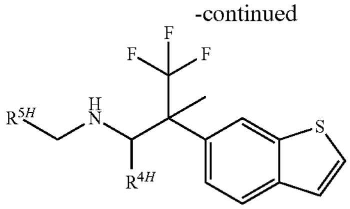
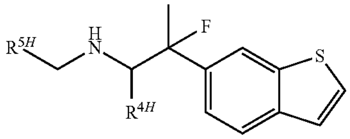
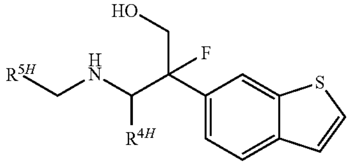
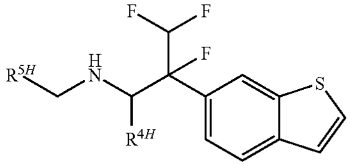
and
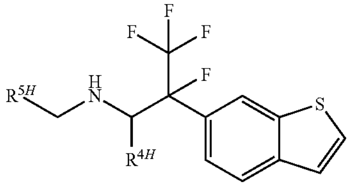
.
In certain embodiments, the compound of the present invention is selected from:
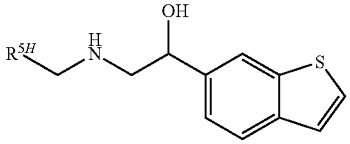
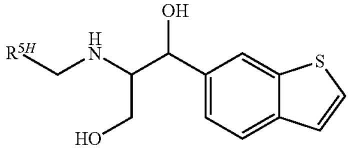
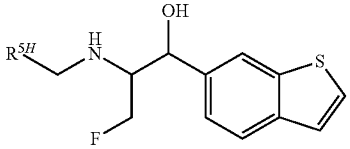
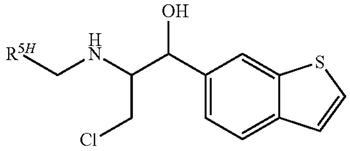
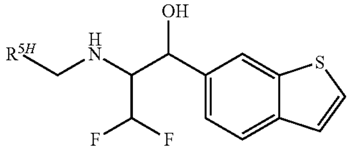
-continued
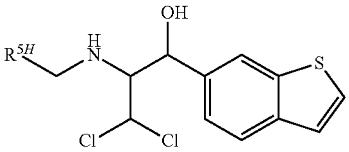
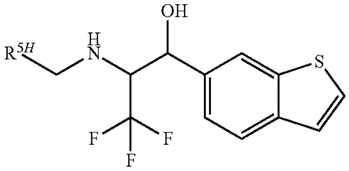
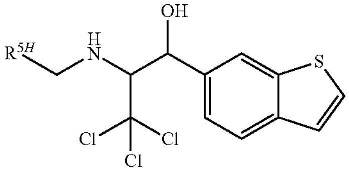
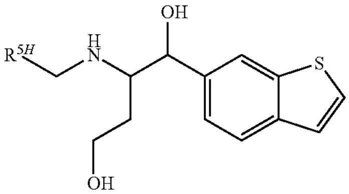
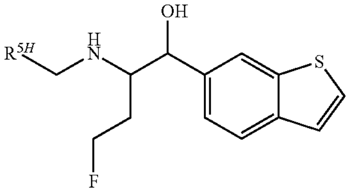
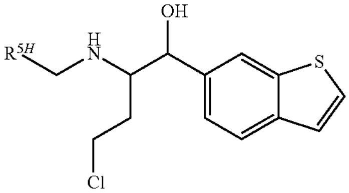
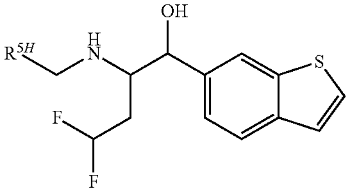
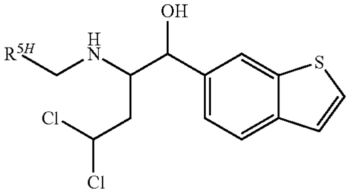
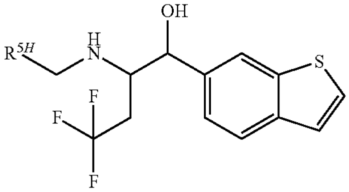

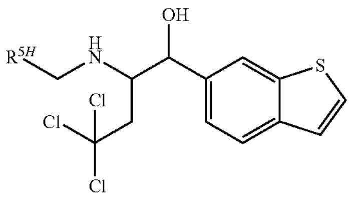
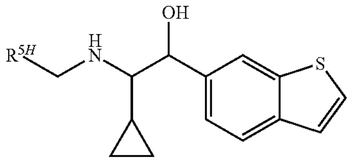
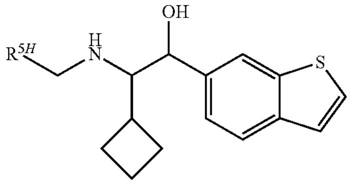
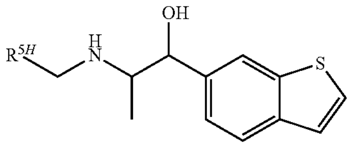
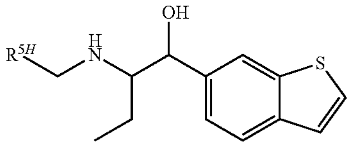
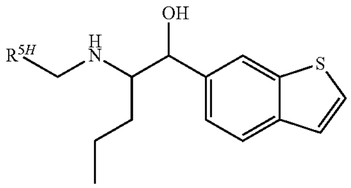
and
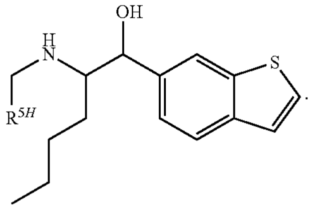
.
In certain embodiments, the compound of the present invention is selected from:
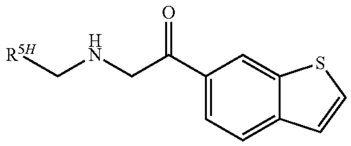
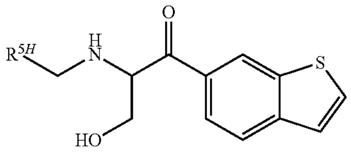
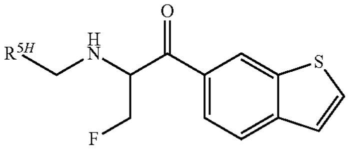
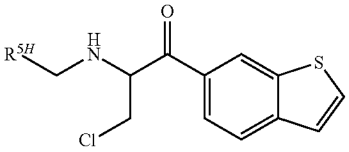
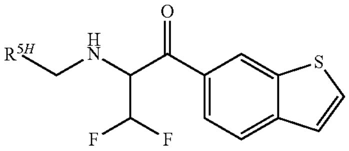
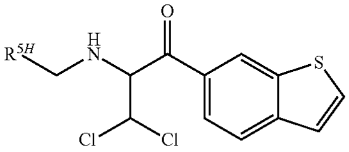
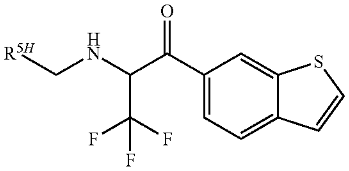
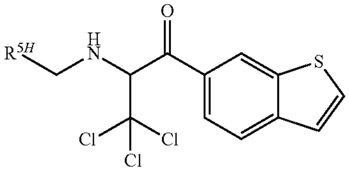
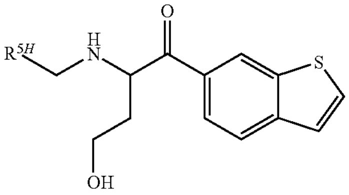
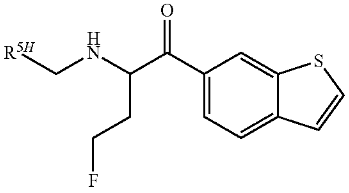
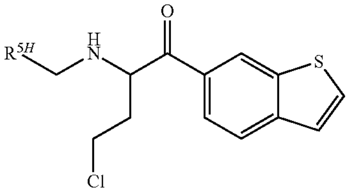
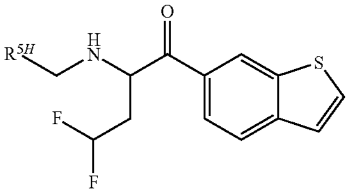

-continued
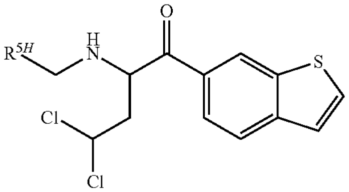
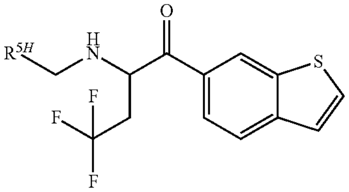
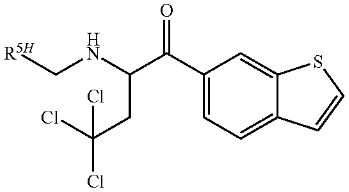
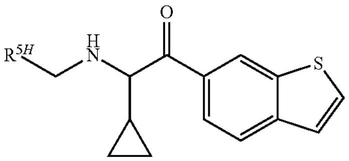
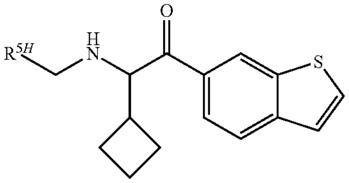
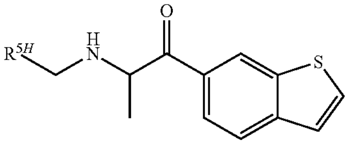
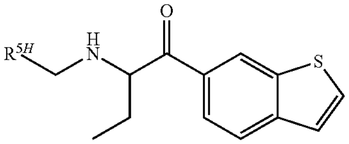
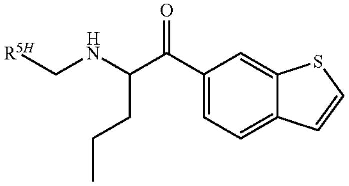
and
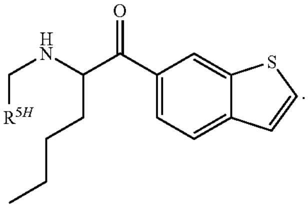
In certain embodiments, the compound of the present invention is selected from:
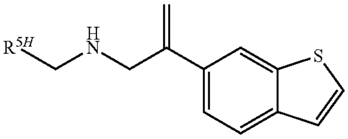
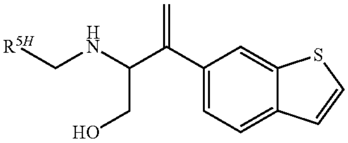
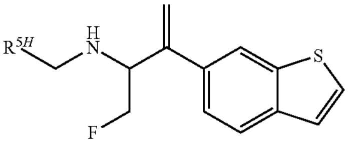
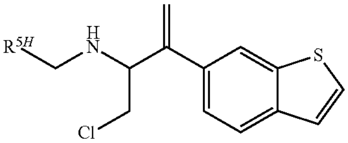
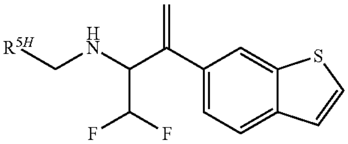
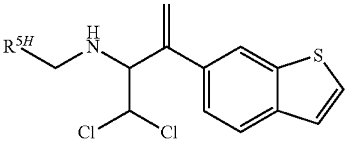
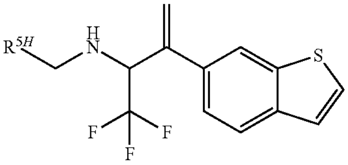
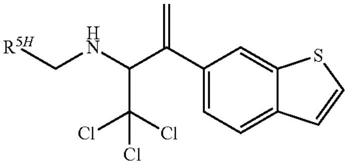
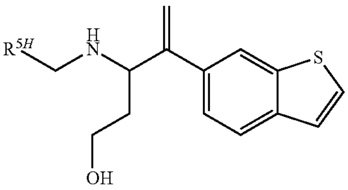
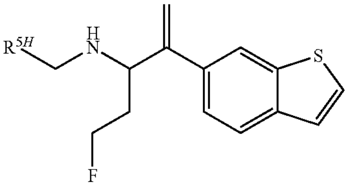

-continued
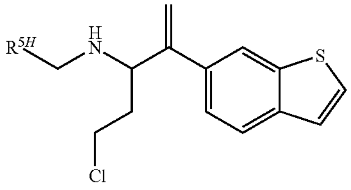
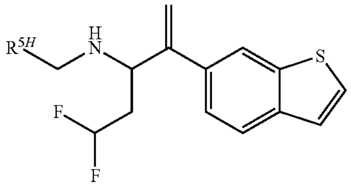
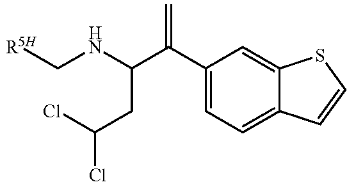
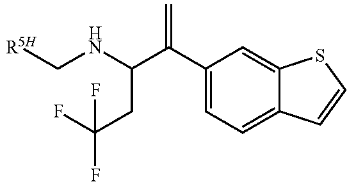
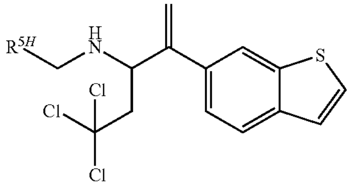
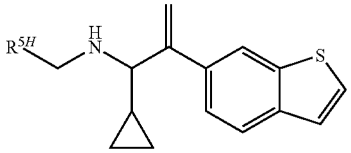
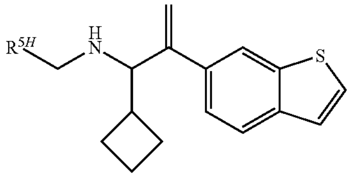
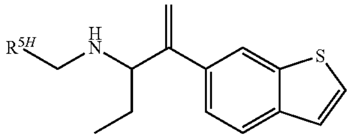
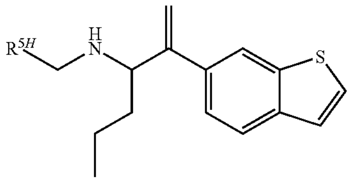
and
-continued
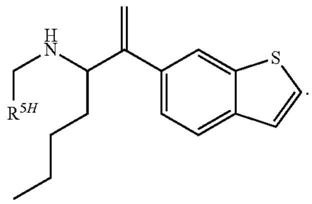
.
In certain embodiments, the compound of the present invention is selected from:
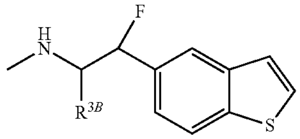
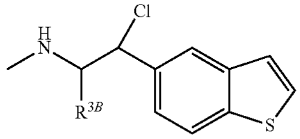
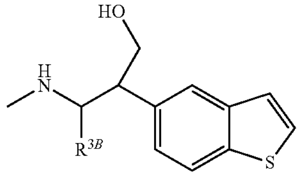
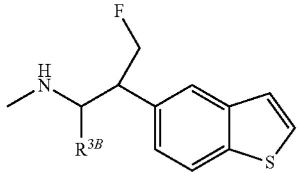
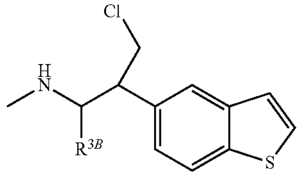
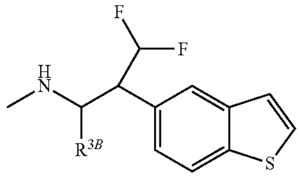
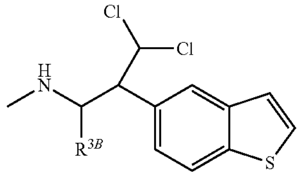
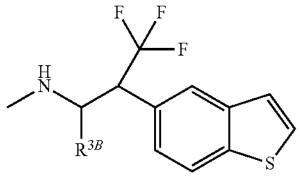

-continued
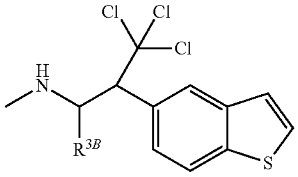
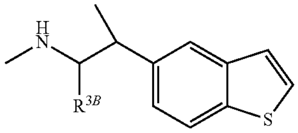
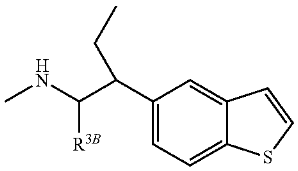
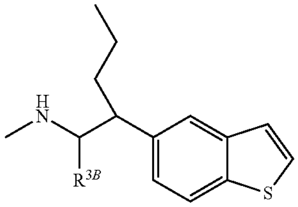
and
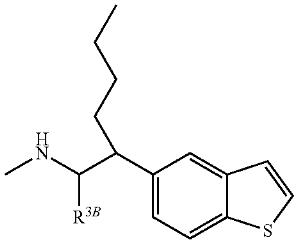
.
In certain embodiments, the compound of the present invention is selected from:
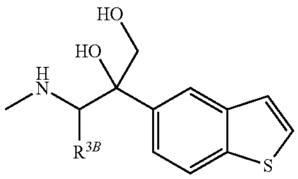
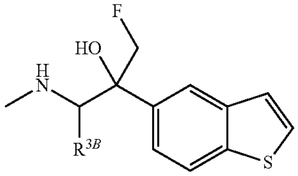
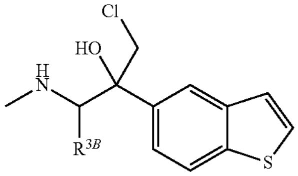
-continued
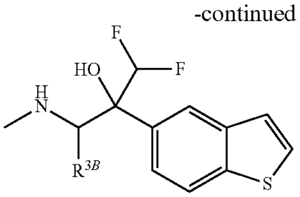
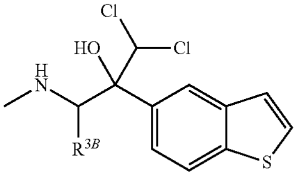
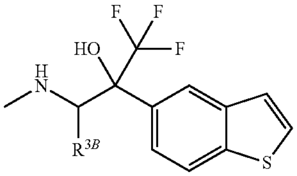
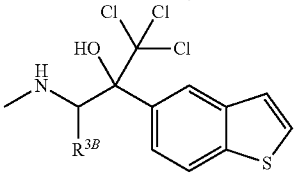
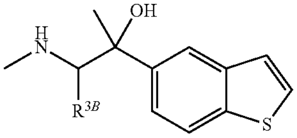
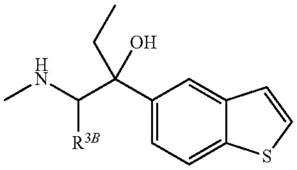
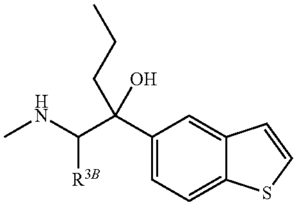
and
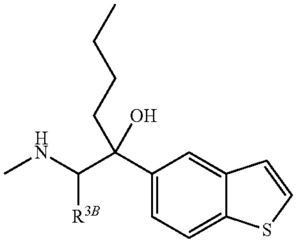
.
In certain embodiments, the compound of the present invention is selected from:
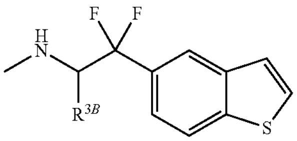

-continued
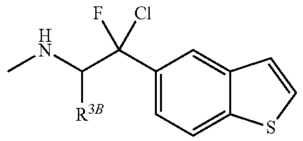
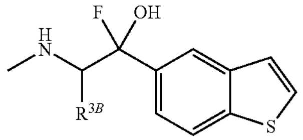
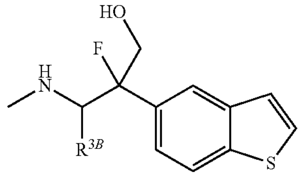
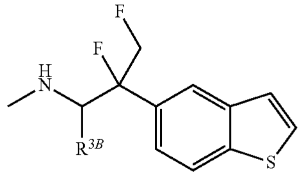
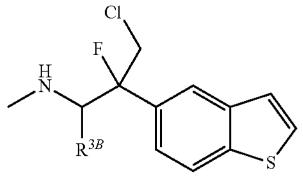
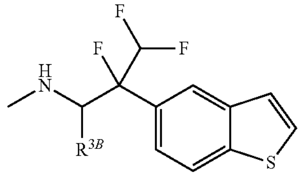
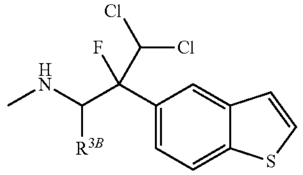
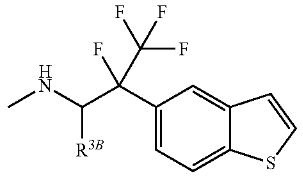
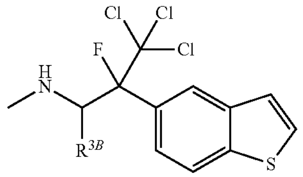
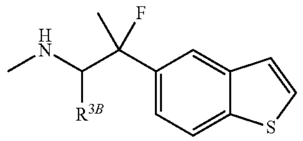
-continued
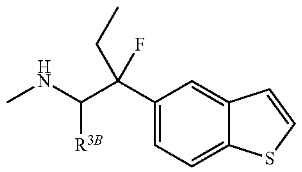
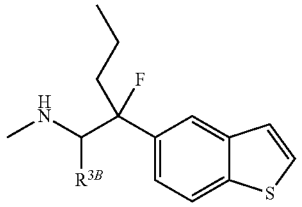
and
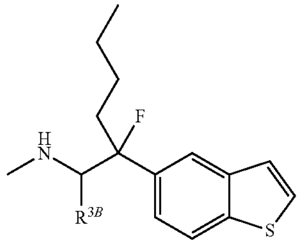
.
In certain embodiments, the compound of the present invention is selected from:
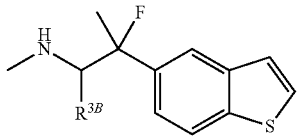
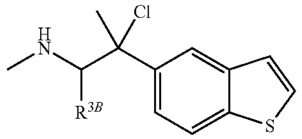
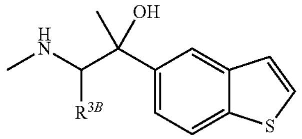
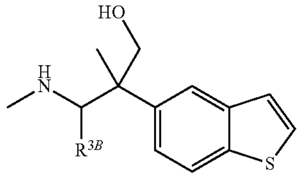
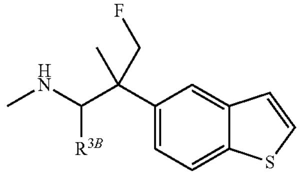
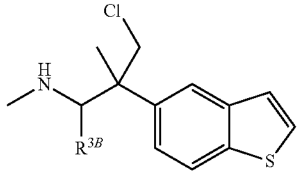

-continued
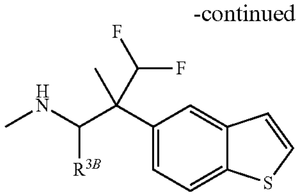
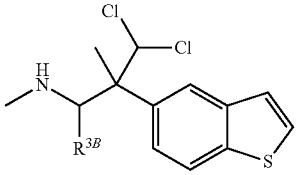
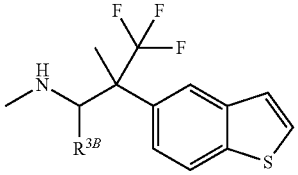
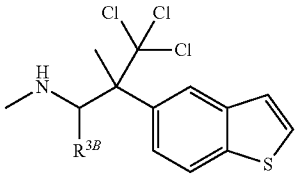
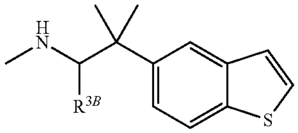
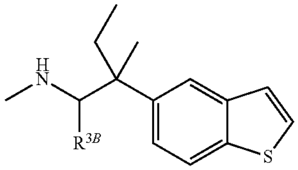
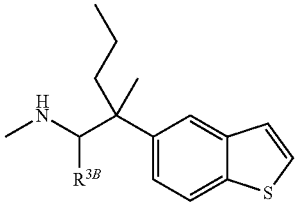
and
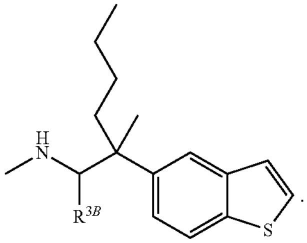
In certain embodiments, the compound of the present invention is selected from:
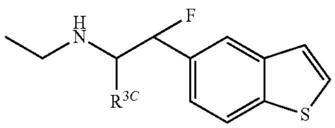
-continued
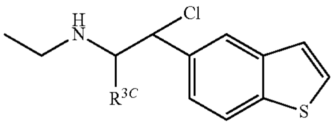
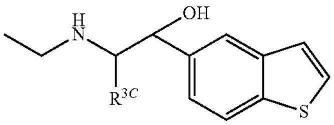
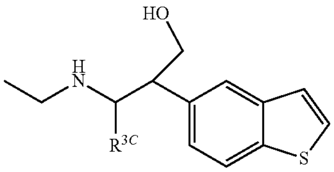
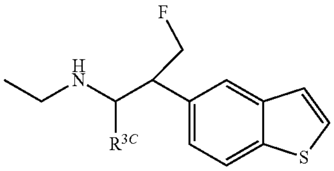
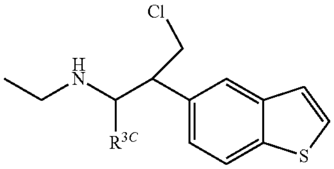
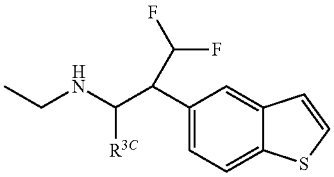
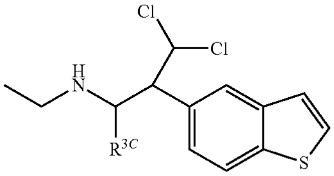
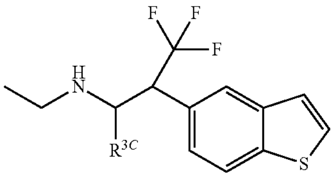
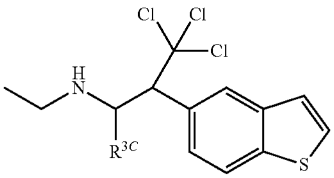
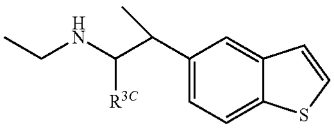

-continued
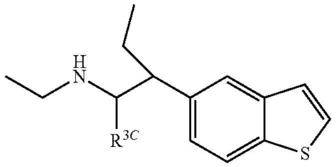
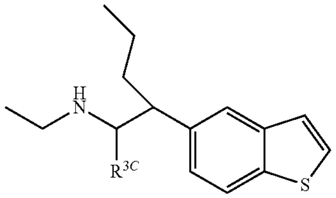
and
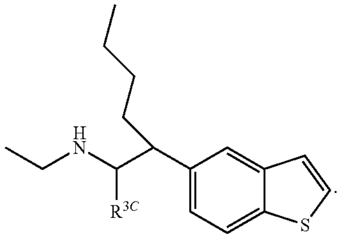
In certain embodiments, the compound of the present invention is selected from:
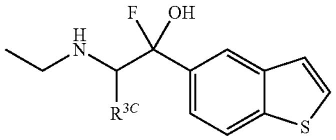
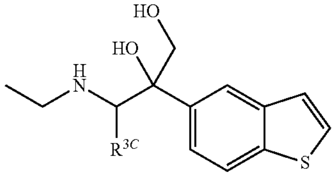
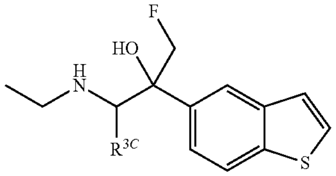
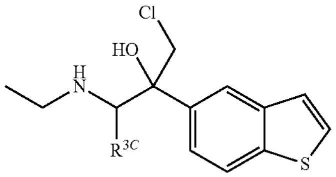
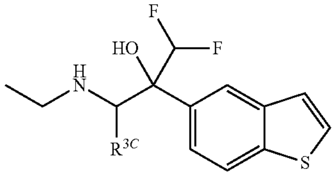
-continued
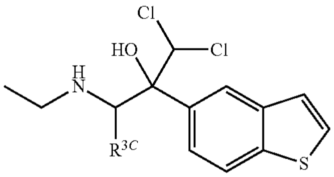
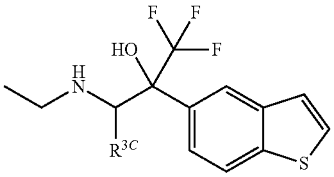
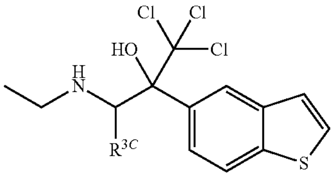
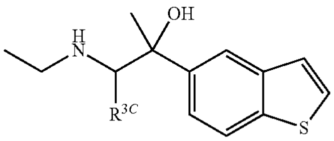
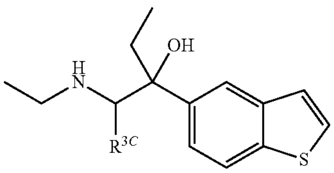
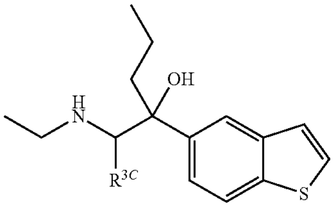
and
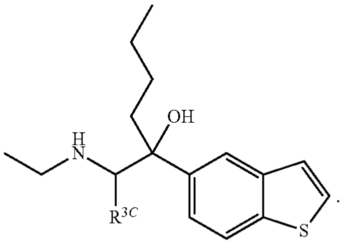
In certain embodiments, the compound of the present invention is selected from:
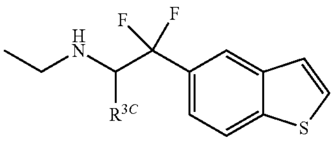
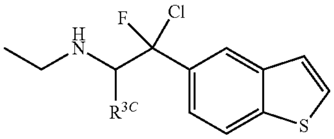

-continued
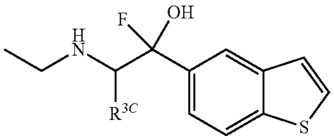
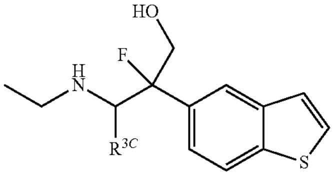
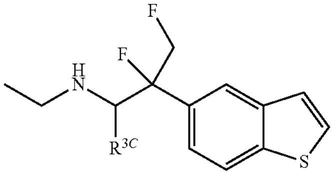
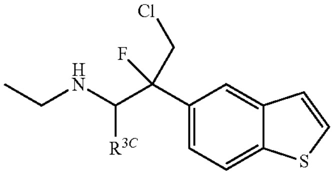
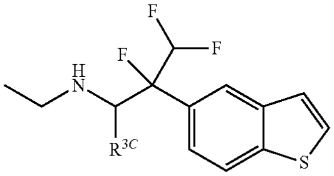
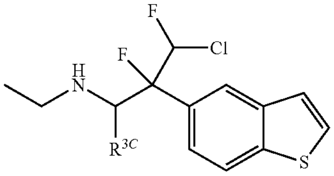
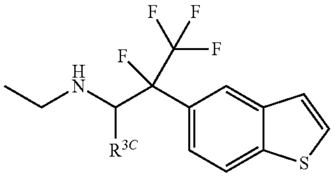
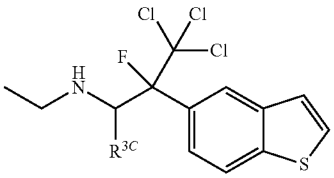
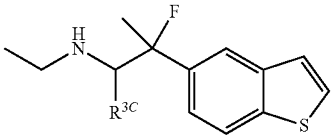
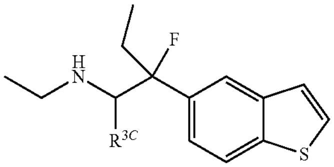
-continued
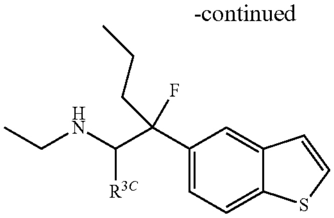
and
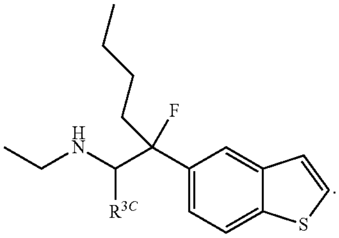
In certain embodiments, the compound of the present invention is selected from:
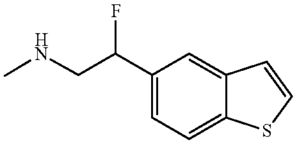
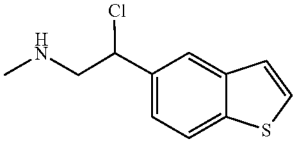
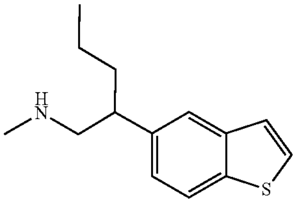
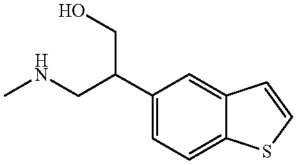
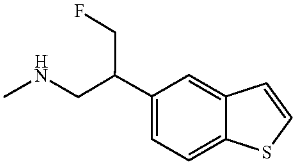
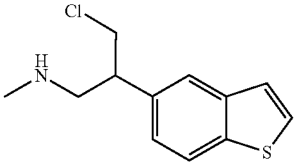
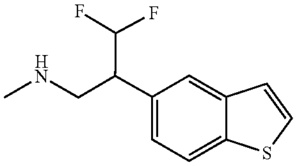
and -continued
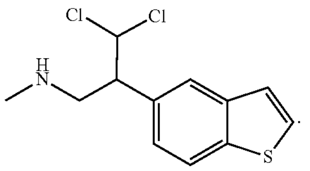
In certain embodiments the compound of the present invention is selected from:
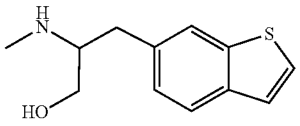
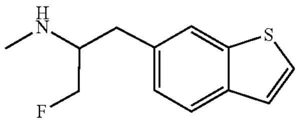
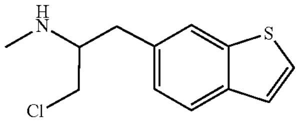
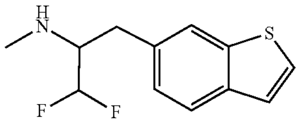
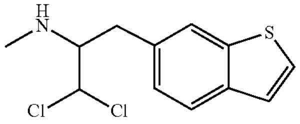
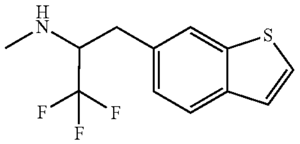
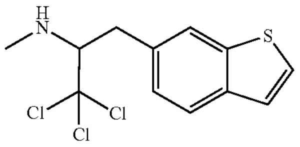
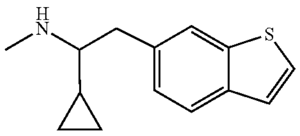
and
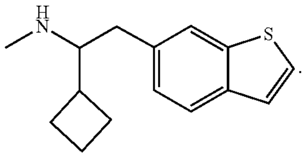
In certain embodiments, the compound of the present invention is selected from:
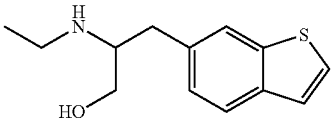
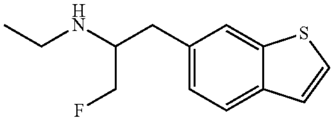
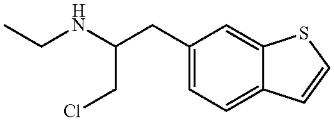
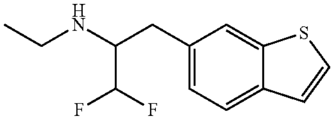
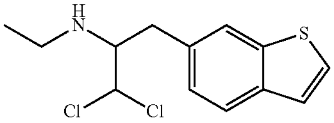
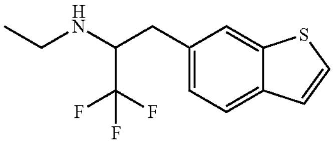
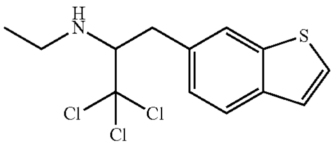
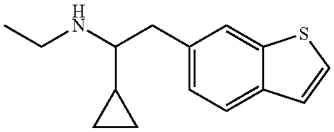
and
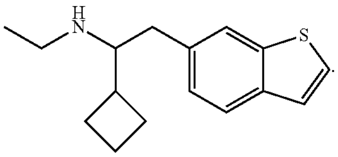
In certain embodiments, the compound of the present invention is selected from:
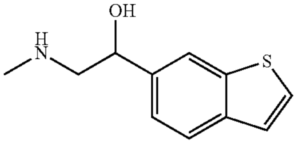
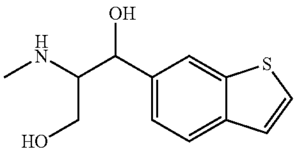

-continued
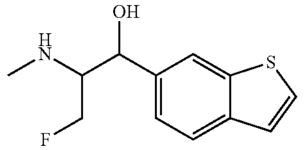
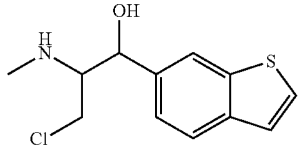
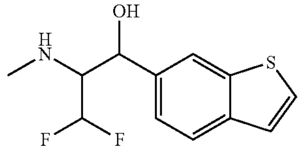
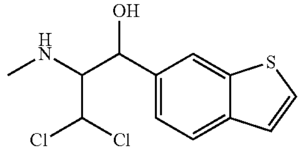
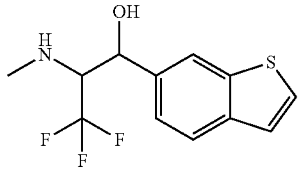
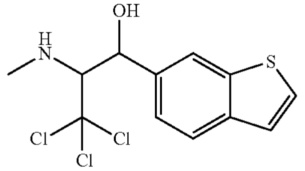
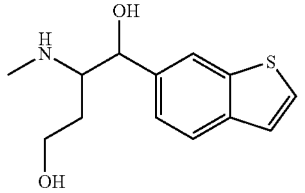
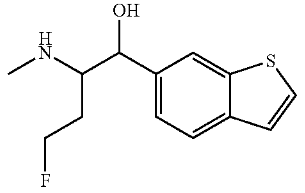
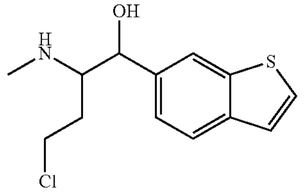
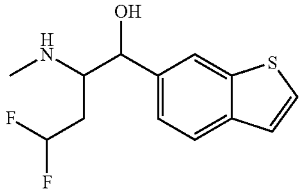
-continued
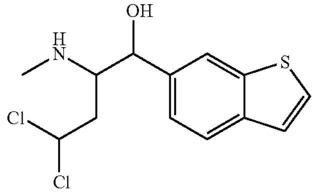
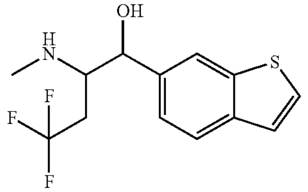
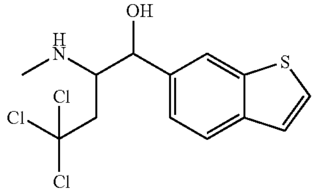
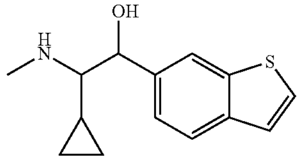
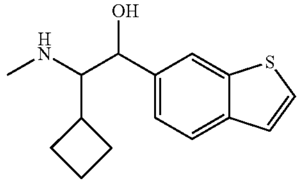
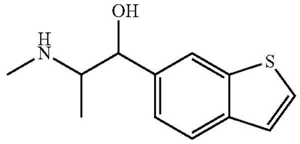
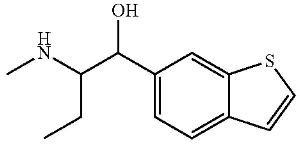
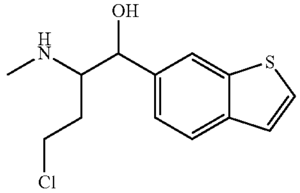
and
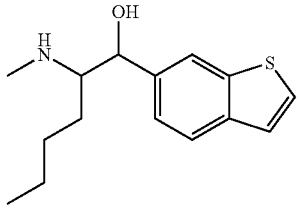
.
In certain embodiments, the compound of the present invention is selected from:

-continued
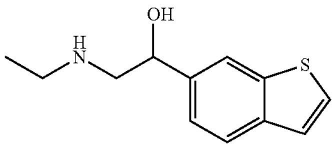
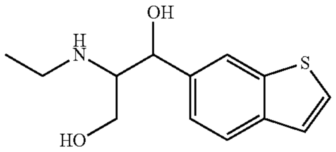
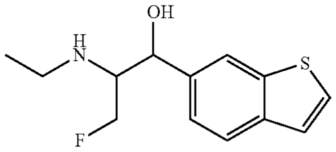
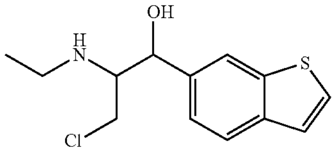
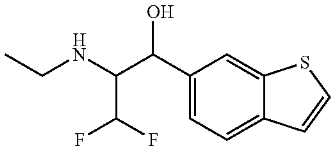
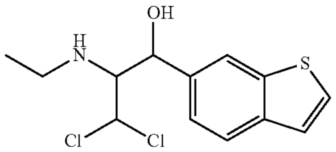
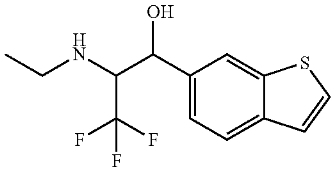
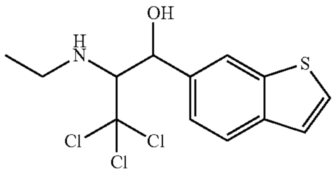
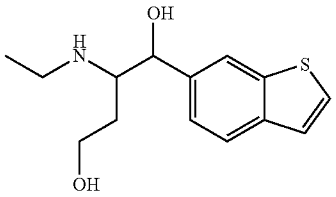
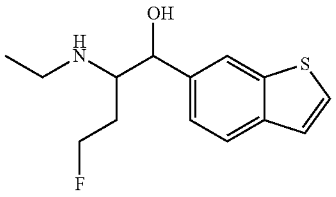
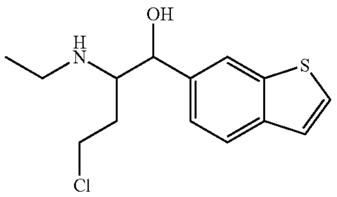
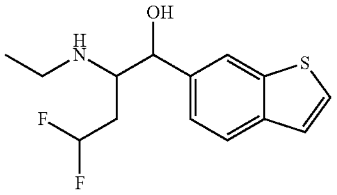
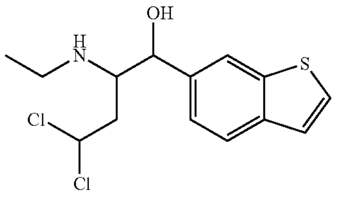
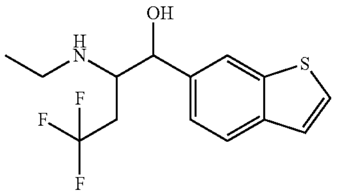
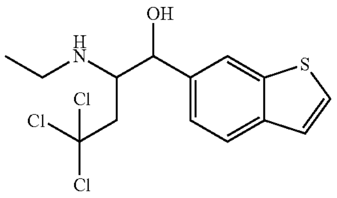
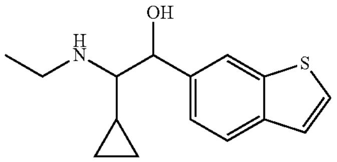
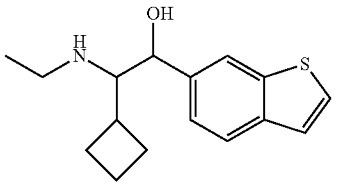
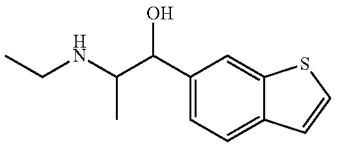
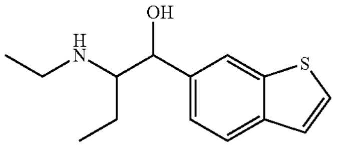

-continued
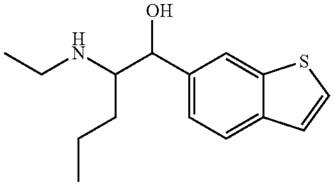
and
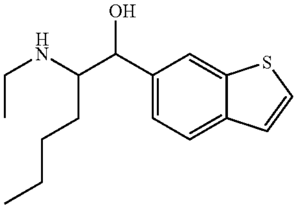
.
In certain embodiments, the compound of the present invention is selected from:
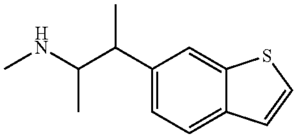
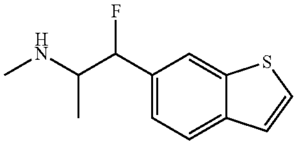
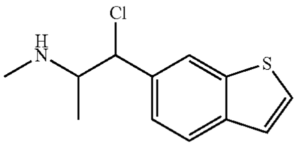
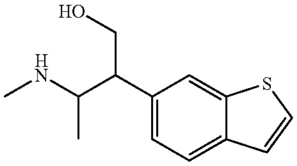
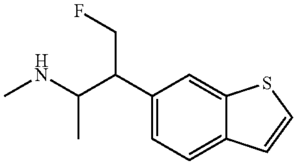
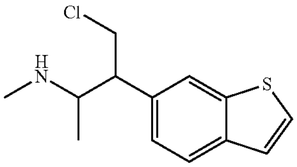
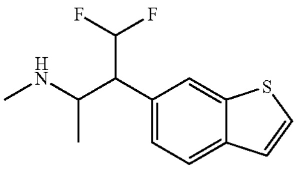
-continued
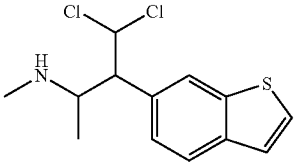
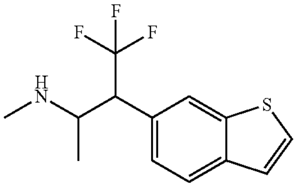
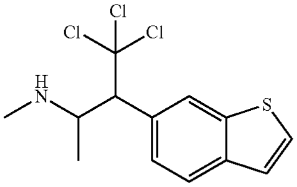
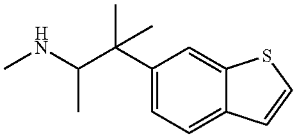
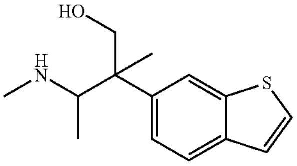
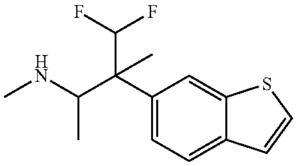
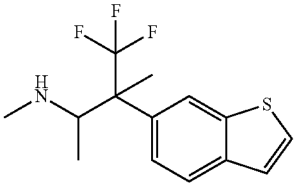
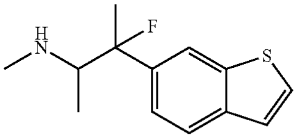
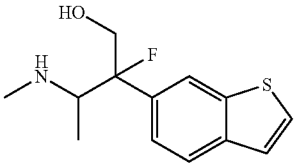
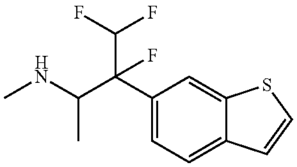
and -continued
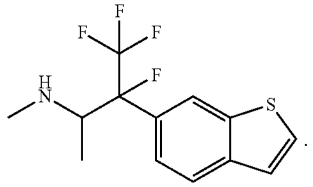
In certain embodiments, the compound of the present invention is selected from:
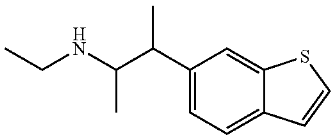
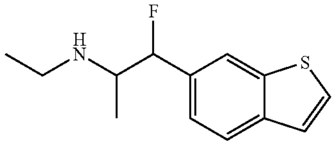
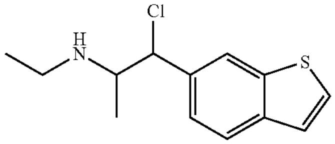
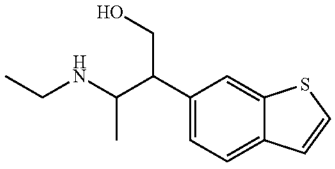
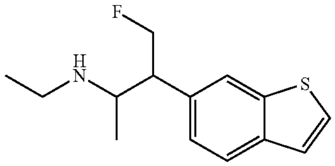
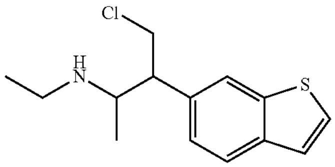
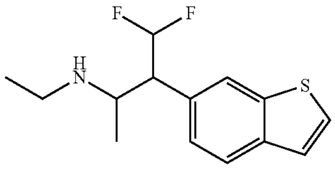
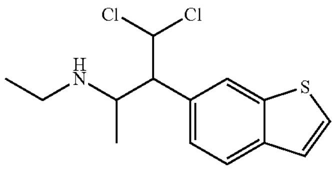
-continued
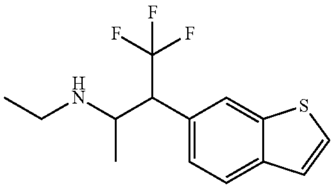
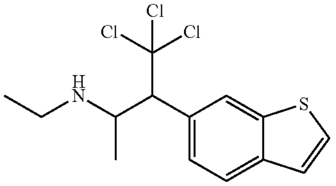
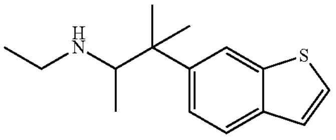
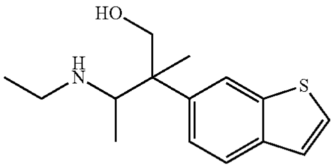
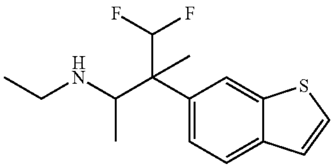
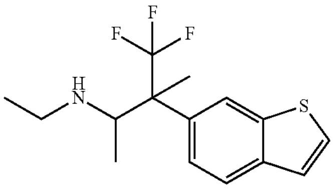
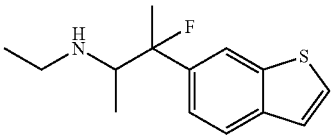
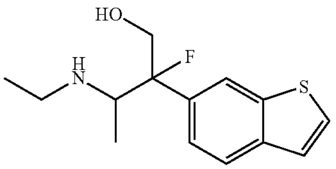
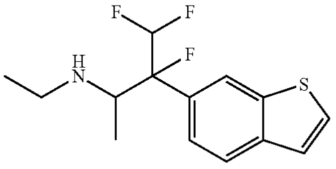
and
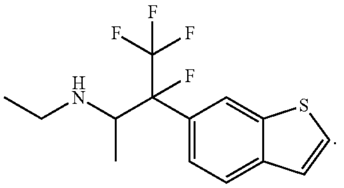

In certain embodiments, the compound of the present invention is selected from:
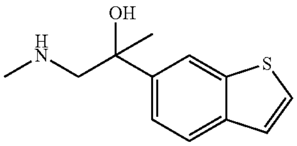
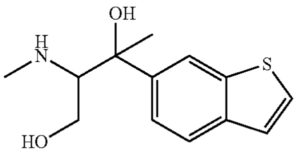
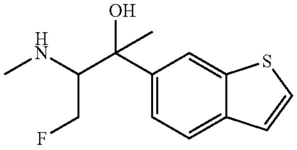
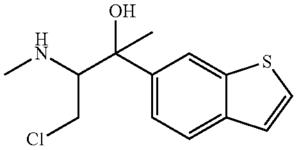
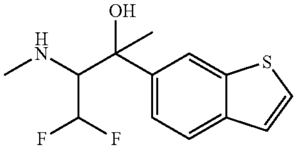
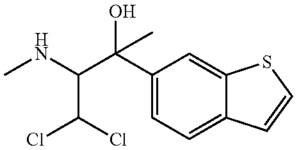
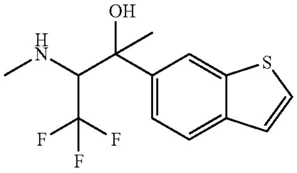
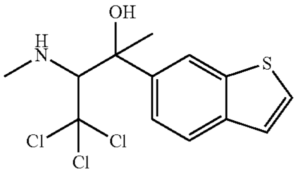
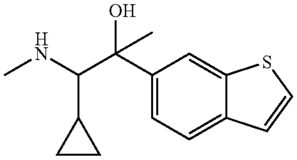
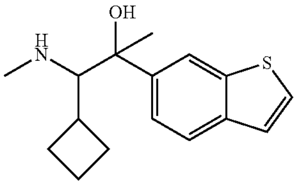
and
-continued
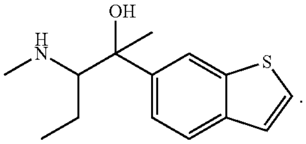
In certain embodiments, the compound of the present invention is selected from:
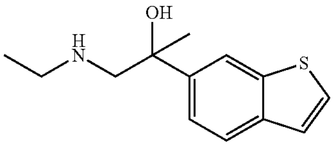
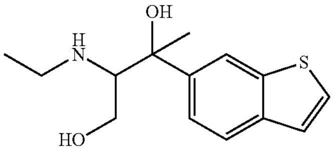
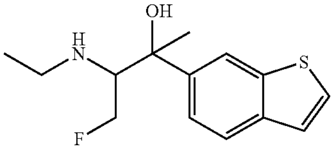
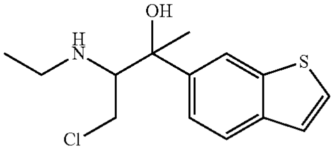
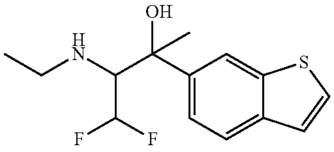
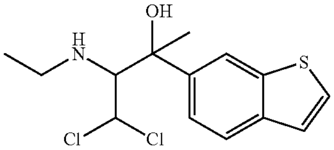
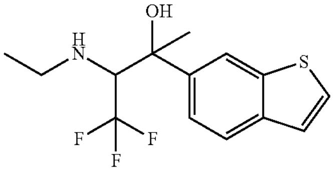
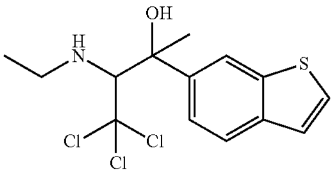
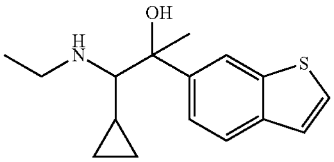

-continued
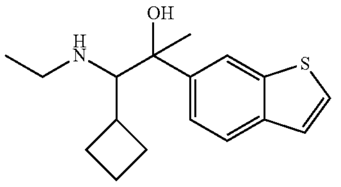
and
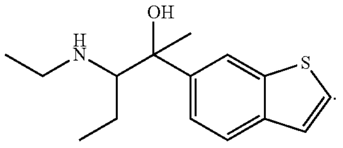
In certain embodiments, the compound of the present invention is selected from:
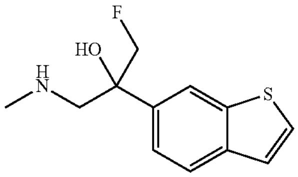
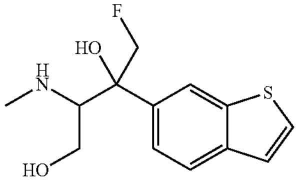
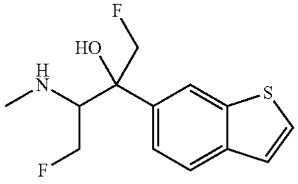
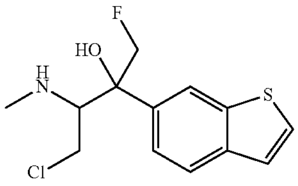
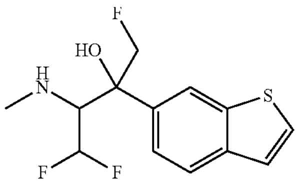
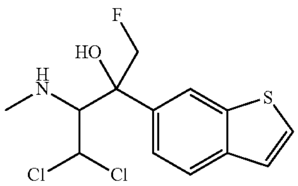
-continued
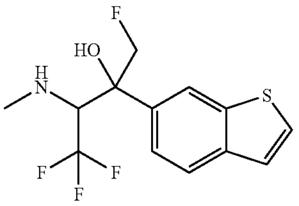
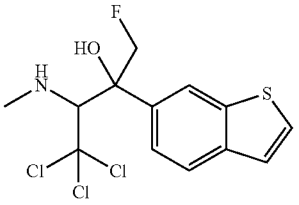
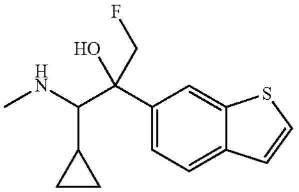
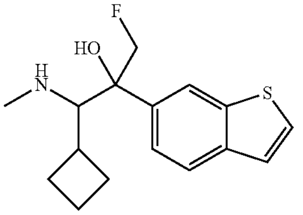
and
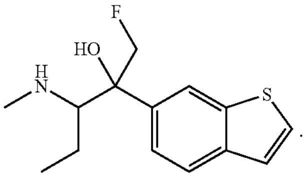
In certain embodiments, the compound of the present invention is selected from:
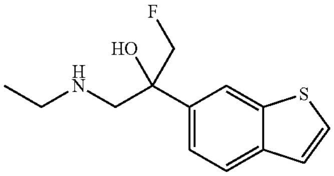
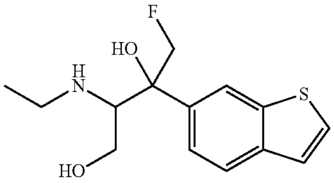
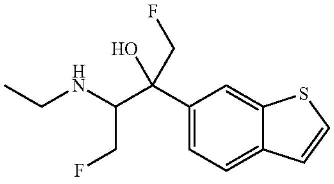

-continued
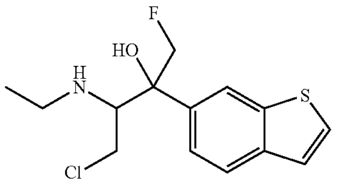
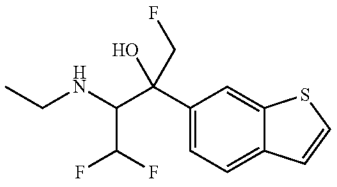
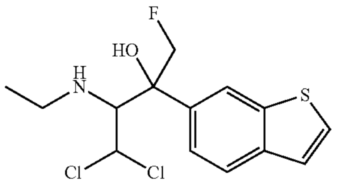
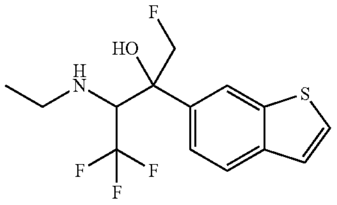
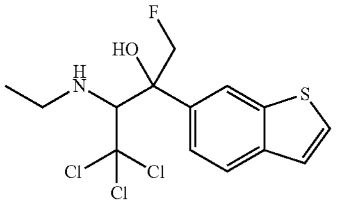
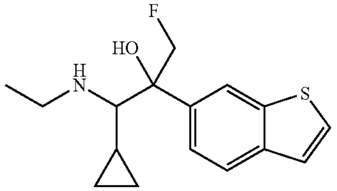
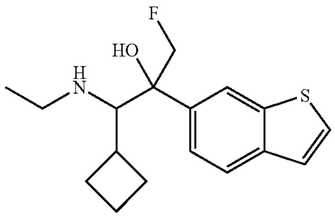
and
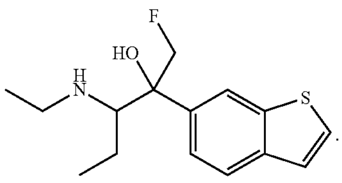
.
In certain embodiments, the compound of the present invention is selected from:
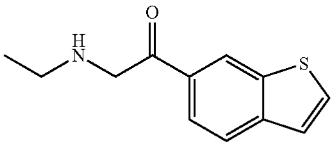
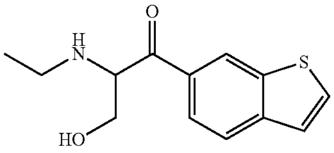
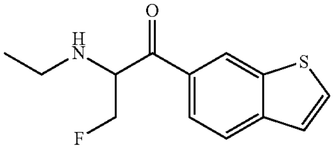
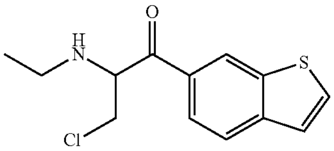
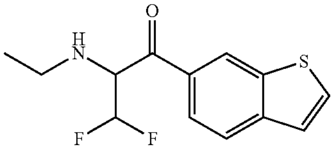
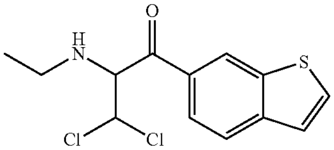
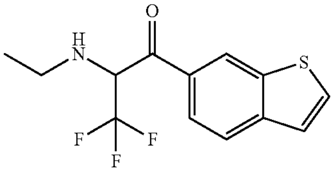
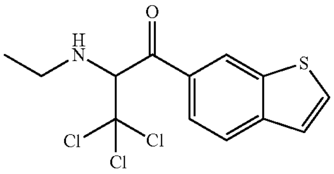
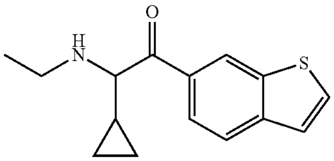
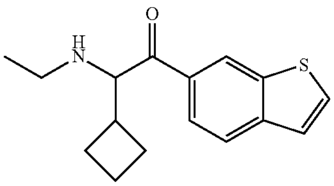
and -continued
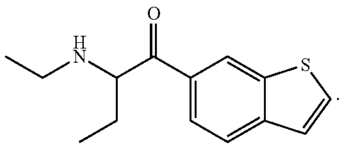
In certain embodiments, the compound of the present invention is selected from:
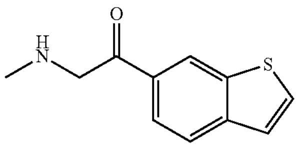
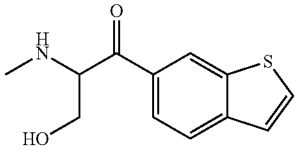
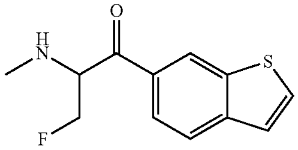
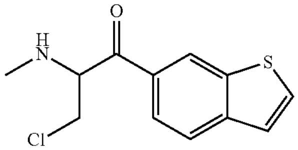
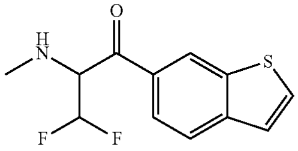
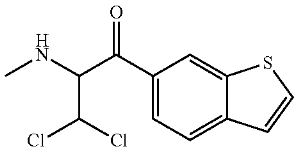
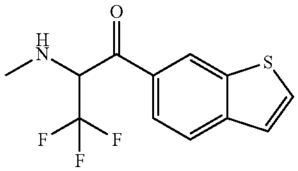
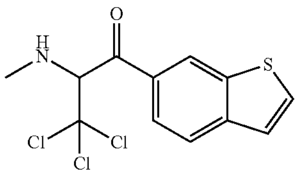
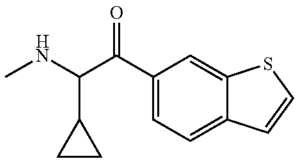
-continued
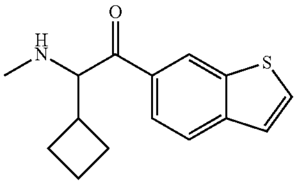
and
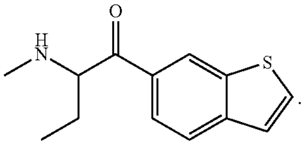
In certain embodiments, the compound of the present invention is selected from:
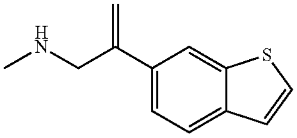
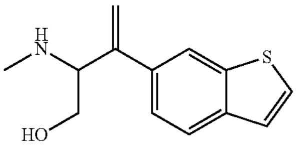
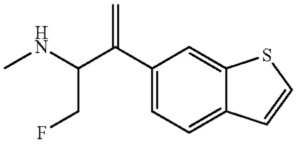
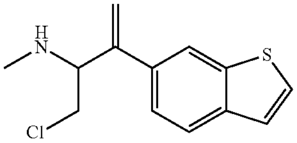
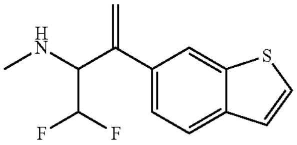
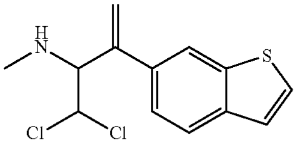
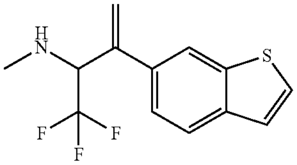
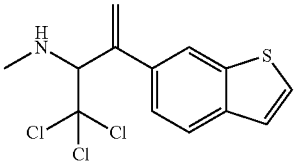

-continued
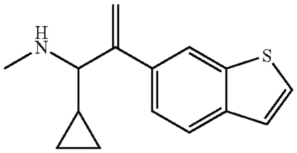
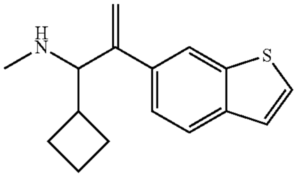
and
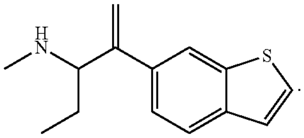
In certain embodiments, the compound of the present invention is selected from:
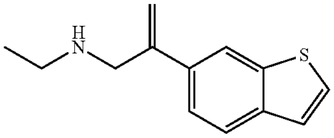
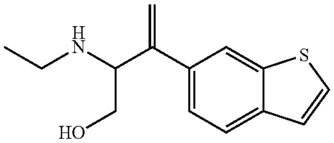
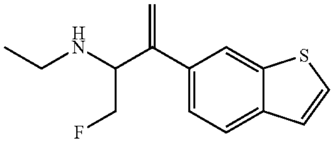
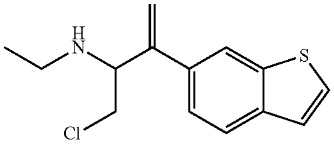
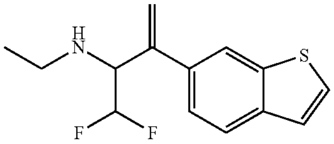
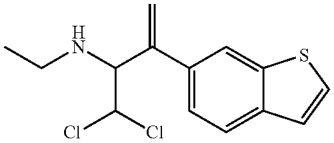
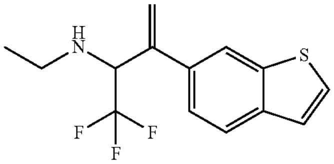
-continued
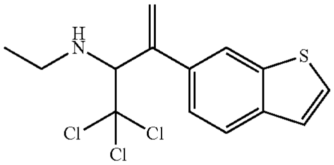
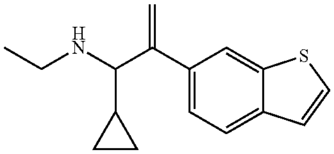
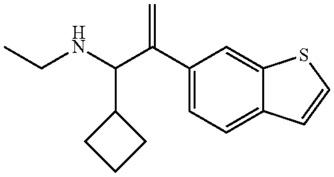
and
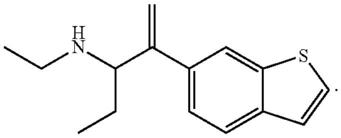
In certain embodiments, the compound of the present invention is selected from:
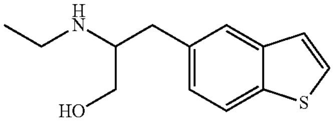
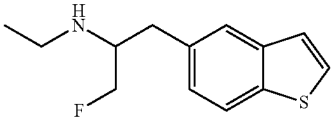
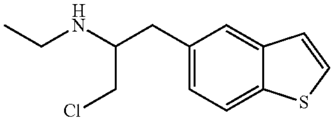
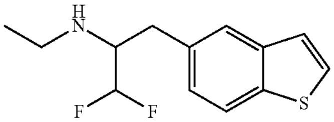
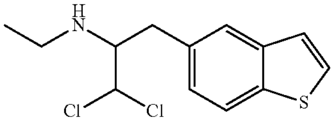
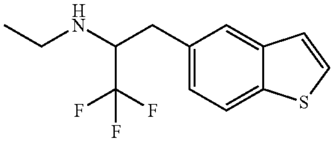
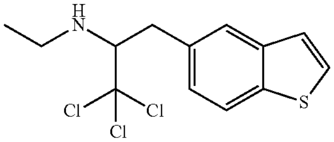

-continued
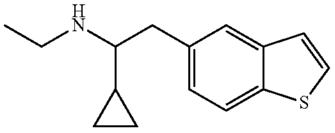
and
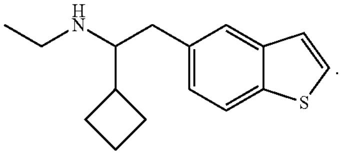 [SMILES: CCNC(Cc1ccc2c(c1)SCC2)C1CCC1]
In certain embodiments, the compound of the present invention is selected from:
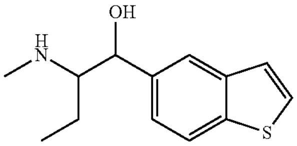
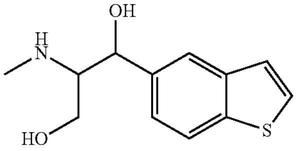
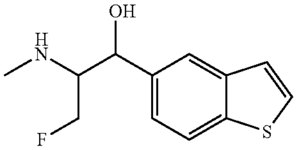
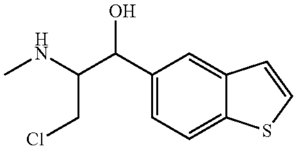
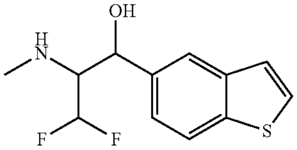
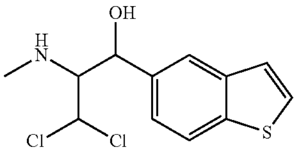
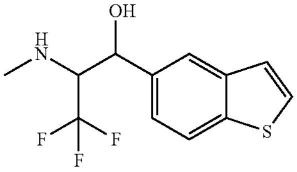
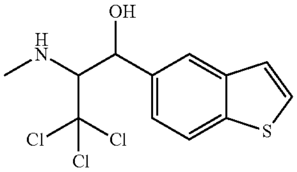
-continued
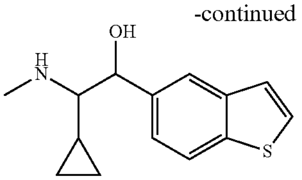
and
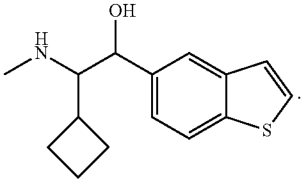
In certain embodiments, the compound of the present invention is selected from:
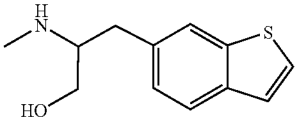
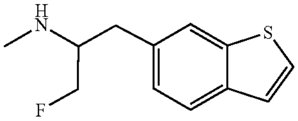
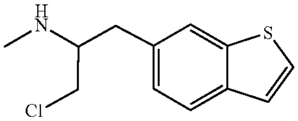
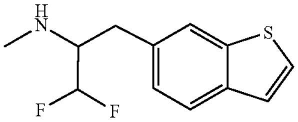
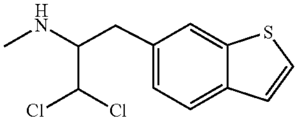
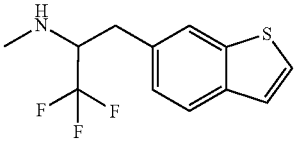
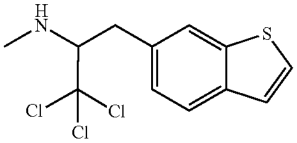
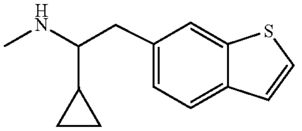
and
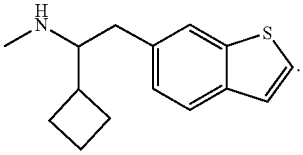
In certain embodiments, the compound of the present invention is selected from:

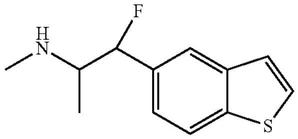
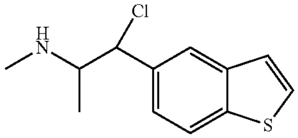
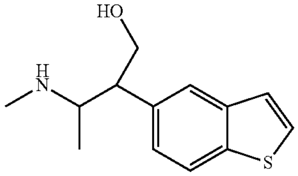
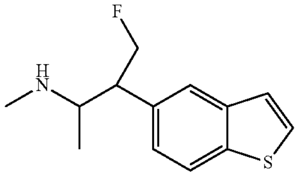
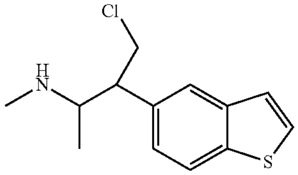
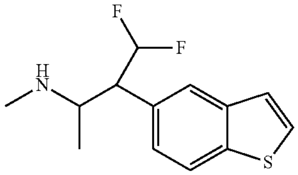
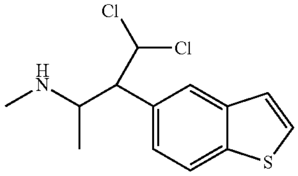
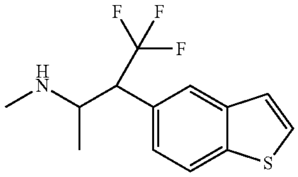
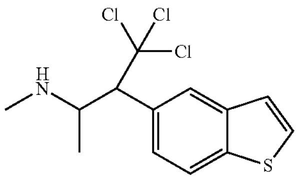
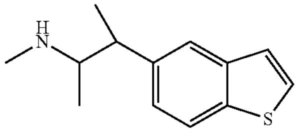
-continued
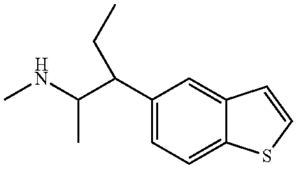
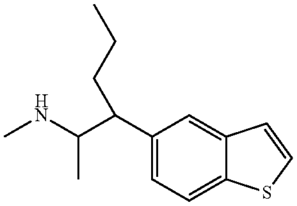
and
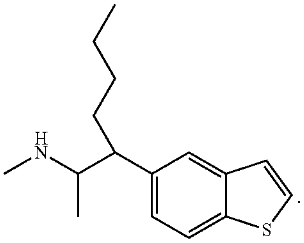
.
In certain embodiments, the compound of the present invention is selected from:
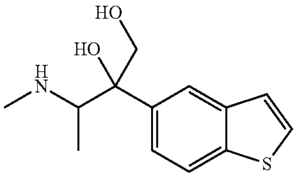
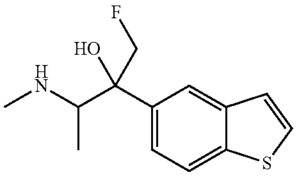
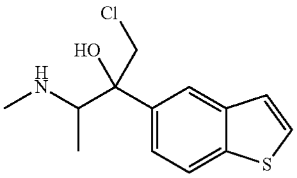
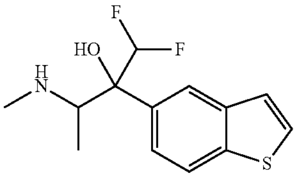
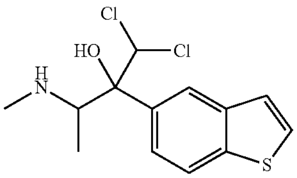

-continued
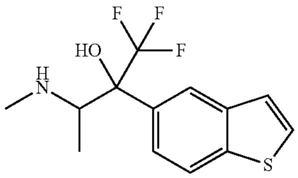
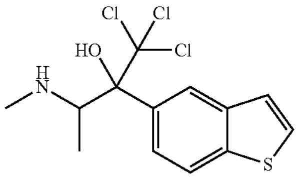
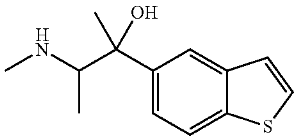
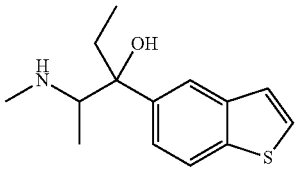
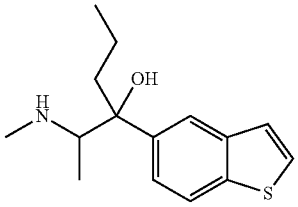
and
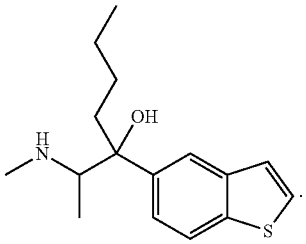
In certain embodiments, the compound of the present invention is selected from:
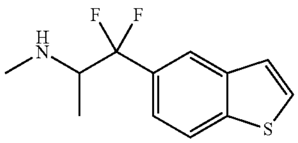
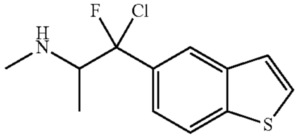
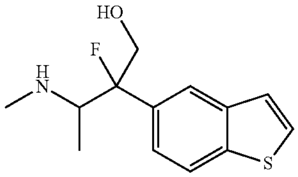
-continued
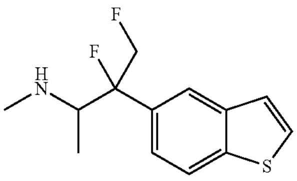
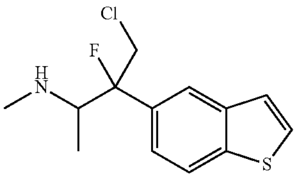
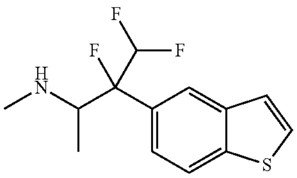
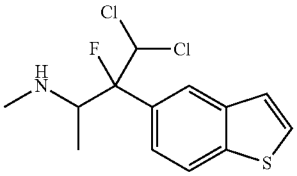
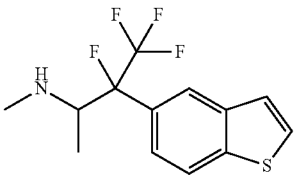
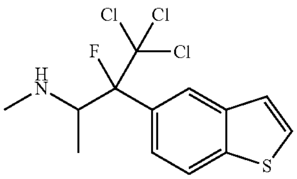
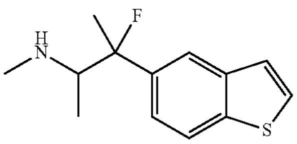
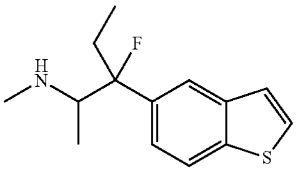
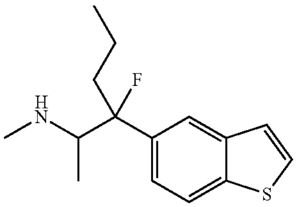
and -continued
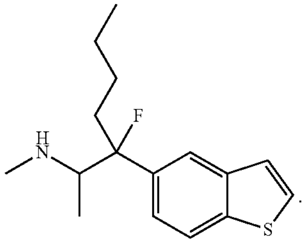
In certain embodiments, the compound of the present invention is selected from:
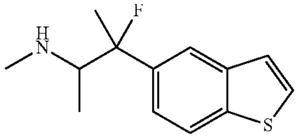
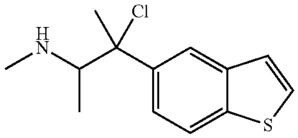
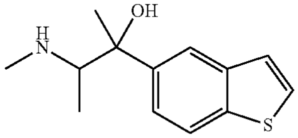
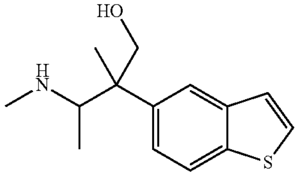
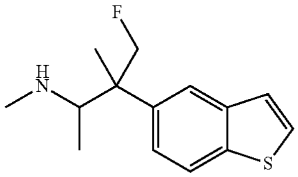
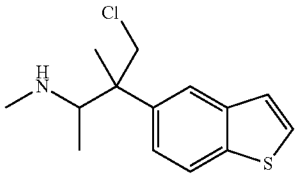
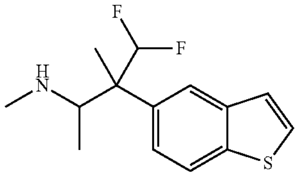
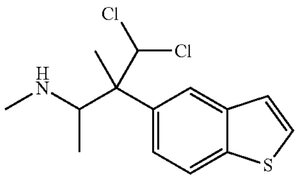
-continued
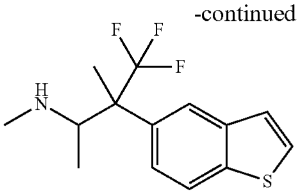
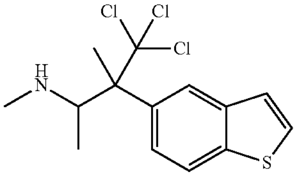
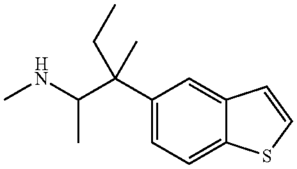
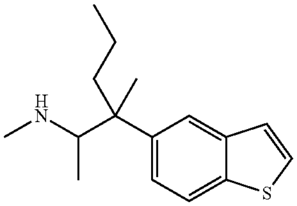
and
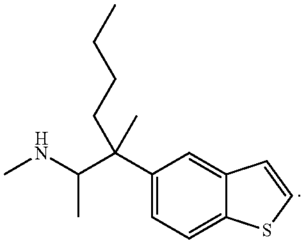
In certain embodiments, the compound of the present invention is selected from:
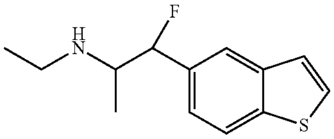
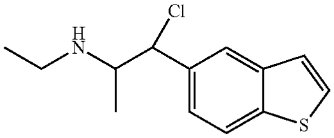
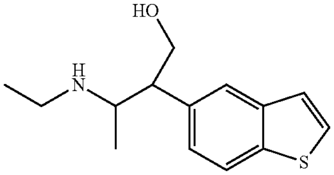
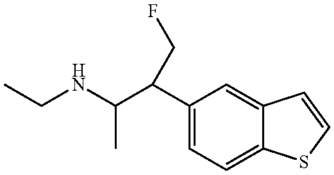

-continued
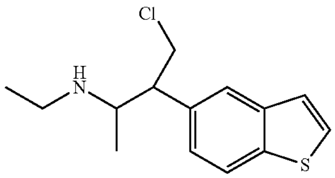
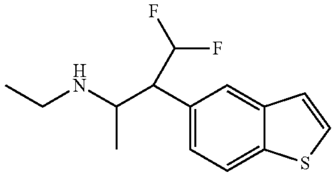
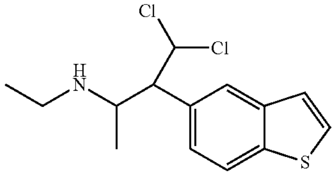
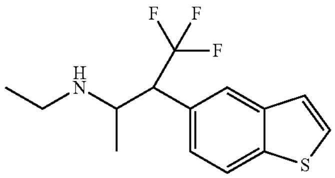
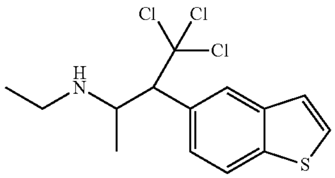
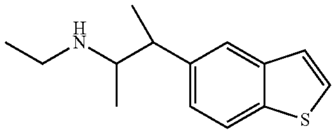
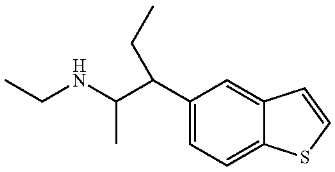
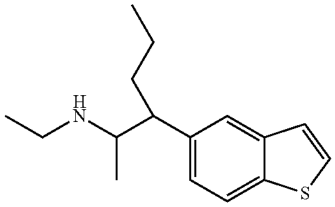
and
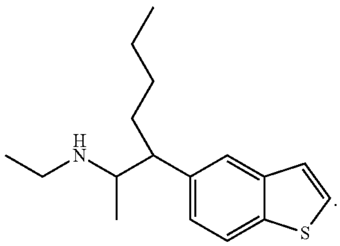
.
In certain embodiments, the compound of the present invention is selected from:
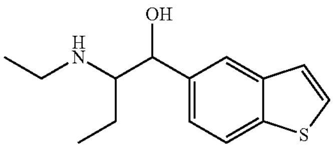
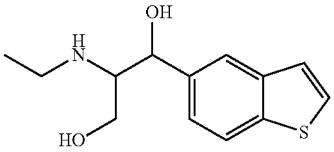
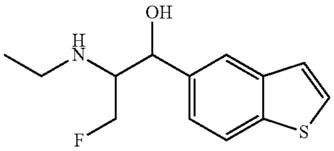
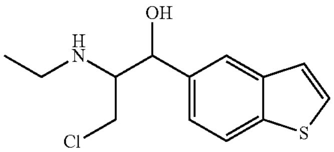
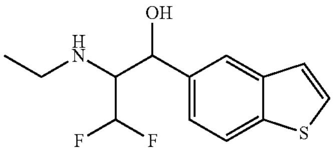
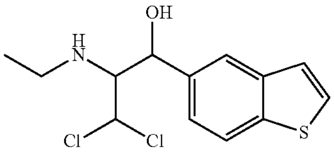
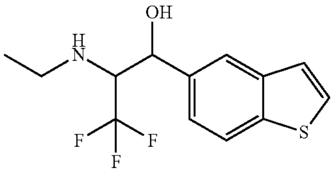
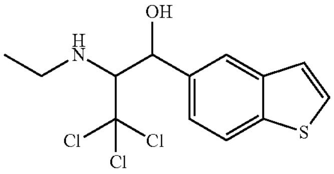
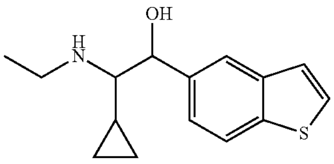
and
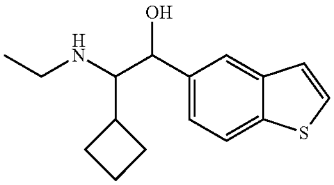
.

In certain embodiments, the compound of the present invention is selected from:
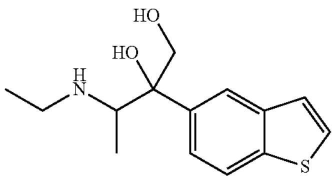
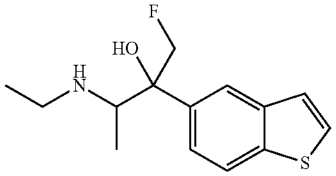
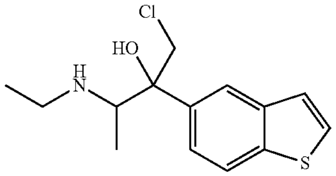
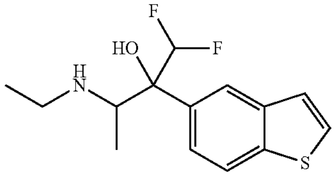
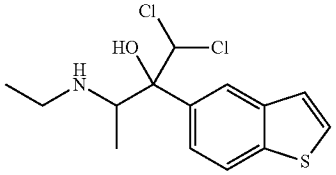
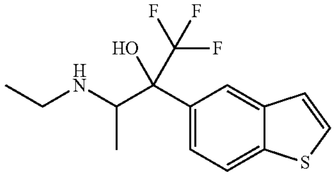
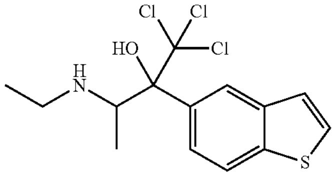
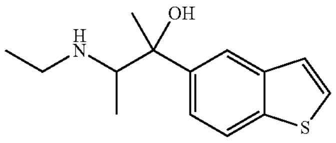
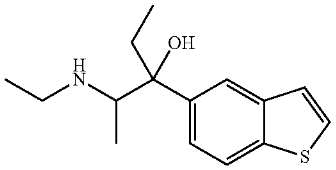
-continued
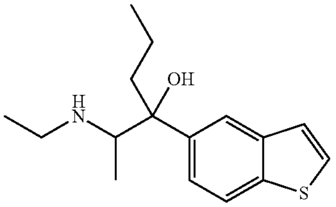
and
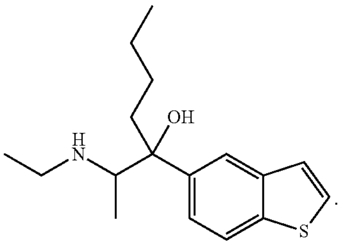
In certain embodiments, the compound of the present invention is selected from:
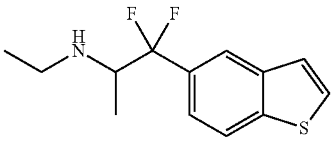
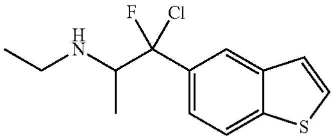
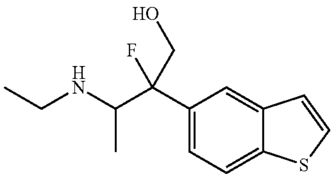
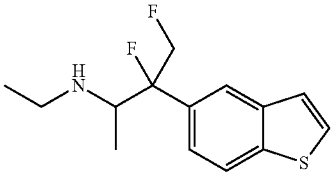
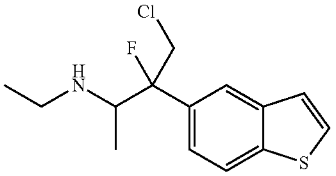
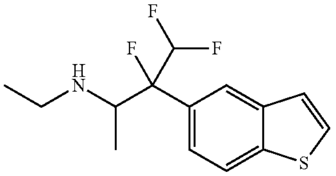

-continued
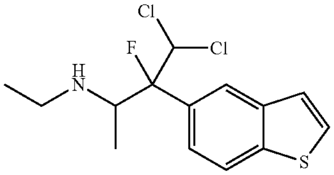
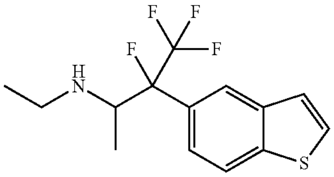
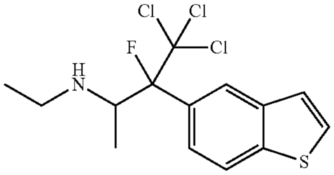
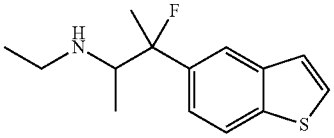
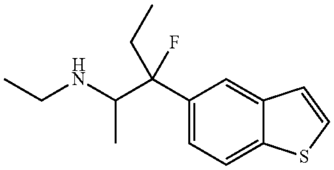
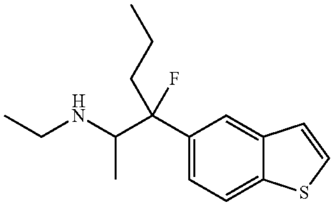
and
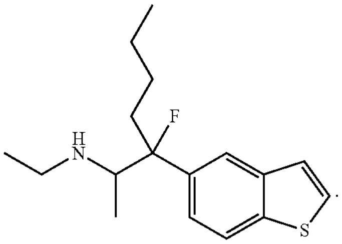
In certain embodiments, the compound of the present invention is selected from:
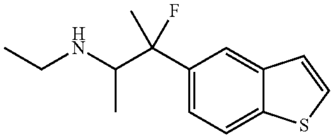
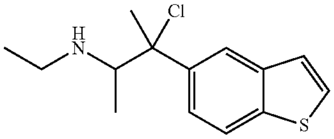
-continued
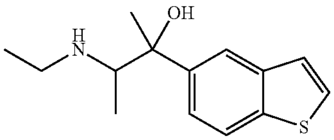
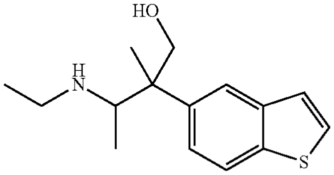
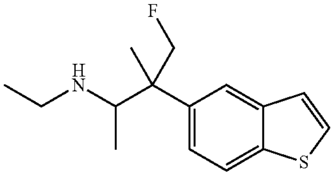
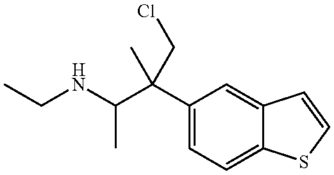
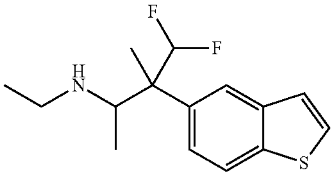
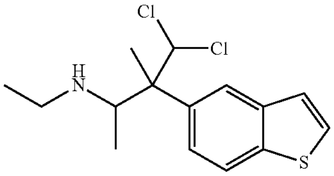
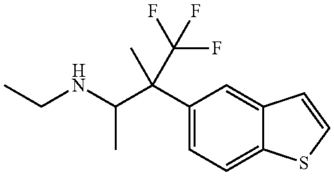
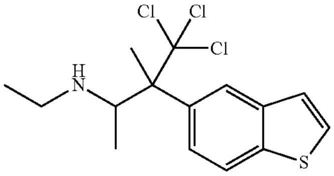
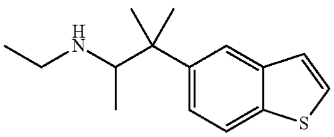
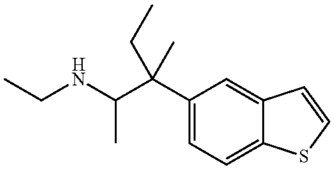

-continued
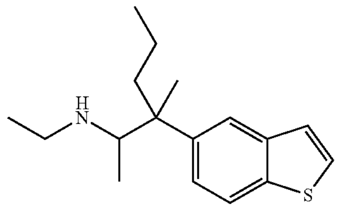
and
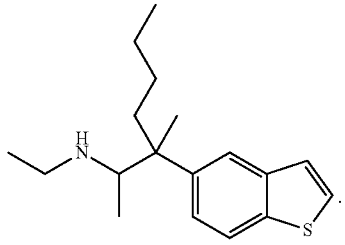
In certain embodiments, the compound of the present invention is selected from:
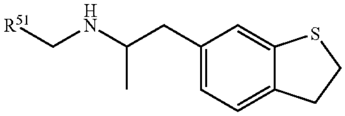
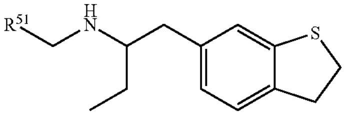
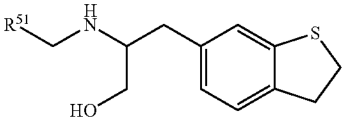
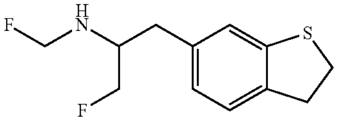
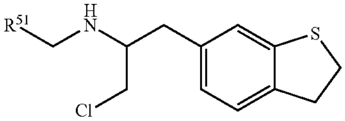
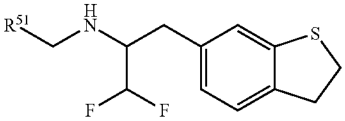
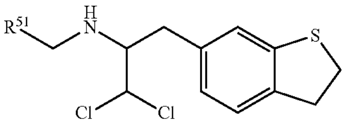
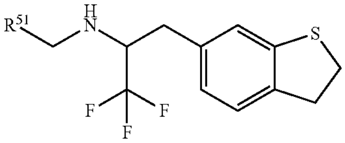
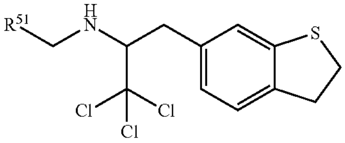
-continued
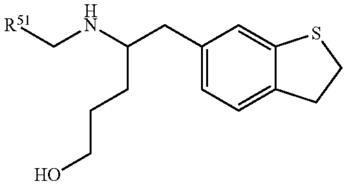
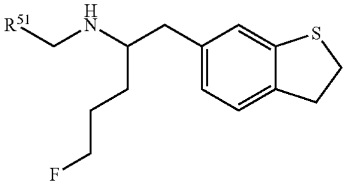
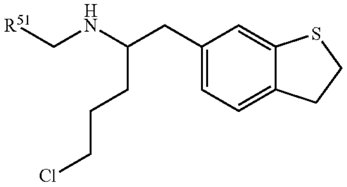
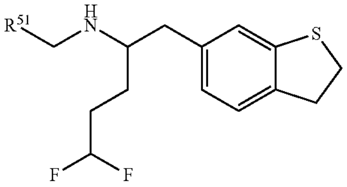
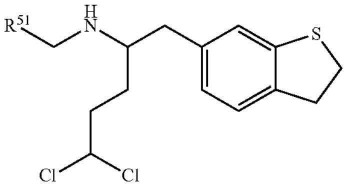
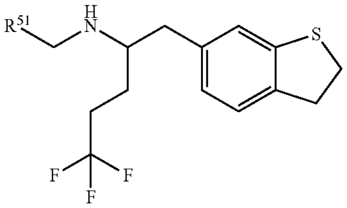
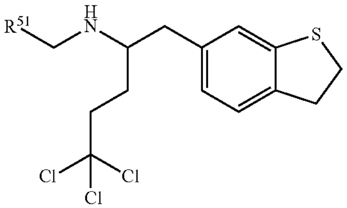
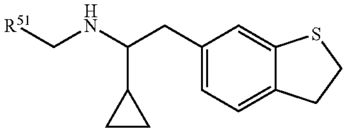
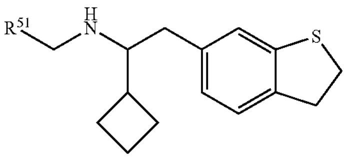

-continued
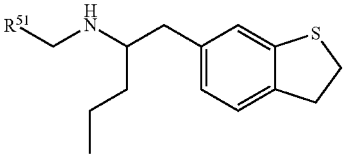
and
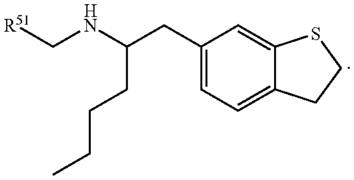
In certain embodiments, the compound of the present invention is selected from:
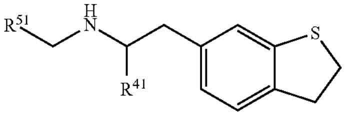
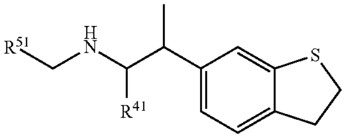
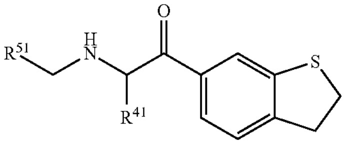
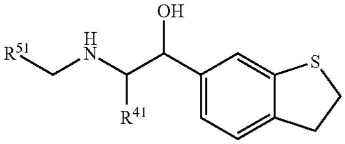
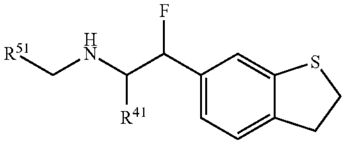
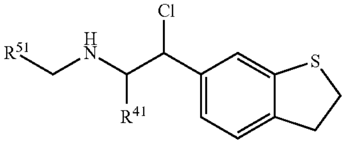
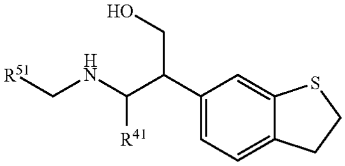
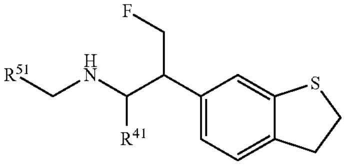
-continued
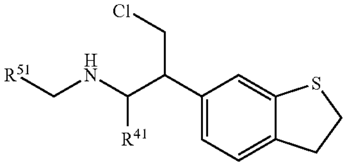
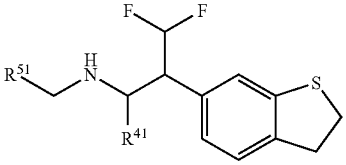
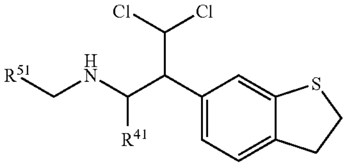
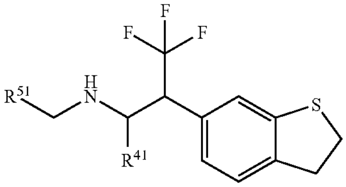
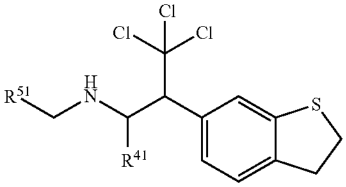
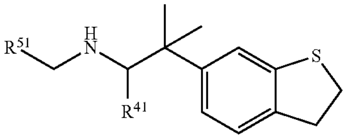
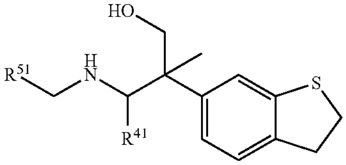
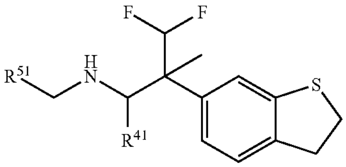
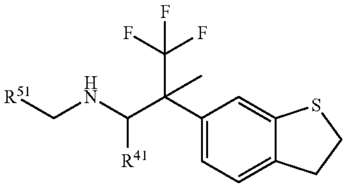
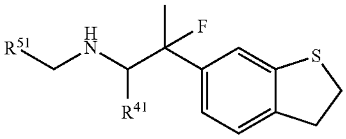

-continued
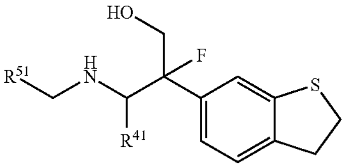
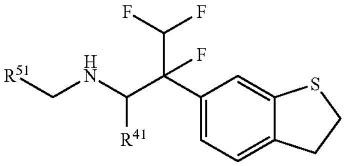
and
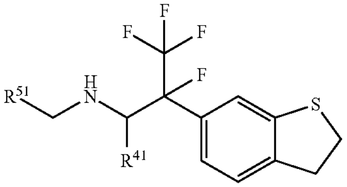
.
In certain embodiments, the compound of the present invention is selected from:
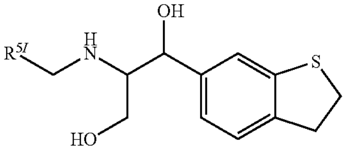
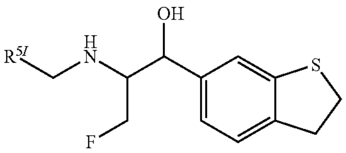
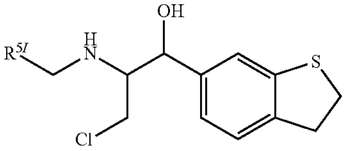
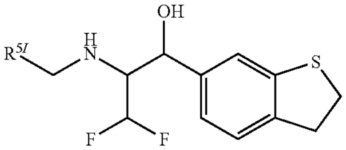
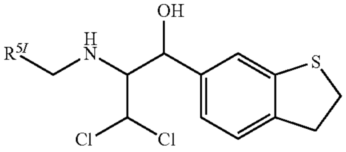
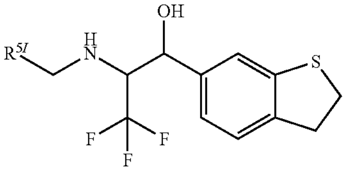
-continued
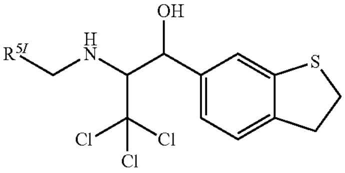
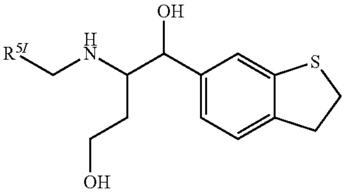
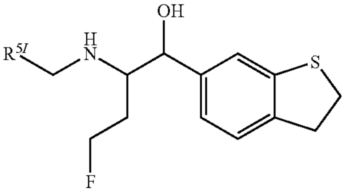
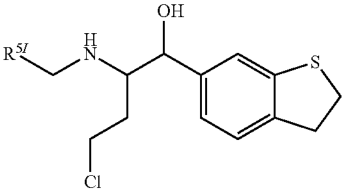
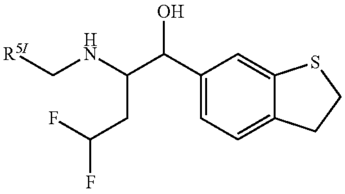
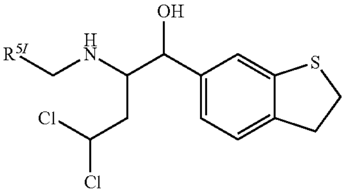
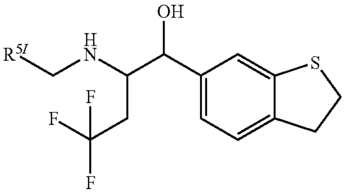
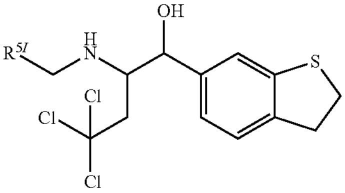
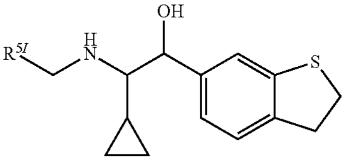

-continued
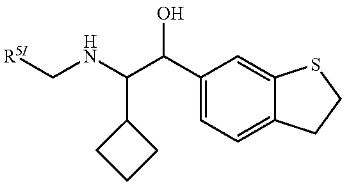
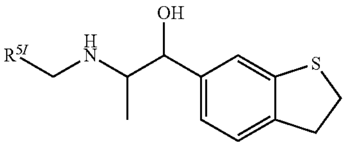
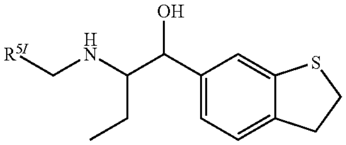
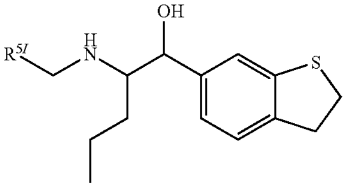
and
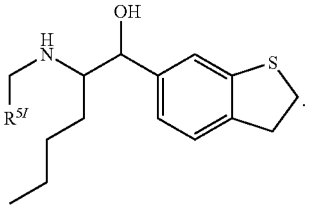
In certain embodiments, the compound of the present invention is selected from:
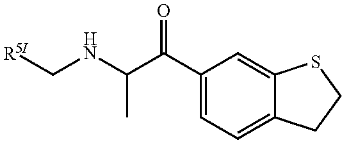
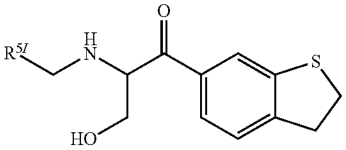
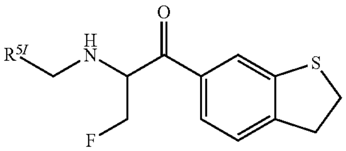
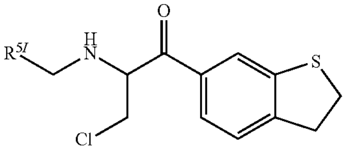
-continued
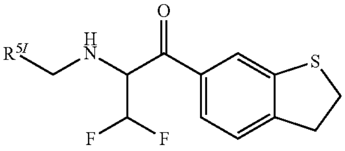
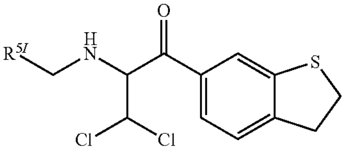
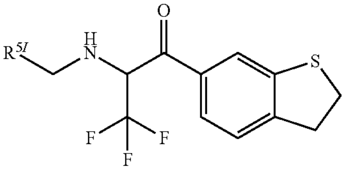
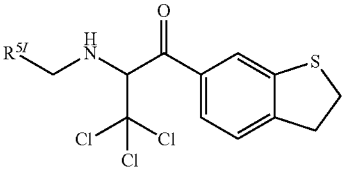
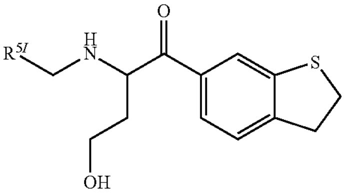
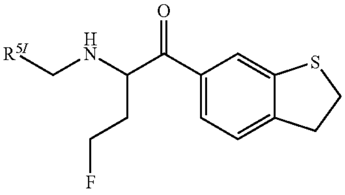
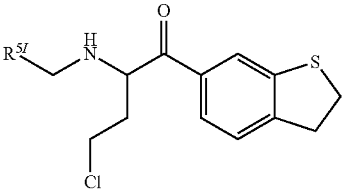
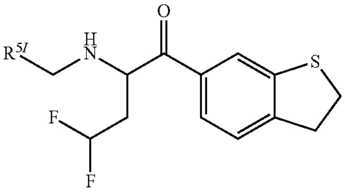
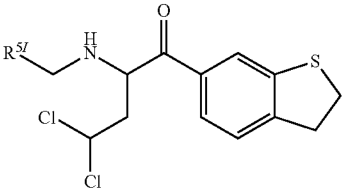

-continued
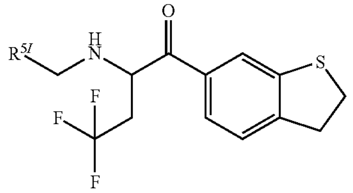
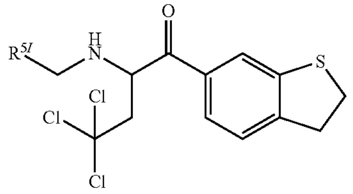
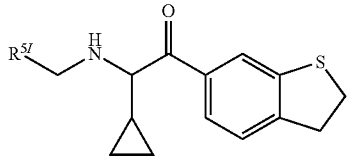
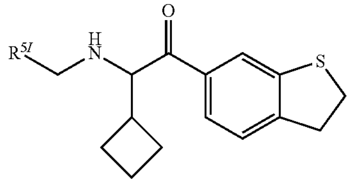
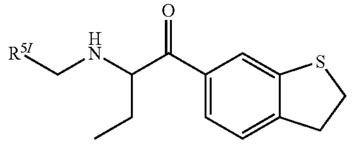
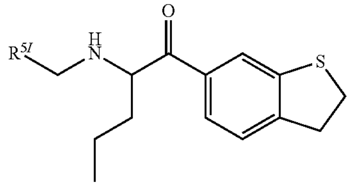
and
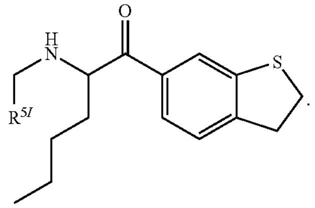
In certain embodiments, the compound of the present invention is selected from:
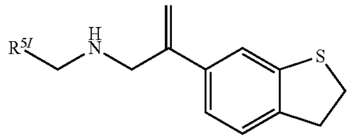
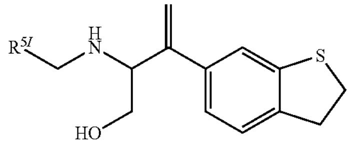
-continued
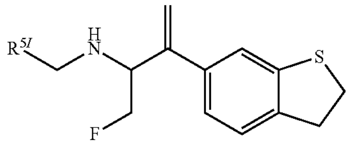
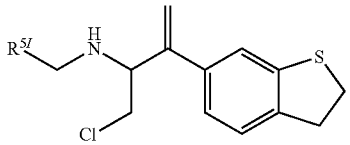
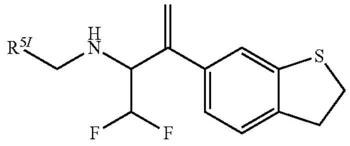
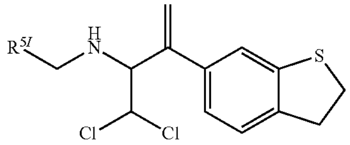
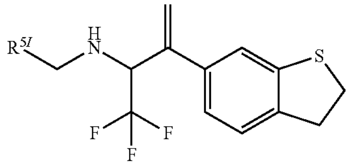
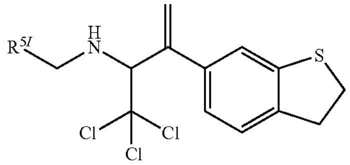
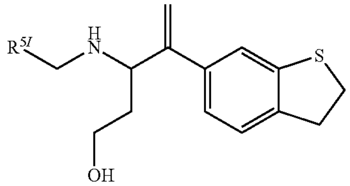
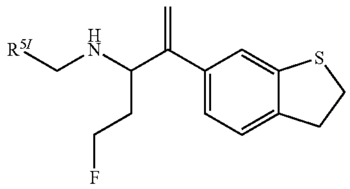
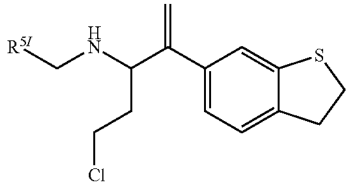
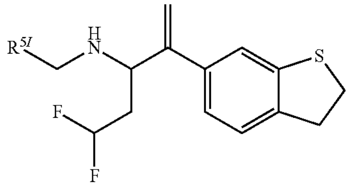

-continued
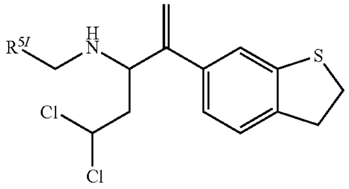
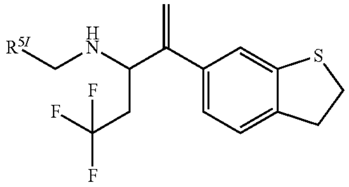
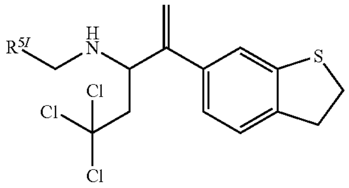
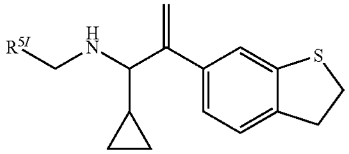
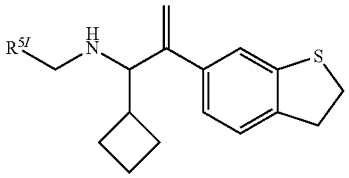
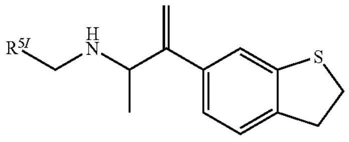
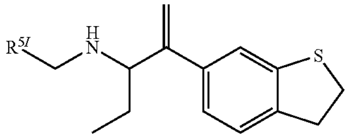
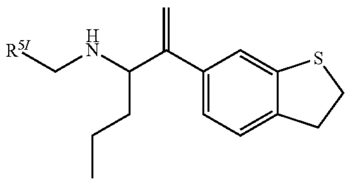
and
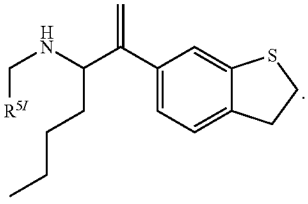
.
In certain embodiments, the compound of the present invention is selected from:
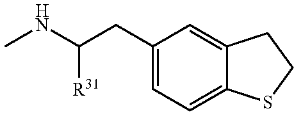
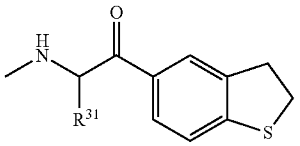
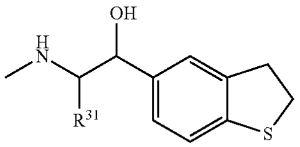
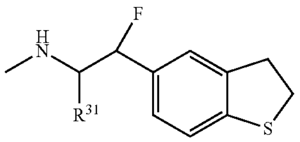
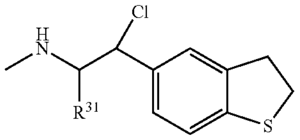
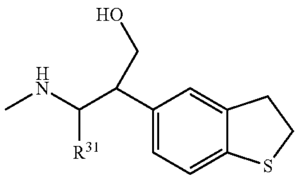
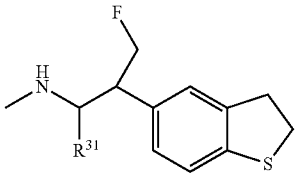
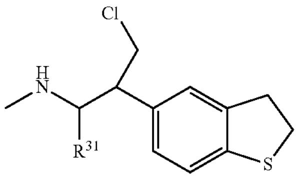
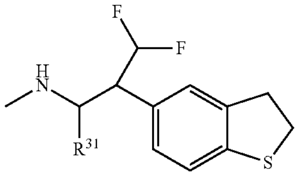
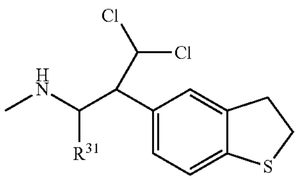

-continued
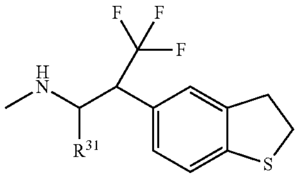
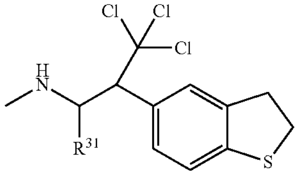
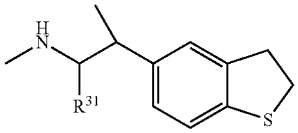
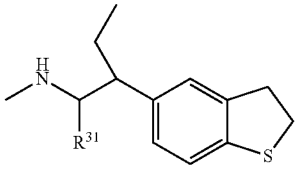
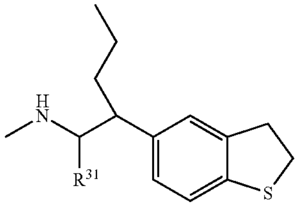
and
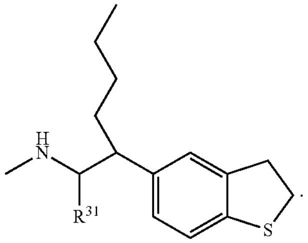
In certain embodiments, the compound of the present invention is selected from:
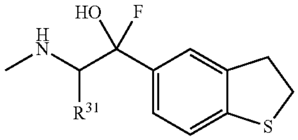
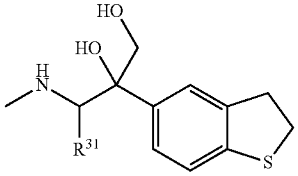
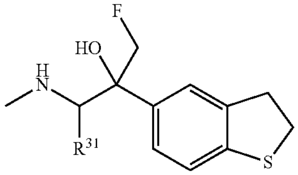
-continued
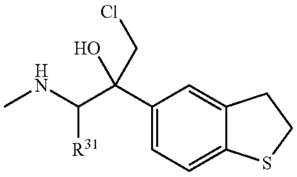
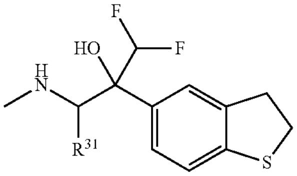
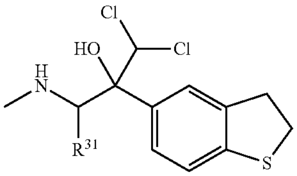
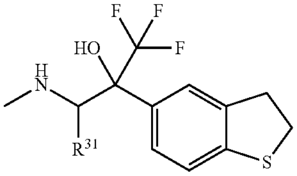
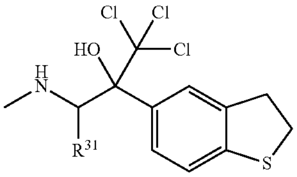
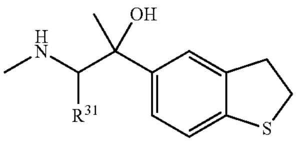
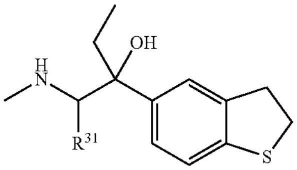
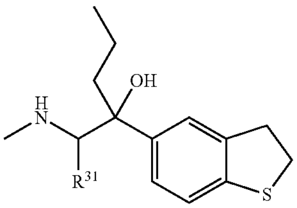
and
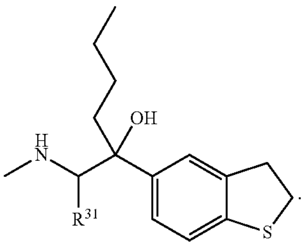
In certain embodiments, the compound of the present invention is selected from:

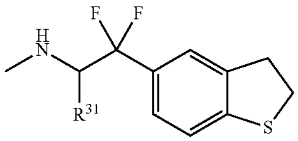
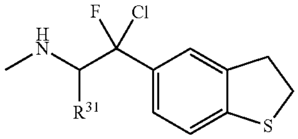
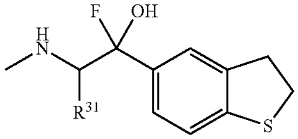
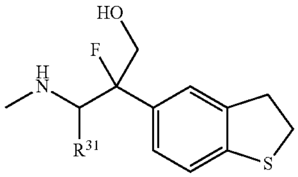
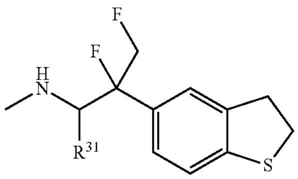
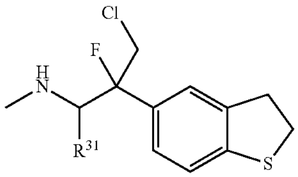
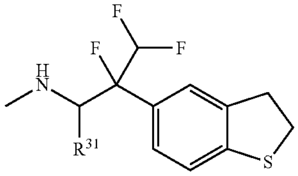
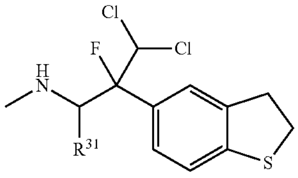
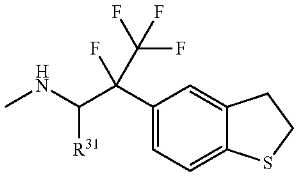
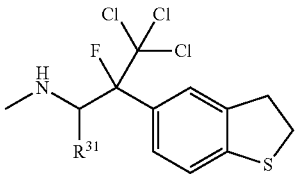
-continued
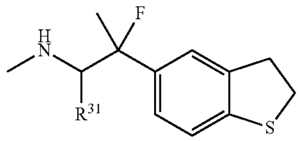
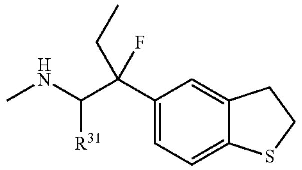
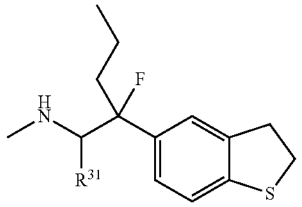
and
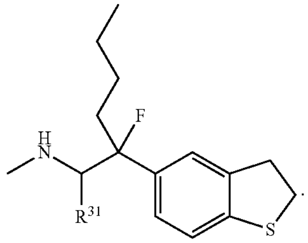
In certain embodiments, the compound of the present invention is selected from:
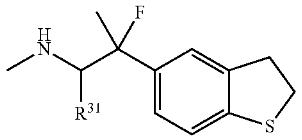
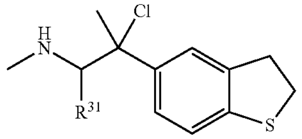
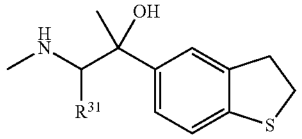
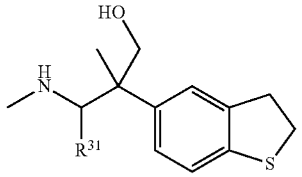
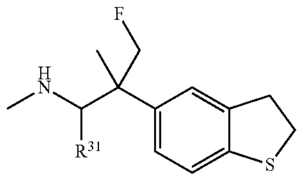

-continued
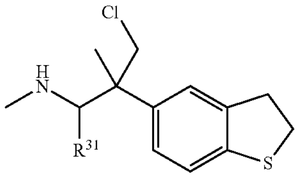
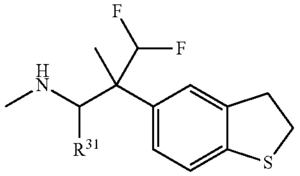
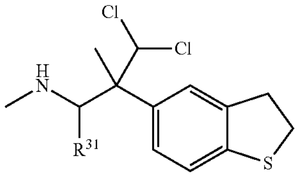
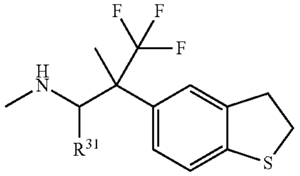
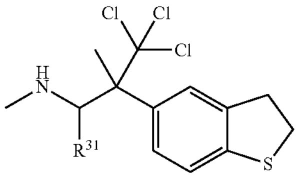
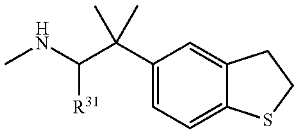
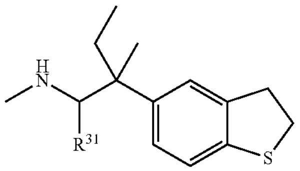
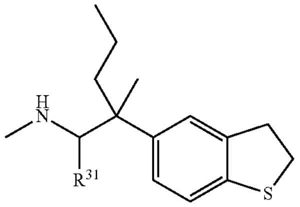
and
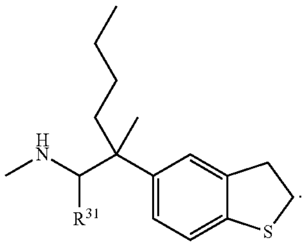
In certain embodiments, the compound of the present invention is selected from:
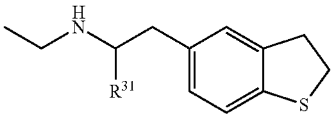
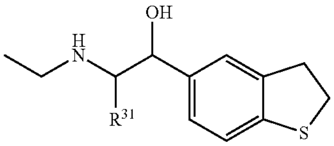
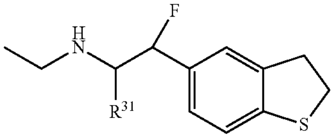
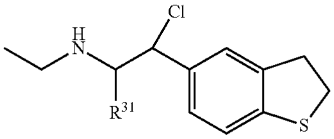
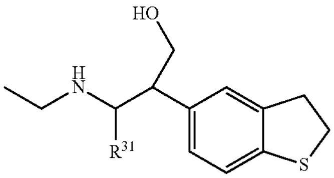
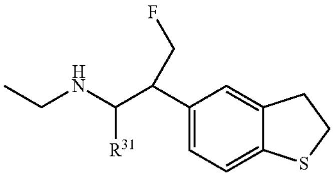
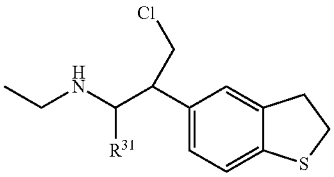
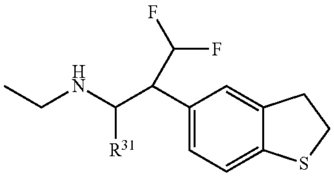
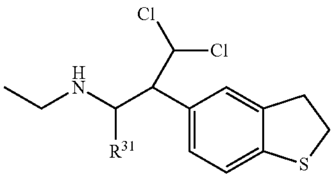
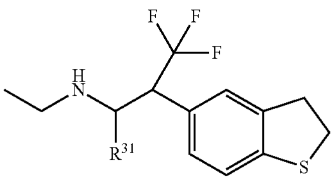

-continued
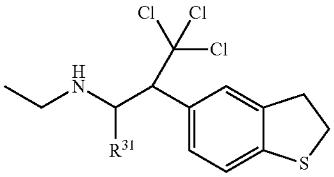
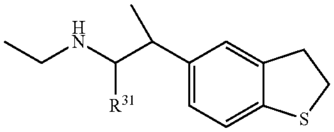
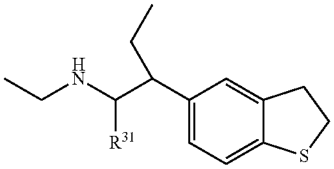
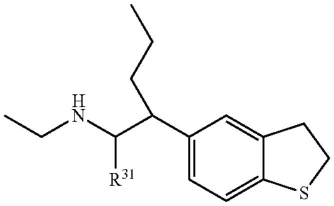
and
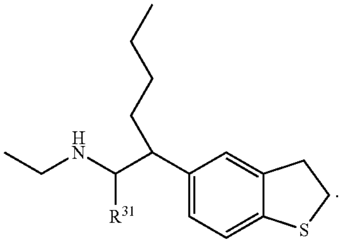
In certain embodiments, the compound of the present invention is selected from:
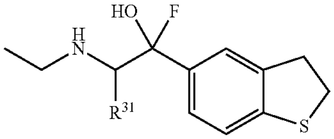
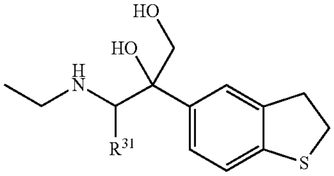
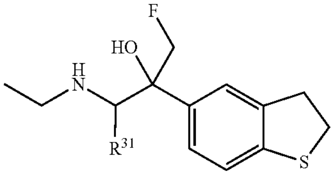
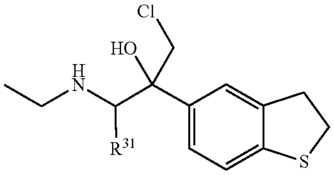
-continued
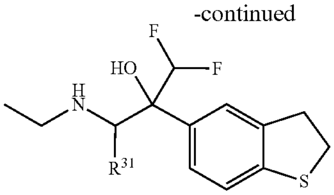
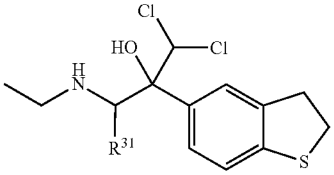
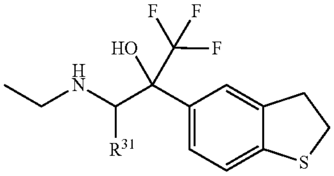
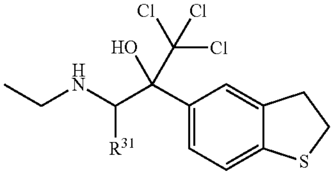
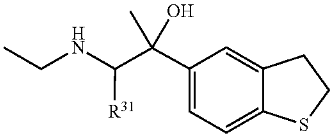
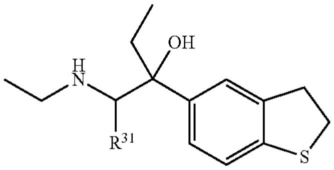
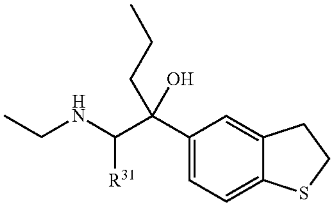
and
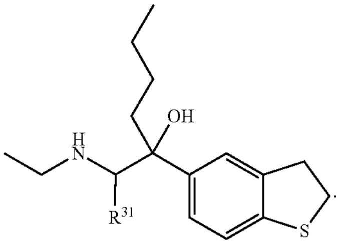
In certain embodiments, the compound of the present invention is selected from:
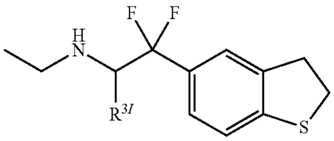

-continued
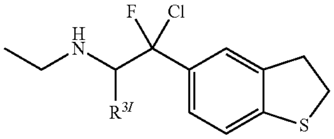
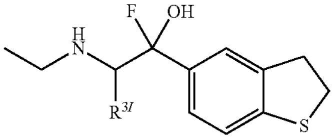
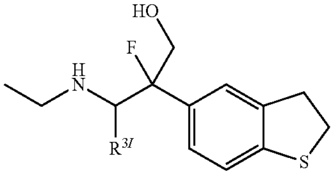
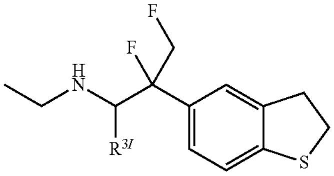
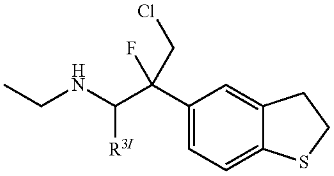
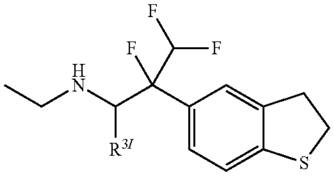
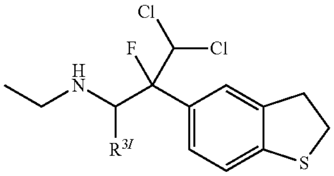
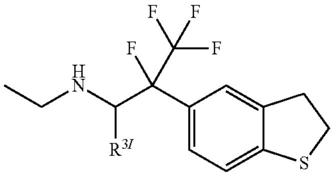
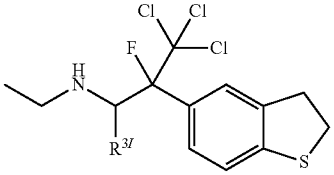
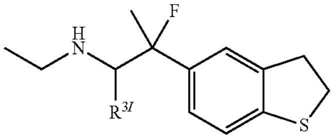
-continued
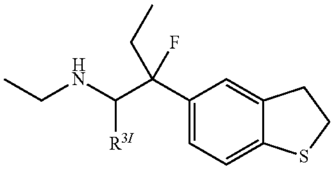
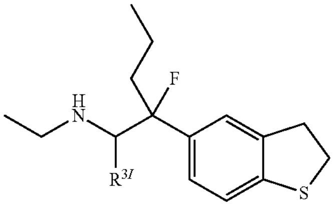
and
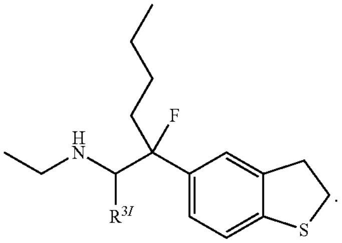
.
In certain embodiments, the compound of the present invention is selected from:
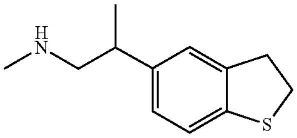
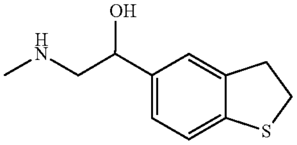
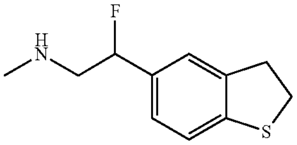
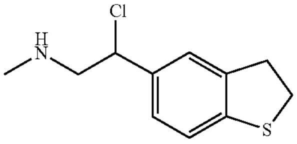
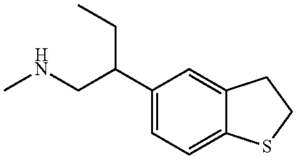
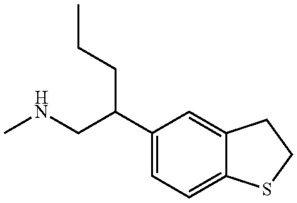

-continued
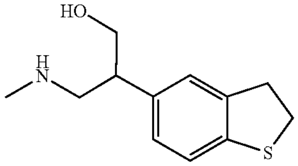
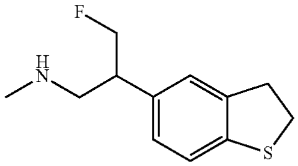
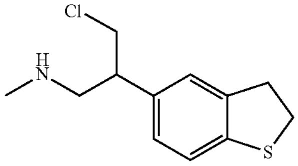
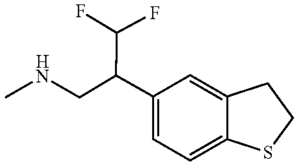
and
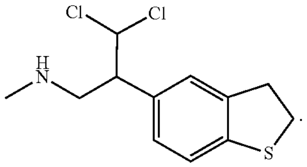
In certain embodiments, the compound of the present invention is selected from:
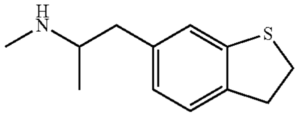
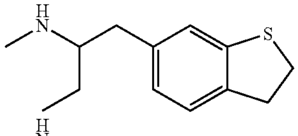
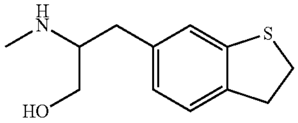
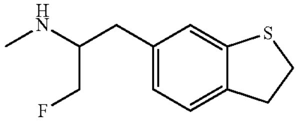
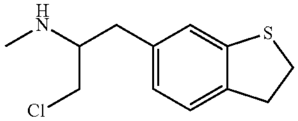
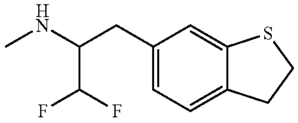
-continued
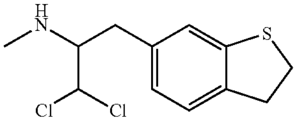
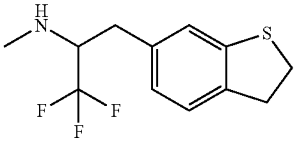
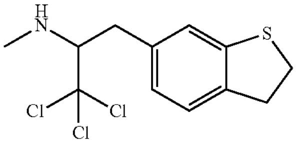
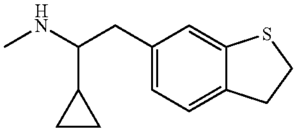
and
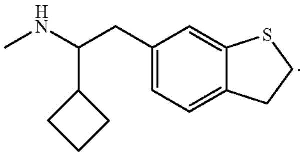
In certain embodiments, the compound of the present invention is selected from:
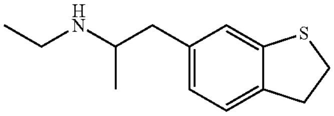
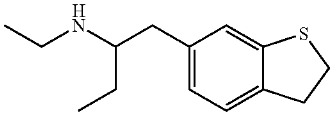
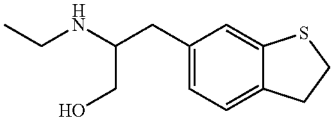
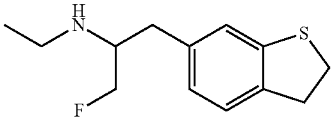
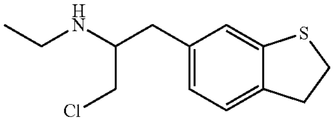
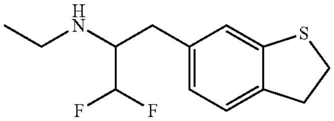
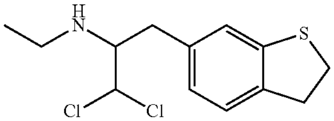

-continued
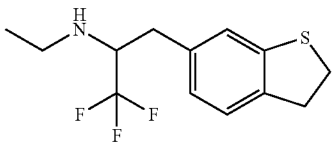
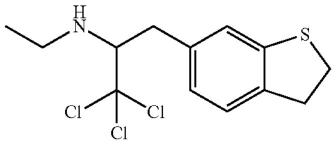
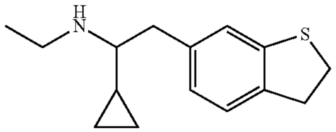
and
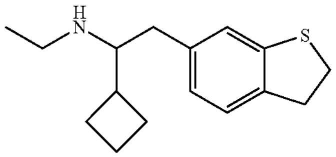
.
In certain embodiments, the compound of the present invention is selected from:
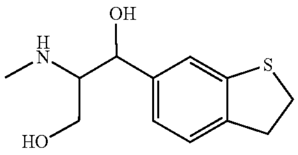
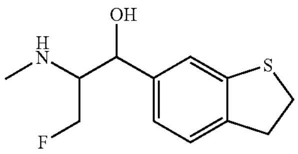
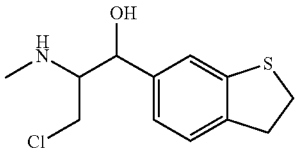
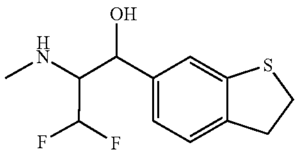
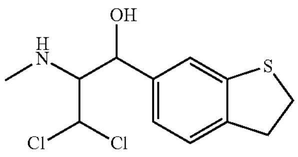
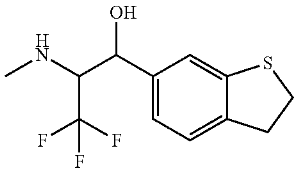
-continued
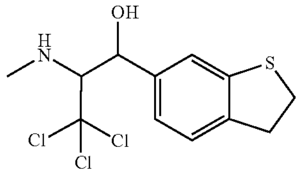
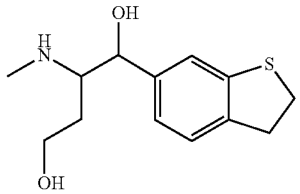
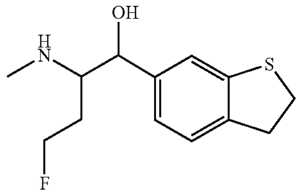
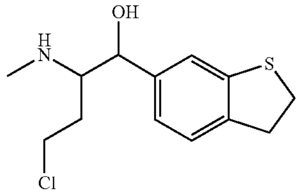
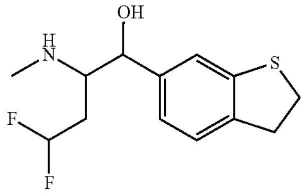
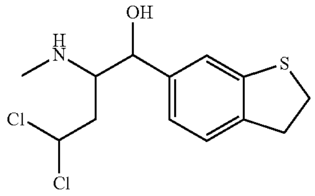
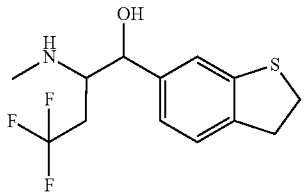
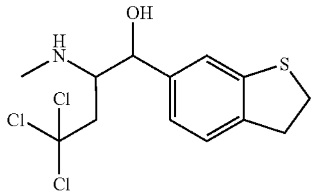
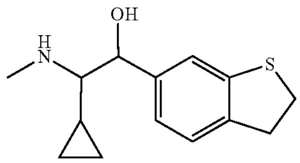

-continued
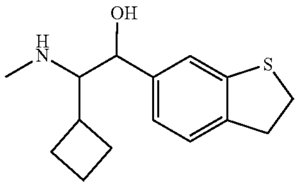
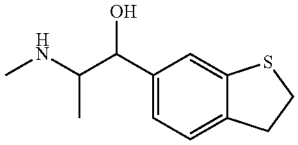
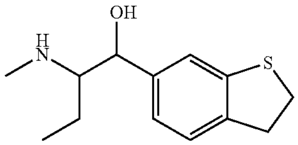
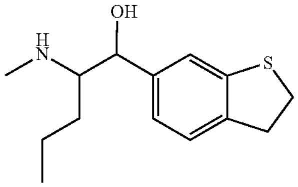
and
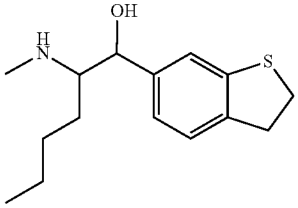
.
In certain embodiments, the compound of the present invention is selected from:
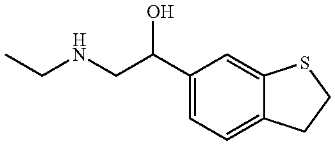
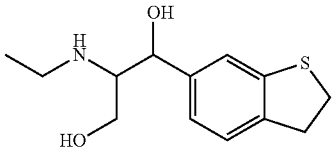
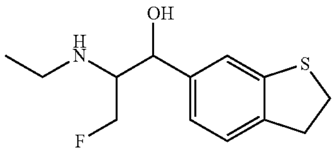
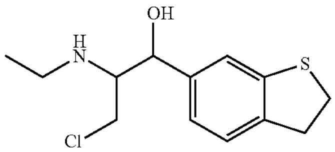
-continued
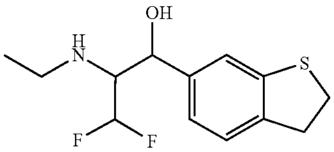
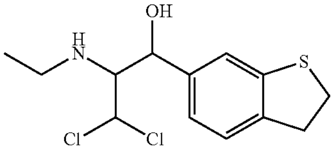
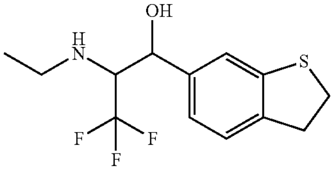
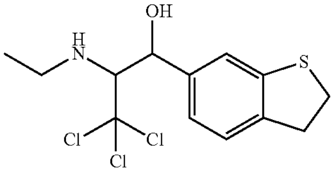
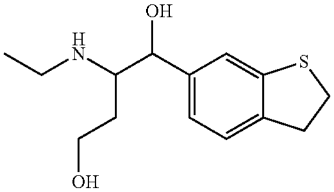
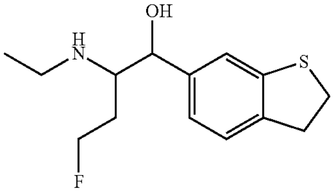
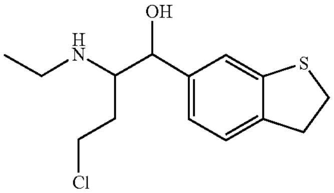
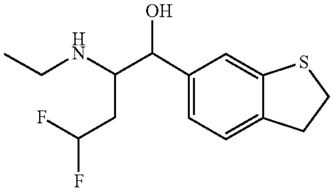
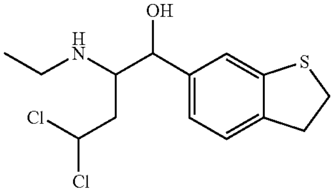

-continued
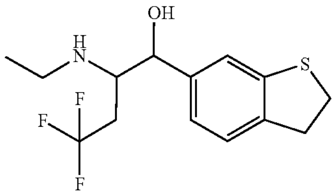
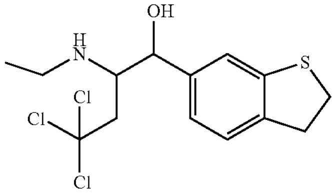
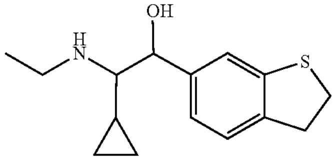
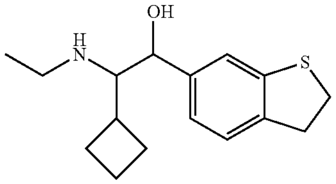
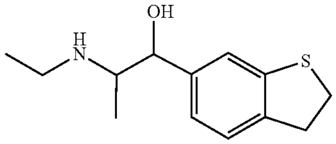
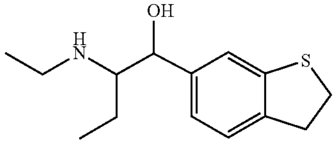
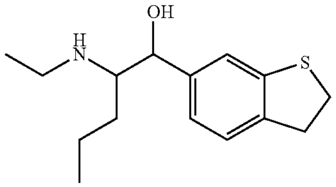
and
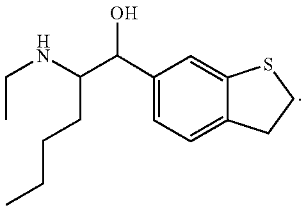
.
In certain embodiments, the compound of the present invention is selected from:
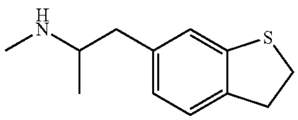
-continued
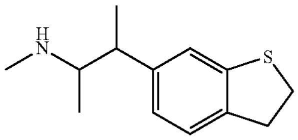
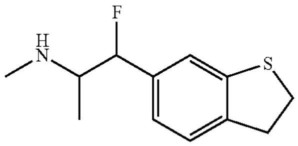
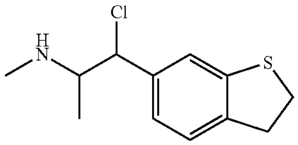
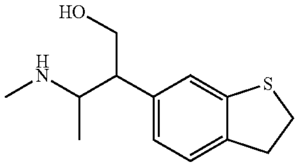
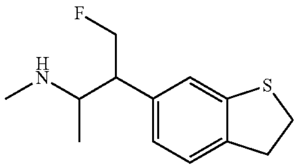
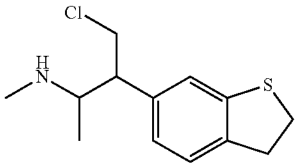
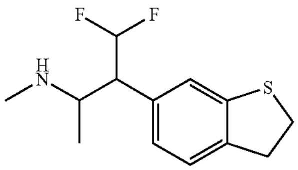
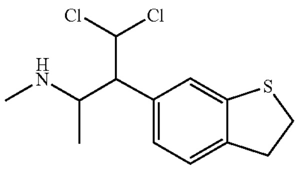
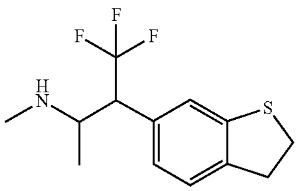
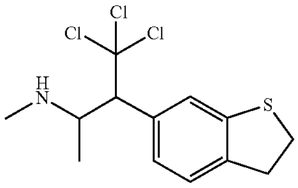

-continued
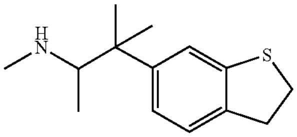
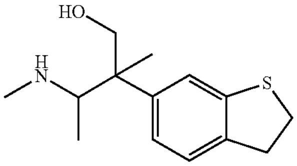
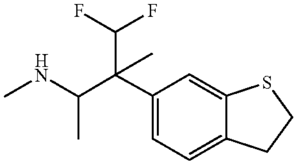
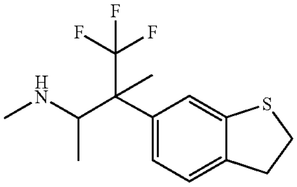
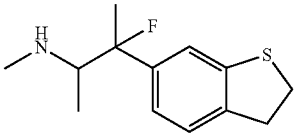
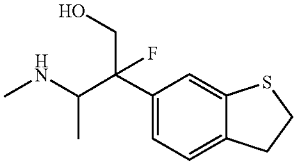
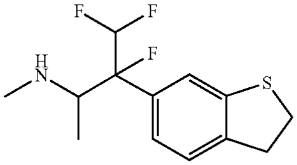
and
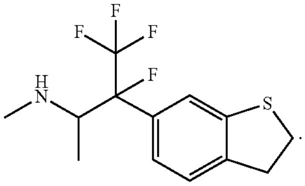
In certain embodiments, the compound of the present invention is selected from:
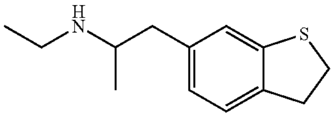
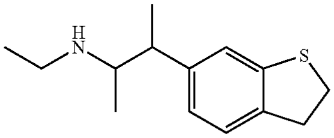
-continued
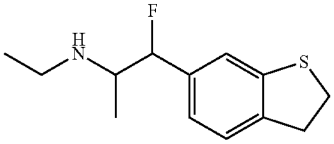
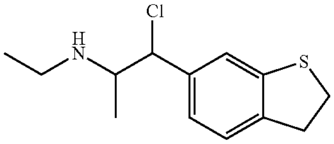
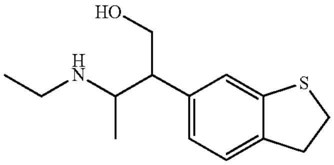
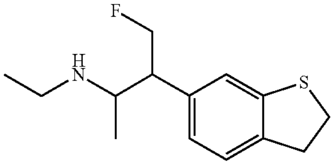
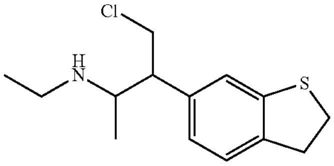
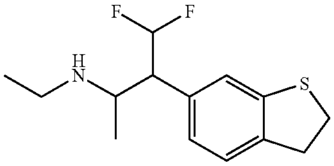
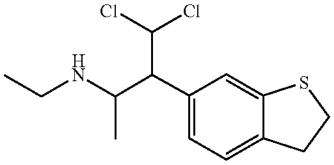
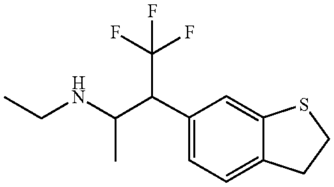
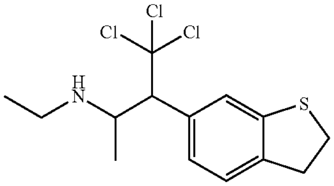
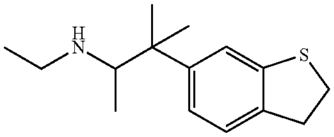

-continued
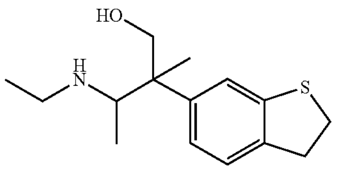
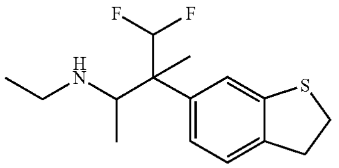
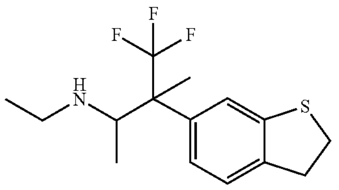
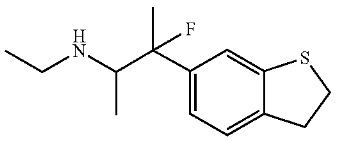
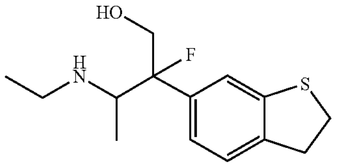
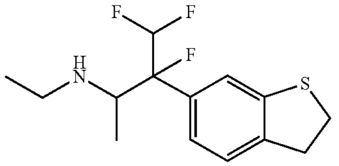
and
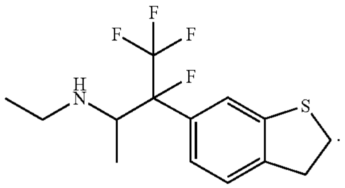
In certain embodiments, the compound of the present invention is selected from:
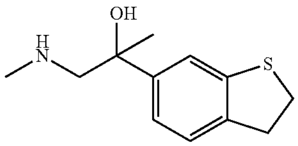
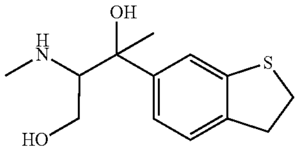
-continued
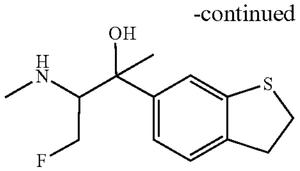
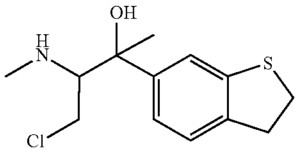
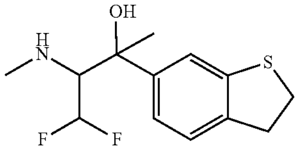
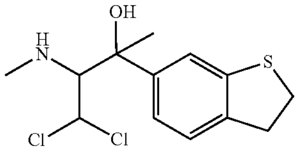
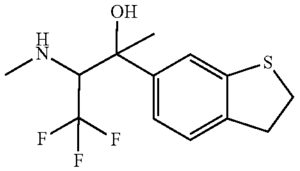
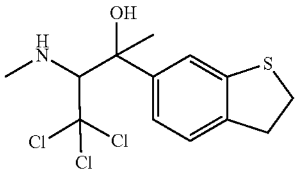
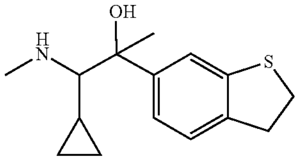
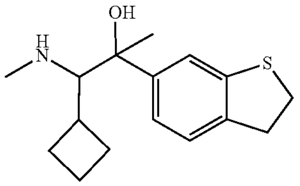
and
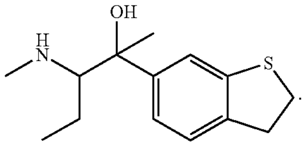
In certain embodiments, the compound of the present invention is selected from:
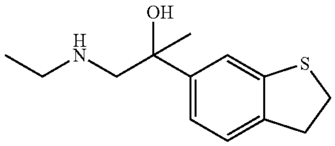

-continued
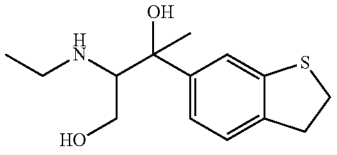
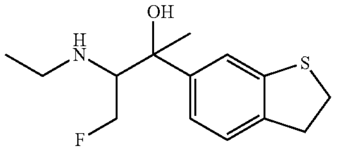
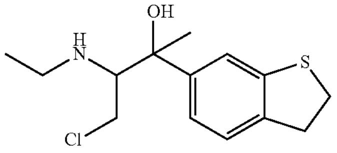
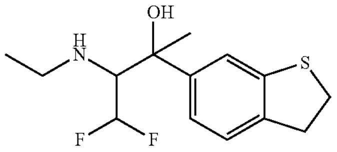
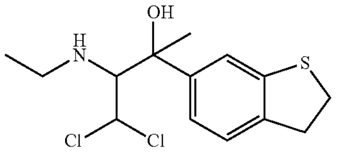
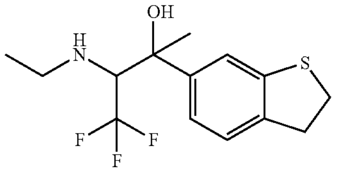
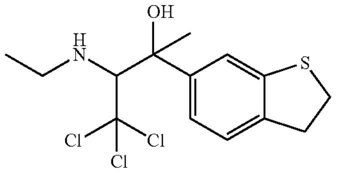
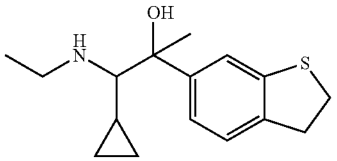
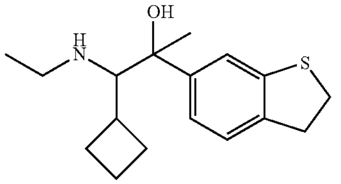
and
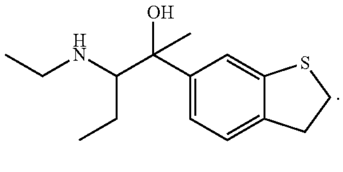
In certain embodiments, the compound of the present invention is selected from:
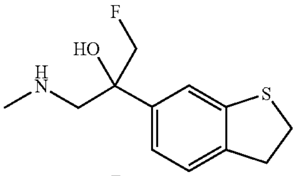
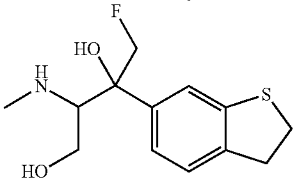
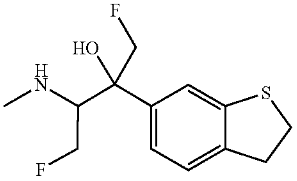
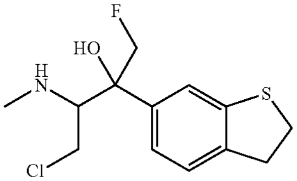
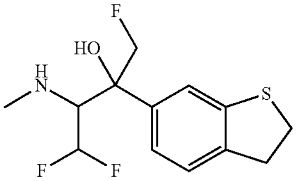
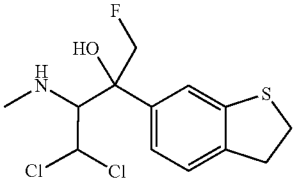
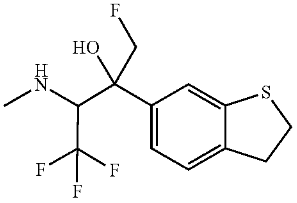
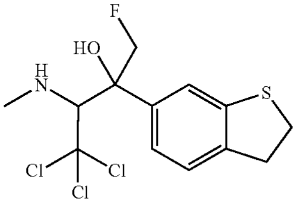
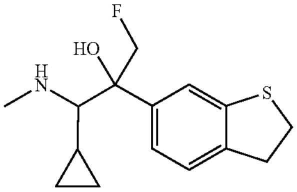

-continued
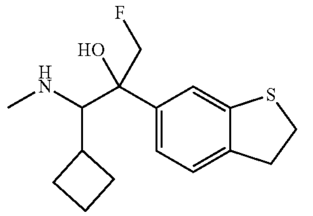
and
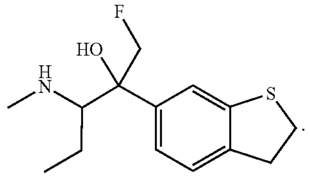
In certain embodiments, the compound of the present invention is selected from:
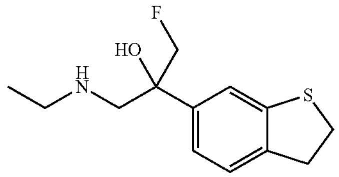
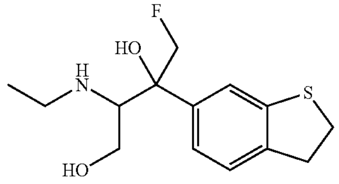
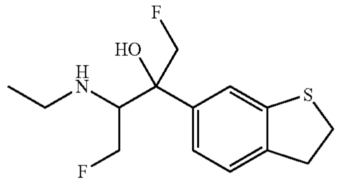
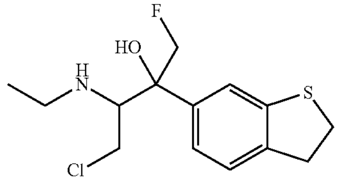
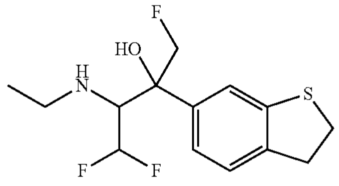
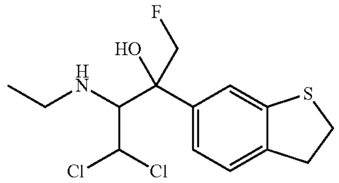
-continued
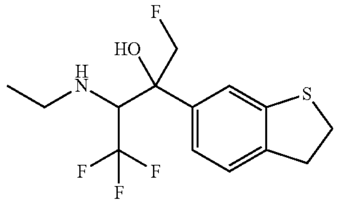
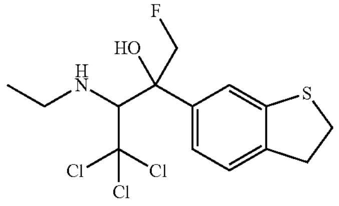
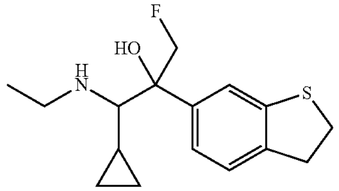
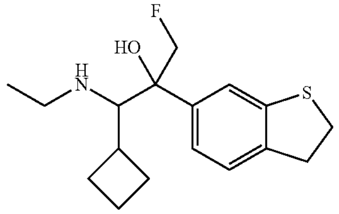
and
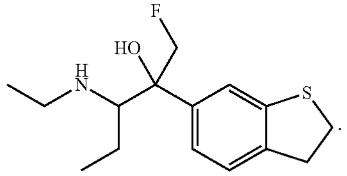
In certain embodiments, the compound of the present invention is selected from:
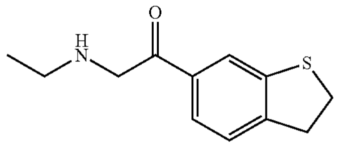
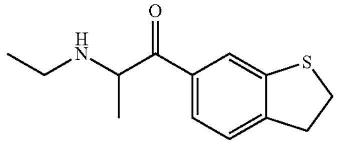
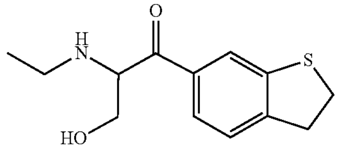
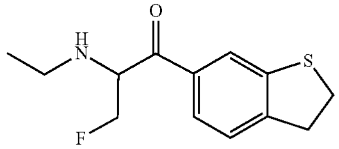

-continued
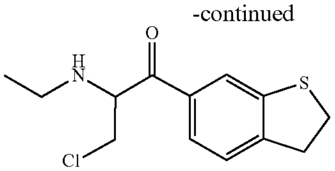
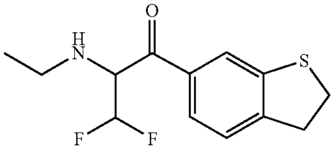
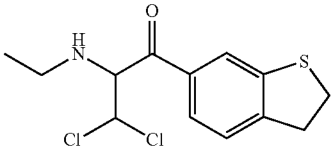
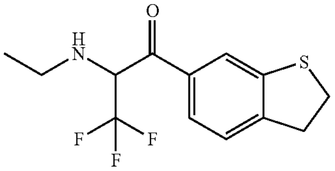
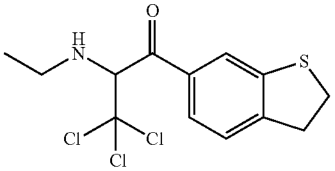
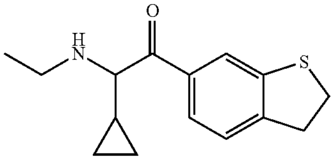
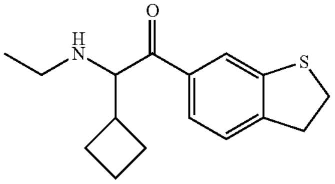
and
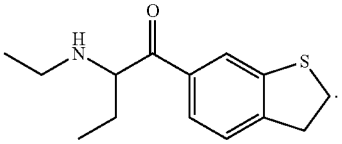 [SMILES: CCNC(CC)C(=O)c1ccc2c(c1)SCC2]
In certain embodiments, the compound of the present invention is selected from:
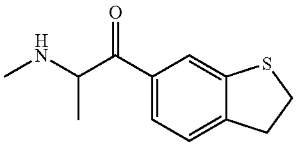
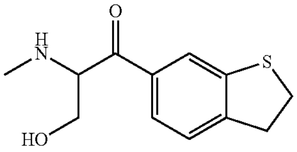
-continued
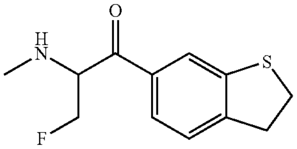
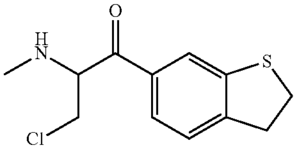
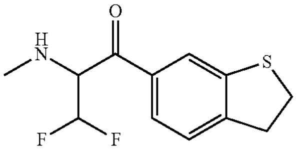
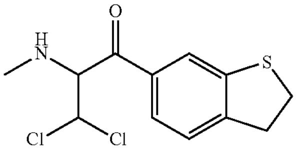
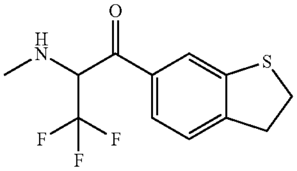
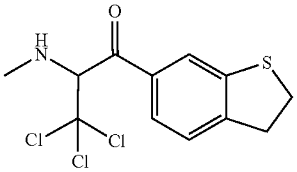
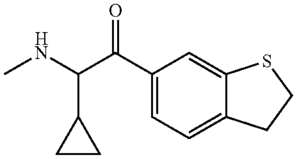
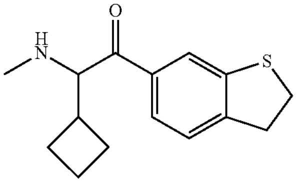
and
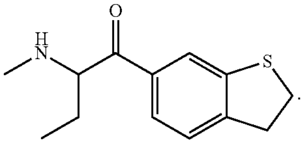 [SMILES: CCC(NC)C(=O)c1ccc2c(c1)SCC2]
In certain embodiments, the compound of the present invention is selected from:
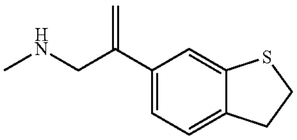

-continued
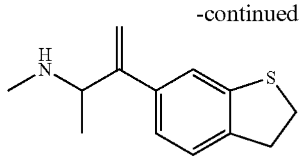
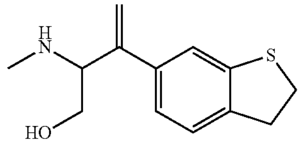
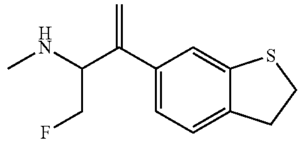
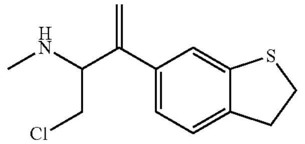
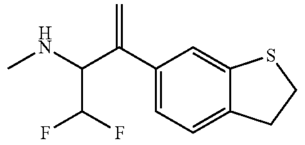
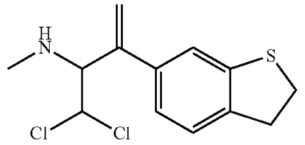
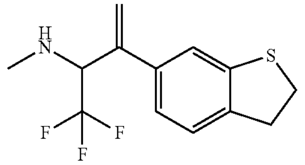
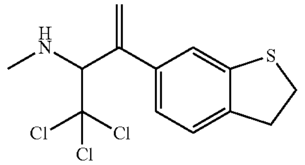
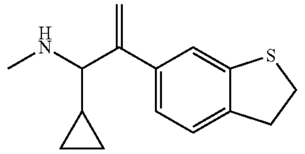
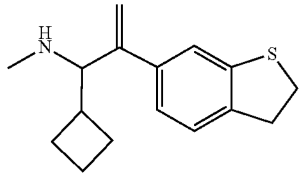
and
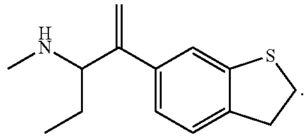 [SMILES: C=C(c1ccc2c(c1)SCC2)C(CC)NC]
In certain embodiments, the compound of the present invention is selected from:
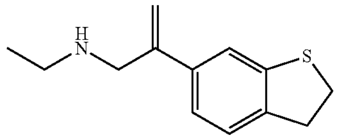
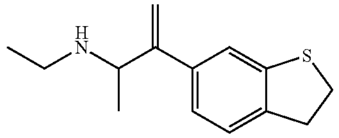
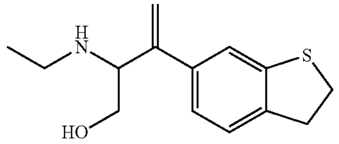
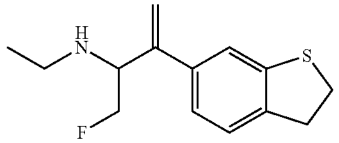
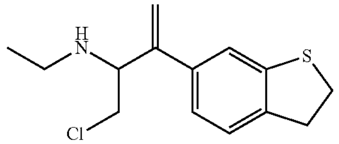
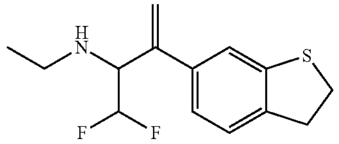
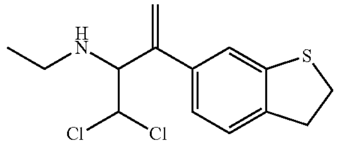
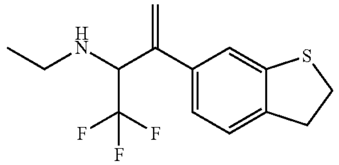
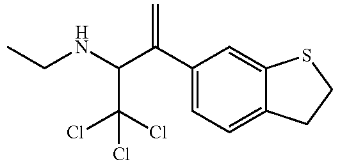
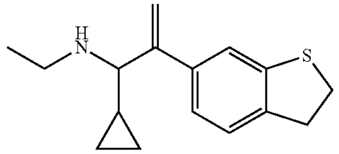
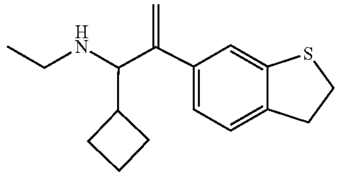
and -continued
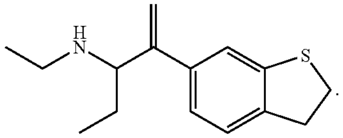 [SMILES: C=C(c1ccc2c(c1)SCC2)C(CC)NCC]
In certain embodiments, the compound of the present invention is selected from:
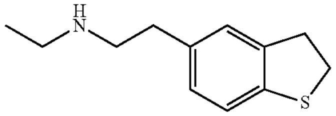
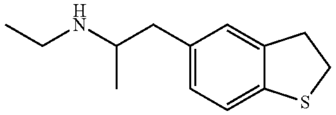
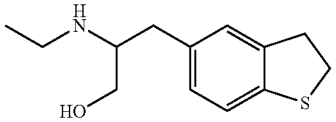
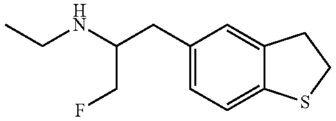
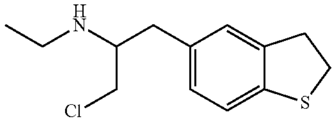
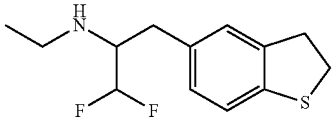
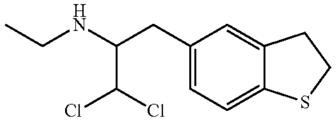
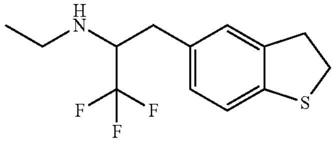
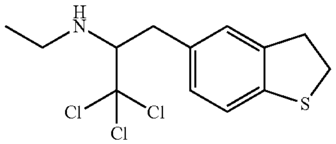
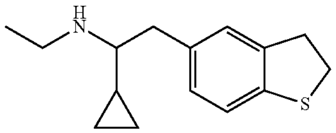
and
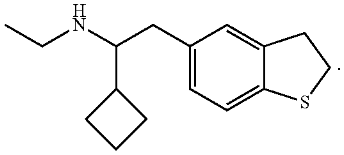
In certain embodiments, the compound of the present invention is selected from:
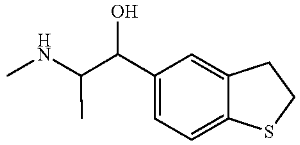
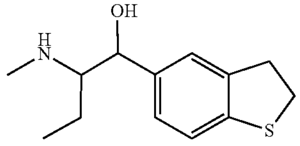
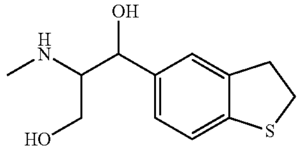
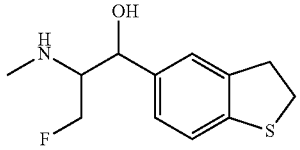
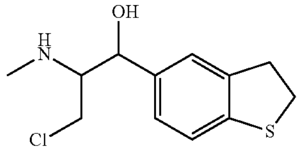
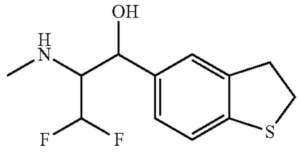
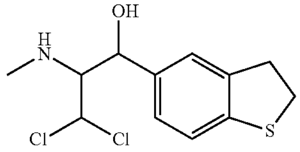
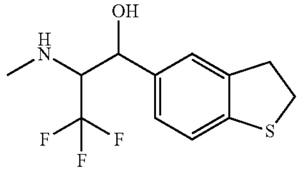
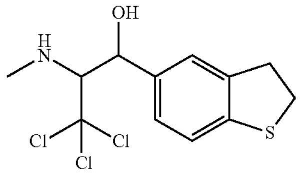
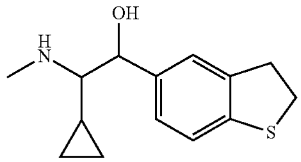
and -continued
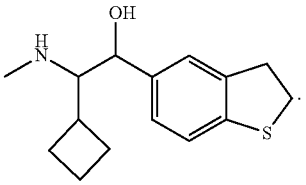
In certain embodiments, the compound of the present invention is selected from:
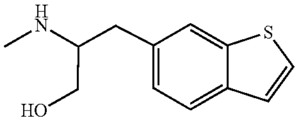
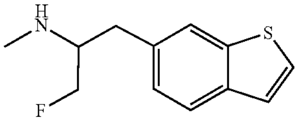
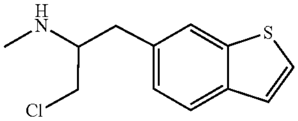
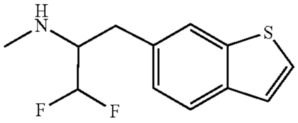
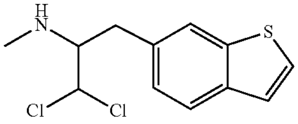
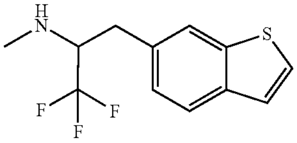
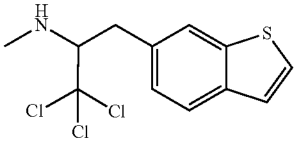
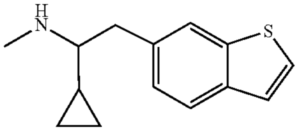
and
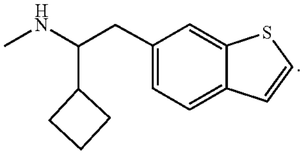
In certain embodiments, the compound of the present invention is selected from:
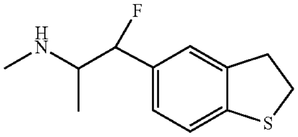
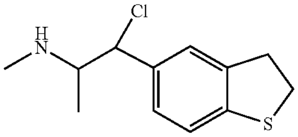
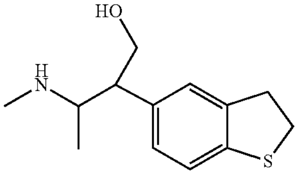
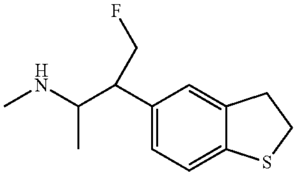
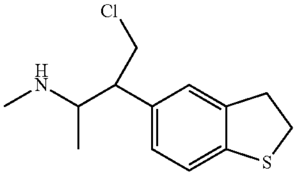
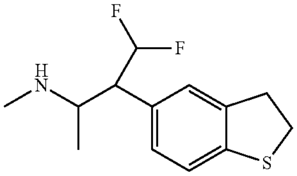
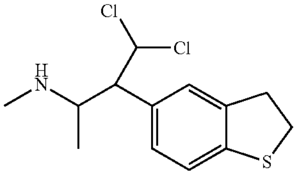
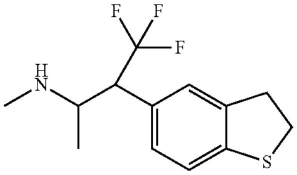
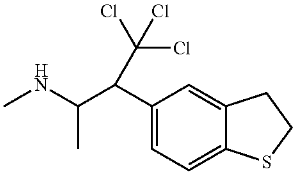
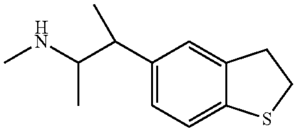

-continued
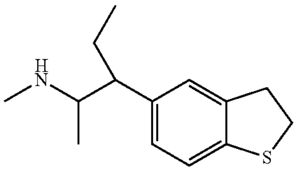
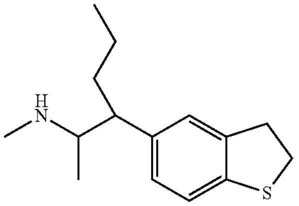
and
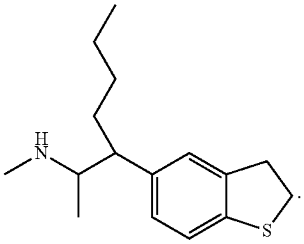
.
In certain embodiments, the compound of the present invention is selected from:
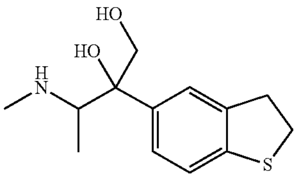
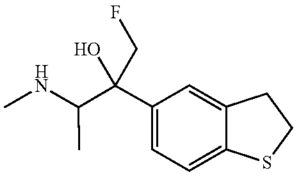
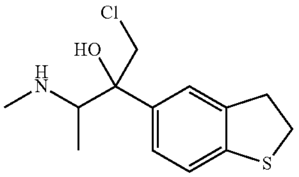
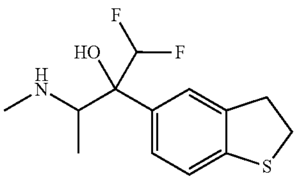
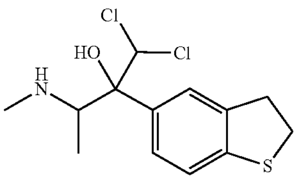
-continued
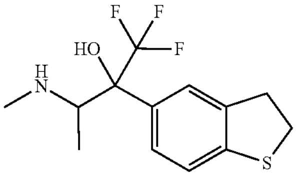
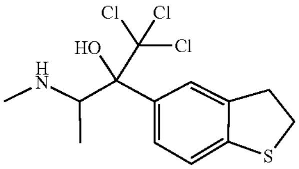
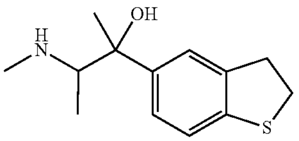
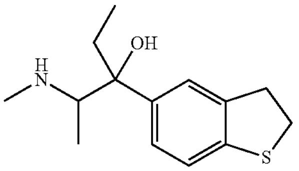
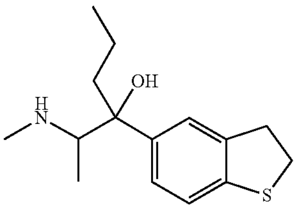
and
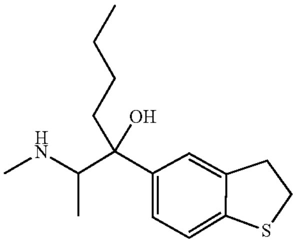
.
In certain embodiments the compound of the present invention is selected from:
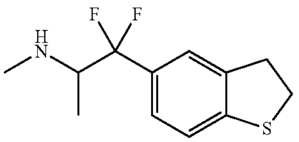
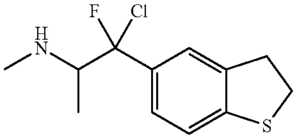
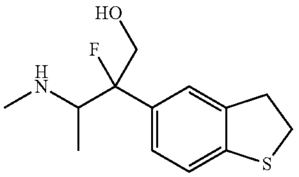

-continued
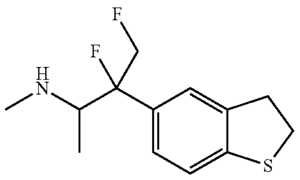
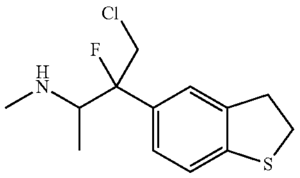
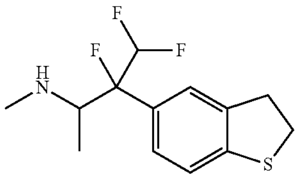
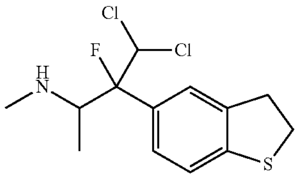
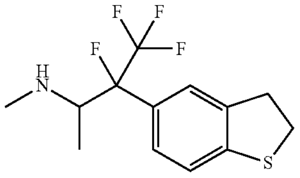
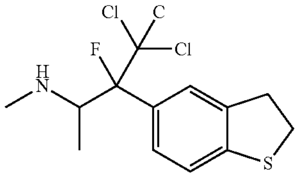
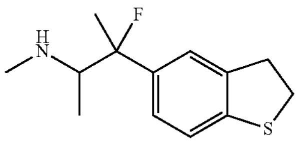
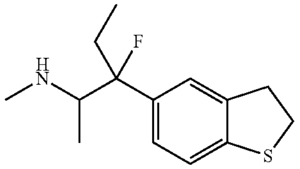
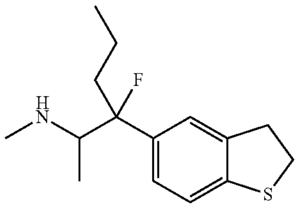
and
-continued
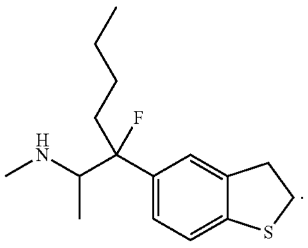
In certain embodiments, the compound of the present invention is selected from:
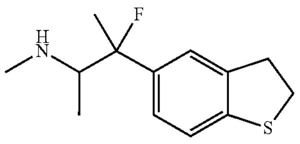
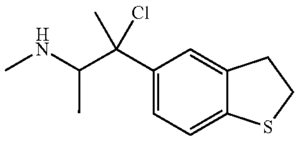
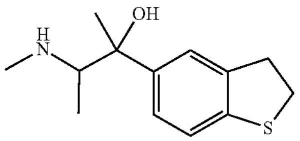
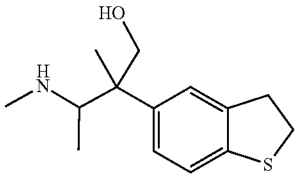
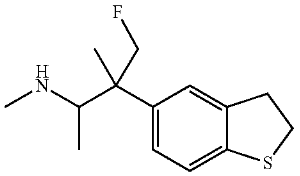
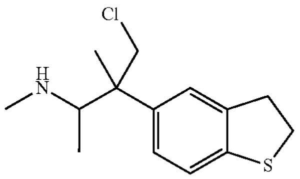
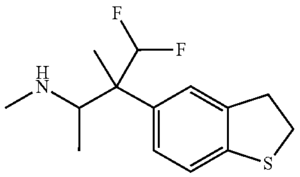
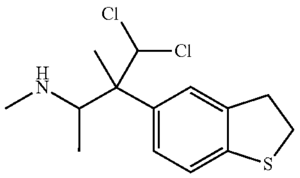

-continued
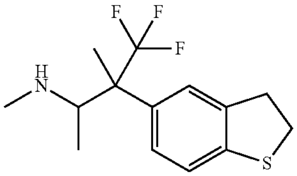
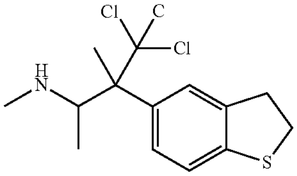
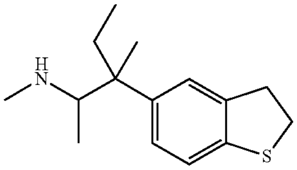
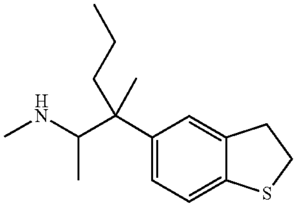
and
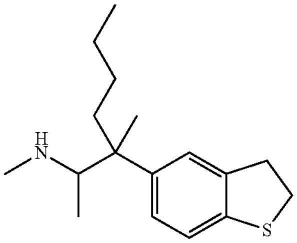
.
In certain embodiments, the compound of the present invention is selected from:
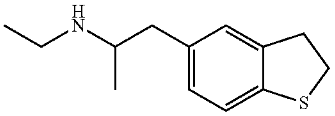
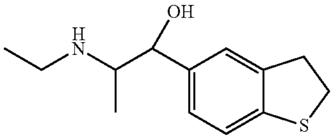
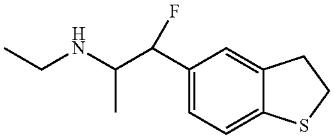
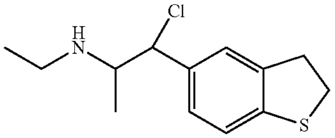
-continued
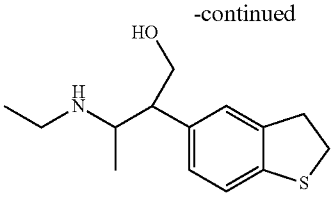
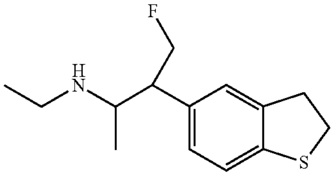
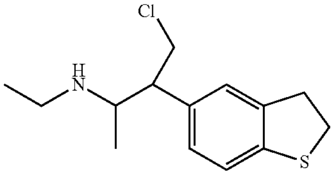
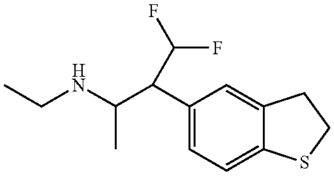
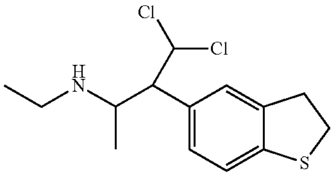
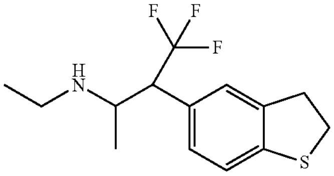
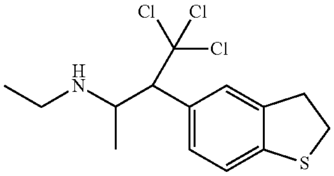
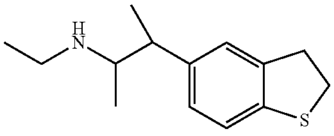
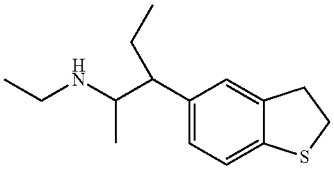
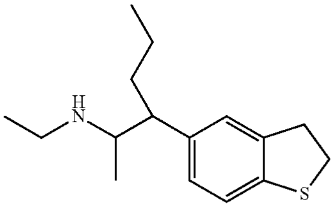
and -continued
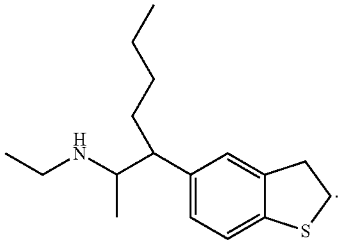
In certain embodiments, the compound of the present invention is selected from:
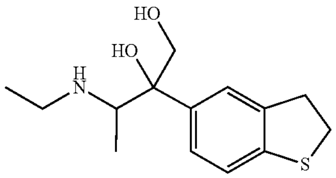
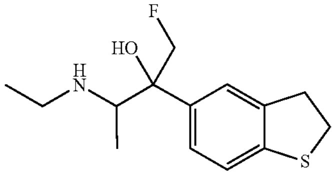
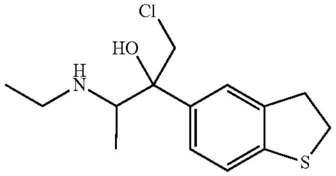
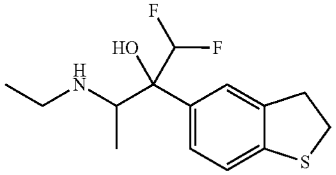
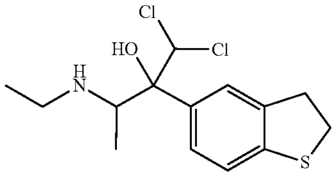
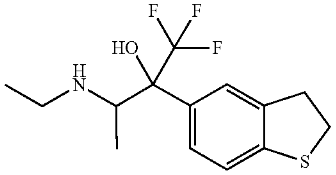
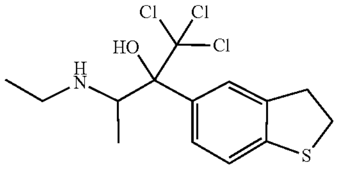
-continued
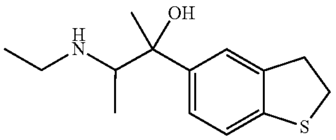
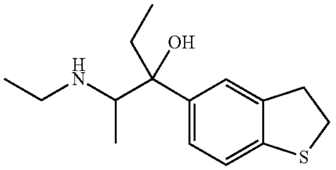
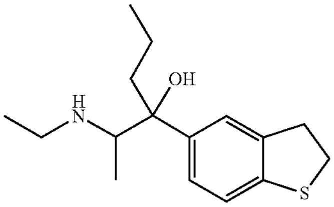
and
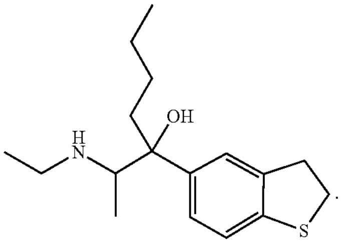 [SMILES: CCCCC(O)(c1ccc2c(c1)CCS2)C(C)NCC]
In certain embodiments, the compound of the present invention is selected from:
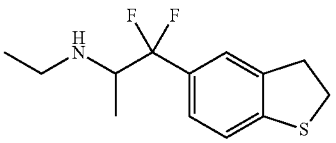
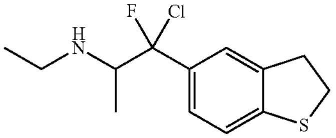
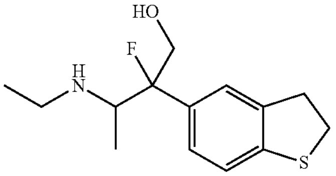
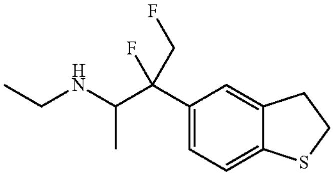
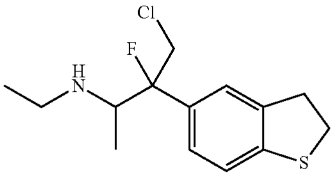

-continued
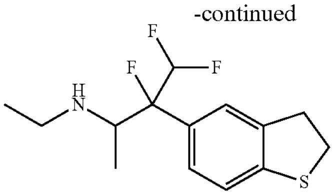
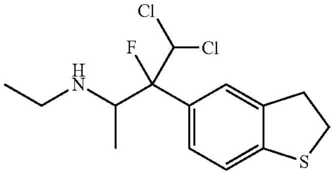
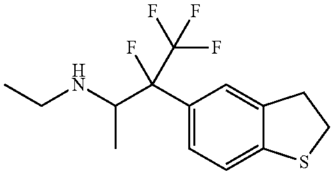
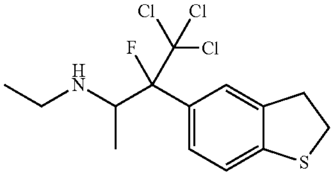
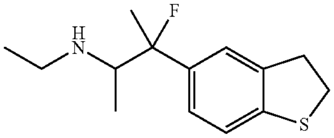
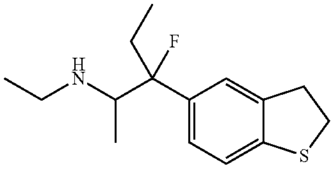
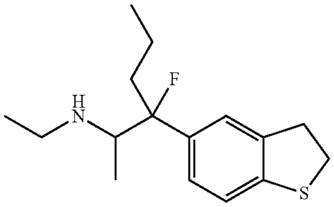
and
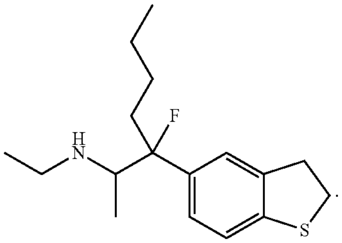
In certain embodiments, the compound of the present invention is selected from:
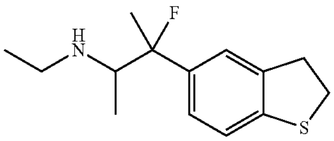
-continued
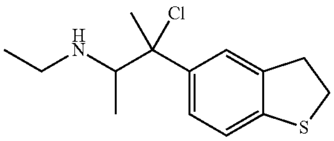
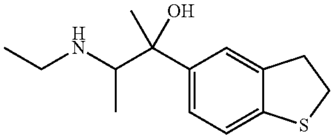
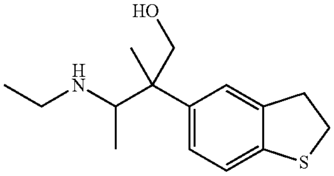
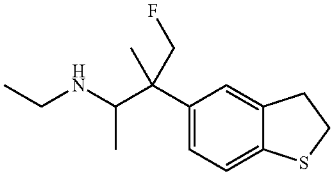
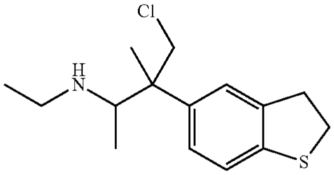
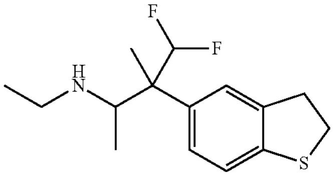
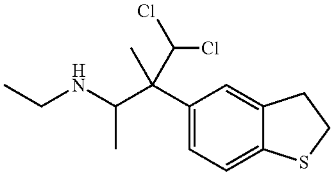
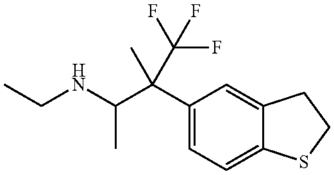
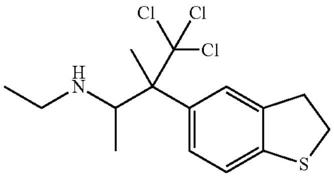
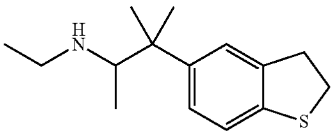

-continued

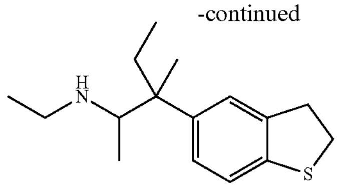

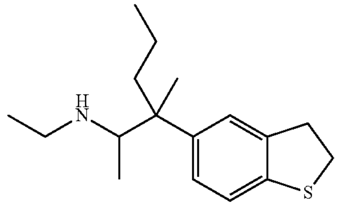

and

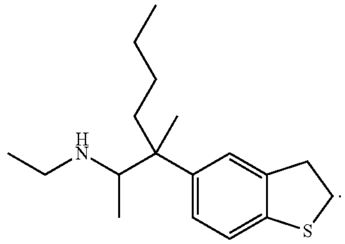

Certain compounds of the invention may also exist in several tautomeric forms including the enol form, the keto form, and mixtures thereof. Accordingly, the chemical structures depicted herein encompass all possible tautomeric forms of the illustrated compounds. Keto-enol tautomerism, for example, is the reversible transfer of a hydrogen from the alpha carbon adjacent to a carbonyl group followed by a double bond transfer. In solution, compounds will spontaneously undergo a kinetic transformation from one tautomer to the other until equilibrium is reached, generally strongly favoring the keto tautomer over the enol tautomer, but dependent on factors such as solvent, pH, and temperature. Keto and enol tautomers may have distinguishable physicochemical properties; however, because they will interconvert in solution, reference to a compound in its keto form (e.g., where $Q^2$ is

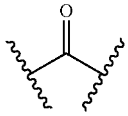

)

will be understood to refer to and include the compound in its enol form (e.g., where $Q^2$ is

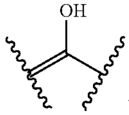

), unless context clearly indicates otherwise. The compounds may also exist as ring-chain tautomers, as discussed below.

Preparation of Enantiomeric Compounds

Various methods are known in the art for preparing optically active forms and determining activity. Such methods include standard processes described herein and other similar assays which are well known in the art. Examples of methods that can be used to obtain optical isomers of the compounds according to the present disclosure include but are not limited to the following:

a) physical separation of crystals whereby macroscopic crystals of the individual enantiomers are manually separated. This technique may particularly be used if crystals of the separate enantiomers exist (i.e., the material is a conglomerate), and the crystals are visually distinct;
b) simultaneous crystallization whereby the individual enantiomers are separately crystallized from a solution of the racemate, possible only if the latter is a conglomerate in the solid state;
c) enzymatic resolutions whereby partial or complete separation of a racemate by virtue of differing rates of reaction for the enantiomers with an enzyme;
d) enzymatic asymmetric synthesis, a synthetic technique whereby at least one step of the synthesis uses an enzymatic reaction to obtain an enantiomerically pure or enriched synthetic precursor of the desired enantiomer;
e) chemical asymmetric synthesis whereby the desired enantiomer is synthesized from an achiral precursor under conditions that produce asymmetry (i.e., chirality) in the product, which may be achieved using chiral catalysts or chiral auxiliaries;
f) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;
g) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;
h) kinetic resolutions comprising partial or complete resolution of a racemate (or of a further resolution of a partially resolved compound) by virtue of unequal reaction rates of the enantiomers with a chiral, enantiomerically enriched reagent or catalyst under kinetic conditions;
i) enantiospecific synthesis from enantiomerically enriched precursors whereby the desired enantiomer is obtained from non-chiral starting materials and where the stereochemical integrity is not or is only minimally compromised over the course of the synthesis;
j) chiral liquid chromatography whereby the enantiomers of a racemate are separated in a liquid mobile phase by virtue of their differing interactions with a stationary phase. The stationary phase can be made of chiral material, or the mobile phase can contain an additional chiral material to provoke the differing interactions;
k) chiral gas chromatography whereby the racemate is volatilized and enantiomers are separated by virtue of their differing interactions in the gaseous mobile phase with a column containing a fixed enantiomerically enriched chiral adsorbent phase;

l) extraction with chiral solvents whereby the enantiomers are separated by virtue of preferential dissolution of one enantiomer into a particular chiral solvent; and m) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the enantiomerically enriched chiral nature of the membrane, which allows only one enantiomer of the racemate to pass through.

Enantiomerically Enriched Pharmaceutical Compositions

Chiral compounds of the invention may be prepared by chiral chromatography from the racemic or enantiomerically enriched free amine. Pharmaceutically acceptable salts of chiral compounds may be prepared from fractional crystallization of salts from a racemic or an enantiomerically enriched free amine and a chiral acid. Alternatively, the free amine may be reacted with a chiral auxiliary and the enantiomers separated by chromatography followed by removal of the chiral auxiliary to regenerate the free amine. Furthermore, separation of enantiomers may be performed at any convenient point in the synthesis of the compounds of the invention. The compounds of the invention may also be prepared using a chiral synthesis.

An enantiomerically enriched mixture is a mixture that contains one enantiomer in a greater amount than the other. An enantiomerically enriched mixture of an S-enantiomer contains at least 55% of the S-enantiomer, and more typically at least about 60%, 65%, 70%, 75%, 80%, 85%, 90%, 95% of the S-enantiomer. An enantiomerically enriched mixture of an R-enantiomer contains at least 55% of the R-enantiomer, more typically at least about 55%, 60%, 65%, 70%, 75%, 80%, 85%, 90%, 95% of the R-enantiomer.

In one embodiment, enantiomerically enriched mixtures are created that have a greater amount of the nicotinic-receptor-dependent therapeutic effects. In one embodiment, enantiomerically enriched mixtures are created that have a greater amount of the serotonin-receptor-dependent therapeutic effects.

In one embodiment, enantiomerically enriched mixtures are created that have a greater amount of the dopaminergic effects. In one embodiment, enantiomerically enriched mixtures are created that have a greater amount of the serotonin-receptor-dependent therapeutic effects.

Non-limiting examples of unwanted effects that can be minimized include psychoactive effects (such as excess stimulation or sedation), physiological effects (such as transient hypertension or appetite suppression), toxic effects (such as to the brain or liver), effects contributing to abuse liability (such as euphoria or dopamine release), and other side effects.

One aspect of the present invention is a balanced mixture of S-5-MAPBT and R-5-MAPBT (not the racemate) or a balanced mixture of S-6-MAPBT and R-6-MAPBT (including possibly the racemate) that achieves a predetermined combination of serotonin-receptor-dependent therapeutic effects and nicotinic-receptor-dependent therapeutic effects.

One aspect of the present invention is a balanced mixture of S-5-MAPBT and R-5-MAPBT (not the racemate) or a balanced mixture of S-6-MAPBT and R-6-MAPBT (including possibly the racemate) that achieves a predetermined combination of serotonin-receptor-dependent therapeutic effects and dopaminergic effects.

In certain embodiments, pharmaceutical compositions of enantiomerically enriched preparations of 5-MAPBT or 6-MAPBT are provided. In one embodiment, the pharmaceutical composition is enriched with S-5-MAPBT. In one embodiment, the pharmaceutical composition is enriched with R-5-MAPBT. In one embodiment, the pharmaceutical composition is enriched with S-6-MAPBT. In one embodiment, the pharmaceutical composition is enriched with R-6-MAPBT.

Example 2 provides non-limiting examples for the preparation of certain enantiomerically enriched preparations of 5-MAPBT (i.e., comprising S-5-MAPBT and R-5-MAPBT). Enantiomerically enriched preparations of 6-MAPBT (i.e., S-6-MAPBT, R-6-MAPBT) can be similarly produced using racemic 6-MAPBT HCl.

Particular embodiments for pharmaceutical compositions, including enantiomerically enriched pharmaceutical compositions, of the present invention include:

a) S-5-MAPBT;
b) R-5-MAPBT;
c) S-6-MAPBT;
d) R-6-MAPBT;
e) Embodiments (a)-(d) wherein the compound is a free base;
f) Embodiments (a)-(d) wherein the compound is a salt;
g) Embodiment (f) wherein the compound is the hydrochloride salt;
h) A mixture of S-5-MAPBT, R-5-MAPBT and there is more S-enantiomer than R-enantiomer;
i) A mixture of S-5-MAPBT, R-5-MAPBT and there is less S-enantiomer than R-enantiomer;
j) A mixture of S-6-MAPBT, R-6-MAPBT and there is more S-enantiomer than R-enantiomer;
k) A mixture of S-6-MAPBT, R-6-MAPBT and there is less S-enantiomer than R-enantiomer;
l) A mixture of S-5-MAPBT, R-5-MAPBT and at least about 65% is the S-enantiomer while no more than 35% is the R-enantiomer;
m) A mixture of S-5-MAPBT, R-5-MAPBT and greater than 65% is the S-enantiomer while less than 35% is the R-enantiomer;
n) A mixture of S-5-MAPBT, R-5-MAPBT and greater than 90% is the S-enantiomer while less than 10% is the R-enantiomer;
o) A mixture of S-5-MAPBT, R-5-MAPBT and at least about 35% is the S-enantiomer while not more than 65% is the R-enantiomer;
p) A mixture of S-5-MAPBT, R-5-MAPBT and less than 35% is the S-enantiomer while greater than 65% is the R-enantiomer;
q) A mixture of S-5-MAPBT, R-5-MAPBT and less than 10% is the S-enantiomer while greater than 90% is the R-enantiomer;
r) A mixture of S-6-MAPBT, R-6-MAPBT and at least about 65% is the S-enantiomer while no more than 35% is the R-enantiomer;
s) A mixture of S-6-MAPBT, R-6-MAPBT and at least about 65% is the S-enantiomer while not more than 35% is the R-enantiomer;
t) A mixture of S-6-MAPBT, R-6-MAPBT and at least about than 90% is the S-enantiomer while not more than 10% is the R-enantiomer;
u) A mixture of S-6-MAPBT, R-6-MAPBT and 35% or less is the S-enantiomer while 65% or more is the R-enantiomer;
v) A mixture of S-6-MAPBT, R-6-MAPBT and at least about 35% is the S-enantiomer while not more than 65% is the R-enantiomer; and w) A mixture of S-6-MAPBT, R-6-MAPBT and less than 10% is the S-enantiomer while greater than 90% is the R-enantiomer.
x) S-5-MBPBT;
y) R-5-MBPBT;
z) S-6-MBPBT;
aa) R-6-MBPBT;
bb) Embodiments (x)-(aa) wherein the compound is a free base;
cc) Embodiments (x)-(aa) wherein the compound is a salt;
dd) Embodiment (cc) wherein the compound is the hydrochloride salt;
ee) A mixture of S-5-MBPBT, R-5-MBPBT and there is more S-enantiomer than R-enantiomer;
ff) A mixture of S-5-MBPBT, R-5-MBPBT and there is less S-enantiomer than R-enantiomer;
gg) A mixture of S-6-MBPBT, R-6-MBPBT and there is more S-enantiomer than R-enantiomer;
hh) A mixture of S-6-MBPBT, R-6-MBPBT and there is less S-enantiomer than R-enantiomer;
ii) A mixture of S-5-MBPBT, R-5-MBPBT and at least about 65% is the S-enantiomer while not more than 35% is the R-enantiomer;
jj) A mixture of S-5-MBPBT, R-5-MBPBT and greater than about 65% is the S-enantiomer while less than about 35% is the R-enantiomer;
kk) A mixture of S-5-MBPBT, R-5-MBPBT and greater than about 90% is the S-enantiomer while less than about 10% is the R-enantiomer;
ll) A mixture of S-5-MBPBT, R-5-MBPBT and at least about 35% is the S-enantiomer while not more than 65% is the R-enantiomer;
mm) A mixture of S-5-MBPBT, R-5-MBPBT and less than about 35% is the S-enantiomer while greater than about 65% is the R-enantiomer;
nn) A mixture of S-5-MBPBT, R-5-MBPBT and less than about 10% is the S-enantiomer while greater than about 90% is the R-enantiomer;
oo) A mixture of S-6-MBPBT, R-6-MBPBT and at least about 65% is the S-enantiomer while not more than 35% is the R-enantiomer;
pp) A mixture of S-6-MBPBT, R-6-MBPBT and greater than about 65% is the S-enantiomer while less than about 35% is the R-enantiomer;
qq) A mixture of S-6-MBPBT, R-6-MBPBT and greater than about 90% is the S-enantiomer while less than about 10% is the R-enantiomer;
rr) A mixture of S-6-MBPBT, R-6-MBPBT and at least about 35% or less is the S-enantiomer while not more than 65% or more is the R-enantiomer;
ss) A mixture of S-6-MBPBT, R-6-MBPBT and about 35% is the S-enantiomer while about 65% is the R-enantiomer; and
tt) A mixture of S-6-MBPBT, R-6-MBPBT and less than about 10% is the S-enantiomer while greater than about 90% is the R-enantiomer.
uu) S-Bk-5-MAPBT;
vv) R-Bk-5-MAPBT;
ww) S-Bk-6-MAPBT;
xx) R-Bk-6-MAPBT;
yy) Embodiments (uu)-(xx) wherein the compound is a free base;
zz) Embodiments (uu)-(xx) wherein the compound is a salt;
aaa) Embodiment (zz) wherein the compound is the hydrochloride salt;
bbb) A mixture of S-Bk-5-MAPBT, R-Bk-5-MAPBT and there is more S-enantiomer than R-enantiomer;
ccc) A mixture of S-Bk-5-MAPBT, R-Bk-5-MAPBT and there is less S-enantiomer than R-enantiomer;
ddd) A mixture of S-Bk-6-MAPBT, R-Bk-6-MAPBT and there is more S-enantiomer than R-enantiomer;
eee) A mixture of S-Bk-6-MAPBT, R-Bk-6-MAPBT and there is less S-enantiomer than R-enantiomer;
fff) A mixture of S-Bk-5-MAPBT, R-Bk-5-MAPBT and at least about 65% is the S-enantiomer while not more than 35% is the R-enantiomer;
ggg) A mixture of S-Bk-5-MAPBT, R-Bk-5-MAPBT and greater than about 65% is the S-enantiomer while less than about 35% is the R-enantiomer;
hhh) A mixture of S-Bk-5-MAPBT, R-Bk-5-MAPBT and greater than about 90% is the S-enantiomer while less than about 10% is the R-enantiomer;
iii) A mixture of S-Bk-5-MAPBT, R-Bk-5-MAPBT and about 35% is the S-enantiomer while about 65% is the R-enantiomer;
jjj) A mixture of S-Bk-5-MAPBT, R-Bk-5-MAPBT and less than about 35% is the S-enantiomer while greater than about 65% is the R-enantiomer;
kkk) A mixture of S-Bk-5-MAPBT, R-Bk-5-MAPBT and less than about 10% is the S-enantiomer while greater than about 90% is the R-enantiomer;
lll) A mixture of S-Bk-6-MAPBT, R-Bk-6-MAPBT and at least about 65% is the S-enantiomer while not more than 35% is the R-enantiomer;
mmm) A mixture of S-Bk-6-MAPBT, R-Bk-6-MAPBT and greater than about 65% is the S-enantiomer while less than about 35% is the R-enantiomer;
nnn) A mixture of S-Bk-6-MAPBT, R-Bk-6-MAPBT and greater than about 90% is the S-enantiomer while less than about 10% is the R-enantiomer;
ooo) A mixture of S-Bk-6-MAPBT, R-Bk-6-MAPBT and at least about 35% or less is the S-enantiomer while not more than 65% or more is the R-enantiomer;
ppp) A mixture of S-Bk-6-MAPBT, R-Bk-6-MAPBT and at least about 35% is the S-enantiomer while not more than 65% is the R-enantiomer; and
qqq) A mixture of S-Bk-6-MAPBT, R-Bk-6-MAPBT and less than about 10% is the S-enantiomer while greater than about 90% is the R-enantiomer.
rrr) S-Bk-5-MBPBT;
sss) R-Bk-5-MBPBT;
ttt) S-Bk-6-MBPBT;
uuu) R-Bk-6-MBPBT;
vvv) Embodiments (rrr)-(uuu) wherein the compound is a free base;
www) Embodiments (rrr)-(uuu) wherein the compound is a salt;
xxx) Embodiment (www) wherein the compound is the hydrochloride salt;
yyy) A mixture of S-Bk-5-MBPBT, R-Bk-5-MBPBT and there is more S-enantiomer than R-enantiomer;
zzz) A mixture of S-Bk-5-MBPBT, R-Bk-5-MBPBT and there is less S-enantiomer than R-enantiomer;
aaaa) A mixture of S-Bk-6-MBPBT, R-Bk-6-MBPBT and there is more S-enantiomer than R-enantiomer;
bbbb) A mixture of S-Bk-6-MBPBT, R-Bk-6-MBPBT and there is less S-enantiomer than R-enantiomer;
cccc) A mixture of S-Bk-5-MBPBT, R-Bk-5-MBPBT and at least about 65% is the S-enantiomer while not more than 35% is the R-enantiomer;

dddd) A mixture of S-Bk-5-MBPBT, R-Bk-5-MBPBT and greater than about 65% is the S-enantiomer while less than about 35% is the R-enantiomer;

eeee) A mixture of S-Bk-5-MBPBT, R-Bk-5-MBPBT and greater than about 90% is the S-enantiomer while less than about 10% is the R-enantiomer;

ffff) A mixture of S-Bk-5-MBPBT, R-Bk-5-MBPBT and about 35% is the S-enantiomer while about 65% is the R-enantiomer;

gggg) A mixture of S-Bk-5-MBPBT, R-Bk-5-MBPBT and less than about 35% is the S-enantiomer while greater than about 65% is the R-enantiomer;

hhhh) A mixture of S-Bk-5-MBPBT, R-Bk-5-MBPBT and less than about 10% is the S-enantiomer while greater than about 90% is the R-enantiomer;

iiii) A mixture of S-Bk-6-MBPBT, R-Bk-6-MBPBT and at least about 65% is the S-enantiomer while not more than 35% is the R-enantiomer;

jjjj) A mixture of S-Bk-6-MBPBT, R-Bk-6-MBPBT and greater than about 65% is the S-enantiomer while less than about 35% is the R-enantiomer;

kkkk) A mixture of S-Bk-6-MBPBT, R-Bk-6-MBPBT and greater than about 90% is the S-enantiomer while less than about 10% is the R-enantiomer;

llll) A mixture of S-Bk-6-MBPBT, R-Bk-6-MBPBT and about 35% or less is the S-enantiomer while about 65% or more is the R-enantiomer;

mmmm) A mixture of S-Bk-6-MBPBT, R-Bk-6-MBPBT and at least about 35% is the S-enantiomer while not more than 65% is the R-enantiomer; and nnnn) A mixture of S-Bk-6-MBPBT, R-Bk-6-MBPBT and less than about 10% is the S-enantiomer while greater than about 90% is the R-enantiomer.

It will be understood that the above embodiments and classes of embodiments can be combined to form additional embodiments.

The Present Invention is Described According to the Embodiments

1. A compound selected from:

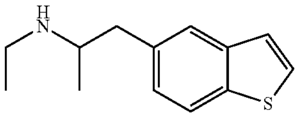

5-EAPBT

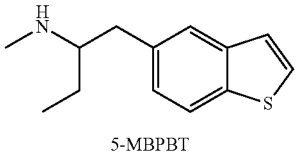

5-MBPBT

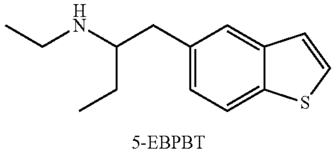

5-EBPBT

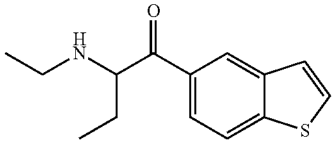

Bk-5-EBPBT

-continued

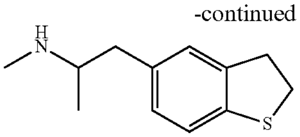

5-MAPDBT

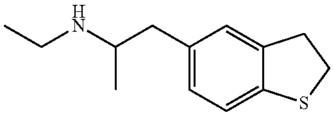

5-EAPDBT

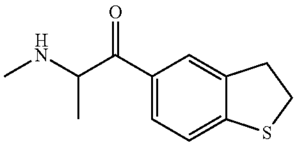

Bk-5-MAPDBT

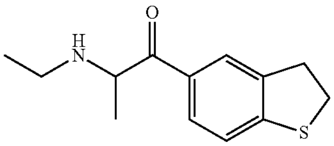

Bk-5-EAPDBT

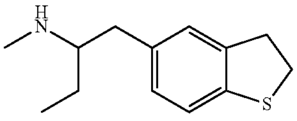

5-MBPDBT

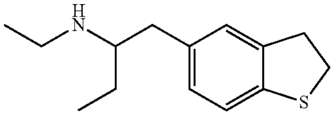

5-EBPDBT

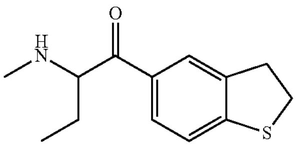

Bk-5-MBPDBT

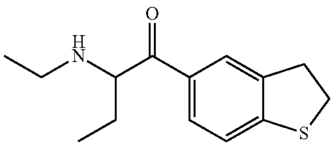

Bk-5-EBPDBT

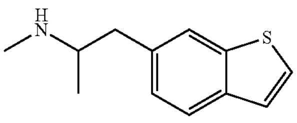

6-MAPBT

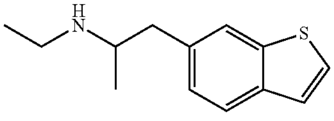

6-EAPBT

-continued
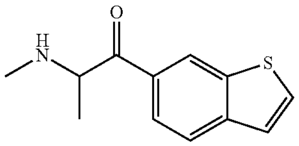
Bk-6-MAPBT
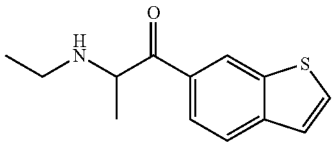
Bk-6-EAPBT
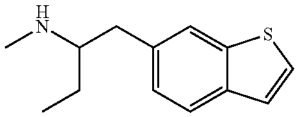
6-MBPBT
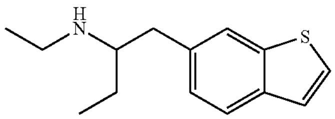
6-EBPBT
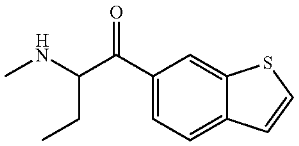
Bk-6-MBPBT
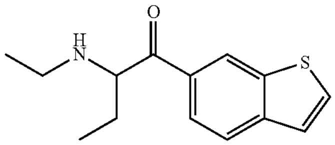
Bk-6-EBPBT
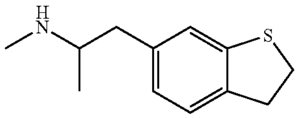
6-MAPDBT
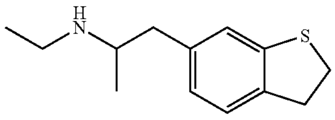
6-EAPDBT
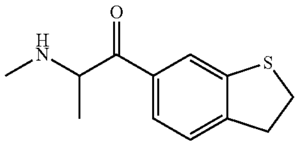
Bk-6-MAPDBT
-continued
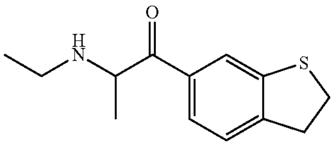
Bk-6-EAPDBT
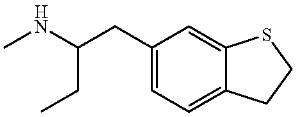
6-MBPDBT
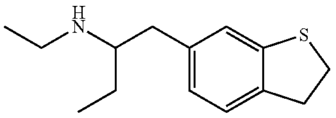
6-EBPDBT
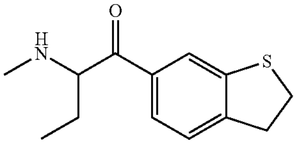
Bk-6-MBPDBT
and
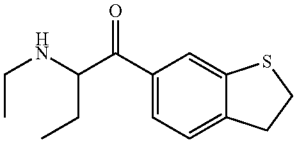
Bk-6-EBPDBT
or a pharmaceutically acceptable salt or salt mixtures thereof.
2. The compound of embodiment 1 selected from:
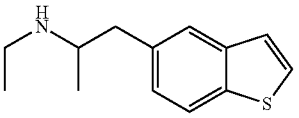
5-EAPBT
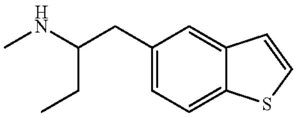
5-MBPBT
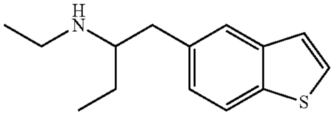
5-EBPBT
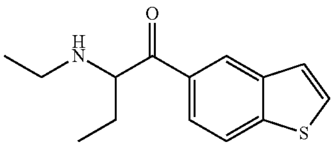
Bk-5-EBPBT -continued
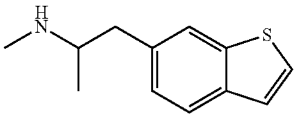
6-MAPBT
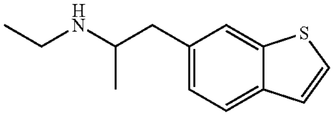
6-EAPBT
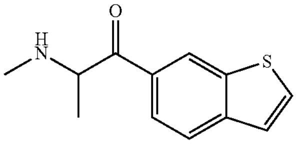
Bk-6-MAPBT
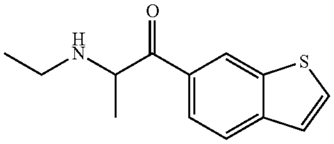
Bk-6-EAPBT
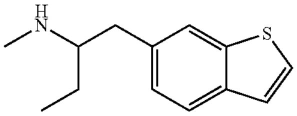
6-MBPBT
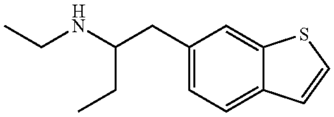
6-EBPBT
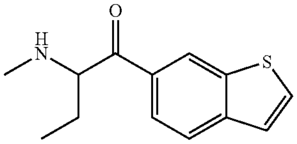
and
Bk-6-MBPBT
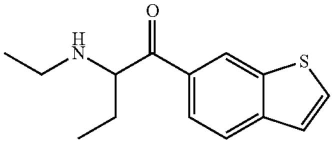
Bk-6-EBPBT
or a pharmaceutically acceptable salt or salt mixtures thereof.
3. The compound of embodiment 1 selected from:
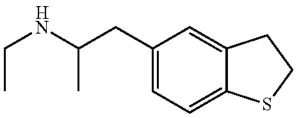
5-MAPDBT
-continued
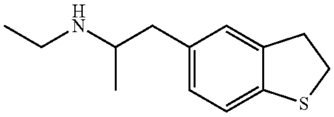
5-EAPDBT
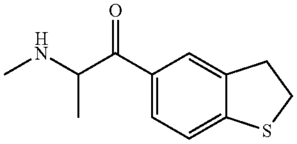
Bk-5-MAPDBT
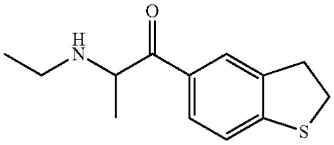
Bk-5-EAPDBT
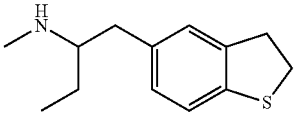
5-MBPDBT
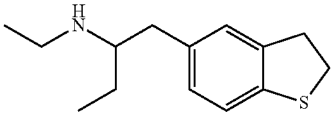
5-EBPDBT
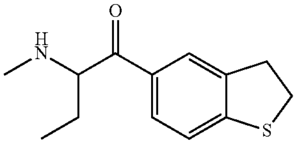
Bk-5-MBPDBT
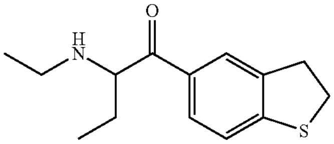
Bk-5-EBPDBT
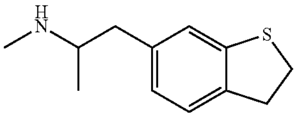
6-MAPDBT
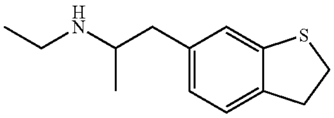
6-EAPDBT
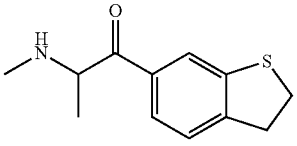
Bk-6-MAPDBT -continued

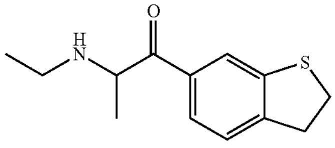

Bk-6-EAPDBT

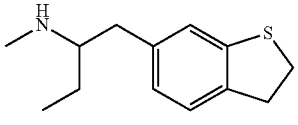

6-MBPDBT

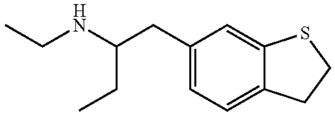

6-EBPDBT

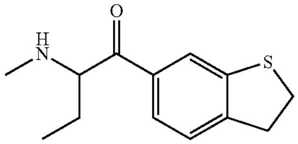

and

Bk-6-MBPDBT

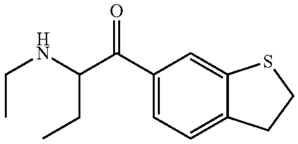

Bk-6-EBPDBT or a pharmaceutically acceptable salt or salt mixtures thereof.

4. The compound of embodiment 1 or 2 of structure:

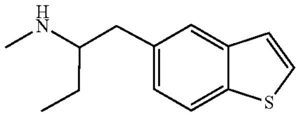

5-MBPBT or a pharmaceutically acceptable salt or salt mixtures thereof.

5. The compound of embodiment 1 or 2 of structure:

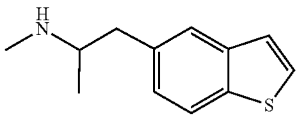

6-MAPBT or a pharmaceutically acceptable salt or salt mixtures thereof.

6. The compound of embodiment 1 or 2 of structure:

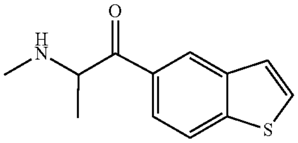

Bk-6-MAPBT or a pharmaceutically acceptable salt or salt mixtures thereof.

7. The compound of embodiment 1 or 2 of structure:

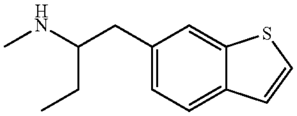

6-MBPBT or a pharmaceutically acceptable salt or salt mixtures thereof.

8. The compound of embodiment 1 or 2 of structure:

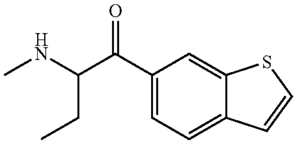

Bk-6-MBPBT or a pharmaceutically acceptable salt or salt mixtures thereof.

9. The compound of embodiment 1 or 2 of structure:

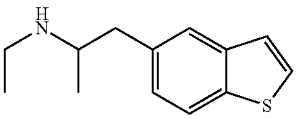

5-EAPBT or a pharmaceutically acceptable salt or salt mixtures thereof.

10. The compound of embodiment 1 or 2 of structure:

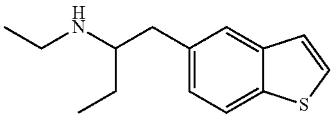

5-EBPBT or a pharmaceutically acceptable salt or salt mixtures thereof.

11. The compound of embodiment 1 or 2 of structure:

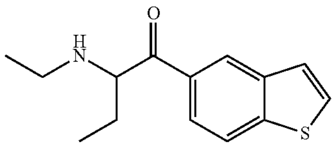

Bk-5-EBPBT or a pharmaceutically acceptable salt or salt mixtures thereof.

12. The compound of embodiment 1 or 2 of structure:

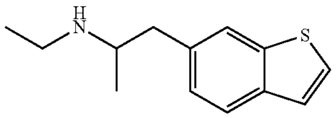

6-EAPBT or a pharmaceutically acceptable salt or salt mixtures thereof.

13. The compound of embodiment 1 or 2 of structure:

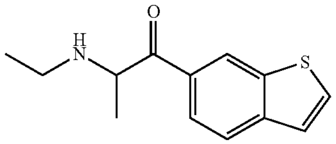

Bk-6-EAPBT or a pharmaceutically acceptable salt or salt mixtures thereof.

14. The compound of embodiment 1 or 2 of structure:

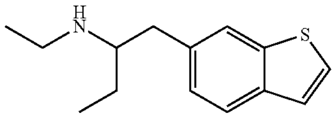

6-EBPBT or a pharmaceutically acceptable salt or salt mixtures thereof.

15. The compound of embodiment 1 or 2 of structure:

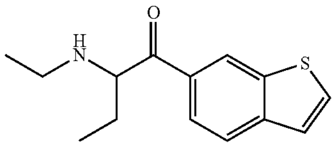

Bk-6-EBPBT or a pharmaceutically acceptable salt or salt mixtures thereof.

16. The compound of embodiment 1 or 3 of structure:

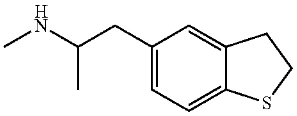

5-MAPDBT or a pharmaceutically acceptable salt or salt mixtures thereof.

17. The compound of embodiment 1 or 3 of structure:

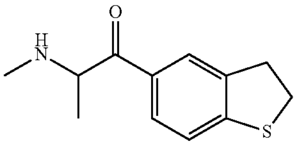

Bk-5-MAPDBT or a pharmaceutically acceptable salt or salt mixtures thereof.

18. The compound of embodiment 1 or 3 of structure:

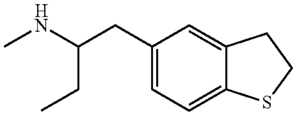

5-MBPDBT or a pharmaceutically acceptable salt or salt mixtures thereof.

19. The compound of embodiment 1 or 3 of structure:

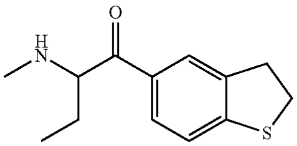

Bk-5-MBPDBT or a pharmaceutically acceptable salt or salt mixtures thereof.

20. The compound of embodiment 1 or 3 of structure:

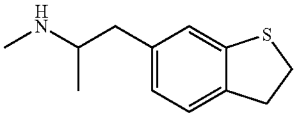

6-MAPDBT or a pharmaceutically acceptable salt or salt mixtures thereof.

21. The compound of embodiment 1 or 3 of structure:

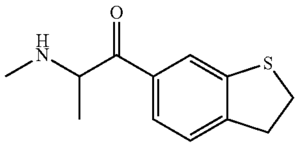

Bk-6-MAPDBT or a pharmaceutically acceptable salt or salt mixtures thereof.

22. The compound of embodiment 1 or 3 of structure:

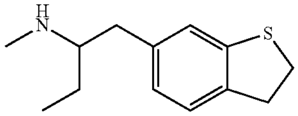

6-MBPDBT or a pharmaceutically acceptable salt or salt mixtures thereof.

23. The compound of embodiment 1 or 3 of structure:

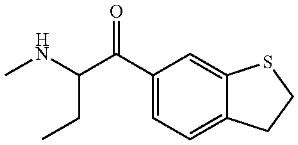

Bk-6-MBPDBT or a pharmaceutically acceptable salt or salt mixtures thereof.

24. The compound of embodiment 1 or 3 of structure:

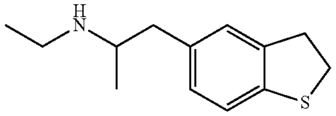

5-EAPDBT or a pharmaceutically acceptable salt or salt mixtures thereof.

25. The compound of embodiment 1 or 3 of structure:

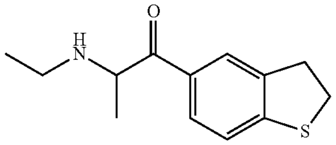

Bk-5-EAPDBT or a pharmaceutically acceptable salt or salt mixtures thereof.

26. The compound of embodiment 1 or 3 of structure:

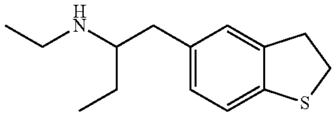

5-EBPDBT or a pharmaceutically acceptable salt or salt mixtures thereof.

27. The compound of embodiment 1 or 3 of structure:

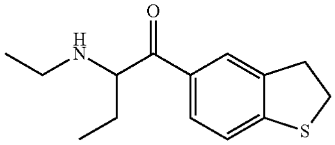

Bk-5-EBPDBT or a pharmaceutically acceptable salt or salt mixtures thereof.

28. The compound of embodiment 1 or 3 of structure:

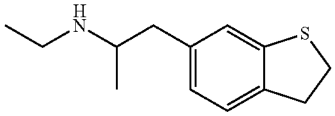

6-EAPDBT or a pharmaceutically acceptable salt or salt mixtures thereof.

29. The compound of embodiment 1 or 3 of structure:

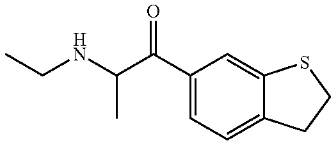

Bk-6-EAPDBT or a pharmaceutically acceptable salt or salt mixtures thereof.

30. The compound of embodiment 1 or 3 of structure:

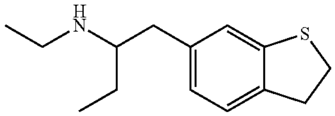

6-EBPDBT or a pharmaceutically acceptable salt or salt mixtures thereof.

31. The compound of embodiment 1 or 3 of structure:

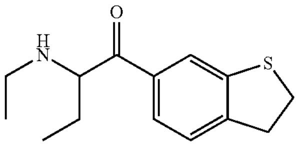

Bk-6-EBPDBT or a pharmaceutically acceptable salt or salt mixtures thereof.

32. A compound of Formula I, Formula II, Formula III, Formula IV, Formula V, Formula VI, Formula VII Formula VIII or Formula IX:

(I)

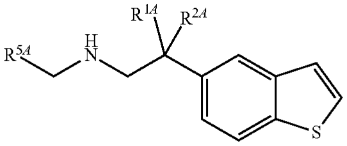

(II)

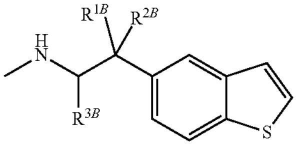

(III)

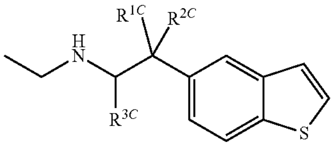

(IV)

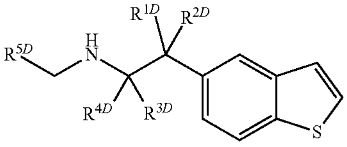

(V)

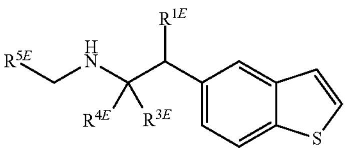

(VI)

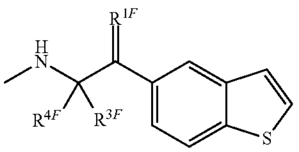

(VII)

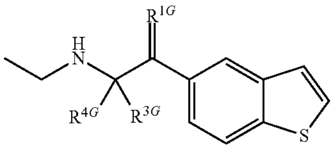

-continued (VIII)

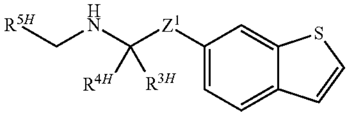

(IX)

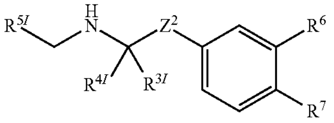

or a pharmaceutically acceptable salt or salt mixtures thereof, wherein:

$Z^1$ is selected from

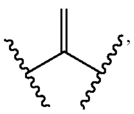, 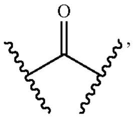, and 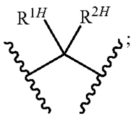;

$Z^2$ is selected from

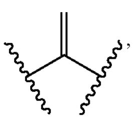, 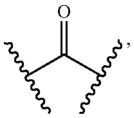, and 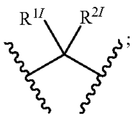;

$R^{1A}$, $R^{1D}$, and $R^{2D}$ are independently selected from —X, —OH, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{1B}$, $R^{1C}$, $R^{1E}$, $R^{1H}$, $R^{1I}$, $R^{2B}$, $R^{2C}$, $R^{2H}$, and $R^{2I}$ are independently selected from —H, —X, —OH, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{1F}$ and $R^{1G}$ are independently selected from $CH_2$ and O;

$R^{2A}$ is selected from —H, —X, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein if $R^{1A}$ is —OH, $R^{2A}$ is not —H or $C_1$ alkyl;

$R^{3B}$ is selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl; wherein if $R^{3B}$ is $C_1$ alkyl and one of $R^{2B}$ and $R^{1B}$ is —H, then the other of $R^{2B}$ and $R^{1B}$ cannot be —H or —OH;

$R^{3C}$ is selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl; wherein if $R^{3C}$ is $C_1$ alkyl and one of $R^{2C}$ and $R^{1C}$ is —H, then the other of $R^{2C}$ and $R^{1C}$ cannot be —OH or $C_1$ alkyl;

$R^{3D}$, $R^{3F}$, and $R^{4D}$ are independently selected from —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{3E}$ and $R^{4E}$ are independently selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein when $R^{3E}$ and $R^{4E}$ are both $C_1$ alkyl, $R^{1E}$ cannot be —OH or —F;

$R^{3G}$ and $R^{4G}$ are independently selected from —H, —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein if $R^{1G}$ is O and one of $R^{3G}$ and $R^{4G}$ is —H, then the other of $R^{3G}$ and $R^{4G}$ cannot be —H or $C_1$ alkyl;

$R^{3H}$, $R^{3I}$, $R^{4H}$, and $R^{4I}$ are independently selected from —H, —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{4F}$ is selected from —H, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein if $R^{4F}$ is —H and $R^{1F}$ is O, then $R^{3F}$ cannot be $C_1$ or $C_2$ alkyl;

$R^{5A}$, $R^{5D}$, $R^{5E}$, and $R^{5H}$ are independently selected from —H or —$CH_3$;

$R^{5I}$ is selected from —H and —$CH_3$, wherein if $R^{3I}$, $R^{4I}$, and $R^{5I}$ are all —H, then $Z^2$ cannot be

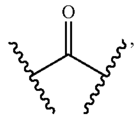, 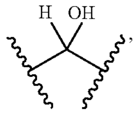, and 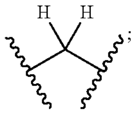;

$R^6$ and $R^7$ are taken together as —$SCH_2CH_2$— or —$CH_2CH_2S$—; and

X is independently selected from —F, —Cl, and —Br.

33. The compound of embodiment 32 wherein the compound is of Formula I.

(I)

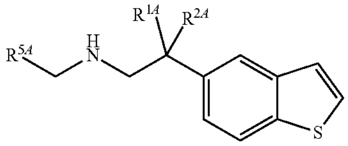

or a pharmaceutically acceptable salt or salt mixtures thereof.

34. The compound of embodiment 32 wherein the compound is of Formula II:

(II)

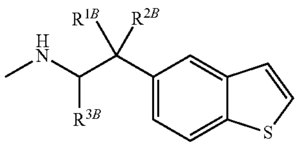

or a pharmaceutically acceptable salt or salt mixtures thereof.

35. The compound of embodiment 36 wherein the compound is of Formula III:

(III)

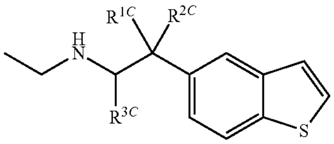

or a pharmaceutically acceptable salt or salt mixtures thereof.

36. The compound of embodiment 32 wherein the compound is of Formula IV:

(IV)

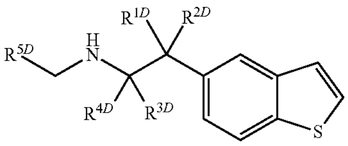

or a pharmaceutically acceptable salt or salt mixtures thereof.

37. The compound of embodiment 32 wherein the compound is of Formula V:

(V)

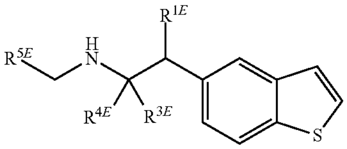

or a pharmaceutically acceptable salt or salt mixtures thereof.

38. The compound of embodiment 32 wherein the compound is of Formula VI:

(VI)

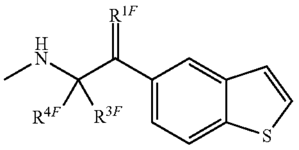

or a pharmaceutically acceptable salt or salt mixtures thereof.

39. The compound of embodiment 32 wherein the compound is of Formula VII:

(VII)

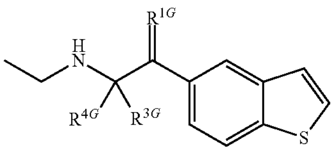

or a pharmaceutically acceptable salt or salt mixtures thereof.

40. The compound of embodiment 32 wherein the compound is of Formula VIII:

(VIII)

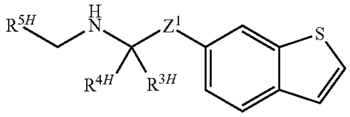

or a pharmaceutically acceptable salt or salt mixtures thereof.

41. The compound of embodiment 32 wherein the compound is of Formula IX:

(IX)

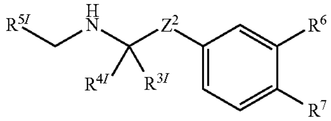

or a pharmaceutically acceptable salt or salt mixtures thereof.

42. The compound of embodiment 32 or 34 wherein the compound is selected from:

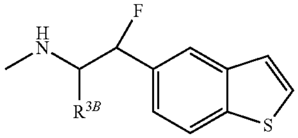

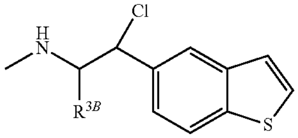

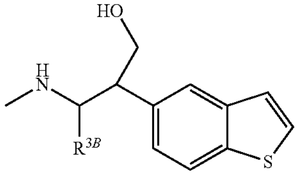

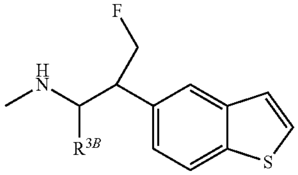

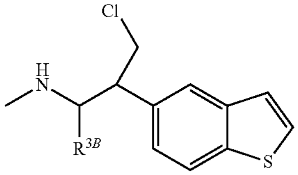

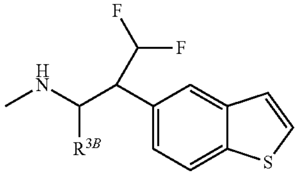

-continued

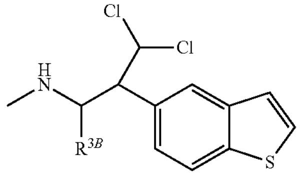

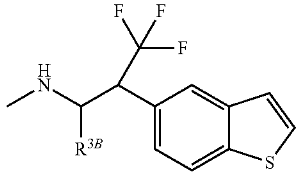

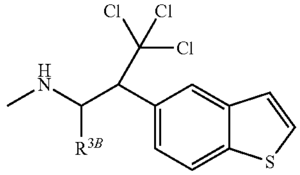

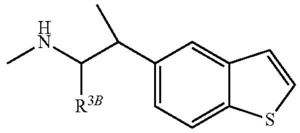

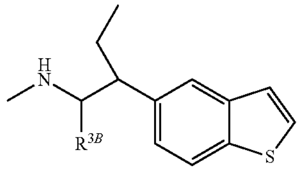

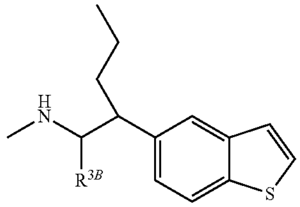

and

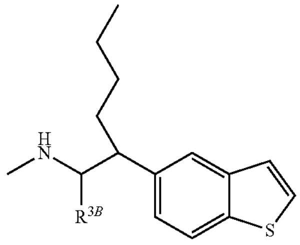

or a pharmaceutically acceptable salt or salt mixtures thereof.

43. The compound of embodiment 32 or 35 wherein the compound is selected from:

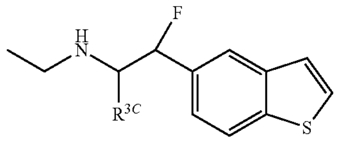

-continued
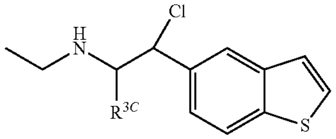
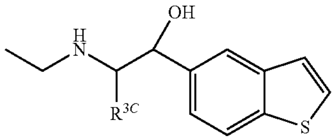
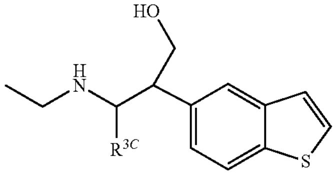
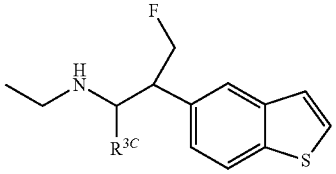
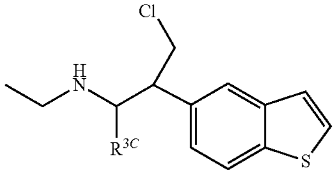
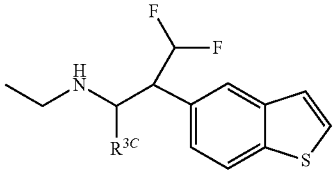
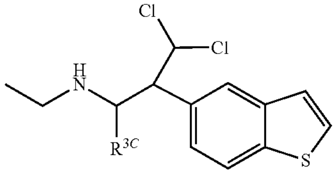
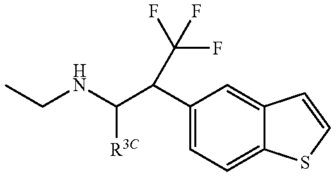
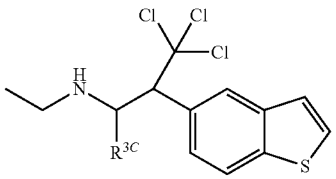
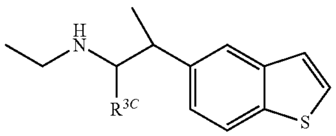
-continued
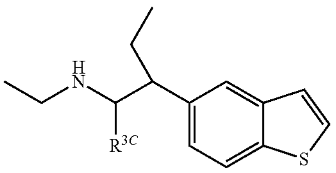
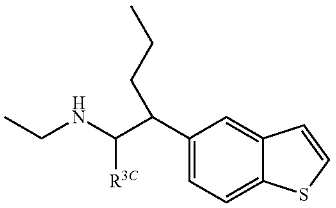
and
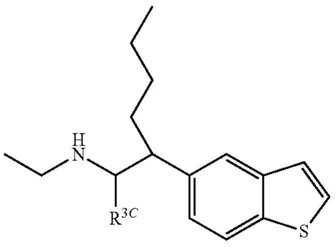
or a pharmaceutically acceptable salt or salt mixtures thereof.
44. The compound of embodiment 32 or 40 wherein the compound is selected from:
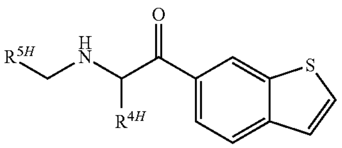
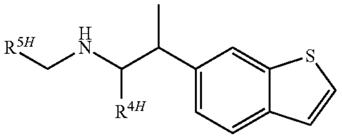
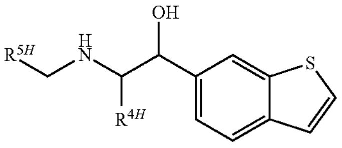
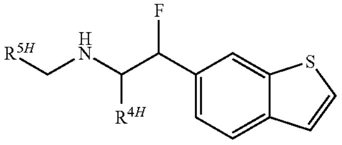
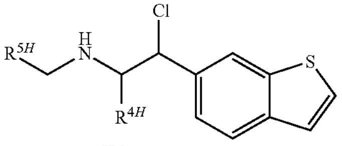
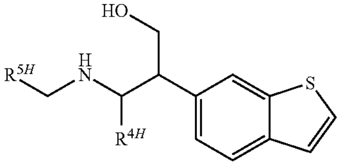

-continued
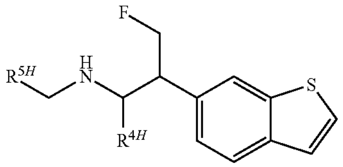
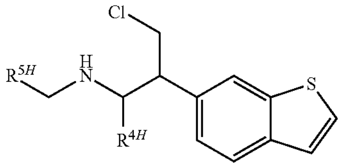
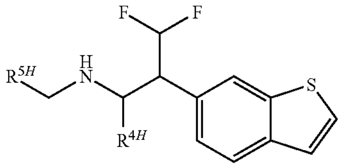
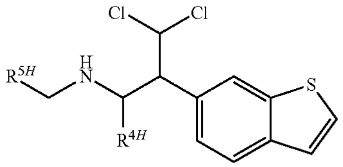
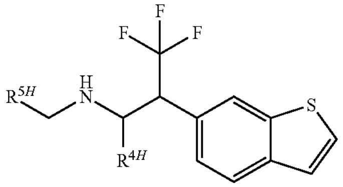
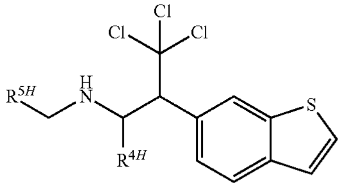
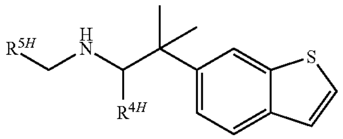
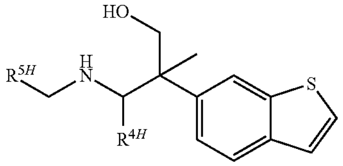
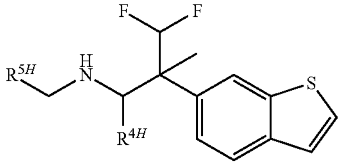
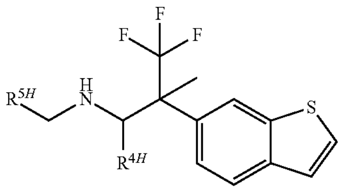
-continued
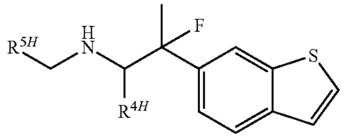
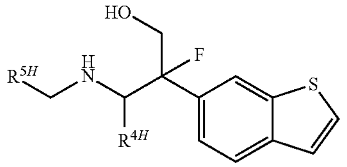
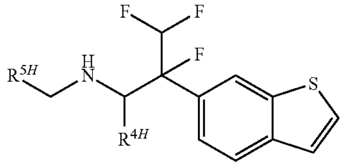
and
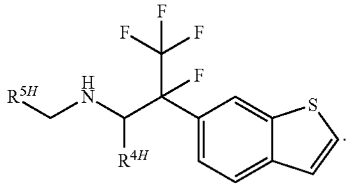
or a pharmaceutically acceptable salt or salt mixtures thereof.
45. The compound of embodiment 32 or 41 wherein the compound is selected from:
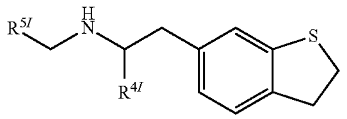
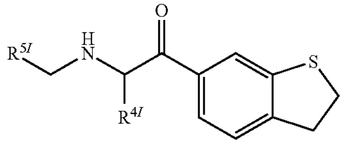
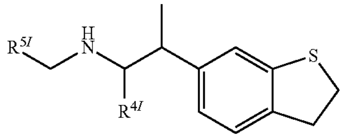
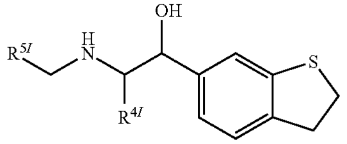
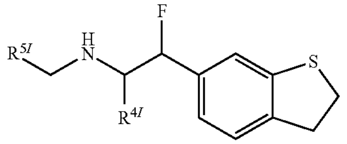
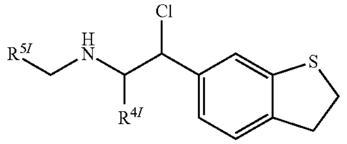

-continued
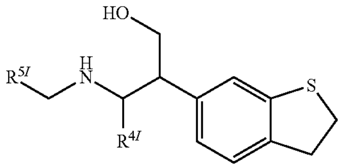
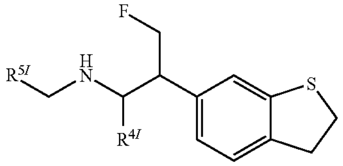
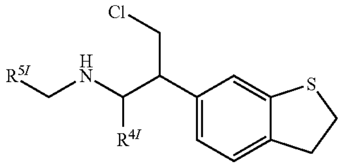
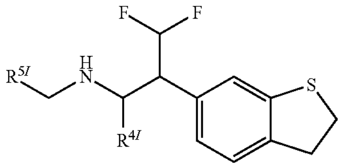
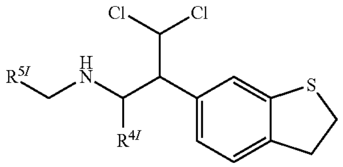
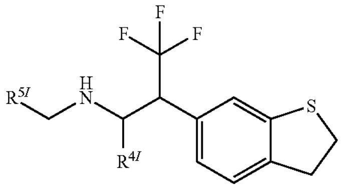
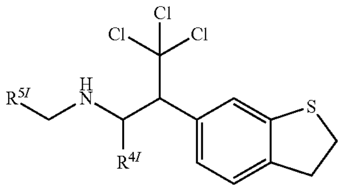
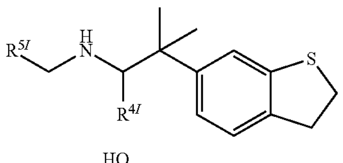
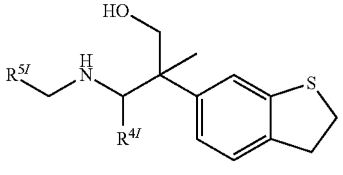
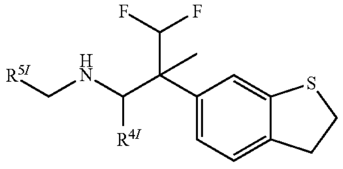
-continued
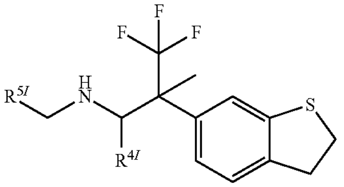
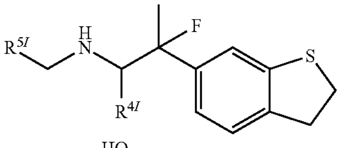
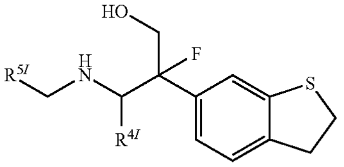
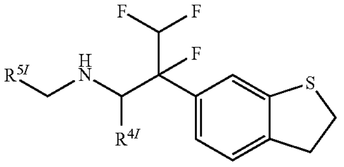
and
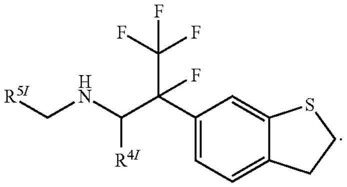
or a pharmaceutically acceptable salt or salt mixtures thereof.
46. The compound of embodiment 32 or 41 wherein the compound is selected from:
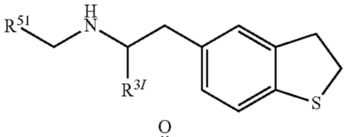
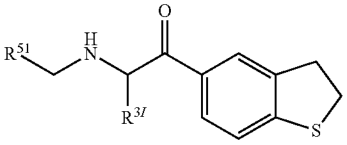
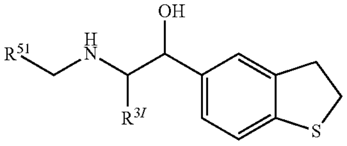
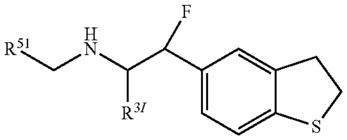
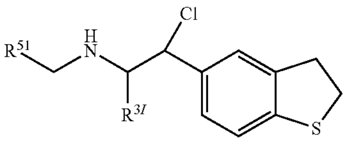

-continued

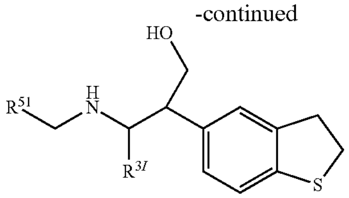

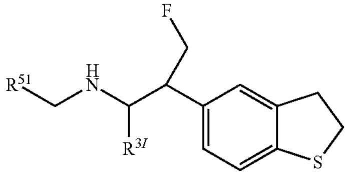

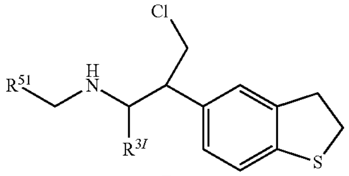

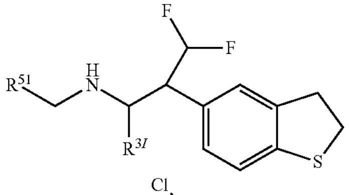

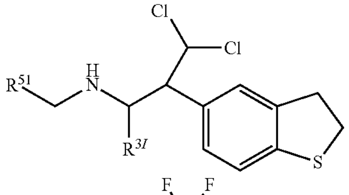

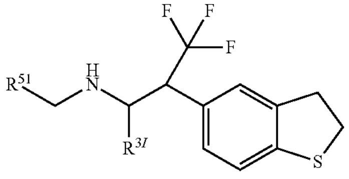

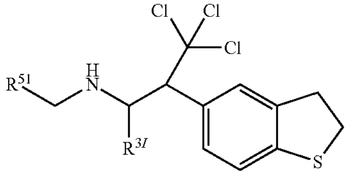

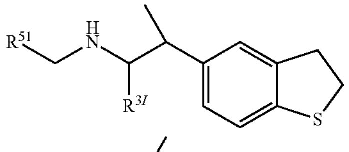

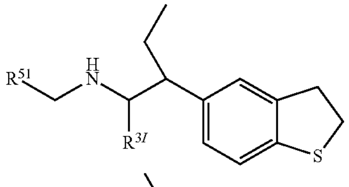

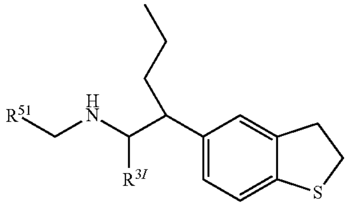

and

-continued

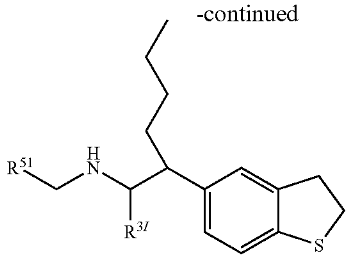

or a pharmaceutically acceptable salt or salt mixtures thereof.

47. The compound of any of embodiments 1-46, wherein the compound has entactogenic properties.
48. The compound of any of embodiments 1-46, wherein the compound has nicotinic-receptor-dependent properties.
49. The compound of any of embodiments 1-46, wherein the compound has serotonin-receptor-dependent properties.
50. The compound of any of embodiments 1-46, wherein the compound has dopamine-receptor-dependent properties.
51. The compound of any of embodiments 1-46, wherein the compound enhances serotonin-receptor-dependent therapeutic properties and decreases nicotinic properties or dopaminergic properties relative to MDMA.
52. The compound of any of embodiments 1-46, with decreased hallucinogenic effects relative to MDMA.
53. The compound of any of embodiments 1-46, with decreased unwanted psychoactive effects relative to MDMA.
54. The compound of any of embodiments 1-46, with decreased physiological effect relative to MDMA.
55. The compound of any of embodiments 1-46, with at least one decreased toxic effect relative to MDMA.
56. The compound of any of embodiments 1-46, with decreased abuse potential relative to MDMA.
57. The compound of any of embodiments 1-46 in an enantiomerically enriched form that has at least about 60% S-enantiomer.
58. The compound of any of embodiments 1-46 in an enantiomerically enriched form that has at least about 70% S-enantiomer.
59. The compound of any of embodiments 1-46 in an enantiomerically enriched form that has at least about 80% S-enantiomer.
60. The compound of any of embodiments 1-46 in an enantiomerically enriched form that has at least about 90% S-enantiomer.
61. The compound of any of embodiments 1-46 in an enantiomerically enriched form that has at least about 60% R-enantiomer.
62. The compound of any of embodiments 1-46 in an enantiomerically enriched form that has at least about 70% R-enantiomer.
63. The compound of any of embodiments 1-46 in an enantiomerically enriched form that has at least about 80% R-enantiomer.
64. The compound of any of embodiments 1-46 in an enantiomerically enriched form that has at least about 90% R-enantiomer.
65. The compound of any of embodiments 1-64 that shows the therapeutic effect of emotional openness.

66. The compound of any of embodiments 1-65 wherein the pharmaceutically acceptable salt(s) is selected from HCl, sulfate, aspartate, saccharate, phosphate, oxalate, acetate, amino acid anion, gluconate, maleate, malate, citrate, mesylate, nitrate or tartrate, or a mixture thereof.
67. The compound of any of embodiments 1-66 that is both a direct 5-$HT_{1B}$ agonist and a serotonin releasing agent.
68. The compound of embodiment 67 that is also a serotonin reuptake inhibitor.
69. The compound of any one of embodiments 1-68 that has minimal or no direct agonism of 5-$HT_{2A}$.
70. An enantiomerically enriched mixture or pure enantiomer of a compound selected from:

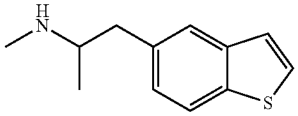

5-MAPBT

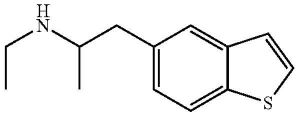

5-EAPBT

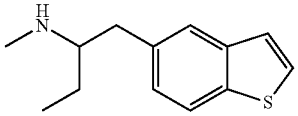

5-MBPBT

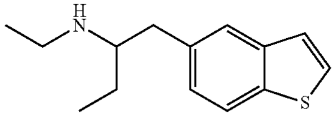

5-EBPBT

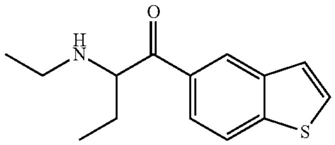

Bk-5-EBPBT

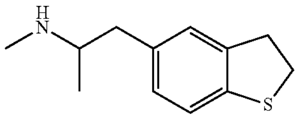

5-MAPDBT

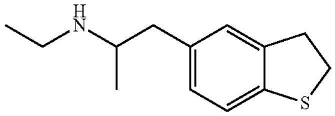

5-EAPDBT

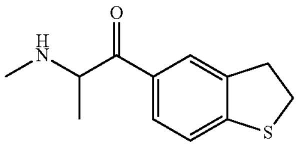

Bk-5-MAPDBT

-continued

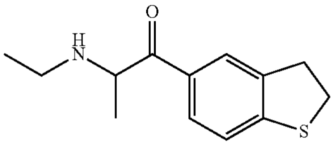

Bk-5-EAPDBT

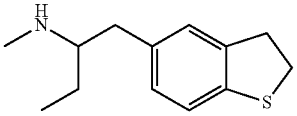

5-MBPDBT

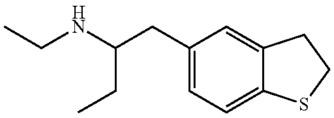

5-EBPDBT

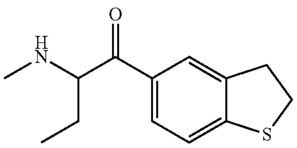

Bk-5-MBPDBT

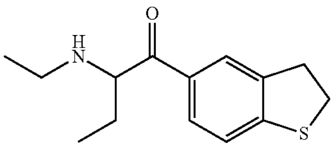

Bk-5-EBPDBT

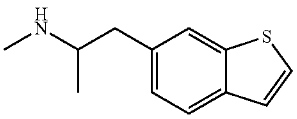

6-MAPBT

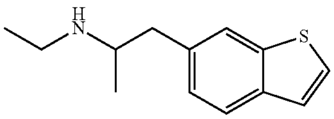

6-EAPBT

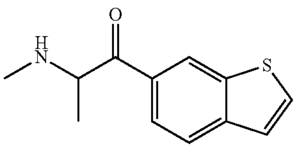

Bk-6-MAPBT

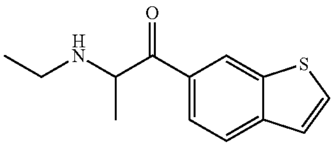

Bk-6-EAPBT

-continued
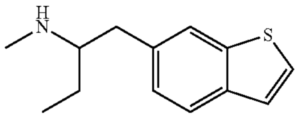
6-MBPBT
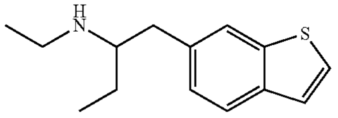
6-EBPBT
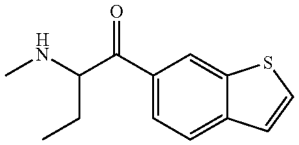
Bk-6-MBPBT
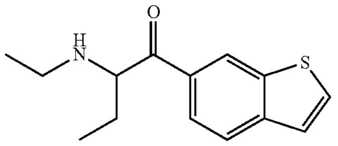
Bk-6-EBPBT
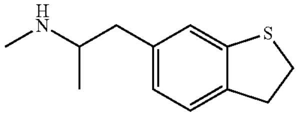
6-MAPDBT
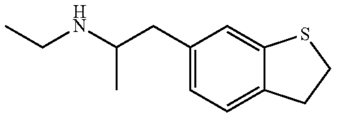
6-EAPDBT
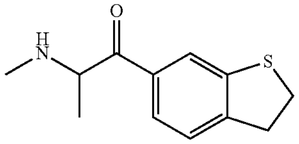
Bk-6-MAPDBT
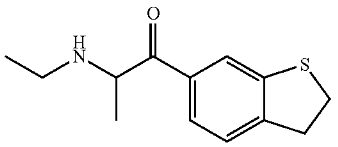
Bk-6-EAPDBT
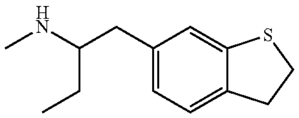
6-MBPDBT
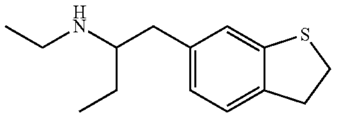
6-EBPDBT
-continued
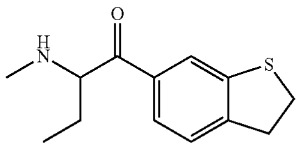
and
Bk-6-MBPDBT
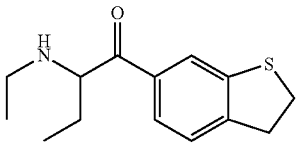
Bk-6-EBPDBT
or a pharmaceutically acceptable salt or salt mixtures thereof.
71. The enantiomerically enriched mixture or pure enantiomer of embodiment 70 selected from:
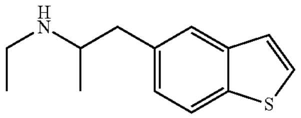
5-MAPBT
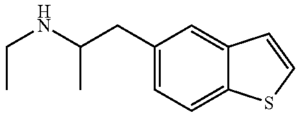
5-EAPBT
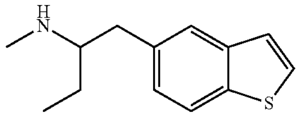
5-MBPBT
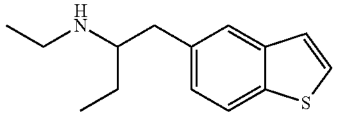
5-EBPBT
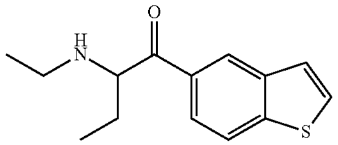
Bk-5-EBPBT
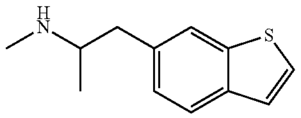
6-MAPBT
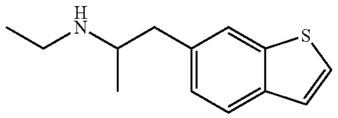
6-EAPBT -continued
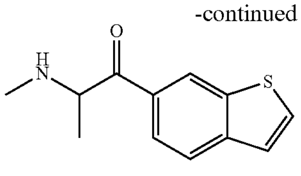
Bk-6-MAPBT
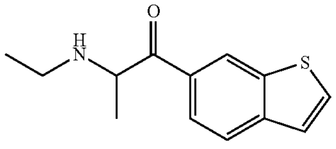
Bk-6-EAPBT
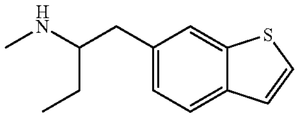
6-MBPBT
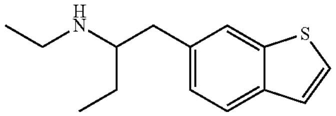
6-EBPBT
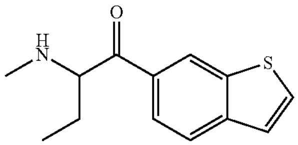
and
Bk-6-MBPBT
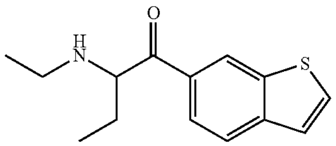
Bk-6-EBPBT
or a pharmaceutically acceptable salt or salt mixtures thereof.
72. The enantiomerically enriched mixture or pure enantiomer of embodiment 70 selected from:
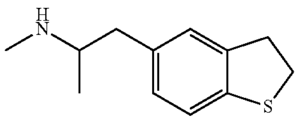
5-MAPDBT
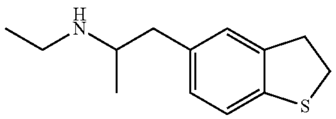
5-EAPDBT
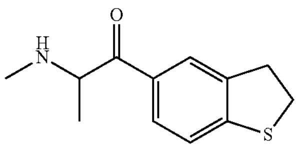
Bk-5-MAPDBT
-continued
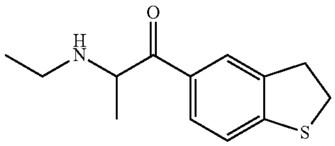
Bk-5-EAPDBT
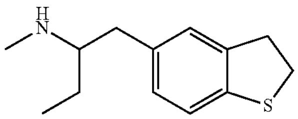
5-MBPDBT
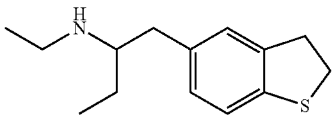
5-EBPDBT
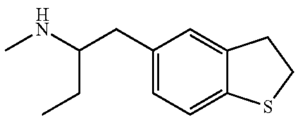
Bk-5-MBPDBT
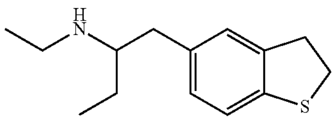
Bk-5-EBPDBT
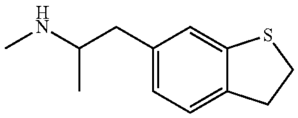
6-MAPDBT
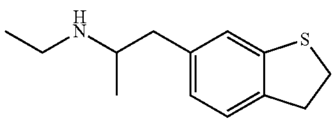
6-EAPDBT
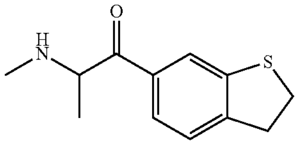
Bk-6-MAPDBT
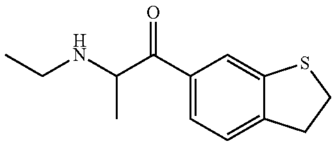
Bk-6-EAPDBT
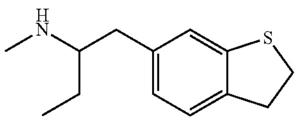
6-MBPDBT -continued

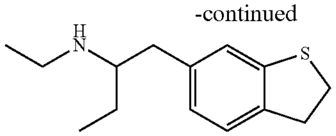

6-EBPDBT

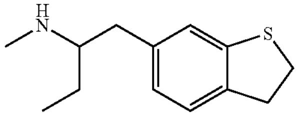

and

Bk-6-MBPDBT

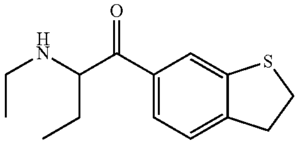

Bk-6-EBPDBT or a pharmaceutically acceptable salt or salt mixtures thereof.

73. The enantiomerically enriched mixture or pure enantiomer of embodiment 70 or 71 of structure:

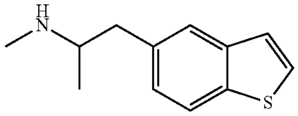

5-MAPBT or a pharmaceutically acceptable salt or salt mixtures thereof.

74. The enantiomerically enriched mixture or pure enantiomer of embodiment 70 or 71 of structure:

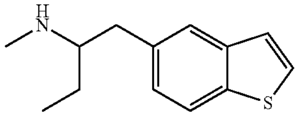

5-MBPBT or a pharmaceutically acceptable salt or salt mixtures thereof.

75. The enantiomerically enriched mixture or pure enantiomer of embodiment 70 or 71 of structure:

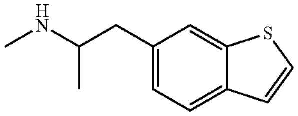

6-MAPBT or a pharmaceutically acceptable salt or salt mixtures thereof.

76. The enantiomerically enriched mixture or pure enantiomer of embodiment 70 or 71 of structure:

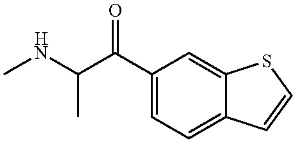

Bk-6-MAPBT or a pharmaceutically acceptable salt or salt mixtures thereof.

77. The enantiomerically enriched mixture or pure enantiomer of embodiment 70 or 71 of structure:

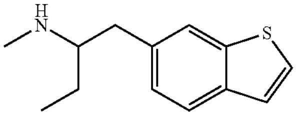

6-MBPBT or a pharmaceutically acceptable salt or salt mixtures thereof.

78. The enantiomerically enriched mixture or pure enantiomer of embodiment 70 or 71 of structure:

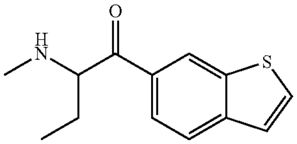

Bk-6-MBPBT or a pharmaceutically acceptable salt or salt mixtures thereof.

79. The enantiomerically enriched mixture or pure enantiomer of embodiment 70 or 71 of structure:

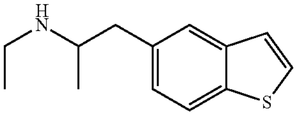

5-EAPBT or a pharmaceutically acceptable salt or salt mixtures thereof.

80. The enantiomerically enriched mixture or pure enantiomer of embodiment 70 or 71 of structure:

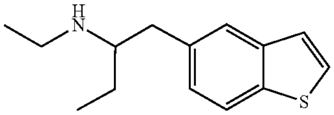

5-EBPBT or a pharmaceutically acceptable salt or salt mixtures thereof.

81. The enantiomerically enriched mixture or pure enantiomer of embodiment 70 or 71 of structure:

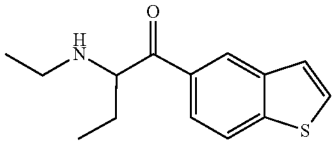

Bk-5-EBPBT or a pharmaceutically acceptable salt or salt mixtures thereof.

82. The enantiomerically enriched mixture or pure enantiomer of embodiment 70 or 71 of structure:

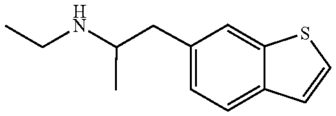

6-EAPBT or a pharmaceutically acceptable salt or salt mixtures thereof.

83. The enantiomerically enriched mixture or pure enantiomer of embodiment 70 or 71 of structure:

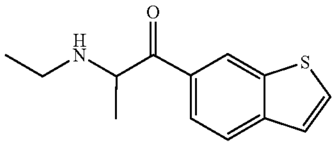

Bk-6-EAPBT or a pharmaceutically acceptable salt or salt mixtures thereof.

84. The enantiomerically enriched mixture or pure enantiomer of embodiment 70 or 71 of structure:

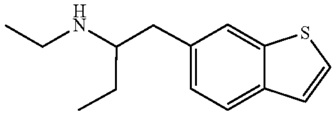

6-EBPBT or a pharmaceutically acceptable salt or salt mixtures thereof.

85. The enantiomerically enriched mixture or pure enantiomer of embodiment 70 or 71 of structure:

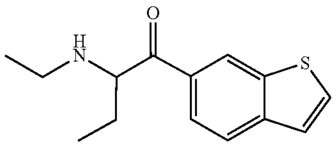

Bk-6-EBPBT or a pharmaceutically acceptable salt or salt mixtures thereof.

86. The enantiomerically enriched mixture or pure enantiomer of embodiment 70 or 72 of structure:

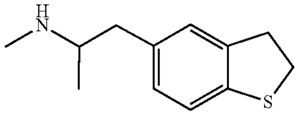

5-MAPDBT or a pharmaceutically acceptable salt or salt mixtures thereof.

87. The enantiomerically enriched mixture or pure enantiomer of embodiment 70 or 72 of structure:

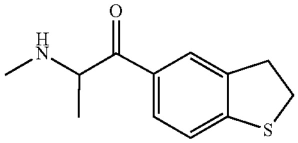

Bk-5-MAPDBT or a pharmaceutically acceptable salt or salt mixtures thereof.

88. The enantiomerically enriched mixture or pure enantiomer of embodiment 70 or 72 of structure:

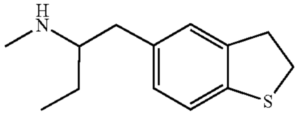

5-MBPDBT or a pharmaceutically acceptable salt or salt mixtures thereof.

89. The enantiomerically enriched mixture or pure enantiomer of embodiment 70 or 72 of structure:

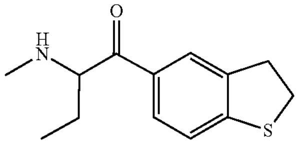

Bk-5-MBPDBT or a pharmaceutically acceptable salt or salt mixtures thereof.

90. The enantiomerically enriched mixture or pure enantiomer of embodiment 70 or 72 of structure:

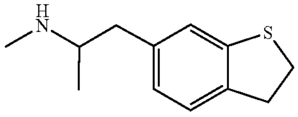

6-MAPDBT or a pharmaceutically acceptable salt or salt mixtures thereof.

91. The enantiomerically enriched mixture or pure enantiomer of embodiment 70 or 72 of structure:

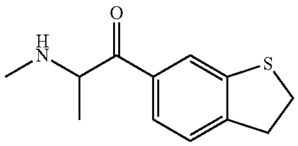

Bk-6-MAPDBT or a pharmaceutically acceptable salt or salt mixtures thereof.

92. The enantiomerically enriched mixture or pure enantiomer of embodiment 70 or 72 of structure:

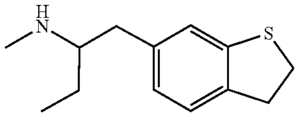

6-MBPDBT or a pharmaceutically acceptable salt or salt mixtures thereof.

93. The enantiomerically enriched mixture or pure enantiomer of embodiment 70 or 72 of structure:

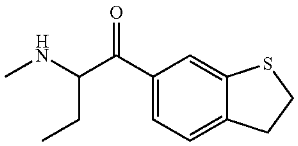

Bk-6-MBPDBT or a pharmaceutically acceptable salt or salt mixtures thereof.

94. The enantiomerically enriched mixture or pure enantiomer of embodiment 70 or 72 of structure:

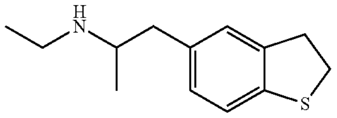

5-EAPDBT or a pharmaceutically acceptable salt or salt mixtures thereof.

95. The enantiomerically enriched mixture or pure enantiomer of embodiment 70 or 72 of structure:

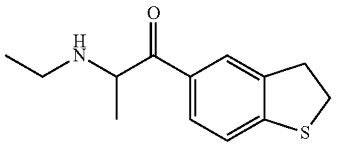

Bk-5-EAPDBT or a pharmaceutically acceptable salt or salt mixtures thereof.

96. The enantiomerically enriched mixture or pure enantiomer of embodiment 70 or 72 of structure:

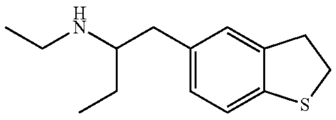

5-EBPDBT or a pharmaceutically acceptable salt or salt mixtures thereof.

97. The enantiomerically enriched mixture or pure enantiomer of embodiment 70 or 72 of structure:

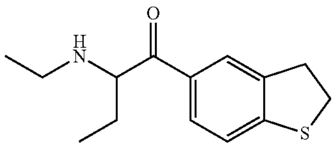

Bk-5-EBPDBT or a pharmaceutically acceptable salt or salt mixtures thereof.

98. The enantiomerically enriched mixture or pure enantiomer of embodiment 70 or 72 of structure:

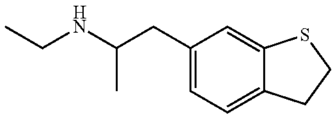

6-EAPDBT or a pharmaceutically acceptable salt or salt mixtures thereof.

99. The enantiomerically enriched mixture or pure enantiomer of embodiment 70 or 72 of structure:

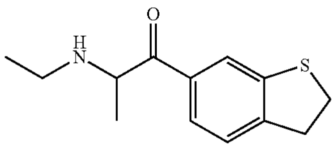

Bk-6-EAPDBT or a pharmaceutically acceptable salt or salt mixtures thereof.

100. The enantiomerically enriched mixture or pure enantiomer of embodiment 70 or 72 of structure:

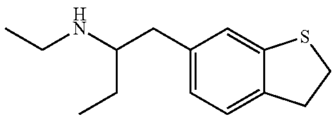

6-EBPDBT or a pharmaceutically acceptable salt or salt mixtures thereof.

101. The enantiomerically enriched mixture or pure enantiomer of embodiment 70 or 72 of structure:

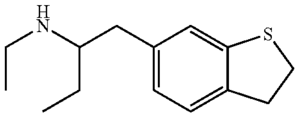

Bk-6-EBPDBT or a pharmaceutically acceptable salt or salt mixtures thereof.

102. An enantiomerically enriched mixture or pure enantiomer of Formula VIII, Formula X, Formula XI, Formula XII, or Formula XIII:

(VIII)

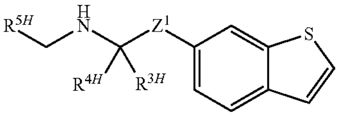

(X)

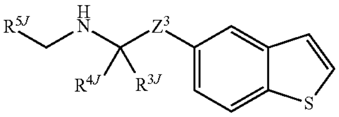

(XI)

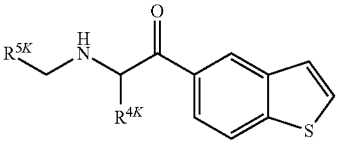

(XII)

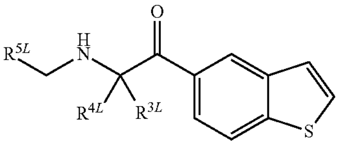

(XIII)

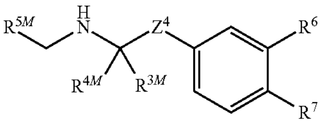

or a pharmaceutically acceptable salt or salt mixtures thereof, wherein:

$Z^1$ is selected from

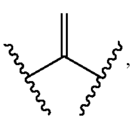, 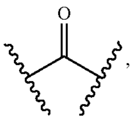, and 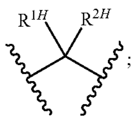;

$Z^3$ is selected from

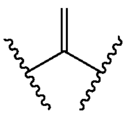 and 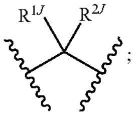;

$Z^4$ is selected from

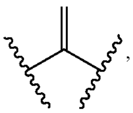, 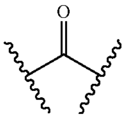, and 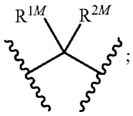;

$R^{1H}$, $R^{1J}$, $R^{1M}$, $R^{2H}$, $R^{2J}$, and $R^{2M}$ are independently selected from —H, —X, —OH, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{3H}$, $R^{3J}$, $R^{3M}$, $R^{4H}$, $R^{4J}$, and $R^{4M}$ are independently selected from —H, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{3L}$ and $R^{4L}$ are independently selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{4K}$ is selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_2$-$C_4$ alkyl;

$R^{5H}$, $R^{5L}$, and $R^{5M}$ are independently selected from —H and —$CH_3$;

$R^{5J}$ is selected from —H and —$CH_3$, wherein if $R^{5J}$ is —H, $Z^3$ is

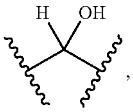 [SMILES: *C(*)O], and one of $R^{3J}$ and $R^{4J}$ is —H, then the other of $R^{3J}$ and $R^{4J}$ cannot be $C_1$ alkyl;

$R^{5K}$ is selected from —H and —$CH_3$, wherein if $R^{5K}$ is —H, then $R^{4K}$ cannot be $C_2$ alkyl;

$R^6$ and $R^7$ are taken together as —$SCH_2CH_2$— or —$CH_2CH_2S$—; and

X is independently selected from —F, —Cl, and —Br.

103. The enantiomerically enriched mixture or pure enantiomer of embodiment 102 wherein the pure enantiomer or enantiomerically enriched mixture is of Formula VIII:

(VIII)

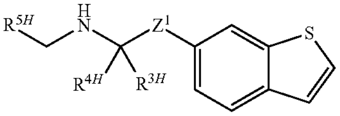

or a pharmaceutically acceptable salt or salt mixtures thereof.

104. The enantiomerically enriched mixture or pure enantiomer of embodiment 102 wherein the pure enantiomer or enantiomerically enriched mixture is of Formula X:

(X)

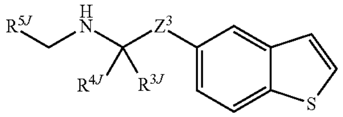

or a pharmaceutically acceptable salt or salt mixtures thereof.

105. The enantiomerically enriched mixture or pure enantiomer of embodiment 102 wherein the pure enantiomer or enantiomerically enriched mixture is of Formula XI:

(XI)

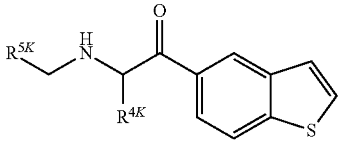

or a pharmaceutically acceptable salt or salt mixtures thereof.

106. The enantiomerically enriched mixture or pure enantiomer of embodiment 102 wherein the pure enantiomer or enantiomerically enriched mixture is of Formula XII:

(XII)

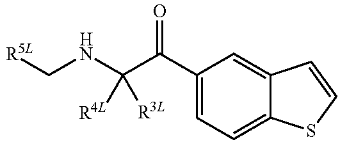

or a pharmaceutically acceptable salt or salt mixtures thereof.

107. The enantiomerically enriched mixture or pure enantiomer of embodiment 102 wherein the pure enantiomer or enantiomerically enriched mixture is of Formula XIII:

(XIII)

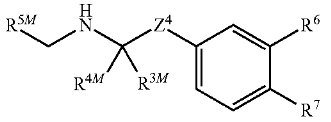

or a pharmaceutically acceptable salt or salt mixtures thereof.

108. The enantiomerically enriched mixture or pure enantiomer of any of embodiments 102-107, wherein the compound has entactogenic properties.

109. The enantiomerically enriched mixture or pure enantiomer of any of embodiments 102-107, wherein the compound has nicotinic-receptor-dependent properties.

110. The enantiomerically enriched mixture or pure enantiomer of any of embodiments 102-107, wherein the compound has serotonin-receptor-dependent properties.

111. The enantiomerically enriched mixture or pure enantiomer of any of embodiments 102-107, wherein the compound has dopamine-receptor-dependent properties.

112. The enantiomerically enriched mixture or pure enantiomer of any of embodiments 102-107, wherein the compound enhances serotonin-receptor-dependent properties and decreases nicotinic properties or dopaminergic properties relative to the racemate.

113. The enantiomerically enriched mixture or pure enantiomer of any of embodiments 102-107, in an enantiomerically enriched form that decreases a hallucinogenic effect relative to the racemate.

114. The enantiomerically enriched mixture or pure enantiomer of any of embodiments 102-107, in an enantiomerically enriched form that decreases an unwanted psychoactive effect relative to the racemate.

115. The enantiomerically enriched mixture or pure enantiomer of any of embodiments 102-107, in an enantiomerically enriched form that decreases a physiological effect relative to the racemate.

116. The enantiomerically enriched mixture or pure enantiomer of any of embodiments 102-107, in an enantiomerically enriched form that decreases at least one toxic effect relative to the racemate.

117. The enantiomerically enriched mixture or pure enantiomer of any of embodiments 102-107, in an enantiomerically enriched form that decreases abuse potential relative to the racemate.

118. The enantiomerically enriched mixture or pure enantiomer of any of embodiments 102-107 in an enantiomerically enriched form that has at least about 60% S-enantiomer.

119. The enantiomerically enriched mixture or pure enantiomer of any of embodiments 102-107 in an enantiomerically enriched form that has at least about 70% S-enantiomer.

120. The enantiomerically enriched mixture or pure enantiomer of any of embodiments 102-107 in an enantiomerically enriched form that has at least about 80% S-enantiomer.

121. The enantiomerically enriched mixture or pure enantiomer of any of embodiments 102-107 in an enantiomerically enriched form that has at least about 90% S-enantiomer.

122. The enantiomerically enriched mixture or pure enantiomer of any of embodiments 102-107 in an enantiomerically enriched form that has at least about 60% R-enantiomer.

123. The enantiomerically enriched mixture or pure enantiomer of any of embodiments 102-107 in an enantiomerically enriched form that has at least about 70% R-enantiomer.

124. The enantiomerically enriched mixture or pure enantiomer of any of embodiments 102-107 in an enantiomerically enriched form that has at least about 80% R-enantiomer.

125. The enantiomerically enriched mixture or pure enantiomer of any of embodiments 102-107 in an enantiomerically enriched form that has at least about 90% R-enantiomer.

126. The enantiomerically enriched mixture or pure enantiomer of any of embodiments 102-107 that shows the therapeutic effect of emotional openness.

127. The enantiomerically enriched mixture or pure enantiomer of any of embodiments 102-126 wherein the pharmaceutically acceptable salt(s) is selected from HCl, sulfate, aspartate, saccharate, phosphate, oxalate, acetate, amino acid anion, gluconate, maleate, malate, citrate, mesylate, nitrate or tartrate, or a mixture thereof.

128. The enantiomerically enriched mixture or pure enantiomer of any of embodiments 102-127 that is both a direct 5-$HT_{1B}$ agonist and a serotonin releasing agent.

129. The enantiomerically enriched mixture or pure enantiomer of embodiment 128 that is also a serotonin reuptake inhibitor.

130. The enantiomerically enriched mixture or pure enantiomer of any one of embodiments 102-129 that has minimal or no direct agonism of 5-$HT_{2A}$.

131. An enantiomerically enriched mixture of a compound selected from:

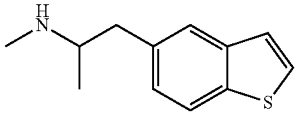

5-MAPBT

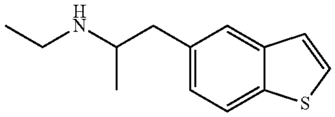

5-EAPBT

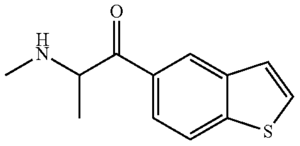

Bk-5-MAPBT

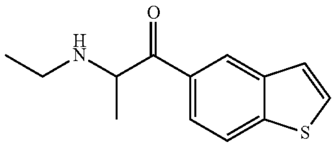

Bk-5-EAPBT

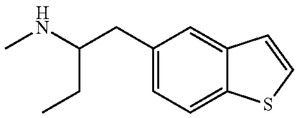

5-MBPBT

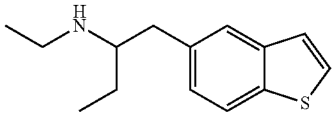

5-EBPBT

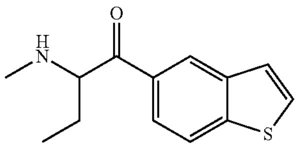

Bk-5-MBPBT

-continued

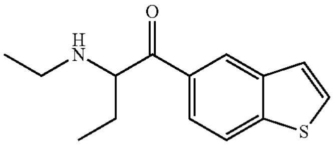

Bk-5-EBPBT

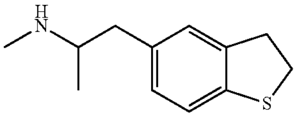

6-MAPDBT

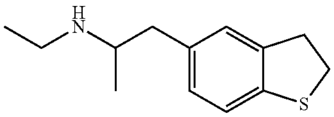

5-EAPDBT

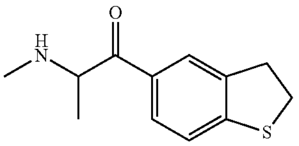

Bk-5-MAPDBT

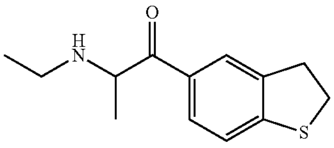

Bk-5-EAPDBT

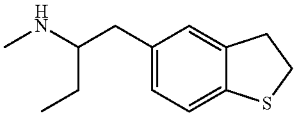

5-MBPDBT

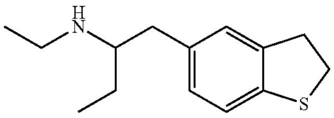

5-EBPDBT

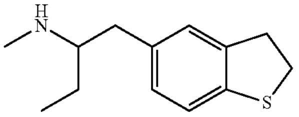

Bk-5-MBPDBT

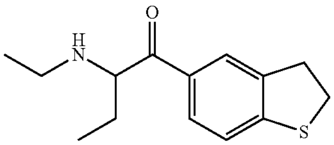

Bk-5-EBPDBT

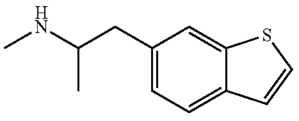

6-MAPBT

-continued
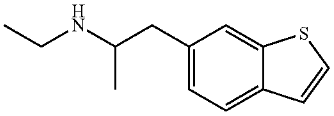
6-EAPBT
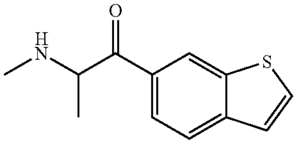
Bk-6-MAPBT
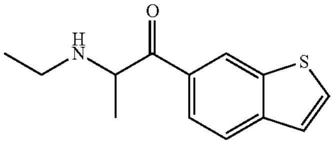
Bk-6-EAPBT
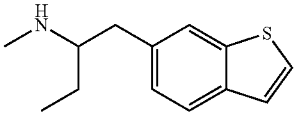
6-MBPBT
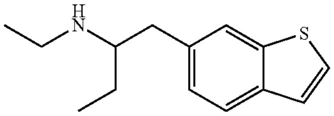
6-EBPBT
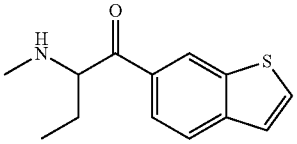
Bk-6-MBPBT
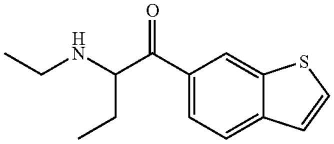
Bk-6-EBPBT
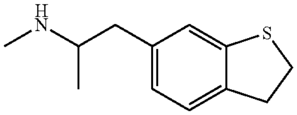
6-MAPDBT
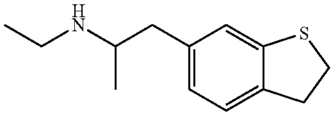
6-EAPDBT
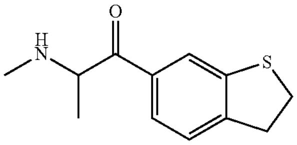
Bk-6-MAPDBT
-continued
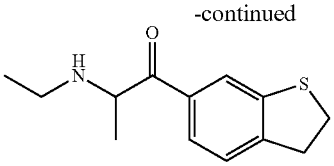
Bk-6-EAPDBT
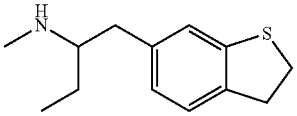
6-MBPDBT
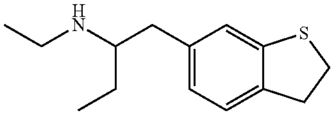
6-EBPDBT
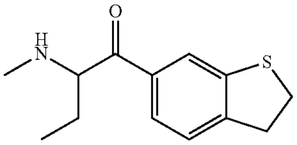
Bk-6-MBPDBT
and
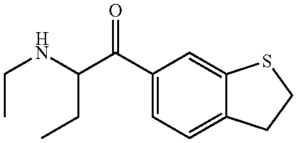
Bk-6-EBPDBT
or a pharmaceutically acceptable salt or salt mixtures thereof.
132. The enantiomerically enriched mixture of embodiment 131 selected from:
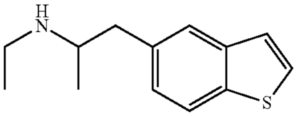
5-MAPBT
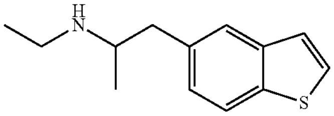
5-EAPBT
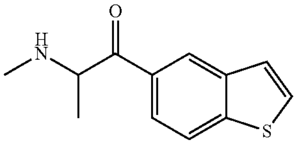
Bk-5-MAPBT
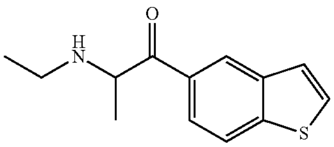
Bk-5-EAPBT -continued
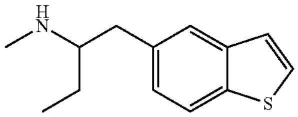
5-MBPBT
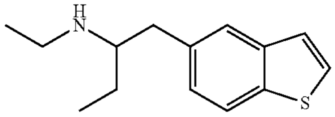
5-EBPBT
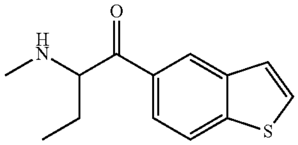
Bk-5-MBPBT
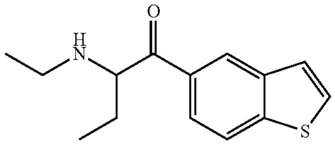
Bk-5-EBPBT
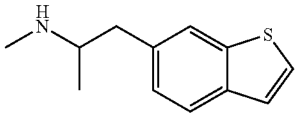
6-MAPBT
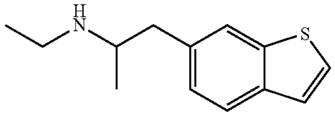
6-EAPBT
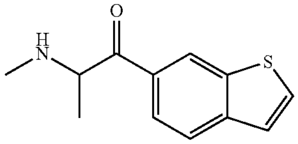
Bk-6-MAPBT
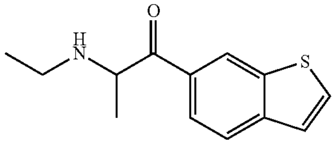
Bk-6-EAPBT
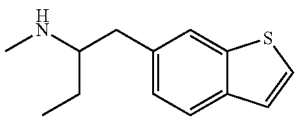
6-MBPBT
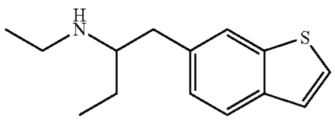
6-EBPBT
-continued
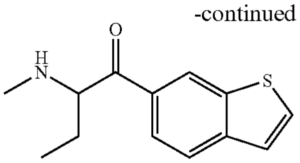
and
Bk-6-MBPBT
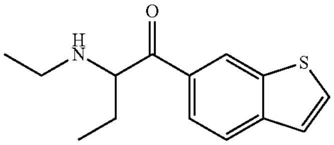
Bk-6-EBPBT
or a pharmaceutically acceptable salt or salt mixtures thereof.
133. The enantiomerically enriched mixture of embodiment 131 selected from:
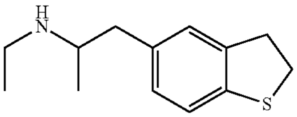
5-MAPDBT
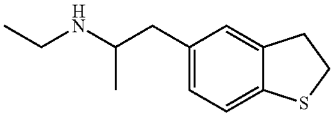
5-EAPDBT
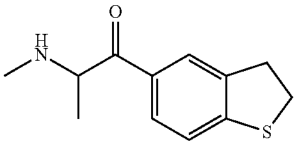
Bk-5-MAPDBT
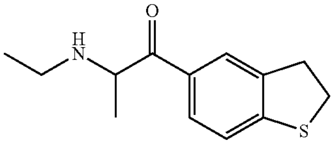
Bk-5-EAPDBT
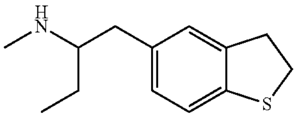
5-MBPDBT
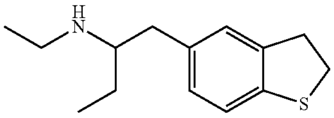
5-EBPDBT
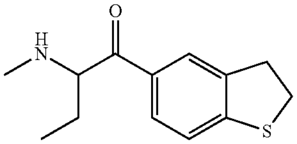
Bk-5-MBPDBT -continued

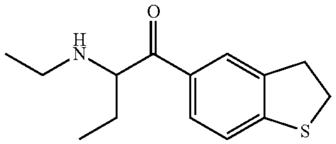

Bk-5-EBPDBT

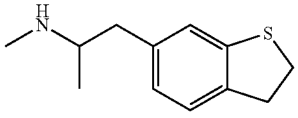

6-MAPDBT

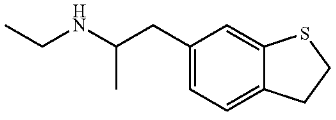

6-EAPDBT

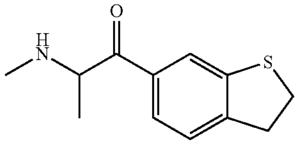

Bk-6-MAPDBT

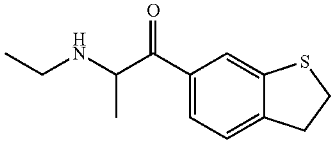

Bk-6-EAPDBT

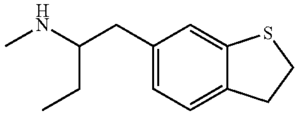

6-MBPDBT

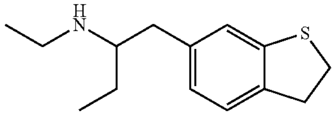

6-EBPDBT

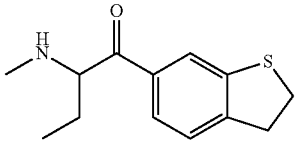

Bk-6-MBPDBT and

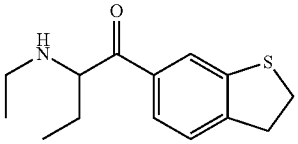

Bk-6-EBPDBT or a pharmaceutically acceptable salt or salt mixtures thereof.

134. The enantiomerically enriched mixture of embodiment 131 or 132 of structure:

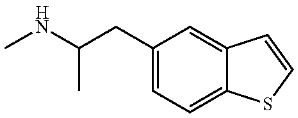

5-MAPBT or a pharmaceutically acceptable salt or salt mixtures thereof.

135. The enantiomerically enriched mixture of embodiment 131 or 132 of structure:

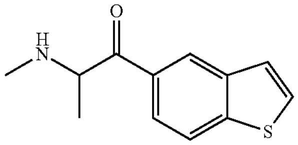

Bk-5-MAPBT or a pharmaceutically acceptable salt or salt mixtures thereof.

136. The enantiomerically enriched mixture of embodiment 131 or 132 of structure:

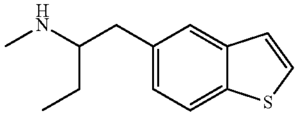

5-MBPBT or a pharmaceutically acceptable salt or salt mixtures thereof.

137. The enantiomerically enriched mixture of embodiment 131 or 132 of structure:

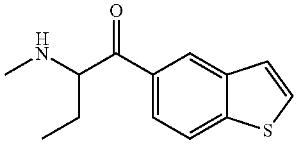

Bk-5-MBPBT or a pharmaceutically acceptable salt or salt mixtures thereof.

138. The enantiomerically enriched mixture of embodiment 131 or 132 of structure:

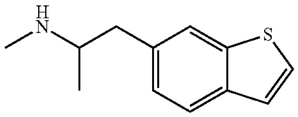

6-MAPBT or a pharmaceutically acceptable salt or salt mixtures thereof.

139. The enantiomerically enriched mixture of embodiment 131 or 132 of structure:

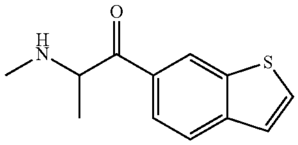

Bk-6-MAPBT or a pharmaceutically acceptable salt or salt mixtures thereof.

140. The enantiomerically enriched mixture of embodiment 131 or 132 of structure:

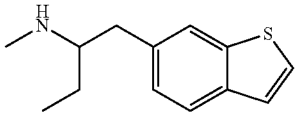

6-MBPBT or a pharmaceutically acceptable salt or salt mixtures thereof.

141. The enantiomerically enriched mixture of embodiment 131 or 132 of structure:

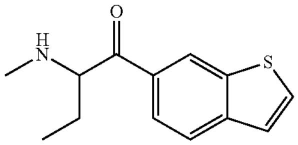

Bk-6-MBPBT or a pharmaceutically acceptable salt or salt mixtures thereof.

142. The enantiomerically enriched mixture of embodiment 131 or 132 of structure:

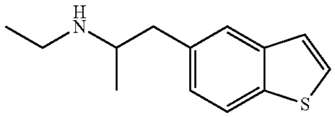

5-EAPBT or a pharmaceutically acceptable salt or salt mixtures thereof.

143. The enantiomerically enriched mixture of embodiment 131 or 132 of structure:

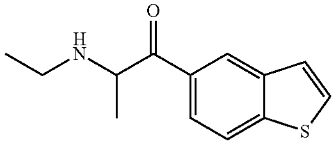

Bk-5-EAPBT or a pharmaceutically acceptable salt or salt mixtures thereof.

144. The enantiomerically enriched mixture of embodiment 131 or 132 of structure:

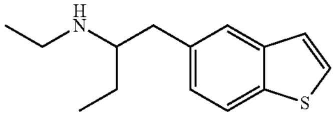

5-EBPBT or a pharmaceutically acceptable salt or salt mixtures thereof.

145. The enantiomerically enriched mixture of embodiment 131 or 132 of structure:

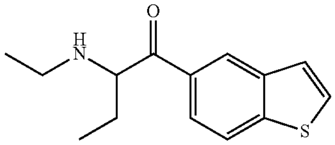

Bk-5-EBPBT or a pharmaceutically acceptable salt or salt mixtures thereof

146. The enantiomerically enriched mixture of embodiment 131 or 132 of structure:

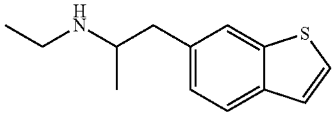

6-EAPBT or a pharmaceutically acceptable salt or salt mixtures thereof.

147. The enantiomerically enriched mixture of embodiment 131 or 132 of structure:

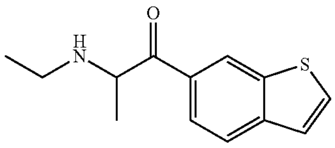

Bk-6-EAPBT or a pharmaceutically acceptable salt or salt mixtures thereof.

148. The enantiomerically enriched mixture of embodiment 131 or 132 of structure:

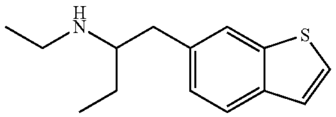

6-EBPT or a pharmaceutically acceptable salt or salt mixtures thereof.

149. The enantiomerically enriched mixture of embodiment 131 or 132 of structure:

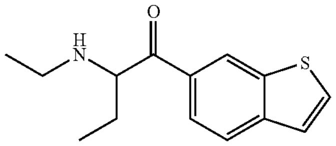

Bk-6-EBPBT or a pharmaceutically acceptable salt or salt mixtures thereof.

150. The enantiomerically enriched mixture of embodiment 131 or 133 of structure:

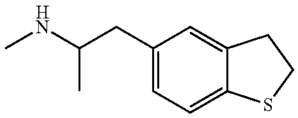

5-MAPDBT or a pharmaceutically acceptable salt or salt mixtures thereof.

151. The enantiomerically enriched mixture of embodiment 131 or 133 of structure:

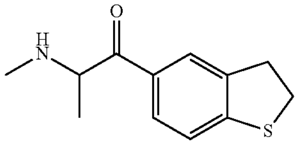

Bk-6-MAPDBT or a pharmaceutically acceptable salt or salt mixtures thereof.

152. The enantiomerically enriched mixture of embodiment 131 or 133 of structure:

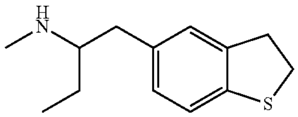

5-MBPDBT or a pharmaceutically acceptable salt or salt mixtures thereof.

153. The enantiomerically enriched mixture of embodiment 131 or 133 of structure:

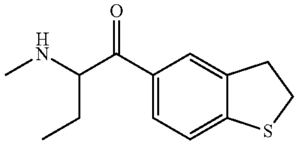

Bk-5-MBPDBT or a pharmaceutically acceptable salt or salt mixtures thereof.

154. The enantiomerically enriched mixture of embodiment 131 or 133 of structure:

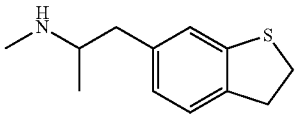

6-MAPDBT or a pharmaceutically acceptable salt or salt mixtures thereof.

155. The enantiomerically enriched mixture of embodiment 131 or 133 of structure:

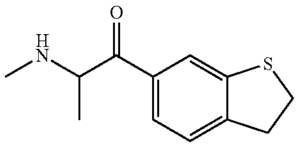

Bk-6-MAPDBT or a pharmaceutically acceptable salt or salt mixtures thereof.

156. The enantiomerically enriched mixture of embodiment 131 or 133 of structure:

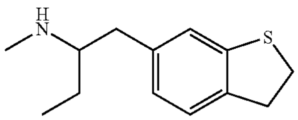

6-MBPDBT or a pharmaceutically acceptable salt or salt mixtures thereof.

157. The enantiomerically enriched mixture of embodiment 131 or 133 of structure:

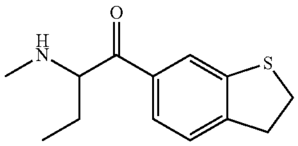

Bk-6-MBPDBT or a pharmaceutically acceptable salt or salt mixtures thereof.

158. The enantiomerically enriched mixture of embodiment 131 or 133 of structure:

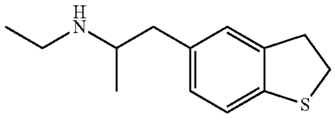

5-EAPDBT or a pharmaceutically acceptable salt or salt mixtures thereof.

159. The enantiomerically enriched mixture of embodiment 131 or 133 of structure:

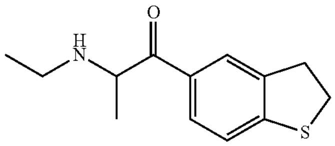

Bk-5-EAPDBT or a pharmaceutically acceptable salt or salt mixtures thereof.

160. The enantiomerically enriched mixture of embodiment 131 or 133 of structure:

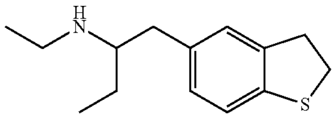

5-EBPDBT or a pharmaceutically acceptable salt or salt mixtures thereof.

161. The enantiomerically enriched mixture of embodiment 131 or 133 of structure:

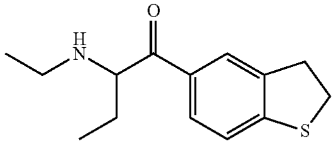

Bk-5-EBPDBT or a pharmaceutically acceptable salt or salt mixtures thereof.

162. The enantiomerically enriched mixture of embodiment 131 or 133 of structure:

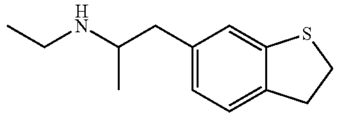

6-EAPDBT or a pharmaceutically acceptable salt or salt mixtures thereof.

163. The enantiomerically enriched mixture of embodiment 131 or 133 of structure:

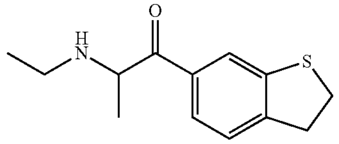

Bk-6-EAPDBT or a pharmaceutically acceptable salt or salt mixtures thereof.

164. The enantiomerically enriched mixture of embodiment 131 or 133 of structure:

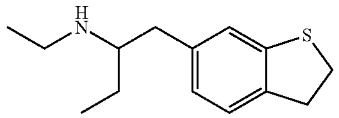

6-EBPDBT or a pharmaceutically acceptable salt or salt mixtures thereof.

165. The enantiomerically enriched mixture of embodiment 131 or 133 of structure:

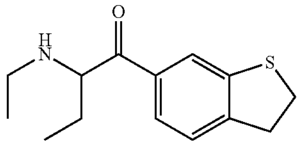

Bk-6-EBPDBT or a pharmaceutically acceptable salt or salt mixtures thereof.

166. An enantiomerically enriched mixture of Formula A, Formula B, Formula C, or Formula D:

Formula A

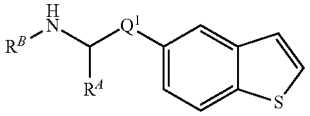

Formula B

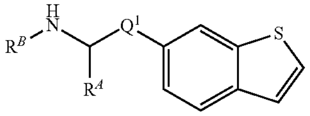

-continued

Formula C

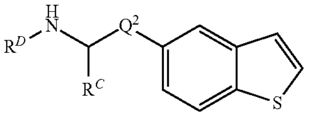

Formula D

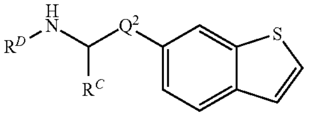

or a pharmaceutically acceptable salt or salt mixtures thereof, wherein:

$R^A$ and $R^B$ are independently selected from $—CH_3$ and $—CH_2CH_3$;

$R^C$ is selected from $—CH_3$, $—CH_2Y$, $—CHY_2$, $—CY_3$, $—CH_2CH_2Y$, $—CH_2CHY_2$, $—CH_2CY_3$, $—CH_2CH_3$, $—CH_2OH$, or $—CH_2CH_2OH$;

$R^D$ is selected from $—CH_3$ and $—CH_2CH_3$;

$Q^1$ is selected from

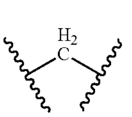 and 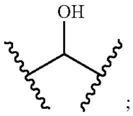 ;

$Q^2$ is selected from:

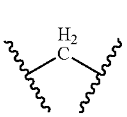 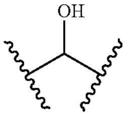 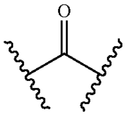

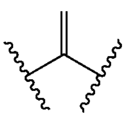 and 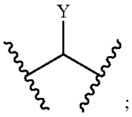 ;

and

Y is halogen.

167. The enantiomerically enriched mixture of embodiment 166 wherein the mixture is of Formula A:

Formula A

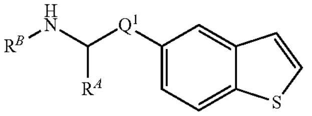

or a pharmaceutically acceptable salt or salt mixtures thereof.

168. The enantiomerically enriched mixture of embodiment 166 wherein the mixture is of Formula B

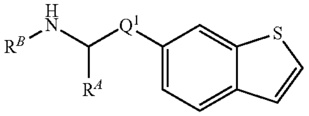

or a pharmaceutically acceptable salt or salt mixtures thereof.

169. The enantiomerically enriched mixture of embodiment 166 wherein the mixture is of Formula C

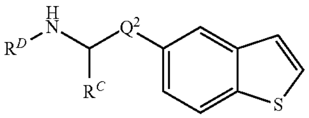

or a pharmaceutically acceptable salt or salt mixtures thereof.

170. The enantiomerically enriched mixture of embodiment 166 wherein the mixture is of Formula D:

Formula D

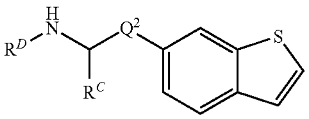

or a pharmaceutically acceptable salt or salt mixtures thereof.

171. The enantiomerically enriched mixture of any one of embodiment 166, 167, or 169 wherein the mixture is selected from:

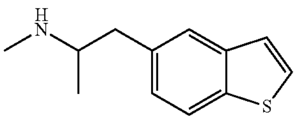

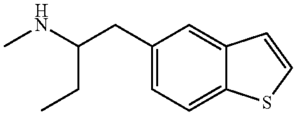

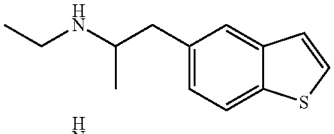 and

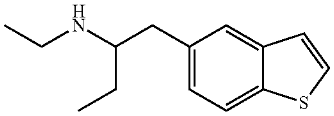

or a pharmaceutically acceptable salt or salt mixtures thereof.

172. The enantiomerically enriched mixture of embodiment 166, 167, or 169 wherein the mixture is selected from:

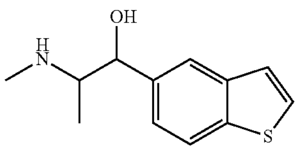

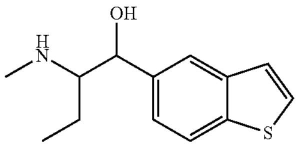

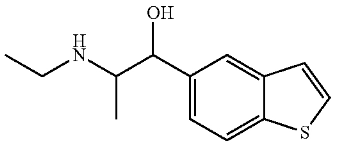

and

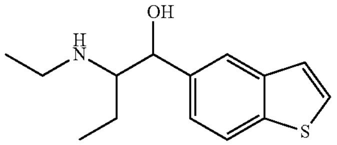

or a pharmaceutically acceptable salt or salt mixtures thereof.

173. The enantiomerically enriched mixture of embodiment 166, 168, or 170 wherein the mixture is selected from:

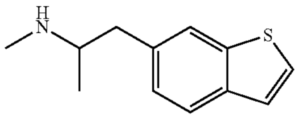

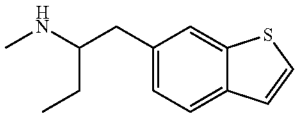

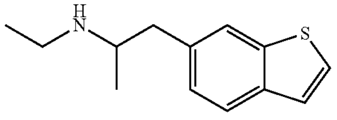

and

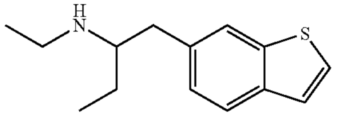

or a pharmaceutically acceptable salt or salt mixtures thereof.

174. The enantiomerically enriched mixture of embodiment 166, 168, or 170 wherein the mixture is selected from:

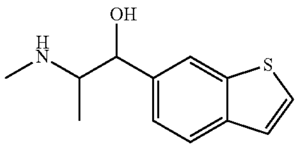

-continued

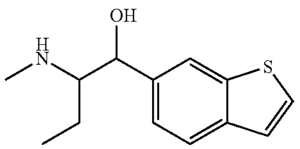

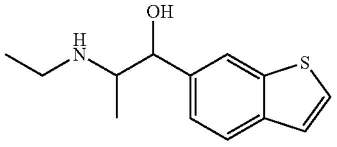

and

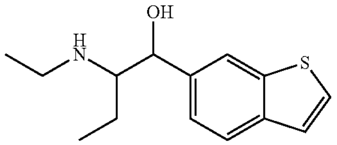

or a pharmaceutically acceptable salt or salt mixtures thereof.

175. The enantiomerically enriched mixture of embodiment 166 or 169 wherein the mixture is of the structure:

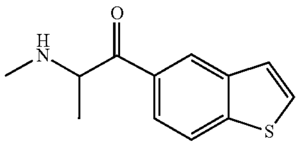

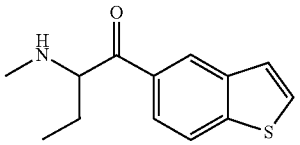

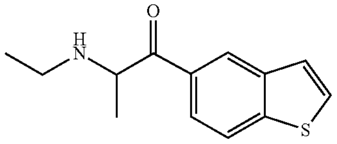

and

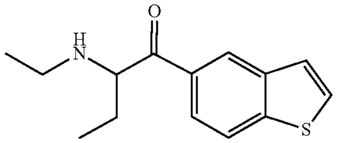

or a pharmaceutically acceptable salt or salt mixtures thereof.

176. The enantiomerically enriched mixture of embodiment 166 or 169 wherein the mixture is of the structure:

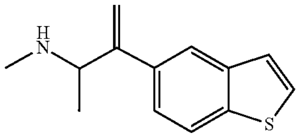

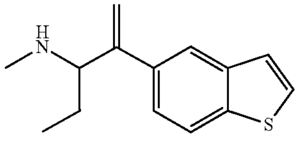

-continued

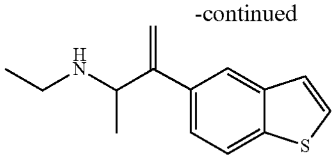

and

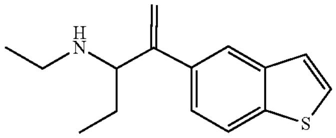

or a pharmaceutically acceptable salt or salt mixtures thereof.

177. The enantiomerically enriched mixture of embodiment 166 or 169 wherein the mixture is of the structure:

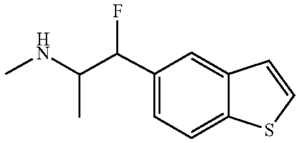

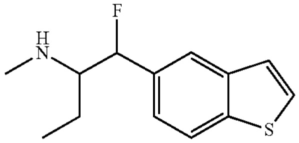

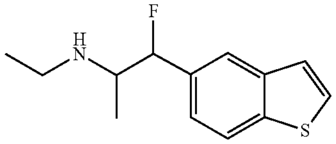

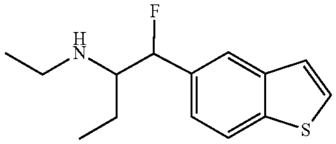

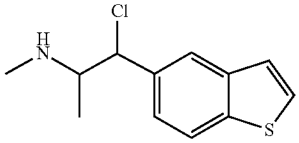

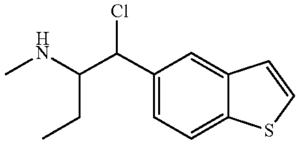

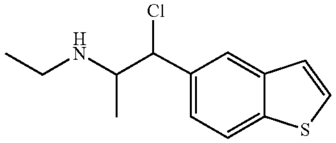

and

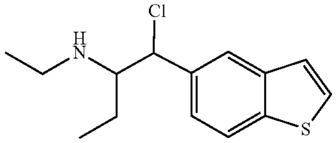

or a pharmaceutically acceptable salt or salt mixtures thereof.

178. The enantiomerically enriched mixture of embodiment 166 or 170 wherein the mixture is of the structure:

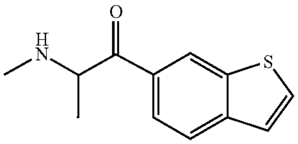

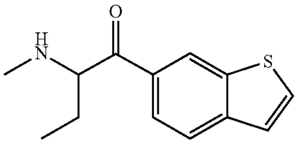

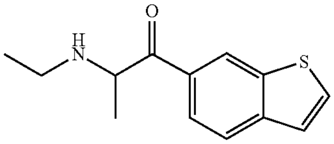

and

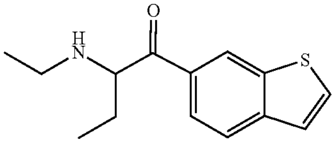

or a pharmaceutically acceptable salt or salt mixtures thereof

179. The enantiomerically enriched mixture of embodiment 166 or 170 wherein the mixture is of the structure:

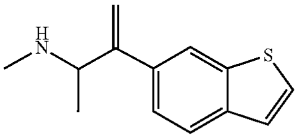

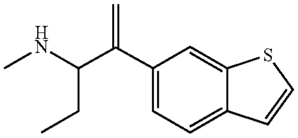

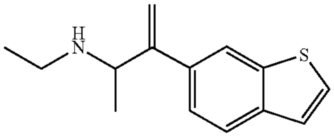

and

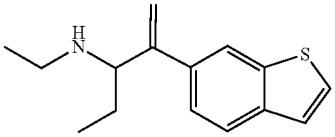

or a pharmaceutically acceptable salt or salt mixtures thereof.

180. The enantiomerically enriched mixture of embodiment 166 or 170 wherein the mixture is of the structure:

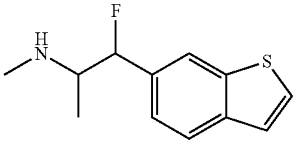

-continued

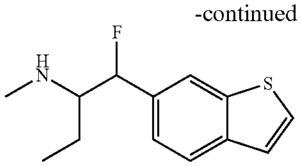

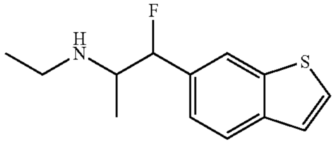

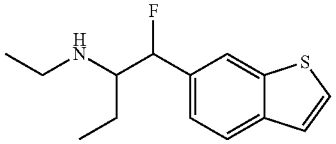

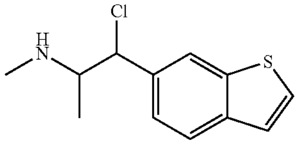

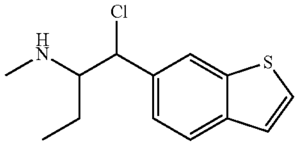

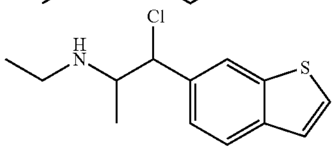

and

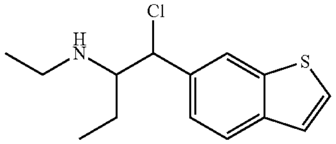

or a pharmaceutically acceptable salt or salt mixtures thereof

181. An enantiomerically enriched mixture of Formula XIV:

(XIV)

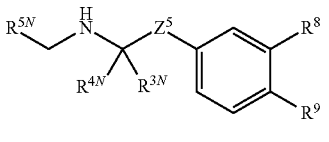

or a pharmaceutically acceptable salt or salt mixtures thereof, wherein:

$Z^5$ is selected from

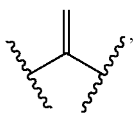

,

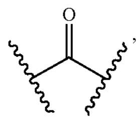

, and

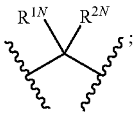

;

$R^{1N}$ and $R^{2N}$ are independently selected from —H, —X, —OH, —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{3N}$ and $R^{4N}$ are independently selected from —H, —$CH_2OH$, —$CH_2X$, —$CHX_2$, —$CX_3$, —$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{5N}$ is selected from —H and —$CH_3$;

$R^8$ and $R^9$ are taken together as —$SCH_2CH_2$—, —$CH_2CH_2S$—, —SCH═CH—, or —CH═CHS—; and X is independently selected from —F, —Cl, and —Br.

182. The enantiomerically enriched mixture of any of embodiments 131-181, wherein the compound has entactogenic properties.

183. The enantiomerically enriched mixture of any of embodiments 131-181, wherein the compound has nicotinic-receptor-dependent therapeutic properties.

184. The enantiomerically enriched mixture of any of embodiments 131-181, wherein the compound has serotonin-receptor-dependent therapeutic properties.

185. The enantiomerically enriched mixture of any of embodiments 131-181, wherein the compound has dopamine-receptor-dependent therapeutic properties.

186. The enantiomerically enriched mixture of any of embodiments 131-181, wherein the compound enhances serotonin-receptor-dependent properties and decreases nicotinic properties or dopaminergic properties relative to the racemate.

187. The enantiomerically enriched mixture of any of embodiments 131-181, in an enantiomerically enriched form that decreases a hallucinogenic effect relative to the racemate.

188. The enantiomerically enriched mixture of any of embodiments 131-181, in an enantiomerically enriched form that decreases an unwanted psychoactive effect relative to the racemate.

189. The enantiomerically enriched mixture of any of embodiments 131-181, in an enantiomerically enriched form that decreases a physiological effect relative to the racemate.

190. The enantiomerically enriched mixture of any of embodiments 131-181, in an enantiomerically enriched form that decreases at least one toxic effect relative to the racemate.

191. The enantiomerically enriched mixture of any of embodiments 131-181, in an enantiomerically enriched form that decreases abuse potential relative to the racemate.

192. The enantiomerically enriched mixture of any of embodiments 131-181 in an enantiomerically enriched form that has at least about 60% S-enantiomer.

193. The enantiomerically enriched mixture of any of embodiments 131-181 in an enantiomerically enriched form that has at least about 70% S-enantiomer.

194. The enantiomerically enriched mixture of any of embodiments 131-181 in an enantiomerically enriched form that has at least about 80% S-enantiomer.

195. The enantiomerically enriched mixture of any of embodiments 131-181 in an enantiomerically enriched form that has at least about 90% S-enantiomer.

196. The enantiomerically enriched mixture of any of embodiments 131-181 in an enantiomerically enriched form that has at least about 60% R-enantiomer.

197. The enantiomerically enriched mixture of any of embodiments 131-181 in an enantiomerically enriched form that has at least about 70% R-enantiomer.

198. The enantiomerically enriched mixture of any of embodiments 131-181 in an enantiomerically enriched form that has at least about 80% R-enantiomer.

199. The enantiomerically enriched mixture of any of embodiments 131-181 in an enantiomerically enriched form that has at least about 90% R-enantiomer.

200. The enantiomerically enriched mixture of any of embodiments 131-199 that shows the therapeutic effect of emotional openness.

201. The enantiomerically enriched mixture of any of embodiments 131-199 wherein the pharmaceutically acceptable salt(s) is selected from HCl, sulfate, aspartate, saccharate, phosphate, oxalate, acetate, amino acid anion, gluconate, maleate, malate, citrate, mesylate, nitrate or tartrate, or a mixture thereof.

202. The enantiomerically enriched mixture of any of embodiments 131-201 that is both a direct 5-$HT_{1B}$ agonist and a serotonin releasing agent.

203. The enantiomerically enriched mixture of embodiment 202 that is also a serotonin reuptake inhibitor.

204. The enantiomerically enriched mixture of any one of embodiments 131-203 that has minimal or no direct agonism of 5-$HT_{2A}$.

205. A method for treating a central nervous system disorder comprising administering an effective amount of a compound, pure R- or S-enantiomer, or enantiomerically enriched mixture of any one of embodiments 1-204 to a host in need thereof.

206. The method of embodiment 205 wherein the administered compound is a compound of Formula I, Formula II, Formula III, Formula IV, Formula V, Formula VI, Formula VII, Formula VIII, or Formula IX:

(I)

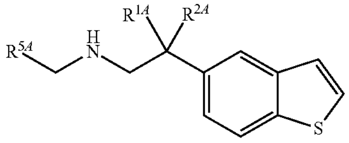

(II)

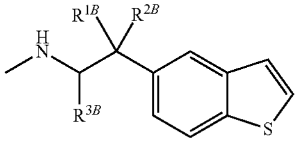

(III)

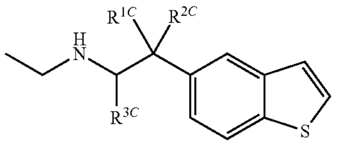

(IV)

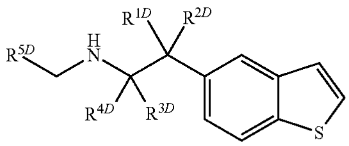

(V)

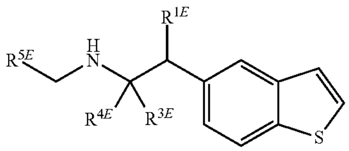

-continued (VI)

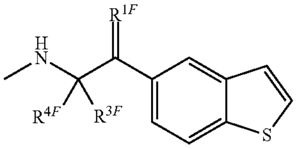

(VII)

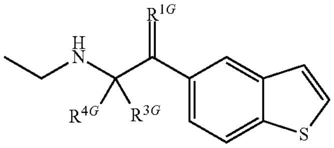

(VIII)

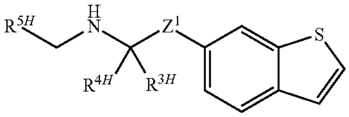

(IX)

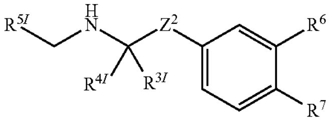

or a pharmaceutically acceptable salt or salt mixtures thereof, wherein:

$Z^1$ is selected from

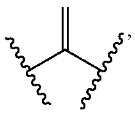, 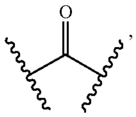, and 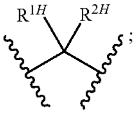;

$Z^2$ is selected from

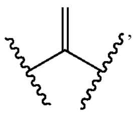, 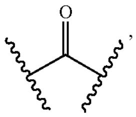, and 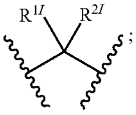;

$R^{1A}$, $R^{1D}$, and $R^{2D}$ are independently selected from —X, —OH, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{1B}$, $R^{1C}$, $R^{1E}$, $R^{1H}$, $R^{1I}$, $R^{2B}$, $R^{2C}$, $R^{2H}$, and $R^{2I}$ are independently selected from —H, —X, —OH, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl;

$R^{1F}$ and $R^{1G}$ are independently selected from $CH_2$ and O;

$R^{2A}$ is selected from —H, —X, —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl, wherein if $R^{1A}$ is —OH, $R^{2A}$ is not —H or $C_1$ alkyl;

$R^{3B}$ is selected from —$CH_2OH$, —$CH_2X$, —$CHX_2$, —$CX_3$,—$CH_2CH_2OH$, —$CH_2CH_2X$, —$CH_2CHX_2$, —$CH_2CX_3$, $C_3$-$C_4$ cycloalkyl, and $C_1$-$C_4$ alkyl; wherein if $R^{3B}$ is $C_1$ alkyl and one of $R^{2B}$ and $R^{1B}$ is —H, then the other of $R^{2B}$ and $R^{1B}$ cannot be —H or —OH;

$R^{3C}$ is selected from $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_1$-$C_4$ alkyl; wherein if $R^{3C}$ is $C_1$ alkyl and one of $R^{2C}$ and $R^{1C}$ is —H, then the other of $R^{2C}$ and $R^{1C}$ cannot be —OH or $C_1$ alkyl;

$R^{3D}$, $R^{3F}$, and $R^{4D}$ are independently selected from $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_1$-$C_4$ alkyl;

$R^{3E}$ and $R^{4E}$ are independently selected from $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_1$-$C_4$ alkyl, wherein when $R^{3E}$ and $R^{4E}$ are both $C_1$ alkyl, $R^{1E}$ cannot be —OH or —F;

$R^{3G}$ and $R^{4G}$ are independently selected from —H, $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_1$-$C_4$ alkyl, wherein if $R^{1G}$ is O and one of $R^{3G}$ and $R^{4G}$ is —H, then the other of $R^{3G}$ and $R^{4G}$ cannot be —H or $C_1$ alkyl;

$R^{3H}$, $R^{3I}$, $R^{4H}$, and $R^{4I}$ are independently selected from —H, $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_1$-$C_4$ alkyl;

$R^{4F}$ is selected from —H, $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_1$-$C_4$ alkyl, wherein if $R^{4F}$ is —H and $R^{1F}$ is O, then $R^{3F}$ cannot be $C_1$ or $C_2$ alkyl;

$R^{5A}$, $R^{5D}$, $R^{5E}$, and $R^{5H}$ are independently selected from —H or $—CH_3$;

$R^{5I}$ is selected from —H and $—CH_3$, wherein if $R^{3I}$, $R^{4I}$, and $R^{5I}$ are all —H, then $Z^2$ cannot be

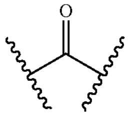, 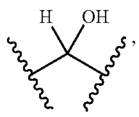, or 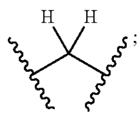;

$R^6$ and $R^7$ are taken together as $—SCH_2CH_2—$ or $—CH_2CH_2S—$; and

X is independently selected from —F, —Cl, and —Br.

207. The method of embodiment 205 wherein the administered compound is a compound of Formula XIV:

(XIV)

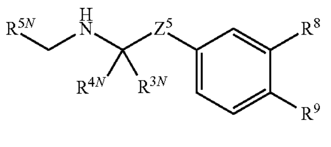

or a pharmaceutically acceptable salt or salt mixtures thereof, wherein:

$Z^5$ is selected from

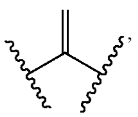, 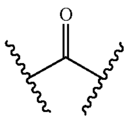, and 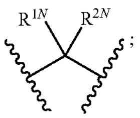;

$R^{1N}$ and $R^{2N}$ are independently selected from —H, —X, —OH, $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_1$-$C_4$ alkyl;

$R^{3N}$ and $R^{4N}$ are independently selected from —H, $—CH_2OH$, $—CH_2X$, $—CHX_2$, $—CX_3$, $—CH_2CH_2OH$, $—CH_2CH_2X$, $—CH_2CHX_2$, $—CH_2CX_3$, $C_3$-$C_4$ cycloalkyl, and $C_1$-$C_4$ alkyl;

$R^{5N}$ is selected from —H and $—CH_3$;

$R^8$ and $R^9$ are taken together as $—SCH_2CH_2—$, $—CH_2CH_2S—$, $—SCH{=}CH—$, or $—CH{=}CHS—$; and X is independently selected from —F, —Cl, and —Br.

208. The method of embodiment 205 wherein the administered compound is a compound of Formula A or Formula B:

Formula A

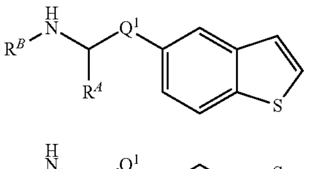

Formula B

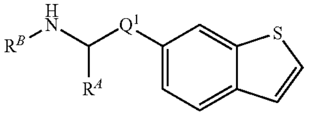

or a pharmaceutically acceptable salt or salt mixtures thereof, wherein:

$R^A$ and $R^B$ are independently selected from $—CH_3$ and $—CH_2CH_3$;

$Q^1$ is selected from

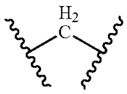 and 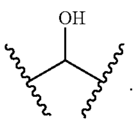.

209. The method of embodiment 205 wherein the administered compound is a compound of Formula C or Formula D:

Formula C

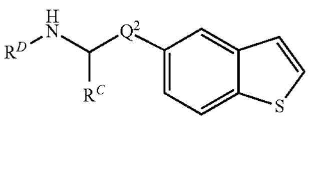

-continued

Formula D

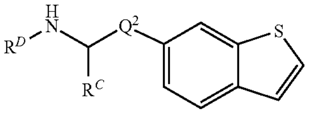

or a pharmaceutically acceptable salt or salt mixtures thereof, wherein:

$R^C$ is selected from $—CH_3$, $—CH_2Y$, $—CHY_2$, $—CY_3$, $—CH_2CH_2Y$, $—CH_2CHY_2$, $—CH_2CY_3$, $—CH_2CH_3$, $—CH_2OH$, or $—CH_2CH_2OH$;

$R^D$ is selected from $—CH_3$ and $—CH_2CH_3$;

$Q^2$ is selected from:

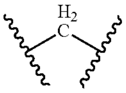
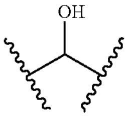
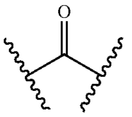
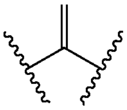
and
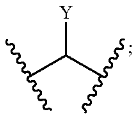

and

Y is halogen.

210. The method of any one of embodiments 205-209 wherein the administered compound is selected from:

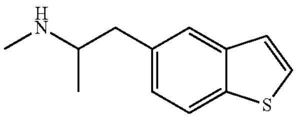
and

5-MAPBT

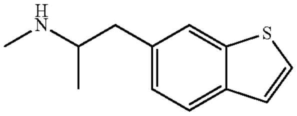

6-MAPBT or a pharmaceutically acceptable salt or salt mixtures thereof.

211. A method for treating a central nervous system disorder comprising administering an effective amount of a compound, pure R- or S-enantiomer, or enantiomerically enriched mixture selected from:

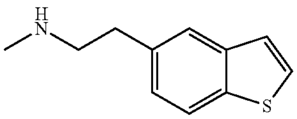

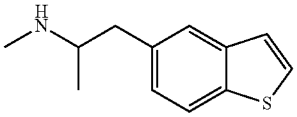

-continued

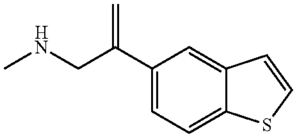

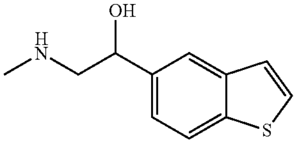

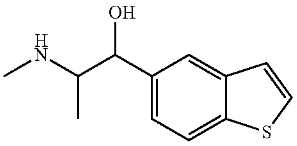

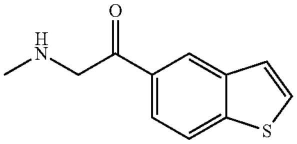

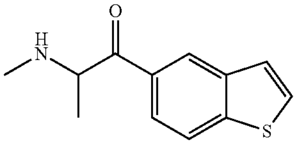

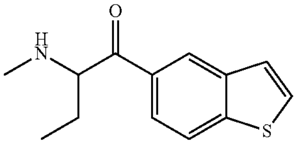

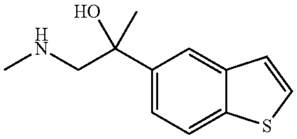

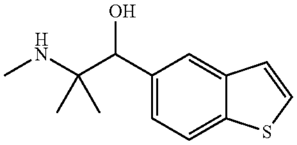

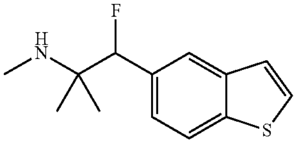

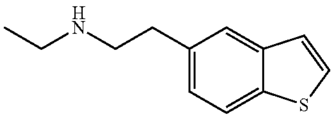

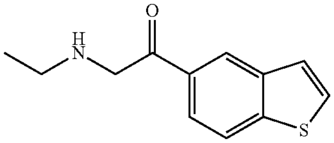

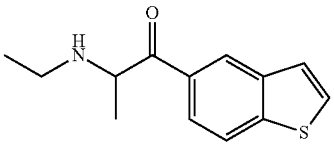

-continued

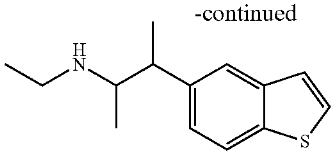

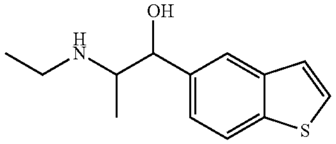

and

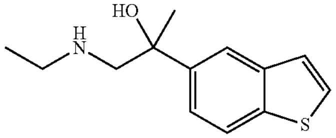

to a host in need thereof.

212. A method for treating a central nervous system disorder comprising administering an effective amount of a compound, pure R- or S-enantiomer, or enantiomerically enriched mixture of structure:

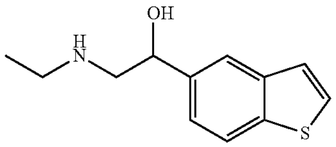

to a host in need thereof.

213. The method of any one of embodiments 205-212 wherein the central nervous system disorder is selected from: post-traumatic stress disorder, depression, dysthymia, anxiety, generalized anxiety, social anxiety, panic, adjustment disorders, feeding and eating disorders, binge behaviors, body dysmorphic syndromes, addiction, drug abuse or dependence disorders, substance use disorders, disruptive behavior disorders, impulse control disorders, gaming disorders, gambling disorders, memory loss, dementia of aging, attention deficit hyperactivity disorder, personality disorders, attachment disorders, autism and dissociative disorders.

214. The method of any one of embodiments 205-212 wherein the host is a human.

215. The method of any one of embodiments 205-212 wherein the central nervous system disorder is post-traumatic stress disorder.

216. The method of any one of embodiments 205-212 wherein the central nervous system disorder is adjustment disorder.

217. The method of any one of embodiments 205-212 wherein the central nervous system disorder is generalized anxiety.

218. The method of any one of embodiments 205-212 wherein the central nervous system disorder is social anxiety.

219. The method of any one of embodiments 205-212 wherein the central nervous system disorder is depression.

220. The method of any one of embodiments 205-212 wherein the central nervous system disorder is addiction.

221. The method of any one of embodiments 205-212 wherein the central nervous system disorder is an attachment disorder.

222. The method of any one of embodiments 205-212 wherein the central nervous system disorder is schizophrenia.

223. The method of any one of embodiments 205-212 wherein the central nervous system disorder is an eating disorder.

224. The method of embodiment 223 wherein the eating disorder is bulimia.

225. The method of embodiment 223 wherein the eating disorder is binge eating.

226. The method of embodiment 223 wherein the eating disorder is anorexia.

227. The method of any one of embodiments 205-226 wherein the compound, pure R- or S-enantiomer, or enantiomerically enriched mixture is administered in a clinical setting.

228. The method of any one of embodiments 205-226 wherein the compound, pure R- or S-enantiomer, or enantiomerically enriched mixture is administered in an at-home setting.

229. The method of any one of embodiments 205-226 wherein the compound, pure R- or S-enantiomer, or enantiomerically enriched mixture is administered during a psychotherapy session.

230. The method of any one of embodiments 205-226 wherein the compound, pure R- or S-enantiomer, or enantiomerically enriched mixture is administered during a counseling session.

231. A pharmaceutical composition comprising an effective patient-treating amount of a compound, pure R- or S-enantiomer, or enantiomerically enriched mixture of any one of embodiments 1-204 and a pharmaceutically acceptable carrier or excipient.

232. A pharmaceutical composition comprising an effective patient-treating amount of a compound, pure R- or S-enantiomer, or enantiomerically enriched mixture, with a pharmaceutically acceptable carrier or excipient, wherein the compound, pure R- or S-enantiomer, or enantiomerically enriched mixture is of a compound selected from:

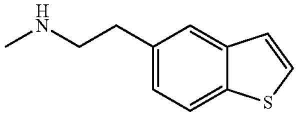

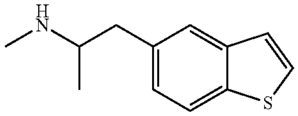

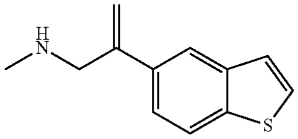

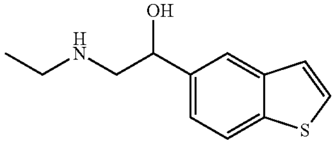

-continued

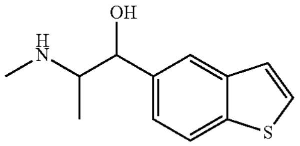

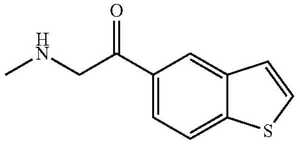

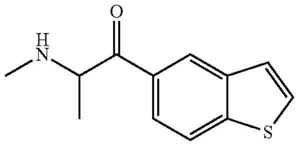

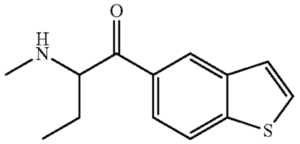

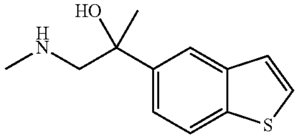

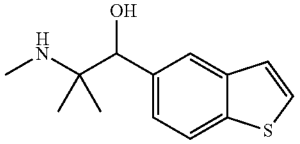

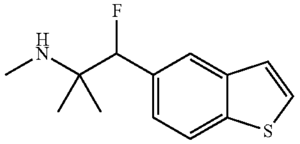

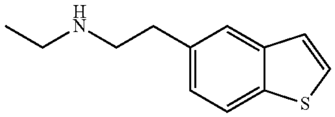

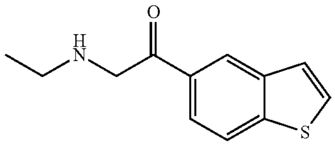

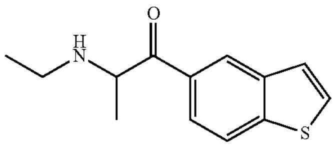

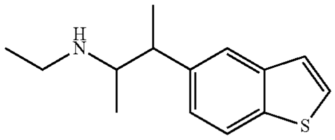

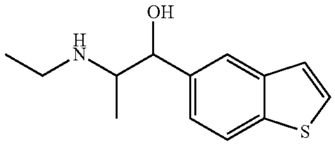

and

-continued

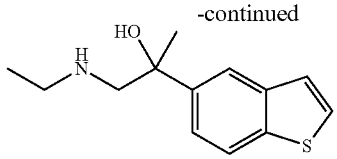

.

233. A pharmaceutical composition comprising an effective patient-treating amount of a compound, pure R- or S-enantiomer, or enantiomerically enriched mixture, with a pharmaceutically acceptable carrier or excipient, wherein the compound, pure R- or S-enantiomer, or enantiomerically enriched mixture is the compound:

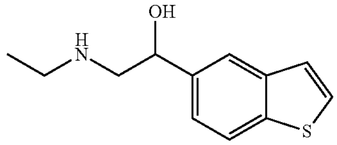

234. The pharmaceutical composition of any one of embodiments 231-233 wherein the composition is administered systemically.

235. The pharmaceutical composition of any one of embodiments 231-233 wherein the composition is administered orally.

236. The pharmaceutical composition of any one of embodiments 231-233 wherein the composition is administered to mucosal tissue.

237. The pharmaceutical composition of any one of embodiments 231-233 wherein the composition is administered rectally.

238. The pharmaceutical composition of any one of embodiments 231-233 wherein the composition is administered topically.

239. The pharmaceutical composition of any one of embodiments 231-233 wherein the composition is administered subcutaneously.

240. The pharmaceutical composition of any one of embodiments 231-233 wherein the composition is administered intravenously.

241. The pharmaceutical composition of any one of embodiments 231-233 wherein the composition is administered intramuscularly.

242. The pharmaceutical composition of any one of embodiments 231-233 wherein the composition is administered via inhalation.

243. The pharmaceutical composition of embodiment 235 wherein the composition is administered as a tablet.

244. The pharmaceutical composition of embodiment 235 wherein the composition is administered as a gelcap.

245. The pharmaceutical composition of embodiment 235 wherein the composition is administered as a capsule.

246. The pharmaceutical composition of embodiment 235 wherein the composition is administered as an aqueous emulsion.

247. The pharmaceutical composition of embodiment 235 wherein the composition is administered as an aqueous solution.

248. The pharmaceutical composition of embodiment 235 wherein the composition is administered as a pill.

249. The pharmaceutical composition of embodiment 235 wherein the composition is administered as a buccal tablet.

250. The pharmaceutical composition of embodiment 236 wherein the composition is administered as a sublingual tablet.
251. The pharmaceutical composition of embodiment 236 wherein the composition is administered as a sublingual strip.
252. The pharmaceutical composition of embodiment 236 wherein the composition is administered as a sublingual liquid.
253. The pharmaceutical composition of embodiment 236 wherein the composition is administered as a sublingual spray.
254. The pharmaceutical composition of embodiment 236 wherein the composition is administered as a sublingual gel.
255. The pharmaceutical composition of embodiment 238 wherein the composition is administered as a cream.
256. The pharmaceutical composition of embodiment 238 wherein the composition is administered as a topical solution.
257. The pharmaceutical composition of embodiment 240 wherein the composition is administered as an aqueous solution.
258. The pharmaceutical composition of embodiment 242 wherein the composition is administered as a powder.
259. The pharmaceutical composition of embodiment 242 wherein the composition is administered as an aerosol.
260. A compound, pure R- or S-enantiomer, or enantiomerically enriched mixture or pharmaceutical composition thereof according to any one of embodiments 1-204 or 231-256 for use in the treatment of a central nervous system disorder in a host.
261. A compound, pure R- or S-enantiomer, or enantiomerically enriched mixture or pharmaceutically acceptable salt thereof selected from:

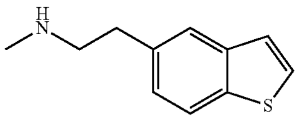

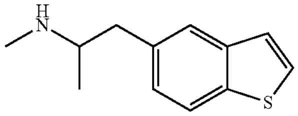

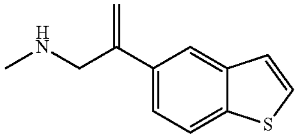

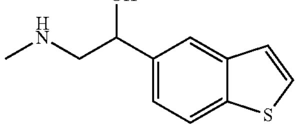

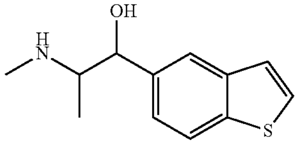

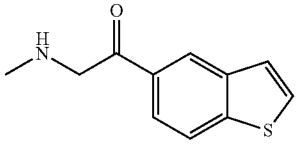

-continued

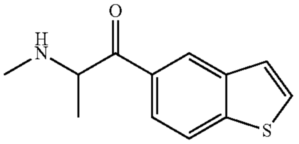

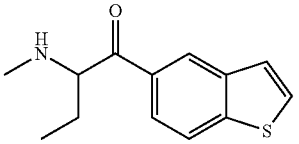

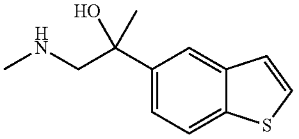

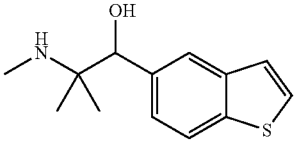

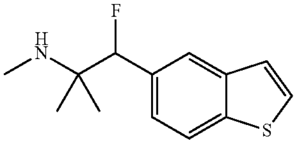

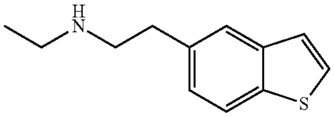

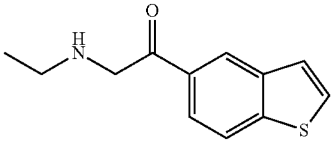

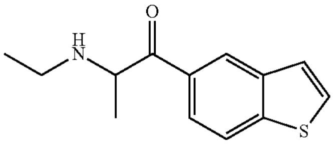

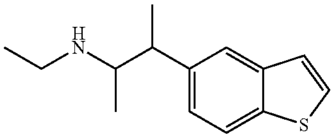

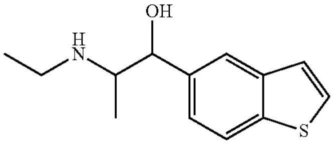

and

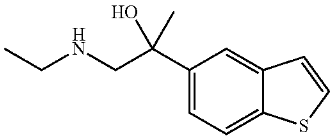

, for use in the treatment of a central nervous system disorder in a host.

262. A compound, pure R- or S-enantiomer, or enantiomerically enriched mixture or pharmaceutically acceptable salt thereof of structure:

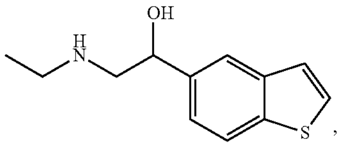

for use in the treatment of a central nervous system disorder in a host.

263. The compound, pure R- or S-enantiomer, enantiomerically enriched mixture, pharmaceutically acceptable salt, or pharmaceutical composition of any one of embodiments 260-262 for use in the treatment of a central nervous system disorder selected from: post-traumatic stress disorder, depression, dysthymia, anxiety, generalized anxiety, social anxiety, panic, adjustment disorders, feeding and eating disorders, binge behaviors, body dysmorphic syndromes, addiction, drug abuse or dependence disorders, substance use disorders, disruptive behavior disorders, impulse control disorders, gaming disorders, gambling disorders, memory loss, dementia of aging, attention deficit hyperactivity disorder, personality disorders, attachment disorders, autism and a dissociative disorder in a host in need thereof.

264. The compound, pure R- or S-enantiomer, or enantiomerically enriched mixture of any one of embodiments 260-263 wherein the host is a human.

265. The compound, pure R- or S-enantiomer, or enantiomerically enriched mixture of any one of embodiments 260-264 wherein the central nervous system disorder is an anxiety disorder.

266. The compound, pure R- or S-enantiomer, or enantiomerically enriched mixture of embodiment 265 wherein the anxiety disorder is generalized anxiety.

267. The compound, pure R- or S-enantiomer, or enantiomerically enriched mixture of embodiment 265 wherein the anxiety disorder is social anxiety.

268. The compound, pure R- or S-enantiomer, or enantiomerically enriched mixture of any one of embodiments 260-264 wherein the central nervous system disorder is depression.

269. The compound, pure R- or S-enantiomer, or enantiomerically enriched mixture of any one of embodiments 260-264 wherein the central nervous system disorder is post-traumatic stress disorder.

270. The compound, pure R- or S-enantiomer, or enantiomerically enriched mixture of any one of embodiments 260-264 wherein the central nervous system disorder is adjustment disorder.

271. The compound, pure R- or S-enantiomer, or enantiomerically enriched mixture of any one of embodiments 260-264 wherein the central nervous system disorder is addiction.

272. The compound, pure R- or S-enantiomer, or enantiomerically enriched mixture of any one of embodiments 260-264 wherein the central nervous system disorder is an attachment disorder.

273. The compound, pure R- or S-enantiomer, or enantiomerically enriched mixture of any one of embodiments 260-264 wherein the central nervous system disorder is schizophrenia.

274. The compound, pure R- or S-enantiomer, or enantiomerically enriched mixture of any one of embodiments 260-264 wherein the central nervous system disorder is an eating disorder.

275. The compound, pure R- or S-enantiomer, or enantiomerically enriched mixture of embodiment 274 wherein the eating disorder is bulimia.

276. The compound, pure R- or S-enantiomer, or enantiomerically enriched mixture of embodiment 274 wherein the eating disorder is binge eating.

277. The compound, pure R- or S-enantiomer, or enantiomerically enriched mixture of embodiment 274 wherein the eating disorder is anorexia.

278. The compound, pure R- or S-enantiomer, or enantiomerically enriched mixture of any one of embodiments 260-277 wherein the compound or enantiomerically enriched mixture is administered in a clinical setting.

279. The compound, pure R- or S-enantiomer, or enantiomerically enriched mixture of any one of embodiments 260-277 wherein the compound or enantiomerically enriched mixture is administered in an at-home setting.

280. The compound, pure R- or S-enantiomer, or enantiomerically enriched mixture of any one of embodiments 260-277 wherein the compound or enantiomerically enriched mixture is administered during a psychotherapy session.

281. The compound, pure R- or S-enantiomer, or enantiomerically enriched mixture of any one of embodiments 260-277 wherein the compound or enantiomerically enriched mixture is administered during a counseling session.

282. Use of a compound, pure R- or S-enantiomer, or enantiomerically enriched mixture or pharmaceutical composition thereof according to any one of embodiments 1-204 or 231-259 in the treatment of a central nervous system disorder in a host.

283. The use of embodiment 282 wherein the central nervous system disorder is selected from: post-traumatic stress disorder, depression, dysthymia, anxiety, generalized anxiety, social anxiety, panic, adjustment disorders, feeding and eating disorders, binge behaviors, body dysmorphic syndromes, addiction, drug abuse or dependence disorders, substance use disorders, disruptive behavior disorders impulse control disorders, gaming disorders, gambling disorders, memory loss, dementia of aging, attention deficit hyperactivity disorder, personality disorders, attachment disorders, autism and a dissociative disorder.

284. Use of a compound, pure R- or S-enantiomer, or enantiomerically enriched mixture or pharmaceutical composition thereof according to any one of embodiments 1-204 or 231-259 in the manufacture of a medicament for the treatment of a central nervous system disorder in a host.

285. Use of a compound, pure R- or S-enantiomer, or enantiomerically enriched mixture or pharmaceutical composition thereof selected from:

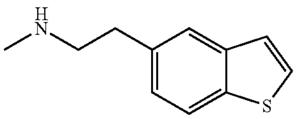

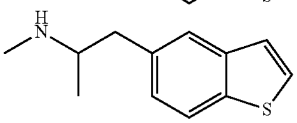

-continued

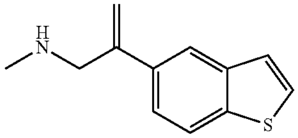

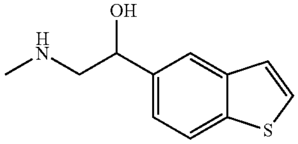

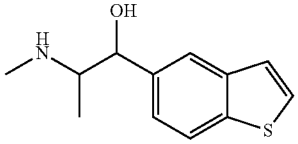

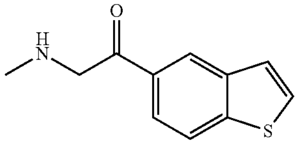

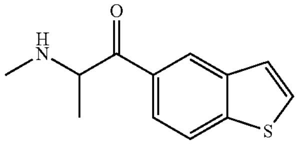

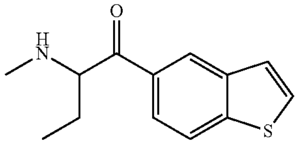

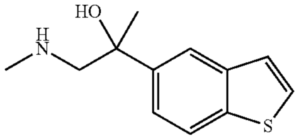

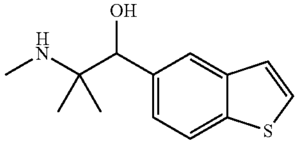

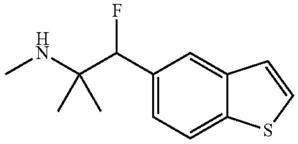

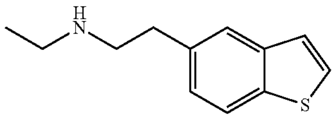

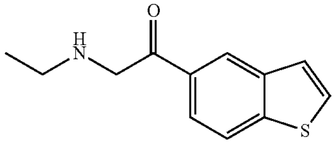

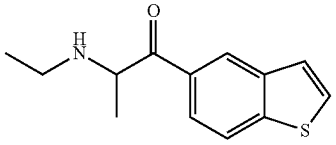

-continued

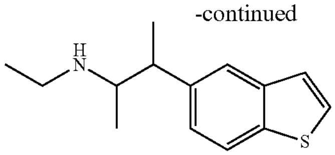

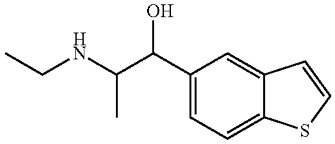

and

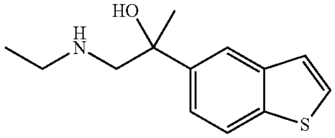

, in the manufacture of a medicament for the treatment of a central nervous system disorder in a host.

286. Use of a compound, pure R- or S-enantiomer, or enantiomerically enriched mixture or pharmaceutical composition thereof of structure:

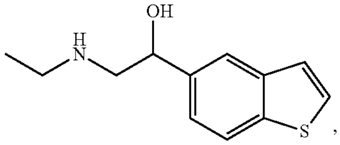

, in the manufacture of a medicament for the treatment of a central nervous system disorder in a host.

287. The use of any one of embodiments 284-286 wherein the central nervous system disorder is selected from: post-traumatic stress disorder, depression, dysthymia, anxiety, generalized anxiety, social anxiety, panic, adjustment disorders, feeding and eating disorders, binge behaviors, body dysmorphic syndromes, addiction, drug abuse or dependence disorders, substance use disorders, disruptive behavior disorders, impulse control disorders, gaming disorders, gambling disorders, memory loss, dementia of aging, attention deficit hyperactivity disorder, personality disorders, attachment disorders, autism and a dissociative disorder.

288. The use of any one of embodiments 284-287 wherein the host is a human.

289. The use of any one of embodiments 284-288 wherein the central nervous system disorder is an anxiety disorder.

290. The use of embodiment 289 wherein the anxiety disorder is generalized anxiety.

291. The use of embodiment 289 wherein the anxiety disorder is social anxiety.

292. The use of any one of embodiments 284-288 wherein the central nervous system disorder is depression.

293. The use of any one of embodiments 284-288 wherein the central nervous system disorder is post-traumatic stress disorder.

294. The use of any one of embodiments 284-288 wherein the central nervous system disorder is adjustment disorder.

295. The use of any one of embodiments 284-288 wherein the central nervous system disorder is addiction.

296. The use of any one of embodiments 284-288 wherein the central nervous system disorder is an eating disorder.

297. The compound, pure R- or S-enantiomer, or enantiomerically enriched mixture of any one of embodiments 1-204 wherein the compound has both serotonin-receptor dependent and dopamine-receptor-dependent activity.

III. Methods to Treat CNS Disorders Including Mental Disorders and for Mental Enhancement The present invention provides methods and uses for the treatment of CNS disorders, including, but not limited to, mental disorders as described herein, including post-traumatic stress and adjustment disorders, and other disorders described in the Background, Summary or Description herein, comprising administering the benzothiophene compounds or composition or a pharmaceutically acceptable salt or salt mixture thereof as described herein. It has been discovered that these compounds display many pharmacological properties that are beneficial to their use as therapeutics and represent an improvement over existing therapeutics.

The present invention provides, for example, methods for the treatment of disorders, including, but not limited to depression, dysthymia, anxiety and phobia disorders (including generalized anxiety, social anxiety, panic, post-traumatic stress and adjustment disorders), feeding and eating disorders (including binge eating, bulimia, and anorexia nervosa), other binge behaviors, body dysmorphic syndromes, alcoholism, tobacco abuse, drug abuse or dependence disorders, disruptive behavior disorders, impulse control disorders, gaming disorders, gambling disorders, memory loss, dementia of aging, attention deficit hyperactivity disorder, personality disorders (including antisocial, avoidant, borderline, histrionic, narcissistic, obsessive compulsive, paranoid, schizoid and schizotypal personality disorders), attachment disorders, autism, and dissociative disorders.

In addition to treating various diseases and disorders, the employed methods of modulating activity of the serotonergic system in particular can be used to improve CNS functioning in non-disease states, such as reducing neuroticism and psychological defensiveness, increasing openness to experience, increasing creativity, and aiding decision-making.

In other embodiments, a compound or composition of the present invention is provided in an effective amount to treat a host, typically a human, with a CNS disorder that can be either a neurological condition (one that is typically treated by a neurologist) or a psychiatric condition (one that is typically treated by a psychiatrist). Neurological disorders are typically those affecting the structure, biochemistry or cause electrical abnormalities of the brain, spinal cord or other nerves. Psychiatric conditions are more typically thought of as mental disorders, which are primarily abnormalities of thought, feeling or behavior that cause significant distress or impairment of personal functioning.

Thus, the disclosed compounds can be used in an effective amount to improve neurological or psychiatric functioning in a patient in need thereof. Neurological indications include, but are not limited to improved neuroplasticity, including treatment of stroke, brain trauma, dementia, and neurodegenerative diseases. MDMA has been reported to have an EC50 of 7.41 nM for promoting neuritogenesis and an $E_{max}$ approximately twice that of ketamine, which has fast acting psychiatric benefits that are thought to be mediated by its ability to promote neuroplasticity, including the growth of dendritic spines, increased synthesis of synaptic proteins, and strengthening synaptic responses (FIG. S3. in Ly et al. Cell reports 23, no. 11 (2018): 3170-3182). The compounds of the current invention can similarly be considered psychoplastogens, that is, small molecules that are able to induce rapid neuroplasticity (Olson, 2018, Journal of experimental neuroscience, 12, 1179069518800508). For example, in certain embodiments, the disclosed compounds and compositions can be used to improve stuttering and other dyspraxias or to treat Parkinson's disease or schizophrenia.

The term "improving psychiatric function" is intended to include mental health and life conditions that are not traditionally treated by neurologists but sometimes treated by psychiatrists and can also be treated by psychotherapists, life coaches, personal fitness trainers, meditation teachers, counselors, and the like. For example, it is contemplated that the disclosed compounds will allow individuals to effectively contemplate actual or possible experiences that would normally be upsetting or even overwhelming. This includes individuals with fatal illnesses planning their last days and the disposition of their estate. This also includes couples discussing difficulties in their relationship and how to address them. This also includes individuals who wish to more effectively plan their career.

In other embodiments, the benzothiophene compounds and compositions of the present invention may be used in an effective amount to treat a host, typically a human, to modulate an immune or inflammatory response. The compounds disclosed herein alter extracellular serotonin, which is known to alter immune functioning. MDMA produces acute time-dependent increases and decreases in immune response.

The following nonlimiting examples are relevant to any of the disorders, indications, methods of use or dosing regimes described herein.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt or salt mixture, isotopic derivative, or prodrug thereof, wherein the percent of S enantiomer is greater than about 95 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, or Formula XIV, Formula XV or Formula XVI or a pharmaceutically acceptable salt or salt mixture, isotopic derivative, or prodrug thereof, wherein the percent of S enantiomer is greater than about 90 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI Formula XII, Formula XIII, or Formula XIV, Formula XV or Formula XVI or a pharmaceutically acceptable salt or salt mixture, isotopic derivative, or prodrug thereof, wherein the percent of S enantiomer is greater than about 85 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, or Formula XIV, Formula V or Formula VI or a pharmaceutically acceptable salt or salt mixture, isotopic derivative, or prodrug thereof, wherein the percent of S enantiomer is greater than about 80 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt, salt mixture, isotopic derivative, or prodrug thereof, wherein the percent of S enantiomer is greater than about 75 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt, salt mixture, isotopic derivative, or prodrug thereof, wherein the percent of S enantiomer is greater than about 70 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt, salt mixture, isotopic derivative, or prodrug thereof, wherein the percent of S enantiomer is greater than about 65 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt, salt mixture, isotopic derivative, or prodrug thereof, wherein the percent of S enantiomer is greater than about 60 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt, salt mixture, isotopic derivative, or prodrug thereof, wherein the percent of S enantiomer is greater than about 55 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt, salt mixture, isotopic derivative, or prodrug thereof, wherein the percent of S enantiomer is greater than about 55 or 60 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt or salt mixture, isotopic derivative, or prodrug thereof, wherein the percent of R enantiomer is greater than about 95 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt mixture, isotopic derivative, or prodrug thereof, wherein the percent of R enantiomer is greater than about 90 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt or salt mixture, isotopic derivative, or prodrug thereof, wherein the percent of R enantiomer is greater than about 85 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt or salt mixture, isotopic derivative, or prodrug thereof, wherein the percent of R enantiomer is greater than about 80 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt or salt mixture, isotopic derivative, or prodrug thereof, wherein the percent of R enantiomer is greater than about 75 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt, salt mixture, isotopic derivative, or prodrug thereof, wherein the percent of R enantiomer is greater than about 70 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt, salt mixture, isotopic derivative, or prodrug thereof, wherein the percent of R enantiomer is greater than about 65 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt, salt mixture, isotopic derivative, or prodrug thereof, wherein the percent of R enantiomer is greater than about 60 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt, salt mixture, isotopic derivative, or prodrug thereof, wherein the percent of R enantiomer is greater than about 55 percent.

In certain embodiments, a host, for example a human, is treated with an effective amount of an enantiomerically enriched mixture of enantiomers of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt, salt mixture, isotopic derivative, or prodrug thereof, wherein the percent of R enantiomer is greater than about 55 or 60 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of S enantiomer is greater than about 95 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of S enantiomer is greater than about 90 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of S enantiomer is greater than about 85 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of S enantiomer is greater than about 80 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of S enantiomer is greater than about 75 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of S enantiomer is greater than about 70 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of S enantiomer is greater than about 65 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of S enantiomer is greater than about 60 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of S enantiomer is greater than about 55 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of S enantiomer is greater than about 55 or 60 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of R enantiomer is greater than about 95 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of R enantiomer is greater than about 90 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of R enantiomer is greater than about 85 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of R enantiomer is greater than about 80 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of R enantiomer is greater than about 75 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of R enantiomer is greater than about 70 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of R enantiomer is greater than about 65 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of R enantiomer is greater than about 60 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, salt mixture, isotopic derivative, or prodrug thereof, wherein the percent of R enantiomer is greater than about 55 percent.

In certain embodiments, a host, for example a human, is treated with an effective amount of an enantiomerically enriched mixture of enantiomers of compounds of Formula A, Formula B, Formula C, or Formula D, or a pharmaceutically acceptable salt, salt mixture, isotopic derivative, or prodrug thereof, wherein the percent of R enantiomer is greater than about 55 or 60 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of R enantiomer is greater than about 95 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of R enantiomer is greater than about 90 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of R enantiomer is greater than about 85 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of R enantiomer is greater than about 80 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of R enantiomer is greater than about 75 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of R enantiomer is greater than about 70 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of R enantiomer is greater than about 65 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of R enantiomer is greater than about 60 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of R enantiomer is greater than about 55 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of R enantiomer is greater than about 55 or 60 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of S enantiomer is greater than about 95 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of S enantiomer is greater than about 90 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of S enantiomer is greater than about 85 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of S enantiomer is greater than about 80 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of S enantiomer is greater than about 75 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of S enantiomer is greater than about 70 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of S enantiomer is greater than about 65 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of S enantiomer is greater than about 60 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of S enantiomer is greater than about 55 percent.

In certain embodiments, a host, for example a human, is treated with an effective amount of an enantiomerically enriched mixture of enantiomers of a compound shown in FIG. 2, or a pharmaceutically acceptable salt, salt mixture, isotopic derivative, or prodrug thereof, wherein the percent of S enantiomer is greater than about 55 or 60 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of R enantiomer is greater than about 95 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of R enantiomer is greater than about 90 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of R enantiomer is greater than about 85 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of R enantiomer is greater than about 80 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of R enantiomer is greater than about 75 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of R enantiomer is greater than about 70 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of R enantiomer is greater than about 65 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of R enantiomer is greater than about 60 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of R enantiomer is greater than about 55 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of R enantiomer is greater than about 55 or 60 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of S enantiomer is greater than about 95 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of S enantiomer is greater than about 90 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of S enantiomer is greater than about 85 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of S enantiomer is greater than about 80 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of S enantiomer is greater than about 75 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of S enantiomer is greater than about 70 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of S enantiomer is greater than about 65 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of S enantiomer is greater than about 60 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of S enantiomer is greater than about 55 percent.

In certain embodiments, a host, for example a human, is treated with an effective amount of an enantiomerically enriched mixture of enantiomers of 5-MAPBT, 6-MAPBT, 5-MBPBT, 6-MBPBT, Bk-5-MAPBT, Bk-6-MAPBT, Bk-5-MBPBT, or Bk-6-MBPBT, or a pharmaceutically acceptable salt, salt mixture, isotopic derivative, or prodrug thereof, wherein the percent of S enantiomer is greater than about 55 or 60 percent.

The present invention also provides methods for modulating the CNS in a mammal in need thereof, including a human, by administering a pharmaceutically effective amount of a compound of the present invention, including S-5-MAPBT, R-5-MAPBT, S-6-MAPBT, and/or R-6-MAPBT or a pharmaceutically acceptable salt or salt mixture thereof.

In some embodiments, a method is provided for modulating the CNS in a mammal in need thereof, including a human, by administering a pharmaceutically effective amount of 5-MBPBT and/or 6-MBPBT or a pharmaceutically acceptable salt thereof. In one embodiment, a method is provided for modulating the CNS in a mammal in need thereof, including a human, by administering a pharmaceutically effective amount of Formula A and/or Formula B or a pharmaceutically acceptable salt thereof. In one embodiment, a method is provided for modulating the CNS in a mammal in need thereof, including a human, by administering a pharmaceutically effective amount of Formula C and/or Formula D or a pharmaceutically acceptable salt thereof. In one embodiment, a method is provided for modulating the CNS in a mammal in need thereof, including a human, by administering a pharmaceutically effective amount of a compound shown in FIG. 2, or a pharmaceutically acceptable salt thereof. In one embodiment, a method is provided for modulating the CNS in a mammal in need thereof, including a human, by administering a pharmaceutically effective amount of a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof.

In one embodiment, a method is provided to treat diseases or disorders linked to inadequate functioning of neurotransmission in the CNS comprising administering 5-MAPBT and 6-MAPBT or a pharmaceutically acceptable salt thereof in a host in need thereof.

In one embodiment, a method is provided to treat diseases or disorders linked to inadequate functioning of neurotransmission in the CNS comprising administering 5-MBPBT and 6-MBPBT or a pharmaceutically acceptable salt thereof in a host in need thereof.

In one embodiment, a method is provided to treat diseases or disorders linked to inadequate functioning of neurotransmission in the CNS comprising administering Bk-5-MAPBT and Bk-6-MAPBT or a pharmaceutically acceptable salt thereof in a host in need thereof.

In one embodiment, a method is provided to treat diseases or disorders linked to inadequate functioning of neurotransmission in the CNS comprising administering Bk-5-MBPBT and Bk-6-MBPBT or a pharmaceutically acceptable salt thereof in a host in need thereof.

In one embodiment, a method is provided to treat diseases or disorders linked to inadequate functioning of neurotransmission in the CNS comprising administering Formula A and Formula B or a pharmaceutically acceptable salt thereof in a host in need thereof.

In one embodiment, a method is provided to treat diseases or disorders linked to inadequate functioning of neurotransmission in the CNS comprising administering Formula C and Formula D or a pharmaceutically acceptable salt thereof in a host in need thereof.

In one embodiment, a method is provided to treat diseases or disorders linked to inadequate functioning of neurotransmission in the CNS comprising administering a compound shown in FIG. 2 or a pharmaceutically acceptable salt thereof in a host in need thereof.

In one embodiment, a method is provided to treat diseases or disorders linked to inadequate functioning of neurotransmission in the CNS comprising administering a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt thereof in a host in need thereof.

This invention also provides the use of 5-MAPBT or 6-MAPBT for the manufacture of a medicament for the treatment of maladaptive responses to perceived psychological threats. Additionally, this invention provides a pharmaceutical formulation adapted for the treatment of maladaptive response to perceived psychological threats containing a 5-MAPBT or 6-MAPBT. Furthermore, this invention includes a method for the treatment of maladaptive response to perceived psychological threats that comprises administering an effective amount of 5-MAPBT or 6-MAPBT, given either in the context of psychotherapy or as a stand-alone treatment.

This invention also provides the use of compounds of Formula A or Formula B for the manufacture of a medicament for the treatment of maladaptive response to perceived psychological threats. Additionally, this invention provides a pharmaceutical formulation adapted for the treatment of maladaptive response to perceived psychological threats containing a compound of Formula A or Formula B. Furthermore, this invention includes a method for the treatment of maladaptive response to perceived psychological threats that comprises administering an effective amount of a compound of Formula A or Formula B, given either in the context of psychotherapy or as a stand-alone treatment.

This invention also provides the use of compounds of Formula C or Formula D for the manufacture of a medicament for the treatment of maladaptive response to perceived psychological threats. Additionally, this invention provides a pharmaceutical formulation adapted for the treatment of maladaptive response to perceived psychological threats containing a compound of Formula C or Formula D. Furthermore, this invention includes a method for the treatment of maladaptive response to perceived psychological threats that comprises administering an effective amount of a compound of Formula C or Formula D, given either in the context of psychotherapy or as a stand-alone treatment.

This invention also provides the use of compounds shown in FIG. 2 for the manufacture of a medicament for the treatment of maladaptive response to perceived psychological threats. Additionally, this invention provides a pharmaceutical formulation adapted for the treatment of maladaptive response to perceived psychological threats containing a compound shown in FIG. 2. Furthermore, this invention includes a method for the treatment of maladaptive response to perceived psychological threats that comprises administering an effective amount of a compound of FIG. 2, given either in the context of psychotherapy or as a stand-alone treatment.

This invention also provides the use of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI for the manufacture of a medicament for the treatment of maladaptive response to perceived psychological threats. Additionally, this invention provides a pharmaceutical formulation adapted for the treatment of maladaptive response to perceived psychological threats containing a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI Furthermore, this invention includes a method for the treatment of maladaptive response to perceived psychological threats that comprises administering an effective amount of a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI given either in the context of psychotherapy or as a stand-alone treatment.

This invention also provides the use S-5-MAPBT, R-5-MAPBT, S-6-MAPBT, and/or R-6-MAPBT or a pharmaceutically acceptable salt or composition to treat a maladaptive response to perceived psychological threats. In one embodiment, S-5-MAPBT, R-5-MAPBT, S-6-MAPBT, and/or R-6-MAPBT or a pharmaceutically acceptable salt or composition is administered in the context of psychotherapy. In one embodiment, S-5-MAPBT, R-5-MAPBT, S-6-MAPBT, and/or R-6-MAPBT or a pharmaceutically acceptable salt or composition is administered as a stand-alone treatment.

This invention also provides the administration of an effective amount of 5-MBPBT and/or 6-MBPBT or a pharmaceutically acceptable salt or composition to a host, typically a human, to treat a maladaptive response to perceived psychological threats. In one embodiment, 5-MBPBT and/or 6-MBPBT or a pharmaceutically acceptable salt or composition is administered in the context of psychotherapy. In one embodiment, 5-MBPBT and/or 6-MBPBT or a pharmaceutically acceptable salt or composition is administered as a stand-alone treatment.

This invention also provides the use Formula A or Formula B or a pharmaceutically acceptable salt or composition in an effective amount to treat a maladaptive response to perceived psychological threats. In one embodiment, Formula A or Formula B or a pharmaceutically acceptable salt or composition is administered in the context of psychotherapy. In one embodiment, Formula A or Formula B or a pharmaceutically acceptable salt or composition is administered as a stand-alone treatment.

This invention also provides the use Formula C or Formula D or a pharmaceutically acceptable salt or composition to treat a maladaptive response to perceived psychological threats. In one embodiment, Formula C or Formula D or a pharmaceutically acceptable salt or composition is administered in the context of psychotherapy. In one embodiment, Formula C or Formula D or a pharmaceutically acceptable salt or composition is administered as a stand-alone treatment.

This invention also provides the use Bk-5-MAPBT and/or Bk-6-MAPBT or a pharmaceutically acceptable salt or composition to treat a maladaptive response to perceived psychological threats. In one embodiment, Bk-5-MAPBT and/or Bk-6-MAPBT or a pharmaceutically acceptable salt or composition is administered in the context of psychotherapy. In one embodiment, Bk-5-MAPBT and/or Bk-6-MAPBT or a pharmaceutically acceptable salt or composition is administered as a stand-alone treatment.

This invention also provides the use Bk-5-MBPBT and/or Bk-6-MBPBT or a pharmaceutically acceptable salt or composition to treat a maladaptive response to perceived psychological threats. In one embodiment, Bk-5-MBPBT and/or Bk-6-MBPBT or a pharmaceutically acceptable salt or composition is administered in the context of psychotherapy. In one embodiment, Bk-5-MBPBT and/or Bk-6-MBPBT or a pharmaceutically acceptable salt or composition is administered as a stand-alone treatment.

This invention also provides the use of a compound shown in FIG. 2 or a pharmaceutically acceptable salt or composition to treat a maladaptive response to perceived psychological threats. In one embodiment, a compound shown in FIG. 2, or a pharmaceutically acceptable salt or composition is administered in the context of psychotherapy.

In one embodiment, a compound of FIG. 2 or a pharmaceutically acceptable salt or composition is administered as a stand-alone treatment.

Non-Limiting Examples of Pharmacotherapeutic Counseling Use

Psychotherapy, cognitive enhancement, or life coaching conducted with the compounds or pharmaceutically acceptable salts as described herein employed as an adjunct (hereafter, "pharmacotherapy" or "pharmacotherapy counseling") is typically conducted in widely spaced sessions with one, two, or rarely three or more administrations of an entactogen per session. These sessions can be as frequent as weekly but are more often approximately monthly or even less frequently. In most cases, a small number of pharmacotherapy counseling sessions, on the order of one to three, is needed for the patient to experience significant clinical progress, as indicated, for example, by a reduction in signs and symptoms of mental distress, by improvement in functioning in some domain of life, by arrival at a satisfactory solution to some problem, or by increased feelings of closeness to and understanding of some other person. In some embodiments, the psychotherapy, cognitive enhancement, or life coaching is conducted with an effective amount of enantiomerically enriched S-5-MAPBT, R-5-MAPBT, S-6-MAPBT, and/or R-6-MAPBT or a pharmaceutically acceptable salt thereof. In some embodiments, the psychotherapy, cognitive enhancement, or life coaching is conducted with an effective amount of enantiomerically enriched Bk-5-MAPBT and/or Bk-6-MAPBT or a pharmaceutically acceptable salt thereof. Alternatively, the psychotherapy, cognitive enhancement, or life coaching is conducted with an effective amount of enantiomerically enriched Bk-5-MBPBT and/or Bk-6-MBPBT or a pharmaceutically acceptable salt thereof. In one embodiment, the psychotherapy, cognitive enhancement, or life coaching is conducted with an effective amount of enantiomerically enriched Formula A and/or Formula B or a pharmaceutically acceptable salt thereof. In one embodiment, the psychotherapy, cognitive enhancement, or life coaching is conducted with an effective amount of enantiomerically enriched Formula C and/or Formula D or a pharmaceutically acceptable salt thereof. In one embodiment, the psychotherapy, cognitive enhancement, or life coaching is conducted with an effective amount of enantiomerically enriched compound shown in FIG. 2 or a pharmaceutically acceptable salt thereof.

In one embodiment, the psychotherapy, cognitive enhancement, or life coaching is conducted with an effective amount of Formula I, Formula II, Formula III, Formula IV, Formula V, Formula VI, Formula VII, Formula VIII, Formula IX, Formula X, Formula XI, Formula XII, Formula XIII, Formula XIV, Formula XV and/or Formula XVI or a pharmaceutically acceptable salt thereof.

The following sections provide detailed examples of pharmacotherapy counseling. While common procedures are described, these are intended as illustrative, non-limiting examples. It is anticipated that the prescribing physician and therapy team may wish to specify different procedures than those described here based on their clinical judgment concerning the needs of the patient.

The example methods of treatment can also be modified with very minor changes to treat multiple patients at once, including couples or families. Hence, "patient" should be understood to mean one or more individuals.

Use of a Compound or Composition of the Present Invention in Conjunction with Conventional Psychotherapy or Coaching In one embodiment, the use of a described benzothiophene compound or composition of the present invention as pharmacotherapy is integrated into the patient's ongoing psychotherapy or coaching (hereafter abbreviated as "psychotherapy"). If a patient in need of the pharmacotherapy counseling is not in ongoing psychotherapy, then psychotherapy may be initiated and the pharmacotherapy counseling added later, after the prescribing physician and treating psychotherapist, physician, coach, member of the clergy, or other similar professional or someone acting under the supervision of such a professional (hereafter, "therapist") agree that the pharmacotherapy counseling is indicated and that there have been sufficient meetings between the patient and therapist to establish an effective therapeutic alliance.

If the patient is not experienced with the pharmacotherapy, a conversation typically occurs in which the therapist or other members of the therapy team addresses the patient's questions and concerns about the medicine and familiarizes the patient with the logistics of pharmacotherapy-assisted session. The therapist describes the kinds of experience that can be expected during the pharmacotherapy counseling session. Optionally, parts of this conversation employ written, recorded, or interactive digital explanations, as might be used in the informed consent process in a clinical trial. The therapist may additionally make commitments to support the participant's healthcare and wellness process. In turn, the patient may be asked to make commitments of their own (such as not to hurt themselves or others and to abstain from contraindicated medicines or drugs for an adequate period before and after the pharmacotherapy counseling).

The compounds and compositions of the invention (or alternately herein for convenience, the "medicine") is administered shortly before or during a scheduled psychotherapy session, with timing optionally selected so that therapeutic effects begin by the time the psychotherapy session begins. It is to be understood that references to administering the medicine "during" a psychotherapeutic or other session are intended to refer to timing the administration of the medicine such that the therapeutic effects of the medicine at least partly temporally overlap with the therapeutic effects of the session. Either shortly before or after administration of the medicine, it is common for the therapist to provide some reminder of their mutual commitments and expected events during the session.

The psychotherapy session is carried out by the therapist, who, optionally, may be remote and in communication with the patient using a communication means suitable for telehealth or telemedicine, such as a phone, video, or other remote two-way communication method. Optionally, video or other monitoring of the patient's response or behavior is used to document or measure the session. The therapist uses their clinical judgment and available data to adjust the session to the needs of the patient. Many therapists view their responsibility as being to facilitate rather than direct the patient's experience. This may sometimes involve silent empathic listening, while other times it may include more active support to help the patient arrive at new perspectives on their life.

It is anticipated that the therapeutic effects of the medicine will allow the patient to make more rapid therapeutic progress than would normally be possible. These effects include decreased neuroticism and increased feelings of authenticity. Patients are often able to calmly contemplate actual or possible experiences that would normally be upsetting or even overwhelming. This can facilitate decision making and creativity in addition to mental wellness.

Optionally, the prescribing physician may allow a second or even third administration of the medicine or another psychotherapeutic agent in order to extend the therapeutic effects. Optionally, a pharmaceutical preparation with modified release is employed to make this unnecessary.

Because the duration of the scheduled psychotherapy session may be shorter than the therapeutic effects of the medicine, the therapist may suggest to the patient activities to support further psychotherapeutic progress after the psychotherapy session has ended. Alternatively, the therapist may continue to work with the patient until the therapeutic effects of the medicine have become clinically minimal.

In a subsequent non-pharmacological psychotherapy session, the therapist and patient will typically discuss the patient's experiences from the pharmacotherapy counseling session and the therapist will often aid the patient in recalling the therapeutic effects and help them to incorporate the experiences into their everyday lives.

Pharmacotherapy counseling sessions may be repeated as needed, based on the judgment of the treating physician and therapy team regarding the needs of the patient.

Use of a Compound or Composition of the Present Invention Outside of Conventional Psychotherapy In one embodiment, a compound or composition of the present invention is administered outside of a conventional psychotherapy. This example method is a broader, more flexible approach to pharmacotherapy that is not centered on supervision by a therapist. These pharmacotherapy counseling sessions can take place in many different quiet and safe settings, including the patient's home. The setting is typically chosen to offer a quiet setting, with minimal disruptions, where the patient feels psychologically safe and emotionally relaxed. The setting may be the patient's home but may alternatively be a clinic, retreat center, or hotel room.

In one alternative embodiment, the medicine is taken by the patient regularly to maintain therapeutic concentrations of the active compound in the blood. In another alternative embodiment, the medicine is taken, as needed, for defined psychotherapy sessions.

Optionally, a checklist may be followed to prepare the immediate environment to minimize distractions and maximize therapeutic or decision-making benefits. This checklist can include items such as silencing phones and other communications devices, cleaning and tidying the environment, preparing light refreshments, preparing playlists of appropriate music, and pre-arranging end-of-session transportation if the patient is not undergoing pharmacotherapy counseling at home.

Before the pharmacotherapy counseling session, there may be an initial determination of the therapeutic or other life-related goals (for example, decision-making, increasing creativity, or simply appreciation of life) that will be a focus of the session. These goals can optionally be determined in advance with support from a therapist.

Optionally, the therapist may help the patient select stimuli, such as photographs, videos, augmented or virtual reality scenes, or small objects such as personal possessions, that will help focus the patient's attention on the goals of the session or on the patient's broader life journey. As examples that are intended to be illustrative and not restrictive, these stimuli can include photographs of the patient from when they were young, which can increase self-compassion, or can include stimuli relating to traumatic events or phobias experienced by the patient, which can help the patient reevaluate and change their response to such stimuli. Optionally, the patient selects these stimuli without assistance (e.g., without the involvement of the therapist) or does not employ any stimuli. Optionally, stimuli are selected in real time by the therapist, or an algorithm based on the events of the session with the goal of maximizing benefits to the patient.

If the patient is not experienced with the pharmacotherapy, a conversation occurs in which the therapist addresses the patient's questions and concerns about the medicine and familiarizes the patient with the logistics of a pharmacotherapy-assisted counseling session. The therapist describes the kinds of experience that can be expected during the pharmacotherapy-assisted counseling session. Optionally, parts of this conversation employ written, recorded, or interactive digital explanations, as might be used in the informed consent process in a clinical trial. The therapist may additionally make commitments to support the participant's healthcare and wellness process. In turn, the patient may be asked to make commitments of their own (such as not to hurt themselves or others and to abstain from contraindicated medicines or drugs for an adequate period before and after the pharmacotherapy counseling).

Selected session goals and any commitments or other agreements regarding conduct between the patient and therapy team are reviewed immediately before administration of the medicine. Depending on the pharmaceutical preparation and route of administration, the therapeutic effects of the medicine usually begin within one hour. Typical therapeutic effects include decreased neuroticism and increased feelings of authenticity. Patients are often able to calmly contemplate experiences or possible experiences that would normally be upsetting or even overwhelming. This can facilitate decision making and creativity in addition to mental wellness.

Optionally, sleep shades and earphones with music or soothing noise may be used to reduce distractions from the environment. Optionally, a virtual reality or immersive reality system may be used to provide stimuli that support the therapeutic process. Optionally, these stimuli are preselected; optionally, they are selected in real time by a person, or an algorithm based on events in the session with the goal of maximizing benefits to the patient. Optionally, a therapist or other person well-known to the patient is present or available nearby or via phone, video, or other communication method in case the patient wishes to talk, however the patient may optionally undergo a session without the assistance of a therapist. Optionally, the patient may write or create artwork relevant to the selected session goals. Optionally, the patient may practice stretches or other beneficial body movements, such as yoga ("movement activity").

Optionally, in other embodiments the patient may practice movement activity that includes more vigorous body movements, such as dance or other aerobic activity. Movement activity also may make use of exercise equipment such as a treadmill or bicycle.

In some additional embodiments, the patient may be presented with music, video, auditory messages, or other perceptual stimuli. Optionally, these stimuli may be adjusted based on the movements or other measurable aspects of the patient. Such adjustment may be done by the therapist with or without the aid of a computer, or by a computer alone in response to said patient aspects, including by an algorithm or artificial intelligence, and "computer" broadly meaning any electronic tool suitable for such purposes, whether worn or attached to a patient (e.g., watches, fitness trackers, "wearables," and other personal devices; biosensors or medical sensors; medical devices), whether directly coupled or wired to a patient or wirelessly connected (and including desktop, laptop, and notebook computers; tablets, smartphones, and other mobile devices; and the like), and whether within the therapy room or remote (e.g., cloud-based systems).

For example, measurable aspects of a patient (e.g., facial expression, eye movements, respiration rate, pulse rate, skin color change, patient voice quality or content, patient responses to questions) from these tools may be individually transformed into scores on standardized scales by subtracting a typical value and then multiplying by a constant and these scores may be further multiplied by constants and added together to create an overall score that can optionally be transformed by multiplication with a link function, such as the logit function, to create an overall score. This score may be used to select or adjust stimuli such as selecting music with higher or lower beats-per-minute or with faster or slower notes, selecting images, audio, or videos with different emotionality or autobiographical meaning, or selecting activities for the patient to engage in (such as specific movements, journaling prompts, or meditation mantras).

It should be readily appreciated that a patient can participate in numerous therapeutically beneficial activities, where such participation follows or is in conjunction with the administration of a compound or composition of the invention, including writing about a preselected topic, engaging in yoga or other movement activity, meditating, creating art, viewing of photographs or videos or emotionally evocative objects, using a virtual reality or augmented reality system, talking with a person, and thinking about a preselected problem or topic, and it should be understood that such participation can occur with or without the participation or guidance of a therapist.

Optionally, the prescribing physician may allow a second or even third administration of the medicine or another psychotherapeutic agent in order to extend the therapeutic effects. Optionally, a pharmaceutical preparation with modified release is employed to make this unnecessary.

The patient typically remains in the immediate environment until the acute therapeutic effects of the medicine are clinically minimal, usually within eight hours. After this point, the session is considered finished.

The treatment plan will often include a follow-up session with a therapist. This follow-up session occurs after the pharmacotherapy counseling session has ended, often the next day but sometimes several days later. In this session, the patient discusses their experiences from the pharmacotherapy counseling session with the therapist, who can aid them in recalling the therapeutic effects and help them to incorporate the experiences into their everyday lives.

Pharmacotherapy counseling sessions may be repeated as needed, based on the judgment of the treating physician and therapy team regarding the needs of the patient.

IV. Pharmaceutical Compositions and Salts

The described benzothiophene compounds and compositions described herein can be administered in an effective amount as the neat chemical but are more typically administered as a pharmaceutical composition for a host, typically a human, in need of such treatment in an effective amount for any of the disorders described herein. The compounds or compositions disclosed herein may be administered orally, topically, systemically, parenterally, by inhalation, insufflation, or spray, mucosally (e.g., buccal, sublingual), sublingually, transdermally, rectally, intravenous, intra-aortal, intracranial, subdermal, intraperitoneal, intramuscularly, inhaled, intranasal, subcutaneous, transnasal, or by other means, in dosage unit formulations containing conventional pharmaceutically acceptable carriers. Such compositions are prepared in a manner well known in the pharmaceutical art and comprise at least one active compound. (See, e.g., Remington, 2005, Remington: The science and practice of pharmacy, 21st ed., Lippincott Williams & Wilkins.)

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, a suppository, a buccal or sublingual formulation, a parenteral formulation, an ophthalmic solution, or in a medical device. Some dosage forms, such as tablets and capsules, are subdivided into suitably sized unit doses containing appropriate quantities of the active components, e.g., an effective amount to achieve the desired purpose.

A "pharmaceutically acceptable composition" thus refers to at least one compound (which may be a mixture of enantiomers or diastereomers, as fully described herein) of the invention and a pharmaceutically acceptable vehicle, excipient, diluent or other carrier in an effective amount to treat a host, typically a human, who may be a patient.

In certain nonlimiting embodiments the pharmaceutical composition is a dosage form that contains from about 0.1 mg to about 1500 mg, from about 10 mg to about 1000 mg, from about 100 mg to about 800 mg, or from about 200 mg to about 600 mg of the active compound and optionally from about 0.1 mg to about 1500 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 20, 25, 40, 50, 100, 125, 150, 200, 250, 300, 400, 500, 600, 700, or 750 mg of active compound, or its salt or salt mixture.

The pharmaceutical compositions described herein can be formulated into any suitable dosage form, including tablets, capsules, gelcaps, aqueous oral dispersions, aqueous oral suspensions, solid dosage forms including oral solid dosage forms, aerosols, controlled release formulations, fast melt formulations, effervescent formulations, self-emulsifying dispersions, solid solutions, liposomal dispersions, lyophilized formulations, pills, powders, delayed-release formulations, immediate-release formulations, modified release formulations, extended-release formulations, pulsatile release formulations, multi particulate formulations, and mixed immediate release and controlled release formulations. Generally speaking, the composition should be administered in an effective amount to administer an amount of the active agents of the present invention achieves a plasma level commensurate with the concentrations found to be effective in vivo for a period of time effective to elicit a desired therapeutic effect without abuse liability.

In making the compositions employed in the present invention the active ingredient is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets (including orally disintegrating, swallowable, sublingual, buccal, and chewable tablets), pills, powders, lozenges, troches, oral films, thin strips, sachets, cachets, elixirs, suspensions, emulsions, solutions, slurries, syrups, aerosols (as a solid or in a liquid medium), ointments containing for example up to 10% by weight of the active compound, soft and hard gelatin capsules, suppositories, dry powders for inhalation, liquid preparations for vaporization and inhalation, topical preparations, transdermal patches, sterile injectable solutions, and sterile packaged powders. Compositions may be formulated as immediate release, controlled release, sustained (extended) release or modified release formulations.

The compositions of the present invention can be administered by multiple routes, which may differ in different patients according to their preference, co-morbidities, side effect profile, and other factors (IV, PO, transdermal, etc.). In one embodiment, the pharmaceutical composition includes the presence of other substances with the active drugs, known to those skilled in the art, such as fillers, carriers, gels, skin patches, lozenges, or other modifications in the preparation to facilitate absorption through various routes (such as, but not limited to, gastrointestinal, transdermal, etc.) and/or to extend the effect of the drugs, and/or to attain higher or more stable serum levels or to enhance the therapeutic effect of the active drugs in the combination.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, but are not limited to, lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are in certain embodiments formulated in a unit dosage form, each dosage containing from at least about 0.05 to about 350 mg or less, more typically at least about 5.0 to about 180 mg or less, of the active ingredients. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier, diluent, or excipient.

The active compounds are effective over a wide dosage range. For example, as-needed dosages normally fall within the range of at least about 0.01 to about 4 mg/kg or less. In the treatment of adult humans, the range of at least about 0.2 to about 3 mg/kg or less, in single dose may be useful.

It will be understood that the amount of the compound actually administered will be determined by a physician, in light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way.

In some instances, dosage levels below the lower limit of the aforesaid range may be more than adequate, while in other cases still larger doses may be employed without causing any harmful side effects, provided for instance that such larger doses may be first divided into several smaller doses for administration.

Generally, the pharmaceutical compositions of the invention may be administered and dosed in accordance with good medical practice, taking into account the method and scheduling of administration, prior and concomitant medications and medical supplements, the clinical condition of the individual patient and the severity of the underlying disease, the patient's age, sex, body weight, and other such factors relevant to medical practitioners, and knowledge of the particular compound(s) used. Starting and maintenance dosage levels thus may differ from patient to patient, for individual patients across time, and for different pharmaceutical compositions, but shall be able to be determined with ordinary skill.

In one embodiment, a powder comprising the active agents of the present invention described herein may be formulated to comprise one or more pharmaceutical excipients and flavors. Such a powder may be prepared, for example, by mixing the active agents of the present invention and optional pharmaceutical excipients to form a bulk blend composition. Additional embodiments also comprise a suspending agent and/or a wetting agent. This bulk blend is uniformly subdivided into unit dosage packaging or multi-dosage packaging units. The term "uniform" means the homogeneity of the bulk blend is substantially maintained during the packaging process.

Oral Formulations

In certain embodiments, any selected compound(s) of the present invention is formulated in an effective amount in a pharmaceutically acceptable oral dosage form. In one embodiment, the compound(s) is 5-MBPBT and/or 6-MBPBT or a pharmaceutically acceptable salt thereof. In one embodiment, the compound(s) is Bk-5-MAPBT and/or Bk-6-MAPBT or a pharmaceutically acceptable salt thereof. In one embodiment, the compound(s) is Bk-5-MBPBT and/or Bk-6-MBPBT or a pharmaceutically acceptable salt thereof. In one embodiment, the compound(s) is Formula A and/or Formula B or a pharmaceutically acceptable salt thereof. In one embodiment, the compound(s) is Formula C and/or Formula D or a pharmaceutically acceptable salt thereof. In one embodiment, the compound(s) is a compound shown in FIG. 2 or a pharmaceutically acceptable salt thereof. In one embodiment, the compound(s) is a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof. Oral dosage forms may include, but are not limited to, oral solid dosage forms and oral liquid dosage forms. Oral solid dosage forms may include but are not limited to, tablets, capsules, caplets, powders, pellets, multiparticulates, beads, spheres and/or any combinations thereof. The oral solid dosage forms may be formulated as immediate release, controlled release, sustained (extended) release or modified release formulations.

The oral solid dosage forms of the present invention may also contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof.

In some embodiments, the solid dosage forms of the present invention may be in the form of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including a fast-melt tablet. Additionally, pharmaceutical formulations of the present invention may be administered as a single capsule or in multiple capsule dosage form. In some embodiments, the pharmaceutical formulation is administered in two, or three, or four, capsules or tablets.

The pharmaceutical solid dosage forms described herein can comprise the active agent of the present invention compositions described herein and one or more pharmaceutically acceptable additives such as a compatible carrier, binder, complexing agent, ionic dispersion modulator, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

Alternatively, the pharmaceutical solid dosage forms described herein can comprise the active agent or agents of the present invention (i.e., the "active agent(s)"; but for convenience herein, both "active agent" and "active agents" shall mean "active agent(s)" unless context clearly indicates that what is intended or would be suitable is only one agent or only two or more agents) and one or more pharmaceutically acceptable additives such as a compatible carrier, binder, complexing agent, ionic dispersion modulator, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the active agent of the present invention formulation. In one embodiment, some or all of the active agent of the present invention particles are coated. In another embodiment, some or all of the active agent of the present invention particles are microencapsulated. In yet another embodiment, some or all of the active agent of the present invention is amorphous material coated and/or microencapsulated with inert excipients. In still another embodiment, the active agent of the present invention particles are not microencapsulated and are uncoated.

Suitable carriers for use in the solid dosage forms described herein include acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include lactose, calcium carbonate, calcium phosphate, dibasic calcium phosphate, calcium sulfate, microcrystalline cellulose (e.g., Avicel®, Avicel® PH101, Avicel® PH102, Avicel® PH105, etc.), cellulose powder, dextrose, dextrates, dextrose, dextran, starches, pregelatinized starch, hydroxypropylmethylcellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

If needed, suitable disintegrants for use in the solid dosage forms described herein include natural starch such as corn starch or potato starch, a pregelatinized starch such as National 1551 or Amijel®, or a sodium starch glycolate such as Promogel® or Explotab®, a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, Ac-Di-Sol, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder-filled capsule formulation, they aid in plug formation that can be filled into soft- or hard-shell capsules and in tablet formulation, binders ensure that the tablet remains intact after compression and help assure blend uniformity prior to a compression or fill step. Materials suitable for use as binders in the solid dosage forms described herein include carboxymethylcellulose, methylcellulose (e.g., Methocel®), hydroxypropylmethylcellulose (e.g., Hypromellose USP Pharmacoat-603, hydroxypropylmethylcellulose acetate stearate (Agoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crosspovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like. In general, binder levels of 20-70% are typically used in powder-filled gelatin capsule formulations. Binder usage level in tablet formulations is a function of whether direct compression, wet granulation, roller compaction, or usage of other excipients such as fillers which itself can act as moderate binders are used. Formulators skilled in the art can determine the binder level for the formulations, but binder usage level of up to 70% in tablet formulations is common.

Suitable lubricants or glidants for use in the solid dosage forms described herein include stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include sugars (including lactose, sucrose, and dextrose), polysaccharides (including dextrates and maltodextrin), polyols (including mannitol, xylitol, and sorbitol), cyclodextrins and the like.

Non-water-soluble diluents are compounds typically used in the formulation of pharmaceuticals, such as calcium phosphate, calcium sulfate, starches, modified starches and microcrystalline cellulose, and micro cellulose (e.g., having a density of about 0.45 g/cm3, e.g. Avicel®, powdered cellulose), and talc.

Suitable wetting agents for use in the solid dosage forms described herein include oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like. Wetting agents include surfactants.

Suitable surfactants for use in the solid dosage forms described herein include docusate and its pharmaceutically acceptable salts, sodium lauryl sulfate, sorbitan monooleate, polyoxyethylene sorbitan monooleate, polysorbates, poloxamers, bile salts, glyceryl monostearate, copolymers of ethylene oxide and propylene oxide, e.g., Pluronic® (BASF), and the like.

Suitable suspending agents for use in the solid dosage forms described here include polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 18000, vinylpyrrolidone/vinyl acetate copolymer (S630), sodium alginate, gums, such as, e.g., gum tragacanth and gum acacia, guar gum, xanthans, including xanthan gum, sugars, cellulosic, such as, e.g., sodium carboxymethylcellulose, methylcellulose, sodium carboxymethylcellulose, hydroxypropylmethylcellulose, hydroxyethylcellulose, polysorbate-80, polyethoxylated sorbitan monolaurate, polyethoxylated sorbitan monolaurate, povidone and the like.

Suitable antioxidants for use in the solid dosage forms described herein include, e.g., butylated hydroxytoluene (BHT), butyl hydroxyanisole (BHA), sodium ascorbate, Vitamin E TPGS, ascorbic acid, sorbic acid and tocopherol.

Immediate-release formulations may be prepared by combining superdisintegrants such as Croscarmellose sodium and different grades of microcrystalline cellulose in different ratios. To aid disintegration, sodium starch glycolate will be added.

The above-listed additives should be taken as merely examples and not limiting, of the types of additives that can be included in solid dosage forms of the present invention. The amounts of such additives can be readily determined by one skilled in the art, according to the particular properties desired.

Oral liquid dosage forms include solutions, emulsions, suspensions, and syrups. These oral liquid dosage forms may be formulated with any pharmaceutically acceptable excipient known to those of skill in the art for the preparation of liquid dosage forms. For example, water, glycerin, simple syrup, alcohol, and combinations thereof.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as but not limited to, an oil, water, an alcohol, and combinations of these pharmaceutically suitable surfactants, suspending agents, emulsifying agents, may be added for oral or parenteral administration. Suspensions may include oils. Such oils include peanut oil, sesame oil, cottonseed oil, corn oil, and olive oil. Suspension preparation may also contain esters of fatty acids such as ethyl oleate, isopropyl myristate, fatty acid glycerides, and acetylated fatty acid glycerides. Suspension formulations may include alcohols, such as ethanol, isopropyl alcohol, hexadecyl alcohol, glycerol, and propylene glycol. Ethers, such as poly(ethylene glycol), petroleum hydrocarbons such as mineral oil and petrolatum, and water may also be used in suspension formulations.

In some embodiments, formulations are provided comprising particles of 5-MAPBT and/or 6-MAPBT and at least one dispersing agent or suspending agent for oral administration to a subject in need thereof. In some embodiments, formulations are provided comprising particles of 5-MBPBT and/or 6-MBPBT and at least one dispersing agent or suspending agent for oral administration to a subject in need thereof. In some embodiments, formulations are provided comprising particles of Bk-5-MAPBT and/or Bk-6-MAPBT and at least one dispersing agent or suspending agent for oral administration to a subject in need thereof. In some embodiments, formulations are provided comprising particles of Bk-5-MBPBT and/or Bk-6-MBPBT and at least one dispersing agent or suspending agent for oral administration to a subject in need thereof. In some embodiments, formulations are provided comprising particles of compounds of Formula A and/or Formula B and at least one dispersing agent or suspending agent for oral administration to a subject in need thereof. In some embodiments, formulations are provided comprising particles of compounds of Formula C and/or Formula D and at least one dispersing agent or suspending agent for oral administration to a subject in need thereof. In some embodiments, formulations are provided comprising particles of compounds shown in FIG. 2 and at least one dispersing agent or suspending agent for oral administration to a subject in need thereof. In some embodiments, formulations are provided comprising particles of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof and at least one dispersing agent or suspending agent for oral administration to a subject in need thereof.

The formulation may be a powder and/or granules for suspension, and upon admixture with water, a substantially uniform suspension is obtained. As described herein, the aqueous dispersion can comprise amorphous and non-amorphous particles consisting of multiple effective particle sizes such that the drug is absorbed in a controlled manner over time. In certain embodiments, the aqueous dispersion or suspension is an immediate-release formulation. In another embodiment, an aqueous dispersion comprising amorphous particles is formulated such that a portion of the particles of the present invention are absorbed within, e.g., about 0.75 hours after administration and the remaining particles are absorbed 2 to 4 hours after absorption of the earlier particles.

In other embodiments, addition of a complexing agent to the aqueous dispersion results in a larger span of the particles to extend the drug absorption phase of the active agent such that 50-80% of the particles are absorbed in the first hour and about 90% are absorbed by about 4 hours. Dosage forms for oral administration can be aqueous suspensions selected from the group including pharmaceutically acceptable aqueous oral dispersions, emulsions, solutions, and syrups. See, e.g., Singh et al., Encyclopedia of Pharm. Tech., 2nd Ed., 754-757 (2002). In addition to the active agents of the present invention particles, the liquid dosage forms may comprise additives, such as (a) disintegrating agents; (b) dispersing agents; (c) wetting agents; (d) at least one preservative; (e) viscosity enhancing agents; (f) at least one sweetening agent; and (g) at least one flavoring agent.

Examples of disintegrating agents for use in the aqueous suspensions and dispersions include a starch, e.g., a natural starch such as corn starch or potato starch, a pregelatinized starch such as National 1551 or Amijel®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corp., Parsippany, N.J.)).

In other embodiments, the dispersing agent is selected from a group not comprising one of the following agents: hydrophilic polymers; electrolytes; Tween® 60 or 80; PEG; polyvinylpyrrolidone (PVP); hydroxypropyl cellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethylcellulose phthalate; hydroxypropylmethylcellulose acetate stearate; noncrystalline cellulose; magnesium aluminum silicate; triethanolamine; polyvinyl alcohol (PVA); 4-(1,1,3,3-tetramethyl butyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908® or Poloxamine 908®).

Wetting agents (including surfactants) suitable for the aqueous suspensions and dispersions described herein are known in the art and include acetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carpool 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphatidylcholine and the like.

Suitable preservatives for the aqueous suspensions or dispersions described herein include potassium sorbate, parabens (e.g., methylparaben and propylparaben) and their salts, benzoic acid and its salts, other esters of para hydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

In one embodiment, the aqueous liquid dispersion can comprise methylparaben and propylparaben in a concentration ranging from at least about 0.01% to about 0.3% or less methylparaben by weight to the weight of the aqueous dispersion and at least about 0.005% to about 0.03% or less propylparaben by weight to the total aqueous dispersion weight. In yet another embodiment, the aqueous liquid dispersion can comprise methylparaben from at least about 0.05 to about 0.1 or less weight % and propylparaben from at least about 0.01 to about 0.02 or less weight % of the aqueous dispersion.

Suitable viscosity enhancing agents for the aqueous suspensions or dispersions described herein include methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans and combinations thereof. The concentration of the viscosity-enhancing agent will depend upon the agent selected and the viscosity desired.

In addition to the additives listed above, the liquid formulations of the present invention can also comprise inert diluents commonly used in the art, such as water or other solvents, solubilizing agents, emulsifiers, and/or sweeteners.

In one embodiment, the formulation for oral delivery is an effervescent powder containing 5-MAPBT and/or 6-MAPBT or a pharmaceutically acceptable salt thereof. In one embodiment, the formulation for oral delivery is an effervescent powder containing 5-MBPBT and/or 6-MBPBT or a pharmaceutically acceptable salt thereof. In one embodiment, the formulation for oral delivery is an effervescent powder containing Bk-5-MAPBT and/or Bk-6-MAPBT or a pharmaceutically acceptable salt thereof. In one embodiment, the formulation for oral delivery is an effervescent powder containing Bk-5-MBPBT and/or Bk-6-MBPBT or a pharmaceutically acceptable salt thereof. In one embodiment, the formulation for oral delivery is an effervescent powder containing a compound of Formula A and/or Formula B or a pharmaceutically acceptable salt thereof. In one embodiment, the formulation for oral delivery is an effervescent powder containing a compound of Formula C and/or Formula D or a pharmaceutically acceptable salt thereof. In one embodiment, the formulation for oral delivery is an effervescent powder containing a compound shown in FIG. 2 or a pharmaceutically acceptable salt thereof. Effervescent salts have been used to disperse medicines in water for oral administration. In one embodiment, the formulation for oral delivery is an effervescent powder containing a compound of Formula I, Formula II, Formula III, Formula IV, Formula V, Formula VI, Formula VII, Formula VIII, Formula IX, Formula X, Formula XI, Formula XII, Formula XIII, Formula XIV Formula XV, or Formula XVI or a pharmaceutically acceptable salt thereof. Effervescent salts have been used to disperse medicines in water for oral administration. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the present invention are added to water, the acids and the base react to liberate carbon dioxide gas, thereby causing "effervescence." Examples of effervescent salts include sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

Tablets of the invention described here can be prepared by methods well known in the art. Various methods for the preparation of the immediate release, modified release, controlled release, and extended-release dosage forms (e.g., as matrix tablets, tablets having one or more modified, controlled, or extended-release layers, etc.) and the vehicles therein are well known in the art. Generally recognized compendia of methods include: Remington: The Science and Practice of Pharmacy, Alfonso R. Gennaro, Editor, 20th Edition, Lippincott Williams & Wilkins, Philadelphia, PA; and Sheth et al. (1980), Compressed tablets, in Pharmaceutical dosage forms, Vol. 1, edited by Lieberman and Lachtman, Dekker, N.Y.

In certain embodiments, solid dosage forms, e.g., tablets, effervescent tablets, and capsules, are prepared by mixing the active agents of the present invention particles with one or more pharmaceutical excipients to form a bulk blend composition. When referring to these bulk blend compositions as homogeneous, it is meant that the active agents of the present invention particles are dispersed evenly throughout the composition so that the composition may be readily subdivided into equally effective unit dosage forms, such as tablets, pills, and capsules. The individual unit dosages may also comprise film coatings, which disintegrate upon oral ingestion or upon contact with diluents. These the active agents of the present invention formulations can be manufactured by conventional pharmaceutical techniques.

Conventional pharmaceutical techniques for preparation of solid dosage forms include, e.g., one or a combination of methods: (1) dry mixing, (2) direct compression, (3) milling, (4) dry or non-aqueous granulation, (5) wet granulation, or (6) fusion. See, e.g., Lachman et al., Theory and Practice of Industrial Pharmacy (1986). Other methods include, e.g., spray drying, pan coating, melt granulation, granulation, fluidized bed spray drying or coating (e.g., Wurster coating), tangential coating, top spraying, tableting, extruding and the like.

Compressed tablets are solid dosage forms prepared by compacting the bulk blend the active agents of the present invention formulations described above. In various embodiments, compressed tablets which are designed to dissolve in the mouth will comprise one or more flavoring agents. In other embodiments, the compressed tablets will comprise a film surrounding a final compressed tablet. In some embodiments, the film coating can provide a delayed release of the active agents of the present invention formulation. In other embodiments, the film coating aids in patient compliance (e.g., Opadry® coatings or sugar coating). Film coatings comprising Opadry® typically range from about 1% to about 3% of the tablet weight. Film coatings for delayed-release usually comprise 2-6% of a tablet weight or 7-15% of a spray-layered bead weight. In other embodiments, the compressed tablets comprise one or more excipients.

A capsule may be prepared, e.g., by placing the bulk blend of the active agents of the present invention formulation, described above, inside of a capsule. In some embodiments, the formulations of the present invention (non-aqueous suspensions and solutions) are placed in a soft gelatin capsule. In other embodiments, the formulations of the present invention are placed in standard gelatin capsules or non-gelatin capsules such as capsules comprising HPMC. In other embodiments, the formulations of the present invention are placed in a sprinkle capsule, wherein the capsule may be swallowed whole, or the capsule may be opened, and the contents sprinkled on food prior to eating. In some embodiments of the present invention, the therapeutic dose is split into multiple (e.g., two, three, or four) capsules. In some embodiments, the entire dose of the active agents of the present invention is delivered in a capsule form.

In certain embodiments, ingredients (including or not including the active agent) of the invention are wet granulated. The individual steps in the wet granulation process of tablet preparation include milling and sieving of the ingredients, dry powder mixing, wet massing, granulation, drying, and final grinding. In various embodiments, the active agents of the present invention composition are added to the other excipients of the pharmaceutical formulation after they have been wet granulated. Alternatively, the ingredients may be subjected to dry granulation, e.g., via compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). No wet binder or moisture is involved in any of the steps.

In some embodiments, the active agents of the present invention formulation are dry granulated with other excipients in the pharmaceutical formulation. In other embodiments, the active agents of the present invention formulation are added to other excipients of the pharmaceutical formulation after they have been dry granulated.

In other embodiments, the formulation of the present invention formulations described herein is a solid dispersion. Methods of producing such solid dispersions are known in the art and include U.S. Pat. Nos. 4,343,789; 5,340,591; 5,456,923; 5,700,485; 5,723,269; and U.S. Pub. No. 2004/0013734. In some embodiments, the solid dispersions of the invention comprise both amorphous and non-amorphous active agents of the present invention and can have enhanced bioavailability as compared to conventional active agents of the present invention formulations. In still other embodiments, the active agents of the present invention formulations described herein are solid solutions. Solid solutions incorporate a substance together with the active agent and other excipients such that heating the mixture results in the dissolution of the drug and the resulting composition is then cooled to provide a solid blend that can be further formulated or directly added to a capsule or compressed into a tablet.

Non-Limiting Examples of Formulations for Oral Delivery

The examples below provide non-limiting embodiments of formulations for oral delivery, which can be used to deliver any of the compounds described herein in enantiomerically enriched form, pure form or even a racemic mixture. Therefore, while the compounds below are specified, any desired purity form or compound can be used if it achieves the desired goal of treatment.

In one non-limiting embodiment, hard gelatin capsules comprising the following ingredients are prepared by mixing the ingredients and filling into hard gelatin capsules in 340 mg quantities. In one non-limiting embodiment, hard gelatin capsules comprising the following ingredients are prepared by mixing the ingredients and filling into hard gelatin capsules in 340 mg quantities.

| Ingredient | Quantity (mg/capsule) |
|---|---|
| S-6-MAPBT | 30.0 |
| Starch | 205.0 |
| Alpha lipoic acid | 100.0 |
| Magnesium stearate | 5.0 |

In one non-limiting embodiment, hard gelatin capsules comprising the following ingredients are prepared by mixing the ingredients and filling into hard gelatin capsules in 340 mg quantities.

| Ingredient | Quantity (mg/capsule) |
|---|---|
| 6-MBPBT (100% R-enantiomer) | 30.0 |
| Starch | 205.0 |
| Alpha lipoic acid | 100.0 |
| Magnesium stearate | 5.0 |

In one non-limiting embodiment, hard gelatin capsules comprising the following ingredients are prepared by mixing the ingredients and filling into hard gelatin capsules in 340 mg quantities.

| Ingredient | Quantity (mg/capsule) |
|---|---|
| Compound of Formula B (100% R-enantiomer) | 30.0 |
| Starch | 205.0 |
| Alpha lipoic acid | 100.0 |
| Magnesium stearate | 5.0 |

In one non-limiting embodiment, hard gelatin capsules comprising the following ingredients are prepared by mixing the ingredients and filling into hard gelatin capsules in 340 mg quantities.

| Ingredient | Quantity (mg/capsule) |
|---|---|
| compound of Formula D (100% R-enantiomer) | 30.0 |
| Starch | 205.0 |
| Alpha lipoic acid | 100.0 |
| Magnesium stearate | 5.0 |

In one non-limiting embodiment, hard gelatin capsules comprising the following ingredients are prepared by mixing the ingredients and filling into hard gelatin capsules in 340 mg quantities.

| Ingredient | Quantity (mg/capsule) |
|---|---|
| Bk-6-MAPBT (100% R-enantiomer) | 30.0 |
| Starch | 205.0 |
| Alpha lipoic acid | 100.0 |
| Magnesium stearate | 5.0 |

In one non-limiting embodiment, a tablet formulation is prepared comprising the ingredients below. The components are blended and compressed to form tablets, each weighing 240 mg.

| Ingredient | Quantity (mg/tablet) |
|---|---|
| R-5-MAPBT | 25.0 |
| Cellulose, microcrystalline | 200.0 |
| Colloidal silicon dioxide | 10.0 |
| Stearic acid | 5.0 |

In one non-limiting embodiment, a tablet formulation is prepared comprising the ingredients below. The components are blended and compressed to form tablets, each weighing 240 mg.

| Ingredient | Quantity (mg/tablet) |
|---|---|
| 6-MBPBT (70% R-enantiomer, 30% S-enantiomer) | 25.0 |
| Cellulose, microcrystalline | 200.0 |
| Colloidal silicon dioxide | 10.0 |
| Stearic acid | 5.0 |

In one non-limiting embodiment, a tablet formulation is prepared comprising the ingredients below. The components are blended and compressed to form tablets, each weighing 240 mg.

| Ingredient | Quantity (mg/tablet) |
|---|---|
| Compound of Formula B (70% R-enantiomer, 30% S-enantiomer) | 25.0 |
| Cellulose, microcrystalline | 200.0 |
| Colloidal silicon dioxide | 10.0 |
| Stearic acid | 5.0 |

In one non-limiting embodiment, a tablet formulation is prepared comprising the ingredients below. The components are blended and compressed to form tablets, each weighing 240 mg.

| Ingredient | Quantity (mg/tablet) |
|---|---|
| Compound of Formula D (70% R-enantiomer, 30% S-enantiomer) | 25.0 |
| Cellulose, microcrystalline | 200.0 |
| Colloidal silicon dioxide | 10.0 |
| Stearic acid | 5.0 |

In one non-limiting embodiment, a tablet formulation is prepared comprising the ingredients below. The components are blended and compressed to form tablets, each weighing 240 mg.

| Ingredient | Quantity (mg/tablet) |
|---|---|
| Bk-6-MAPBT (70% R-enantiomer, 30% S-enantiomer) | 25.0 |
| Cellulose, microcrystalline | 200.0 |
| Colloidal silicon dioxide | 10.0 |
| Stearic acid | 5.0 |

In one non-limiting embodiment, a tablet, comprising the components below, including R-6-MAPBT and S-6-MAPBT, is prepared. The active ingredients, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Ingredient | Quantity (mg/tablet) |
|---|---|
| R-6-MAPBT | 20.0 |
| S-6-MAPBT | 10.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |

In one non-limiting embodiment, a tablet, comprising the components below, including R-5-MBPBT and 6-MBPBT, is prepared. The active ingredients, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Ingredient | Quantity (mg/tablet) |
|---|---|
| 5-MBPBT (R-enantiomer) | 20.0 |
| 6-MBPBT (Racemic) | 10.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |

In one non-limiting embodiment, a tablet, comprising the components below, including an R-enantiomer of a compound of Formula A and a racemic compound of Formula B, is prepared. The active ingredients, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Ingredient | Quantity (mg/tablet) |
|---|---|
| Compound of Formula A (R-enantiomer) | 20.0 |
| Compound of Formula B (Racemic) | 10.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |

In one non-limiting embodiment, a tablet, comprising the components below, including an R-enantiomer of a compound of Formula C and a racemic compound of Formula D, is prepared. The active ingredients, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Ingredient | Quantity (mg/tablet) |
|---|---|
| compound of Formula C (R-enantiomer) | 20.0 |
| compound of Formula D (Racemic) | 10.0 |
| Starch | 45.0 |
| Microcrystalline cellulose | 35.0 |

-continued

| Ingredient | Quantity (mg/tablet) |
| --- | --- |
| Polyvinylpyrrolidone (as 10% solution in water) | 4.0 |
| Sodium carboxymethyl starch | 4.5 |
| Magnesium stearate | 0.5 |
| Talc | 1.0 |

In one non-limiting embodiment, a tablet, comprising the components below, including R-Bk-5-MAPBT and Bk-6-MAPBT, is prepared. The active ingredients, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

| Ingredient | Quantity (mg/tablet) |
| --- | --- |
| Bk-5-MAPBT (R-enantiomer) | 20.0 |
| Bk-6-MAPBT (Racemic) | 10.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |

In one non-limiting embodiment, a capsule, comprising the components below, including R-5-MAPBT and S-5-MAPBT, is prepared. The active ingredients, cellulose, starch, and magnesium stearate are blended, passed through a No. 20 mesh U.S. sieve, and filled into hard gelatin capsules in 150 mg quantities.

| Ingredient | Quantity (mg/capsule) |
| --- | --- |
| S-5-MAPBT | 10.0 |
| R-5-MAPBT | 30.0 |
| Starch | 109.0 |
| Magnesium stearate | 1.0 |

In one non-limiting embodiment, a capsule, comprising the components below, including R-6-MBPBT and 5-MBPBT, is prepared. The active ingredients, cellulose, starch, and magnesium stearate are blended, passed through a No. 20 mesh U.S. sieve, and filled into hard gelatin capsules in 150 mg quantities.

| Ingredient | Quantity (mg/capsule) |
| --- | --- |
| 5-MBPBT (racemic) | 10.0 |
| 6-MBPBT (R-enantiomer) | 30.0 |
| Starch | 109.0 |
| Magnesium stearate | 1.0 |

In one non-limiting embodiment, a capsule, comprising the components below, including a racemic compound of Formula A and an R-enantiomer of a compound of Formula B, is prepared. The active ingredients, cellulose, starch, and magnesium stearate are blended, passed through a No. 20 mesh U.S. sieve, and filled into hard gelatin capsules in 150 mg quantities.

| Ingredient | Quantity (mg/capsule) |
| --- | --- |
| Compound of Formula A (racemic) | 10.0 |
| Compound of Formula B (R-enantiomer) | 30.0 |
| Starch | 109.0 |
| Magnesium stearate | 1.0 |

In one non-limiting embodiment, a capsule, comprising the components below, including a racemic compound of Formula C and an R-enantiomer of a compound of Formula D, is prepared. The active ingredients, cellulose, starch, and magnesium stearate are blended, passed through a No. 20 mesh U.S. sieve, and filled into hard gelatin capsules in 150 mg quantities.

| Ingredient | Quantity (mg/capsule) |
| --- | --- |
| compound of Formula C (racemic) | 10.0 |
| compound of Formula D (R-enantiomer) | 30.0 |
| Starch | 109.0 |
| Magnesium stearate | 1.0 |

In one non-limiting embodiment, a capsule, comprising the components below, including R-Bk-6-MAPBT and Bk-5-MAPBT, is prepared. The active ingredients, cellulose, starch, and magnesium stearate are blended, passed through a No. 20 mesh U.S. sieve, and filled into hard gelatin capsules in 150 mg quantities.

| Ingredient | Quantity (mg/capsule) |
| --- | --- |
| Bk-5-MAPBT (racemic) | 10.0 |
| Bk-6-MAPBT (R-enantiomer) | 30.0 |
| Starch | 109.0 |
| Magnesium stearate | 1.0 |

In one non-limiting embodiment, a capsule, comprising 15 mg of S-5-MAPBT, is prepared using the ingredients below. The active ingredient, cellulose, starch, and magnesium stearate are blended, passed through a No. 20 mesh U.S. sieve, and filled into hard gelatin capsules in 425 mg quantities.

| Ingredient | Amount (mg/capsule) |
| --- | --- |
| S-5-MAPBT | 15.0 |
| Starch | 407.0 |
| Magnesium stearate | 3.0 |

In one non-limiting embodiment, a capsule, comprising 100 mg of R-5-MBPBT, is prepared using the ingredients below. The active ingredient, cellulose, starch, and magnesium stearate are blended, passed through a No. 20 mesh U.S. sieve, and filled into hard gelatin capsules in 510 mg quantities.

| Ingredient | Amount (mg/capsule) |
| --- | --- |
| 5-MBPBT (R-enantiomer) | 100.0 |
| Starch | 407.0 |
| Magnesium stearate | 3.0 |

In one non-limiting embodiment, a capsule, comprising 100 mg of an R-enantiomer of a compound of Formula A, is prepared using the ingredients below. The active ingredient, cellulose, starch, and magnesium stearate are blended, passed through a No. 20 mesh U.S. sieve, and filled into hard gelatin capsules in 510 mg quantities.

| Ingredient | Amount (mg/capsule) |
|---|---|
| Compound of Formula A (R-enantiomer) | 100.0 |
| Starch | 407.0 |
| Magnesium stearate | 3.0 |

In one non-limiting embodiment, a capsule, comprising 100 mg of an R-enantiomer of a compound of Formula C, is prepared using the ingredients below. The active ingredient, cellulose, starch, and magnesium stearate are blended, passed through a No. 20 mesh U.S. sieve, and filled into hard gelatin capsules in 510 mg quantities.

| Ingredient | Amount (mg/capsule) |
|---|---|
| compound of Formula C (R-enantiomer) | 100.0 |
| Starch | 407.0 |
| Magnesium stearate | 3.0 |

In one non-limiting embodiment, a capsule, comprising 100 mg of R-Bk-5-MAPBT, is prepared using the ingredients below. The active ingredient, cellulose, starch, and magnesium stearate are blended, passed through a No. 20 mesh U.S. sieve, and filled into hard gelatin capsules in 510 mg quantities.

| Ingredient | Amount (mg/capsule) |
|---|---|
| Bk-5-MAPBT (R-enantiomer) | 100.0 |
| Starch | 407.0 |
| Magnesium stearate | 3.0 |

Extended-Release Formulations

Depending on the desired release profile, the pharmaceutical formulation, for example, an oral solid dosage form, may contain a suitable amount of controlled-release agents, extended-release agents, and/or modified-release agents (e.g., delayed-release agents). The pharmaceutical solid oral dosage forms comprising the active agents of the present invention described herein can be further formulated to provide a modified or controlled release of the active agents of the present invention. In some embodiments, the solid dosage forms described herein can be formulated as a delayed release dosage form such as an enteric-coated delayed release oral dosage forms, i.e., as an oral dosage form of a pharmaceutical composition as described herein which uses an enteric coating to affect release in the small intestine of the gastrointestinal tract. The enteric-coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated. Enteric coatings may also be used to prepare other controlled release dosage forms including extended-release and pulsatile release dosage forms.

In other embodiments, the active agents of the formulations described herein are delivered using a pulsatile dosage form. Pulsatile dosage forms comprising the active agents of the present invention described herein may be administered using a variety of formulations known in the art. For example, such formulations include those described in U.S. Pat. Nos. 5,011,692; 5,017,381; 5,229,135; and 5,840,329. Other dosage forms suitable for use with the active agents of the present invention are described in, for example, U.S. Pat. Nos. 4,871,549; 5,260,068; 5,260,069; 5,508,040; 5,567,441; and 5,837,284.

In one embodiment, the controlled release dosage form is pulsatile release solid oral dosage form comprising at least two groups of particles, each containing active agents of the present invention as described herein. The first group of particles provides a substantially immediate dose of the active agents of the present invention upon ingestion by a subject. The first group of particles can be either uncoated or comprise a coating and/or sealant. The second group of particles comprises coated particles, which may comprise from at least about 2% to about 75% or less, typically from at least about 2.5% to about 70% or less, or from at least about 40% to about 70% or less, by weight of the total dose of the active agents of the present invention in said formulation, in admixture with one or more binders.

In one embodiment, a coating for providing a controlled, delayed, or extended-release is applied to 5-MAPBT and/or 6-MAPBT or to a core containing 5-MAPBT and/or 6-MAPBT. In one embodiment, a coating for providing a controlled, delayed, or extended-release is applied to 5-MBPBT and/or 6-MBPBT or to a core containing 5-MBPBT and/or 6-MBPBT. In one embodiment, a coating for providing a controlled, delayed, or extended-release is applied to Bk-5-MAPBT and/or Bk-6-MAPBT or to a core containing Bk-5-MAPBT and/or Bk-6-MAPBT. In one embodiment, a coating for providing a controlled, delayed, or extended-release is applied to Bk-5-MBPBT and/or Bk-6-MBPBT or to a core containing Bk-5-MBPBT and/or Bk-6-MBPBT. In one embodiment, a coating for providing a controlled, delayed, or extended-release is applied to a compound of Formula A and/or Formula B or to a core containing a compound of Formula A and/or Formula B. In one embodiment, a coating for providing a controlled, delayed, or extended-release is applied to a compound of Formula C and/or Formula D or to a core containing a compound of Formula C and/or Formula D. In one embodiment, a coating for providing a controlled, delayed, or extended-release is applied to a compound shown in FIG. 2 or to a core containing a compound shown in FIG. 2. In one embodiment, a coating for providing a controlled, delayed, or extended-release is applied to a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or to a core containing a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI.

The coating may comprise a pharmaceutically acceptable ingredient in an amount sufficient, e.g., to provide an extended release from e.g., about 1 hours to about 7 hours following ingestion before release of the active agent. Suitable coatings include one or more differentially degradable coatings such as, by way of example only, pH-sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the active agents of the present invention formulation.

Many other types of controlled/delayed/extended-release systems known to those of ordinary skill in the art and are suitable for use with the active agents of the present invention formulations described herein. Examples of such delivery systems include polymer-based systems, such as polylactic and polyglycolic acid, polyanhydrides and polycaprolactone, cellulose derivatives (e.g., ethylcellulose), porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, 2nd Ed., pp. 751-753 (2002); U.S. Pat. Nos. 4,327,725; 4,624,848; 4,968,509; 5,461,140; 5,456,923, 5,516,527; 5,622,721, 5,686,105; 5,700,410; 5,977,175; 6,465,014 and 6,932,983.

In certain embodiments, the controlled release systems may comprise the controlled/delayed/extended-release material incorporated with the drug(s) into a matrix, whereas in other formulations, the controlled release material may be applied to a core containing the drug(s). In certain embodiments, one drug may be incorporated into the core while the other drug is incorporated into the coating. In some embodiments, materials include shellac, acrylic polymers, cellulosic derivatives, polyvinyl acetate phthalate, and mixtures thereof. In other embodiments, materials include Eudragit® series E, L, RL, RS, NE, L, L300, S, 100-55, cellulose acetate phthalate, Aquateric, cellulose acetate trimellitate, ethyl cellulose, hydroxypropylmethylcellulose phthalate, hydroxypropylmethylcellulose acetate succinate, polyvinyl acetate phthalate, and Cotteric.

The controlled/delayed/extended-release systems may use a hydrophilic polymer, including a water-swellable polymer (e.g., a natural or synthetic gum). The hydrophilic polymer may be any pharmaceutically acceptable polymer which swells and expands in the presence of water to slowly release the active agents of the present invention. These polymers include polyethylene oxide, methylcellulose, hydroxypropyl cellulose, hydroxypropylmethylcellulose, and the like.

The performance of acrylic polymers (primarily their solubility in biological fluids) can vary based on the degree and type of substitution. Examples of suitable acrylic polymers which may be used in matrix formulations or coatings include methacrylic acid copolymers and ammonia methacrylate copolymers. The Eudragit series E, L, S, RL, RS and NE (Rohm Pharma) are available as solubilized in an organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in the stomach and dissolve in the intestine; Opadry Enteric is also insoluble in the stomach and dissolves in the intestine.

Examples of suitable cellulose derivatives for use in matrix formulations or coatings include ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous-based system and is a spray-dried CAP psuedolatex with particles <1 μm. Other components in Aquateric can include pluronic, Tweens, and acetylated monoglycerides. Other suitable cellulose derivatives include cellulose acetate trimellitate (Eastman); methylcellulose (Pharmacoat, Methocel); hydroxypropylmethylcellulose phthalate (HPMCP); hydroxypropylmethylcellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-555, HP-55F grades are suitable. The performance can vary based on the degree and type of substitution. For example, suitable grades of hydroxypropylmethylcellulose acetate succinate include AS-LG (LF), which dissolves at pH 5, AS-MG (MF), which dissolves at pH 5.5, and AS-HG (HF), which dissolves at higher pH. These polymers are offered as granules or as fine powders for aqueous dispersions. Other suitable cellulose derivatives include hydroxypropylmethylcellulose.

In some embodiments, the coating may contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate, and triacetin. Conventional coating techniques such as spray or pan coating are employed to apply coatings. The coating thickness must be sufficient to ensure that the oral dosage form remains intact until the desired site of topical delivery in the intestinal tract is reached.

Multilayer tablet delivery (e.g., such as that used in the GeoMatrix™ technology) comprises a hydrophilic matrix core containing the active ingredient and one or two impermeable or semi-permeable polymeric coatings. This technology uses films or compressed polymeric barrier coatings on one or both sides of the core. The presence of polymeric coatings (e.g., such as that used in the GeoMatrix™ technology) modifies the hydration/swelling rates of the core and reduces the surface area available for drug release. These partial coatings provide modulation of the drug dissolution profile: they reduce the release rate from the device and shift the typical time-dependent release rate toward constant release. This technology enables customized levels of controlled release of specific active agents and/or simultaneous release of two different active agents at different rates that can be achieved from a single tablet. The combination of layers, each with different rates of swelling, gelling and erosion, is used for the rate of drug release in the body. Exposure of the multilayer tablet as a result of the partial coating may affect the release and erosion rates, therefore, transformation of a multilayered tablet with exposure on all sides to the gastrointestinal fluids upon detachment of the barrier layer will be considered.

Multi-layered tablets containing combinations of immediate release and modified/extended release of two different active agents or dual release rate of the same drug in a single dosage form may be prepared by using hydrophilic and hydrophobic polymer matrices. Dual release repeat action multi-layered tablets may be prepared with an outer compression layer with an initial dose of rapidly disintegrating matrix in the stomach and a core inner layer tablet formulated with components that are insoluble in the gastric media but release efficiently in the intestinal environment.

In certain embodiments, the dosage form is a solid oral dosage form which is an immediate release dosage form whereby >80% of the active agents of the present invention are released within 2 hours after administration. In other embodiments, the invention provides an (e.g., solid oral) dosage form that is a controlled release or pulsatile release dosage form. In such instances, the release may be, e.g., 30 to 60% of the active agents of the present invention particles by weight are released from the dosage form within about 2 hours after administration and about 90% by weight of the active agents of the present invention released from the dosage form, e.g., within about 4 hours after administration. In yet other embodiments, the dosage form includes at least one active agent in an immediate-release form and at least one active agent in the delayed-release form or sustained-release form. In yet other embodiments, the dosage form includes at least two active agents that are released at different rates as determined by in-vitro dissolution testing or via oral administration.

The various release dosage formulations discussed above, and others known to those skilled in the art can be characterized by their disintegration profile. A profile is characterized by the test conditions selected. Thus, the disintegration profile can be generated at a pre-selected apparatus type, shaft speed, temperature, volume, and pH of the dispersion media. Several disintegration profiles can be obtained. For example, a first disintegration profile can be measured at a pH level approximating that of the stomach (about pH 1.2); a second disintegration profile can be measured at a pH level approximating that of one point in the intestine or several pH levels approximating multiple points in the intestine (about 6.0 to about 7.5, more specifically, about 6.5 to 7.0). Another disintegration profile can be measured using distilled water. The release of formulations may also be characterized by their pharmacokinetic parameters, for example, $C_{max}$, $T_{max}$, and AUC (0-τ).

In certain embodiments, the controlled, delayed or extended-release of one or more of the active agents of the fixed-dose combinations of the invention may be in the form of a capsule having a shell comprising the material of the rate-limiting membrane, including any of the coating materials previously discussed, and filled with the active agents of the present invention particles. A particular advantage of this configuration is that the capsule may be prepared independently of the active agent of the present invention particles; thus, process conditions that would adversely affect the drug can be used to prepare the capsule.

Alternatively, the formulation may comprise a capsule having a shell made of a porous or a pH-sensitive polymer made by a thermal forming process. Another alternative is a capsule shell in the form of an asymmetric membrane, i.e., a membrane that has a thin skin on one surface and most of whose thickness is constituted of a highly permeable porous material. The asymmetric membrane capsules may be prepared by a solvent exchange phase inversion, wherein a solution of polymer, coated on a capsule-shaped mold, is induced to phase separate by exchanging the solvent with a miscible non-solvent. In another embodiment, spray layered active agents of the present invention particles are filled in a capsule.

An exemplary process for manufacturing the spray layered the active agents of the present invention is the fluidized bed spraying process. The active agents of the present invention suspensions or the active agents of the present invention complex suspensions described above may be sprayed onto sugar or microcrystalline cellulose (MCC) beads (20-35 mesh) with Wurster column insert at an inlet temperature of 50° C. to 60° C. and air temp of 30° C. to 50° C. A 15 to 20 wt % total solids content suspension containing 45 to 80 wt % the active agents of the present invention, 10 to 25 wt % hydroxymethylpropylcellulose, 0.25 to 2 wt % of SLS, 10 to 18 wt % of sucrose, 0.01 to 0.3 wt % simethicone emulsion (30% emulsion) and 0.3 to 10% NaCl, based on the total weight of the solid content of the suspension, are sprayed (bottom spray) onto the beads through 1.2 mm nozzles at 10 mL/min and 1.5 bar of pressure until a layering of 400 to 700% wt % is achieved as compared to initial beads weight. The resulting spray layered the active agents of the present invention particles, or the active agents of the present invention complex particles comprise about 30 to 70 wt % of the active agents of the present invention based on the total weight of the particles.

In one embodiment the capsule is a size 0 soft gelatin capsule. In one embodiment, the capsule is a swelling plug device. In another embodiment, the swelling plug device is further coated with cellulose acetate phthalate or copolymers of methacrylic acid and methylmethacrylate. In some embodiments, the capsule includes at least 40 mg (or at least 100 mg or at least 200 mg) of the active agents of the present invention and has a total weight of less than 800 mg (or less than 700 mg). The capsule may contain a plurality of the active agents of the present invention-containing beads, for example, spray layered beads. In some embodiments, the beads are 12-25% the active agents of the present invention by weight. In some embodiments, some or all of the active agents of the present invention containing beads are coated with a coating comprising 6 to 15% (or 8 to 12%) of the total bead weight. Optimization work typically involves lower loading levels, and the beads constitute 30 to 60% of the finished bead weight. The capsule may contain a granulated composition, wherein the granulated composition comprises the active agents of the present invention.

The capsule may provide pulsatile release of the active agents of the present invention oral dosage form. In one embodiment, the formulations comprise: (a) a first dosage unit comprising 5-MBPBT and/or 6-MBPBT that is released substantially immediately following oral administration of the dosage form to a patient; (b) a second dosage unit comprising 5-MBPBT and/or 6-MBPBT that is released approximately 2 to 6 hours following administration of the dosage form to a patient.

The capsule may provide pulsatile release of the active agents of the present invention oral dosage form. In one embodiment, the formulations comprise: (a) a first dosage unit comprising 5-MAPBT and/or 6-MAPBT that is released substantially immediately following oral administration of the dosage form to a patient; (b) a second dosage unit comprising 5-MAPBT and/or 6-MAPBT that is released approximately 2 to 6 hours following administration of the dosage form to a patient. In one embodiment, the formulation comprises: (a) a first dosage unit comprising compounds of Formula A and/or Formula B that is released substantially immediately following oral administration of the dosage form to a patient; (b) a second dosage unit comprising compounds of Formula A and/or Formula B that is released approximately 2 to 6 hours following administration of the dosage form to a patient.

In one embodiment, the formulations comprises: (a) a first dosage unit comprising compounds of Formula C and/or Formula D that is released substantially immediately following oral administration of the dosage form to a patient; (b) a second dosage unit comprising compounds of Formula C and/or Formula D that is released approximately 2 to 6 hours following administration of the dosage form to a patient.

In one embodiment, the formulation comprises: (a) a first dosage unit comprising Bk-5-MAPBT and/or Bk-6-MAPBT that is released substantially immediately following oral administration of the dosage form to a patient; (b) a second dosage unit comprising Bk-5-MAPBT and/or Bk-6-MAPBT that is released approximately 2 to 6 hours following administration of the dosage form to a patient.

In one embodiment, the formulation comprises: (a) a first dosage unit comprising Bk-5-MAPBT and/or Bk-6-MAPBT that is released substantially immediately following oral administration of the dosage form to a patient; (b) a second dosage unit comprising Bk-5-MAPBT and/or Bk-6-MAPBT that is released approximately 2 to 6 hours following administration of the dosage form to a patient.

In one embodiment, the formulation comprises: (a) a first dosage unit comprising a compound shown in FIG. 2 that is released substantially immediately following oral administration of the dosage form to a patient; (b) a second dosage unit comprising a compound shown in FIG. 2 that is released approximately 2 to 6 hours following administration of the dosage form to a patient.

In one embodiment, the formulation comprises: (a) a first dosage unit comprising a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof that is released substantially immediately following oral administration of the dosage form to a patient; (b) a second dosage unit comprising a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof that is released approximately 2 to 6 hours following administration of the dosage form to a patient.

For pulsatile release capsules containing beads, the beads can be coated with a coating comprising 6 to 15% (or 8 to 12%) of the total bead weight. In some embodiments, the coating is a coating that is insoluble at pH 1 to 2 and soluble at pH greater than 5.5. In other embodiments, the pulsatile release capsule contains a plurality of beads formulated for modified release and the at least one agent of the present invention is, for example, spray granulated for immediate release.

In some embodiments, the release of the active agents of the present invention particles can be modified with a modified release coating, such as an enteric coating using cellulose acetate phthalate or a sustained release coating comprising copolymers of methacrylic acid and methylmethacrylate. In one embodiment, the enteric coating may be present in an amount of about 0.5 to about 15 wt %, more specifically, about 8 to about 12 wt %, based on the weight of, e.g., the spray layered particles. In one embodiment, the spray layered particles coated with the delayed and/or sustained release coatings can be filled in a modified release capsule in which both enteric-coated particles and immediate release particles of the present invention beads are filled into a soft gelatin capsule. Additional suitable excipients may also be filled with the coated particles in the capsule. The uncoated particles release the active agent of the present invention immediately upon administration while the coated particles do not release the active agent of the present invention until these particles reach the intestine. By controlling the ratios of the coated and uncoated particles, desirable pulsatile release profiles also may be obtained. In some embodiments, the ratios between the uncoated and the coated particles are e.g., 20/80, or 30/70, or 40/60, or 50/50, w/w to obtain desirable release.

In certain embodiments, spray layered active agents of the present invention can be compressed into tablets with commonly used pharmaceutical excipients. Any appropriate apparatus for forming the coating can be used to make the enteric coated tablets, e.g., fluidized bed coating using a Wurster column, powder layering in coating pans or rotary coaters; dry coating by double compression technique; tablet coating by film coating technique, and the like. See, e.g., U.S. Pat. No. 5,322,655; Remington's Pharmaceutical Sciences Handbook: Chapter 90 "Coating of Pharmaceutical Dosage Forms," 1990.

In certain embodiments, the spray layered active agents of the present invention described above and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the active agents of the present invention formulation into the gastrointestinal fluid. In other embodiments, the spray layered active agents of the present invention particles or spray layered active agents complex particles with enteric coatings described above and one or more excipients are dry blended and compressed into a mass, such as a tablet.

In certain embodiments, a pulsatile release of the active agent of the present invention formulation comprises a first dosage unit comprising a formulation made from the active agent of the present invention containing granules made from a spray drying or spray granulated procedure or a formulation made from the active agent of the present invention complex containing granules made from a spray drying or spray granulated procedure without enteric or sustained-release coatings and a second dosage unit comprising spray layered the active agent of the present invention particles or spray layered the active agent of the present invention complex particles with enteric or sustained-release coatings. In one embodiment, the active agent is wet or dry blended and compressed into a mass to make a pulsatile release tablet.

In certain embodiments, binding, lubricating and disintegrating agents are blended (wet or dry) to the spray layered active agent of the present invention to make a compressible blend. In one embodiment, the dosage unit containing 5-MBPBT and/or 6-MBPBT and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing 5-MBPBT and/or 6-MBPBT. In yet another embodiment, the dosage unit containing 5-MBPBT and/or 6-MBPBT is in the form of an overcoat and completely covers the second dosage unit containing the other pharmacological agent.

In certain embodiments, binding, lubricating and disintegrating agents are blended (wet or dry) to the spray layered active agent of the present invention to make a compressible blend. In one embodiment, the dosage unit containing 5-MAPBT and/or 6-MAPBT and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing 5-MAPBT and/or 6-MAPBT. In yet another embodiment, the dosage unit containing 5-MAPBT and/or 6-MAPBT is in the form of an overcoat and completely covers the second dosage unit containing the other pharmacological agent.

In one embodiment, the dosage unit containing Bk-5-MAPBT and/or Bk-6-MAPBT and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing Bk-5-MAPBT and/or Bk-6-MAPBT. In yet another embodiment, the dosage unit containing Bk-5-MAPBT and/or Bk-6-MAPBT is in the form of an overcoat and completely covers the second dosage unit containing the other pharmacological agent.

In one embodiment, the dosage unit containing Bk-5-MBPBT and/or Bk-6-MBPBT and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing Bk-5-MBPBT and/or Bk-6-MBPBT. In yet another embodiment, the dosage unit containing Bk-5-MBPBT and/or Bk-6-MBPBT is in the form of an overcoat and completely covers the second dosage unit containing the other pharmacological agent.

In one embodiment, the dosage unit containing a compound of Formula A and/or Formula B and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing a compound of Formula A and/or Formula B. In yet another embodiment, the dosage unit containing a compound of Formula A and/or Formula B is in the form of an overcoat and completely covers the second dosage unit containing the other pharmacological agent.

In one embodiment, the dosage unit containing a compound of Formula C and/or Formula D and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing a compound of Formula C and/or Formula D. In yet another embodiment, the dosage unit containing a compound of Formula C and/or Formula D is in the form of an overcoat and completely covers the second dosage unit containing the other pharmacological agent.

In one embodiment, the dosage unit containing a compound shown in FIG. 2 and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing a compound shown in FIG. 2. In yet another embodiment, the dosage unit containing a compound shown in FIG. 2 is in the form of an overcoat and completely covers the second dosage unit containing the other pharmacological agent.

In one embodiment, the dosage unit containing a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI and the dosage unit containing the other pharmacological agent are compressed separately and then compressed together to form a bilayer tablet. In yet another embodiment, the dosage unit containing the other pharmacological agent is in the form of an overcoat and completely covers the second dosage unit containing a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI. In yet another embodiment, the dosage unit containing a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI is in the form of an overcoat and completely covers the second dosage unit containing the other pharmacological agent.

Systemic Formulations

The formulations of the present invention can include any selected compound of the present invention for any of the disclosed indications in a form suitable for intramuscular, subcutaneous, or intravenous injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propylene glycol, polyethylene-glycol, glycerol, cremophor and the like), suitable mixtures thereof, vegetable oils (such as olive oil) and injectable organic esters such as ethyl oleate. Additionally, the active agents of the present invention can be dissolved at concentrations of greater than about 1 mg/ml using water-soluble beta cyclodextrins (e.g., beta-sulfobutyl-cyclodextrin and 2-hydroxypropyl-beta-cyclodextrin. Proper fluidity can be maintained, for example, by the use of a coating such as a lecithin, by the maintenance of the required particle size in the case of dispersions, and by the use of surfactants.

The formulations of the present invention suitable for subcutaneous injection may also contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, sorbic acid, and the like. It may also be desirable to include isotonic agents, such as sugars, sodium chloride, and the like. Prolonged drug absorption of the injectable pharmaceutical form can be brought about by the use of agents delaying absorption, such as aluminum monostearate and gelatin. The formulations of the present invention designed for extended-release via subcutaneous or intramuscular injection can avoid first-pass metabolism and lower dosages of the active agents of the present invention will be necessary to maintain plasma levels of about 50 ng/ml. In such formulations, the particle size of the active agents of the present invention and the range of the particle sizes of the active agents of the present invention particles can be used to control the release of the drug by controlling the rate of dissolution in fat or muscle.

In one embodiment, a pharmaceutical composition containing 5-MAPBT and/or 6-MAPBT or a pharmaceutically acceptable salt thereof is formulated into a dosage form suitable for parenteral use. In one embodiment, a pharmaceutical composition containing 5-MBPBT and/or 6-MBPBT or a pharmaceutically acceptable salt thereof is formulated into a dosage form suitable for parenteral use. In one embodiment, pharmaceutical compositions containing compounds of Formula A and/or Formula B or a pharmaceutically acceptable salt thereof is formulated into a dosage form suitable for parenteral use. In one embodiment, pharmaceutical compositions containing compounds of Formula C and/or Formula D or a pharmaceutically acceptable salt thereof is formulated into a dosage form suitable for parenteral use. In one embodiment, pharmaceutical compositions containing Bk-5-MAPBT and/or Bk-6-MAPBT or a pharmaceutically acceptable salt thereof is formulated into a dosage form suitable for parenteral use. In one embodiment, pharmaceutical compositions containing Bk-5-MBPBT and/or Bk-6-MBPBT or a pharmaceutically acceptable salt thereof is formulated into a dosage form suitable for parenteral use. In one embodiment, pharmaceutical compositions containing a compound shown in FIG. 2 or a pharmaceutically acceptable salt thereof is formulated into a dosage form suitable for parenteral use. In one embodiment, pharmaceutical compositions containing a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt thereof is formulated into a dosage form suitable for parenteral use. The dosage form may be selected from, but not limited to, a lyophilized powder, a solution, or a suspension (e.g., a depot suspension).

In one embodiment, a pharmaceutical composition containing 5-MBPBT and/or 6-MBPBT or a pharmaceutically acceptable salt thereof is formulated into a topical dosage form. In one embodiment, a pharmaceutical composition containing Bk-5-MAPBT and/or Bk-6-MAPBT or a pharmaceutically acceptable salt thereof is formulated into a topical dosage form. In one embodiment, a pharmaceutical composition containing 5-MAPBT and/or 6-MAPBT or a pharmaceutically acceptable salt thereof is formulated into a topical dosage form. In one embodiment, a pharmaceutical composition containing Bk-5-MBPBT and/or Bk-6-MBPBT or a pharmaceutically acceptable salt thereof is formulated into a topical dosage form. In one embodiment, a pharmaceutical composition containing a compound of Formula A and/or Formula B or a pharmaceutically acceptable salt thereof is formulated into a topical dosage form. In one embodiment, a pharmaceutical composition containing a compound of Formula C and/or Formula D or a pharmaceutically acceptable salt thereof is formulated into a topical dosage form. In one embodiment, a pharmaceutical composition containing a compound shown in FIG. 2 or a pharmaceutically acceptable salt thereof is formulated into a topical dosage form. In one embodiment, a pharmaceutical composition containing a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV or Formula XVI or a pharmaceutically acceptable salt thereof is formulated into a topical dosage form. The topical dosage form is selected from, but not limited to, a patch, a gel, a paste, a cream, an emulsion, a liniment, a balm, a lotion, and an ointment.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. Indirect techniques, which are generally useful, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Non-Limiting Examples of Formulations for Systemic Delivery

The examples below provide non-limiting embodiments of formulations, which can be used to deliver any of the compounds described herein in enantiomerically enriched form, pure form or even a racemic mixture. Therefore, while the compounds below are specified, any desired purity form or compound can be used if it achieves the desired goal of treatment.

In one non-limiting embodiment, a suppository, comprising 25 mg of S-6-MAPBT, is prepared. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Ingredient | Quantity (mg) |
|---|---|
| S-6-MAPBT | 25.0 |
| Saturated fatty acid glycerides | 2000.0 |

In one non-limiting embodiment, a suppository, comprising 25 mg of R-5-MBPBT, is prepared. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Ingredient | Quantity (mg) |
|---|---|
| R-5-MBPBT | 25.0 |
| Saturated fatty acid glycerides | 2000.0 |

In one non-limiting embodiment, a suppository, comprising 25 mg of a compound of Formula A, is prepared. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Ingredient | Quantity (mg) |
|---|---|
| Compound of Formula A (R-enantiomer) | 25.0 |
| Saturated fatty acid glycerides | 2000.0 |

In one non-limiting embodiment, a suppository, comprising 25 mg of a compound of Formula C, is prepared. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Ingredient | Quantity (mg) |
|---|---|
| compound of Formula C (R-enantiomer) | 25.0 |
| Saturated fatty acid glycerides | 2000.0 |

In one non-limiting embodiment, a suppository, comprising 25 mg of R-Bk-5-MAPBT, is prepared. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

| Ingredient | Quantity (mg) |
|---|---|
| R-Bk-5-MAPBT | 25.0 |
| Saturated fatty acid glycerides | 2000.0 |

In one non-limiting embodiment, a suspension comprising 50 mg of S-5-MAPBT per 5.0 ml dose is prepared using the ingredients below. The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Ingredient | Amount |
|---|---|
| S-5-MAPBT | 50.0 mg |
| Xanthan gum | 4.0 mg |
| Sodium carboxymethyl cellulose (11%) | 50.0 mg |
| Microcrystalline cellulose (89%) | 50 mg |
| Sucrose | 1.75 g |
| Sodium benzoate | 10.0 mg |
| Flavor and Color | q.v. |
| Purified water | To 5.0 ml |

In one non-limiting embodiment, a suspension comprising 50 mg of R-5-MBPBT per 5.0 ml dose is prepared using the ingredients below. The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Ingredient | Amount |
|---|---|
| 5-MBPBT (R-enantiomer) | 50.0 mg |
| Xanthan gum | 4.0 mg |
| Sodium carboxymethyl cellulose (11%) | 50.0 mg |
| Microcrystalline cellulose (89%) | 50 mg |
| Sucrose | 1.75 g |
| Sodium benzoate | 10.0 mg |
| Flavor and Color | q.v. |
| Purified water | To 5.0 ml |

In one non-limiting embodiment, a suspension comprising 50 mg of an R-enantiomer of a compound of Formula A per 5.0 ml dose is prepared using the ingredients below. The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Ingredient | Amount |
|---|---|
| Compound of Formula A (R-enantiomer) | 50.0 mg |
| Xanthan gum | 4.0 mg |
| Sodium carboxymethyl cellulose (11%) | 50.0 mg |
| Microcrystalline cellulose (89%) | 50 mg |
| Sucrose | 1.75 g |
| Sodium benzoate | 10.0 mg |
| Flavor and Color | q.v. |
| Purified water | To 5.0 ml |

In one non-limiting embodiment, a suspension comprising 50 mg of an R-enantiomer of a compound of Formula C per 5.0 ml dose is prepared using the ingredients below. The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Ingredient | Amount |
|---|---|
| compound of Formula C (R-enantiomer) | 50.0 mg |
| Xanthan gum | 4.0 mg |
| Sodium carboxymethyl cellulose (11%) | 50.0 mg |
| Microcrystalline cellulose (89%) | 50 mg |
| Sucrose | 1.75 g |
| Sodium benzoate | 10.0 mg |
| Flavor and Color | q.v. |
| Purified water | To 5.0 ml |

In one non-limiting embodiment, a suspension comprising 50 mg of R-Bk-5-MAPBT per 5.0 ml dose is prepared using the ingredients below. The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

| Ingredient | Amount |
|---|---|
| Bk-5-MAPBT (R-enantiomer) | 50.0 mg |
| Xanthan gum | 4.0 mg |
| Sodium carboxymethyl cellulose (11%) | 50.0 mg |
| Microcrystalline cellulose (89%) | 50 mg |
| Sucrose | 1.75 g |
| Sodium benzoate | 10.0 mg |
| Flavor and Color | q.v. |
| Purified water | To 5.0 ml |

In one non-limiting embodiment, an intravenous formulation is prepared using the following ingredients:

| Ingredient | Amount |
|---|---|
| R-6-MAPBT | 250.0 mg |
| Isotonic saline | 1000 ml |

In one non-limiting embodiment, an intravenous formulation is prepared using the following ingredients:

| Ingredient | Amount |
|---|---|
| Compound of Formula B (R-enantiomer of beta-ketone) | 250.0 mg |
| Isotonic saline | 1000 ml |

In one non-limiting embodiment, an intravenous formulation is prepared using the following ingredients:

| Ingredient | Amount |
|---|---|
| compound of Formula D (R-enantiomer of beta-ketone) | 250.0 mg |
| Isotonic saline | 1000 ml |

In one non-limiting embodiment, an intravenous formulation is prepared using the following ingredients:

| Ingredient | Amount |
|---|---|
| Bk-6-MAPBT (R-enantiomer) | 250.0 mg |
| Isotonic saline | 1000 ml |

In one non-limiting embodiment, a topical formulation is prepared using the ingredients below. The white soft paraffin is heated until molten. The liquid paraffin and emulsifying wax are incorporated and stirred until dissolved. The active ingredient is added and stirring is continued until dispersed. The mixture is then cooled until solid.

| Ingredient | Amount (g) |
|---|---|
| R-5-MAPBT | 10.0 |
| Emulsifying Wax | 30.0 |
| Liquid Paraffin | 20.0 |
| White Soft Paraffin | To 100 |

In one non-limiting embodiment, a topical formulation is prepared using the ingredients below. The white soft paraffin is heated until molten. The liquid paraffin and emulsifying wax are incorporated and stirred until dissolved. The active ingredient is added and stirring is continued until dispersed. The mixture is then cooled until solid.

| Ingredient | Amount (g) |
|---|---|
| 6-MBPBT (S-enantiomer) | 10.0 |
| Emulsifying Wax | 30.0 |
| Liquid Paraffin | 20.0 |
| White Soft Paraffin | To 100 |

In one non-limiting embodiment, a topical formulation is prepared using the ingredients below. The white soft paraffin is heated until molten. The liquid paraffin and emulsifying wax are incorporated and stirred until dissolved. The active ingredient is added and stirring is continued until dispersed. The mixture is then cooled until solid.

| Ingredient | Amount (g) |
|---|---|
| Compound of Formula B (S-enantiomer) | 10.0 |
| Emulsifying Wax | 30.0 |
| Liquid Paraffin | 20.0 |
| White Soft Paraffin | To 100 |

In one non-limiting embodiment, a topical formulation is prepared using the ingredients below. The white soft paraffin is heated until molten. The liquid paraffin and emulsifying wax are incorporated and stirred until dissolved. The active ingredient is added and stirring is continued until dispersed. The mixture is then cooled until solid.

| Ingredient | Amount (g) |
|---|---|
| compound of Formula D (S-enantiomer) | 10.0 |
| Emulsifying Wax | 30.0 |
| Liquid Paraffin | 20.0 |
| White Soft Paraffin | To 100 |

In one non-limiting embodiment, a topical formulation is prepared using the ingredients below. The white soft paraffin is heated until molten. The liquid paraffin and emulsifying wax are incorporated and stirred until dissolved. The active ingredient is added and stirring is continued until dispersed. The mixture is then cooled until solid.

| Ingredient | Amount (g) |
|---|---|
| Bk-6-MAPBT (S-enantiomer) | 10.0 |
| Emulsifying Wax | 30.0 |
| Liquid Paraffin | 20.0 |
| White Soft Paraffin | To 100 |

In one embodiment, a sublingual or buccal tablet, comprising 10 mg of S-5-MAPBT, is prepared using the following ingredients. The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

| Ingredient | Amount (mg/tablet) |
|---|---|
| S-5-MAPBT | 10.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

In one embodiment, a sublingual or buccal tablet, comprising 20 mg of R-5-MBPBT, is prepared using the following ingredients. The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

| Ingredient | Amount (mg/tablet) |
|---|---|
| 5-MBPBT (R-enantiomer) | 20.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

In one embodiment, a sublingual or buccal tablet, comprising 20 mg of an R-enantiomer of a compound of Formula A, is prepared using the following ingredients. The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

| Ingredient | Amount (mg/tablet) |
|---|---|
| Compound of Formula A (R-enantiomer) | 20.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

In one embodiment, a sublingual or buccal tablet, comprising 20 mg of an R-enantiomer of a compound of Formula C, is prepared using the following ingredients. The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

| Ingredient | Amount (mg/tablet) |
|---|---|
| compound of Formula C (R-enantiomer) | 20.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

In one embodiment, a sublingual or buccal tablet, comprising 20 mg of R-Bk-5-MAPBT, is prepared using the following ingredients. The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

| Ingredient | Amount (mg/tablet) |
|---|---|
| Bk-5-MAPBT (R-enantiomer) | 20.0 |
| Glycerol | 210.5 |
| Water | 143.0 |
| Sodium Citrate | 4.5 |
| Polyvinyl Alcohol | 26.5 |
| Polyvinylpyrrolidone | 15.5 |

In one non-limiting embodiment, a liquid formulation for vaporization comprising R-5-MPBP, is prepared using the ingredients below. The active mixture is mixed and added to a liquid vaporization appliance.

| Ingredient | Quantity (units) |
|---|---|
| 5-MPBP (R-enantiomer) | 500 mg |
| Propylene Glycol | 2 ml |
| Glycerin | 2 ml |

In one non-limiting embodiment, a liquid formulation for vaporization comprising a compound of Formula A, is prepared using the ingredients below. The active mixture is mixed and added to a liquid vaporization appliance.

| Ingredient | Quantity (units) |
|---|---|
| Compound of Formula A (R-enantiomer) | 500 mg |
| Propylene Glycol | 2 ml |
| Glycerin | 2 ml |

In one non-limiting embodiment, a liquid formulation for vaporization comprising a compound of Formula C, is prepared using the ingredients below. The active mixture is mixed and added to a liquid vaporization appliance.

| Ingredient | Quantity (units) |
|---|---|
| compound of Formula C (R-enantiomer) | 500 mg |
| Propylene Glycol | 2 ml |
| Glycerin | 2 ml |

In one non-limiting embodiment, a liquid formulation for vaporization comprising R-Bk-5-MAPBT, is prepared using the ingredients below. The active mixture is mixed and added to a liquid vaporization appliance.

| Ingredient | Quantity (units) |
|---|---|
| Bk-5-MAPBT (R-enantiomer) | 500 mg |
| Propylene Glycol | 2 ml |
| Glycerin | 2 ml |

In one non-limiting embodiment, a formulation of dry powder for insufflation is prepared comprising the components below. The active mixture is mixed with the lactose and the mixture is added to a dry powder inhaling appliance.

| Ingredient | Weight % |
|---|---|
| S-5-MAPBT | 5 |
| Lactose | 95 |

In one non-limiting embodiment, a formulation of dry powder for insufflation is prepared comprising the components below. The active mixture is mixed with the lactose and the mixture is added to a dry powder inhaling appliance.

| Ingredient | Weight % |
|---|---|
| 5-MAPBT (R-enantiomer) | 5 |
| Lactose | 95 |

In one non-limiting embodiment, a formulation of dry powder for insufflation is prepared comprising the components below. The active mixture is mixed with the lactose and the mixture is added to a dry powder inhaling appliance.

| Ingredient | Weight % |
|---|---|
| Compound of Formula A (R-enantiomer) | 5 |
| Lactose | 95 |

In one non-limiting embodiment, a formulation of dry powder for insufflation is prepared comprising the components below. The active mixture is mixed with the lactose and the mixture is added to a dry powder inhaling appliance.

| Ingredient | Weight % |
|---|---|
| compound of Formula C (R-enantiomer) | 5 |
| Lactose | 95 |

In one non-limiting embodiment, a formulation of dry powder for insufflation is prepared comprising the components below. The active mixture is mixed with the lactose and the mixture is added to a dry powder inhaling appliance.

| Ingredient | Weight % |
|---|---|
| Bk-5-MAPBT (R-enantiomer) | 5 |
| Lactose | 95 |

Pharmaceutically Acceptable Salts

The compounds described herein, including enantiomerically enriched mixtures, can be administered if desired as a pharmaceutically acceptable salt or a salt mixture. A salt mixture may be useful to increase solubility of the active substances, to alter pharmacokinetics, or for controlled release or other objective. A salt mixture may comprise 2, 3, 4, 5, 6, or more pharmaceutically acceptable salts together to form a single composition.

The compounds of the present invention are amines and thus basic, and therefore, react with inorganic and organic acids to form pharmaceutically acceptable acid addition salts. In some embodiments, the compounds of the present invention as free amines are oily and have decreased stability at room temperature. In this case it may be beneficial to convert the free amines to their pharmaceutically acceptable acid addition salts for ease of handling and administration because in some embodiments, the pharmaceutically acceptable salt is solid at room temperature.

Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. In one embodiment, the compounds of the present invention are administered as oxalate salts. In one embodiment of the present invention, the compounds are administered as phosphate salts.

Exemplary salts include, but are not limited to, 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, finnarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, sethionate, lactate, lactobionate, laurate, laurylsulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphateldiphosphate, picrate, pivalate, polygalacturonate, propionate, p-toluenesulfonate, saccharate, salicylate, stearate, subacetate, succinate, sulfate, sulfosaliculate, suramate, tannate, tartrate, teoclate, thiocyanate, tosylate, triethiodide, undecanoate, and valerate salts, and the like.

Alternatively, exemplary salts include 2-hydroxyethanesulfonate, 2-naphthalenesulfonate, 2-napsylate, 3-hydroxy-2-naphthoate, 3-phenylpropionate, 4-acetamidobenzoate, acefyllinate, acetate, aceturate, adipate, alginate, aminosalicylate, ammonium, amsonate, ascorbate, aspartate, benzenesulfonate, benzoate, besylate, bicarbonate, bisulfate, bitartrate, borate, butyrate, calcium edetate, calcium, camphocarbonate, camphorate, camphorsulfonate, camsylate, carbonate, cholate, citrate, clavulariate, cyclopentanepropionate, cypionate, d-aspartate, d-camsylate, d-lactate, decanoate, dichloroacetate, digluconate, dodecylsulfate, edentate, edetate, edisylate, estolate, esylate, ethanesulfonate, ethyl sulfate, finnarate, fumarate, furate, fusidate, galactarate (mucate), galacturonate, gallate, gentisate, gluceptate, glucoheptanoate, gluconate, glucuronate, glutamate, glutarate, glycerophosphate, glycolate, glycollylarsanilate, hemisulfate, heptanoate (enanthate), heptanoate, hexafluorophosphate, hexanoate, hexylresorcinate, sethiona, hybenzate, hydrabamine, hydrobromide, hydrobromide/bromide, hydrochloride, hydroiodide, hydroxide, hydroxybenzoate, hydroxynaphthoate, iodide, isethionate, sethionate, 1-aspartate, 1-camsylate, 1-lactate, lactate, lactobionate, laurate, laurylsulphonate, lithium, magnesium, malate, maleate, malonate, mandelate, meso-tartrate, mesylate, methanesulfonate, methylbromide, methylnitrate, methylsulfate, mucate, myristate, N-methylglucamine ammonium salt, napadisilate, naphthylate, napsylate, nicotinate, nitrate, octanoate, oleate, orotate, oxalate, p-toluenesulfonate, palmitate, pamoate, pantothenate, pectinate, persulfate, phenylpropionate, phosphate, phosphateldiphosphate, picrate, pivalate, polygalacturonate, potassium, propionate, pyrophosphate, saccharate, salicylate, salicylsulfate, sodium, stearate, subacetate, succinate, sulfate, sulfosaliculate, sulfosalicylate, suramate, tannate, tartrate, teoclate, terephthalate, thiocyanate, thiosalicylate, tosylate, tribrophenate, triethiodide, undecanoate, undecylenate, valerate, valproate, xinafoate, zinc and the like. (See Berge et al. (1977) "Pharmaceutical Salts," J. Pharm. Sci. 66:1-19.) Pharmaceutically acceptable salts include those employing a hydrochloride anion.

While salts of 5-MAPBT or 6-MAPBT are illustrated, any of the compounds described herein can be substituted, including but not limited to 5-MBPBT, 6-MBPBT, Bk-5-MAPBT, Bk-6-MAPBT, Bk-5-MBPBT, Bk-6-MBPBT, or any compound shown in FIG. 2. The compounds can be used as salts or salt mixtures in enantiomerically enriched form, or in pure enantiomeric form. Nonlimiting examples are the oxalate and phosphate salts (and wherein MAPBT is used solely for exemplary purposes for ease of drafting, but can be substituted for any of the other compounds herein):

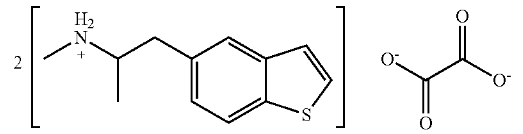

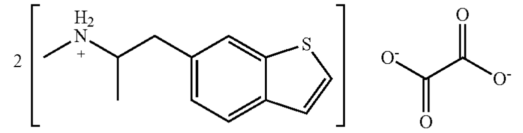

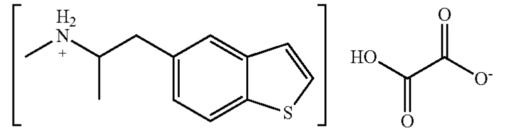

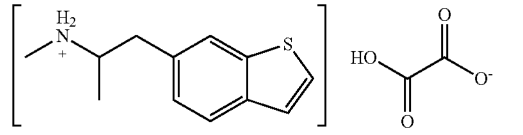

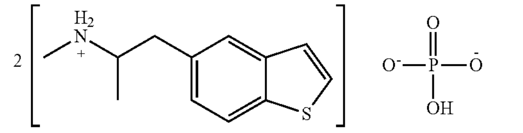

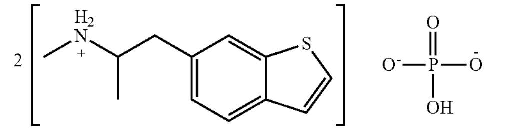

-continued

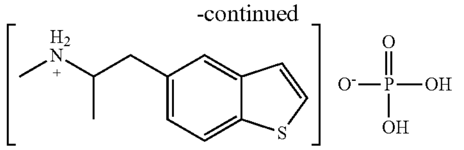

and

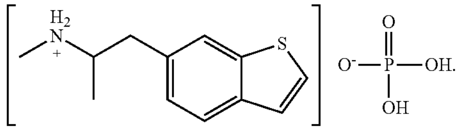

In certain illustrative nonlimiting embodiments, the pharmaceutically acceptable salt of 5-MAPBT or 6-MAPBT, including enantiomerically enriched 5-MAPBT or 6-MAPBT, is selected from:

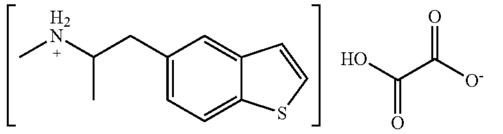

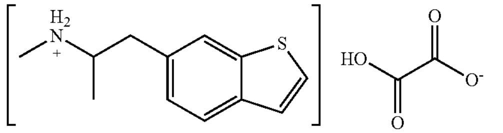

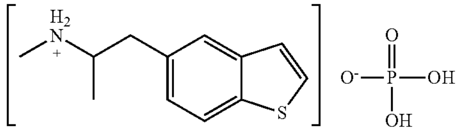

and

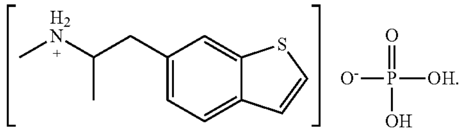

In certain illustrative nonlimiting embodiments, the pharmaceutically acceptable salt of 5-MAPBT or 6-MAPBT, including enantiomerically enriched 5-MAPBT or 6-MAPBT, is selected from:

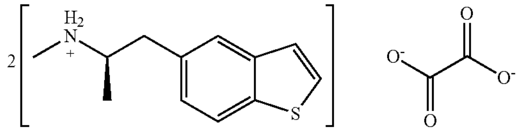

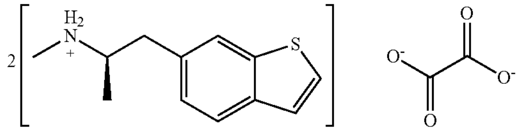

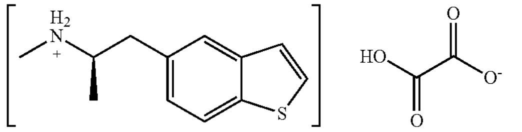

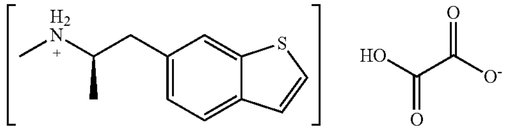

-continued

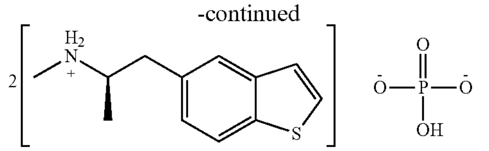

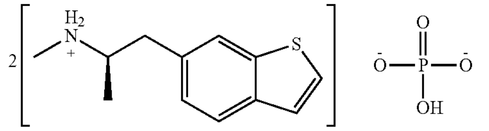

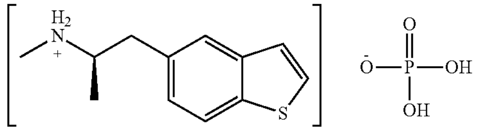

and

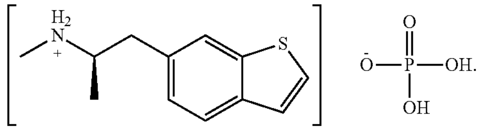

In certain illustrative nonlimiting embodiments, the pharmaceutically acceptable salt of 5-MAPBT or 6-MAPBT, including enantiomerically enriched 5-MAPBT or 6-MAPBT, is selected from:

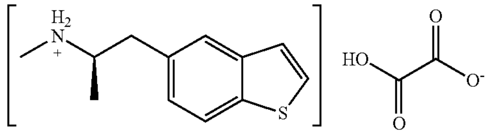

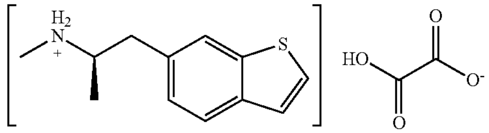

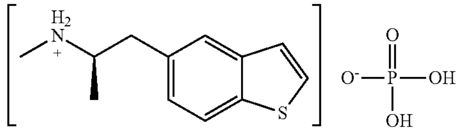

and

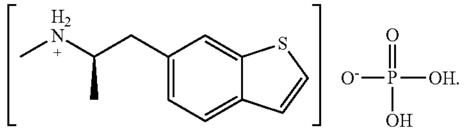

In certain illustrative nonlimiting embodiments, the pharmaceutically acceptable salt of 5-MAPBT or 6-MAPBT, including enantiomerically enriched 5-MAPBT or 6-MAPBT, is selected from:

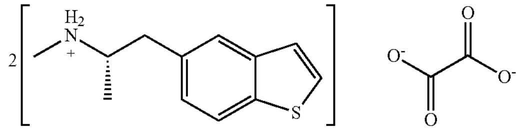

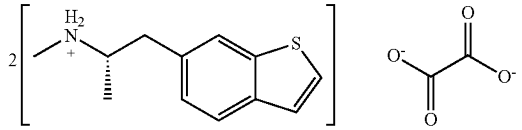

-continued

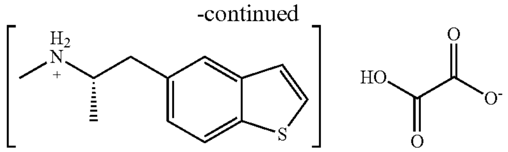

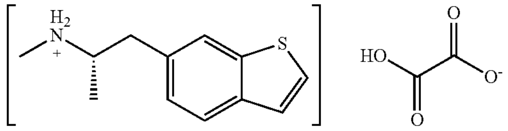

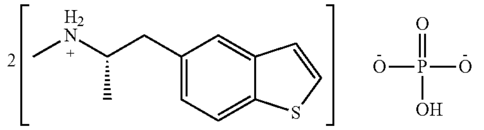

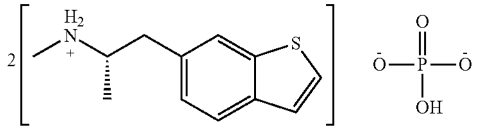

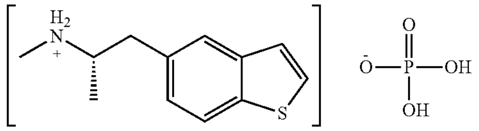

and

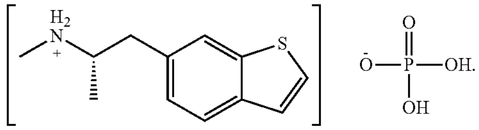

In certain illustrative nonlimiting embodiments, the pharmaceutically acceptable salt of 5-MAPBT or 6-MAPBT, including enantiomerically enriched 5-MAPBT or 6-MAPBT, is selected from:

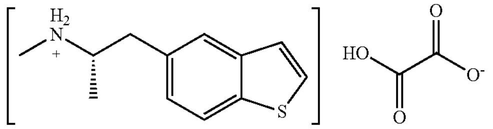

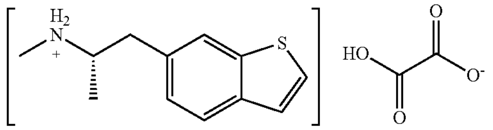

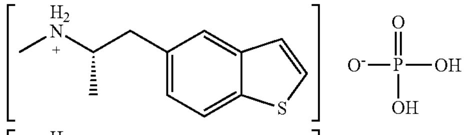

and

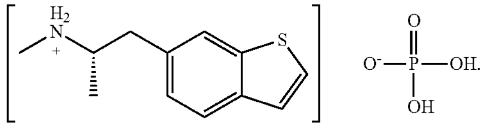

Prodrugs

In certain aspects, the compounds of the present invention are administered as prodrugs. Prodrugs are compounds that are metabolized or otherwise transformed inside the body to the active pharmacologic agent(s) of interest. Thus, prodrug will contain the "active" component (for example, Bk-5-MBPBT, Bk-6-MBPBT, 5-MBPBT, 6-MBPBT, 5-MAPBT, 6-MAPBT, Bk-6-MAPBT, Bk-5-MAPBT, or a compound of Formula A, Formula B, Formula C, or Formula D, or a compound shown in FIG. 2, and a prodrug moiety). Examples include N-alpha-acyloxyalkoxycarbonyl derivatives or addition of amino acids to the amine, which can be removed within the body by esterases or similar enzymes, and reactions at the keto-group to form enol ethers, enol esters, and imines. Prodrugs are frequently (though not necessarily) pharmacologically less active or inactive until converted to the parent drug. This is done in the body by a chemical or biological reaction. In some cases, the moiety or chemicals formed from it may also have beneficial effects, including increasing therapeutic effects, decreasing undesirable side effects, or otherwise altering the pharmacokinetics or pharmacodynamics of the active drug. When the chemical formed from the prodrug moiety has beneficial effects that contribute to the overall beneficial effects of administering the prodrug, then the formed chemical is considered a "codrug."

Types of prodrugs contemplated to be within the scope of the invention include compounds that are transformed in various organs or locations in the body (e.g., liver, kidney, G.I., lung, tissue) to release the active compound. For example, liver prodrugs will include active compounds conjugated with a polymer or chemical moiety that is not released until acted upon by liver cytochrome enzymes and CYP metabolism includes dealkylation, dehydrogenation, reduction, hydrolysis, oxidation, and the breakdown of aromatic rings. Kidney prodrugs will include active compounds conjugated to L-gamma-glutamyl or N-acetyl-L-gamma glutamic moieties so that they are metabolized by gamma-glutamyl transpeptidase before they are bioactive. Alternatively, the compounds may be conjugated to alkyl-glucoside moieties to create glycosylation-based prodrugs. Digestive or G.I. prodrugs will include those where an active compound is, e.g., formulated into microspheres or nanospheres that do not degrade until the spheres are subjected to an acidic pH; formulated with an amide that will resist biochemical degradation until colonic pH is achieved; or, conjugated with a linear polysaccharide such as pectin that will delay activation until the combination reaches the bacteria in the colon. Besides these exemplary prodrug forms, many others will be known to those of ordinary skill.

Among derivatives of a compound are included its "physiologically functional derivatives," which refers to physiologically tolerated chemical derivatives of the compound having the same physiological function thereof, for example, by being convertible in the body thereto, and which on administration to a mammal such as a human is able to form (directly or indirectly) the compound or an active metabolite thereof (acting therefore, like a prodrug), or by otherwise having the same physiological function, despite one or more structural differences. According to the present invention, examples of physiologically functional derivatives include esters, amides, carbamates, ureas, and heterocycles.

V. Combination Therapy

In certain embodiments the compositions of the invention are not limited to combinations of a single compound, and a single carrier, diluent, or excipient alone, but also include combinations of multiple such compounds, and/or multiple carriers, diluents, and excipients. In certain embodiments, a pharmaceutical composition can be provided to the host, for example a human who can be a patient, with an effective amount of one or more other compounds either of the present invention or other active compounds, in combination, together with one or more other active compounds, and one or more pharmaceutically acceptable carriers, diluents, and/or excipients.

In some aspects, a compound of the present invention is formulated in a pharmaceutical preparation with other active compounds to increase therapeutic efficacy, decrease unwanted effects, increase stability/shelf-life, and/or alter pharmacokinetics. Such other active compounds include, but are not limited to antioxidants (such alpha-lipoate in acid or salt form, ascorbate in acid or salt form, selenium, or N-acetylcysteine); H2-receptor agonists or antagonists (such as famotidine); stimulants (such as dextroamphetamine, amphetamine, lisdexamphetamine, methylphenidate, or methamphetamine); entactogens (such as MDMA); anti-inflammatories (such as ibuprofen or ketoprofen); matrix metalloproteinase inhibitors (such as doxycycline); NOS inhibitors (such as S-methyl-L-thiocitrulline); proton pump inhibitors (such as omeprazole); phosphodiesterase 5 inhibitors (such as sildenafil); drugs with cardiovascular effects (beta antagonists such as propranolol, mixed alpha and beta antagonists such as carvedilol, alpha antagonists such as prazosin, imidazoline receptor agonists such as rilmenidine or moxonidine; serotonin antagonists such as ketanserin or lisuride); norepinephrine transporter blockers (such as reboxetine); acetylcholine nicotinic receptor modulators (such as bupropion, hydroxybupropion, methyllycaconitine, memantine, or mecamylamine); gastrointestinal acidifying agents (such as ascorbic acid or glutamic acid hydrochloride); alkalinizing agents (such as sodium bicarbonate), NMDA receptor antagonists (such as ketamine); TrkB agonists (such as 7,8-dihydroxyflavone, 7,8,3'-trihydroxyflavone, or N-acetylserotonin), or serotonin receptor agonists (such as 5-methoxy-N-methyl-N-isopropyltryptamine, N,N-Dimethyl-2-(2-methyl-1H-indol-1-yl)ethan-1-amine, psilocin, or psilocybin). The ingredients may be in ion, freebase, or salt form and may be isomers or prodrugs.

The pharmacological agents that make up the combination therapy disclosed herein may be a combined dosage form or in separate dosage forms intended for substantially simultaneous administration. The pharmacological agents that make up the combination therapy may also be administered sequentially, with either therapeutic compound being administered by a regimen calling for two-step administration. The two-step administration regimen may call for sequential administration of the active agents or spaced-apart administration of the separate active agents.

The time period between the multiple administration steps may range from, a few minutes to several hours, depending upon the properties of each pharmacological agent, such as potency, solubility, bioavailability, plasma half-life and kinetic profile of the pharmacological agent. Circadian variation of the target molecule concentration may also determine the optimal dose interval. For example, a compound of the present invention may be administered while the other pharmacological agent is being administered (concurrent administration) or may be administered before or after other pharmacological agent is administered (sequential administration).

In cases where the two (or more) drugs are included in the fixed-dose combinations of the present invention are incompatible, cross-contamination can be avoided, e.g., by incorporation of the drugs in different drug layers in the oral dosage form with the inclusion of a barrier layer(s) between the different drug layers, wherein the barrier layer(s) comprise one or more inert/non-functional materials.

In certain embodiments, the formulations of the present invention are fixed-dose combinations of a compound of the present invention or a pharmaceutically acceptable salt thereof and at least one other pharmacological agent. Fixed-dose combination formulations may contain, but are not limited to, the following combinations in the form of single-layer monolithic tablet or multi-layered monolithic tablet or in the form of a core tablet-in-tablet or multi-layered multi-disk tablet or beads inside a capsule or tablets inside a capsule.

In one embodiment, the fixed-dose combination is a therapeutically efficacious fixed-dose combinations of immediate-release formulations of 5-MBPBT and/or 6-MBPBT and other pharmacological agents.

In one embodiment, the fixed-dose combination is a therapeutically efficacious fixed-dose combinations of extended-release formulations of 5-MBPBT and/or 6-MBPBT and delayed and/or extended-release other pharmacological agents contained in a single dosage form.

In one embodiment, the fixed-dose combination is a therapeutically efficacious fixed-dose combinations of immediate-release formulations of 5-MAPBT and/or 6-MAPBT and other pharmacological agents.

In one embodiment, the fixed-dose combination is a therapeutically efficacious fixed-dose combinations of extended-release formulations of 5-MAPBT and/or 6-MAPBT and delayed and/or extended-release other pharmacological agents contained in a single dosage form.

In one embodiment, the fixed-dose combination is a therapeutically efficacious fixed-dose combinations of immediate-release formulations of compounds of Formula A and/or Formula B and other pharmacological agents.

In one embodiment, the fixed-dose combination is a therapeutically efficacious fixed-dose combinations of extended-release formulations of compounds of Formula A and/or Formula B and delayed and/or extended-release other pharmacological agents contained in a single dosage form.

In one embodiment, the fixed-dose combination is a therapeutically efficacious fixed-dose combinations of immediate-release formulations of compounds of Formula C and/or Formula D and other pharmacological agents.

In one embodiment, the fixed-dose combination is a therapeutically efficacious fixed-dose combinations of extended-release formulations of compounds of Formula C and/or Formula D and delayed and/or extended-release other pharmacological agents contained in a single dosage form.

In one embodiment, the fixed-dose combination is a therapeutically efficacious fixed-dose combinations of immediate-release formulations of compounds shown in FIG. 2 and other pharmacological agents.

In one embodiment, the fixed-dose combination is a therapeutically efficacious fixed-dose combinations of extended-release formulations of compounds shown in FIG. 2 and delayed and/or extended-release other pharmacological agents contained in a single dosage form.

In one embodiment, the fixed-dose combination is a therapeutically efficacious fixed-dose combinations of immediate-release formulations of Bk-5-MAPBT and/or Bk-6-MAPBT and other pharmacological agents.

In one embodiment, the fixed-dose combination is a therapeutically efficacious fixed-dose combinations of extended-release formulations of Bk-5-MAPBT and/or Bk-6-MAPBT and delayed and/or extended-release other pharmacological agents contained in a single dosage form.

In one embodiment, the fixed-dose combination is a therapeutically efficacious fixed-dose combinations of immediate-release formulations of compounds of Bk-5-MBPBT and/or Bk-6-MBPBT and other pharmacological agents.

In one embodiment, the fixed-dose combination is a therapeutically efficacious fixed-dose combinations of extended-release formulations of Bk-5-MBPBT and/or Bk-6-MBPBT and delayed and/or extended-release other pharmacological agents contained in a single dosage form.

In one embodiment, the fixed-dose combination is a therapeutically efficacious fixed-dose combinations of immediate-release formulations of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof, and other pharmacological agents.

In one embodiment, the fixed-dose combination is a therapeutically efficacious fixed-dose combinations of extended-release formulations of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof, and other pharmacological agents.

In certain embodiments, the invention includes pharmaceutically acceptable complex derivatives of the compound or composition, including solvates, salts, esters, enantiomers, isomers (stereoisomers and/or constitutional, including ones based on substituting deuterium for hydrogen), derivatives or prodrugs of 5-MAPBT or 6-MAPBT.

In certain embodiments, the invention includes pharmaceutically acceptable complex derivatives of the compound or composition, including solvates, salts, esters, enantiomers, isomers (stereoisomers and/or constitutional, including ones based on substituting deuterium for hydrogen), derivatives or prodrugs of compounds of Formula I, Formula II, Formula III, Formula IV, Formula V, Formula VI, Formula VII, Formula VIII, Formula IX, Formula X, Formula XI, Formula XII, Formula XIII, or Formula XIV.

In certain embodiments, the invention includes pharmaceutically acceptable complex derivatives of the compound or composition, including solvates, salts, esters, enantiomers, isomers (stereoisomers and/or constitutional, including ones based on substituting deuterium for hydrogen), derivatives or prodrugs of compounds of Formula A or Formula B.

In certain embodiments, the invention includes pharmaceutically acceptable complex derivatives of the compound or composition, including solvates, salts, esters, enantiomers, isomers (stereoisomers and/or constitutional, including ones based on substituting deuterium for hydrogen), derivatives or prodrugs of compounds of Formula C or Formula D.

In certain embodiments, the invention includes pharmaceutically acceptable complex derivatives of the compound or composition, including solvates, salts, esters, enantiomers, isomers (stereoisomers and/or constitutional, including ones based on substituting deuterium for hydrogen), derivatives or prodrugs of a compound shown in FIG. 2.

In one embodiment, extended-release multi-layered matrix tablets are prepared using fixed-dose combinations of 5-MAPBT and/or 6-MAPBT with another pharmacological agent. In one embodiment, extended-release multi-layered matrix tablets are prepared using fixed-dose combinations of 5-MBPBT and/or 6-MBPBT with another pharmacological agent. In one embodiment, extended-release multi-layered matrix tablets are prepared using fixed-dose combinations of compounds of Formula A and/or Formula B with another pharmacological agent. In one embodiment, extended-release multi-layered matrix tablets are prepared using fixed-dose combinations of compounds of Formula C and/or Formula D with another pharmacological agent.

In one embodiment, extended-release multi-layered matrix tablets are prepared using fixed-dose combinations of a compound shown in FIG. 2 with another pharmacological agent. In one embodiment, extended-release multi-layered matrix tablets are prepared using fixed-dose combinations of Bk-5-MAPBT and/or Bk-6-MAPBT with another pharmacological agent. In one embodiment, extended-release multi-layered matrix tablets are prepared using fixed-dose combinations of Bk-5-MBPBT and/or Bk-6-MBPBT with another pharmacological agent. Such formulations may comprise one or more of the active agents within a hydrophilic or hydrophobic polymer matrix. In one embodiment, extended-release multi-layered matrix tablets are prepared using fixed-dose combinations of compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof, with another pharmacological agent. In one embodiment, extended-release multi-layered matrix tablets are prepared using fixed-dose combinations of 5-MAPBT and/or 6-MAPBT with another pharmacological agent. For example, a hydrophilic polymer may comprise guar gum, hydroxypropylmethylcellulose, and xanthan gum as matrix formers. Lubricated formulations may be compressed by a wet granulation method.

Another embodiment of the invention includes multiple variations in the pharmaceutical dosages of each drug in the combination as further outlined below. Another embodiment of the invention includes various forms of preparations including using solids, liquids, immediate or delayed or extended-release forms. Many types of variations are possible as known to those skilled in the art.

Pharmaceutical Combinations with Dextroamphetamine

In certain embodiments, 5-MAPBT or 6-MAPBT, either an enantiomer or a mixture of enantiomers, with zero to five or zero to seven hydrogens replaced with deuterium, is formulated in a pharmaceutical composition that contains a pharmaceutically acceptable salt of dextroamphetamine in the amount of 2 mg, 4 mg, 5 mg, 7 mg, 10 mg, 15 mg, 20 mg, or 25 mg. The required amount of dextroamphetamine will vary depending on the needs of the patient.

In other embodiments, a compound of 5-MAPBT or 6-MAPBT, with zero to five or zero to seven hydrogens replaced with deuterium, is formulated in a pharmaceutical composition that contains a pharmaceutically acceptable salt of dextroamphetamine with dextroamphetamine in a ratio by weight of 1:2, 1:3, 1:4, or 1:5 to a compound of Formula A or Formula B. The required amount of dextroamphetamine will vary depending on the needs of the patient.

In certain embodiments, a compound of Formula A or Formula B, with zero to five or zero to seven hydrogens replaced with deuterium, is formulated in a pharmaceutical composition that contains a pharmaceutically acceptable salt of dextroamphetamine in the amount of 2 mg, 4 mg, 5 mg, 7 mg, 10 mg, 15 mg, 20 mg, or 25 mg. The required amount of dextroamphetamine will vary depending on the needs of the patient.

In another embodiments, a compound of Formula A or Formula B, with zero to five or zero to seven hydrogens replaced with deuterium, is formulated in a pharmaceutical composition that contains a pharmaceutically acceptable salt of dextroamphetamine with dextroamphetamine in a ratio by weight of 1:2, 1:3, 1:4, or 1:5 to a compound of Formula A or Formula B. The required amount of dextroamphetamine will vary depending on the needs of the patient.

In certain embodiments, a compound of Formula C or Formula D, with zero to five or zero to seven hydrogens replaced with deuterium, is formulated in a pharmaceutical composition that contains a pharmaceutically acceptable salt of dextroamphetamine in the amount of 2 mg, 4 mg, 5 mg, 7 mg, 10 mg, 15 mg, 20 mg, or 25 mg. The required amount of dextroamphetamine will vary depending on the needs of the patient.

In certain embodiments, a compound of Formula C or Formula D, with zero to five or zero to seven hydrogens replaced with deuterium, is formulated in a pharmaceutical composition that contains a pharmaceutically acceptable salt of dextroamphetamine with dextroamphetamine in a ratio by weight of 1:2, 1:3, 1:4, or 1:5 to a compound of Formula C or Formula D. The required amount of dextroamphetamine will vary depending on the needs of the patient.

In certain embodiments, a compound shown in FIG. 2, with zero to five or zero to seven hydrogens replaced with deuterium, is formulated in a pharmaceutical composition that contains a pharmaceutically acceptable salt of dextroamphetamine in the amount of 2 mg, 4 mg, 5 mg, 7 mg, 10 mg, 15 mg, 20 mg, or 25 mg. The required amount of dextroamphetamine will vary depending on the needs of the patient.

In certain embodiments, a compound shown in FIG. 2, with zero to five or zero to seven hydrogens replaced with deuterium, is formulated in a pharmaceutical composition that contains a pharmaceutically acceptable salt of dextroamphetamine with dextroamphetamine in a ratio by weight of 1:2, 1:3, 1:4, or 1:5 to a compound of Formula C or Formula D. The required amount of dextroamphetamine will vary depending on the needs of the patient.

In other embodiments, a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI with zero to five or zero to seven hydrogens replaced with deuterium, is formulated in a pharmaceutical composition that contains a pharmaceutically acceptable salt of dextroamphetamine in the amount of 2 mg, 4 mg, 5 mg, 7 mg, 10 mg, 15 mg, 20 mg, or 25 mg. The required amount of dextroamphetamine will vary depending on the needs of the patient.

In yet other embodiments, a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI with zero to five or zero to seven hydrogens replaced with deuterium, is formulated in a pharmaceutical composition that contains a pharmaceutically acceptable salt of dextroamphetamine with dextroamphetamine in a ratio by weight of 1:2, 1:3, 1:4, or 1:5 to a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI. The required amount of dextroamphetamine will vary depending on the needs of the patient.

In certain other embodiments, 5-MBPBT and/or 6-MBPBT or a pharmaceutically acceptable salt thereof is formulated in a pharmaceutical composition that also contains dextroamphetamine or a pharmaceutically acceptable salt thereof in the amount of at least about 2 mg, 4 mg, 5 mg, 7 mg, 10 mg, 15 mg, 20 mg, or 25 mg. The required amount of dextroamphetamine will vary depending on the needs of the patient. The compound of 5-MBPBT and/or 6-MBPBT can be a racemic compound, an R- or S-enantiomer, or an enantiomerically enriched mixture of R- or S-enantiomers. In one embodiment, the compound of 5-MBPBT and/or 6-MBPBT is deuterated wherein one to five hydrogens have been replaced with deuterium.

In one embodiment, the ratio of dextroamphetamine (with or without salt) to 5-MBPBT and/or 6-MBPBT (with or without salt) is about 1:2, about 1:3, about 1:4, or about 1:5 by weight.

In one embodiment, 5-MAPBT and/or 6-MAPBT or a pharmaceutically acceptable salt thereof is formulated in a pharmaceutical composition that also contains dextroamphetamine or a pharmaceutically acceptable salt thereof in the amount of at least about 2 mg, 4 mg, 5 mg, 7 mg, 10 mg, 15 mg, 20 mg, or 25 mg. The required amount of dextroamphetamine will vary depending on the needs of the patient. The compound of 5-MAPBT and/or 6-MAPBT can be a racemic compound, an R- or S-enantiomer, or an enantiomerically enriched mixture of R- or S-enantiomers. In one embodiment, the compound of 5-MAPBT and/or 6-MAPBT is deuterated wherein one to five hydrogens have been replaced with deuterium.

In one embodiment, the ratio of dextroamphetamine (with or without salt) to 5-MAPBT and/or 6-MAPBT (with or without salt) is about 1:2, about 1:3, about 1:4, or about 1:5 by weight.

In one embodiment, a compound of Formula A and/or Formula B or a pharmaceutically acceptable salt thereof is formulated in a pharmaceutical composition that also contains dextroamphetamine or a pharmaceutically acceptable salt thereof in the amount of at least about 2 mg, 4 mg, 5 mg, 7 mg, 10 mg, 15 mg, 20 mg, or 25 mg. The required amount of dextroamphetamine will vary depending on the needs of the patient. The compound of Formula A and/or Formula B can be a racemic compound, an R- or S-enantiomer, or an enantiomerically enriched mixture of R- or S-enantiomers. In one embodiment, the compound of Formula A and/or B is deuterated wherein one to five hydrogens have been replaced with deuterium.

In one embodiment, the ratio of dextroamphetamine (with or without salt) to the compound of Formula A and/or Formula B (with or without salt) is about 1:2, about 1:3, about 1:4, or about 1:5 by weight.

In one embodiment, a compound of Formula C and/or Formula D or a pharmaceutically acceptable salt thereof is formulated in a pharmaceutical composition that also contains dextroamphetamine or a pharmaceutically acceptable salt of in the amount of at least about 2 mg, 4 mg, 5 mg, 7 mg, 10 mg, 15 mg, 20 mg, or 25 mg. The required amount of dextroamphetamine will vary depending on the needs of the patient. The compound of Formula C and/or Formula D can be a racemic compound, an R- or S-enantiomer, or an enantiomerically enriched mixture of R- or S-enantiomers. In one embodiment, the compound of Formula C and/or D is deuterated wherein one to five hydrogens have been replaced with deuterium.

In one embodiment, the ratio of dextroamphetamine (with or without salt) to the compound of Formula C and/or Formula D (with or without salt) is about 1:2, about 1:3, about 1:4, about 1:5 by weight.

In one embodiment, a compound shown in FIG. 2, or a pharmaceutically acceptable salt thereof is formulated in a pharmaceutical composition that also contains dextroamphetamine or a pharmaceutically acceptable salt of in the amount of at least about 2 mg, 4 mg, 5 mg, 7 mg, 10 mg, 15 mg, 20 mg, or 25 mg. The required amount of dextroamphetamine will vary depending on the needs of the patient. The compound shown in FIG. 2 can be a racemic compound, an R- or S-enantiomer, or an enantiomerically enriched mixture of R- or S-enantiomers. In one embodiment, the compound shown in FIG. 2 is deuterated wherein one to five hydrogens have been replaced with deuterium.

In one embodiment, the ratio of dextroamphetamine (with or without salt) to the compound shown in FIG. 2 (with or without salt) is about 1:2, about 1:3, about 1:4, or about 1:5 by weight, about 1:6, about 1:7, about 1:8, about 1:9, or about 1:10 by weight.

In one embodiment, Bk-5-MAPBT and/or Bk-6-MAPBT is formulated in a pharmaceutical composition that also contains dextroamphetamine or a pharmaceutically acceptable salt of in the amount of at least about 2 mg, 4 mg, 5 mg, 7 mg, 10 mg, 15 mg, 20 mg, or 25 mg. The required amount of dextroamphetamine will vary depending on the needs of the patient. The compound of Bk-5-MAPBT and/or Bk-6-MAPBT can be a racemic compound, an R- or S-enantiomer, or an enantiomerically enriched mixture of R- or S-enantiomers. In one embodiment, the compound of Bk-5-MAPBT and/or Bk-6-MAPBT is deuterated wherein one to five hydrogens have been replaced with deuterium.

In one embodiment, the ratio of dextroamphetamine (with or without salt) to Bk-5-MAPBT and/or Bk-6-MAPBT (with or without salt) is at least about 1:2, about 1:3, about 1:4, about 1:5, about 1:6, about 1:7, about 1:8, about 1:9, or about 1:10 by weight.

In one embodiment, Bk-5-MBPBT and/or Bk-6-MBPBT is formulated in a pharmaceutical composition that also contains dextroamphetamine or a pharmaceutically acceptable salt of in the amount of at least about 2 mg, 4 mg, 5 mg, 7 mg, 10 mg, 15 mg, 20 mg, or 25 mg. The required amount of dextroamphetamine will vary depending on the needs of the patient. The compound of Bk-5-MBPBT and/or Bk-6-MBPBT can be a racemic compound, an R- or S-enantiomer, or an enantiomerically enriched mixture of R- or S-enantiomers. In one embodiment, the compound of Bk-5-MBPBT and/or Bk-6-MBPBT is deuterated wherein one to five hydrogens have been replaced with deuterium.

In one embodiment, the ratio of dextroamphetamine (with or without salt) to Bk-5-MBPBT and/or Bk-6-MBPBT (with or without salt) is at least about 1:2, about 1:3, about 1:4, about 1:5, about 1:6, about 1:7, about 1:8, about 1:9, or about 1:10 by weight.

In one embodiment, a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof is formulated in a pharmaceutical composition that also contains dextroamphetamine or a pharmaceutically acceptable salt of in the amount of at least about 2 mg, 4 mg, 5 mg, 7 mg, 10 mg, 15 mg, 20 mg, or 25 mg. The required amount of dextroamphetamine will vary depending on the needs of the patient. The compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof, can be a racemic compound, an R- or S-enantiomer, or an enantiomerically enriched mixture of R- or S-enantiomers. In one embodiment, the compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof is deuterated wherein one to five hydrogens have been replaced with deuterium.

In one embodiment, the ratio of dextroamphetamine (with or without salt) to the compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof is at least about 1:2, about 1:3, about 1:4, about 1:5, about 1:6, about 1:7, about 1:8, about 1:9, or about 1:10 by weight.

In one embodiment, 5-MAPBT and/or 6-MAPBT or a pharmaceutically acceptable salt thereof is formulated in a pharmaceutical composition that also contains dextroamphetamine or a pharmaceutically acceptable salt thereof in the amount of at least about 2 mg, 4 mg, 5 mg, 7 mg, 10 mg, 15 mg, 20 mg, or 25 mg. The required amount of dextroamphetamine will vary depending on the needs of the patient. The compound of 5-MAPBT and/or 6-MAPBT can be a racemic compound, an R- or S-enantiomer, or an enantiomerically enriched mixture of R- or S-enantiomers. In one embodiment, the compound of 5-MAPBT and/or 6-MAPBT is deuterated wherein one to five hydrogens have been replaced with deuterium.

In one embodiment, the ratio of dextroamphetamine (with or without salt) to 5-MAPBT and/or 6-MAPBT (with or without salt) is at least about 1:2, about 1:3, about 1:4, about 1:5, about 1:6, about 1:7, about 1:8, about 1:9, or about 1:10 by weight.

Pharmaceutical Combinations with MDMA

In one embodiment, 5-MBPBT and/or 6-MBPBT is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The required amount of MDMA will vary depending on the needs of the patient. The compound of 5-MBPBT and/or 6-MBPBT can be a racemic compound, an R- or S-enantiomer, or an enantiomerically enriched mixture of R- or S-enantiomers. In one embodiment, the compound of 5-MBPBT and/or 6-MBPBT is deuterated wherein one to five hydrogens have been replaced with deuterium.

In one embodiment, the ratio of MDMA (with or without salt) to 5-MBPBT and/or 6-MBPBT (with or without salt) is at least about 3:1, about 2:1, about 1:1, about 1:2, about 1:3, about 1:4, or about 1:5 by weight.

In one embodiment, 5-MAPBT and/or 6-MAPBT is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The required amount of MDMA will vary depending on the needs of the patient. The compound of 5-MAPBT and/or 6-MAPBT can be a racemic compound, an R- or S-enantiomer, or an enantiomerically enriched mixture of R- or S-enantiomers. In one embodiment, the compound of 5-MAPBT and/or 6-MAPBT is deuterated wherein one to five hydrogens have been replaced with deuterium.

In one embodiment, the ratio of MDMA (with or without salt) to 5-MAPBT and/or 6-MAPBT (with or without salt) is at least about 3:1, about 2:1, about 1:1, about 1:2, about 1:3, about 1:4, or about 1:5 by weight.

In one embodiment, a compound of Formula A and/or Formula B is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The compound of Formula A and/or Formula B can be a racemic compound, an R- or S-enantiomer, or an enantiomerically enriched mixture of R- or S-enantiomers. In one embodiment, the compound of Formula A and/or Formula B is deuterated wherein one to five hydrogens have been replaced with deuterium.

In one embodiment, the ratio of MDMA (with or without salt) to the compound of Formula A and/or Formula B (with or without salt) is at least about 3:1, about 2:1, about 1:1, about 1:2, about 1:3, about 1:4, or about 1:5 by weight.

In one embodiment, a compound of Formula C and/or Formula D is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The compound of Formula C and/or Formula D can be a racemic compound, an R- or S-enantiomer, or an enantiomerically enriched mixture of R- or S-enantiomers. In one embodiment, the compound of Formula C and/or Formula D is deuterated wherein one to five hydrogens have been replaced with deuterium.

In one embodiment, the ratio of MDMA (with or without salt) to the compound of Formula C and/or Formula D (with or without salt) is at least about 3:1, about 2:1, about 1:1, about 1:2, about 1:3, about 1:4, or about 1:5 by weight.

In one embodiment, a compound shown in FIG. 2 is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The compound shown in FIG. 2 can be a racemic compound, an R- or S-enantiomer, or an enantiomerically enriched mixture of R- or S-enantiomers. In one embodiment, the compound shown in FIG. 2 is deuterated wherein one to five hydrogens have been replaced with deuterium.

In one embodiment, the ratio of MDMA (with or without salt) to the compound shown in FIG. 2 (with or without salt) is at least about 3:1, about 2:1, about 1:1, about 1:2, about 1:3, about 1:4, or about 1:5 by weight.

In one embodiment, Bk-5-MAPBT and/or Bk-6-MAPBT is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The Bk-5-MAPBT and/or Bk-6-MAPBT can be a racemic compound, an R- or S-enantiomer, or an enantiomerically enriched mixture of R- or S-enantiomers. In one embodiment, the Bk-5-MAPBT and/or Bk-6-MAPBT is deuterated wherein one to five hydrogens have been replaced with deuterium.

In one embodiment, the ratio of MDMA (with or without salt) to Bk-5-MAPBT and/or Bk-6-MAPBT (with or without salt) is at least about 3:1, about 2:1, about 1:1, about 1:2, about 1:3, about 1:4, or about 1:5 by weight.

In one embodiment, Bk-5-MBPBT and/or Bk-6-MBPBT is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The Bk-5-MBPBT and/or Bk-6-MBPBT can be a racemic compound, an R- or S-enantiomer, or an enantiomerically enriched mixture of R- or S-enantiomers. In one embodiment, the Bk-5-MBPBT and/or Bk-6-MBPBT is deuterated wherein one to five hydrogens have been replaced with deuterium.

In one embodiment, the ratio of MDMA (with or without salt) to Bk-5-MBPBT and/or Bk-6-MBPBT (with or without salt) is at least about 3:1, about 2:1, about 1:1, about 1:2, about 1:3, about 1:4, or about 1:5 by weight.

In other embodiments, 5-MAPBT or 6-MAPBT, either as an enantiomer or a mixture of enantiomers, and with zero to five or zero to seven hydrogens replaced with deuterium, are formulated in a pharmaceutical composition that contains a pharmaceutically acceptable salt of MDMA, in an amount between 5 and 180 mg, typically 15-60 mg. The required amount of MDMA will vary depending on the needs of the patient.

In yet another embodiment, 5-MAPBT or 6-MAPBT, either as an enantiomer or a mixture of enantiomers, and with zero to five or zero to seven hydrogens replaced with deuterium, are formulated in a pharmaceutical composition that contains a pharmaceutically acceptable salt of MDMA with MDMA in a ratio by weight of 1:2, 1:3, 1:4, or 1:5 to 5-MAPBT or 6-MAPBT. The required amount of MDMA will vary depending on the needs of the patient.

In still another embodiment, a compound of Formula A or Formula B, as a mixture of enantiomers, with zero to five or zero to seven hydrogens replaced with deuterium, are formulated in a pharmaceutical composition that contains a pharmaceutically acceptable salt of MDMA, in an amount between 5 and 180 mg, typically 15-60 mg. The required amount of MDMA will vary depending on the needs of the patient.

In some embodiments, a compound of Formula A or Formula B, as a mixture of enantiomers, with zero to five or zero to seven hydrogens replaced with deuterium, are formulated in a pharmaceutical composition that contains a pharmaceutically acceptable salt of MDMA with MDMA in a ratio by weight of 1:2, 1:3, 1:4, or 1:5 to a compound of Formula A or Formula B. The required amount of MDMA will vary depending on the needs of the patient.

In yet other embodiments, a compound of Formula C or Formula D, as a mixture of enantiomers, with zero to five or zero to seven hydrogens replaced with deuterium, are formulated in a pharmaceutical composition that contains a pharmaceutically acceptable salt of MDMA, in an amount between 5 and 180 mg, typically 15-60 mg. The required amount of MDMA will vary depending on the needs of the patient.

In certain other embodiments, a compound of Formula C or Formula D, as a mixture of enantiomers, with zero to five or zero to seven hydrogens replaced with deuterium, are formulated in a pharmaceutical composition that contains a pharmaceutically acceptable salt of MDMA with MDMA in a ratio by weight of 1:2, 1:3, 1:4, or 1:5 to a compound of Formula C or Formula D. The required amount of MDMA will vary depending on the needs of the patient.

In other aspects, a compound shown in FIG. 2, as a mixture of enantiomers, with zero to five or zero to seven hydrogens replaced with deuterium, are formulated in a pharmaceutical composition that contains a pharmaceutically acceptable salt of MDMA, in an amount between 5 and 180 mg, typically 15-60 mg. The required amount of MDMA will vary depending on the needs of the patient.

In other embodiments, a compound shown in FIG. 2, as a mixture of enantiomers, with zero to five or zero to seven hydrogens replaced with deuterium, are formulated in a pharmaceutical composition that contains a pharmaceutically acceptable salt of MDMA with MDMA in a ratio by weight of 1:2, 1:3, 1:4, or 1:5 to a compound shown in FIG. 2. The required amount of MDMA will vary depending on the needs of the patient.

In yet additional embodiments, a compound of Formula I, Formula II, Formula III, Formula IV, Formula V, Formula VI, Formula VII, Formula VIII, or Formula IX, as a racemate, an enantiomer, or a mixture of enantiomers, and with zero to five or zero to seven hydrogens replaced with deuterium, are formulated in a pharmaceutical composition that contains a pharmaceutically acceptable salt of MDMA, in an amount between 5 and 180 mg, typically 15-60 mg. The required amount of MDMA will vary depending on the needs of the patient.

In additional embodiments, a compound of Formula I, Formula II, Formula III, Formula IV, Formula V, Formula VI, Formula VII, Formula VIII, or Formula IX, as a racemate, an enantiomer, or a mixture of enantiomers, and with zero to five or zero to seven hydrogens replaced with deuterium, is formulated in a pharmaceutical composition that contains a pharmaceutically acceptable salt of MDMA with MDMA in a ratio by weight of 1:2, 1:3, 1:4, or 1:5 to a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI. The required amount of MDMA will vary depending on the needs of the patient.

In other aspects, a compound of Formula VIII, Formula X, Formula XI, Formula XII, or Formula XIII, either as an enantiomer or a mixture of enantiomers, and with zero to five or zero to seven hydrogens replaced with deuterium, is formulated in a pharmaceutical composition that contains a pharmaceutically acceptable salt of MDMA, in an amount between 5 and 180 mg, typically 15-60 mg. The required amount of MDMA will vary depending on the needs of the patient.

In yet more aspects, a compound of Formula VIII, Formula X, Formula XI, Formula XII, or Formula XIII, either as an enantiomer or a mixture of enantiomers, and with zero to five or zero to seven hydrogens replaced with deuterium, is formulated in a pharmaceutical composition that contains a pharmaceutically acceptable salt of MDMA with MDMA in a ratio by weight of 1:2, 1:3, 1:4, or 1:5 to a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI. The required amount of MDMA will vary depending on the needs of the patient.

In some embodiments, a compound of Formula XIV, as a mixture of enantiomers, and with zero to five or zero to seven hydrogens replaced with deuterium, is formulated in a pharmaceutical composition that contains a pharmaceutically acceptable salt of MDMA, in an amount between 5 and 180 mg, typically 15-60 mg. The required amount of MDMA will vary depending on the needs of the patient.

In another embodiment, a compound of Formula XIV, as a mixture of enantiomers, and with zero to five or zero to seven hydrogens replaced with deuterium, is formulated in a pharmaceutical composition that contains a pharmaceutically acceptable salt of MDMA with MDMA in a ratio by weight of 1:2, 1:3, 1:4, or 1:5 to a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI. The required amount of MDMA will vary depending on the needs of the patient.

In one embodiment, a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof is formulated in a pharmaceutical composition that contains MDMA or a pharmaceutically acceptable salt thereof. In one embodiment, the composition comprises between about at least 5 and about 180 mg or less of MDMA or a pharmaceutically acceptable salt thereof. In one embodiment, the composition comprises between about 15-60 mg of MDMA or a pharmaceutically acceptable salt thereof. The compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof can be a racemic compound, an R- or S-enantiomer, or an enantiomerically enriched mixture of R- or S-enantiomers. In one embodiment, the compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof is deuterated wherein one to five hydrogens have been replaced with deuterium.

In one embodiment, the ratio of MDMA (with or without salt) to the compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof (with or without salt) is at least about 3:1, about 2:1, about 1:1, about 1:2, about 1:3, about 1:4, or about 1:5 by weight.

Pharmaceutical Combinations with Psilocybin

In one embodiment, 5-MBPBT and/or 6-MBPBT or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of 5-MBPBT and/or 6-MBPBT can be a racemic compound, an R- or S-enantiomer, or an enantiomerically enriched mixture of R- or S-enantiomers. In one embodiment, the compound of 5-MBPBT and/or 6-MBPBT is deuterated wherein one to five hydrogens have been replaced with deuterium.

In one embodiment, a compound of Formula A and/or Formula B or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Formula A and/or Formula B can be a racemic compound, an R- or S-enantiomer, or an enantiomerically enriched mixture of R- or S-enantiomers. In one embodiment, the compound of Formula A and/or B is deuterated wherein one to five hydrogens have been replaced with deuterium.

In one embodiment, a compound of Formula C and/or Formula D or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Formula C and/or Formula D can be a racemic compound, an R- or S-enantiomer, or an enantiomerically enriched mixture of R- or S-enantiomers. In one embodiment, the compound of Formula C and/or D is deuterated wherein one to five hydrogens have been replaced with deuterium.

In one embodiment, a compound shown in FIG. 2, or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound shown in FIG. 2 can be a racemic compound, an R- or S-enantiomer, or an enantiomerically enriched mixture of R- or S-enantiomers. In one embodiment, the compound shown in FIG. 2 is deuterated wherein one to five hydrogens have been replaced with deuterium.

In one embodiment, Bk-5-MAPBT and/or Bk-6-MAPBT is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Bk-5-MAPBT and/or Bk-6-MAPBT can be a racemic compound, an R- or S-enantiomer, or an enantiomerically enriched mixture of R- or S-enantiomers. In one embodiment, the compound of Bk-5-MAPBT and/or Bk-6-MAPBT is deuterated wherein one to five hydrogens have been replaced with deuterium.

In one embodiment, a compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof, can be a racemic compound, an R- or S-enantiomer, or an enantiomerically enriched mixture of R- or S-enantiomers. In one embodiment, the compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, or Formula XVI or a pharmaceutically acceptable salt thereof is deuterated wherein one to five hydrogens have been replaced with deuterium.

In one embodiment, 5-MAPBT and/or 6-MAPBT or a pharmaceutically acceptable salt thereof is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of 5-MAPBT and/or 6-MAPBT can be a racemic compound, an R- or S-enantiomer, or an enantiomerically enriched mixture of R- or S-enantiomers. In one embodiment, the compound of 5-MAPBT and/or 6-MAPBT is deuterated wherein one to five hydrogens have been replaced with deuterium.

In one embodiment, Bk-5-MBPBT and/or Bk-6-MBPBT is formulated in a pharmaceutical composition that also contains psilocybin or a pharmaceutically acceptable salt thereof in the amount of at least about 0.01 mg, 0.1 mg, 0.5 mg, 1 mg, 2 mg, 3 mg, 4 mg, 5 mg, 10 mg, 15 mg, 20 mg, 25 mg, or 30 mg. The required amount of psilocybin will vary depending on the needs of the patient. The compound of Bk-5-MBPBT and/or Bk-6-MBPBT can be a racemic compound, an R- or S-enantiomer, or an enantiomerically enriched mixture of R- or S-enantiomers. In one embodiment, the compound of Bk-5-MBPBT and/or Bk-6-MBPBT is deuterated wherein one to five hydrogens have been replaced with deuterium.

Non-Limiting Examples of Combination Formulations

The examples below provide non-limiting embodiments of combination formulations, which can be used to deliver any of the compounds described herein in enantiomerically enriched form, pure form or even a racemic mixture. Therefore, while the compounds below are specified, any desired purity form or compound can be used if it achieves the desired goal of treatment.

In one non-limiting embodiment, a capsule comprising S-5-MAPBT, R-5-MAPBT, and amphetamine sulfate is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
|---|---|
| S-5-MAPBT | 30.0 |
| R-5-MAPBT | 10.0 |
| Amphetamine sulfate | 5.0 |
| Starch | 109.0 |
| Magnesium stearate | 1.0 |

In one non-limiting embodiment, a capsule comprising deuterated R-5-MBPBT, R-6-MBPBT, and amphetamine sulfate is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
|---|---|
| 5-MBPBT (R-enantiomer, D3-N-Deuterated) | 10.0 |
| 6-MBPBT (R-enantiomer, D3-N-Deuterated) | 30.0 |
| Amphetamine sulfate | 5.0 |
| Starch | 109.0 |
| Magnesium stearate | 1.0 |

In one non-limiting embodiment, a capsule, comprising a deuterated compound of Formula A, a deuterated compound of Formula B, and amphetamine sulfate is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
|---|---|
| Compound of Formula A (R-enantiomer, D3-N-Deuterated) | 10.0 |
| Compound of Formula B (R-enantiomer, D3-N-Deuterated) | 30.0 |
| Amphetamine sulfate | 5.0 |
| Starch | 109.0 |
| Magnesium stearate | 1.0 |

In one non-limiting embodiment, a capsule, comprising a deuterated compound of Formula C, a deuterated compound of Formula D, and amphetamine sulfate is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
|---|---|
| compound of Formula C (R-enantiomer, D3-N-Deuterated) | 10.0 |
| compound of Formula D (R-enantiomer, D3-N-Deuterated) | 30.0 |
| Amphetamine sulfate | 5.0 |
| Starch | 109.0 |
| Magnesium stearate | 1.0 |

In one non-limiting embodiment, a capsule, comprising deuterated R-Bk-5-MAPBT, deuterated R-Bk-6-MAPBT, and amphetamine sulfate is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
|---|---|
| Bk-5-MAPBT (R-enantiomer, D3-N-Deuterated) | 10.0 |
| Bk-6-MAPBT (R-enantiomer, D3-N-Deuterated) | 30.0 |
| Amphetamine sulfate | 5.0 |
| Starch | 109.0 |
| Magnesium stearate | 1.0 |

In one non-limiting embodiment, a capsule, comprising deuterated R-6-MBPBT and amphetamine sulfate, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
|---|---|
| 6-MBPBT (R-enantiomer, D3-N-Deuterated) | 40.0 |
| Amphetamine sulfate | 5.0 |
| Starch | 109.0 |
| Magnesium stearate | 1.0 |

In one non-limiting embodiment, a capsule, comprising R-6-MAPBT, S-6-MAPBT, and psilocybin hydrochloride, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
|---|---|
| R-6-MAPBT | 30.0 |
| S-6-MAPBT | 10.0 |
| Psilocybin hydrochloride | 2.0 |
| Alpha lipoic acid | 40.0 |
| Starch | 72.0 |
| Magnesium stearate | 1.0 |

In one non-limiting embodiment, a capsule, comprising enantiomerically enriched 5-MBPBT, enantiomerically enriched 6-MBPBT, and psilocybin hydrochloride, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
|---|---|
| 5-MBPBT (70% R-enantiomer) | 30.0 |
| 6-MBPBT (70% S-enantiomer) | 10.0 |
| Psilocybin hydrochloride | 2.0 |
| Alpha lipoic acid | 40.0 |
| Starch | 72.0 |
| Magnesium stearate | 1.0 |

In one non-limiting embodiment, a capsule, comprising a non-racemic compound of Formula A, a non-racemic compound of Formula B, and psilocybin hydrochloride, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
|---|---|
| Compound of Formula A (70% R-enantiomer) | 30.0 |
| Compound of Formula B (70% S-enantiomer) | 10.0 |
| Psilocybin hydrochloride | 2.0 |
| Alpha lipoic acid | 40.0 |
| Starch | 72.0 |
| Magnesium stearate | 1.0 |

In one non-limiting embodiment, a capsule, comprising an enantiomerically enriched compound of Formula C, an enantiomerically enriched compound of Formula D, and psilocybin hydrochloride, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
|---|---|
| compound of Formula C (70% R-enantiomer) | 30.0 |
| compound of Formula D (70% S-enantiomer) | 10.0 |
| Psilocybin hydrochloride | 2.0 |
| Alpha lipoic acid | 40.0 |
| Starch | 72.0 |
| Magnesium stearate | 1.0 |

In one non-limiting embodiment, a capsule, comprising enantiomerically enriched Bk-5-MAPBT, enantiomerically enriched Bk-6-MAPBT, and psilocybin hydrochloride, is prepared using the ingredients below. The active ingredients, cellulose, starch, and magnesium stearate are blended, passed through a No. 20 mesh U.S. sieve, and filled into hard gelatin capsules in 155 mg quantities.

| Ingredient | Quantity (mg/capsule) |
|---|---|
| Bk-5-MAPBT (70% R-enantiomer) | 30.0 |
| Bk-6-MAPBT (70% S-enantiomer) | 10.0 |
| Psilocybin hydrochloride | 2.0 |
| Alpha lipoic acid | 40.0 |
| Starch | 72.0 |
| Magnesium stearate | 1.0 |

It should be readily appreciated that the above formulation examples are illustrative only. Accordingly, it should be understood that reference to particular compounds(s) is likewise illustrative, and the compounds(s) in any of the non-limiting examples of combination formulations may be substituted by other compounds(s) of the invention. Likewise, any of the other active compounds (e.g., amphetamine sulfate or psilocybin hydrochloride as described above) may be substituted by a different other active compound, as may the inactive compounds.

Moreover, for any of S-5-MAPBT, R-5-MAPBT, S-6-MAPBT, R-6-MAPBT, 5-MBPBT, 6-MBPBT, Bk-5-MAPBT, Bk-6-MAPBT, Formulas I-XVI, Formula A, Formula B, Formula C, and Formula D, or for any other active compounds of the invention, substitution of the compound by its prodrug, free base, salt, or hydrochloride salt shall be understood to provide merely an alternative embodiment still within the scope of the invention. Further, compositions within the scope of the invention should be understood to be open-ended and may include additional active or inactive compounds and ingredients.

The type of formulation employed for the administration of the compounds employed in the methods of the present invention generally may be dictated by the compound(s) employed, the type of pharmacokinetic profile desired from the route of administration and the compound(s), and the state of the patient.

VI. Dosage Regimes

The compounds or pharmaceutically acceptable formulations of the present invention can be administered to the host in any amount, and with any frequency, that achieves the goals of the invention as used by the healthcare provider, or otherwise by the host in need thereof, typically a human, as necessary or desired.

In certain embodiments, the composition as described herein is provided only in a controlled counseling session, and administered only once, or perhaps 2, 3, 4, or 5 or more times in repeated counseling sessions to address a mental disorder as described herein.

In other embodiments, the composition as described herein is provided outside of a controlled counseling session, and perhaps self-administered, as needed to perhaps 2, 3, 4, or 5 or more times in to address a mental disorder as described herein.

In other embodiments, the composition of the present invention may be administered on a routine basis for mental wellbeing or for entactogenic treatment.

The compounds of the current invention can be administered in a variety of doses, routes of administration, and dosing regimens, based on the indication and needs of the patient. Non-limiting examples of therapeutic use include discrete psychotherapeutic sessions, ad libitum use for treatment of episodic disorders, and ongoing use for treatment of subchronic and chronic disorders.

Psychotherapeutic Sessions

For some indications, the medicine is taken in discrete psychotherapy or other beneficial sessions. It is anticipated that these sessions will typically be separated by more than 5 half-lives of the medicine and, for most patients, will typically occur only 1 to 5 times each year.

For these sessions, it will typically be desirable to induce clearly perceptible entactogenic effects that will facilitate fast therapeutic progress. Non-exhaustive examples of oral doses of medicine that produce clearly perceptible entactogenic effects for exemplary purposes for any of the compounds described herein include (using compounds for illustrative purposes only): about 40 to about 120 mg of non-racemic 5-MAPBT, about 40 to about 120 mg of non-racemic 6-MAPBT, about 50 to about 300 mg of 5-MBPBT, about 50 to about 300 mg of 6-MBPBT, about 75 to about 500 mg of BK-5-MAPBT, about 75 to about 500 mg of BK-6-MAPBT, about 75 to about 800 mg of BK-5-MBPBT, about 75 to about 800 mg of BK-6-MBPBT.

It is anticipated that the medicine would be taken once or, more rarely, two or three times in a single therapeutic session. In these cases, it is common for each subsequent dose to be half of the previous dose or lower. Multiple doses within a session typically occur because either the patient's sensitivity to the medicine was unknown and too low of an initial dose was employed or because the patient is experiencing a productive session and it is desirable to extend the duration of therapeutic effects. Controlled release preparations may be used to lengthen the duration of therapeutic effects from a single administration of the medicine. In cases where multiple administrations are used in a session, it is anticipated that individual doses will be lower so that plasma concentrations remain within a desired therapeutic range.

Non-limiting, non-exhaustive examples of indications that may benefit from psychotherapeutic sessions include post-traumatic stress disorder, depression, dysthymia, anxiety and phobia disorders, feeding, eating, and binge disorders, body dysmorphic syndromes, alcoholism, tobacco abuse, drug abuse or dependence disorders, disruptive behavior disorders, impulse control disorders, gaming disorders, gambling disorders, personality disorders, attachment disorders, autism, and dissociative disorders. Also included as exemplary situations where an individual would benefit from a psychotherapeutic session are situations from a reduction of neuroticism or psychological defensiveness, an increase in openness to experience, an increase in creativity, or an increase in decision-making ability.

Ad Libitum Use for Treatment of Episodic Disorders

For some indications, such as social anxiety, where the patient has need for relief from episodic occurrence of a disorder, it is anticipated that the medicine would be taken as needed but that uses should be separated by more than 5 half-lives of the medicine to avoid bioaccumulation and formation of tolerance.

For treating episodic disorders, clearly perceptible entactogenic effects are often not desirable, as they can impair some aspects of functioning. Non-exhaustive examples of oral doses of medicine for any of the compounds described herein include (using compounds for illustrative purposes only) that produce subtle, barely perceptible therapeutic effects include: about 10 to about 60 mg of non-racemic 5-MAPBT, about 10 to about 60 mg of non-racemic 6-MAPBT, about 10 to about 100 mg of 5-MBPBT, about 10 to about 100 mg of 6-MBPBT, about 20 to about 150 mg of BK-5-MAPBT, about 20 to about 150 mg of BK-6-MAPBT, about 20 to about 200 mg of BK-5-MBPBT, and about 20 to about 200 mg of BK-6-MBPBT.

Non-limiting, non-exhaustive examples of indications that may benefit from episodic treatment include post-traumatic stress disorder, depression, dysthymia, anxiety and phobia disorders, feeding, eating, and binge disorders, body dysmorphic syndromes, alcoholism, tobacco abuse, drug abuse or dependence disorders, disruptive behavior disorders, impulse control disorders, gaming disorders, gambling disorders, personality disorders, attachment disorders, autism, and dissociative disorders, provided that clinically significant signs and symptoms worsen episodically or in predictable contexts.

Ongoing Use for Treatment of Subchronic and Chronic Disorders

For some indications, such as substance use disorders, inflammatory conditions, and neurological indications, including treatment of stroke, brain trauma, dementia, and neurodegenerative diseases, where the patient has need for ongoing treatment, it is anticipated that the medicine would be taken daily, twice daily, or three times per day. With some indications (subchronic disorders), such as treatment of stroke or traumatic brain injury, it is anticipated that treatment duration will be time-limited and dosing will be tapered when the patient has recovered. An example dose taper regimen is a reduction in dose of 10% of the original dose per week for nine weeks. With other, chronic disorders, such as dementia, it is anticipated that treatment will be continued as long as the patient continues to receive clinically significant benefits.

For treating subchronic and chronic disorders, clearly perceptible entactogenic effects are often not desirable. Non-exhaustive examples of oral doses of medicine for any of the compounds described herein include (using compounds for illustrative purposes only) that produce subtle, barely perceptible therapeutic effects with ongoing dosing include: about 5 to about 60 mg of non-racemic 5-MAPBT, about 5 to about 60 mg of non-racemic 6-MAPBT, about 5 to about 100 mg of 5-MBPBT, about 5 to about 100 mg of 6-MBPBT, about 10 to about 150 mg of BK-5-MAPBT, about 10 to about 150 mg of BK-6-MAPBT, about 10 to about 200 mg of BK-5-MBPBT, and about 10 to about 200 mg of BK-6-MBPBT.

Non-limiting, non-exhaustive examples of subchronic and chronic disorders that may benefit from regular treatment include migraine, headaches (e.g., cluster headache), neurodegenerative disorders, Alzheimer's disease, Parkinson's disease, schizophrenia, stroke, traumatic brain injury, phantom limb syndrome, and other conditions where increasing neuronal plasticity is desirable.

VII. Examples

Example 1: Synthesis of Select Compounds of the Present Invention

Methods for synthesis of the compounds described herein and/or starting materials are either described in the art or will be readily apparent to the skilled artisan in view of general references well-known in the art (see, e.g., Green et al., "Protective Groups in Organic Chemistry," (Wiley, 2nd ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al, "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995) and may be used to synthesize the compounds of the invention.

In general, the approaches used for similar compounds (Shulgin & Shulgin. 1992. PiHKAL. A chemical love story, Transform Press, Berkeley CA; Glennon et al. 1986. Journal of medicinal chemistry, 29(2), 194-199; Nichols et al. 1991. Journal of medicinal chemistry, 34(1), 276-281; Kedrowski et al. 2007. Organic Letters, 9(17), 3205-3207; Heravi & Zadsirjan. 2016. Current Organic Synthesis, 13(6), 780-833; Keri et al. 2017. European journal of medicinal chemistry, 138, 1002-1033; Perez-Silanes et al. 2001. Journal of Heterocyclic Chemistry, 38(5), 1025-1030; and references therein), such adaptation being that known and understood to those of ordinary skill.

The following two schemes summarize synthetic methods for producing 5-MAPBT and 6-MAPBT. These are meant to be illustrative as there are a large number of potential synthetic methods that can be employed.

Synthesis 1. Synthesis of 6-MAPBT

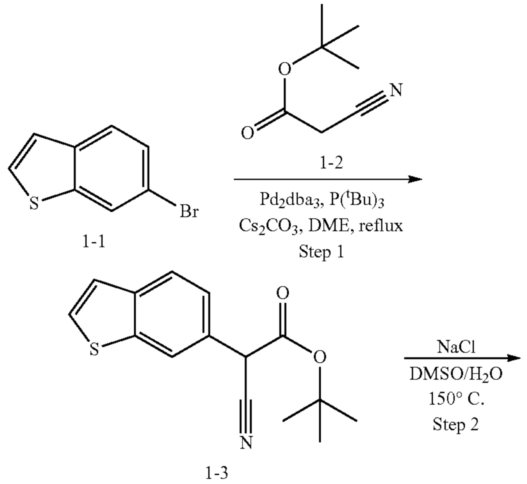

1-1
1-2
1-3

-continued

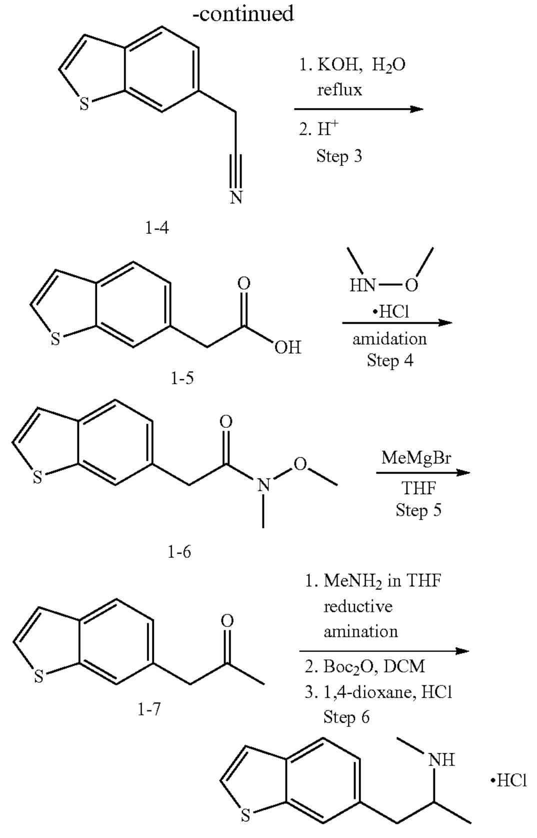

1-4
1-5
1-6
1-7
6-MAPBT

Synthesis 2. Synthesis of 5-MAPBT

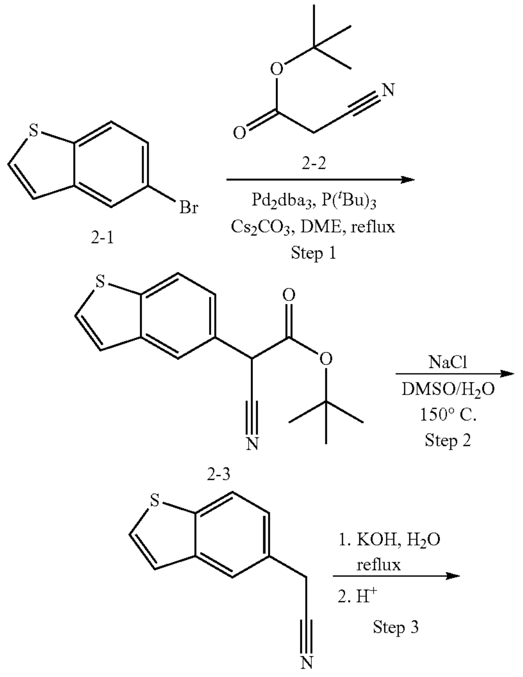

2-1
2-2
2-3
2-4

-continued

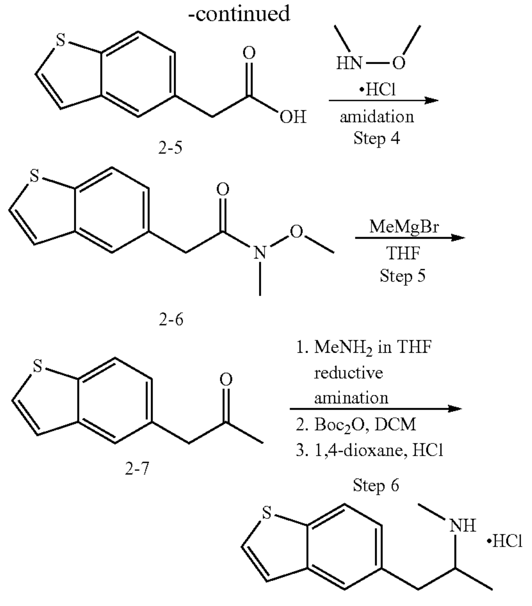

2-5

2-6

2-7

5-MAPBT

Synthesis 3. Synthesis of 5-MBPDBT

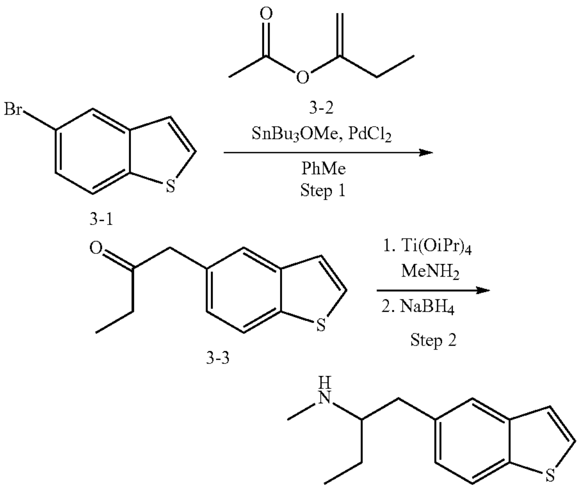

3-1

3-3

5-MBPBT

Step 1: A round-bottom flask is charged with 3-1, tributyltin methoxide, and palladium(II) chloride. The flask is then evacuated and refilled with anhydrous nitrogen three times before adding toluene and 3-2. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 3-3. This crude material can be taken to the next step without further purification or purified by standard techniques of the art to obtain the pure compound.

Step 2: In a round-bottom flask, 3-3, methylamine, and titanium (IV) isopropoxide are dissolved in ethanol and stirred under nitrogen. Once there is no remaining 3-3 as judged by TLC, IPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 5-MBPDBT. This crude material can be purified by standard techniques of the art to obtain the pure compound.

The individual enantiomers of 5-MBPDBT can be separated using the methods described herein or others known in the art. Following isolation of the pure enantiomers, they can be mixed again in any ratio necessary to obtain the desired effects.

Synthesis 4. Synthesis of 5-EBPDBT

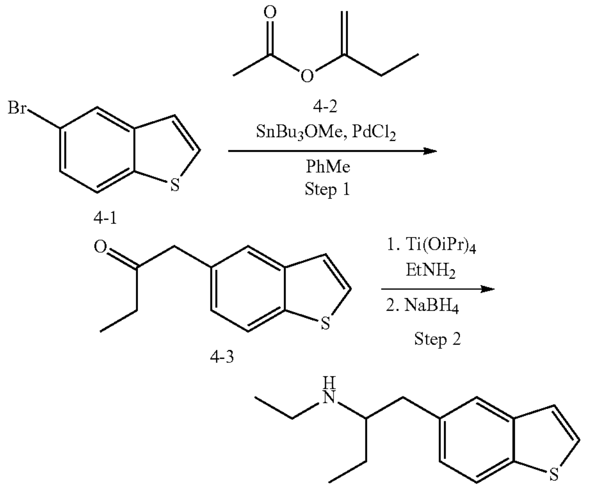

4-1

4-3

5-EBPBT

Step 1: A round-bottom flask is charged with 4-1, tributyltin methoxide, and palladium(II) chloride. The flask is then evacuated and refilled with anhydrous nitrogen three times before adding toluene and 4-2. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 4-3. This crude material can be taken to the next step without further purification or purified by standard techniques of the art to obtain the pure compound.

Step 2: In a round-bottom flask, 4-3, ethylamine, and titanium (IV) isopropoxide are dissolved in ethanol and stirred under nitrogen. Once there is no remaining 4-3 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 5-EBPBT. This crude material can be purified by standard techniques of the art to obtain the pure compound.

The individual enantiomers of 5-EBPBT can be separated using the methods described herein or others known in the art. Following isolation of the pure enantiomers, they can be mixed again in any ratio necessary to obtain the desired effects.

Synthesis 5. Synthesis of Bk-5-EAPBT

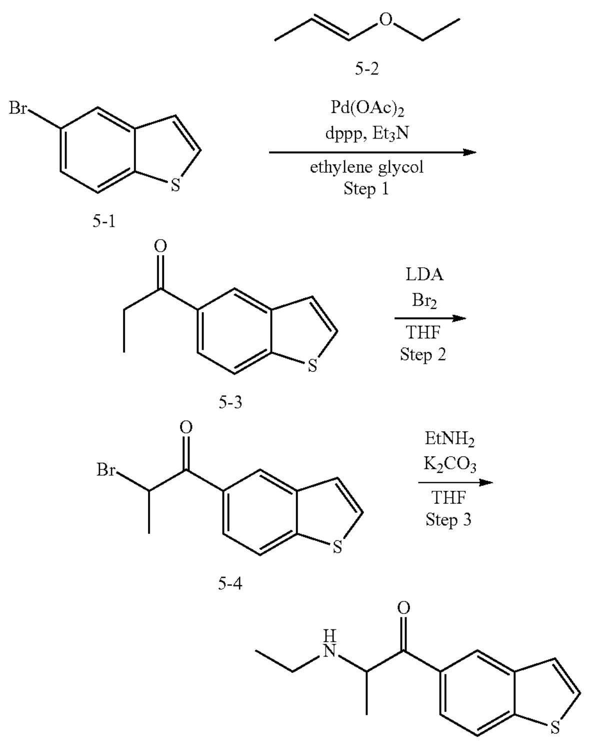

Bk-5-EAPBT

Step 1: A round-bottom flask is charged with 5-1, palladium(II) acetate, and 1,3-bis(diphenylphosphino)propane. The flask is then evacuated and refilled with anhydrous nitrogen three times before adding ethylene glycol, triethylamine, and 5-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 5-3. This crude material can be taken to the next step without further purification or purified by standard techniques of the art to obtain the pure compound.

Step 2: A round-bottom flask is charged with 5-3. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 5-4. This crude material can be taken to the next step without further purification or purified by standard techniques of the art to obtain the pure compound.

Step 3: A round-bottom flask is charged with 5-4, potassium carbonate, anhydrous DMF, and a 2M solution of ethylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-5-EAPBT. This crude material can be purified by standard techniques of the art to obtain the pure compound.

The individual enantiomers of Bk-5-EAPBT can be separated using the methods described herein or others known in the art. Following isolation of the pure enantiomers, they can be mixed again in any ratio necessary to obtain the desired effects.

Synthesis 6. Synthesis of Bk-5-MBPBT

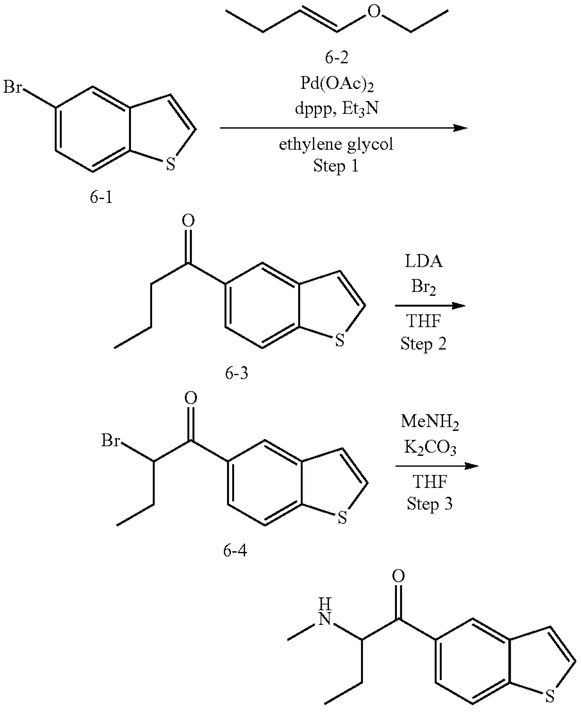

Bk-5-MBPBT

Step 1: A round-bottom flask is charged with 6-1, palladium(II) acetate, and 1,3-bis(diphenylphosphino)propane. The flask is then evacuated and refilled with anhydrous nitrogen three times before adding ethylene glycol, triethylamine, and 6-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 6-3. This crude material can be taken to the next step without further purification or purified by standard techniques of the art to obtain the pure compound.

Step 2: A round-bottom flask is charged with 6-3. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 6-4. This crude material can be taken to the next step without further purification or purified by standard techniques of the art to obtain the pure compound.

Step 3: A round-bottom flask is charged with 6-4, potassium carbonate, anhydrous DMF, and a 2M solution of methylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-5-MBPBT. This crude material can be purified by standard techniques of the art to obtain the pure compound.

The individual enantiomers of Bk-5-MBPBT can be separated using the methods described herein or others known in the art. Following isolation of the pure enantiomers, they can be mixed again in any ratio necessary to obtain the desired effects.

Synthesis 7. Synthesis of Bk-5-EBPBT

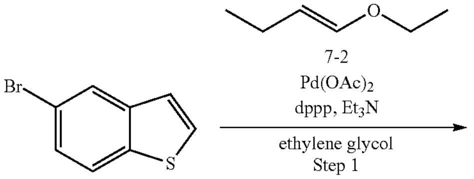

7-1

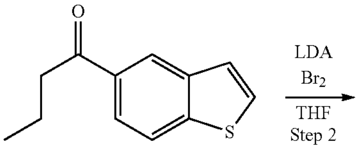

7-3

-continued

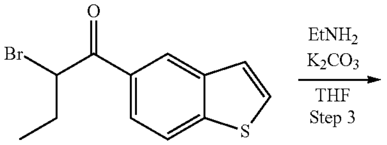

7-4

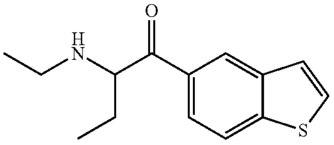

Bk-5-EBPBT

Step 1: A round-bottom flask is charged with 7-1, palladium(II) acetate, and 1,3-bis(diphenylphosphino)propane. The flask is then evacuated and refilled with anhydrous nitrogen three times before adding ethylene glycol, triethylamine, and 7-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 7-3. This crude material can be taken to the next step without further purification or purified by standard techniques of the art to obtain the pure compound.

Step 2: A round-bottom flask is charged with 7-3. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 7-4. This crude material can be taken to the next step without further purification or purified by standard techniques of the art to obtain the pure compound.

Step 3: A round-bottom flask is charged with 7-4, potassium carbonate, anhydrous DMF, and a 2M solution of ethylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-5-EBPBT. This crude material can be purified by standard techniques of the art to obtain the pure compound.

The individual enantiomers of Bk-5-EBPBT can be separated using the methods described herein or others known in the art. Following isolation of the pure enantiomers, they can be mixed again in any ratio necessary to obtain the desired effects.

Synthesis 8. Synthesis of 5-MAPDBT

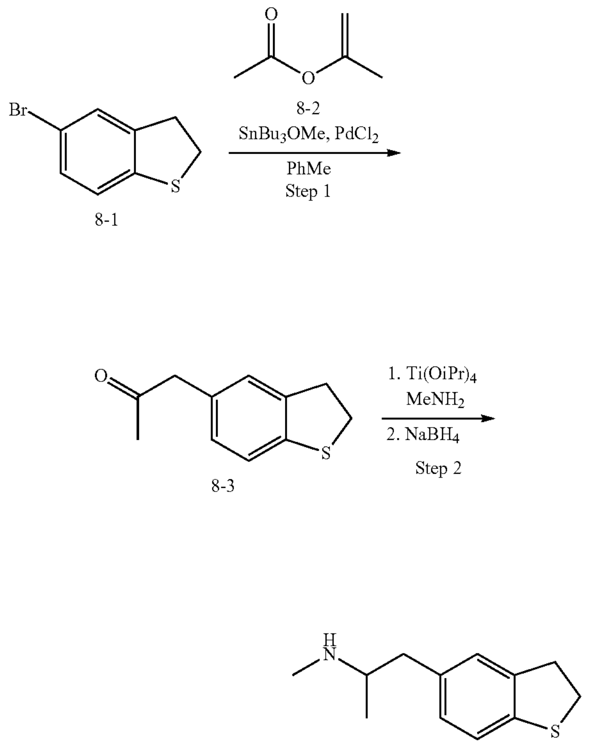

5-MAPDBT

Step 1: A round-bottom flask is charged with 8-1, tributyltin methoxide, and palladium(II) chloride. The flask is then evacuated and refilled with anhydrous nitrogen three times before adding toluene and isopropenyl acetate (8-2). The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 8-3. This crude material can be taken to the next step without further purification or purified by standard techniques of the art to obtain the pure compound.

Step 2: In a round-bottom flask, 8-3, methylamine, and titanium (IV) isopropoxide are dissolved in ethanol and stirred under nitrogen. Once there is no remaining 8-3 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 5-MAPDBT. This crude material can be purified by standard techniques of the art to obtain the pure compound.

The individual enantiomers of 5-MAPDBT can be separated using the methods described herein or others known in the art. Following isolation of the pure enantiomers, they can be mixed again in any ratio necessary to obtain the desired effects.

Synthesis 9. Synthesis of 5-EAPDBT

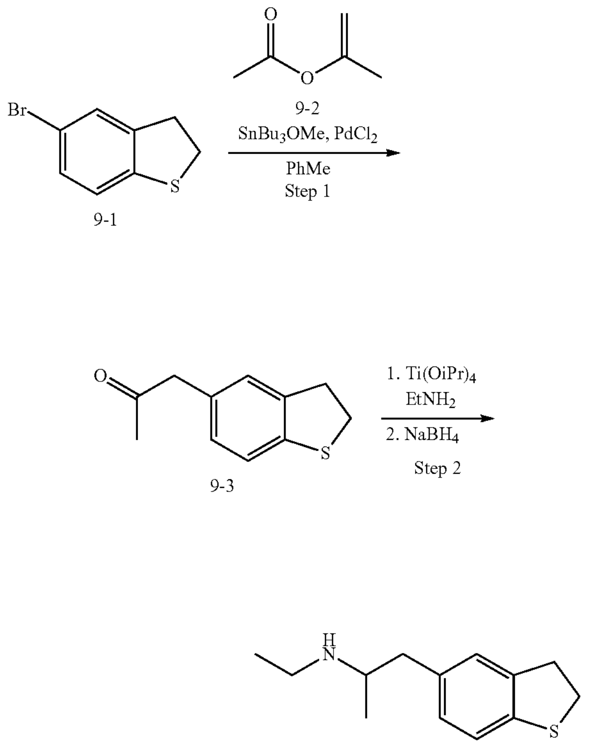

5-EAPDBT

Step 1: A round-bottom flask is charged with 9-1, tributyltin methoxide, and palladium(II) chloride. The flask is then evacuated and refilled with anhydrous nitrogen three times before adding toluene and isopropenyl acetate (9-2). The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 9-3. This crude material can be taken to the next step without further purification or purified by standard techniques of the art to obtain the pure compound.

Step 2: In a round-bottom flask, 9-3, ethylamine, and titanium (IV) isopropoxide are dissolved in ethanol and stirred under nitrogen. Once there is no remaining 9-3 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 5-EAPDBT. This crude material can be purified by standard techniques of the art to obtain the pure compound.

The individual enantiomers of 5-EAPDBT can be separated using the methods described herein or others known in the art. Following isolation of the pure enantiomers, they can be mixed again in any ratio necessary to obtain the desired effects.

Synthesis 10. Synthesis of 5-MBPDBT

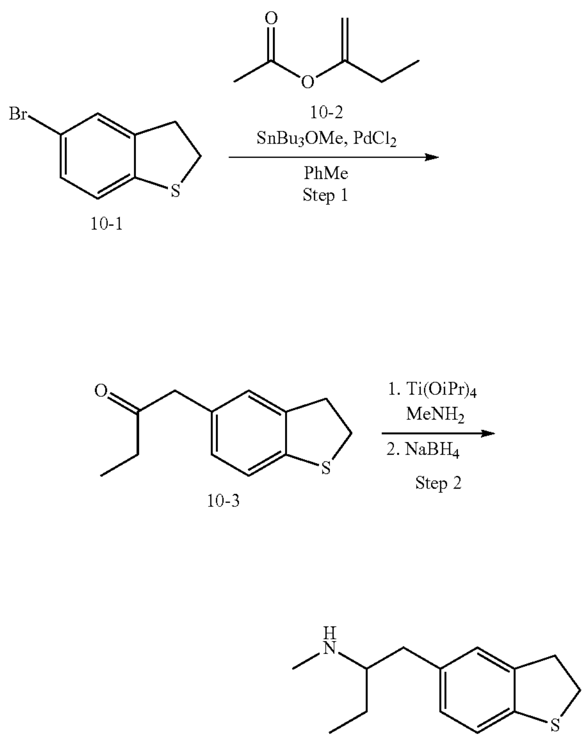

10-1
10-3
5-MBPDBT

Step 1: A round-bottom flask is charged with 10-1, tributyltin methoxide, and palladium(II) chloride. The flask is then evacuated and refilled with anhydrous nitrogen three times before adding toluene and 10-2. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 10-3. This crude material can be taken to the next step without further purification or purified by standard techniques of the art to obtain the pure compound.

Step 2: In a round-bottom flask, 10-3, methylamine, and titanium (IV) isopropoxide are dissolved in ethanol and stirred under nitrogen. Once there is no remaining 10-3 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 5-MBPDBT. This crude material can be purified by standard techniques of the art to obtain the pure compound.

The individual enantiomers of 5-MBPDBT can be separated using the methods described herein or others known in the art. Following isolation of the pure enantiomers, they can be mixed again in any ratio necessary to obtain the desired effects.

Synthesis 11. Synthesis of 5-EBPDBT

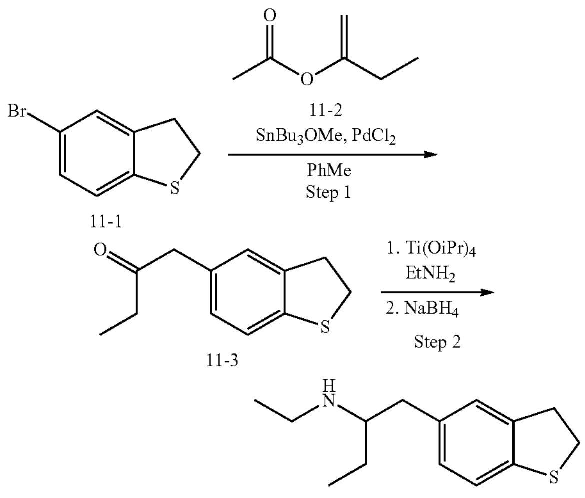

11-1
11-3
5-EBPDBT

Step 1: A round-bottom flask is charged with 11-1, tributyltin methoxide, and palladium(II) chloride. The flask is then evacuated and refilled with anhydrous nitrogen three times before adding toluene and 11-2. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 11-3. This crude material can be taken to the next step without further purification or purified by standard techniques of the art to obtain the pure compound.

Step 2: In a round-bottom flask, 11-3, ethylamine, and titanium (IV) isopropoxide are dissolved in ethanol and stirred under nitrogen. Once there is no remaining 11-3 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 5-EBPDBT. This crude material can be purified by standard techniques of the art to obtain the pure compound.

The individual enantiomers of 5-EBPDBT can be separated using the methods described herein or others known in the art. Following isolation of the pure enantiomers, they can be mixed again in any ratio necessary to obtain the desired effects.

Synthesis 12. Synthesis of Bk-5-MAPDBT

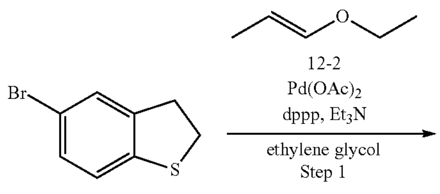

12-1

-continued

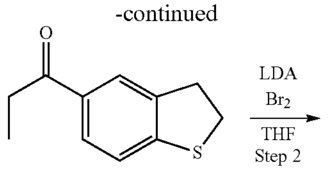

12-3

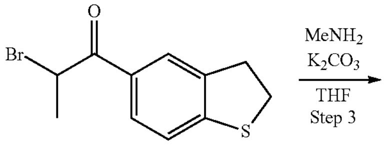

12-4

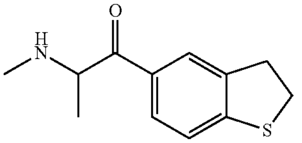

Bk-5-MAPDBT

Step 1: A round-bottom flask is charged with 12-1, palladium(II) acetate, and 1,3-bis(diphenylphosphino)propane. The flask is then evacuated and refilled with anhydrous nitrogen three times before adding ethylene glycol, triethylamine, and 12-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 12-3. This crude material can be taken to the next step without further purification or purified by standard techniques of the art to obtain the pure compound.

Step 2: A round-bottom flask is charged with 12-3. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 12-4. This crude material can be taken to the next step without further purification or purified by standard techniques of the art to obtain the pure compound.

Step 3: A round-bottom flask is charged with 12-4, potassium carbonate, anhydrous DMF, and a 2M solution of methylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-5-MAPDBT. This crude material can be purified by standard techniques of the art to obtain the pure compound.

The individual enantiomers of Bk-5-MAPDBT can be separated using the methods described herein or others known in the art. Following isolation of the pure enantiomers, they can be mixed again in any ratio necessary to obtain the desired effects.

Synthesis 13. Synthesis of Bk-5-EAPDBT

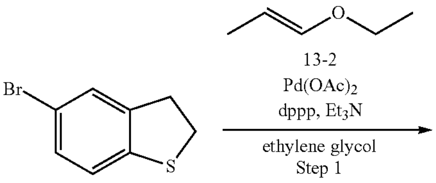

13-1

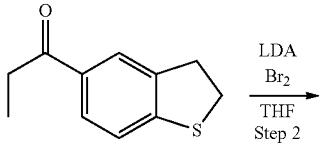

13-3

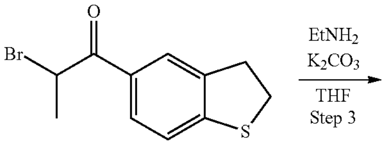

13-4

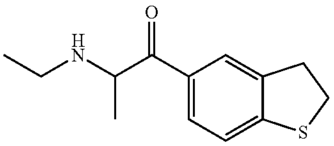

Bk-5-EAPDBT

Step 1: A round-bottom flask is charged with 13-1, palladium(II) acetate, and 1,3-bis(diphenylphosphino)propane. The flask is then evacuated and refilled with anhydrous nitrogen three times before adding ethylene glycol, triethylamine, and 13-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 13-3. This crude material can be taken to the next step without further purification or purified by standard techniques of the art to obtain the pure compound.

Step 2: A round-bottom flask is charged with 13-3. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 13-4. This crude material can be taken to the next step without further purification or purified by standard techniques of the art to obtain the pure compound.

Step 3: A round-bottom flask is charged with 13-4, potassium carbonate, anhydrous DMF, and a 2M solution of ethylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-5-EAPDBT. This crude material can be purified by standard techniques of the art to obtain the pure compound.

The individual enantiomers of Bk-5-EAPDBT can be separated using the methods described herein or others known in the art. Following isolation of the pure enantiomers, they can be mixed again in any ratio necessary to obtain the desired effects.

Synthesis 14. Synthesis of Bk-5-MBPDBT

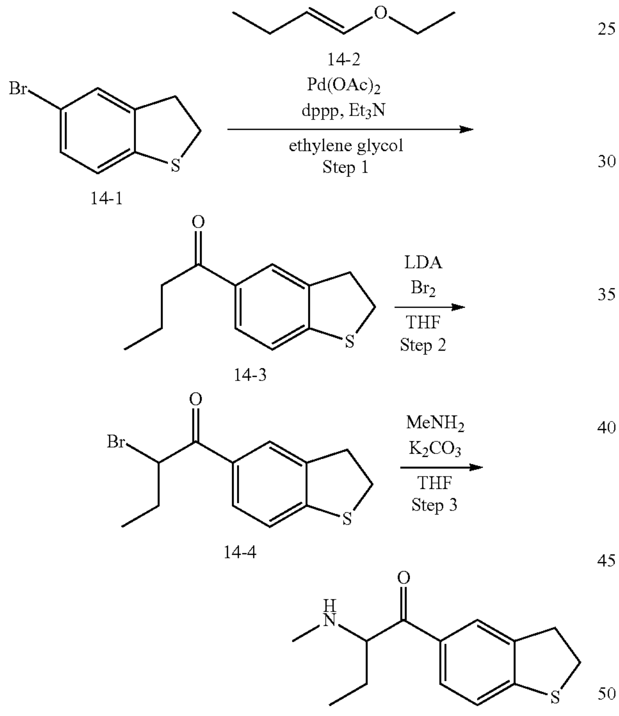

Bk-5-MBPDBT

Step 1: A round-bottom flask is charged with 14-1, palladium(II) acetate, and 1,3-bis(diphenylphosphino)propane. The flask is then evacuated and refilled with anhydrous nitrogen three times before adding ethylene glycol, triethylamine, and 14-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 14-3. This crude material can be taken to the next step without further purification or purified by standard techniques of the art to obtain the pure compound.

Step 2: A round-bottom flask is charged with 14-3. The flask is then evacuated and refilled with anhydrous nitrogen three times before adding anhydrous THF and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 14-4. This crude material can be taken to the next step without further purification or purified by standard techniques of the art to obtain the pure compound.

Step 3: A round-bottom flask is charged with 14-4, potassium carbonate, anhydrous DMF, and a 2M solution of methylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-5-MBPDBT. This crude material can be purified by standard techniques of the art to obtain the pure compound.

The individual enantiomers of Bk-5-MBPDBT can be separated using the methods described herein or others known in the art. Following isolation of the pure enantiomers, they can be mixed again in any ratio necessary to obtain the desired effects.

Synthesis 15. Synthesis of Bk-5-EBPDBT

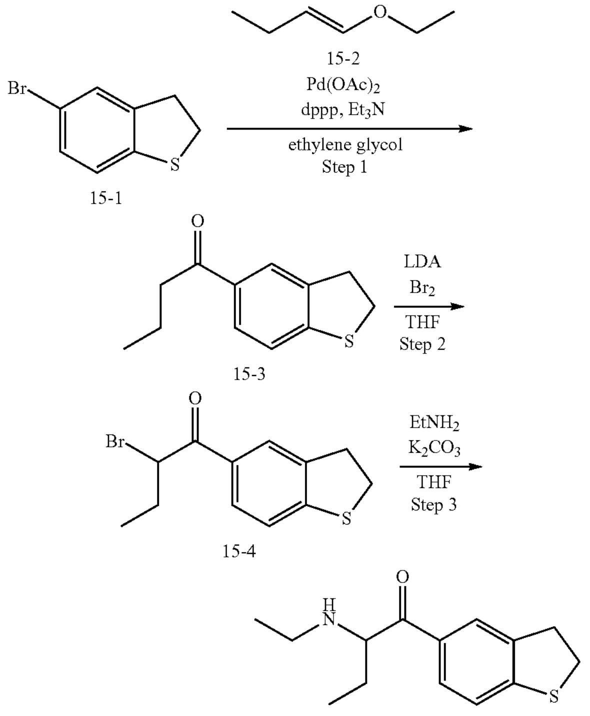

Bk-5-EBPDBT

Step 1: A round-bottom flask is charged with 15-1, palladium(II) acetate, and 1,3-bis(diphenylphosphino)propane. The flask is then evacuated and refilled with anhydrous nitrogen three times before adding ethylene glycol, triethylamine, and 15-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 15-3. This crude material can be taken to the next step without further purification or purified by standard techniques of the art to obtain the pure compound.

Step 2: A round-bottom flask is charged with 15-3. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 15-4. This crude material can be taken to the next step without further purification or purified by standard techniques of the art to obtain the pure compound.

Step 3: A round-bottom flask is charged with 15-4, potassium carbonate, anhydrous DMF, and a 2M solution of ethylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-5-EBPDBT. This crude material can be purified by standard techniques of the art to obtain the pure compound.

The individual enantiomers of Bk-5-EBPDBT can be separated using the methods described herein or others known in the art. Following isolation of the pure enantiomers, they can be mixed again in any ratio necessary to obtain the desired effects.

Synthesis 16. Synthesis of 6-EAPBT

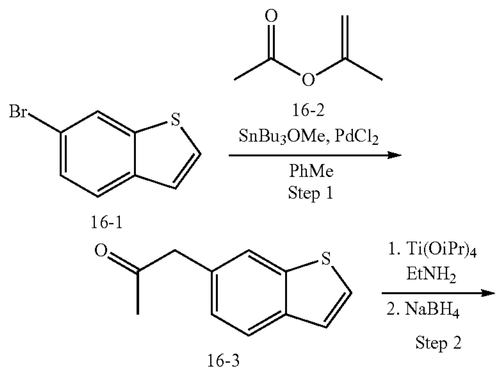

-continued

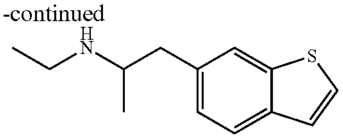

5-EAPBT

Step 1: A round-bottom flask is charged with 16-1, tributyltin methoxide, and palladium(II) chloride. The flask is then evacuated and refilled with anhydrous nitrogen three times before adding toluene and isopropenyl acetate (16-2). The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 16-3. This crude material can be taken to the next step without further purification or purified by standard techniques of the art to obtain the pure compound.

Step 2: In a round-bottom flask, 16-3, ethylamine, and titanium (IV) isopropoxide are dissolved in ethanol and stirred under nitrogen. Once there is no remaining 16-3 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 6-EAPBT. This crude material can be purified by standard techniques of the art to obtain the pure compound.

The individual enantiomers of 6-EAPBT can be separated using the methods described herein or others known in the art. Following isolation of the pure enantiomers, they can be mixed again in any ratio necessary to obtain the desired effects.

Synthesis 17. Synthesis of 6-MBPBT

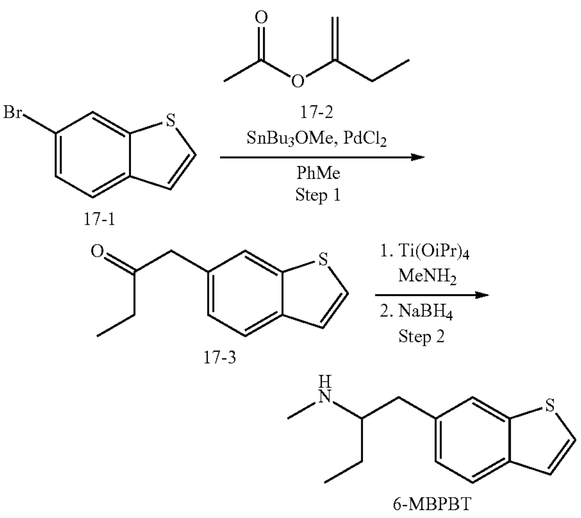

Step 1: A round-bottom flask is charged with 17-1, tributyltin methoxide, and palladium(II) chloride. The flask is then evacuated and refilled with anhydrous nitrogen three times before adding toluene and 17-2. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 17-3. This crude material can be taken to the next step without further purification or purified by standard techniques of the art to obtain the pure compound.

Step 2: In a round-bottom flask, 17-3, methylamine, and titanium (IV) isopropoxide are dissolved in ethanol and stirred under nitrogen. Once there is no remaining 17-3 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 6-MBPBT. This crude material can be purified by standard techniques of the art to obtain the pure compound.

The individual enantiomers of 6-MBPBT can be separated using the methods described herein or others known in the art. Following isolation of the pure enantiomers, they can be mixed again in any ratio necessary to obtain the desired effects.

Synthesis 18. Synthesis of 6-EBPBT

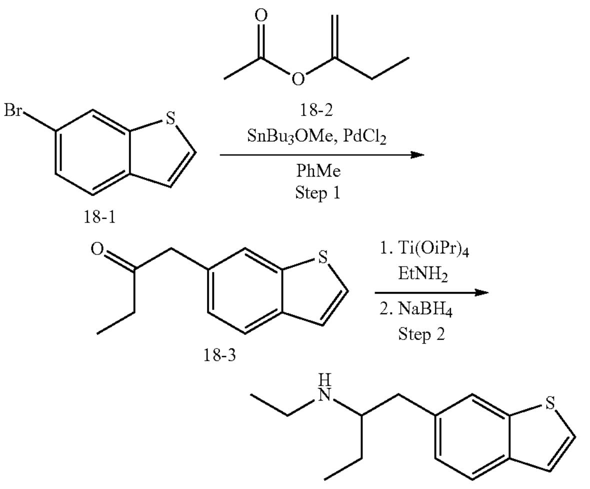

18-2

18-1

18-3

6-EBPBT

Step 1: A round-bottom flask is charged with 18-1, tributyltin methoxide, and palladium(II) chloride. The flask is then evacuated and refilled with anhydrous nitrogen three times before adding toluene and 18-2. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 18-3. This crude material can be taken to the next step without further purification or purified by standard techniques of the art to obtain the pure compound.

Step 2: In a round-bottom flask, 1-3, ethylamine, and titanium (IV) isopropoxide are dissolved in ethanol and stirred under nitrogen. Once there is no remaining 18-3 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 6-EBPBT. This crude material can be purified by standard techniques of the art to obtain the pure compound.

The individual enantiomers of 6-EBPBT can be separated using the methods described herein or others known in the art. Following isolation of the pure enantiomers, they can be mixed again in any ratio necessary to obtain the desired effects.

Synthesis 19. Synthesis of Bk-6-MAPBT

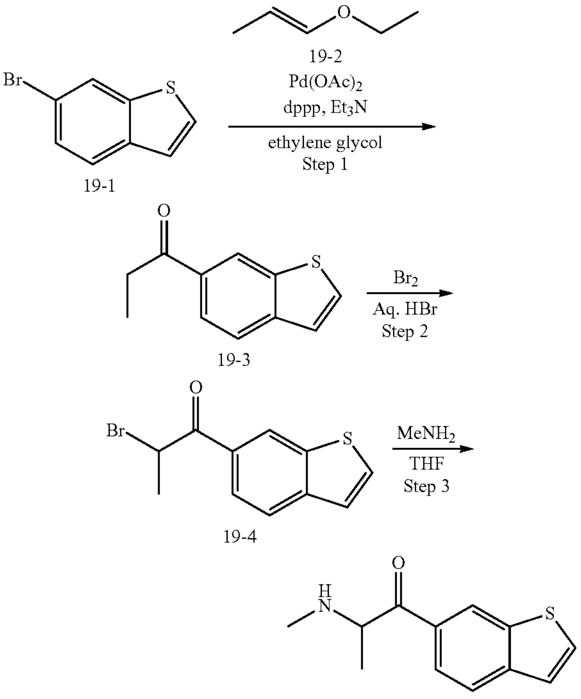

19-2

19-1

19-3

19-4

Bk-6-MAPBT

Step 1: A round-bottom flask is charged with 19-1, palladium(II) acetate, and 1,3-bis(diphenylphosphino)propane. The flask is then evacuated and refilled with anhydrous nitrogen three times before adding ethylene glycol, triethylamine, and 19-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 19-3. This crude material can be taken to the next step without further purification or purified by standard techniques of the art to obtain the pure compound.

Step 2: A round-bottom flask is charged with 19-3 and anhydrous THE then cooled to 0° C. and stirred. Hydrobromic acid (48% in water) and bromine are added dropwise to the cooled and stirred solution. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$ and $NaHCO_3$, and washed three times with water. The organic layer is then dried over anhydrous $Na_2SO_4$, filtered, and concentrated to collect crude 19-4. This crude material can be taken to the next step without further purification or purified by standard techniques of the art to obtain the pure compound.

Step 3: A round-bottom flask is charged with 19-4, potassium carbonate, anhydrous DMF, and a 2M solution of methylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-6-MAPBT. This crude material can be purified by standard techniques of the art to obtain the pure compound.

The individual enantiomers of Bk-6-MAPBT can be separated using the methods described herein or others known in the art. Following isolation of the pure enantiomers, they can be mixed again in any ratio necessary to obtain the desired effects.

Synthesis 20. Synthesis of Bk-6-EAPBT

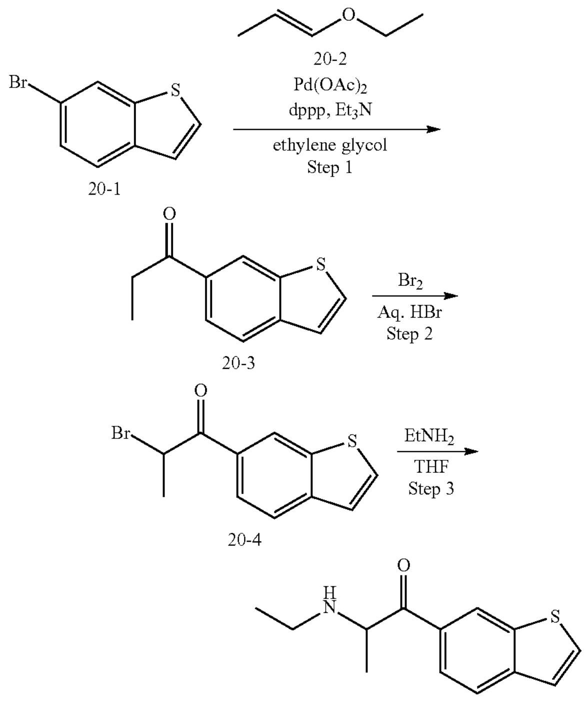

Bk-6-EAPBT

Step 1: A round-bottom flask is charged with 20-1, palladium(II) acetate, and 1,3-bis(diphenylphosphino)propane. The flask is then evacuated and refilled with anhydrous nitrogen three times before adding ethylene glycol, triethylamine, and 20-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 20-3. This crude material can be taken to the next step without further purification or purified by standard techniques of the art to obtain the pure compound.

Step 2: A round-bottom flask is charged with 20-3 and anhydrous THE then cooled to 0° C. and stirred. Hydrobromic acid (48% in water) and bromine are added dropwise to the cooled and stirred solution. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$ and $NaHCO_3$, and washed three times with water. The organic layer is then dried over anhydrous $Na_2SO_4$, filtered, and concentrated to collect crude 20-4. This crude material can be taken to the next step without further purification or purified by standard techniques of the art to obtain the pure compound.

Step 3: A round-bottom flask is charged with 20-4, potassium carbonate, anhydrous DMF, and a 2M solution of ethylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-6-EAPBT. This crude material can be purified by standard techniques of the art to obtain the pure compound.

The individual enantiomers of Bk-6-EAPBT can be separated using the methods described herein or others known in the art. Following isolation of the pure enantiomers, they can be mixed again in any ratio necessary to obtain the desired effects.

Synthesis 21. Synthesis of Bk-6-MBPBT

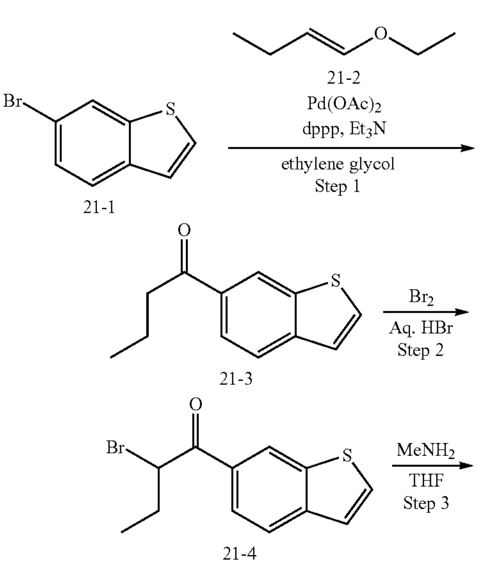

21-4

-continued

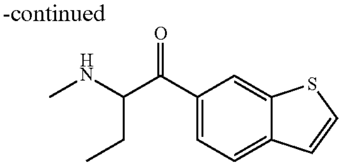

Bk-6-MBPBT

Step 1: A round-bottom flask is charged with 21-1, palladium(II) acetate, and 1,3-bis(diphenylphosphino)propane. The flask is then evacuated and refilled with anhydrous nitrogen three times before adding ethylene glycol, triethylamine, and 21-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 21-3. This crude material can be taken to the next step without further purification or purified by standard techniques of the art to obtain the pure compound.

Step 2: A round-bottom flask is charged with 21-3 and anhydrous THE then cooled to 0° C. and stirred. Hydrobromic acid (48% in water) and bromine are added dropwise to the cooled and stirred solution. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$ and $NaHCO_3$, and washed three times with water. The organic layer is then dried over anhydrous $Na_2SO_4$, filtered, and concentrated to collect crude 21-4. This crude material can be taken to the next step without further purification or purified by standard techniques of the art to obtain the pure compound.

Step 3: A round-bottom flask is charged with 21-4, potassium carbonate, anhydrous DMF, and a 2M solution of methylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-6-MBPBT. This crude material can be purified by standard techniques of the art to obtain the pure compound.

The individual enantiomers of Bk-6-MBPBT can be separated using the methods described herein or others known in the art. Following isolation of the pure enantiomers, they can be mixed again in any ratio necessary to obtain the desired effects.

Synthesis 22. Synthesis of Bk-6-EBPBT

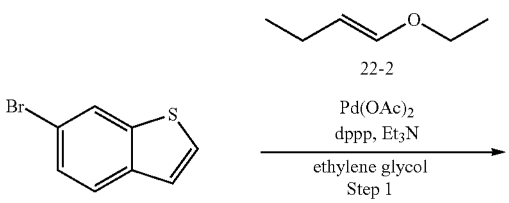

22-1

-continued

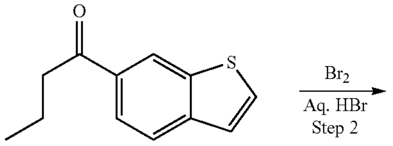

22-3

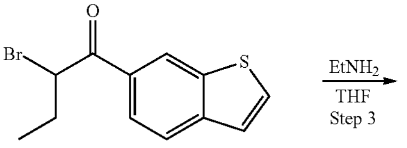

22-4

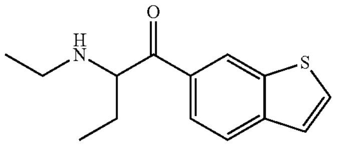

Bk-6-EBPBT

Step 1: A round-bottom flask is charged with 22-1, palladium(II) acetate, and 1,3-bis(diphenylphosphino)propane. The flask is then evacuated and refilled with anhydrous nitrogen three times before adding ethylene glycol, triethylamine, and 22-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 22-3. This crude material can be taken to the next step without further purification or purified by standard techniques of the art to obtain the pure compound.

Step 2: A round-bottom flask is charged with 22-3 and anhydrous THE then cooled to 0° C. and stirred. Hydrobromic acid (48% in water) and bromine are added dropwise to the cooled and stirred solution. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$ and $NaHCO_3$, and washed three times with water. The organic layer is then dried over anhydrous $Na_2SO_4$, filtered, and concentrated to collect crude 22-4. This crude material can be taken to the next step without further purification or purified by standard techniques of the art to obtain the pure compound.

Step 3: A round-bottom flask is charged with 22-4, potassium carbonate, anhydrous DMF, and a 2M solution of ethylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-6-EBPBT. This crude material can be purified by standard techniques of the art to obtain the pure compound.

The individual enantiomers of Bk-6-EBPBT can be separated using the methods described herein or others known in the art. Following isolation of the pure enantiomers, they can be mixed again in any ratio necessary to obtain the desired effects.

Synthesis 23. Synthesis of 6-MAPDBT

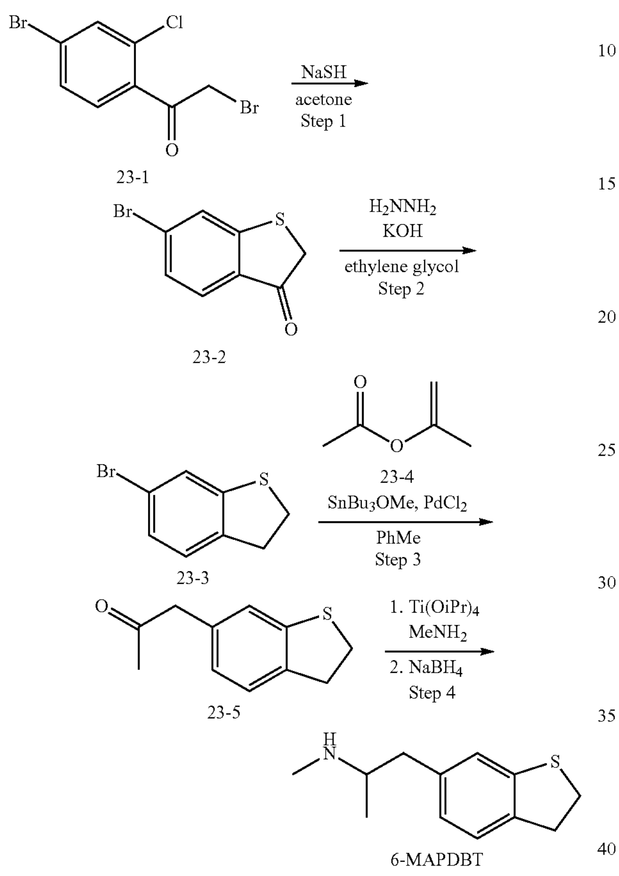

Step 1: A round-bottom flask is charged with 23-1 and acetone then cooled to 0° C. and stirred. Sodium hydrosulfide is then added to the solution and the reaction is allowed to slowly warm to room temperature. Once the reaction is judged complete by TLC, HPLC, or other analytical method, the mixture is diluted with ethyl acetate and washed three times with water. The organic layer is then dried over anhydrous $Na_2SO_4$, filtered, and concentrated to collect crude 6-2. This crude material can be taken to the next step without further purification or purified by standard techniques of the art to obtain the pure compound.

Step 2: A round-bottom flask is charged with 23-2, potassium hydroxide, hydrazine, and ethylene glycol. The resulting solution is then stirred and heated to reflux until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 23-3. This crude material can be taken to the next step without further purification or purified by standard techniques of the art to obtain the pure compound.

Step 3: A round-bottom flask is charged with 23-3, tributyltin methoxide, and palladium(II) chloride. The flask is then evacuated and refilled with anhydrous nitrogen three times before adding toluene and isopropenyl acetate (23-4). The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 23-5. This crude material can be taken to the next step without further purification or purified by standard techniques of the art to obtain the pure compound.

Step 4: In a round-bottom flask, 23-5, methylamine, and titanium (IV) isopropoxide are dissolved in ethanol and stirred under nitrogen. Once there is no remaining 23-5 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 6-MAPDBT. This crude material can be purified by standard techniques of the art to obtain the pure compound.

The individual enantiomers of 6-MAPDBT can be separated using the methods described herein or others known in the art. Following isolation of the pure enantiomers, they can be mixed again in any ratio necessary to obtain the desired effects.

Synthesis 24. Synthesis of 6-EAPDBT

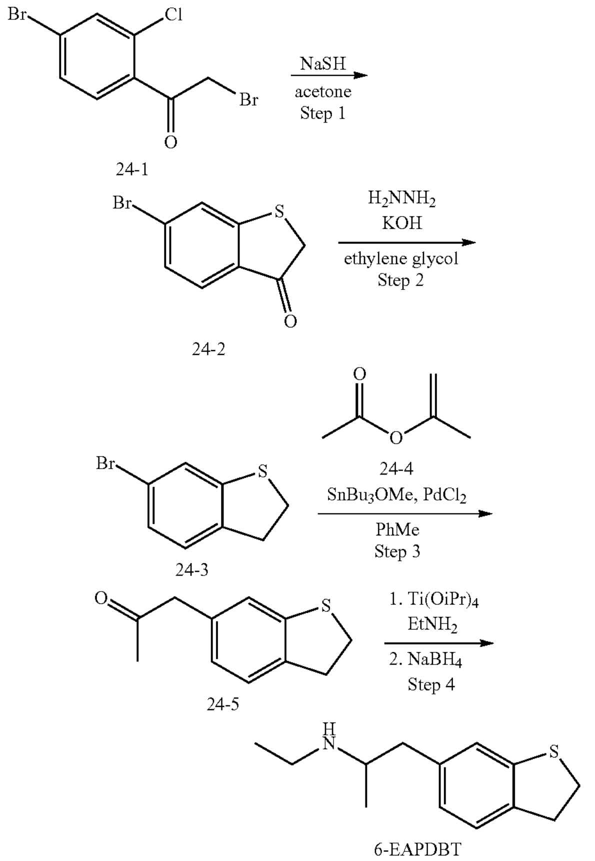

Step 1: A round-bottom flask is charged with 24-1 and acetone then cooled to 0° C. and stirred. Sodium hydrosulfide is then added to the solution and the reaction is allowed to slowly warm to room temperature. Once the reaction is judged complete by TLC, HPLC, or other analytical method, the mixture is diluted with ethyl acetate and washed three times with water. The organic layer is then dried over anhydrous $Na_2SO_4$, filtered, and concentrated to collect crude 24-2. This crude material can be taken to the next step without further purification or purified by standard techniques of the art to obtain the pure compound.

Step 2: A round-bottom flask is charged with 24-2, potassium hydroxide, hydrazine, and ethylene glycol. The resulting solution is then stirred and heated to reflux until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 24-3. This crude material can be taken to the next step without further purification or purified by standard techniques of the art to obtain the pure compound.

Step 3: A round-bottom flask is charged with 24-3, tributyltin methoxide, and palladium(II) chloride. The flask is then evacuated and refilled with anhydrous nitrogen three times before adding toluene and isopropenyl acetate (24-4). The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 24-5. This crude material can be taken to the next step without further purification or purified by standard techniques of the art to obtain the pure compound.

Step 4: In a round-bottom flask, 24-5, ethylamine, and titanium (IV) isopropoxide are dissolved in ethanol and stirred under nitrogen. Once there is no remaining 24-5 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 6-EAPDBT. This crude material can be purified by standard techniques of the art to obtain the pure compound.

The individual enantiomers of 6-EAPDBT can be separated using the methods described herein or others known in the art. Following isolation of the pure enantiomers, they can be mixed again in any ratio necessary to obtain the desired effects.

Synthesis 25. Synthesis of 6-MBPDBT

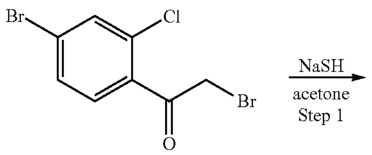

25-1

-continued

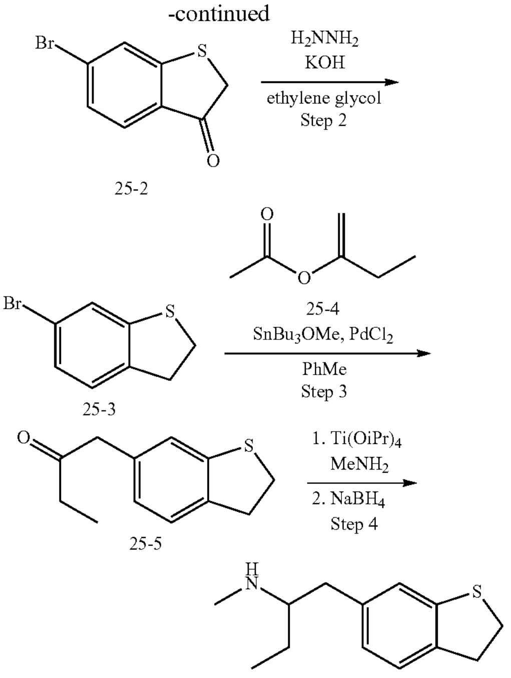

6-MBPDBT

Step 1: A round-bottom flask is charged with 25-1 and acetone then cooled to 0° C. and stirred. Sodium hydrosulfide is then added to the solution and the reaction is allowed to slowly warm to room temperature. Once the reaction is judged complete by TLC, HPLC, or other analytical method, the mixture is diluted with ethyl acetate and washed three times with water. The organic layer is then dried over anhydrous $Na_2SO_4$, filtered, and concentrated to collect crude 25-2. This crude material can be taken to the next step without further purification or purified by standard techniques of the art to obtain the pure compound.

Step 2: A round-bottom flask is charged with 25-2, potassium hydroxide, hydrazine, and ethylene glycol. The resulting solution is then stirred and heated to reflux until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 25-3. This crude material can be taken to the next step without further purification or purified by standard techniques of the art to obtain the pure compound.

Step 3: A round-bottom flask is charged with 25-3, tributyltin methoxide, and palladium(II) chloride. The flask is then evacuated and refilled with anhydrous nitrogen three times before adding toluene and 25-4. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 25-5. This crude material can be taken to the next step without further purification or purified by standard techniques of the art to obtain the pure compound.

Step 4: In a round-bottom flask, 25-5, methylamine, and titanium (IV) isopropoxide are dissolved in ethanol and stirred under nitrogen. Once there is no remaining 25-5 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 6-MBPDBT. This crude material can be purified by standard techniques of the art to obtain the pure compound.

The individual enantiomers of 6-MBPDBT can be separated using the methods described herein or others known in the art. Following isolation of the pure enantiomers, they can be mixed again in any ratio necessary to obtain the desired effects.

Synthesis 26. Synthesis of 6-EBPDBT

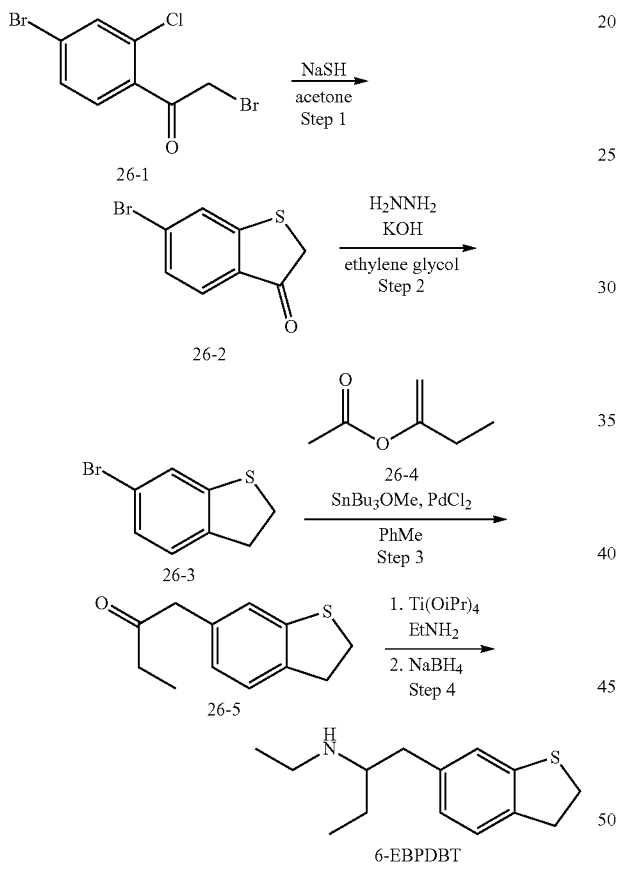

26-1

26-2

26-4

26-3

26-5

6-EBPDBT

Step 1: A round-bottom flask is charged with 26-1 and acetone then cooled to 0° C. and stirred. Sodium hydrosulfide is then added to the solution and the reaction is allowed to slowly warm to room temperature. Once the reaction is judged complete by TLC, HPLC, or other analytical method, the mixture is diluted with ethyl acetate and washed three times with water. The organic layer is then dried over anhydrous $Na_2SO_4$, filtered, and concentrated to collect crude 26-2. This crude material can be taken to the next step without further purification or purified by standard techniques of the art to obtain the pure compound.

Step 2: A round-bottom flask is charged with 26-2, potassium hydroxide, hydrazine, and ethylene glycol. The resulting solution is then stirred and heated to reflux until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 26-3. This crude material can be taken to the next step without further purification or purified by standard techniques of the art to obtain the pure compound.

Step 3: A round-bottom flask is charged with 26-3, tributyltin methoxide, and palladium(II) chloride. The flask is then evacuated and refilled with anhydrous nitrogen three times before adding toluene and 26-4. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 26-5. This crude material can be taken to the next step without further purification or purified by standard techniques of the art to obtain the pure compound.

Step 4: In a round-bottom flask, 26-5, ethylamine, and titanium (IV) isopropoxide are dissolved in ethanol and stirred under nitrogen. Once there is no remaining 26-5 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude 6-EBPDBT. This crude material can be purified by standard techniques of the art to obtain the pure compound.

The individual enantiomers of 6-EBPDBT can be separated using the methods described herein or others known in the art. Following isolation of the pure enantiomers, they can be mixed again in any ratio necessary to obtain the desired effects.

Synthesis 27. Synthesis of Bk-6-MAPDBT

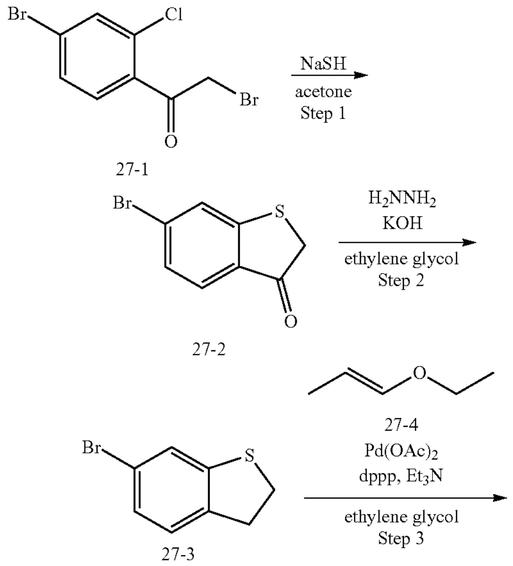

27-1

27-2

27-4

27-3

-continued

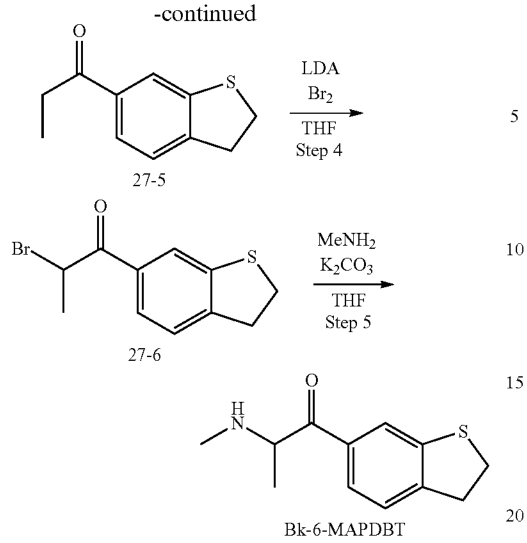

27-5

27-6

Bk-6-MAPDBT

Step 1: A round-bottom flask is charged with 27-1 and acetone then cooled to 0° C. and stirred. Sodium hydrosulfide is then added to the solution and the reaction is allowed to slowly warm to room temperature. Once the reaction is judged complete by TLC, HPLC, or other analytical method, the mixture is diluted with ethyl acetate and washed three times with water. The organic layer is then dried over anhydrous $Na_2SO_4$, filtered, and concentrated to collect crude 27-2. This crude material can be taken to the next step without further purification or purified by standard techniques of the art to obtain the pure compound.

Step 2: A round-bottom flask is charged with 27-2, potassium hydroxide, hydrazine, and ethylene glycol. The resulting solution is then stirred and heated to reflux until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 27-3. This crude material can be taken to the next step without further purification or purified by standard techniques of the art to obtain the pure compound.

Step 3: A round-bottom flask is charged with 27-3, palladium(II) acetate, and 1,3-bis(diphenylphosphino)propane. The flask is then evacuated and refilled with anhydrous nitrogen three times before adding ethylene glycol, triethylamine, and 27-4 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 27-5. This crude material can be taken to the next step without further purification or purified by standard techniques of the art to obtain the pure compound.

Step 4: A round-bottom flask is charged with 27-5. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 27-6. This crude material can be taken to the next step without further purification or purified by standard techniques of the art to obtain the pure compound.

Step 5: A round-bottom flask is charged with 27-6, potassium carbonate, anhydrous DMF, and a 2M solution of methylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-6-MAPDBT. This crude material can be purified by standard techniques of the art to obtain the pure compound.

The individual enantiomers of Bk-6-MAPDBT can be separated using the methods described herein or others known in the art. Following isolation of the pure enantiomers, they can be mixed again in any ratio necessary to obtain the desired effects.

Synthesis 28. Synthesis of Bk-6-EAPDBT

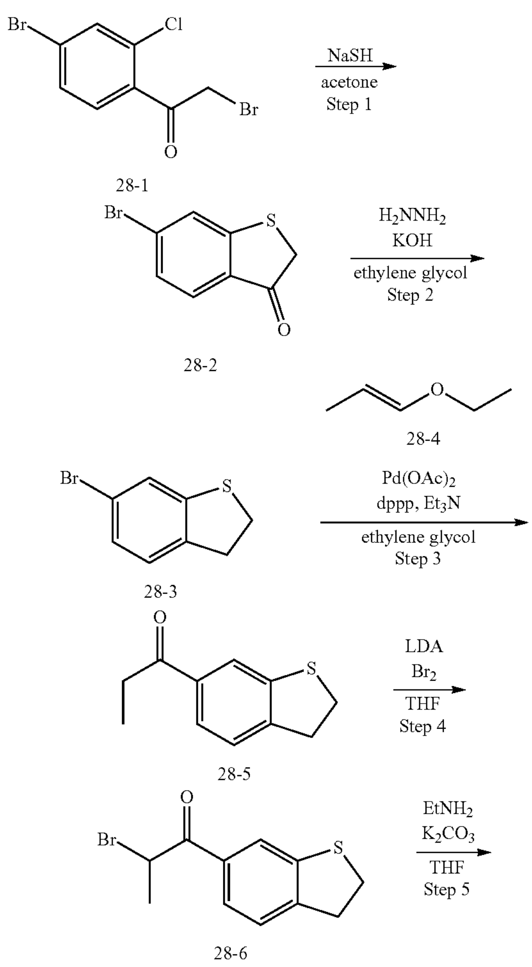

28-1

28-2

28-4

28-3

28-5

28-6

-continued

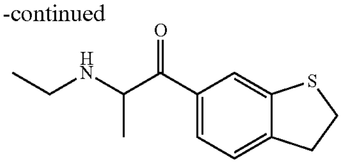

Bk-6-EAPDBT

Step 1: A round-bottom flask is charged with 28-1 and acetone then cooled to 0° C. and stirred. Sodium hydrosulfide is then added to the solution and the reaction is allowed to slowly warm to room temperature. Once the reaction is judged complete by TLC, HPLC, or other analytical method, the mixture is diluted with ethyl acetate and washed three times with water. The organic layer is then dried over anhydrous $Na_2SO_4$, filtered, and concentrated to collect crude 28-2. This crude material can be taken to the next step without further purification or purified by standard techniques of the art to obtain the pure compound.

Step 2: A round-bottom flask is charged with 28-2, potassium hydroxide, hydrazine, and ethylene glycol. The resulting solution is then stirred and heated to reflux until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 28-3. This crude material can be taken to the next step without further purification or purified by standard techniques of the art to obtain the pure compound.

Step 3: A round-bottom flask is charged with 28-3, palladium(II) acetate, and 1,3-bis(diphenylphosphino)propane. The flask is then evacuated and refilled with anhydrous nitrogen three times before adding ethylene glycol, triethylamine, and 28-4 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 28-5. This crude material can be taken to the next step without further purification or purified by standard techniques of the art to obtain the pure compound.

Step 4: A round-bottom flask is charged with 28-5. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 28-6. This crude material can be taken to the next step without further purification or purified by standard techniques of the art to obtain the pure compound.

Step 5: A round-bottom flask is charged with 28-6, potassium carbonate, anhydrous DMF, and a 2M solution of ethylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-6-EAPDBT. This crude material can be purified by standard techniques of the art to obtain the pure compound.

The individual enantiomers of Bk-6-EAPDBT can be separated using the methods described herein or others known in the art. Following isolation of the pure enantiomers, they can be mixed again in any ratio necessary to obtain the desired effects.

Synthesis 29. Synthesis of Bk-6-MBPDBT

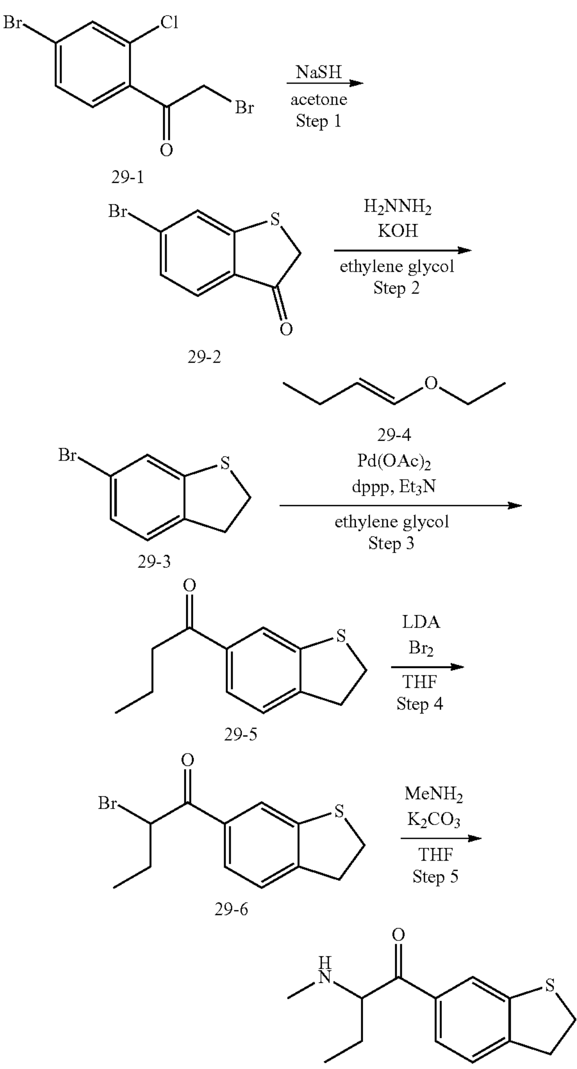

Bk-6-MBPDBT

Step 1: A round-bottom flask is charged with 29-1 and acetone then cooled to 0° C. and stirred. Sodium hydrosulfide is then added to the solution and the reaction is allowed to slowly warm to room temperature. Once the reaction is judged complete by TLC, HPLC, or other analytical method, the mixture is diluted with ethyl acetate and washed three times with water. The organic layer is then dried over anhydrous $Na_2SO_4$, filtered, and concentrated to collect crude 7-2. This crude material can be taken to the next step without further purification or purified by standard techniques of the art to obtain the pure compound.

Step 2: A round-bottom flask is charged with 29-2, potassium hydroxide, hydrazine, and ethylene glycol. The resulting solution is then stirred and heated to reflux until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 29-3. This crude material can be taken to the next step without further purification or purified by standard techniques of the art to obtain the pure compound.

Step 3: A round-bottom flask is charged with 29-3, palladium(II) acetate, and 1,3-bis(diphenylphosphino)propane. The flask is then evacuated and refilled with anhydrous nitrogen three times before adding ethylene glycol, triethylamine, and 29-4 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 29-5. This crude material can be taken to the next step without further purification or purified by standard techniques of the art to obtain the pure compound.

Step 4: A round-bottom flask is charged with 29-5. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 29-6. This crude material can be taken to the next step without further purification or purified by standard techniques of the art to obtain the pure compound.

Step 5: A round-bottom flask is charged with 29-6, potassium carbonate, anhydrous DMF, and a 2M solution of methylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-6-MBPDBT. This crude material can be purified by standard techniques of the art to obtain the pure compound.

The individual enantiomers of Bk-6-MBPDBT can be separated using the methods described herein or others known in the art. Following isolation of the pure enantiomers, they can be mixed again in any ratio necessary to obtain the desired effects.

Synthesis 30. Synthesis of Bk-6-EBPDBT

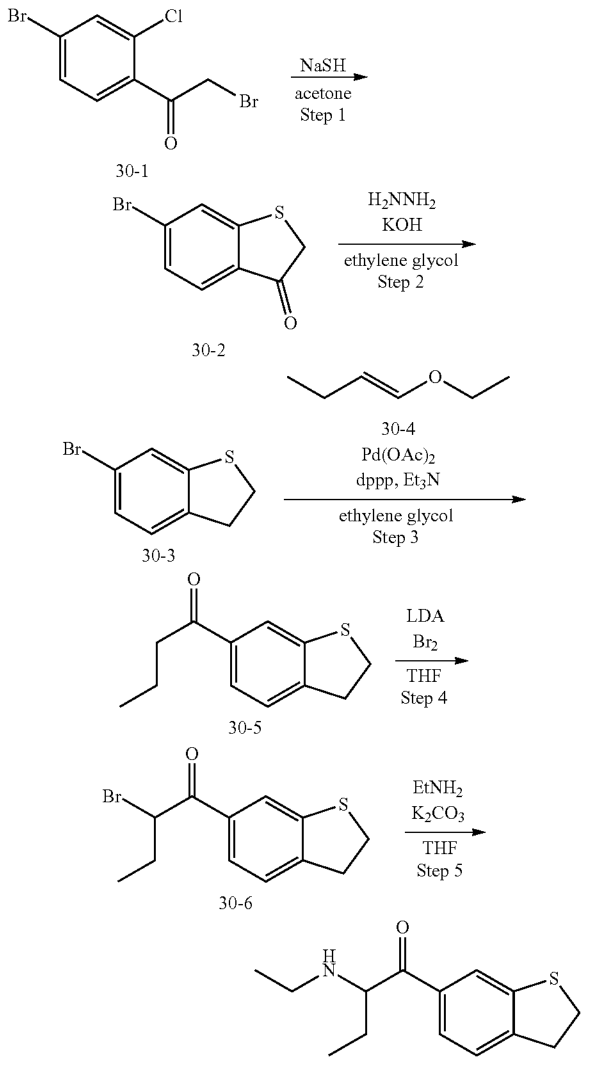

Bk-6-EBPDBT

Step 1: A round-bottom flask is charged with 30-1 and acetone then cooled to 0° C. and stirred. Sodium hydrosulfide is then added to the solution and the reaction is allowed to slowly warm to room temperature. Once the reaction is judged complete by TLC, HPLC, or other analytical method, the mixture is diluted with ethyl acetate and washed three times with water. The organic layer is then dried over anhydrous $Na_2SO_4$, filtered, and concentrated to collect crude 30-2. This crude material can be taken to the next step without further purification or purified by standard techniques of the art to obtain the pure compound.

Step 2: A round-bottom flask is charged with 30-2, potassium hydroxide, hydrazine, and ethylene glycol. The resulting solution is then stirred and heated to reflux until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 30-3. This crude material can be taken to the next step without further purification or purified by standard techniques of the art to obtain the pure compound.

Step 3: A round-bottom flask is charged with 30-3, palladium(II) acetate, and 1,3-bis(diphenylphosphino)propane. The flask is then evacuated and refilled with anhydrous nitrogen three times before adding ethylene glycol, triethylamine, and 30-4 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 30-5. This crude material can be taken to the next step without further purification or purified by standard techniques of the art to obtain the pure compound.

Step 4: A round-bottom flask is charged with 30-5. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 30-6. This crude material can be taken to the next step without further purification or purified by standard techniques of the art to obtain the pure compound.

Step 5: A round-bottom flask is charged with 30-6, potassium carbonate, anhydrous DMF, and a 2M solution of ethylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-6-EBPDBT. This crude material can be purified by standard techniques of the art to obtain the pure compound.

The individual enantiomers of Bk-6-EBPDBT can be separated using the methods described herein or others known in the art. Following isolation of the pure enantiomers, they can be mixed again in any ratio necessary to obtain the desired effects.

Synthesis 31. Synthesis of 1-(benzo[b]thiophen-5-yl)-1-chloro-N-methylpropan-2-amine (Compound 31)

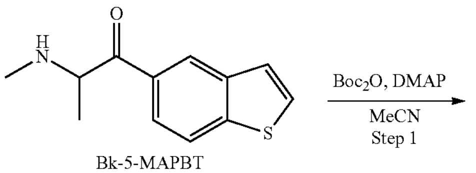

Bk-5-MAPBT

-continued

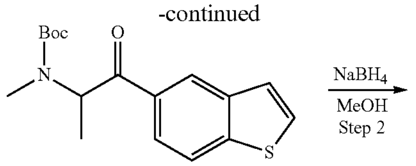

31-1

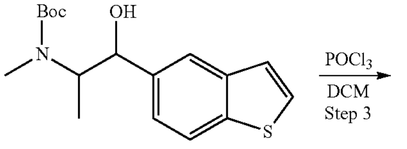

31-2

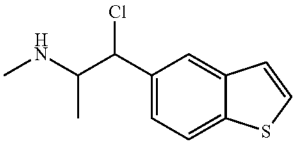

Compound 31

Step 1: A round-bottom flask is charged with Bk-5-MAPBT, di-tert-butyl-dicarbonate, DMAP, and acetonitrile. The reaction solution is then stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 31-1. This crude material can be taken to the next step without further purification or purified by standard techniques of the art to obtain the pure compound.

Step 2: A round-bottom flask is charged with 31-1 and methanol. The reaction solution is then stirred at room temperature and sodium borohydride added slowly. The solution is stirred until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 31-2. This crude material can be taken to the next step without further purification or purified by standard techniques of the art to obtain the pure compound.

Step 3: A round-bottom flask is charged with 31-2 and DCM. The reaction solution is then cooled to 0° C. and phosphorous oxychloride added slowly. The solution is stirred at 0° C. until the reaction is judged complete by TLC, HPLC, or other analytical method. Following the reaction, the mixture is diluted with ethyl acetate, quenched with aqueous $NaHCO_3$, and washed three times with water. The organic layer is then dried over anhydrous $Na_2SO_4$, filtered, and concentrated to collect crude Compound 31. This crude material can be purified by standard techniques of the art to obtain the pure compound.

The individual enantiomers of Compound 31 can be separated using the methods described herein or others known in the art. Following isolation of the pure enantiomers, they can be mixed again in any ratio necessary to obtain the desired effects.

Alternatively, the diastereomers can first be separated by conventional, achiral purification techniques such as silica gel chromatography or preparative HPLC. The two purified diastereomers can then be further separated into the enantiomers as described.

Synthesis 32. Synthesis of 2-(benzo[b]thiophen-5-yl)-1,1,1-trifluoro-3-(methylamino)butan-2-ol (Compound 32)

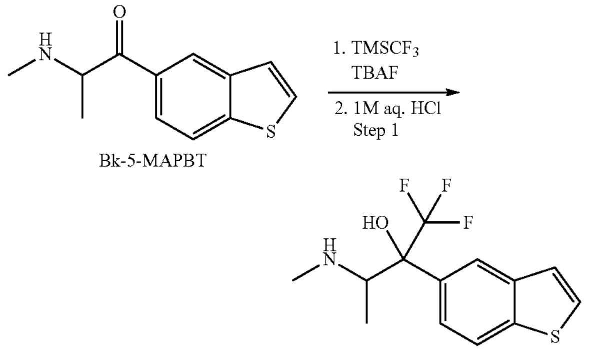

Bk-5-MAPBT

Compound 32

Step 1: A round-bottom flask is charged with Bk-5-MAPBT, $TMSCF_3$, and THF. The resulting mixture is stirred at room temperature and TBAF is added. Once there is no remaining Bk-5-MAPBT as judged by TLC, HPLC, or other analytical method, 1M aqueous HCl is added, and the reaction is again stirred at room temperature or heated as necessary to provide full conversion to Compound 32. Once the reaction is judged complete by TLC, HPLC, or other analytical method, the mixture is diluted with ethyl acetate, quenched with aqueous $NaHCO_3$ and washed three times with water. The organic layer is then dried over anhydrous $Na_2SO_4$, filtered, and concentrated to collect crude Compound 32. This crude material can be purified by standard techniques of the art to obtain the pure compound.

The individual enantiomers of Compound 32 can be separated using the methods described herein or others known in the art. Following isolation of the pure enantiomers, they can be mixed again in any ratio necessary to obtain the desired effects.

Alternatively, the diastereomers can first be separated by conventional, achiral purification techniques such as silica gel chromatography or preparative HPLC. The two purified diastereomers can then be further separated into the enantiomers as described.

Synthesis 33. Synthesis of 1-(benzo[b]thiophen-5-yl)-1-fluoro-N-methylpropan-2-amine (Compound 33)

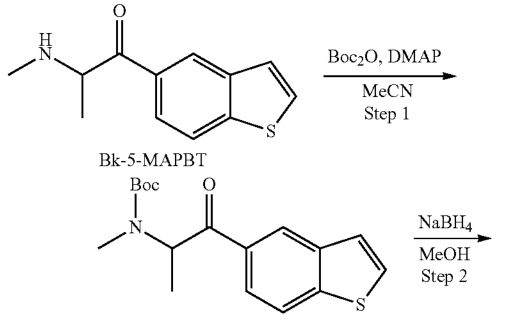

Bk-5-MAPBT 33-1

-continued

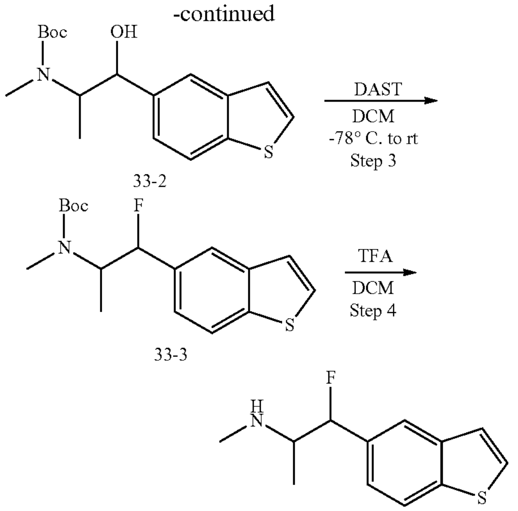

33-2

33-3

Compound 33

Step 1: A round-bottom flask is charged with Bk-5-MAPBT, di-tert-butyl-dicarbonate, DMAP, and acetonitrile. The reaction solution is then stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 33-1. This crude material can be taken to the next step without further purification or purified by standard techniques of the art to obtain the pure compound.

Step 2: A round-bottom flask is charged with 33-1 and methanol. The reaction solution is then stirred at room temperature and sodium borohydride added slowly. The solution is stirred until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 33-2. This crude material can be taken to the next step without further purification or purified by standard techniques of the art to obtain the pure compound.

Step 3: A round-bottom flask is charged with 33-2 and DCM. The reaction solution is then cooled to 0° C. and DAST added slowly. The solution is stirred at 0° C. until the reaction is judged complete by TLC, HPLC, or other analytical method. Following the reaction, the mixture is diluted with ethyl acetate, quenched with aqueous $NaHCO_3$, and washed three times with water. The organic layer is then dried over anhydrous $Na_2SO_4$, filtered, and concentrated to collect crude 10-3. This crude material can be taken to the next step without further purification or purified by standard techniques of the art to obtain the pure compound.

Step 4: A round-bottom flask is charged with 33-3 and DCM. The reaction solution is then cooled to 0° C. and trifluoroacetic acid added slowly. The solution is stirred and allowed to slowly warm to room temperature until the reaction is judged complete by TLC, HPLC, or other analytical method. Following the reaction, the mixture is diluted with ethyl acetate, quenched with aqueous $NaHCO_3$, and washed three times with water. The organic layer is then dried over anhydrous $Na_2SO_4$, filtered, and concentrated to collect crude Compound 33. This crude material can be purified by standard techniques of the art to obtain the pure compound.

The individual enantiomers of Compound 33 can be separated using the methods described herein or others known in the art. Following isolation of the pure enantiomers, they can be mixed again in any ratio necessary to obtain the desired effects.

Alternatively, the diastereomers can first be separated by conventional, achiral purification techniques such as silica gel chromatography or preparative HPLC. The two purified diastereomers can then be further separated into the enantiomers as described.

Synthesis 34. Synthesis of 3-(2,3-dihydrobenzo[b]thiophen-5-yl)-4,4,4-trifluoro-N-methylbutan-2-amine (Compound 34)

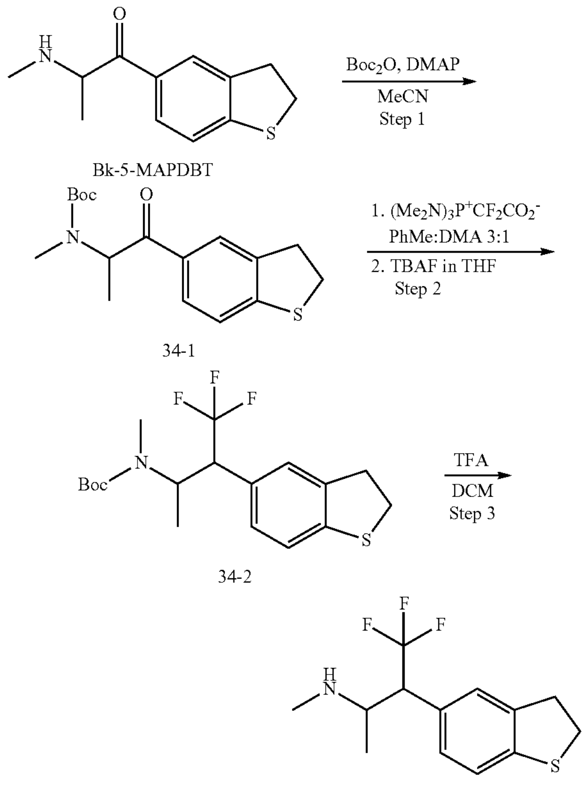

Bk-5-MAPDBT
34-1
34-2
Compound 34

Step 1: A round-bottom flask is charged with Bk-5-MAPDBT, di-tert-butyl-dicarbonate, DMAP, and acetonitrile. The reaction solution is then stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 34-1. This crude material can be taken to the next step without further purification or purified by standard techniques of the art to obtain the pure compound.

Step 2: A round-bottom flask is charged with 34-1, [tris(dimethylamino)phosphonio]difluoroacetate, and a 3:1 mixture of toluene and DMA. The resulting solution is heated to 100° C. until 34-1 is judged to be consumed by TLC, HPLC, or other analytical method. A solution of TBAF in THE is then added and the reaction is further stirred at 100° C. until judged to be complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 34-2. This crude material can be taken to the next step without further purification or purified by standard techniques of the art to obtain the pure compound.

Step 3: A round-bottom flask is charged with 34-2 and DCM. The reaction solution is then cooled to 0° C. and trifluoroacetic acid added slowly. The solution is stirred and allowed to slowly warm to room temperature until the reaction is judged complete by TLC, HPLC, or other analytical method. Following the reaction, the mixture is diluted with ethyl acetate, quenched with aqueous $NaHCO_3$, and washed three times with water. The organic layer is then dried over anhydrous $Na_2SO_4$, filtered, and concentrated to collect crude Compound 34. This crude material can be purified by standard techniques of the art to obtain the pure compound.

The individual enantiomers of Compound 34 can be separated using the methods described herein or others known in the art. Following isolation of the pure enantiomers, they can be mixed again in any ratio necessary to obtain the desired effects.

Alternatively, the diastereomers can first be separated by conventional, achiral purification techniques such as silica gel chromatography or preparative HPLC. The two purified diastereomers can then be further separated into the enantiomers as described.

Synthesis 35. Synthesis of 1-(2,3-dihydrobenzo[b]thiophen-5-yl)-2-methyl-2-(methylamino)propan-1-ol (Compound 35)

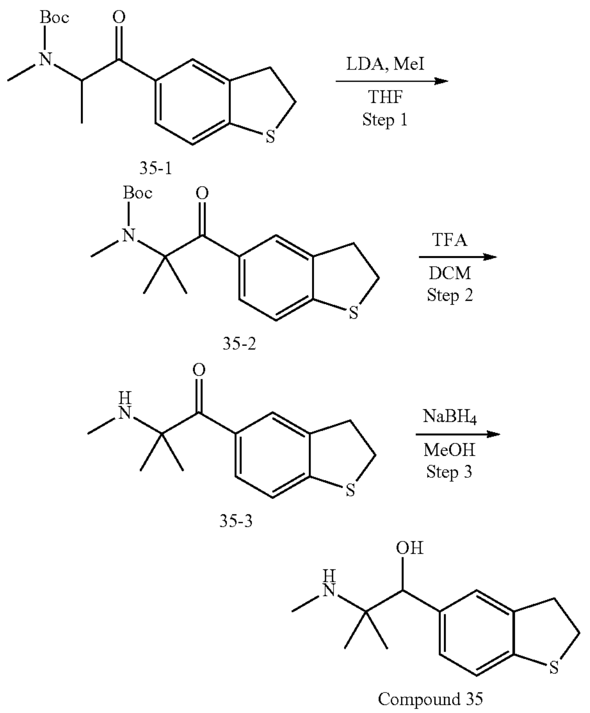

35-1
35-2
35-3
Compound 35

Step 1: A round-bottom flask is charged with 35-1. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of iodomethane is added dropwise. The reaction solution is then stirred under nitrogen until the reaction is judged complete by TLC, HPLC, or other analytical method. Following the reaction, the mixture is warmed to room temperature, diluted with ethyl acetate, quenched with $NaHCO_3$, and washed three times with water. The organic layer is then dried over anhydrous $Na_2SO_4$, filtered, and concentrated to collect crude 35-2. This crude material can be taken to the next step without further purification or purified by standard techniques of the art to obtain the pure compound.

Step 2: A round-bottom flask is charged with 35-2 and DCM. The reaction solution is then cooled to 0° C. and trifluoroacetic acid added slowly. The solution is stirred and allowed to slowly warm to room temperature until the reaction is judged complete by TLC, HPLC, or other analytical method. Following the reaction, the mixture is diluted with ethyl acetate, quenched with aqueous $NaHCO_3$, and washed three times with water. The organic layer is then dried over anhydrous $Na_2SO_4$, filtered, and concentrated to collect crude 35-3. This crude material can be taken to the next step without further purification or purified by standard techniques of the art to obtain the pure compound.

Step 3: A round-bottom flask is charged with 35-3 and methanol. The reaction solution is then stirred at room temperature and sodium borohydride added slowly. The solution is stirred until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Compound 35. This crude material can purified by standard techniques of the art to obtain the pure compound.

The individual enantiomers of Compound 35 can be separated using the methods described herein or others known in the art. Following isolation of the pure enantiomers, they can be mixed again in any ratio necessary to obtain the desired effects.

Synthesis 36. Synthesis of 1-(2,3-dihydrobenzo[b]thiophen-5-yl)-1,1-difluoro-N-methylpropan-2-amine (Compound 36)

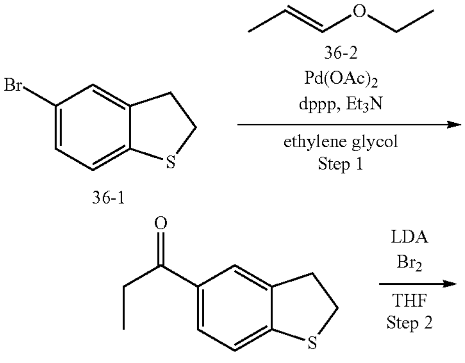

36-3

-continued

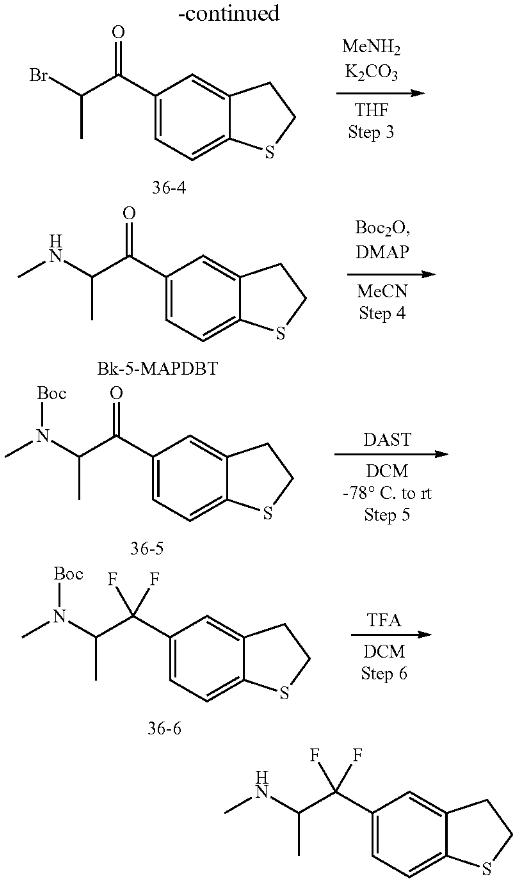

Compound 36

Step 1: A round-bottom flask is charged with 36-1, palladium(II) acetate, and 1,3-bis(diphenylphosphino)propane. The flask is then evacuated and refilled with anhydrous nitrogen three times before adding ethylene glycol, triethylamine, and 36-2 via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 36-3. This crude material can be taken to the next step without further purification or purified by standard techniques of the art to obtain the pure compound.

Step 2: A round-bottom flask is charged with 36-3. The flask is then evacuated and refilled with anhydrous nitrogen three times before adding anhydrous THE and cooling to −78° C. The solution is then stirred and a freshly prepared anhydrous solution of lithium diisopropylamide is added slowly. Once all of the lithium diisopropylamide solution is added, an anhydrous solution of bromine is added dropwise. The reaction solution is then stirred under nitrogen until the reaction is judged complete by TLC, HPLC, or other analytical method. Following the reaction, the mixture is warmed to room temperature, diluted with ethyl acetate, quenched with aqueous $Na_2S_2O_3$, and washed three times with water. The organic layer is then dried over anhydrous $Na_2SO_4$, filtered, and concentrated to collect crude 36-4. This crude material can be taken to the next step without further purification or purified by standard techniques of the art to obtain the pure compound.

Step 3: A round-bottom flask is charged with 36-4, potassium carbonate, anhydrous DMF, and a 2M solution of methylamine in THF. The flask is then sealed, and the solution stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Bk-5-MAPDBT. This crude material can be taken to the next step without further purification or purified by standard techniques of the art to obtain the pure compound.

Step 4: A round-bottom flask is charged with Bk-5-MAPDBT, di-tert-butyl-dicarbonate, DMAP, and acetonitrile. The reaction solution is then stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 36-5. This crude material can be taken to the next step without further purification or purified by standard techniques of the art to obtain the pure compound.

Step 5: A round-bottom flask is charged with 36-5 and DCM. The reaction solution is then cooled to 0° C. and DAST added slowly. The solution is stirred at 0° C. until the reaction is judged complete by TLC, HPLC, or other analytical method. Following the reaction, the mixture is diluted with ethyl acetate, quenched with aqueous $NaHCO_3$, and washed three times with water. The organic layer is then dried over anhydrous $Na_2SO_4$, filtered, and concentrated to collect crude 36-6. This crude material can be taken to the next step without further purification or purified by standard techniques of the art to obtain the pure compound.

Step 6: A round-bottom flask is charged with 36-6 and DCM. The reaction solution is then cooled to 0° C. and trifluoroacetic acid added slowly. The solution is stirred and allowed to slowly warm to room temperature until the reaction is judged complete by TLC, HPLC, or other analytical method. Following the reaction, the mixture is diluted with ethyl acetate, quenched with aqueous $NaHCO_3$, and washed three times with water. The organic layer is then dried over anhydrous $Na_2SO_4$, filtered, and concentrated to collect crude Compound 36. This crude material can be purified by standard techniques of the art to obtain the pure compound.

The individual enantiomers of Compound 36 can be separated using the methods described herein or others known in the art. Following isolation of the pure enantiomers, they can be mixed again in any ratio necessary to obtain the desired effects.

Synthesis 37. Synthesis of 2-(benzo[b]thiophen-6-yl)-3-(methylamino)butan-2-ol (Compound 37)

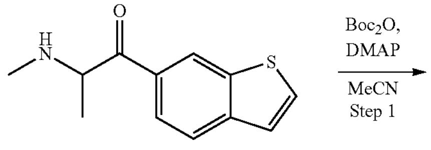

Bk-6-MAPBT

-continued

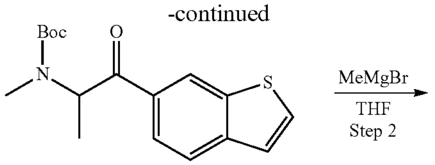

37-1

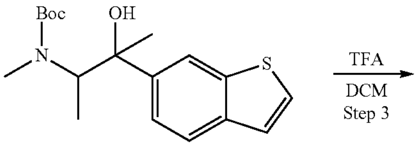

37-2

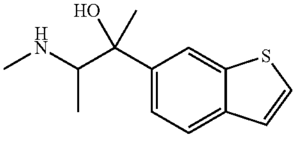

Compound 37

Step 1: A round-bottom flask is charged with Bk-6-MAPBT, di-tert-butyl-dicarbonate, DMAP, and acetonitrile. The reaction solution is then stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 37-1. This crude material can be taken to the next step without further purification or purified by standard techniques of the art to obtain the pure compound.

Step 2: A round-bottom flask is charged with 37-1. The flask is then evacuated and refilled with anhydrous nitrogen three times before adding anhydrous THE and cooling to −78° C. The solution is then stirred and an anhydrous solution of methylmagnesium bromide is added slowly. Once all of the methylmagnesium bromide solution is added, the reaction is then stirred under nitrogen until the reaction is judged complete by TLC, HPLC, or other analytical method. Following the reaction, the mixture is warmed to room temperature, diluted with diethyl ether, quenched with aqueous $NH_4Cl$, and washed three times with water. The organic layer is then dried over anhydrous $Na_2SO_4$, filtered, and concentrated to collect crude 37-2. This crude material can be taken to the next step without further purification or purified by standard techniques of the art to obtain the pure compound.

Step 3: A round-bottom flask is charged with 37-2 and DCM. The reaction solution is then cooled to 0° C. and trifluoroacetic acid added slowly. The solution is stirred and allowed to slowly warm to room temperature until the reaction is judged complete by TLC, HPLC, or other analytical method. Following the reaction, the mixture is diluted with ethyl acetate, quenched with aqueous $NaHCO_3$, and washed three times with water. The organic layer is then dried over anhydrous $Na_2SO_4$, filtered, and concentrated to collect crude Compound 37. This crude material can be purified by standard techniques of the art to obtain the pure compound.

The individual enantiomers of Compound 37 can be separated using the methods described herein or others known in the art. Following isolation of the pure enantiomers, they can be mixed again in any ratio necessary to obtain the desired effects.

Alternatively, the diastereomers can first be separated by conventional, achiral purification techniques such as silica gel chromatography or preparative HPLC. The two purified diastereomers can then be further separated into the enantiomers as described.

Synthesis 38. Synthesis of 3-(benzo[b]thiophen-6-yl)-N-methylbut-3-en-2-amine (Compound 38)

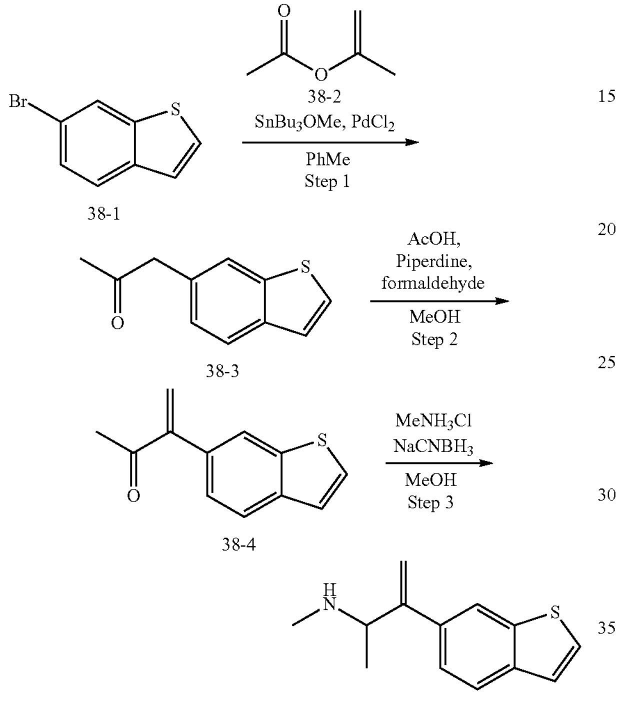

Compound 38

Step 1: A round-bottom flask is charged with 38-1, tributyltin methoxide, and palladium(II) chloride. The flask is then evacuated and refilled with anhydrous nitrogen three times before adding toluene and isopropenyl acetate (38-2). The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 38-3. This crude material can be taken to the next step without further purification or purified by standard techniques of the art to obtain the pure compound.

Step 2: A round-bottom flask is charged with 38-3, acetic acid, piperdine, and formaldehyde. Methanol is then added to dissolve the reaction components and the mixture is stirred until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 15-4. This crude material can be taken to the next step without further purification or purified by standard techniques of the art to obtain the pure compound.

Step 3: In a round-bottom flask, 38-4, methylamine, and sodium cyanoborohydride are dissolved in methanol and stirred under nitrogen. Once there is no remaining 38-4 as judged by TLC, HPLC, or other analytical method, the mixture is diluted with ethyl acetate and washed three times with water. The organic layer is then dried over anhydrous $Na_2SO_4$, filtered, and concentrated to collect crude Compound 38. This crude material can be purified by standard techniques of the art to obtain the pure compound.

The individual enantiomers of Compound 38 can be separated using the methods described herein or others known in the art. Following isolation of the pure enantiomers, they can be mixed again in any ratio necessary to obtain the desired effects.

Synthesis 39. Synthesis of 2-(benzo[b]thiophen-6-yl)-3-(methylamino)butan-1-ol (Compound

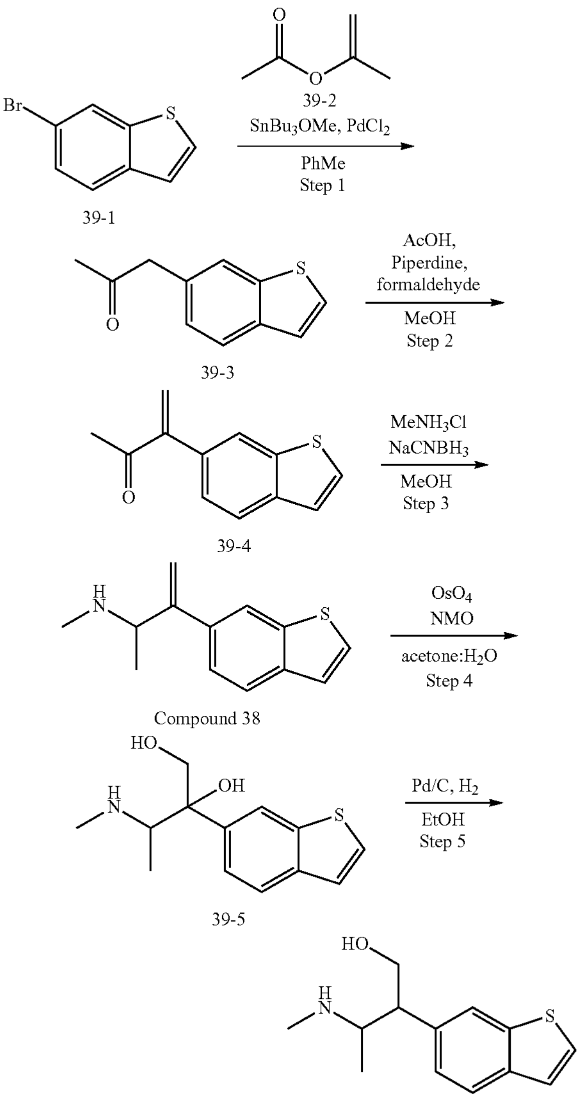

Compound 39

Step 1: A round-bottom flask is charged with 39-1, tributyltin methoxide, and palladium(II) chloride. The flask is then evacuated and refilled with anhydrous nitrogen three times before adding toluene and isopropenyl acetate (39-2). The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 39-3. This crude material can be taken to the next step without further purification or purified by standard techniques of the art to obtain the pure compound.

Step 2: A round-bottom flask is charged with 39-3, acetic acid, piperdine, and formaldehyde. Methanol is then added to dissolve the reaction components and the mixture is stirred until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 16-4. This crude material can be taken to the next step without further purification or purified by standard techniques of the art to obtain the pure compound.

Step 3: In a round-bottom flask, 39-4, methylamine, and sodium cyanoborohydride are dissolved in ethanol and stirred under nitrogen. Once there is no remaining 39-4 as judged by TLC, HPLC, or other analytical method, the mixture is diluted with ethyl acetate and washed three times with water. The organic layer is then dried over anhydrous $Na_2SO_4$, filtered, and concentrated to collect crude Compound 38. This crude material can be purified by standard techniques of the art to obtain the pure compound.

Step 4: To a round-bottom flask containing Compound 38 dissolved in acetone:$H_2O$ is added NMO and a catalytic amount of osmium tetroxide. The resulting mixture is stirred at room temperature until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude 39-5. This crude material can be taken to the next step without further purification or purified by standard techniques of the art to obtain the pure compound.

Step 5: A round-bottom flask containing 39-5 and palladium on carbon is evacuated under vacuum and backfilled with nitrogen three times. Ethanol is then added to the flask and the resulting mixture is sparged with hydrogen gas while stirring. Once the nitrogen atmosphere is displaced by hydrogen, the reaction is stirred at room temperature until the reaction is judged complete by TLC, HPLC, or other analytical method. Following the reaction, the mixture is diluted with ethyl acetate, filtered through diatomaceous earth, and concentrated to collect crude Compound 39. This crude material can be purified by standard techniques of the art to obtain the pure compound.

The individual enantiomers of Compound 39 can be separated using the methods described herein or others known in the art. Following isolation of the pure enantiomers, they can be mixed again in any ratio necessary to obtain the desired effects.

Alternatively, the diastereomers can first be separated by conventional, achiral purification techniques such as silica gel chromatography or preparative HPLC. The two purified diastereomers can then be further separated into the enantiomers as described.

Synthesis 40. Synthesis of 1-(2,3-dihydrobenzo[b]thiophen-6-yl)-2-(methylamino)propan-1-ol (Compound 40)

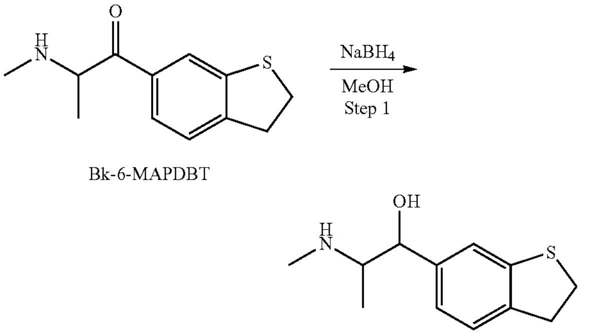

Bk-6-MAPDBT

Compound 40

Step 1: A round-bottom flask is charged with Bk-6-MAPDBT and methanol. The reaction solution is then stirred at room temperature and sodium borohydride added slowly. The solution is stirred until the reaction is judged complete by TLC, HPLC, or other analytical method. Following the reaction, the mixture is diluted with ethyl acetate and washed three times with water. The organic layer is then dried over anhydrous $Na_2SO_4$, filtered, and concentrated to collect crude Compound 40. This crude material can purified by standard techniques of the art to obtain the pure compound.

The individual enantiomers of Compound 40 can be separated using the methods described herein or others known in the art. Following isolation of the pure enantiomers, they can be mixed again in any ratio necessary to obtain the desired effects.

Alternatively, the diastereomers can first be separated by conventional, achiral purification techniques such as silica gel chromatography or preparative HPLC. The two purified diastereomers can then be further separated into the enantiomers as described.

Synthesis 41. Synthesis of 1-cyclopropyl-2-(2,3-dihydrobenzo[b]thiophen-6-yl)-N-methylethan-1-amine (Compound 41)

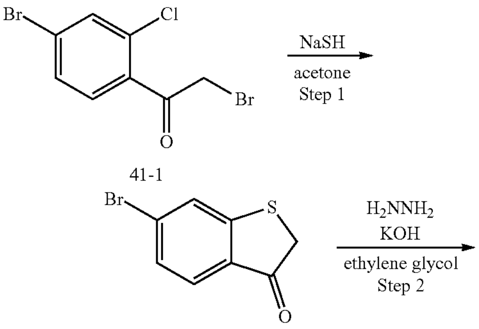

41-1

41-2

-continued

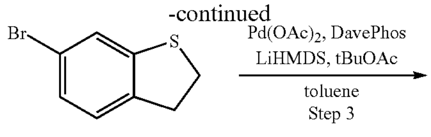

41-3

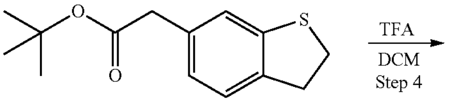

41-4

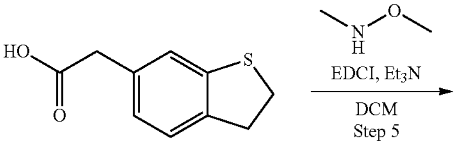

41-5

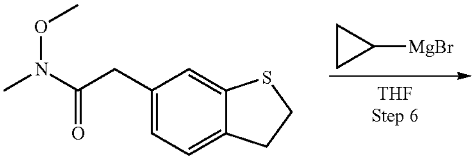

41-6

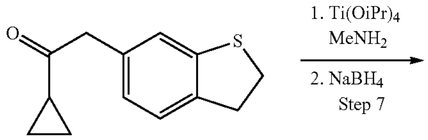

41-7

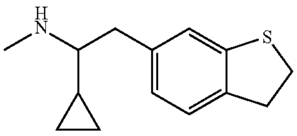

Compound 41

Step 1: A round-bottom flask is charged with 41-1 and acetone then cooled to 0° C. and stirred. Sodium hydrosulfide is then added to the solution and the reaction is allowed to slowly warm to room temperature. Once the reaction is judged complete by TLC, HPLC, or other analytical method, the mixture is diluted with ethyl acetate and washed three times with water. The organic layer is then dried over anhydrous $Na_2SO_4$, filtered, and concentrated to collect crude 41-2. This crude material can be taken to the next step without further purification or purified by standard techniques of the art to obtain the pure compound.

Step 2: A round-bottom flask is charged with 41-2, potassium hydroxide, hydrazine, and ethylene glycol. The resulting solution is then stirred and heated to reflux until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 41-3. This crude material can be taken to the next step without further purification or purified by standard techniques of the art to obtain the pure compound.

Step 3: A round-bottom flask is charged with 41-3, palladium(II) acetate, and DavePhos. The flask is then evacuated and refilled with anhydrous nitrogen three times before adding toluene, lithium bis(trimethylsilyl)amide (1M in toluene), and tert-butyl acetate via syringe. The reaction solution is then stirred with heating under nitrogen until the reaction is judged complete by TLC, HPLC, or other analytical method. Following the reaction, the mixture is cooled to room temperature, diluted with ethyl acetate, and washed three times with water. The organic layer is then dried over anhydrous $Na_2SO_4$, filtered, and concentrated to collect crude 41-4. This crude material can be taken to the next step without further purification or purified by standard techniques of the art to obtain the pure compound.

Step 4: A round-bottom flask is charged with 41-4 and DCM. The reaction solution is then cooled to 0° C. and trifluoroacetic acid added slowly. The solution is stirred and allowed to slowly warm to room temperature until the reaction is judged complete by TLC, HPLC, or other analytical method. Following the reaction, the mixture is diluted with ethyl acetate, quenched with aqueous $NaHCO_3$, and washed three times with water. The organic layer is then dried over anhydrous $Na_2SO_4$, filtered, and concentrated to collect crude 41-5. This crude material can be purified by standard techniques of the art to obtain the pure compound.

Step 5: A round-bottom flask is charged with 41-5, EDCI, N,O-dimethylhydroxylamine, triethylamine, and DCM. The solution is stirred at room temperature until the reaction is judged complete by TLC, HPLC, or other analytical method. Following the reaction, the mixture is diluted with ethyl acetate, quenched with aqueous $NH_4Cl$, and washed three times with water. The organic layer is then dried over anhydrous $Na_2SO_4$, filtered, and concentrated to collect crude 41-6. This crude material can be purified by standard techniques of the art to obtain the pure compound.

Step 6: A round-bottom flask is charged with 41-6. The flask is then evacuated and refilled with anhydrous nitrogen three times before adding anhydrous THE and cooling to −78° C. The solution is then stirred and an anhydrous solution of cyclopropylmagnesium bromide is added slowly. Once all of the cyclopropylmagnesium bromide solution is added, the reaction is then stirred under nitrogen until the reaction is judged complete by TLC, HPLC, or other analytical method. Following the reaction, the mixture is warmed to room temperature, diluted with diethyl ether, quenched with aqueous $NH_4Cl$, and washed three times with water. The organic layer is then dried over anhydrous $Na_2SO_4$, filtered, and concentrated to collect crude 41-7. This crude material can be taken to the next step without further purification or purified by standard techniques of the art to obtain the pure compound.

Step 7: In a round-bottom flask, 41-7, methylamine, and titanium (IV) isopropoxide are dissolved in ethanol and stirred under nitrogen. Once there is no remaining 41-7 as judged by TLC, HPLC, or other analytical method, the flask is opened briefly, and sodium borohydride is added slowly. The resulting slurry is stirred at room temperature overnight. Following the reaction, the mixture is diluted with ethyl acetate and washed three times with water. The organic layer is then dried over anhydrous $Na_2SO_4$, filtered, and concentrated to collect crude Compound 41. This crude material can be purified by standard techniques of the art to obtain the pure compound.

The individual enantiomers of Compound 41 can be separated using the methods described herein or others known in the art. Following isolation of the pure enantiomers, they can be mixed again in any ratio necessary to obtain the desired effects.

Synthesis 42. Synthesis of 1-(benzothiophen-5-yl)-N-methylpropan-2-amine hydrochloride (5-MAPBT)

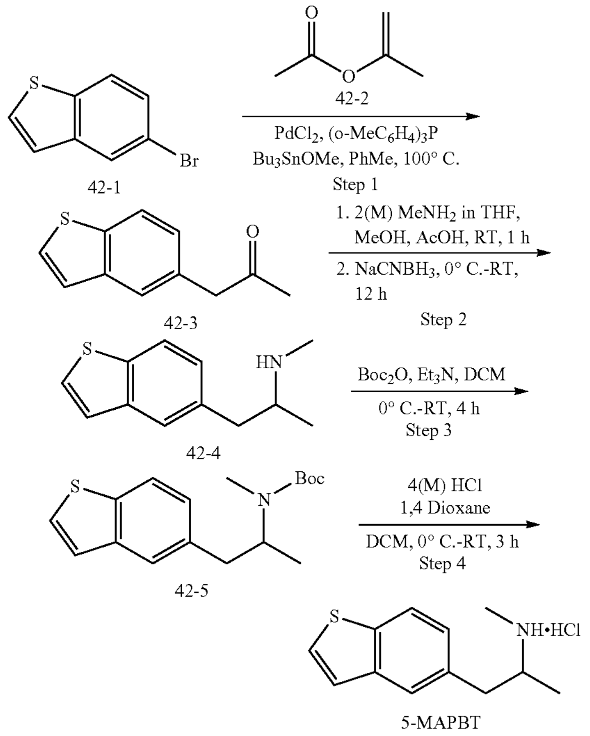

Step 1: To a stirred solution of 5-bromobenzothiophene (42-1) (5 g, 23.46 mmol, 1 eq.) in dry Toluene (100 mL) was added tri(o-tolyl)phosphine (0.43 g, 1.40 mmol, 0.06 eq.), tributyltin methoxide (10.27 ml, 35.19 mmol, 1.5 eq.) and isopropenyl acetate (42-2, 3.92 mL, 36.13 mmol, 1.54 eq.) and the resulting reaction mixture was degassed under nitrogen for 15 minutes. Then palladium (II) chloride (0.29 g, 1.64 mmol, 0.07 eq.) was added to the reaction mixture and the resulting reaction mixture continued to stir at 100° C. for 16 h. Upon completion, as monitored by TLC (10% EA in Hexane), the reaction mixture was cooled to room temperature and evaporated under vacuum. Then the residue was dissolved in ethyl acetate and filtered through celite bed, washed with water, saturated potassium fluoride solution, and brine solution. Combined organic layer was dried over anhydrous sodium sulphate, solvent was removed under vacuum, and crude material purified by silica gel column chromatography using ethyl acetate/hexane (10:90 v/v) as eluent to afford 1-(benzothiophen-5-yl)propan-2-one (42-3) as light yellow solid (3.3 g, 74%). $^1$H NMR (400 MHz, $CDCl_3$) δ 7.84 (d, J=8.24 Hz, 1H), 7.65 (s, 1H), 7.45 (d, J=5.40 Hz, 1H), 7.29 (d, J=5.44 Hz, 1H), 7.18 (d, J=8 Hz, 1H), 3.80 (s, 2H), 2.16 (s, 3H). LCMS: Rt 3.24 min. MS (ES) $C_{11}H_{10}OS$ requires 190, found 191 [M+H]$^+$.

Step 2: To a stirred solution of 1-(benzothiophen-5-yl) propan-2-one (42-3) (3.5 g, 18.39 mmol, 1 eq.) in dry MeOH (35 mL) was added AcOH (0.31 ml, 5.51 mmol, 0.3 eq.) and methylamine in THF 2(M) (18.5 ml, 36.79 mmol, 2 eq.) (In a sealed round-bottom flask) and the resulting reaction mixture was allowed to stir at room temperature for 1 h. Then $NaCNBH_3$ (2.3 g, 36.79 mmol, 2 eq.) was added to the reaction mixture at 0° C. and it was allowed to stir at room temperature for 12 h. Upon completion, as monitored by TLC (20% EA in Hexane), the volatiles were removed under vacuum, the crude was diluted with ethyl acetate (2×100 ml), and organic layer washed with water then brine solution. Combined organic layer was dried over anhydrous sodium sulphate and solvent was removed under vacuum to afford crude 1-(benzothiophen-5-yl)-N-methylpropan-2-amine (42-4) as yellow sticky gum (3.1 g, 82%). Crude $^1$H NMR (400 MHz, $CDCl_3$) δ 7.81 (d, J=8.28 Hz, 1H), 7.63 (s, 1H), 7.43 (d, J=5.44 Hz, 1H), 7.29 (d, J=5.40 Hz, 1H), 7.18 (d, J=8.32 Hz, 1H), 2.93 (m, 2H), 2.80 (m, 1H), 2.43 (s, 3H), 1.12 (d, J=6.04 Hz, 3H). LCMS: Rt 2.56 min. MS (ES) $C_{12}H_{15}NS$, requires 205, found 206 [M+H]$^+$.

Step 3: To a stirred solution of crude 1-(benzothiophen-5-yl)-N-methylpropan-2-amine (42-4) (3.1 g, 15.09 mmol, 1 eq.) in dry DCM (30 mL) was added $Et_3N$ (4.2 mL, 30.19 mmol, 2 eq.) and Boc anhydride (6.9 mL, 30.19 mmol, 2 eq.) then the resulting reaction mixture was allowed to stir at room temperature for 4 h. Upon completion (as monitored by TLC, 10% EA in Hexane), the reaction mixture was evaporated to dryness, diluted with DCM (2×100 mL), and washed with water then brine solution. Combined organic layer was dried over anhydrous sodium sulphate, solvent was evaporated under vacuum and purified by silica gel column chromatography using ethyl acetate/hexane (10:90 v/v) as eluent to afford tert-butyl (1-(benzothiophen-5-yl) propan-2-yl)(methyl)carbamate (42-5) as yellow sticky gum (3 g, 65%). $^1$H NMR (400 MHz, DMSO-$d_6$) δ 7.88 (d, J=7.96 Hz, 1H), 7.70 (d, J=5.40 Hz, 1H), 7.64 (s, 1H), 7.38 (d, J=5.32 Hz, 1H), 7.18 (d, J=8.16 Hz, 1H), 4.40-4.33 (m, 1H), 2.80 (d, J=5.84 Hz, 2H), 2.64 (s, 3H), 1.24 (S, 3H), 1.10 (s, 9H). Rotamers observed. LCMS: Rt 3.35 min. MS (ES) $C_{17}H_{23}NO_2S$, requires 305, found 306 [M+H]$^+$.

Step 4: To a stirred solution of tert-butyl (1-(benzothiophen-5-yl)propan-2-yl)(methyl)carbamate (42-5) (3 g, 9.82 mmol, 1 eq.) in dry DCM (30 mL) was added 4(M) HCl in 1,4 dioxane (30 mL) at 0° C. and the resulting reaction mixture was allowed to stir at room temperature for 3 h. Upon completion of reaction (as monitored by TLC, 10% EA in Hexane), the solvent was evaporated and the crude was washed twice with diethyl ether (2×50 ml) and pentane (1×50 ml) and dried under vacuum to afford 1-(benzothiophen-5-yl)-N-methylpropan-2-amine hydrochloride (5-MAPBT) as white solid (2.1 g, 88%). $^1$H NMR (400 MHz, DMSO-$d_6$) δ 9.10 (s, 2H), 7.98 (d, J=8.28 Hz, 1H), 7.77 (t, J=3.28 Hz, 1.76 Hz, 2H), 7.43 (d, J=5.40 Hz, 1H), 7.28 (d, J=8.28 Hz, 1H), 3.44 (m, 1H), 3.29 (m, 1H), 2.81 (q, 1H), 2.57 (s, 3H), 1.13 (d, J=6.52 Hz, 3H). LCMS: Rt 1.79 min. MS (ES) $C_{12}H_{15}NS$, requires 205, found 206 [M+H]$^+$. HPLC: Rt 6.05 min. Purity (λ 230 nm): 99.26%.

Synthesis 43. Synthesis of 1-(benzothiophen-6-yl)-N-methylpropan-2-amine hydrochloride (6-MAPBT)

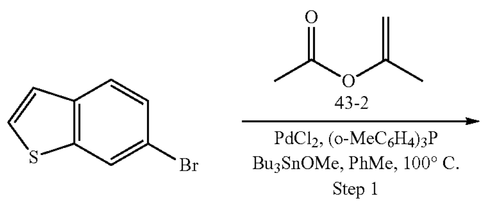

-continued

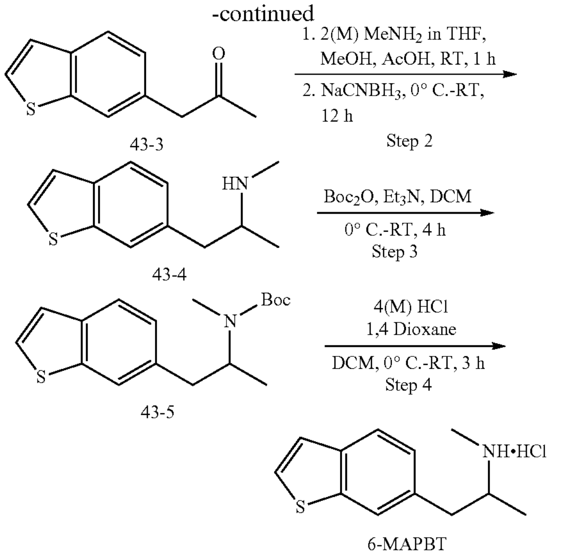

43-3

43-4

43-5

6-MAPBT

Step 1: To a stirred solution of 6-bromobenzothiophene (43-1) (10 g, 46.94 mmol, 1 eq.) in dry toluene (200 mL) was added tri(o-tolyl)phosphine (1.85 g, 6.10 mmol, 0.13 eq.), tributyltin methoxide (34.25 mL, 117.37 mmol, 2.5 eq.) and isopropenyl acetate (43-2, 15.30 mL, 140.84 mmol, 3 eq.) and the resulting reaction mixture was degassed under nitrogen for 15 minutes. Then palladium (II) chloride (0.83 g, 4.69 mmol, 0.1 eq.) was added to the reaction mixture and it continued to stir at 100° C. for 16 h. Upon completion, as monitored by TLC (10% EA in Hexane), the reaction mixture was cooled to room temperature, and evaporated under vacuum. Then the residue was dissolved in ethyl acetate and filtered through celite bed, and washed with water, saturated potassium fluoride solution, and brine solution. Combined organic layer was dried over anhydrous sodium sulphate, solvent was removed under vacuum, and crude material was purified by silica gel column chromatography using ethyl acetate/hexane (10:90 v/v) as eluent to afford 1-(benzothiophen-6-yl)propan-2-one (43-3) as light yellow solid (6 g, 67%). $^1H$ NMR (400 MHz, DMSO-$d_6$) δ 7.82 (d, J=7.72 Hz, 2H), 7.71 (d, J=5.40 Hz, 1H), 7.42 (d, J=5.44 Hz, 1H), 7.20 (d, J=8.28 Hz, 1H), 3.88 (s, 2H), 2.15 (s, 3H). Aliphatic region impurity peak present. LCMS: Rt 3.24 min. MS (ES) $C_{11}H_{10}OS$ requires 190, found 191 $[M+H]^+$.

Step 2: To a stirred solution of 1-(benzothiophen-6-yl) propan-2-one (43-3) (6 g, 31.57 mmol, 1 eq.) in dry MeOH (60 mL) was added AcOH (0.54 mL, 9.47 mmol, 0.3 eq.) and methylamine in THF 2(M) (31.7 mL, 63.15 mmol, 2 eq.) (in a sealed round-bottom flask) and the resulting reaction mixture was allowed to stir at room temperature for 1 h. Then $NaCNBH_3$ (3.96 g, 63.15 mmol, 2 eq.) was added to the reaction mixture at 0° C. and it was allowed to stir at room temperature for 12 h. Upon completion, as monitored by TLC (20% EA in Hexane), the volatiles were removed under vacuum and the crude was extracted with ethyl acetate (2×100 mL) and washed with water then brine solution. Combined organic layer was dried over anhydrous sodium sulphate and the solvent was removed under vacuum to afford crude 1-(benzothiophen-6-yl)-N-methylpropan-2-amine (43-4) as yellow sticky gum (5 g, 77%). 1H NMR (400 MHz, DMSO-$d_6$) δ 7.79 (d, J=7.92 Hz, 2H), 7.67 (d, J=5.40 Hz, 1H), 7.40 (d, J=5.40 Hz, 1H), 7.23 (d, J=9.32 Hz, 1H), 2.92 (m, 2H), 2.60 (q, 1H), 2.34 (s, 3H), 0.95 (d, J=6.12 Hz, 3H). Extra impurity peak present in aliphatic region. LCMS: Rt 1.95 min. MS (ES) $C_{12}H_{15}NS$, requires 205, found 206 $[M+H]^+$.

Step 3: To a stirred solution of crude 1-(benzothiophen-6-yl)-N-methylpropan-2-amine (43-4) (5 g, 24.39 mmol, 1 eq.) in dry DCM (50 mL) was added $Et_3N$ (7.03 mL, 48.78 mmol, 2 eq.) and Boc anhydride (11.19 mL, 48.78 mmol, 2 eq.) and the resulting reaction mixture was allowed to stir at room temperature for 4 h. Upon completion (as monitored by TLC, 10% EA in Hexane), the reaction mixture was evaporated to dryness, diluted with DCM (2×100 mL), and washed with water then brine solution. Combined organic solvent was dried over anhydrous sodium sulphate and evaporated under vacuum. The resulting residue was purified by silica gel column chromatography using ethyl acetate/hexane (10:90 v/v) as eluent to afford tert-butyl (1-(benzothiophen-6-yl)propan-2-yl)(methyl)carbamate (43-5) as yellow sticky gum (3 g, 40%). $^1H$ NMR (400 MHz, DMSO-$d_6$) δ 7.88 (d, J=7.96 Hz, 2H), 7.70 (d, J=5.40 Hz, 1H), 7.64 (s, 1H), 7.38 (d, J=5.32 Hz, 1H), 7.18 (d, J=8.16 Hz, 1H), 4.40-4.33 (m, 1H), 2.80 (s, 2H), 2.64 (s, 3H), 1.24 (s, 3H), 1.10 (S, 9H). Rotamers observed. LCMS: Rt 3.93 min. MS (ES) $C_{17}H_{23}NO_2S$, requires 305, found 306 $[M+H]^+$.

Step 4: To a stirred solution of tert-butyl (1-(benzothiophen-6-yl)propan-2-yl)(methyl)carbamate (43-5) (3 g, 9.83 mmol, 1 eq.) in dry DCM (20 mL) was added 4(M) HCl in 1,4 dioxane (20 mL) at 0° C. and the resulting reaction mixture was allowed to stir at room temperature for 3 h. Upon completion of reaction (as monitored by TLC, 10% EA in Hexane), the solvent was evaporated and the crude was washed twice with diethyl ether (2×50 ml) and pentane (1×50 ml) and dried under vacuum to afford 1-(benzothiophen-6-yl)-N-methylpropan-2-amine hydrochloride (6-MAPBT) as light blue solid (2.27 g, 95%). $^1H$ NMR (400 MHz, DMSO-$d_6$) δ 9.17 (bs, 2H), 7.90 (s, 1H), 7.85 (d, J=8.12 Hz, 1H), 7.73 (d, J=5.36 Hz, 1H), 7.43 (d, J=5.32 Hz, 1H), 7.29 (d, J=7.60 Hz 1H), 3.42 (bs, 1H), 3.30 (bs, 1H), 2.82 (q, 1H), 2.56 (s, 3H), 1.13 (d, J=6.40 Hz, 3H). LCMS: Rt 1.95 min. MS (ES) $C_{12}H_{15}NS$, requires 205, found 206 $[M+H]^+$. HPLC: Rt 4.75 min. Purity (λ 220 nm): 99.52%.

Synthesis 44. Synthesis of 1-(benzo[b]thiophen-5-yl)-2-(methylamino) propan-1-one hydrochloride (Bk-5-MAPBT)

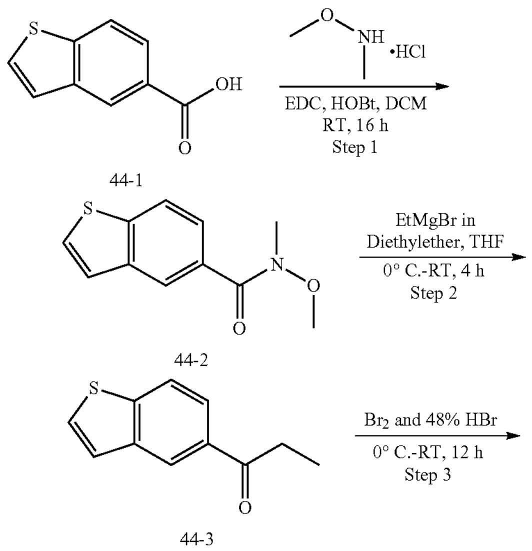

44-1

44-2

44-3

-continued

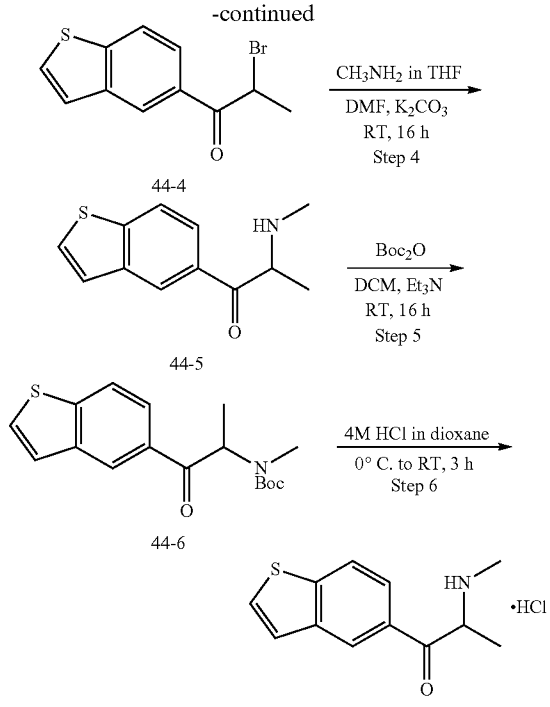

44-4

44-5

44-6

Bk-5-MAPBT

Step 1: To a stirred solution of benzothiophene-5-carboxylic acid (44-1) (1 g, 5.61 mmol, 1 eq.) in dry DCM (20 mL) was added DIPEA (2.93 mL, 16.84 mmol, 3 eq.) followed by EDC.HCl (1.18 g, 6.17 mmol, 1.1 eq.) and HOBT (1.13 g, 8.42 mmol, 1.5 eq.) under nitrogen atmosphere at room temperature and the resulting reaction mixture continued to stir for 15 min. Then N,O-dimethylhydroxylamine hydrochloride (0.60 g, 6.17 mmol, 1.1 eq.) was added to the resulting reaction mixture and was allowed to continue stirring at room temperature for 16 h. Upon completion, as monitored by TLC (20% EA in Hexane), the reaction mixture was diluted with DCM (500 mL) and washed with water then brine solution. Combined organic layer was dried over anhydrous sodium sulphate, solvent was removed under vacuum, and crude material purified by silica gel column chromatography using ethyl acetate/hexane (20:80 v/v) as eluent to afford N-methoxy-N-methylbenzo[b]thiophene-5-carboxamide (44-2) as yellow sticky gum (1.18 g, 95%). $^1$H NMR (400 MHz, $CDCl_3$) δ 8.17 (s, 1H), 7.89 (d, J=8.36 Hz, 1H), 7.67 (d, J=8.32 Hz, 1H), 7.49 (d, J=5.36 Hz, 1H), 7.38 (d, J=5.32 Hz, 1H), 3.55 (s, 3H), 3.39 (s, 3H).

Step 2: To a stirred solution of N-methoxy-N-methylbenzothiophene-5-carboxamide (44-2) (7.5 g, 33.93 mmol, 1 eq.) at 0° C. was added dry THE (100 mL) and 2(M) solution of EtMgBr in Diethylether (23 ml, 67.87 mmol, 2 eq.) to the reaction mixture and allowed to stir at room temperature for 4 h. Upon completion, (monitored by TLC, 20% EA in Hexane) the reaction was quenched with saturated $NH_4Cl$ solution and extracted with ethyl acetate, twice (2×150 ml), then washed with water followed by brine solution. Combined organic layer was dried over anhydrous sodium sulphate, solvent was evaporated under vacuum to get crude 1-(benzothiophene-5-yl) propan-1-one (44-3) as yellow solid (6 g, 93%). $^1$H NMR (400 MHz, $CDCl_3$) δ 8.43 (s, 1H), 7.94-7.91 (bs, 2H), 7.52 (d, J=5.24 Hz, 1H), 7.43 (d, J=5.24 Hz, 1H), 3.11-3.06 (m, 2H), 1.28 (t, J=7.28 Hz, 7.24 Hz, 3H).

Step 3: To a stirred solution of 1-(benzothiophene-5-yl) propan-1-one (44-3) (3.1 g, 16.27 mmol, 1 eq.) in dry THE (30 mL) was added hydrobromic acid (48% in water) (28.2 mL, 520.73 mmol, 32 eq.) and bromine (0.91 mL, 17.9 mmol, 1.1 eq.) dropwise at 0° C. and the reaction mixture was allowed to stir at room temperature for 16 h. Upon completion, (as monitored by TLC, 10% EA in Hexane), reaction mixture was quenched with saturated sodium carbonate solution, extracted with ethyl acetate (2×100 ml), and washed with water and brine solution. Combined organic layer was dried over anhydrous sodium sulphate, solvent was evaporated under reduced pressure and crude material purified by silica gel column chromatography using ethyl acetate/hexane (10:90 v/v) as eluent to get 1-(benzothiophen-5-yl)-2-bromopropan-1-one (44-4) as yellow sticky gum (3 g, 68%). $^1$H NMR (400 MHz, $CDCl_3$) δ 8.50 (d, J=12.1 Hz, 1H), 8.06-7.92 (m, 2H), 7.54 (d, J=4.04 Hz, 2H), 7.45 (d, J=5.28 Hz, 1H), 5.43-5.36 (m, 1H), 1.96 (t, J=6.40 Hz, 3H).

Step 4: To a stirred solution of 1-(benzothiophen-5-yl)-2-bromopropan-1-one (44-4) (4 g, 14.92 mmol, 1 eq.) in dry DMF (40 mL) was added potassium carbonate (3 g, 22.39 mmol, 1.5 eq.) and methylamine 2(M) in THE (45 mL, 89.56 mmol, 6 eq.) in a sealed round-bottom flask and the resulting reaction mixture was allowed to stir at room temperature for 16 h. Upon completion of reaction (monitored by TLC, 10% EA in Hexane), volatiles were evaporated, and the crude was diluted with ethyl acetate (2×100 ml) and washed with water (2×50 ml) followed by brine solution. Combined organic solvent was dried over anhydrous sodium sulphate, and solvent was evaporated under reduced pressure to afford crude 1-(benzothiophen-5-yl)-2-(methylamino) propan-1-one (44-5) as yellow sticky gum (2.9 g, 89%). $^1$H NMR (400 MHz, $CDCl_3$) δ 8.44 (d, J=14.96 Hz, 1H), 8.02 (d, J=8.40 Hz, 1H), 7.95 (s, 1H), 7.53 (d, J=3.64 Hz, 1H), 7.45 (d, J=5.48 Hz, 1H), 4.37-4.28 (m, 1H), 2.41 (d, J=6.92 Hz, 3H), 1.35 (t, J=5.40 Hz, 6.72 Hz, 3H).

Step 5: To a stirred solution of 1-(benzothiophen-5-yl)-2-(methylamino)propan-1-one (44-5) (2.9 g, 13.42 mmol, 1 eq.) in dry DCM (30 mL) was added triethylamine (3.73 mL, 26.84 mmol, 2 eq.) and Boc anhydride (6.1 mL, 26.84 mmol, 2 eq.) and the resulting reaction mixture was allowed to stir at room temperature for 4 h. Upon completion, (as monitored by TLC, 10% EA in Hexane), the reaction mixture was evaporated under reduced pressure, diluted with DCM (200 mL), and washed with water followed by brine solution. Combined organic solvent was dried over anhydrous sodium sulphate, solvent was evaporated under vacuum, and crude material was purified by silica gel column chromatography using ethyl acetate/hexane (10:90 v/v) as eluent to get tert-butyl (1-(benzothiophen-5-yl)-1-oxopropan-2-yl) (methyl) carbamate (44-6) as yellow sticky gum (2.5 g, 58%). $^1$H NMR (400 MHz, $CDCl_3$) δ 8.52 (bs, 1H), 7.91-7.87 (m, 2H), 7.49 (m, 1H), 7.40 (d, J=5.36 Hz, 1H), 5.83-5.79 (q, 1H), 2.60 (s, 3H), 1.55 (s, 3H), 1.44 (s, 9H). Impurity peak present in NMR.

Step 6: To a stirred solution of tert-butyl (1-(benzothiophen-5-yl)-1-oxopropan-2-yl) (methyl) carbamate (44-6) (2.1 g, 6.58 mmol, 1 eq.) in dry DCM (20 mL) was added 4(M) HCl in 1,4 dioxane (20 mL) at 0° C. and the resulting reaction mixture was allowed to stir at room temperature for 3 h. Upon completion of reaction (as monitored by TLC, 10% EA in hexane), the solvent was evaporated and the crude was washed twice with diethyl ether (2×30 mL) and pentane (2×15 mL) and dried under vacuum to afford 1-(benzothiophen-5-yl)-2-(methylamino) propan-1-one hydrochloride (Bk-5-MAPBT) (1.15 g, 79%) as white solid.

$^1$HNMR (400 MHz, DMSO) δ 9.37-9.15 (bs, 2H), 8.66 (s, 1H), 8.26 (d, J=8.52 Hz, 1H), 7.97 (d, J=5.84 Hz, 2H), 7.65 (d, J=5.48 Hz, 1H), 5.28-5.23 (q, 1H), 2.63 (s, 3H), 1.51 (d, J=7.16 Hz, 3H). LCMS: Rt 1.50 min. MS (ES) $C_{12}H_{13}NOS$ requires 219, found 220 $[M+H]^+$. HPLC: Rt 6.13 min. Purity (λ 250 nm): 98.56%.

Synthesis 45. Synthesis of 1-(benzothiophen-5-yl)-N-ethylpropan-2-amine hydrochloride (5-EAPBT)

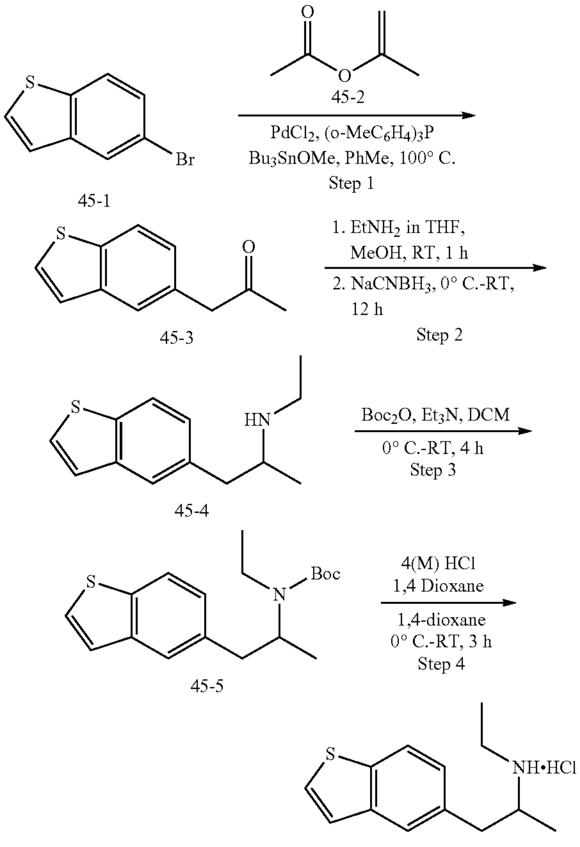

45-1

45-3

45-4

45-5

5-EAPBT

Step 1: To a stirred solution of 5-bromobenzothiophene (45-1, 10 g, 47.17 mmol, 1.0 eq.) in toluene (200 mL), tri(o-tolyl)phosphine (0.86 g, 2.83 mmol, 0.06 eq.), tributyltin methoxide (22.71 mL, 70.75 mmol, 1.5 eq.) and isopropenyl acetate (45-2, 7.9 mL, 72.64 mmol, 1.54 eq.) was added and the reaction mixture was purged with nitrogen for 15 minutes. Then palladium (II) chloride (0.58 g, 3.30 mmol, 0.07 eq.) was added and the reaction mixture was continued to stir at 100° C. for 16 hours. Upon completion, as monitored by TLC (10% EA in Hexane), the reaction mixture was cooled to room temperature and evaporated under vacuum. The reaction mixture was filtered through celite bed, and the residue was dissolved with ethyl acetate (2×400 ml). The organic layer was then washed with water, saturated potassium fluoride solution, and brine solution. Combined organic layer was dried over anhydrous sodium sulphate, solvent was removed under vacuum, and crude material purified by silica gel column chromatography using ethyl acetate/hexane (10% EtOAc\Hex) as eluent to afford 1-(benzothiophen-5-yl)propan-2-one (45-3) (7.5 g, 84%) as colorless sticky gum. $^1$H NMR (400 MHz, DMSO-$d_6$) δ 7.94 (d, J=8.28 Hz, 1H), 7.75 (d, J=5.40 Hz, 1H), 7.69 (s, 1H), 7.42 (d, J=5.44 Hz, 1H), 7.19 (dd, J=8.20 Hz, 1.28 Hz, 1H), 3.87 (s, 2H), 2.14 (s, 3H). LCMS: Rt 1.81 min. MS (ES) $C_{11}H_{10}OS$ requires 190, found 191 $[M+H]^+$.

Step 2: To a stirred solution of 1-(benzothiophen-5-yl) propan-2-one (45-3) (3.0 g, 15.78 mmol, 1.0 eq.) and ethylamine (2M in THF) (2.1 mL, 31.57 mmol, 2.0 eq.) in methanol (30.0 mL) after 1 h of stirring, $NaCNBH_3$ (1.98 g, 31.57 mmol, 2.0 eq.) was added portion wise at 0° C. Then the resulting reaction mixture continued to stir at room temperature for 16 h. Upon completion, as monitored by TLC (20% EA in Hex) the reaction mixture was diluted with water (50 mL) and extracted with DCM (100 mL). Organic layer was collected and dried under sodium sulphate, and solvent was removed under vacuum to afford crude 1-(benzothiophen-5-yl)-N-ethylpropan-2-amine (45-4) (3.5 g) as a light yellow sticky gum, which was used in the next step without further purification. LCMS: Rt 1.50 min. MS (ES) $C_{13}H_{17}NS$, requires 219, found 220 $[M+H]^+$.

Step 3: To stirred solution of 1-(benzothiophen-5-yl)-N-ethylpropan-2-amine (45-4) (3.5 g, 15.98 mmol, 1.0 eq.) in DCM (60.0 mL) was added Boc Anhydride (11.0 mL, 47.94 mmol, 3.0 eq.) and $Et_3N$ (5.57 mL, 39.95 mmol, 2.5 eq.) at room temperature. The resulting reaction mixture was stirred at room temperature for 30 min. After completion, as monitored by TLC (30% EA in Hex), the reaction mixture was washed with water (30 mL) and extracted with ethyl acetate (2×100 mL). Combined organic layer was dried over anhydrous magnesium sulfate, evaporated under reduced pressure, and crude residue purified by column chromatography using 15%-20% ethyl acetate in hexane to afford tert-butyl (1-(benzothiophen-5-yl)propan-2-yl)(ethyl)carbamate (45-5) (3.6 g, 70%) as a colorless sticky gum. 1H NMR (400 MHz, DMSO-$d_6$) δ 7.88 (d, J=7.92, 1H), 7.70 (d, J=5.24 Hz, 1H), 7.64 (s, 1H), 7.38 (d, J=5.16 Hz, 1H), 7.18 (d, J=7.52 Hz, 1H), 4.18-4.15 (bm, 1H), 3.04 (bs, 2H), 2.88 (m, 2H), 1.36-1.19 (m, 12H), 0.97 (t, J=6.52 Hz, 6.36 Hz, 3H). LCMS: Rt 2.23 min. MS (ES) $C_{18}H_{25}NO_2S$ requires 319, found 320 $[M+H]^+$.

Step 4: To a stirred solution of tert-butyl (1-(benzothiophen-5-yl)propan-2-yl)(ethyl)carbamate (45-5) (3.3 g, 10.97 mmol, 1.0 eq.) dissolved in 1, 4 dioxane (30.0 mL) at 0° C. was added 4M HCl in 1, 4 dioxane (15.0 mL). The resultant reaction mixture was stirred at room temperature for 2 h. After completion (as monitored by TLC, 30% EA in Hexane), solvent was evaporated. Then the residue was dissolved in methanol, ether was added, and white precipitate of desired product was observed and filtered to afford the pure 1-(benzothiophen-5-yl)-N-ethylpropan-2-amine hydrochloride (5-EAPBT) (2.4 g, 99%) as a white solid. $^1$H NMR (400 MHz, DMSO-$d_6$) δ 9.17 (bs, 2H), 7.97 (d, J=8.24, 1H), 7.77-7.75 (m, 2H), 7.43 (d, J=5.44 Hz, 1H), 7.28-7.26 (d, J=9.16 Hz, 1H), 3.43-3.36 (m, 2H), 3.01-2.99 (m, 2H), 2.80-2.74 (q, 1H), 1.27 (t, J=7.16 Hz, 7.24 Hz, 3H), 1.13 (d, J=6.44 Hz, 3H). LCMS: Rt 1.51 min. MS (ES) $C_{13}H_{17}NS$, requires 219, found 220 $[M+H]^+$. HPLC: Rt 5.63 min. Purity (λ 220 nm): 99.39%.

Example 2: Production of Enantiomerically Enriched Preparations

Racemic compounds of the present invention are separated into pure enantiomers using the methods described herein or otherwise known to one of skill in the art. Exemplary synthetic transformations and supercritical fluid chiral chromatography conditions are given here as illustrative examples. Although there is variance in the chemical properties of the compounds of the present invention, it is routine to one skilled in the art to determine the exact conditions necessary to achieve separation in each case.

Preparative SFC Method

- Column: 2.1×25.0 cm Chiralpak AD-H (Chiral Technologies, West Chester, PA)
- $CO_2$ Co-solvent (Solvent B): isopropyl alcohol with 0.25% Isopropylamine
- Isocratic Method: 15% Co-solvent at 90 g/min
- System Pressure: 100 bar
- Column Temperature: 25 degrees C.
- Sample Diluent: 3:2 isopropyl alcohol/Methanol Analytical SFC Method

- Column: 4.6×250 mm 3 μm Chiralpak AD-H from Chiral Technologies (West Chester, PA)
- $CO_2$ Co-solvent (Solvent B): isopropyl alcohol with 0.1% Isopropylamine
- Isocratic Method: 10% Co-solvent at 3 mL/min System Pressure: 125 bar
- Column Temperature: 40 degrees C.
- Sample Diluent: isopropyl alcohol Separation of R-5-MAPBT and S-5-MAPBT Additionally, certain compounds may be separated more easily as functionalized derivatives. Therefore, it can be beneficial to separate the enantiomers of racemic compounds as their Fmoc derivatives, as shown below.

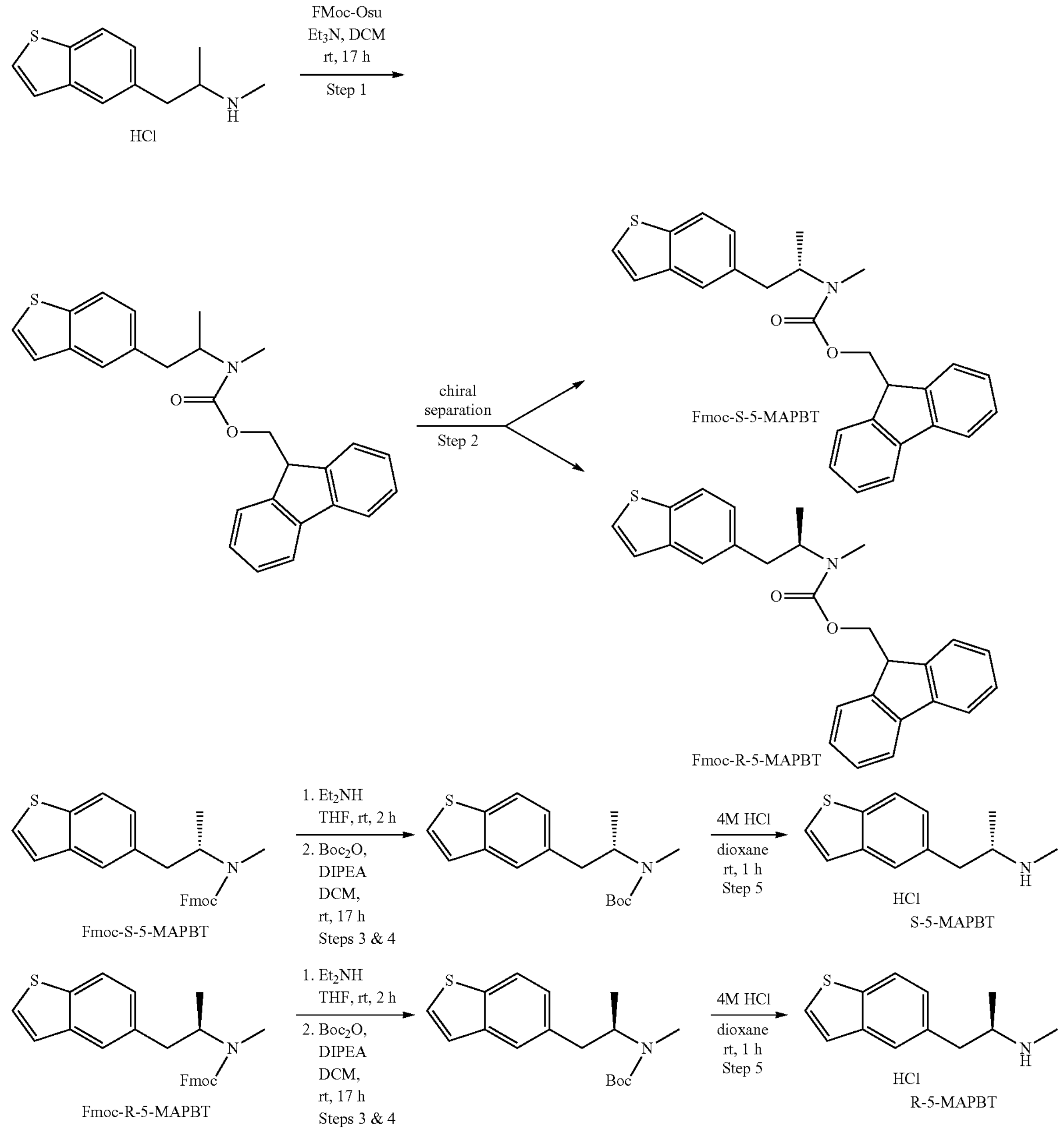

The chiral separation of Step 2 is accomplished with the following method:
Separation SFC Method
Column: 30.0×250 mm Regis Reflect C-Amylose A, 5 μm (Regis Technologies, Morton Grove, IL)
Mobile Phase: 30% $CO_2$+70% MeOH
Flow: 30 g/min
System Pressure: 140 bar
Column Temperature: 35 degrees C.
UV: 240 nm
Diluent: Methanol
Separation of R-6-MAPBT and S-6-MAPBT
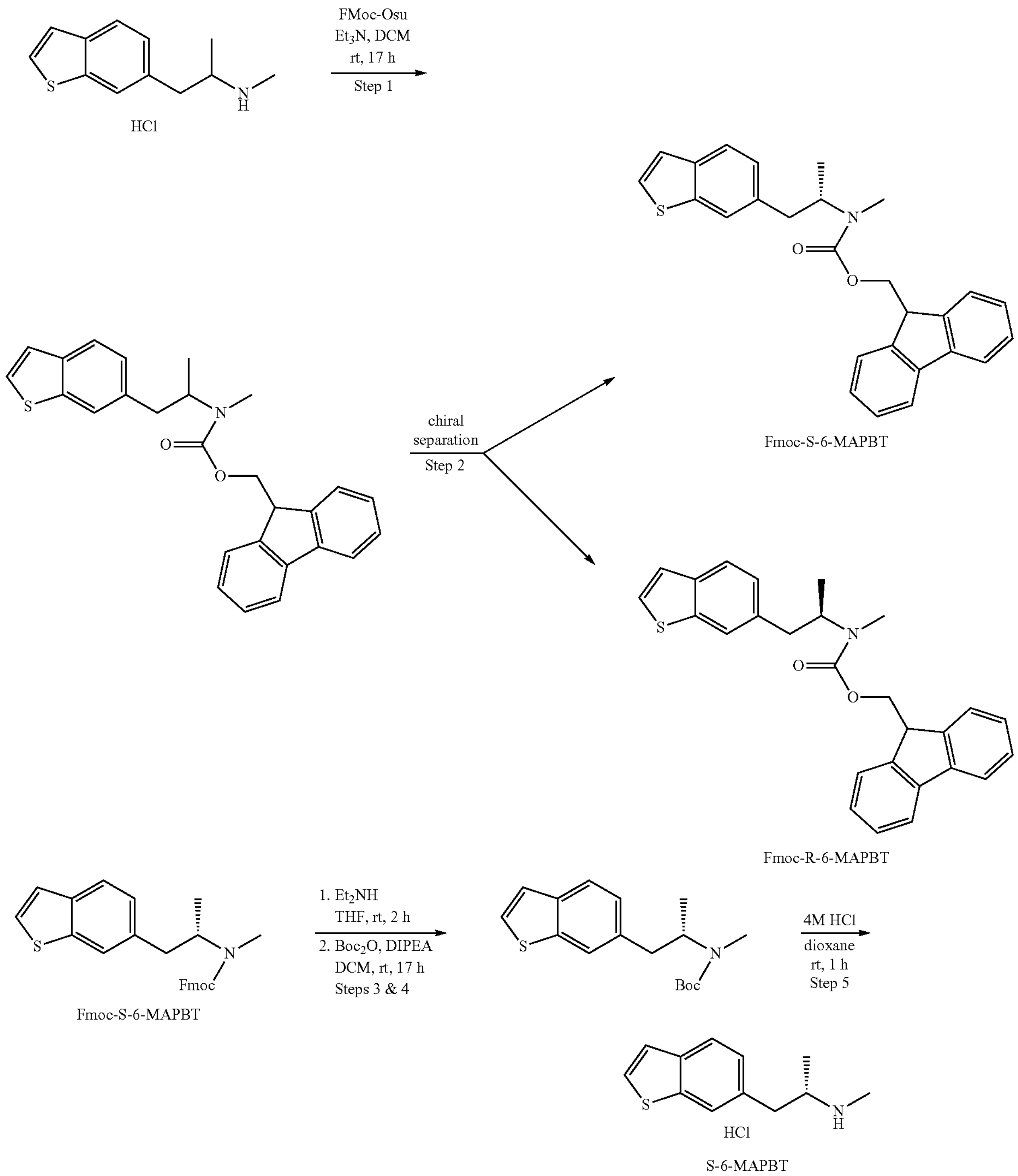
Fmoc-S-6-MAPBT
Fmoc-R-6-MAPBT
Fmoc-S-6-MAPBT
S-6-MAPBT -continued

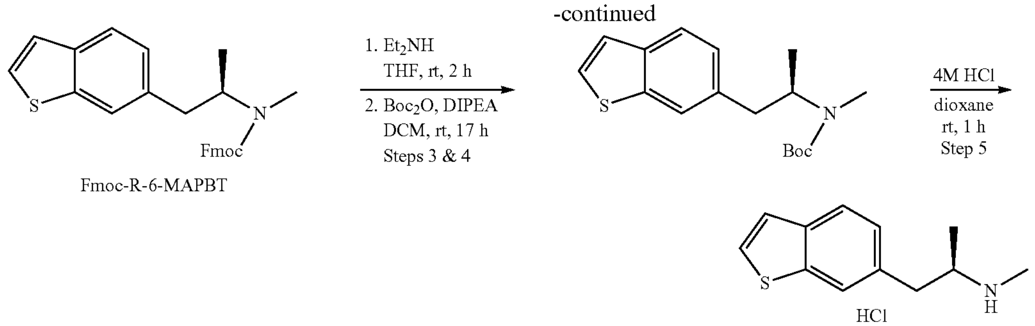

Fmoc-R-6-MAPBT

R-6-MAPBT

The chiral separation method used in Step 2 is performed with the following conditions:

Separation SFC Method

Column: 30.0×250 mm Regis Reflect C-Amylose A, 5 μm (Regis Technologies, Morton Grove, IL)

Mobile Phase: 30% $CO_2$+70% MeOH

Flow: 30 g/min

System Pressure: 140 bar

Column Temperature: 35 degrees C.

UV: 240 nm

Diluent: Methanol

Separation of Bk-5-MAPBT:

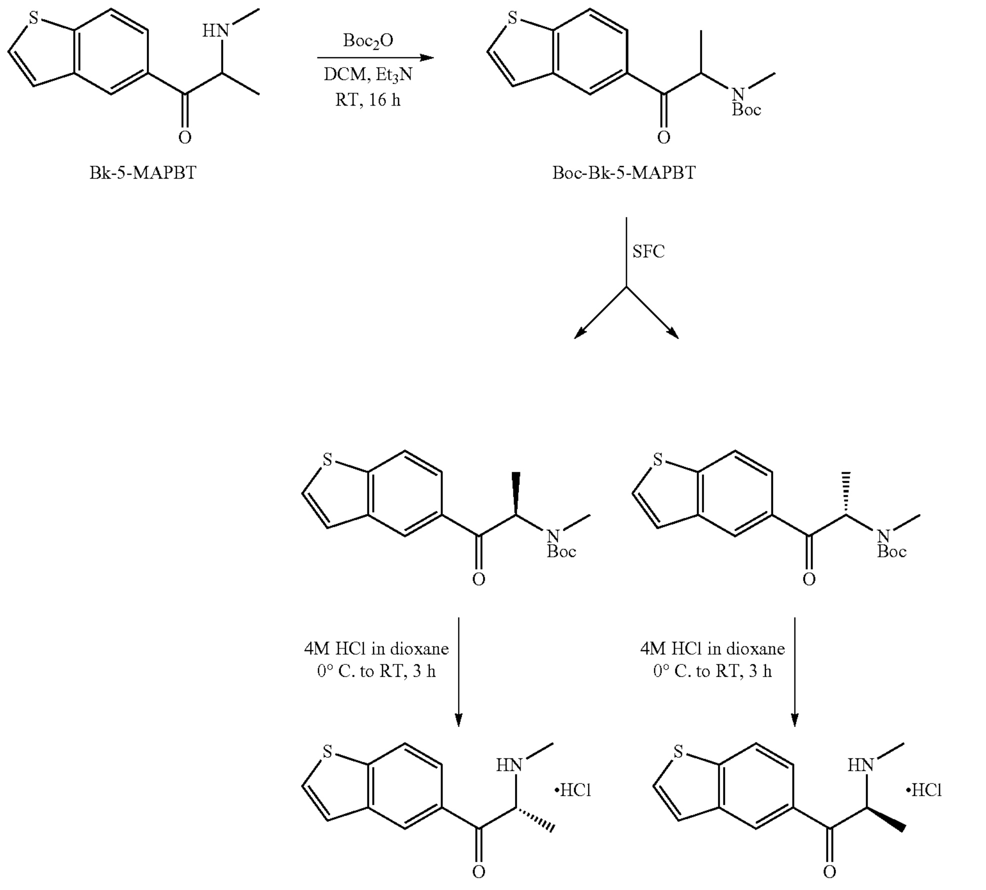

Bk-5-MAPBT

Boc-Bk-5-MAPBT

R-Bk-5-MAPBT

S-Bk-5-MAPBT

Isomeric Separation by SFC:

Isomeric separation of intermediate Boc-Bk-5-MAPBT is performed using SFC and the method of SFC separation given below:

Column: (R,R) Whelk-01 (4.5 mm×250 mm), 5 μm
Flow: 2 g/min
Mobile Phase: 75% CO2+25% (isopropyl alcohol)
ABPR: 100 bar
Temp: 35° C.
UV: 220 nm
Diluent: isopropyl alcohol Separation of Bk-6-MAPBT:

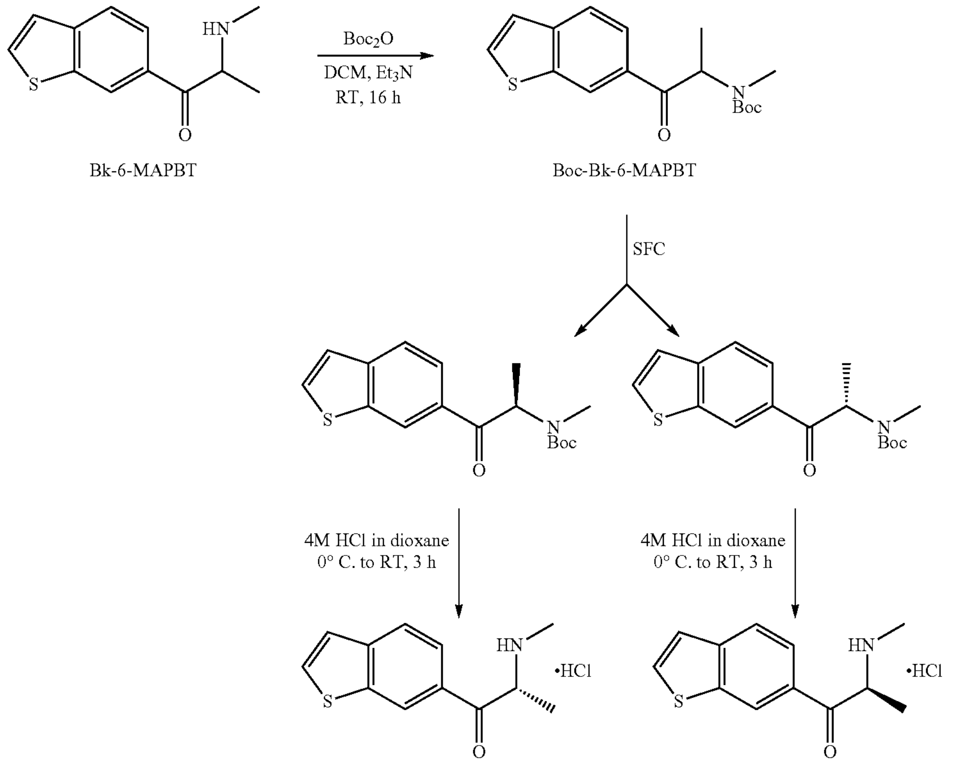

Bk-6-MAPBT
Boc-Bk-6-MAPBT
R-Bk-6-MAPBT
S-Bk-6-MAPBT

Isomeric Separation by SFC:

Isomer separation of Boc-Bk-6-MAPBT is performed using SFC and the method of SFC separation given below:

Column: (R,R) Whelk-01 (4.5 mm×250 mm), 5 μm
Flow: 2 g/min
Mobile Phase: 75% CO2+25% (isopropyl alcohol)
ABPR: 100 bar
Temp: 35° C.
UV: 220 nm
Diluent: isopropyl alcohol Determination of Specific Rotation Specific rotation is determined for individual enantiomers using a Jasco P-2000 Polarimeter, 589 nm Na lamp (Path Length 1 dm, 20° C. temperature, Concentration approx. 1 g/100 mL). EtOH is used as solvent for beta-ketone compounds, while distilled water is used for other compounds. Ten measurements are made for each compound.

Example 3: Serotonin Transporter (SERT, SLC6A4) Release Assay

An alternative, invasive method of measuring compound interactions with the serotonin transporter can be conducted according to the methods of Rothman and Baumann (Partilla et al. 2016. In: Bönisch S, Sitte HH (eds.) Neurotransmitter Transporters Springer; New York, pp. 41-52). In this assay, male Sprague-Dawley rats are euthanized by CO2 narcosis; brains, excluding the striatum and cerebellum, are processed to yield synaptosomes.

Synaptosomes are preloaded (to steady state) with [$^3$H] 5-HT in Krebs-phosphate buffer. Release assays are initiated by adding preloaded synaptosomes to test compound prepared in Krebsphosphate buffer containing BSA. Non-specific binding is determined in the presence of tyramine and total binding is determined in the presence of vehicle. Assays are terminated by rapid vacuum filtration/washing and retained radioactivity is quantified by a PerkinElmer TopCount® or similar.

The selectivity of the SERT assay is optimized for SERT by including unlabeled blockers to prevent uptake of [$^3$H] 5-HT by competing transporters (e.g., nomifensine to block NET and GBR12935 to block DAT). Substrate activity for releasers is confirmed by detecting a significant reversal of the releasing effect of the test compound in the presence of reuptake inhibitors. Release assays can be tested in the presence and absence of a known reuptake inhibitor, such as citalopram, which is a known blocker for the SERT substrate reversal assay.

Example 4: Marble Burying Measure of Decreased Anxiety and Neuroticism

The marble burying test is a model of neophobia, anxiety, and obsessive-compulsive behavior that has been proposed to have predictive validity for the screening of novel anti-depressants and anxiolytics. Rodents use bedding material to bury noxious as well as harmless objects. It is well established to be sensitive to the effects of SSRIs as well as serotonin releasers such as fenfluramine and MDMA (De Brouwer et al., Cognitive, Affective, and Behavioral Neuroscience, 2019, 19(1), 1-39). The test involves the placement of a standardized number of marbles gently onto the surface of a layer of bedding material within a testing arena. Mice are then introduced into the arena for a standardized amount of time and allowed to explore the environment. The outcome measure of the test is the number of marbles covered, as scored by automatic scoring software or blinded observers. Compounds that attenuate anxiety, neuroticism, or obsessive-compulsive behavior decrease marble burying. Racemic 5-MAPBT, 6-MAPBT, 5-EAPBT, and BK-5-MAPBT were assessed with this assay, and every tested compound displayed dose-dependent anxiolytic effects. The results are shown in FIG. 3, FIG. 4, FIG. 5, and FIG. 6.

Marble Burying Experimental Methods

Marble burying experiments were conducted by trained and authorized personnel and were in compliance with applicable guidelines for experiments with laboratory animals. Manipulation of animals was conducted carefully to reduce stress to a minimum. Experimental conditions always included at least 10 animals per group.

Animal Care

Test animals were Swiss CD 1 mice, 5-6 weeks old, that had not been subjected to prior experiments.

Housing Conditions

| | |
|---|---|
| Housing | Group housing (8-9 mice/cage): 1290D Eurostandard Type III cages (Tecniplast, Italy) in transparent polycarbonate (42.5 cm deep; 26.6 cm large; 15.5 cm high, area = 820 $cm^2$). Cages are covered with a stainless-steel grid in which food and a bottle are placed. A stainless-steel removable divider separates food and water |
| Litter | Aspen Small (SDS Dietex, France) |
| Enrichment | Cell huts |
| Temperature | 21.5 ± 1.5° C. |
| Hygrometry | 50 ± 30% (measured but not controlled) |
| Air renewal | Fresh air, 12-25 vol/h |
| Lighting | 20-30 Lux |
| Day/night cycle | Normal 12 h/12 h cycle; light on 8:00-20:00/off: 20:00-8:00 |
| Food | Rat-mouse A04 (Safe, France) available ad libitum |
| Drink | Tap water, available ad libitum |

Experimental Arenas

The experiment was conducted in eight Plexiglas transparent open boxes (42 cm L, 42 cm W, 40 cm H) filled with 5 cm sawdust. Twenty-five clean glass marbles (15 mm diameter) were evenly spaced 5 cm apart on sawdust.

Testing Procedure

Testing was carried out during the dark phase, in standardized conditions (T°=22.0±1.5° C.), with artificial light (20 Lux at the level of the apparatus) and low ambient noise (mostly coming from the ventilation system and the experimental apparatus).

Test compounds or placebo vehicle were administered intraperitoneally 30 minutes before animals were individually placed in an experimental apparatus for a 30-min session.

The number of marbles at least ⅔ buried was counted at the end of the session as the primary outcome measure. Results were generally displayed with scores inverted (proportion of marble left unburied) and expressed as magnitude difference-from-placebo with error bars indicating 95% confidence intervals.

Example 5: In Vitro Activity Studies

Select compounds of the present invention were tested for activity at 47 target sites at ten concentrations up to 10 μM (5-MAPBT and 6-MAPBT) or 30 μM (5-EAPBT and BK-5-MAPBT), with $EC_{50}$ or $IC_{50}$ determined whenever possible. In Table 2 below, $EC_{50}$ values are for the test compound acting as an agonist or opener while $IC_{50}$ values are for the test compound acting as an antagonist, blocker, or inhibitor.

TABLE 2

In Vitro Activity Results

| | 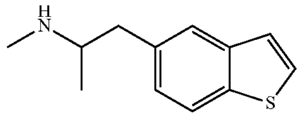 5-MAPBT | | 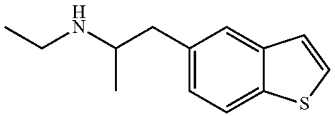 5-EAPBT | | 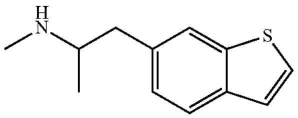 6-MAPBT | | 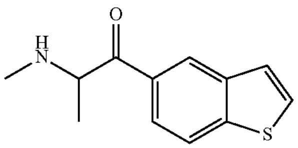 Bk-5-MAPBT | |
|---|---|---|---|---|---|---|---|---|
| Assay Target/ Assay Type | $EC_{50}$ (μM) | $EC_{50}$ (μM) | $EC_{50}$ (μM) | $EC_{50}$ (μM) | $EC_{50}$ (μM) | $EC_{50}$ (μM) | $EC_{50}$ (μM) | $EC_{50}$ (μM) |
| Serotonergic Receptors | | | | | | | | |
| 5-HT1B/cAMP | 0.038 | >10 | 4.578 | >30 | 0.024 | >10 | 0.059 | >30 |
| 5-HT2A/Calcium Flux | 2.728 | 3.840 | >30 | >30 | 0.959 | 1.715 | >30 | >30 |
| 5-HT2B/Calcium Flux | >10 | 0.102 | >30 | >30 | >10 | 0.072 | >30 | 3.20 |
| 5-HT3A/Ion Channel | >10 | >10 | >10 | >30 | >10 | 5.180 | >30 | 15.567 |
| 5-HT1A/cAMP | >10 | >10 | >30 | >30 | >10 | >10 | >30 | >30 |
| Other GPCRs | | | | | | | | |
| ADRA1A/Calcium Flux | >10 | 5.275 | >30 | >30 | >10 | 3.431 | >30 | 19.378 |
| ADRA2A/cAMP | >10 | >10 | >30 | >30 | >10 | >10 | >30 | 27.681 |
| ADRB2/cAMP | >10 | 4.605 | >30 | >30 | >10 | 5.788 | >30 | 9.883 |
| HRH1/Calcium Flux | >10 | 2.244 | >30 | >30 | >10 | >10 | >30 | 9.668 |
| ADORA2A/Calcium Flux | >10 | >10 | >30 | >30 | >10 | >10 | >30 | >30 |
| ADRB1/cAMP | >10 | >10 | >30 | >30 | >10 | >10 | >30 | >30 |
| AVPR1A/Calcium Flux | >10 | >10 | >30 | >30 | >10 | >10 | >30 | >30 |
| CCKAR/Calcium Flux | >10 | >10 | >30 | >30 | >10 | >10 | >30 | >30 |
| CHRM1/Calcium Flux | >10 | >10 | >30 | >30 | >10 | >10 | >30 | >30 |
| CHRM2/cAMP | >10 | >10 | >30 | >30 | >10 | >10 | >30 | >30 |
| CHRM3/Calcium Flux | >10 | >10 | >30 | >30 | >10 | >10 | >30 | >30 |
| CNR1/cAMP | >10 | >10 | >30 | >30 | >10 | >10 | >30 | >30 |
| CNR2/cAMP | >10 | >10 | >30 | >30 | >10 | >10 | >30 | >30 |
| DRD1/cAMP | >10 | >10 | >30 | >30 | >10 | >10 | >30 | >30 |
| DRD2S/cAMP | >10 | >10 | >30 | >30 | >10 | >10 | >30 | >30 |
| EDNRA/Calcium Flux | >10 | >10 | >30 | >30 | >10 | >10 | >30 | >30 |
| HRH2/cAMP | >10 | >10 | >30 | >30 | >10 | >10 | >30 | >30 |
| OPRD1/cAMP | >10 | >10 | >10 | >30 | >10 | >10 | >30 | >30 |
| OPRK1/cAMP | >10 | >10 | >10 | >30 | >10 | >10 | >30 | >30 |
| OPRM1/cAMP | >10 | >10 | >10 | >30 | >10 | >10 | >30 | >30 |
| Other Ion Channels | | | | | | | | |
| nAChR(a4/b2)/Ion Channel | >10 | 7.774 | >10 | >30 | >10 | 4.441 | >30 | >30 |
| NAV1.5/Ion Channel | | >10 | | >30 | | >10 | | 28.888 |
| CAV1.2/Ion Channel | | >10 | | >30 | | >10 | | >30 |
| GABAA/Ion Channel | >10 | >10 | >30 | >30 | >10 | >10 | >30 | >30 |
| hERG/Ion Channel | | >10 | | >30 | | >10 | | >30 |

TABLE 2-continued

In Vitro Activity Results

| | | | | | | | | |
|---|---|---|---|---|---|---|---|---|
| | 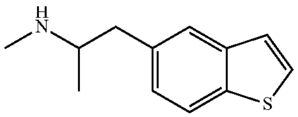 5-MAPBT | | 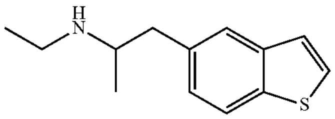 5-EAPBT | | 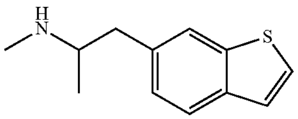 6-MAPBT | | 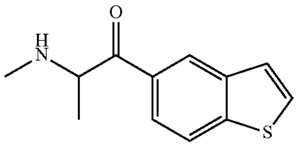 Bk-5-MAPBT | |
| Assay Target/ Assay Type | $EC_{50}$ (μM) | $EC_{50}$ (μM) | $EC_{50}$ (μM) | $EC_{50}$ (μM) | $EC_{50}$ (μM) | $EC_{50}$ (μM) | $EC_{50}$ (μM) | $EC_{50}$ (μM) |
| KvLQT1/minK/Ion Channel | >10 | >10 | >10 | >30 | >10 | >10 | >30 | >30 |
| NMDAR (1A/2B)/Ion Channel | >10 | >10 | >10 | >30 | >10 | >10 | >30 | >30 |
| Monoamine Transporters | | | | | | | | |
| DAT/Transporter | | 0.694 | | 4.344 | | 0.320 | | 2.258 |
| NET/Transporter | | 4.421 | | >30 | | 0.684 | | 1.158 |
| SERT/Transporter | | 6.902 | | >30 | | >10 | | 10.221 |
| Enzymes | | | | | | | | |
| MAOA/Enzymatic | | 0.765 | | 9.763 | | 0.945 | | 14.690 |
| AChE/Enzymatic | | >10 | | >30 | | >10 | | >30 |
| COX1/Enzymatic | | >10 | | >30 | | >10 | | >30 |
| COX2/Enzymatic | | >10 | | >30 | | >10 | | >30 |
| PDE3AEnzymatic/ | | >10 | | >30 | | >10 | | >30 |
| PDE4D2/Enzymatic | | >10 | | >30 | | >10 | | >30 |
| Kinases | | | | | | | | |
| ROCK1/Binding | | >10 | | >30 | | >10 | | 9.331 |
| INSR/Binding | | >10 | | >30 | | >10 | | >30 |
| AR/NHR Nuclear Translocation | >10 | >10 | >30 | >30 | >10 | >10 | >30 | >30 |
| GR/NHR Protein Interaction | >10 | >10 | >30 | >30 | >10 | >10 | >30 | >30 |
| LCK/Binding | | >10 | | >30 | | >10 | | >30 |
| VEGFR2/Binding | | >10 | | >30 | | >10 | | >30 |

In Vitro Assay Methods

Concentrations of test compounds were either 0.00152416, 0.0045724, 0.0137174, 0.041152, 0.123456, 0.37038, 1.11112, 3.3334, 10, and 30 μM (for 5-EAPBT and BK-5-MAPBT) or 0.00050806, 0.00152416, 0.0045724, 0.0137174, 0.041152, 0.123456, 0.37038, 1.11112, 3.3334, and 10 μM (for 5-MAPBT and 6-MAPBT).

CAMP Secondary Messenger Assays

CAMP secondary messenger assays used cell lines that stably expressed non-tagged GPCRs. Hit Hunter® CAMP assays monitored the activation of a GPCR via Gi and Gs secondary messenger signaling in a homogenous, non-imaging assay format using Enzyme Fragment Complementation (EFC) with β-galactosidase (β-gal) as the functional endpoint. For the assay system, exogenously introduced Enzyme Donor (ED) fused to cAMP (ED-cAMP) competed with endogenously generated cAMP for binding to an anti-cAMP-specific antibody. Active β-gal was formed by complementation of exogenous Enzyme Acceptor (EA) to any unbound ED-cAMP. Active enzyme was then converted a chemiluminescent substrate, generating an output signal detected on a standard microplate reader.

Specific assay steps and reference compounds are given below for each assay type.

Calcium Flux Secondary Messenger Assays

The Calcium No Wash$^{PLUS}$ assay was used to monitor GPCR activity via Gq secondary messenger signaling in a live cell, non-imaging assay format. Calcium mobilization in PathHunter® cell lines or other cell lines stably expressing Gq-coupled GPCRs was monitored using calcium-sensitive dye loaded into cells. GPCR activation by a compound resulted in the release of calcium from intracellular stores and an increase in dye fluorescence that was measured in real-time.

Specific assay steps and reference compounds are given below for each assay type.

Nuclear Hormone Receptor Assays

PathHunter® NHR Protein Interaction (NHR Pro) and Nuclear Translocation (NHR NT) assays monitored the activation of specific nuclear hormone receptors in a homogenous, non-imaging assay format using Enzyme Fragment Complementation (EFC). The NHR Pro assay is based on detection of protein-protein interactions between an activated, full length NHR protein and a nuclear fusion protein containing Steroid Receptor Co-activator Peptide (SRCP) domains with one or more canonical LXXLL interaction motifs.

The NHR was tagged with the ProLink™ (PK) component of the DiscoverX EFC assay system, and the SRCP domain was fused to the Enzyme Acceptor component (EA) expressed in the nucleus. When bound by ligand, the NHR migrates to the nucleus and recruits the SRCP domain, whereby complementation occurs, generating a unit of active β-galactosidase (p-gal) and production of chemiluminescent signal upon the addition of PathHunter detection reagents.

The NHR NT assay monitored movement of an NHR between the cytoplasmic and nuclear compartments. The receptor was tagged with the ProLabel™ (PL) component of the EFC assay system, and EA was fused to a nuclear location sequence that restricted the expression of EA to the nucleus. Migration of the NHR to the nucleus resulted in complementation with EA generating a unit of active B-gal and production of a chemiluminescent signal upon the addition of Path Hunter detection reagents.

Specific assay steps and reference compounds are given below for each assay type.

KINOMEscan® Assays

Kinase activity was measured using the KINOMEscan screening platform, which employs a site-directed competition binding assay to quantitatively measure interactions between test compounds and the kinases. Compounds that bind the kinase active site and directly (sterically) or indirectly (allosterically) prevent kinase binding to the immobilized ligand, will reduce the amount of kinase captured on the solid support (A and B). Conversely, test molecules that do not bind the kinase have no effect on the amount of kinase captured on the solid support (C). Screening "hits" were identified by measuring the amount of kinase captured in test versus control samples by using a quantitative, precise and ultra-sensitive qPCR method that detects the associated DNA label (D). In a similar manner, dissociation constants (Kds) for test compound-kinase interactions were calculated by measuring the amount of kinase captured on the solid support as a function of the test compound concentration.

Specific assay steps and reference compounds are given below for each assay type.

Monoamine Transporter Uptake Assays

The Neurotransmitter Transporter Uptake Assay Kit from Molecular Devices was used as a homogeneous fluorescence-based assay for the detection of dopamine, norepinephrine or serotonin transporter activity in cells expressing these transporters. The kit employs a fluorescent substrate that mimics the biogenic amine neurotransmitters that are taken into the cell through these specific transporters, resulting in increased intracellular fluorescence intensity.

It should be noted that fluorescence-based assays for the detection of dopamine, norepinephrine or serotonin transporter activity have poor sensitivity for compounds that are substrates for these monoamine transporters. We therefore separately measured interactions with these transporters using two additional types of assays: an antagonist radioligand assay of inhibition of the human 5-HT transporter (hSERT) expressed in CHO cells (Tatsumi, M. et al. (1999), Eur. J. Pharmacol., 368: 277-283) and an assay measuring release of [$^3$H] Serotonin or [$^3$H] dopamine, respectively, from cells stably expressing SERT or DAT. While the former is sensitive to classic reuptake inhibition, the latter can detect the effects of substrates, which also induce release.

Specific assay steps and reference compounds are given below for each assay type.

Potassium Assay

The FLIPR Potassium Assay Kit from Molecular Devices was used for ion channel assays. This approach exploited the permeability of thallium ions (Tl+) through both voltage and ligand-gated potassium (K+) channels. A highly sensitive Tl+ indicator dye produced a bright fluorescent signal upon the binding to Tl+ conducted through potassium channels. The intensity of the Tl+ signal was proportional to the number of potassium channels in the open state and therefore provided a functional indication of the potassium channel activities. In addition, a masking dye was included to reduce background fluorescence for improved signal/noise ratio.

Specific assay steps and reference compounds are given below for each assay type.

Membrane Potential Assay

The FLIPR® Membrane Potential Assay Kit was used which employs a fluorescent indicator dye in combination with a quencher to reflect real-time membrane potential changes associated with ion channel activation and ion transporter proteins. Unlike traditional dyes such as DiBAC, the FLIPR Membrane Potential Assay Kit detects bidirectional ion fluxes so both variable and control conditions can be monitored within a single experiment.

Specific assay steps and reference compounds are given below for each assay type.

Calcium Assays

The DiscoveRx Calcium NWPLUS Assay Kit was used for detection of changes in intracellular calcium. Cells expressing a receptor of interest that signals through calcium were preloaded with a calcium sensitive dye and then treated with compound. Upon stimulation, the receptor signaled release of intracellular calcium, which resulted in an increase of dye fluorescence. Signal was measured on a fluorescent plate reader equipped with fluidic handling capable of detecting rapid changes in fluorescence upon compound stimulation.

Specific assay steps and reference compounds are given below for each assay type.

Enzymatic Assays

Enzymatic assays determined enzymatic activity by measuring either the consumption of substrate or production of product over time. Different detection methods were used in each enzymatic assay to measure the concentrations of substrates and products, including spectrophotometric, fluorometric, and luminescent readouts.

Specific assay steps and reference compounds are given below for each assay type.

Assay Design: GPCR cAMP Modulation

Cell Handling 1. cAMP Hunter cell lines were expanded from freezer stocks according to standard procedures.
2. Cells were seeded in a total volume of 20 μL into white walled, 384-well microplates and incubated at 37° C. for the appropriate time prior to testing.
3. cAMP modulation was determined using the DiscoverX HitHunter cAMP XS+ assay.

Gs Agonist Format

1. For agonist determination, cells were incubated with sample to induce response.
2. Media was aspirated from cells and replaced with 15 μL 2:1 HBSS/10 mM Hepes: cAMP XS+ Ab reagent.
3. Intermediate dilution of sample stocks was performed to generate 4× sample in assay buffer.
4. 5 μL of 4× sample was added to cells and incubated at 37° C. or room temperature for 30 or 60 minutes.

Gi Agonist Format

1. For agonist determination, cells were incubated with sample in the presence of $EC_{80}$ forskolin to induce response.
2. Media was aspirated from cells and replaced with 15 μL 2:1 HBSS/10 MM Hepes: cAMP XS+ Ab reagent.
3. Intermediate dilution of sample stocks was performed to generate 4× sample in assay buffer containing 4× $EC_{80}$ forskolin.
4. 5 μL of 4× sample was added to cells and incubated at 37° C. or room temperature for 30 or 60 minutes.

Antagonist Format

1. For antagonist determination, cells were pre-incubated with sample followed by agonist challenge at the EC80 concentration.
2. Media was aspirated from cells and replaced with 10 μL 1:1 HBSS/Hepes: cAMP XS+ Ab reagent.
3. 5 μL of 4× compound was added to the cells and incubated at 37° C. or room temperature for 30 minutes.
4. 5 μL of 4× $EC_{80}$ agonist was added to cells and incubated at 37° C. or room temperature for 30 or 60 minutes. For Gi coupled GPCRs, $EC_{80}$ forskolin was included.

Signal Detection

1. After appropriate compound incubation, assay signal was generated through incubation with 20 μL cAMP XS+ ED/CL lysis cocktail for one hour followed by incubation with 20 μL cAMP XS+ EA reagent for three hours at room temperature.
2. Microplates were read following signal generation with PerkinElmer Envision instrument for chemiluminescent signal detection.

Data Analysis

Compound activity was analyzed using CBIS data analysis suite (ChemInnovation, CA). For Gs agonist mode assays, percentage activity was calculated using the following formula: % Activity=100%×(mean RLU of test sample−mean RLU of vehicle control)/(mean RLU of MAX control−mean RLU of vehicle control).

For Gs antagonist mode assays, percentage inhibition was calculated using the following formula: % Inhibition=100%×(1−(mean RLU of test sample−mean RLU of vehicle control)/(mean RLU of $EC_{80}$ control−mean RLU of vehicle control)).

For Gi agonist mode assays, percentage activity was calculated using the following formula: % Activity=100%×(1−(mean RLU of test sample−mean RLU of MAX control)/(mean RLU of vehicle control−mean RLU of MAX control)).

For Gi antagonist or negative allosteric mode assays, percentage inhibition was calculated using the following formula: % Inhibition=100%×(mean RLU of test sample−mean RLU of $EC_{80}$ control)/(mean RLU of forskolin positive control−mean RLU of $EC_{80}$ control).

For Primary screens, percent response was capped at 0% or 100% where calculated percent response returned a negative value or a value greater than 100, respectively.

Assay Design: Calcium Mobilization

Cell Handling

1. Cell lines were expanded from freezer stocks according to standard procedures.
2. Cells (10,000 cells/well) were seeded in a total volume of 50 μL (200 cells/μL) into black-walled, clear-bottom, Poly-D-lysine coated 384-well microplates and incubated at 37° C. for the appropriate time prior to testing.

Dye Loading

1. Assays were performed in 1× Dye Loading Buffer consisting of 1× Dye (DiscoverX, Calcium No Wash PLUS kit, Catalog No. 90-0091), 1× Additive A and 2.5 mM Probenecid in HBSS/20 mM Hepes. Probenecid was prepared fresh.
2. Cells were loaded with dye prior to testing. Media was aspirated from cells and replaced with 25 μL Dye Loading Buffer.
3. Cells were incubated for 45 minutes at 37° C. and then 20 minutes at room temperature.

Agonist Format

1. For agonist determination, cells were incubated with sample to induce response.
2. After dye loading, cells were removed from the incubator and 25 μL of 2× compound in HBSS/20 mM Hepes was added using a FLIPR Tetra (MDS).
3. Compound agonist activity was measured on a FLIPR Tetra. Calcium mobilization was monitored for 2 minutes with a 5 second baseline read.

Antagonist Format

1. For antagonist determination, cells were pre-incubated with sample followed by agonist challenge at the $EC_{80}$ concentration.
2. After dye loading, cells were removed from the incubator and 25 μL 2× sample was added. Cells were incubated for 30 minutes at room temperature in the dark to equilibrate plate temperature.
3. After incubation, antagonist determination was initiated with addition of 25 μL 1× compound with 3× $EC_{80}$ agonist using FLIPR
4. Compound antagonist activity was measured on a FLIPR Tetra (MDS). Calcium mobilization was monitored for 2 minutes with a 5 second baseline read.

Data Analysis

FLIPR read—Area under the curve was calculated for the entire two minute read.

Compound activity was analyzed using CBIS data analysis suite (ChemInnovation, CA).

For agonist mode assays, percentage activity was calculated as: % Activity=100%×(mean RFU of test sample−mean RFU of vehicle control)/(mean MAX RFU control ligand−mean RFU of vehicle control).

For antagonist mode assays, percentage inhibition was calculated as: % Inhibition=100%×(1−(mean RFU of test sample−mean RFU of vehicle control)/(mean RFU of EC80 control−mean RFU of vehicle control)).

For Primary screens, percent response was capped at 0% or 100% where calculated percent response returned a negative value or a value greater than 100, respectively.

Assay Design: Nuclear Hormone Receptor

Cell Handling

1. PathHunter NHR cell lines were expanded from freezer stocks according to standard procedures.
2. Cells were seeded in a total volume of 20 μL into white walled, 384-well microplates and incubated at 37° C. for the appropriate time prior to testing. Assay media contained charcoal-dextran filtered serum to reduce the level of hormones present.

Agonist Format

1. For agonist determination, cells were incubated with sample to induce response.
2. Intermediate dilution of sample stocks was performed to generate 5× sample in assay buffer.
3. 5 μL of 5× sample was added to cells and incubated at 37° C. or room temperature for 3-16 hours.

Antagonist Format

1. For antagonist determination, cells were pre-incubated with antagonist followed by agonist challenge at the $EC_{80}$ concentration.
2. Intermediate dilution of sample stocks was performed to generate 5× sample in assay buffer.
3. 5 μL of 5× sample was added to cells and incubated at 37° C. or room temperature for 60 minutes. Vehicle concentration was 1%.
4. 5 μL of 6× EC80 agonist in assay buffer was added to the cells and incubated at 37° C. or room temperature for 3-16 hours.

Signal Detection

1. Assay signal was generated through a single addition of 12.5 or 15 μL (50% v/v) of PathHunter Detection reagent cocktail, followed by a one hour incubation at room temperature.
2. Microplates were read following signal generation with a PerkinElmer Envision instrument for chemiluminescent signal detection.

Data Analysis

Compound activity was analyzed using CBIS data analysis suite (ChemInnovation, CA).

For agonist mode assays, percentage activity was calculated as: % Activity=100%×(mean RLU of test sample−mean RLU of vehicle control)/(mean MAX control ligand−mean RLU of vehicle control).

For antagonist mode assays, percentage inhibition was calculated as: % Inhibition=100%×(1−(mean RLU of test sample−mean RLU of vehicle control)/(mean RLU of EC80 control−mean RLU of vehicle control)).

Note that for select assays, the ligand response produces a decrease in receptor activity (inverse agonist with a constitutively active target). For those assays inverse agonist activity was calculated as: % Inverse Agonist Activity=100%×((mean RLU of vehicle control−mean RLU of test sample)/(mean RLU of vehicle control−mean RLU of MAX control)).

For Primary screens, percent response was capped at 0% or 100% where calculated percent response returned a negative value or a value greater than 100, respectively.

Assay Design: KINOMEscan Binding Assays

Protein Expression

For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 μM) to remove cell debris. The remaining kinases were produced in HEK-293 cells and subsequently tagged with DNA for qPCR detection.

Capture Ligand Production

Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding.

Binding Reaction Assembly

Binding reactions were assembled by combining kinases, liganded affinity beads, and test compounds in 1× binding buffer (20% SeaBlock, 0.17×PBS, 0.05% Tween 20, 6 mM DTT). All reactions were performed in polypropylene 384-well plates in a final volume of 0.02 mL. The assay plates were incubated at room temperature with shaking for 1 hour and the affinity beads were washed with wash buffer (lx PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Signal Detection

The kinase concentration in the eluates was measured by qPCR. qPCR reactions were assembled by adding 2.5 μL of kinase eluate to 7.5 μL of qPCR master mix containing 0.15 μM amplicon primers and 0.15 μM amplicon probe. The qPCR protocol consisted of a 10 minute hot start at 95° C., followed by 35 cycles of 95° C. for 15 seconds, 60° C. for 1 minute.

Data Analysis

Percent response was calculated using the formula:

100*(test compound signal−positive control signal)/(negative compound signal−positive control signal)

where:

Test compound=compound submitted by Customer

Negative control=DMSO (100% Ctrl)

Positive control=control compound (0% Ctrl)

Percent of Control was converted to Percent Response with the conversion:

Percent Response=(100−Percent Control).

For Primary screens, percent response was capped at 0% or 100% where calculated percent response returned a negative value or a value greater than 100, respectively.

Binding Constants (Kds)

Binding constants (Kds) were calculated with a standard dose response curve using the Hill equation with Hill Slope set to −1. Curves were fitted using a non-linear least square fit with the Levenberg-Marquardt algorithm.

Assay Design: Ion Channel Assays

Cell Handling

1. Cell lines were expanded from freezer stocks according to standard procedures.
2. Cells were seeded in a total volume of 20 μL into black-walled, clear-bottom, Poly-D-lysine coated 384-well microplates and incubated at 37° C. for the appropriate time prior to testing.

Dye Loading

1. Assays were performed in 1× Dye Loading Buffer consisting of 1× Dye, and 2.5 mM Probenecid when applicable. Probenecid was prepared fresh.
2. Cells were loaded with dye prior to testing.
3. Cells were incubated for 30-60 minutes at 37° C.

Agonist/Opener Format

1. For agonist determination, cells were incubated with sample to induce response.
2. Intermediate dilution of sample stocks was performed to generate 2-5× sample in assay buffer.
3. 10-25 μL of 2-5× sample was added to cells and incubated at 37° C. or room temperature for 30 minutes.

Antagonist/Blocker Format

1. For antagonist determination, cells were pre-incubated with sample.
2. Intermediate dilution of sample stocks was performed to generate 2-5× sample in assay buffer.
3. After dye loading, cells were removed from the incubator and 10-25 μL 2-5× sample was added to cells in the presence of EC80 agonist when appropriate. Cells were incubated for 30 minutes at room temperature in the dark to equilibrate plate temperature.

Signal Detection

Compound activity was measured on a FLIPR Tetra (MDS).

Data Analysis

Compound activity was analyzed using CBIS data analysis suite (ChemInnovation, CA). For agonist mode assays, percentage activity was calculated using the following formula: % Activity=100%×(mean RLU of test sample−mean RLU of vehicle control)/(mean MAX control ligand−mean RLU of vehicle control).

For antagonist percentage inhibition was calculated using the following formula: % Inhibition=100%×(1−(mean RLU of test sample−mean RLU of vehicle control)/(mean RLU of EC80 control−mean RLU of vehicle control)).

For Primary screens, percent response was capped at 0% or 100% where calculated percent response returned a negative value or a value greater than 100, respectively.

Assay Design: Transporter Assays

Cell Handling

1. Cell lines were expanded from freezer stocks according to standard procedures.
2. Cells were seeded in a total volume of 25 μL into black-walled, clear-bottom, Poly-D-lysine coated 384-well microplates and incubated at 37° C. for the appropriate time prior to testing.

Blocker/Antagonist Format

1. After cell plating and incubation, media was removed and 25 μL of 1× compound in 1× HBSS/0.1% BSA was added.
2. Compounds were incubated with cells at 37° C. for 30 minutes.

Dye Loading

1. Assays were performed in 1× Dye Loading Buffer consisting of 1× Dye, 1×HBSS/20 mM Hepes.
2. After compound incubation, 25 μL of 1× dye was added to wells.
3. Cells were incubated for 30-60 minutes at 37° C.

Signal Detection

After dye incubation, microplates were transferred to a PerkinElmer Envision instrument for fluorescence signal detection.

Data Analysis

Compound activity was analyzed using CBIS data analysis suite (ChemInnovation, CA).

For blocker mode assays, percentage inhibition was calculated using the following formula: % Inhibition=100%×(1−(mean RLU of test sample−mean RLU of vehicle control)/(mean RLU of positive control−mean RLU of vehicle control)).

For Primary screens, percent response was capped at 0% or 100% where calculated percent response returned a negative value or a value greater than 100, respectively.

Assay Design: Enzymatic Assays

Enzyme Preparations

Enzyme preparations were sourced from various vendors: AChE (R&D Systems), COX1 and COX2 (BPS Bioscience), MAOA (Sigma), PDE3A and PDE4D2 (Signal Chem).

Enzyme Activity Assays

1. Enzymatic assays determine the enzymatic activity by measuring either the consumption of substrate or production of product over time. Different detection methods were used in each enzymatic assay to measure the concentrations of value greater than 100, respectively. substrates and products.
2. ACHE: Enzyme and test compound were preincubated for 15 minutes at room temp before substrate addition. Acetylthiocholine and DTNB were added and incubated at room temperature for 30 minutes. Signal was detected by measuring absorbance at 405 nm.
3. COX1 & COX2: Enzyme stocks were diluted in Assay Buffer (40 mM Tris-HCl, 1× PBS, 0.5 mM Phenol, 0.01% Tween-20+100 nM Hematin) and allowed to equilibrate with compounds at room temperature for 30 minutes (binding incubation). Arachidonic acid (1.7 μM) and Ampliflu Red (2.5 μM) were prepared and dispensed into a reaction plate. Plates were read immediately on a fluorimeter with the emission detection at 590 nm and excitation wavelength 544 nm.
4. MAOA: Enzyme and test compound were preincubated for 15 minutes at 37° C. before substrate addition. The reaction was initiated by addition of kynuramine and incubated at 37° C. for 30 minutes. The reaction was terminated by addition of NaOH. The amount of 4-hydroquioline formed was determined through spectrofluorimetric readout with the emission detection at 380 nm and excitation wavelength 310 nm.

5. PDE3A & PDE4D2: Enzyme and test compound were preincubated for 15 minutes at room temp before substrate addition. cAMP substrate (at a concentration equal to $EC_{80}$) was added and incubated at room temperature for 30 minutes. Enzyme reaction was terminated by addition of 9 mM IBMX. Signal was detected using the HitHunter® cAMP detection kit.

Signal Detection

For each assay, microplates were transferred to a PerkinElmer Envision instrument and readout as described.

Data Analysis

Compound activity was analyzed using CBIS data analysis suite (ChemInnovation, CA). For enzyme activity assays, percentage inhibition was calculated using the following formula: % Inhibition=100%×(1−(mean RLU of test sample−mean RLU of vehicle control)/(mean RLU of positive control−mean RLU of vehicle control)).

For Primary screens, percent response was capped at 0% or 100% where calculated percent response returned a negative value or a value greater than 100, respectively.

TABLE 3

Target Names and Reference Compound Activity (Positive Controls) in Assays

| Target | Abbreviation | Mode | Reference Compound | Result Type | RC50 (μM) |
|---|---|---|---|---|---|
| 5-Hydroxytryptamine (Serotonin) Receptor 1A | 5-HTR1A | Agonist | Serotonin Hydrochloride | EC50 | 0.00395 |
| 5-Hydroxytryptamine (Serotonin) Receptor 1A | 5-HTR1A | Antagonist | Spiperone | IC50 | 0.10535 |
| 5-Hydroxytryptamine (Serotonin) Receptor 1B | 5-HTR1B | Agonist | Serotonin Hydrochloride | EC50 | 2.00E−04 |
| 5-Hydroxytryptamine (Serotonin) Receptor 1B | 5-HTR1B | Antagonist | SB 224289 | IC50 | 0.00606 |
| 5-Hydroxytryptamine (Serotonin) Receptor 2A | 5-HTR2A | Agonist | Serotonin Hydrochloride | EC50 | 0.00257 |
| 5-Hydroxytryptamine (Serotonin) Receptor 2A | 5-HTR2A | Antagonist | Altanserin | IC50 | 0.01553 |
| 5-Hydroxytryptamine (Serotonin) Receptor 2B | 5-HTR2B | Agonist | Serotonin Hydrochloride | EC50 | 0.00396 |
| 5-Hydroxytryptamine (Serotonin) Receptor 2B | 5-HTR2B | Antagonist | LY 272015 | IC50 | 3.00E−04 |
| 5-Hydroxytryptamine (Serotonin) Receptor 3A | 5-HTR3A | Blocker | Bemesetron | IC50 | 0.00305 |
| 5-Hydroxytryptamine (Serotonin) Receptor 3A | 5-HTR3A | Opener | Serotonin Hydrochloride | EC50 | 0.36698 |
| Acetylcholinesterase | ACHE | Inhibitor | Physostigmine | IC50 | 0.03747 |
| Adenosine Receptor A2A | ADORA2A | Antagonist | SCH 442416 | IC50 | 0.0798 |
| Adenosine Receptor A2A | ADORA2A | Agonist | NECA | EC50 | 0.01783 |
| Adrenergic Receptor on $\alpha_1$A | ADRA1A | Agonist | A 61603 Hydrobromide | EC50 | 9.00E−05 |
| Adrenergic Receptor on $\alpha_1$A | ADRA1A | Antagonist | Tamsulosin | IC50 | 0.00115 |
| Adrenergic Receptor on $\alpha_2$A | ADRA2A | Agonist | UK 14304 | EC50 | 6.00E−05 |
| Adrenergic Receptor on $\alpha_2$A | ADRA2A | Antagonist | Yohimbine | IC50 | 0.00463 |
| Adrenergic Receptor β1 | ADRB1 | Agonist | (−)-Isoproterenol | EC50 | 0.002 |
| Adrenergic Receptor β1 | ADRB1 | Antagonist | Betaxolol | IC50 | 0.0034 |
| Adrenergic Receptor β2 | ADRB2 | Agonist | (−)-Isoproterenol | EC50 | 3.00E−04 |
| Adrenergic Receptor β2 | ADRB2 | Antagonist | ICI 118,551 hydrochloride | IC50 | 0.00056 |
| Nuclear Hormone Androgen Receptor | AR | Agonist | 6a-Fluorotestosterone | EC50 | 0.00195 |
| Nuclear Hormone Androgen Receptor | AR | Antagonist | Geldanamycin | IC50 | 0.09429 |
| Arginine Vasopressin Receptor 1A | AVPR1A | Agonist | [$Arg^8$]-Vasopressin | EC50 | 0.00037 |
| Arginine Vasopressin Receptor 1A | AVPR1A | Antagonist | SR 49059 | IC50 | 0.00182 |
| Voltage-gated L-type calcium channel | CAV1.2 | Blocker | Isradipine | IC50 | 0.01691 |
| Cholecystokinin Receptor A | CCKAR | Agonist | ($Tyr[SO_3H]_{27}$) Cholecystokinin fragment 26-33 Amide | EC50 | 1.00E−04 |
| Cholecystokinin Receptor A | CCKAR | Antagonist | SR 27897 | IC50 | 0.03707 |
| Muscarinic acetylcholine Receptor M1 | CHRM1 | Agonist | Acetylcholine chloride | EC50 | 0.01621 |
| Muscarinic acetylcholine Receptor M1 | CHRM1 | Antagonist | Atropine | IC50 | 0.00306 |
| Muscarinic acetylcholine Receptor M2 | CHRM2 | Agonist | Acetylcholine chloride | EC50 | 0.02486 |
| Muscarinic acetylcholine Receptor M2 | CHRM2 | Antagonist | Atropine | IC50 | 0.00406 |
| Muscarinic acetylcholine Receptor M3 | CHRM3 | Agonist | Acetylcholine chloride | EC50 | 0.03952 |

TABLE 3-continued

Target Names and Reference Compound Activity (Positive Controls) in Assays

| Target | Abbreviation | Mode | Reference Compound | Result Type | RC50 (μM) |
|---|---|---|---|---|---|
| Muscarinic acetylcholine Receptor M3 | CHRM3 | Antagonist | Atropine | IC50 | 0.0015 |
| Cannabinoid Receptor 1 | CNR1 | Agonist | CP 55940 | EC50 | 4.00E−05 |
| Cannabinoid Receptor 1 | CNR1 | Antagonist | AM 251 | IC50 | 0.00324 |
| Cannabinoid Receptor 2 | CNR2 | Agonist | CP 55940 | EC50 | 0.00016 |
| Cannabinoid Receptor 2 | CNR2 | Antagonist | SR 144528 | IC50 | 0.03516 |
| Cyclooxygenase 1 | COX1 | Inhibitor | Indomethacin | IC50 | 0.0329 |
| Cyclooxygenase 2 | COX2 | Inhibitor | NS-398 | IC50 | 0.02245 |
| Dopamine transporter | DAT | Blocker | GBR 12909 | IC50 | 0.01456 |
| Dopamine Receptor D1 | DRD1 | Agonist | Dopamine | EC50 | 0.0855 |
| Dopamine Receptor D1 | DRD1 | Antagonist | SCH 39166 | IC50 | 0.00092 |
| Dopamine Receptor D2 | DRD2S | Agonist | Dopamine | EC50 | 0.001 |
| Dopamine Receptor D2 | DRD2S | Antagonist | Risperidone | IC50 | 0.00158 |
| Endothelin Receptor Type A | EDNRA | Agonist | Endothelin 1 | EC50 | 0.0011 |
| Endothelin Receptor Type A | EDNRA | Antagonist | BMS 182874 | IC50 | 1.10701 |
| Gamma-aminobutyric acid Receptor A | GABAA | Blocker | Picrotoxin | IC50 | 2.77847 |
| Gamma-aminobutyric acid Receptor A | GABAA | Opener | GABA | EC50 | 6.35785 |
| Nuclear Hormone Glucocorticoid Receptor | GR | Agonist | Dexamethasone | EC50 | 0.04971 |
| Nuclear Hormone Glucocorticoid Receptor | GR | Antagonist | Mifepristone | IC50 | 0.07236 |
| Nuclear Hormone Glucocorticoid Receptor | HERG | Blocker | Astemizole | IC50 | 0.22171 |
| Histamine Receptor H1 | HRH1 | Agonist | Histamine | EC50 | 0.03202 |
| Histamine Receptor H1 | HRH1 | Antagonist | Mepyramine | IC50 | 0.00538 |
| Histamine Receptor H2 | HRH2 | Agonist | Histamine | EC50 | 0.26388 |
| Histamine Receptor H2 | HRH2 | Antagonist | Tiotidine | IC50 | 0.13915 |
| Insulin Receptor (tyrosine kinase) | INSR | Inhibitor | BMS-754807 | IC50 | 0.00052 |
| Kv11.1, the alpha subunit of a potassium ion channel | KvLQT1/minK | Blocker | XE 991 | IC50 | 1.66819 |
| Kv11.1, the alpha subunit of a potassium ion channel | KvLQT1/minK | Opener | ML-277 | EC50 | 2.30579 |
| Lymphocyte Cell-Specific Protein-Tyrosine Kinase (Src family) | LCK | Inhibitor | Gleevec | IC50 | 13.36093 |
| Monoamine oxidase type A | MAOA | Inhibitor | Clorgyline | IC50 | 0.00446 |
| Nicotinic acetylcholine Receptor α4 β2 | nACHR (a4/b2) | Blocker | Dihydro-AY-erythroidine | IC50 | 0.68211 |
| Nicotinic acetylcholine Receptor α4 β2 | nACHR (a4/b2) | Opener | (−)-Nicotine | EC50 | 2.3741 |
| A tetrodotoxin-resistant voltage-gated sodium channel N-methyl-D-aspartate (NMDA) Glutamate | NAV1.5 | Blocker | Lidocaine | IC50 | 32.04972 |
| Norepinephrine transporter | NET | Blocker | Desipramine | IC50 | 0.01292 |
| N-methyl-D-aspartate (NMDA) Glutamate Receptor 1A/2B | NMDAR (1A/2B) | Blocker | (+)-MK 801 maleate | IC50 | 0.03884 |
| N-methyl-D-aspartate (NMDA) Glutamate Receptor 1A/2B | NMDAR (1A/2B) | Opener | L-Glutamic Acid | EC50 | 0.413 |
| Opioid Receptor Delta 1 | OPRD1 | Agonist | DADLE | EC50 | 0.00012 |
| Opioid Receptor Delta 1 | OPRD1 | Antagonist | Naltriben | IC50 | 0.00039 |
| Opioid Receptor Kappa 1 | OPRK1 | Agonist | Dynorphin A (1-17) | EC50 | 0.01234 |
| Opioid Receptor Kappa 1 | OPRK1 | Antagonist | nor-Binaltorphimine | IC50 | 0.00724 |
| Opioid Receptor Mu | OPRM1 | Agonist | DAMGO | EC50 | 0.00221 |
| Opioid Receptor Mu | OPRM1 | Antagonist | Naloxone | IC50 | 0.00552 |
| cGMP-inhibited cyclic nucleotide phosphodiesterase 3A | PDE3A | Inhibitor | Cilostamide | IC50 | 0.05554 |

TABLE 3-continued

| Target Names and Reference Compound Activity (Positive Controls) in Assays | | | | | |
|---|---|---|---|---|---|
| Target | Abbreviation | Mode | Reference Compound | Result Type | RC50 (μM) |
| cAMP-specific 3',5'-cyclic phospho-diesterase | PDE4D2 | Inhibitor | Cilomilast | IC50 | 0.01688 |
| Catecholamine Transporters | | | | | |
| Rho Associated Coiled-Coil Containing Protein Kinase 1 (serine-threonine kinase) | ROCK1 | Inhibitor | Staurosporine | IC50 | 8.00E−05 |
| Serotonin transporter | SERT | Blocker | Clomipramine | IC50 | 0.00242 |
| Vascular endothelial growth factor receptor 2 (KDR tyrosine kinase) | VEGFR2 | Inhibitor | SU-11248 | IC50 | 0.00022 |

Example 6: Human Serotonin Transporter (SERT, SLC6A4) Functional Antagonist Uptake Assay Benzothiophene derivatives were evaluated for inhibiting the human 5-HT transporter (hSERT) as expressed in CHO cells using an antagonist radioligand assay (Tatsumi, M. et al. (1999), Eur. J. Pharmacol., 368: 277-283). Compound binding was calculated as a percent inhibition of the binding of 2 nM [$^3$H]imipramine using a scintillation method and inhibition constants (Ki) were calculated using the Cheng Prusoff equation. Test compounds were assayed in three trials at 300, 94.868, 30, 9.4868, 0.3, and 0.94868 μM.

All tested compounds showed inhibition of hSERT within the tested range of concentrations. When compounds are substrates for monoamine transporters instead of solely inhibitors, it is known that IC50 values underestimate their potency for interacting with these transporters (Ilic, M. et al. (2020), Frontiers in Pharmacology 11: 673).

TABLE 4

| Human Serotonin Transporter Functional Antagonist Uptake Assay | | |
|---|---|---|
| Compound | SERT IC50 (μM ) | SERT Ki (μM) |
| 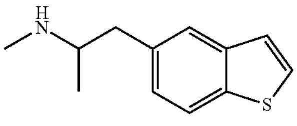 5-MAPBT | 0.25 | 0.12 |
| 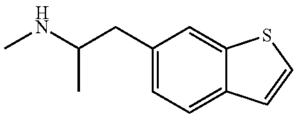 6-MAPBT | 1.5 | 0.68 |
| 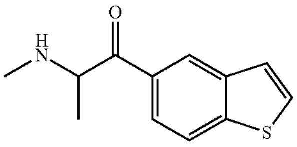 BK-5-MAPBT | 2.0 | 0.90 |

TABLE 4-continued

| Human Serotonin Transporter Functional Antagonist Uptake Assay | | |
|---|---|---|
| Compound | SERT IC50 (μM ) | SERT Ki (μM) |
| 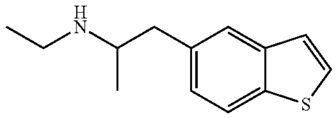 5-EAPBT | 0.10 | 0.05 |

Example 7: Human Monoamine Transporter (hMAT) Release

To assess the effects of benzothiophene derivatives on extracellular dopamine and serotonin concentrations, in vitro measures of serotonin and dopamine release were made using Chinese hamster ovary cells that stably expressed human monoamine transporters, dopamine (hDAT) and serotonin (hSERT) transporter. Dextroamphetamine and norfenfluramine were used as reference releasers of dopamine and serotonin, respectively.

Assay results revealed that the benzothiophene derivatives are more potent at releasing 5-HT than DA, with DAT to SERT ratios suggesting MDMA-like effects and indicating reduced abuse liability compared to amphetamine and other substances with higher DAT to SERT ratios. In addition, 5-EAPBT appeared to be a partial DAT substrate, with high concentrations producing limited dopamine release in comparison to the reference releaser amphetamine. This indicates that 5-EAPBT will display further reductions in abuse liability beyond those predictable from its DAT to SERT ratio.

Figure 7:
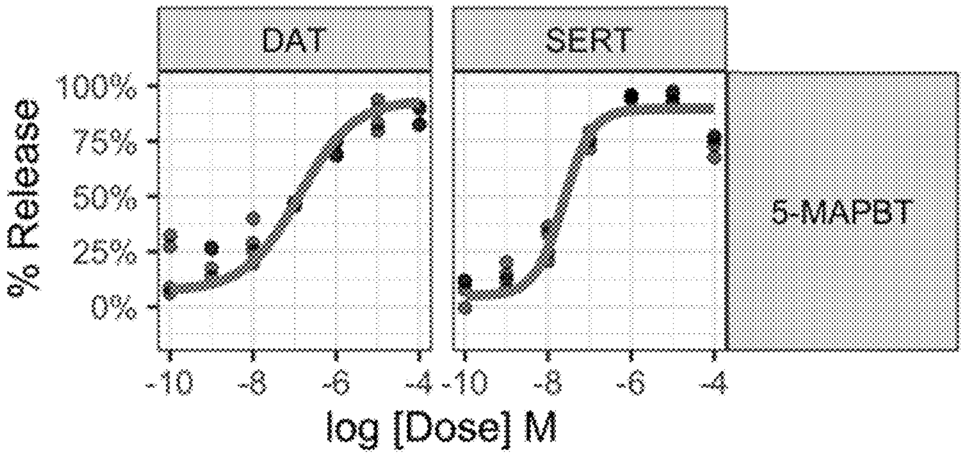
FIG. 7 is a graph showing results from the human monoamine transporter (hMAT) release assay. The graphs display [$^3$H]-labeled serotonin or dopamine release as a function of concentration of 5-MAPBT. The x-axis is the log [dose] concentration measured in molar and the y-axis is the [$^3$H]-labeled serotonin or dopamine release measured in percent of max release compared to a control. Details and procedural information for this assay are described in Example 7. These data indicate that 5-MAPBT rapidly induces extracellular dopamine and serotonin release.
Figure 8:
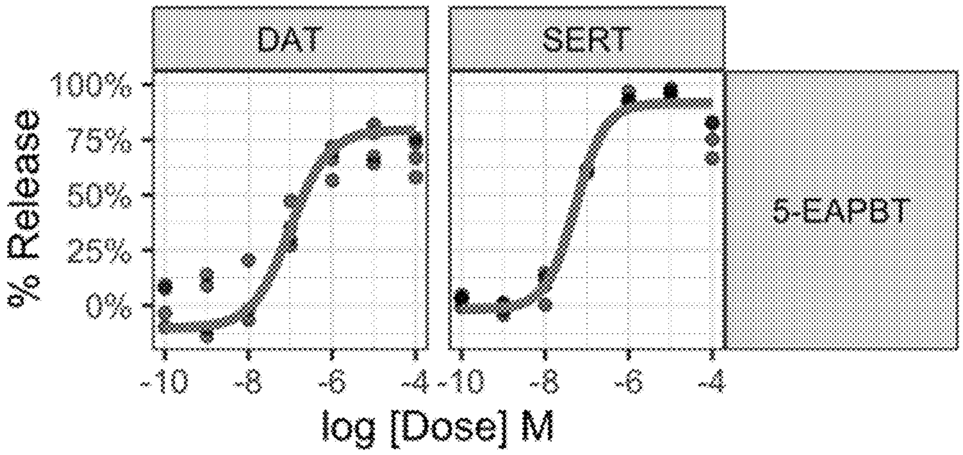
FIG. 8 is a graph showing results from the human monoamine transporter (hMAT) release assay. The graphs display [$^3$H]-labeled serotonin or dopamine release as a function of concentration of 5-EAPBT. The x-axis is the log [dose] concentration measured in molar and the y-axis is the [$^3$H]-labeled serotonin or dopamine release measured in percent of max release compared to a control. Details and procedural information for this assay are described in Example 7. These data indicate that 5-EAPBT rapidly induces extracellular dopamine and serotonin release.
Figure 9:
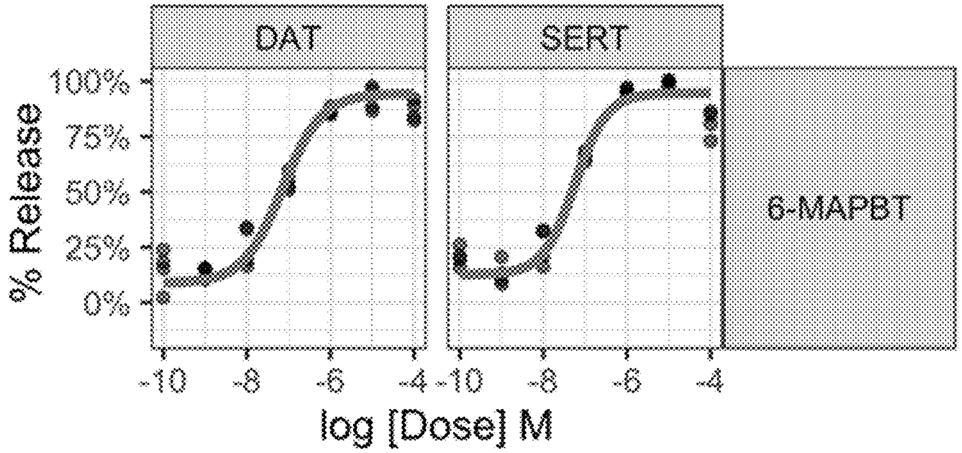
FIG. 9 is a graph showing results from the human monoamine transporter (hMAT) release assay. The graphs display [$^3$H]-labeled serotonin or dopamine release as a function of concentration of 6-MAPBT. The x-axis is the log [dose] concentration measured in molar and the y-axis is the [$^3$H]-labeled serotonin or dopamine release measured in percent of max release compared to a control. Details and procedural information for this assay are described in Example 7. These data indicate that 6-MAPBT rapidly induces extracellular dopamine and serotonin release.
Figure 10:
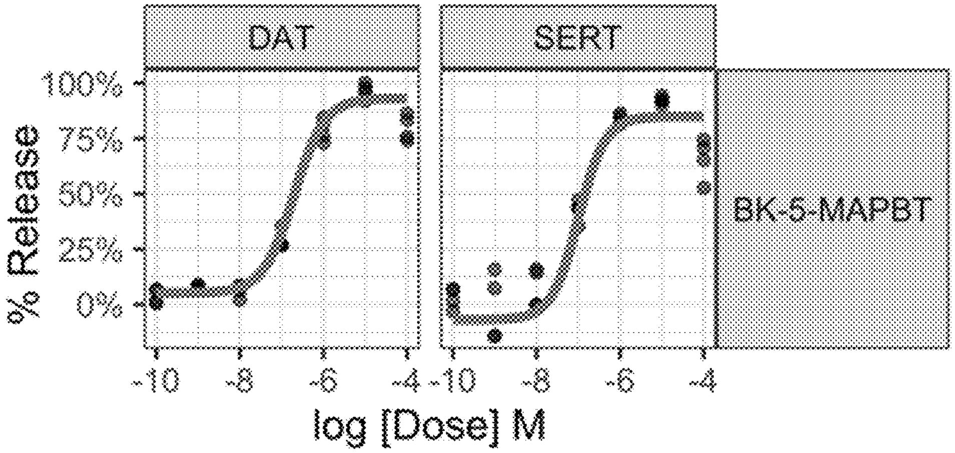
FIG. 10 is a graph showing results from the human monoamine transporter (hMAT) release assay. The graphs display [$^3$H]-labeled serotonin or dopamine release as a function of concentration of Bk-5-MAPBT. The x-axis is the log [dose] concentration measured in molar and the y-axis is the [$^3$H]-labeled serotonin or dopamine release measured in percent of max release compared to a control. Details and procedural information for this assay are described in Example 7. These data indicate that Bk-5-MAPBT rapidly induces extracellular dopamine and serotonin release.
Figure 11:
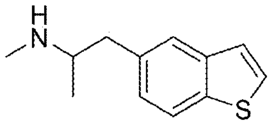
FIG. 11 provides the names and structures of 5-MAPBT and 6-MAPBT referred to herein.
Figure 11:
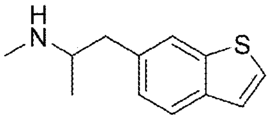

FIG. 7 is a graph of the effect of 5-MAPBT on monoamine release. FIG. 8 is a graph of the effect of 5-EAPBT on monoamine release. FIG. 9 is a graph of the effect of 6-MAPBT on monoamine release. FIG. 10 is a graph of the effect of Bk-5-MAPBT on monoamine release.

TABLE 5

| Effects of 5-MAPB on DAT and SERT | | | |
|---|---|---|---|
| | $EC_{50}$ DAT (nM) | $EC_{50}$ SERT (nM) | DAT/SERT ratio* |
| 5-MAPBT | 129 | 23 | 0.18 |
| 5-EAPBT | 98 | 53 | 0.54 |
| 6-MAPBT | 71 | 57 | 0.80 |
| BK-5-MAPBT | 194 | 101 | 0.52 |

*DAT/SERT ratios are calculated here as $(DAT\ EC_{50})^{-1}/(SERT\ EC_{50})^{-1}$ where larger numbers indicate higher DAT selectivity hSERT Release Measurement Methods Chinese hamster ovary cells expressing human SERT were seeded in Cytostar™ (PerkinElmer) plate with standard culture medium the day before the experiment at a single density (5000 cells/assay). Cells were incubated overnight with 5% $CO_2$ at 37° C. The day of experiment, the medium was replaced by incubation buffer (140 mM NaCl, 4.8 mM KCl, 1.2 mM $MgSO_4$, 0.1 mM $KH_2PO_4$, 10 mM HEPES, pH 7.4) with a single concentration of $[^3H]$serotonin at 150 nM. Experiments comparing release in radioligand-free incubation buffer versus incubation buffer containing $[^3H]$serotonin determined that the latter provided better signal stability. Therefore, this was used for experiments.

In control wells, the specificity of hSERT uptake was verified by adding the reference control imipramine (100 μM).

Two control conditions were used: (1) buffer only (with 1% DMSO concentration to match that in the test compound condition) to verify the background level of release; and (2) one reference SERT substrate compound, norfenfluramine, at 100 μM, to make it possible to calculate a relative $E_{max}$. Pilot studies varying DMSO concentration from 0.1 to 3% indicated that signal decreased at higher DMSO concentrations but that 1% DMSO retained good properties.

Cells were incubated at room temperature at different incubation times and radioactivity counted. Test compounds were measured at concentrations of 1e-10, 1e-09, 1e-08, 1e-07, 1e-06, 1e-05, and 1e-04 M. Each experiment was performed in duplicate (n=2) and results calculated at two inhibition times (60 and 90).

hDAT Release Measurement Methods

Chinese hamster ovary cells expressing human DAT were seeded in Cytostar™ plate with standard culture medium the day before experiment at one single density (2500 cells/assay). Cells were incubated overnight with 5% $CO_2$ at 37° C. The day of experiment, the medium was replaced by incubation buffer (TrisHCl 5 mM, 120 mM NaCl, 5.4 mM KCl, 1.2 mM $MgSO_4$, 1.2 mM $CaCl_2$), Glucose 5 mM, 7.5 mM HEPES, pH 7.4) with a single concentration of $[^3H]$ dopamine at 300 nM. Experiments comparing release in radioligand-free incubation buffer versus incubation buffer containing $[^3H]$dopamine determined that the latter provided better signal stability. Therefore, this was used for experiments.

In control wells, the specificity of DAT uptake was verified by adding the reference control GBR 12909 (10 μM).

For all assays, three reference conditions were employed: (1) radioligand-containing buffer only, to verify the control level of release, (2) buffer with 1% DMSO (solvent used to solubilize the test compounds), (3) 100 μM amphetamine (in 1% DMSO) to make it possible to calculate a relative $E_{max}$.

Cells were incubated at room temperature at different incubation times and radioactivity counted. Test compounds were measured at concentrations of 1e-10, 1e-09, 1e-08, 1e-07, 1e-06, 1e-05, and 1e-04 M. Each experiment was performed in duplicate (n=2) and results calculated at two inhibition times (60 and 90).

Statistical Analysis $EC/IC_{50S}$ were calculated using the R packages drm (to fit the regression model) and LL.4 (to define the structure of the log-logistic regression model). Values were fit to the following function:

$$f(x)=c+(d-c)/(1+\exp(b(\log(x)-\log(e)))$$

where b=the Hill coefficient, c=minimum value, d=maximum value, and e=$EC_{50}/IC_{50}$.

Values were calculated for both experimental repetitions at both stable inhibition times (60 and 90 minutes), resulting in four estimates of $EC_{50}$ and other parameters for each compound and transporter. These four values were averaged to produce final estimates for each compound and transporter.

Example 8: Evaluation of Entactogenic Effect of Decreased Neuroticism

The entactogenic effect of decreased neuroticism can be measured as a decrease in social anxiety using the Brief Fear of Negative Evaluation—revised (BFNE) (Carleton et al., 2006, Depression and Anxiety, 23(5), 297-303; Leary, 1983, Personality and Social Psychology bulletin, 9(3), 371-375). This 12-item Likert scale questionnaire measures apprehension and distress due to concerns about being judged disparagingly or with hostility by others. Ratings use a five-point Likert scale with the lowest, middle, and highest values labeled with "much less than normal," "normal," and "much more than normal." The BFNE can be administered before and repeatedly during therapeutic drug effects. Participants are instructed to answer how they have been feeling for the past hour, or otherwise during the effect of the drug. Baseline-subtracted responses are typically used in statistical models.

Example 9: Evaluation of Entactogenic Effect of Authenticity

The entactogenic effect of authenticity can be measured using the Authenticity Inventory (Kernis & Goldman. 2006. Advances in experimental social psychology, 38, 283-357) as modified by Baggott et al (Journal of Psychopharmacology 2016, 30.4: 378-87). Administration and scoring of the instrument is almost identical to that of the BFNE. The Authenticity Inventory consists of the following items, which are each rated on a 1-5 scale, with select items reverse scored as specified by Kernis & Goldman:

I am confused about my feelings.

I feel that I would pretend to enjoy something when in actuality I really didn't.

For better or worse, I am aware of who I truly am.

I understand why I believe the things I do about myself

I want the people with whom I am close to understand my strengths.

I actively understand which of my self-aspects fit together to form my core or true self.

I am very uncomfortable objectively considering my limitations and shortcomings.

I feel that I would use my silence or head-nodding to convey agreement with someone else's statement or position even though I really disagreed.

I have a very good understanding of why I do the things I do.
I am willing to change myself for others if the reward is desirable enough.
I would find it easy to pretend to be something other than my true self.
I want people with whom I am close to understand my weaknesses.
I find it difficult to critically assess myself (unchanged)
I am not in touch with my deepest thoughts and feelings.
I feel that I would make it a point to express to those I am close with how much I truly care for them.
I have difficulty accepting my personal faults, so I try to cast them in a more positive way.
I feel that I idealize the people close to me rather than objectively see them as they truly are.
If asked, people I am close to could accurately describe what kind of person I am.
I prefer to ignore my darkest thoughts and feelings.
I am aware of times when I am not being my true self.
I am able to distinguish the self-aspects that are important to my core or true self from those that are unimportant.
People close to me would be shocked or surprised if they discovered what I am keeping inside me.
It is important for me to understand the needs and desires of those with whom I am close.
I want people close to me to understand the real me, rather than just my public persona or "image".
I could act in a manner that is consistent with my personally held values, even if others criticized me or rejected me for doing so.
If a close other and I were in disagreement, I would rather ignore the issue than constructively work it out.
I feel that I would do things that I don't want to do merely to avoid disappointing people.
My behavior expresses my values.
I actively attempt to understand myself as well as possible.
I feel that I'd rather feel good about myself than objectively assess my personal limitations and shortcomings.
My behavior expresses my personal needs and desires.
I have on a "false face" for others to see.
I feel that I would spend a lot of energy pursuing goals that are very important to other people even though they are unimportant to me.
I am not in touch with what is important to me.
I try to block out any unpleasant feelings I have about myself.
I question whether I really know what I want to accomplish in my lifetime.
I am overly critical about myself.
I am in touch with my motives and desires.
I feel that I would deny the validity of any compliments that I receive.
I place a good deal of importance on people close to me understanding who I truly am.
I find it difficult to embrace and feel good about the things I have accomplished.
If someone pointed out or focused on one of my shortcomings, I would quickly try to block it out of my mind and forget it.
The people close to me could count on me being who I am, regardless of what setting we were in.
My openness and honesty in close relationships are extremely important to me.
I am willing to endure negative consequences by expressing my true beliefs about things.

Example 10: Evaluation of Side Effects of Entactogens

Adverse effects of an entactogen include formation of tolerance to entactogens, headache, difficulty concentrating, lack of appetite, lack of energy, and decreased mood. To measure these adverse effects, patients can be asked to complete a self-report symptom questionnaire, such as the Subjective Drug Effects Questionnaire (SDEQ) or List of Complaints. The SDEQ is a 272-item self-report instrument measuring perceptual, mood, and somatic changes caused by drugs including hallucinogens like LSD (Katz et al. 1968. J Abnorm Psychology 73:1-14). It has also been used to measure the therapeutic and adverse effects of MDMA (Harris et al. 2002. Psychopharmacology, 162(4), 396-405). The List of Complaints is a 66-item questionnaire that measures physical and general discomfort and is sensitive to entactogen-related complaints (e.g., Vizeli & Liechti. 2017. Journal of Psychopharmacology, 31(5), 576-588).

In addition to these mild toxicities, MDMA is associated with a number of more severe toxicities, including but not limited to acute and chronic cardiovascular changes, hepatotoxicity, hyperthermic syndromes, hyponatremia, and neurotoxicity (see the MDMA Investigator's Brochure, 13th Edition: Mar. 22, 2021, and references therein, available from the sponsor of MDMA clinical trials at MAPS.org).

Alternatively, individual items can be taken from the SDEQ or List of Complaints in order to create more focused questionnaires and reduce the burden of filling out time-consuming paperwork on participants. To measure tolerance formation, a global measure of the intensity of therapeutic effects can be used, such as the question "on a scale from 0 to 100 where 0 is no 'good drug effect' and 100 is the most 'good drug effect' you have ever felt, how would you rate this drug experience?"

In some embodiments, the questionnaire will be administered approximately 7 hours after a patient takes MDMA or another entactogen (with instructions to answer for the time since taking the entactogen) and then daily (with instructions to answer for the last 24 hours) for up to 96 hours after the entactogen was taken. Decreases in adverse effects of a compound compared to MDMA can be shown by comparing the intensity (for the tolerance question) or prevalence (for other symptom questions) of effects that occur. Prevalence of adverse effects including formation of tolerance to entactogens, headache, difficulty concentrating, lack of appetite, lack of energy, and decreased mood may be decreased by approximately 10%, 20%, 30%, 40%, 50%, 60%, 70%, 80%, 90%, 99%, or 100%.

While the present invention is described in terms of particular embodiments and applications, it is not intended that these descriptions in any way limit its scope to any such embodiments and applications, and it will be understood that many modifications, substitutions, changes, and variations in the described embodiments, applications, and details of the invention illustrated herein can be made by those skilled in the art without departing from the spirit of the invention, or the scope of the invention as described in the appended claims.

I claim:

1. A compound selected from:

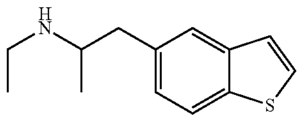

5-EAPBT

-continued
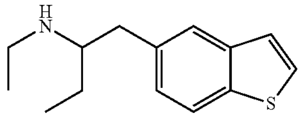
5-MBPBT
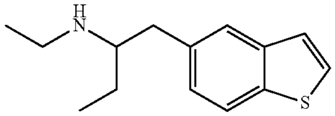
5-EBPBT
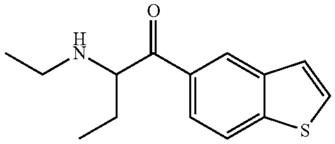
Bk-5-EBPBT
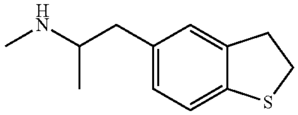
5-MAPDBT
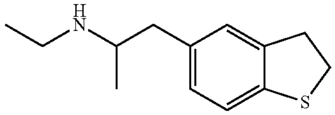
5-EAPDBT
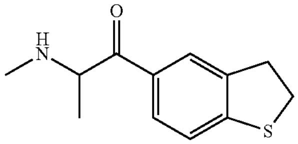
Bk-5-MAPDBT
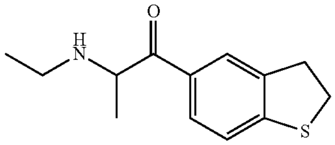
Bk-5-EAPDBT
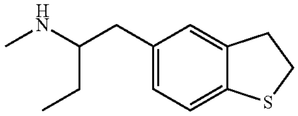
5-MBPDBT
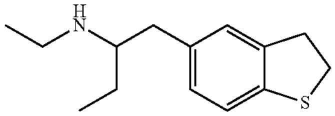
5-EBPDBT
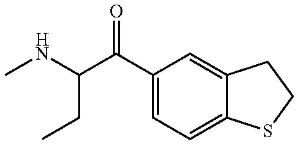
Bk-5-MBPDBT
-continued
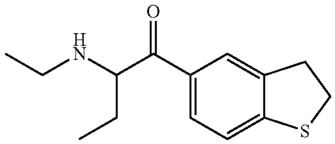
Bk-5-EBPDBT
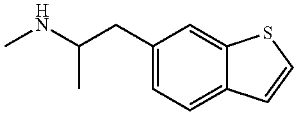
6-MAPBT
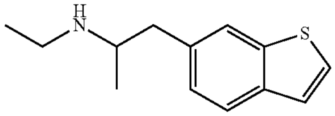
6-EAPBT
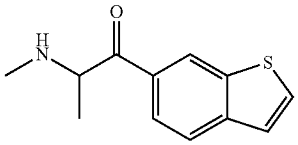
Bk-6-MAPBT
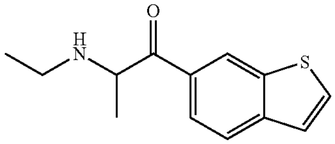
Bk-6-EAPBT
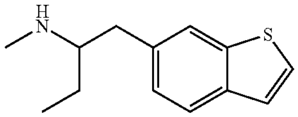
6-MBPBT
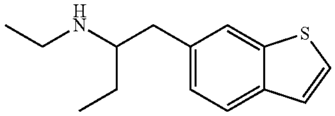
6-EBPBT
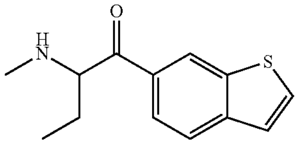
Bk-6-MBPBT
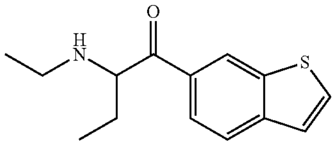
Bk-6-EBPBT
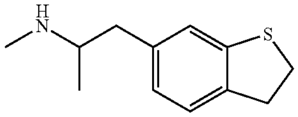
6-MAPDBT -continued

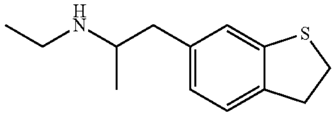

6-EAPDBT

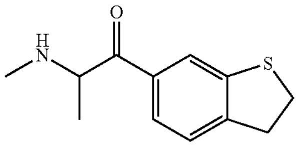

Bk-6-MAPDBT

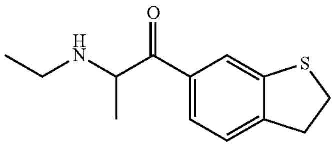

Bk-6-EAPDBT

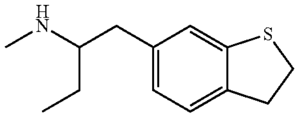

6-MBPDBT

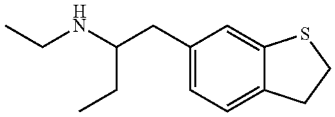

6-EBPDBT

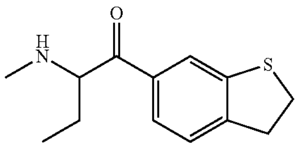

and

Bk-6-MBPDBT

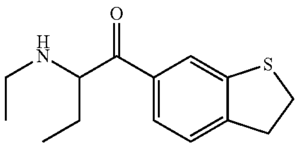

Bk-6-EBPDBT or a pharmaceutically acceptable salt or salt mixture thereof.

2. The compound of claim 1 selected from:

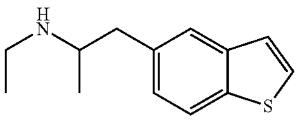

5-EAPBT

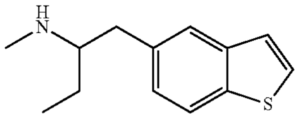

5-MBPBT

-continued

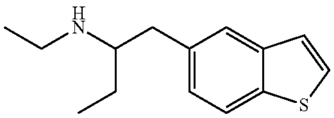

5-EBPBT

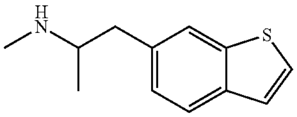

6-MAPBT

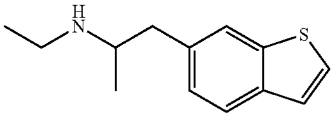

6-EAPBT

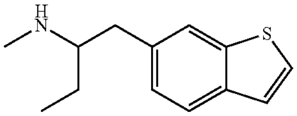

and

6-MBPBT

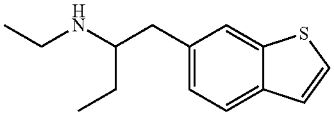

6-EBPBT or a pharmaceutically acceptable salt or salt mixture thereof.

3. The compound of claim 2 of structure:

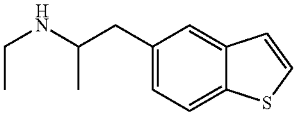

5-EAPBT or a pharmaceutically acceptable salt or salt mixture thereof.

4. The compound of claim 2 of structure:

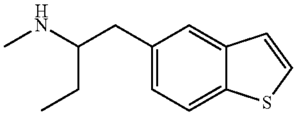

5-MBPBT or a pharmaceutically acceptable salt or salt mixture thereof.

5. The compound of claim 2 of structure:

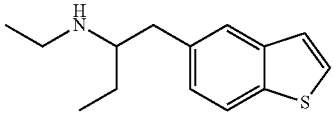

5-EBPBT or a pharmaceutically acceptable salt or salt mixture thereof.

6. The compound of claim 2 of structure:

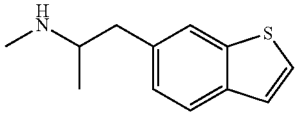

6-MAPBT or a pharmaceutically acceptable salt or salt mixture thereof.

7. The compound of claim 2 of structure:

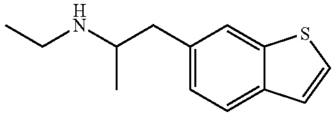

6-EAPBT or a pharmaceutically acceptable salt or salt mixture thereof.

8. The compound of claim 2 of structure:

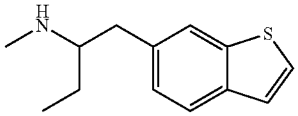

6-MBPBT or a pharmaceutically acceptable salt or salt mixture thereof.

9. The compound of claim 2 of structure:

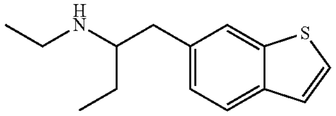

6-EBPBT or a pharmaceutically acceptable salt or salt mixture thereof.

10. The compound of claim 1 selected from

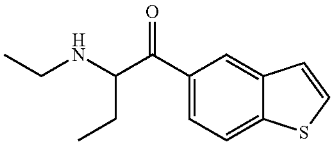

Bk-5-EBPBT

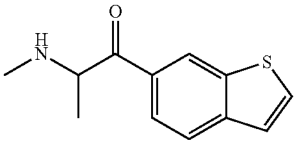

Bk-6-MAPBT

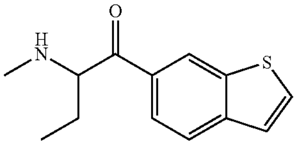

Bk-6-MBPBT

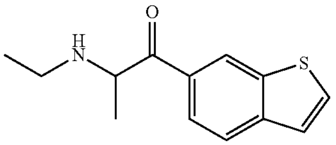

and

Bk-6-EAPBT

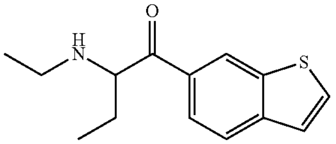

Bk-6-EBPBT or a pharmaceutically acceptable salt or salt mixture thereof.

11. The compound of claim 10 of structure:

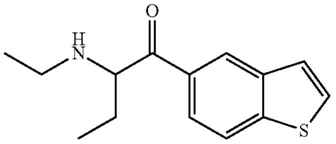

Bk-5-EBPBT or a pharmaceutically acceptable salt or salt mixture thereof.

12. The compound of claim 10 of structure:

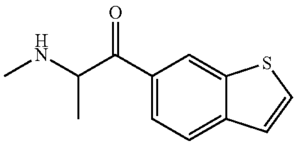

Bk-6-MAPBT or a pharmaceutically acceptable salt or salt mixture thereof.

13. The compound of claim 10 of structure:

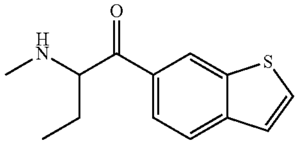

Bk-6-MBPBT or a pharmaceutically acceptable salt or salt mixture thereof.

14. The compound of claim 10 of structure:

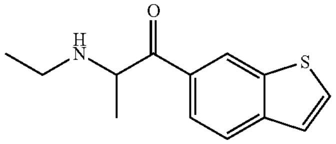

Bk-6-EAPBT or a pharmaceutically acceptable salt or salt mixture thereof.

15. The compound of claim 10 of structure:

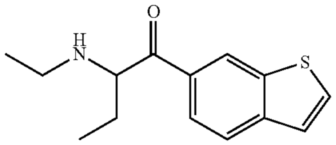

Bk-6-EBPBT or a pharmaceutically acceptable salt or salt mixture thereof.

16. The compound of claim 1 selected from:

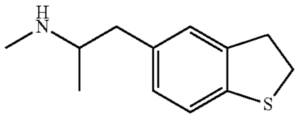

5-MAPDBT

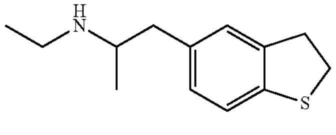

5-EAPDBT

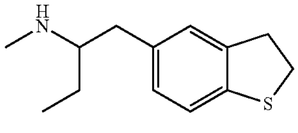

5-MBPDBT

-continued

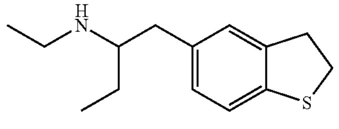

5-EBPDBT

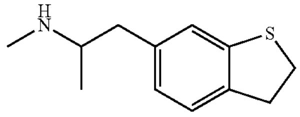

6-MAPDBT

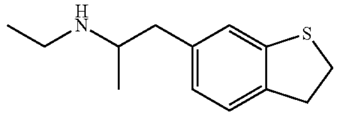

6-EAPDBT

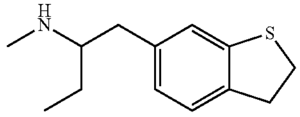

and

6-MBPDBT

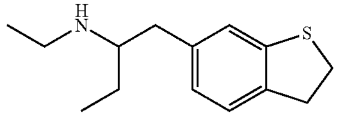

6-EBPDBT or a pharmaceutically acceptable salt or salt mixture thereof.

17. The compound of claim 16 of structure:

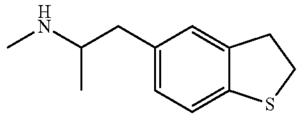

5-MAPDBT or a pharmaceutically acceptable salt or salt mixture thereof.

18. The compound of claim 16 of structure:

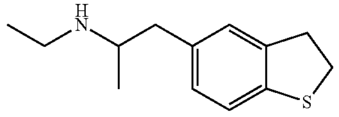

5-EAPDBT or a pharmaceutically acceptable salt or salt mixture thereof.

19. The compound of claim 16 of structure:

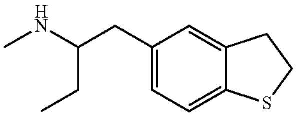

5-MBPDBT or a pharmaceutically acceptable salt or salt mixture thereof.

20. The compound of claim 16 of structure:

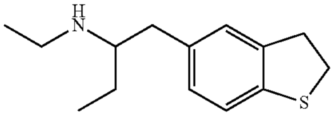

5-EBPDBT or a pharmaceutically acceptable salt or salt mixture thereof.

21. The compound of claim 16 of structure:

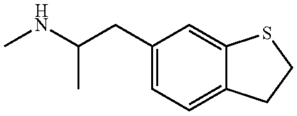

6-MAPDBT or a pharmaceutically acceptable salt or salt mixture thereof.

22. The compound of claim 16 of structure:

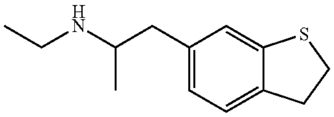

6-EAPDBT or a pharmaceutically acceptable salt or salt mixture thereof.

23. The compound of claim 16 of structure:

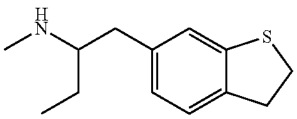

6-MBPDBT or a pharmaceutically acceptable salt or salt mixture thereof.

24. The compound of claim 16 of structure:

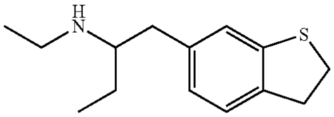

6-EBPDBT or a pharmaceutically acceptable salt or salt mixture thereof.

25. The compound of claim 1 selected from

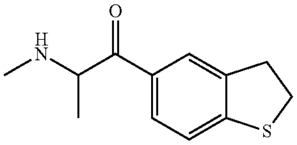

Bk-5-MAPDBT

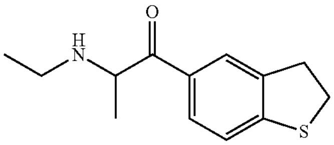

Bk-5-EAPDBT

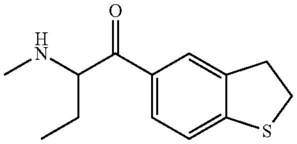

Bk-5-MBPDBT

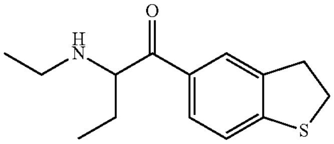

Bk-5-EBPDBT

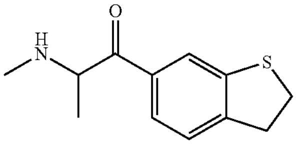

Bk-6-MAPDBT

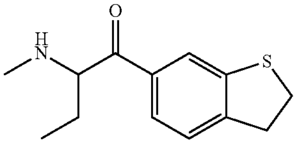

Bk-6-MBPDBT

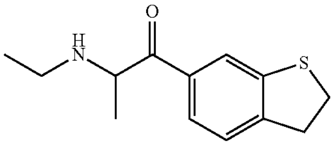

and

Bk-6-EAPDBT

-continued

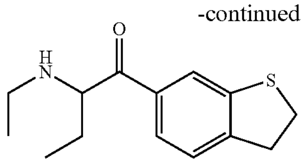

Bk-6-EBPDBT or a pharmaceutically acceptable salt or salt mixture thereof.

26. The compound of claim 25 of structure:

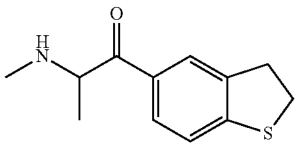

Bk-5-MAPDBT or a pharmaceutically acceptable salt or salt mixture thereof.

27. The compound of claim 25 of structure:

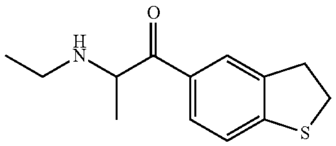

Bk-5-EAPDBT or a pharmaceutically acceptable salt or salt mixture thereof.

28. The compound of claim 25 of structure:

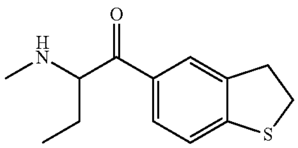

Bk-5-MBPDBT or a pharmaceutically acceptable salt or salt mixture thereof.

29. The compound of claim 25 of structure:

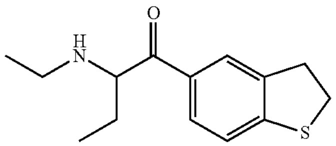

Bk-5-EBPDBT or a pharmaceutically acceptable salt or salt mixture thereof.

30. The compound of claim 25 of structure:

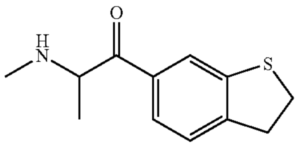

Bk-6-MAPDBT or a pharmaceutically acceptable salt or salt mixture thereof.

31. The compound of claim 25 of structure:

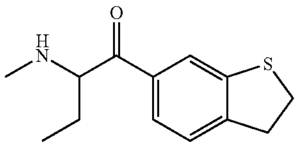

Bk-6-MBPDBT or a pharmaceutically acceptable salt or salt mixture thereof.

32. The compound of claim 25 of structure:

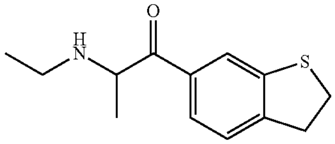

Bk-6-EAPDBT or a pharmaceutically acceptable salt or salt mixture thereof.

33. The compound of claim 25 of structure:

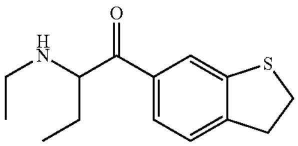

Bk-6-EBPDBT or a pharmaceutically acceptable salt or salt mixture thereof.

34. A pharmaceutical composition comprising a compound of claim 1 or a pharmaceutically acceptable salt or salt mixture thereof and a pharmaceutically acceptable excipient.

35. The pharmaceutical composition of claim 34, wherein the compound is selected from

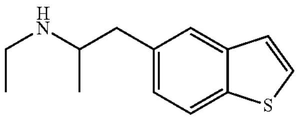

5-EAPBT

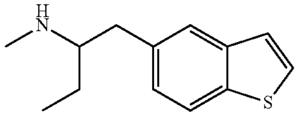

5-MBPBT

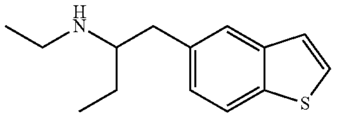

5-EBPBT

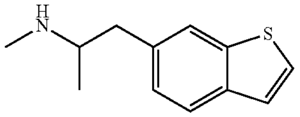

6-MAPBT

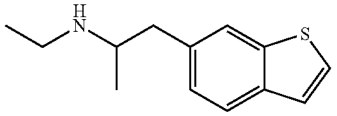

6-EAPBT

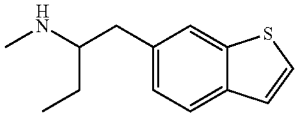

and

6-MBPBT

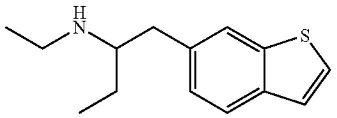

6-EBPBT or a pharmaceutically acceptable salt or salt mixture thereof.

36. The pharmaceutical composition of claim 34, wherein the compound is selected from

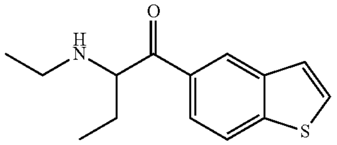

Bk-5-EBPBT

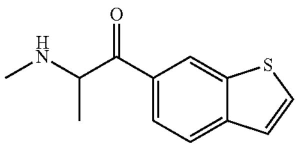

Bk-6-MAPBT

-continued

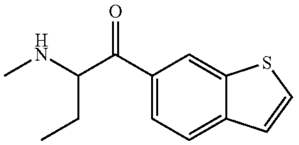

Bk-6-MBPBT

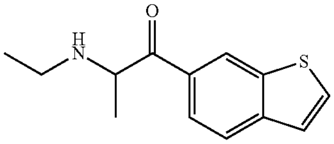

and

Bk-6-EAPBT

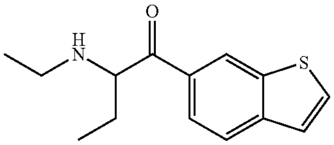

Bk-6-EBPBT or a pharmaceutically acceptable salt or salt mixture thereof.

37. The pharmaceutical composition of claim 34, wherein the compound is selected from

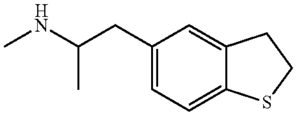

5-MAPDBT

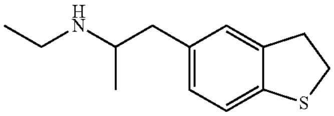

5-EAPDBT

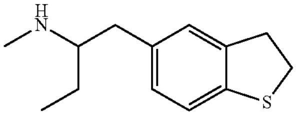

5-MBPDBT

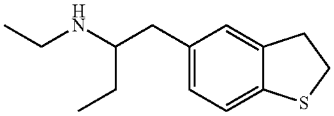

5-EBPDBT

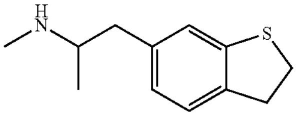

6-MAPDBT

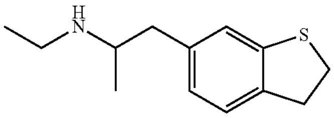

6-EAPDBT

-continued
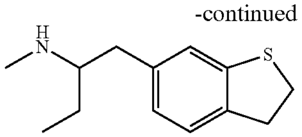
and
6-MBPDBT
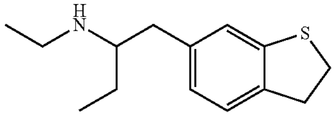
6-EBPDBT
or a pharmaceutically acceptable salt or salt mixture thereof.
38. The pharmaceutical composition of claim 34, wherein the compound is selected from
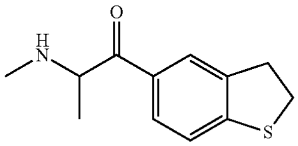
Bk-5-MAPDBT
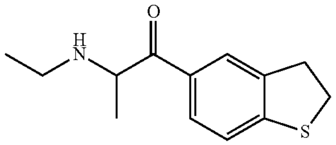
Bk-5-EAPDBT
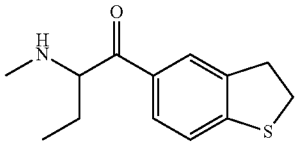
Bk-5-MBPDBT
-continued
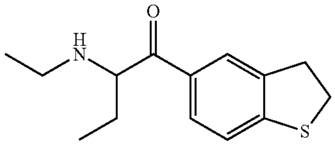
Bk-5-EBPDBT
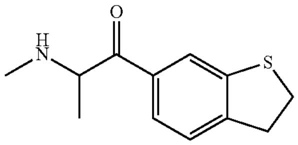
Bk-6-MAPDBT
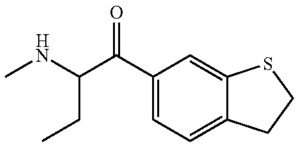
Bk-6-MBPDBT
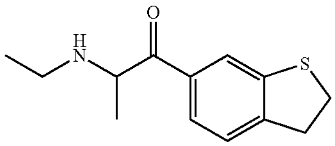
and
Bk-6-EAPDBT
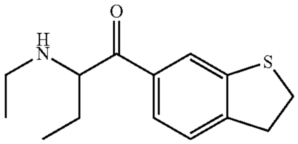
Bk-6-EBPDBT
or a pharmaceutically acceptable salt or salt mixture thereof.
* * * * *